US012077483B2

(12) United States Patent
Scully et al.

(10) Patent No.: US 12,077,483 B2
(45) Date of Patent: Sep. 3, 2024

(54) MODIFIED AMINE LIPIDS

(71) Applicant: Intellia Therapeutics, Inc., Cambridge, MA (US)

(72) Inventors: Stephen S. Scully, Cambridge, MA (US); Micah Maetani, Cambridge, MA (US); Ramsey Majzoub, Cambridge, MA (US)

(73) Assignee: Intellia Therapeutics, Inc., Cambridge, MA (US)

( * ) Notice: Subject to any disclaimer, the term of this patent is extended or adjusted under 35 U.S.C. 154(b) by 651 days.

(21) Appl. No.: 17/299,925

(22) PCT Filed: Dec. 5, 2019

(86) PCT No.: PCT/US2019/064663
§ 371 (c)(1),
(2) Date: Jun. 4, 2021

(87) PCT Pub. No.: WO2020/118041
PCT Pub. Date: Jun. 11, 2020

(65) Prior Publication Data
US 2022/0119341 A1  Apr. 21, 2022

Related U.S. Application Data

(60) Provisional application No. 62/775,783, filed on Dec. 5, 2018.

(51) Int. Cl.
| | |
|---|---|
| *C07C 219/04* | (2006.01) |
| *A61P 1/16* | (2006.01) |
| *C07C 271/20* | (2006.01) |
| *C07D 205/04* | (2006.01) |
| *C07D 207/09* | (2006.01) |
| *C07D 211/46* | (2006.01) |
| *C07D 211/62* | (2006.01) |
| *C07D 271/10* | (2006.01) |
| *C07D 295/08* | (2006.01) |
| *C12N 15/113* | (2010.01) |
| *B82Y 5/00* | (2011.01) |
| *B82Y 30/00* | (2011.01) |
| *B82Y 40/00* | (2011.01) |

(52) U.S. Cl.
CPC .............. *C07C 219/04* (2013.01); *A61P 1/16* (2018.01); *C07C 271/20* (2013.01); *C07D 205/04* (2013.01); *C07D 207/09* (2013.01); *C07D 211/46* (2013.01); *C07D 211/62* (2013.01); *C07D 271/10* (2013.01); *C07D 295/08* (2013.01); *C12N 15/113* (2013.01); *B82Y 5/00* (2013.01); *B82Y 30/00* (2013.01); *B82Y 40/00* (2013.01); *C12N 2310/315* (2013.01); *C12N 2310/321* (2013.01)

(58) Field of Classification Search
CPC ....... C07C 219/04; C07C 271/20; A61P 1/16; C07D 205/04; C07D 207/09; C07D 211/46; C07D 211/62; C07D 271/10; C07D 295/08; C12N 15/113; C12N 2310/315; C12N 2310/321; B82Y 5/00; B82Y 30/00; B82Y 40/00
USPC ......................................................... 514/315
See application file for complete search history.

(56) References Cited

FOREIGN PATENT DOCUMENTS

| WO | WO-2014/093622 A2 | 6/2014 |
|---|---|---|
| WO | WO-2015/095346 A1 | 6/2015 |
| WO | WO-2016/010840 A1 | 1/2016 |
| WO | WO-2016/037053 A1 | 3/2016 |
| WO | WO-2017/173054 A1 | 10/2017 |
| WO | WO-2020/118041 A1 | 6/2020 |

OTHER PUBLICATIONS

International Search Report and Written Opinion for International Application No. PCT/US2019/064663 mailed Mar. 17, 2020.

*Primary Examiner* — Kristin A Vajda
(74) *Attorney, Agent, or Firm* — Foley Hoag LLP; David P. Halstead; Janine S. Ladislaw

(57) ABSTRACT

The disclosure provides ionizable amine lipids and salts thereof (e.g., pharmaceutically acceptable salts thereof) useful for the delivery of biologically active agents, for example delivering biologically active agents to cells to prepare engineered cells. The ionizable amine lipids disclosed herein are useful as ionizable lipids in the formulation of lipid nanoparticle-based compositions.

21 Claims, 33 Drawing Sheets
Specification includes a Sequence Listing.

MODIFIED AMINE LIPIDS

CROSS-REFERENCE TO RELATED APPLICATIONS

This application is the U.S. national phase of International Application No. PCT/US2019/064663, filed Dec. 5, 2019, which claims priority to U.S. Provisional Patent Application No. 62/775,783, filed Dec. 5, 2018, the entire contents of each of these applications are incorporated herein by reference.

BACKGROUND

Lipid nanoparticles formulated with ionizable amine-containing lipids can serve as cargo vehicles for delivery of biologically active agents, in particular polynucleotides, such as RNAs, mRNAs, and guide RNAs into cells. The LNP compositions containing ionizable lipids can facilitate delivery of oligonucleotide agents across cell membranes, and can be used to introduce components and compositions for gene editing into living cells. Biologically active agents that are particularly difficult to deliver to cells include proteins, nucleic acid-based drugs, and derivatives thereof, particularly drugs that include relatively large oligonucleotides, such as mRNA. Compositions for delivery of promising gene editing technologies into cells, such as for delivery of CRISPR/Cas9 system components, are of particular interest (e.g., mRNA encoding a nuclease and associated guide RNA (gRNA)).

Compositions for delivery of the protein and nucleic acid components of CRISPR/Cas to a cell, such as a cell in a patient, are needed. In particular, compositions for delivering mRNA encoding the CRISPR protein component, and for delivering CRISPR guide RNAs are of particular interest. Compositions with useful properties for in vitro and in vivo delivery that can stabilize and deliver RNA components, are also of particular interest.

BRIEF SUMMARY

The present disclosure provides amine-containing lipids useful for the formulation of lipid nanoparticle (LNP) compositions. Such LNP compositions may have properties advantageous for delivery of nucleic acid cargo, such as CRISPR/Cas gene editing components, to cells.

In certain embodiments, the present disclosure relates to a compound having a structure of Formula (IA):

(IA)

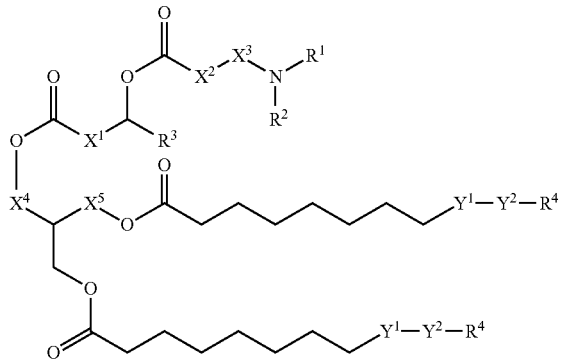

wherein, independently for each occurrence, $X^1$ is $C_{1-3}$ alkylene or

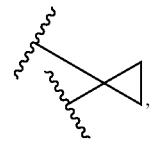 [SMILES: *C1(*)CC1]

$X^2$ is selected from O, NH, NMe, and a bond,
$X^3$ is $C_{2-4}$ alkylene,
$X^4$ is $C_1$ alkylene or a bond,
$X^5$ is $C_1$ alkylene or a bond,
$R^1$ is $C_{1-3}$ alkyl,
$R^2$ is $C_{1-3}$ alkyl, or
$R^2$ taken together with the nitrogen atom and either $R^1$ or a carbon atom of $X^3$ form a 4-membered, 5-membered, or 6-membered ring,
$Y^1$ is selected from a bond, —CH=CH—, —(C=O)O—, and —O(C=O)—,
$Y^2$ is selected from —CH$_2$—CH=CH— and $C_3$-$C_4$ alkylene,
$R^3$ is selected from H, $C_{5-7}$ cycloalkyl, $C_8$-$C_{10}$ alkenyl, and $C_{3-18}$ alkyl,
$R^4$ is $C_{4-8}$ alkyl,
or a salt thereof, with a proviso that when $R^2$ is Me, $R^3$ is linear $C_{12}$ alkyl, $X^1$ is $C_2$ alkylene, $X^2$ is O, $X^3$ is $C_3$ alkylene, $X^4$ is a bond, $X^5$ is $C_1$ alkylene, $Y^1$ is cis —CH=CH—, and —Y$^2$—R$^4$ is cis —CH$_2$—CH=CH—(C$_5$-alkyl), then $R^1$ is $C_{2-3}$ alkyl.

In certain embodiments, the present disclosure relates to a compound having a structure of Formula (I):

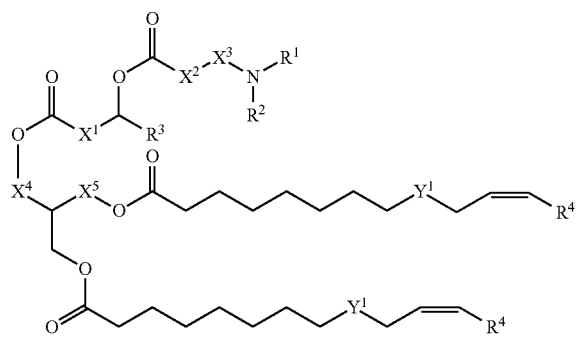

wherein, independently for each occurrence,
$X^1$ is $C_{2-3}$ alkylene,
$X^2$ is selected from O, NH, NMe, and a bond,
$X^3$ is $C_{2-4}$ alkylene,
$X^4$ is $C_1$ alkylene or a bond, $X^5$ is $C_1$ alkylene or a bond,
$R^1$ is $C_{1-2}$ alkyl,
$R^2$ is $C_{1-2}$ alkyl, or
  $R^2$ taken together with the nitrogen atom and either $R^1$ or a carbon atom of
$X^3$ form a 5-membered or a 6-membered ring,
$Y^1$ is selected from —CH=CH—, —(C=O)O—, and —O(C=O)—,
$R^3$ is selected from H, $C_{5-7}$ cycloalkyl, and $C_{3-18}$ alkyl,
$R^4$ is $C_{4-7}$ alkyl,
or a salt thereof,
with a proviso that when $R^2$ is Me, $R^3$ is linear $C_{12}$ alkyl, $X^1$ is $C_2$ alkylene, $X^2$ is O, $X^3$ is $C_3$ alkylene, $X^4$ is a bond, $X^5$ is $C_1$ alkylene, $Y^1$ is cis —CH=CH— and $R^4$ is $C_5$ alkyl, then $R^1$ is $C_2$ alkyl, or a salt thereof, such as a pharmaceutically acceptable salt thereof.

In certain embodiments, the compound is a compound of Formula (I) with a proviso that when $R^2$ is Me, $R^3$ is linear $C_{12}$ alkyl, $X^1$ is $C_2$ alkylene, $X^2$ is O, $X^3$ is $C_3$ alkylene, $X^4$ is a bond, $X^5$ is $C_1$ alkylene, and $Y^1$ is cis —CH=CH—, then $R^1$ is $C_2$ alkyl.

In certain embodiments, $X^1$ is linear $C_2$ alkylene. In other embodiments, $X^1$ is $C_1$ alkylene. In some embodiments, $X^1$ is linear $C_3$ alkylene or branched $C_3$ alkylene.

In some other embodiments, $X^2$ is NH or O. In certain preferred embodiments, $X^2$ is O and $X^3$ is $C_{3-4}$ alkylene. In some embodiments, $X^3$ is $C_{2-3}$ alkylene. In certain embodiments, $X^2$ is NMe or a bond.

In certain embodiments, $R^2$ and a carbon atom of $X^3$ taken together form a 4-membered ring. In certain embodiments, $R^2$ and a carbon atom of $X^3$ taken together form a 5-membered ring. In some embodiments, $R^2$ and a carbon atom of $X^3$ taken together form a 6-membered ring. Alternatively, $R^2$ may be $C_2$ alkyl. In some instances, $R^2$ is $C_1$ alkyl. In some embodiments, $R^2$ is substituted, for example, with a hydroxy group, an example of $R^2$ includes hydroxy-substituted $C_2$ alkyl.

In certain embodiments, $R^1$ is $C_1$ alkyl. Alternatively, $R^1$ may be $C_2$ alkyl. In some embodiments, $R^1$ is substituted, for example, with a hydroxy group, an example of $R^1$ includes hydroxy-substituted $C_2$ alkyl. In other embodiments, $R^1$ and $R^2$ together form a 4-membered ring. In other embodiments, $R^1$ and $R^2$ together form a 5-membered ring. In still other embodiments, $R^1$ and $R^2$ together form a 6-membered ring.

In some embodiments, $R^3$ is linear $C_{8-16}$ alkyl, for example linear $C_{7-12}$ alkyl, such as linear $C_{7-9}$ alkyl. Alternatively, $R^3$ can be linear $C_{3-6}$ alkyl. In some embodiments, $R^3$ is branched $C_{6-10}$ alkyl. In other embodiments, $R^3$ is $C_{5-7}$ cycloalkyl, for example $C_6$ cycloalkyl. In some embodiments, $R^3$ is H. In some embodiments, $R^3$ is $C_{8-10}$ alkenyl.

In certain embodiments, $R^4$ is linear $C_{5-6}$ alkyl.

In some embodiments, $X^4$ is a bond.

In certain embodiments, $X^5$ is a $C_1$ alkylene.

In some embodiments, $Y^2$—$R^4$ is —$CH_2$—CH=CH—$R^4$.

In other embodiments, $Y^2$ is linear $C_3$ alkylene.

In some embodiments, $Y^1$ is selected from a bond, —CH=CH—, and —O(C=O)—, for example, —CH=CH— and —O(C=O)—.

In certain embodiments, the compound is a compound of Formula II:

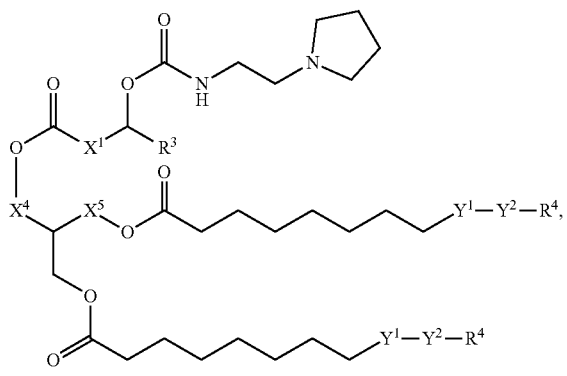

(II)

wherein the variables are defined as for Formula (IA).

In certain embodiments, the compound is a compound of Formula III;

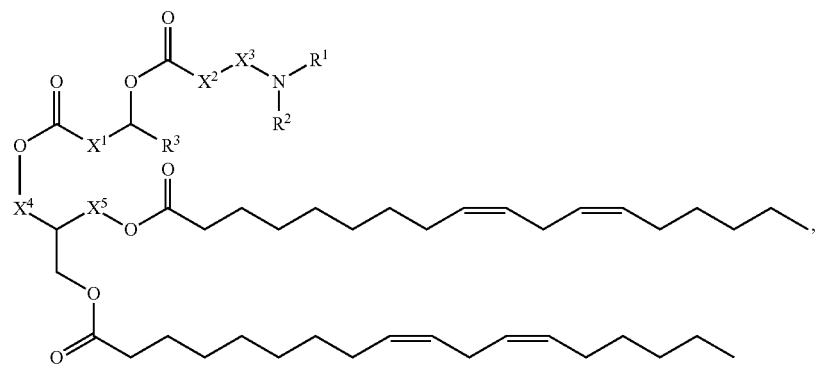

(III)

wherein the variables are defined as for Formula (IA).

Representative compounds of Formula (IA) or (I) include:
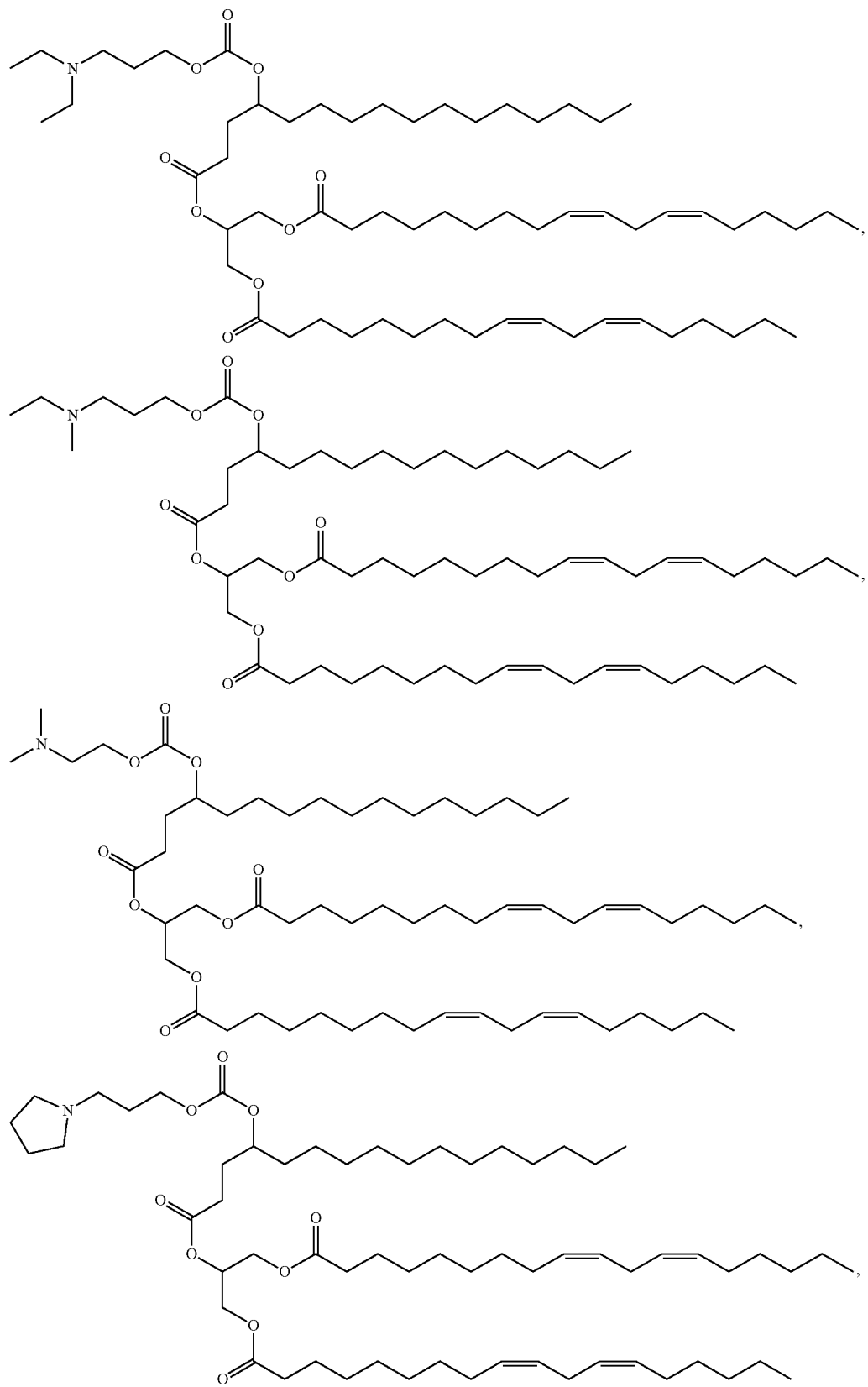

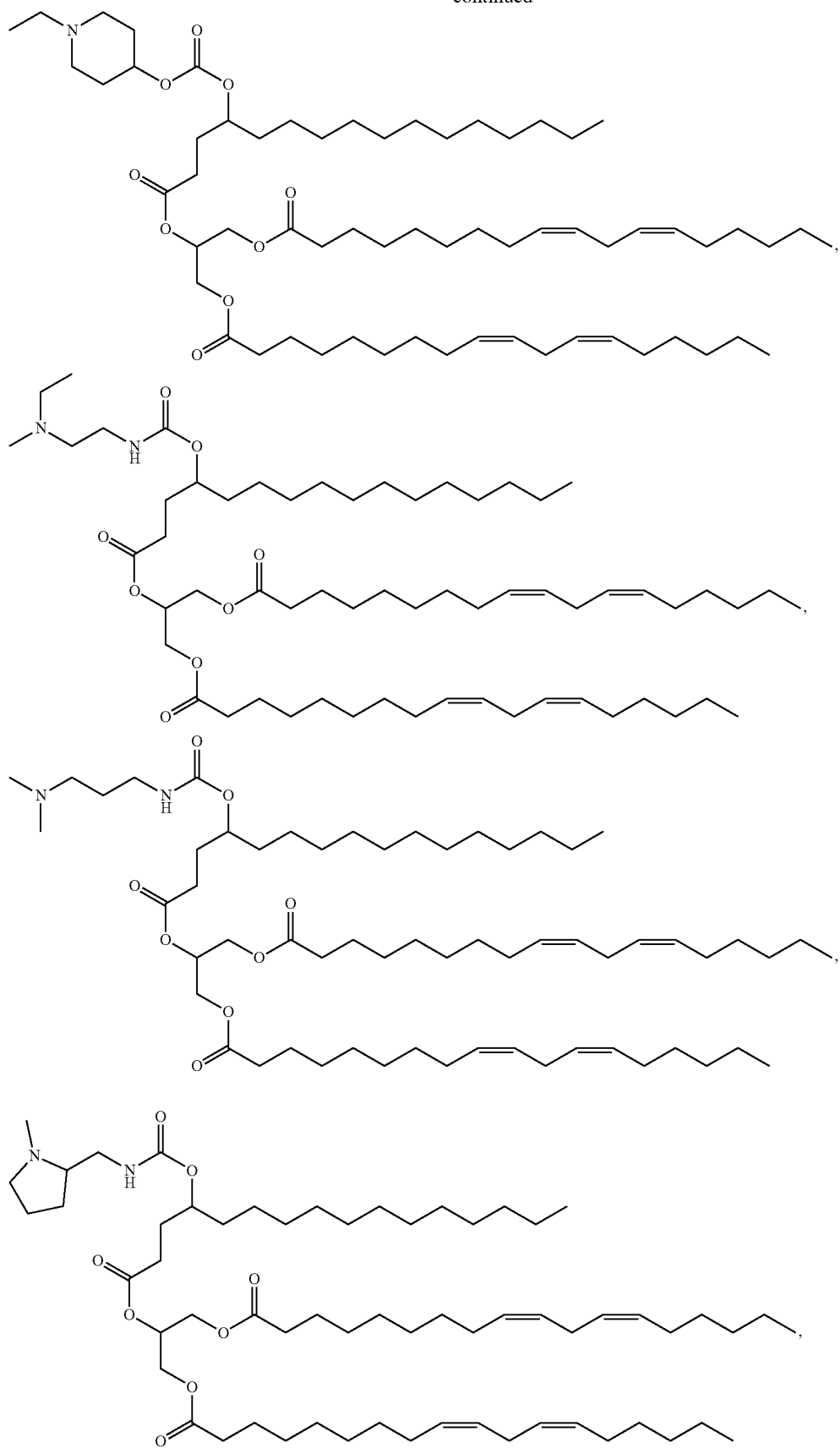

-continued
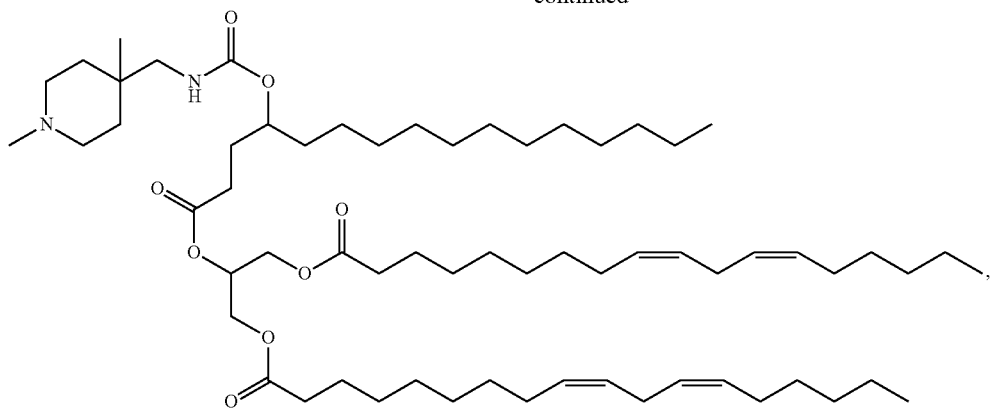
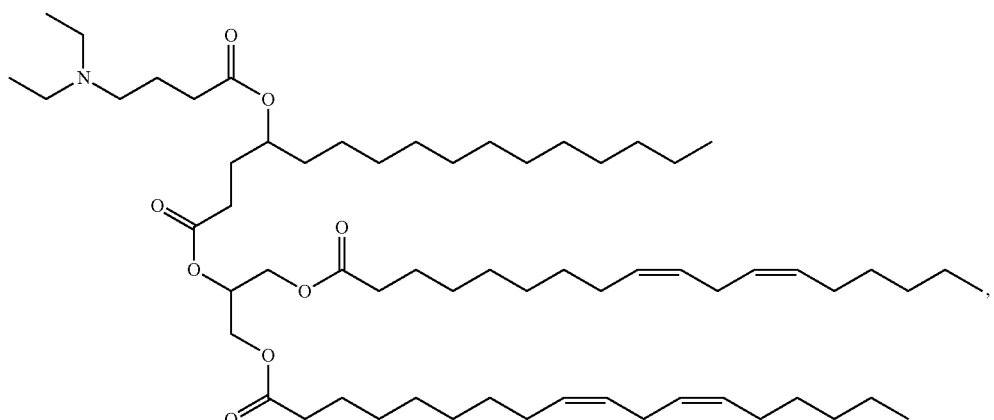
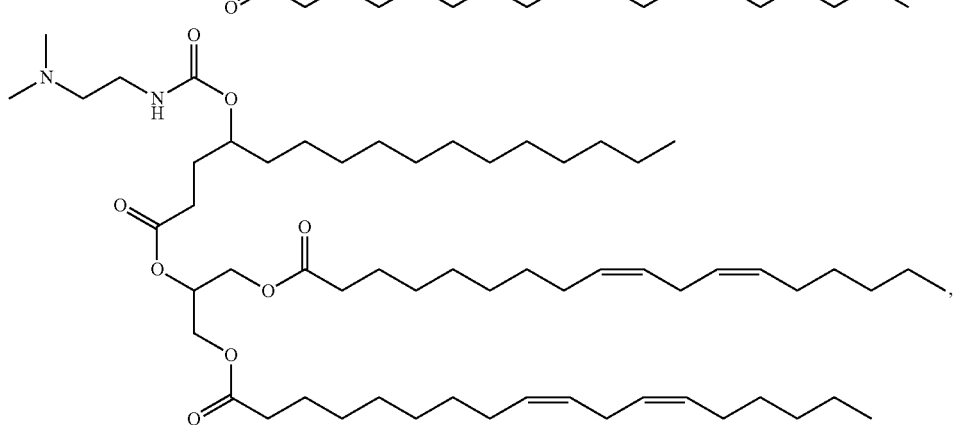
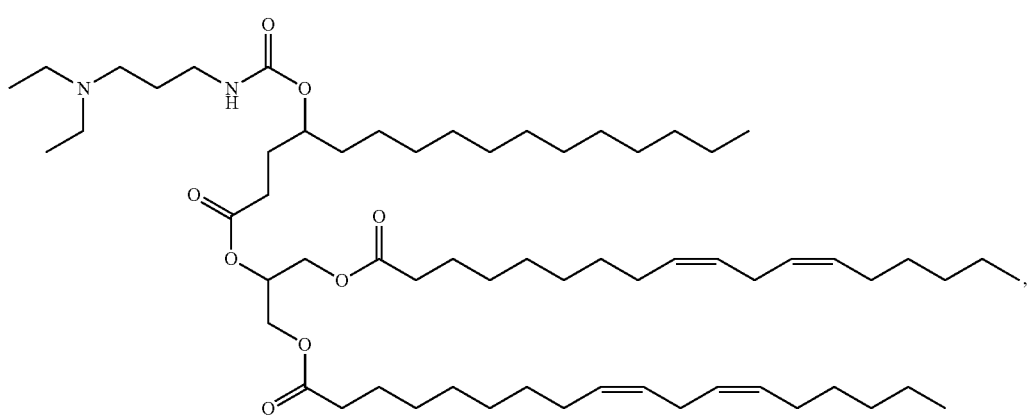

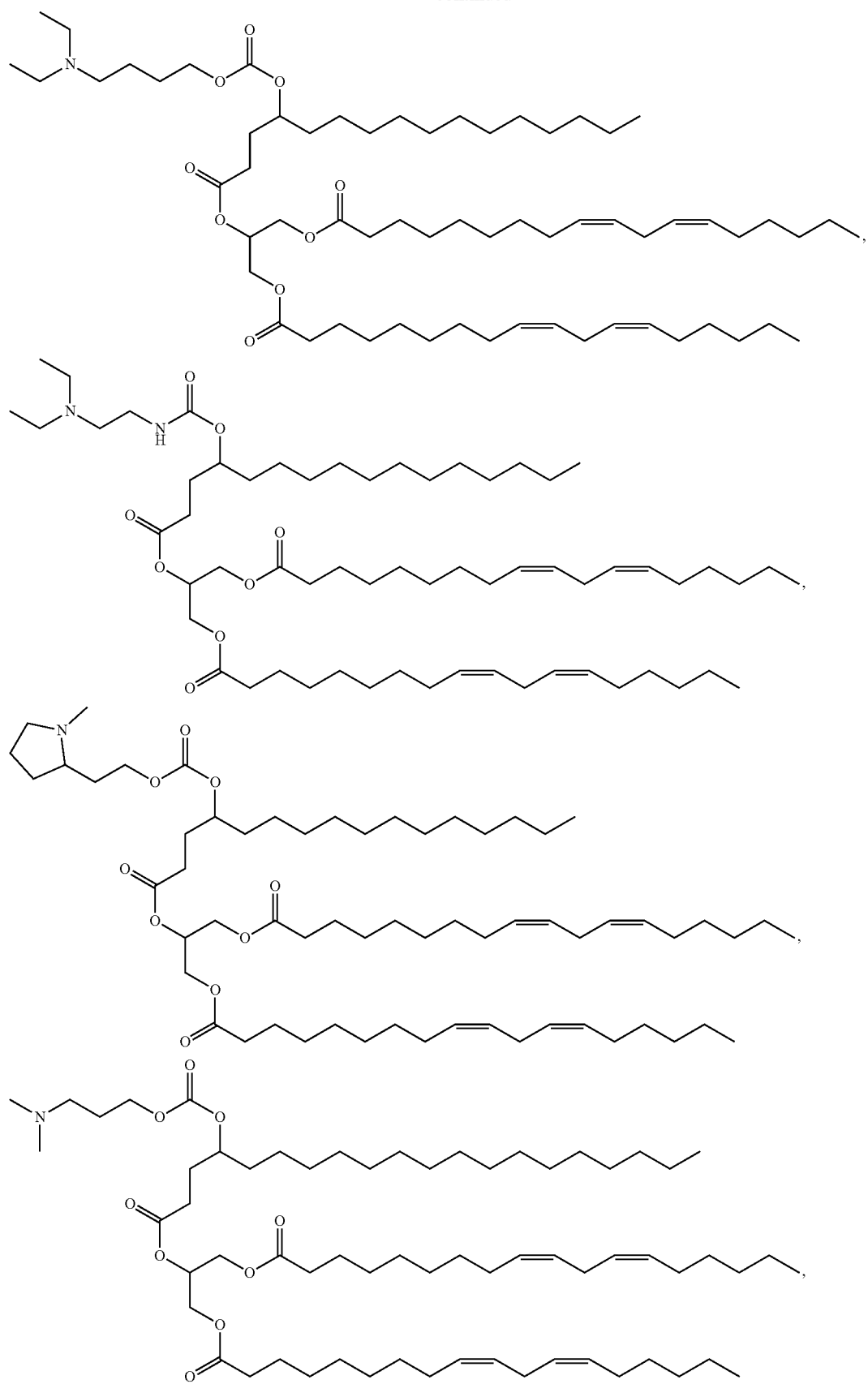

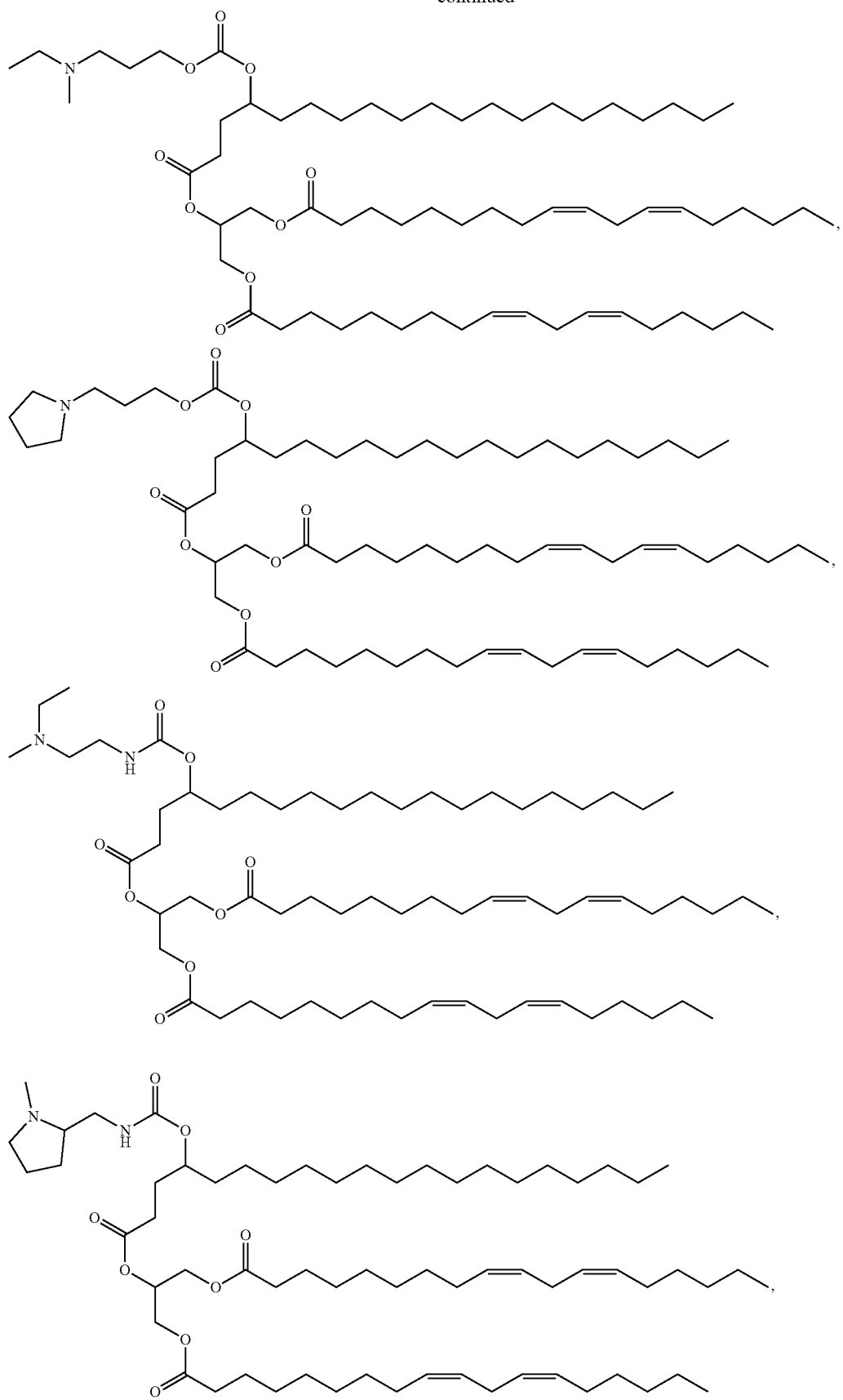

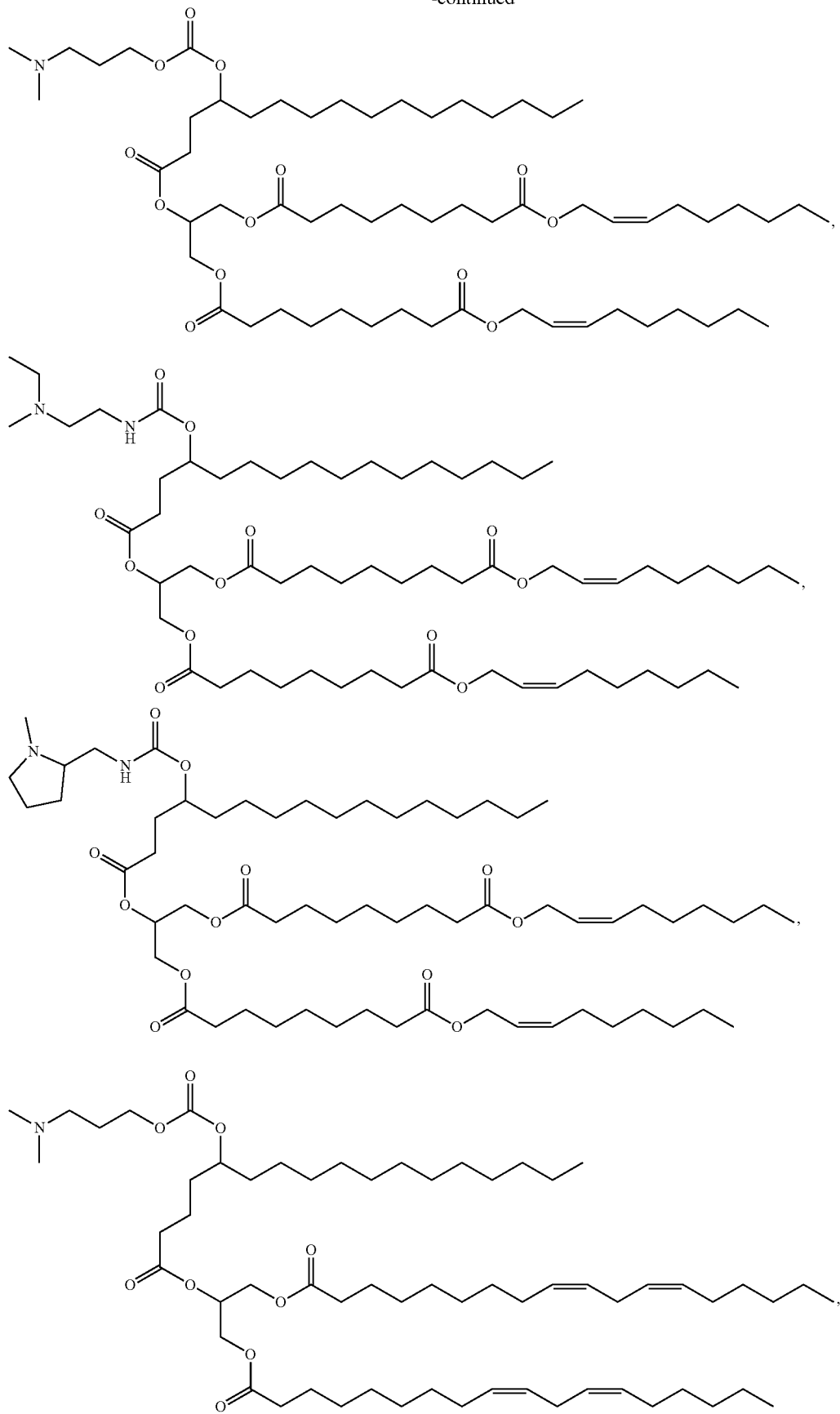

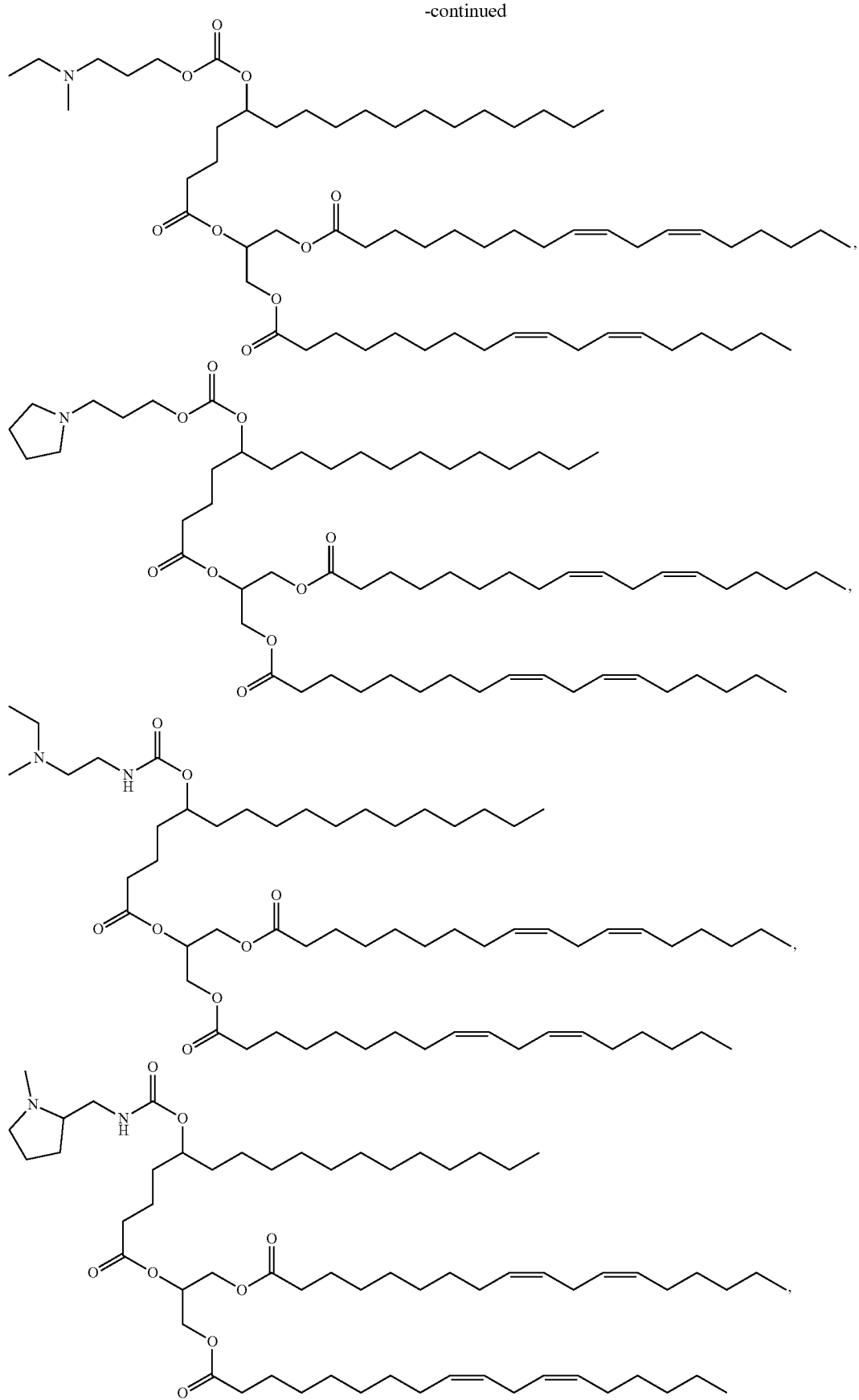

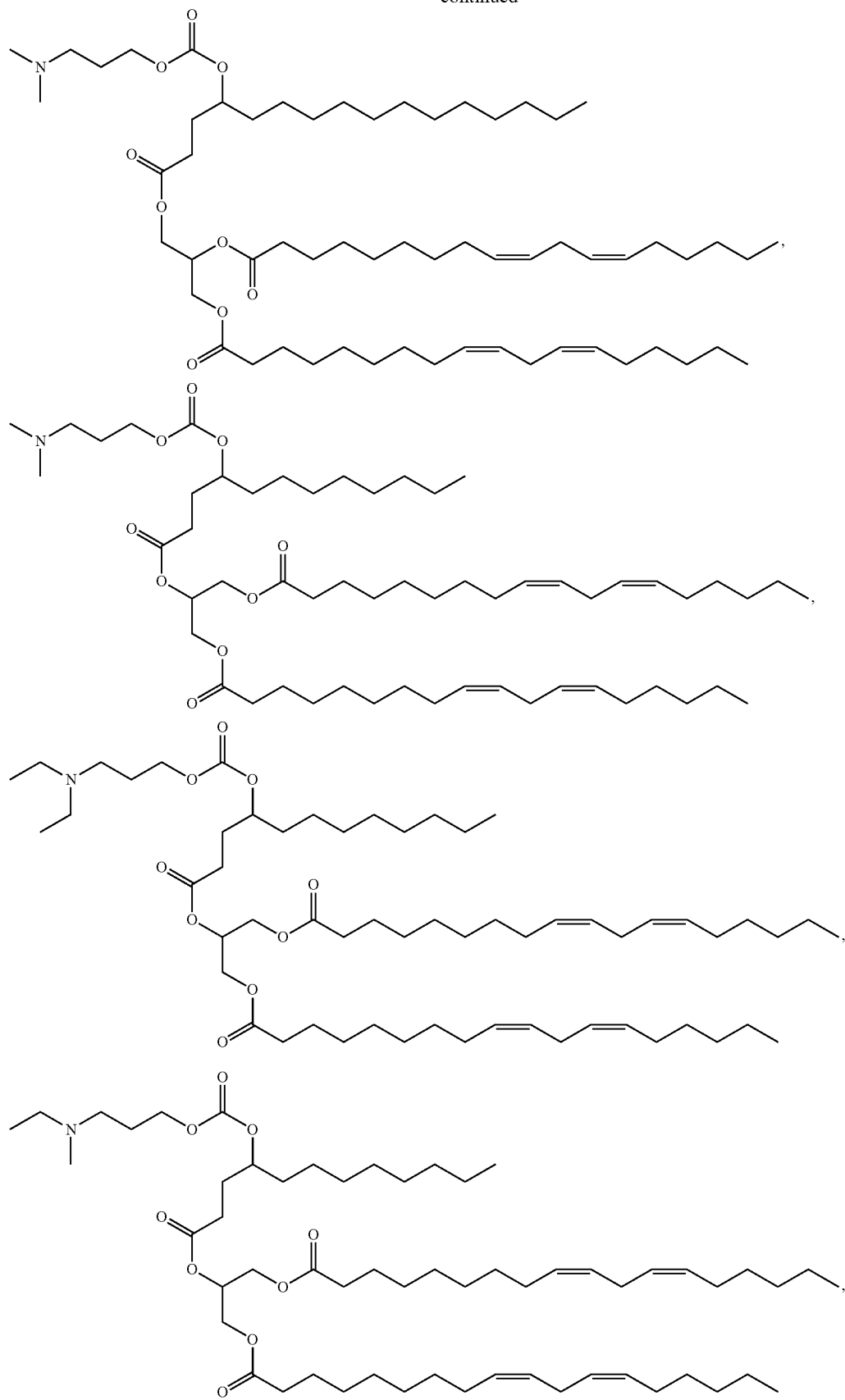

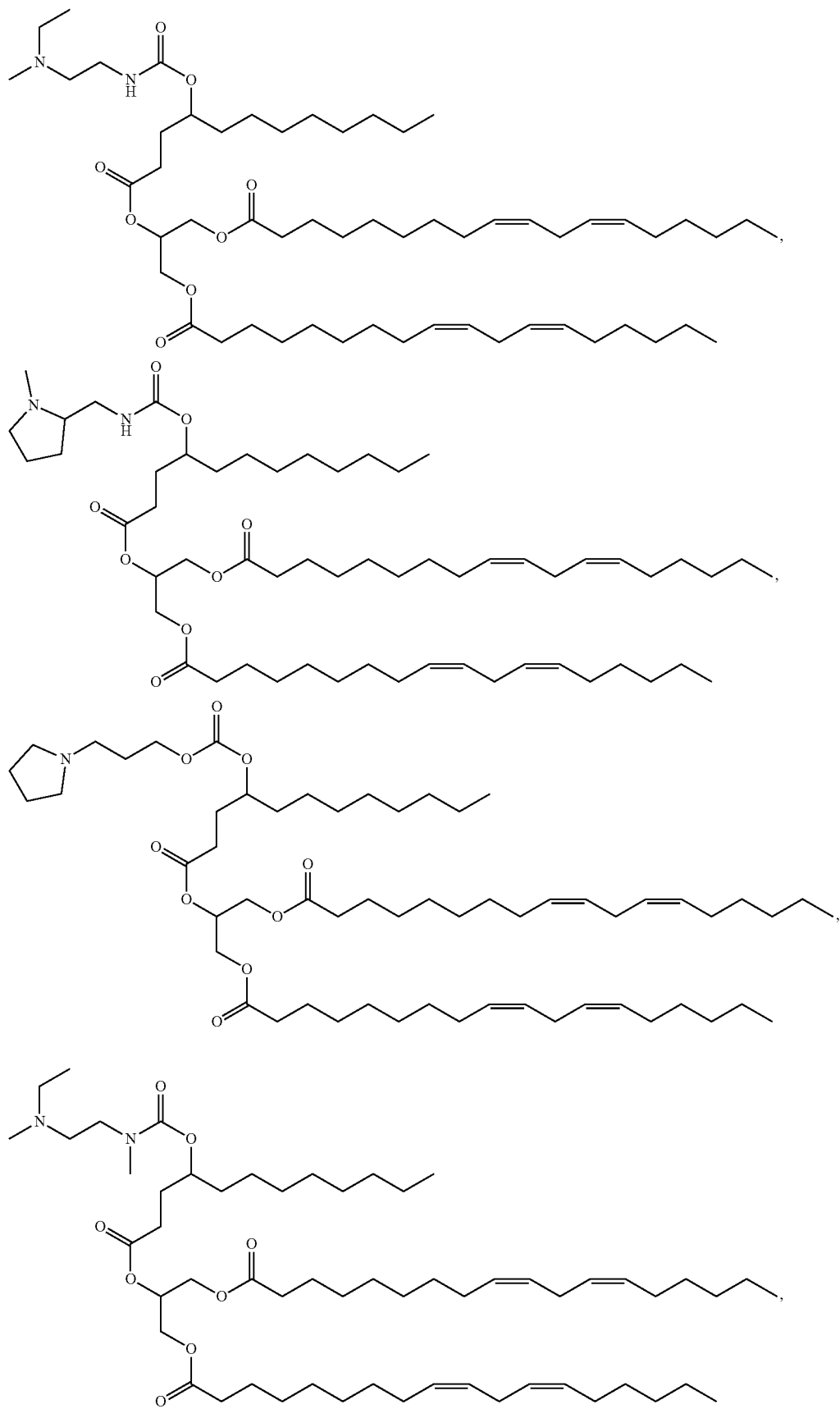

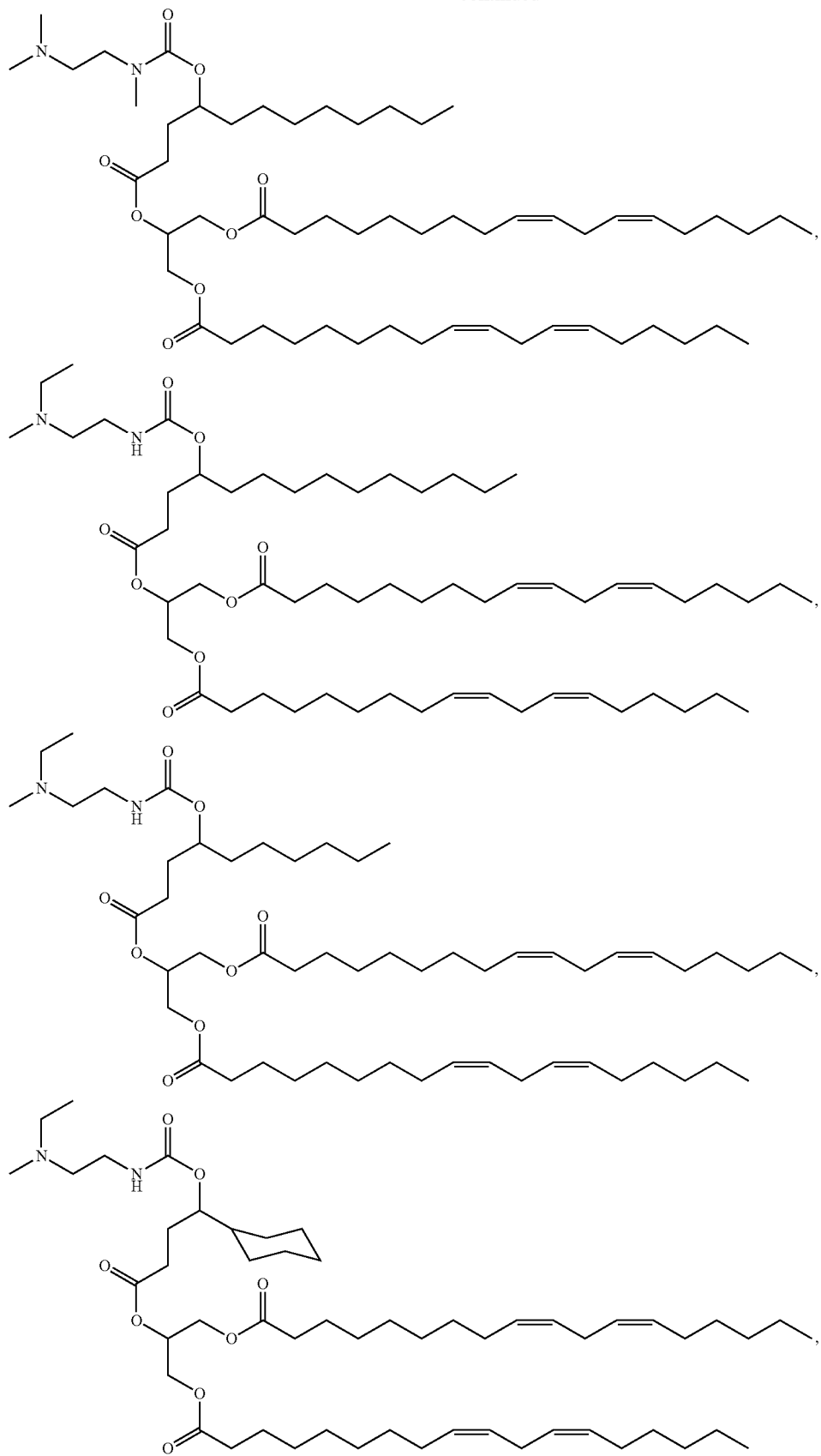

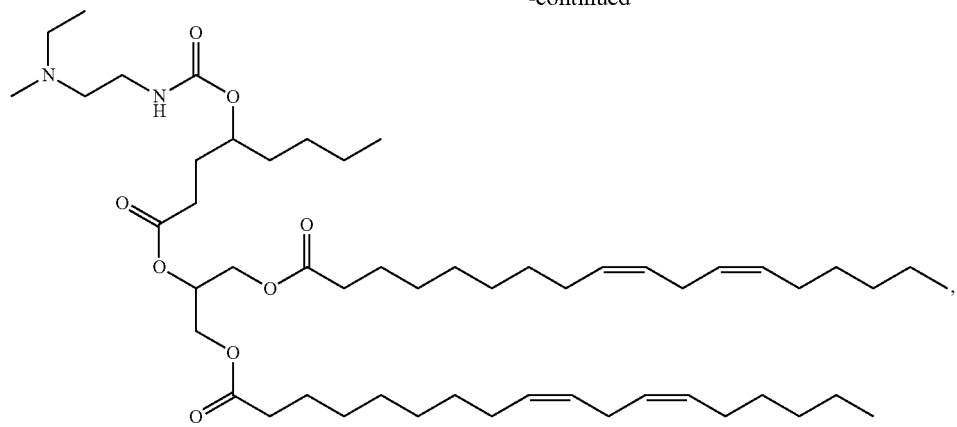,
,
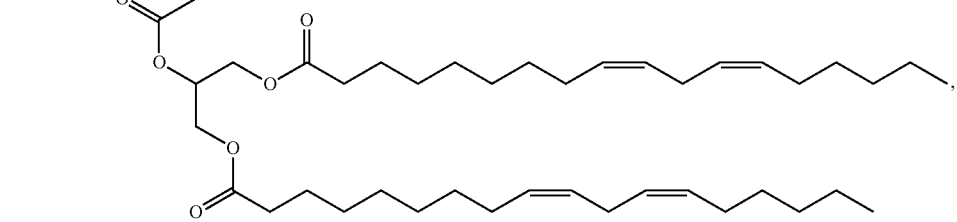,
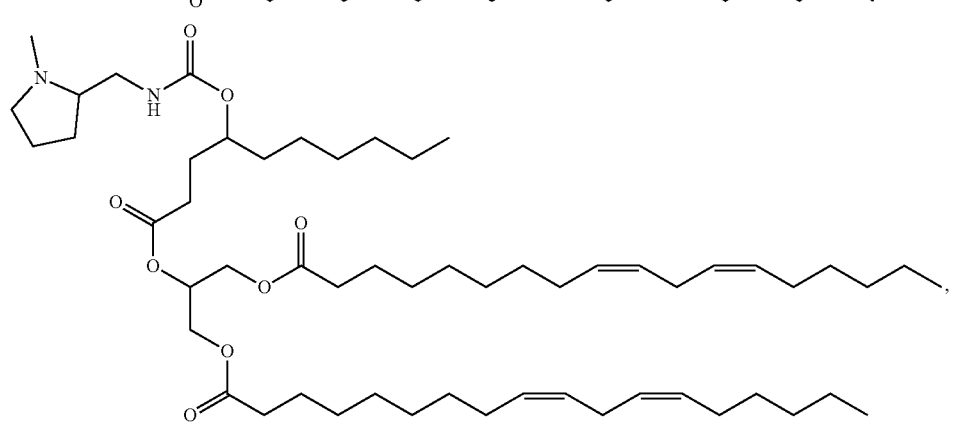,

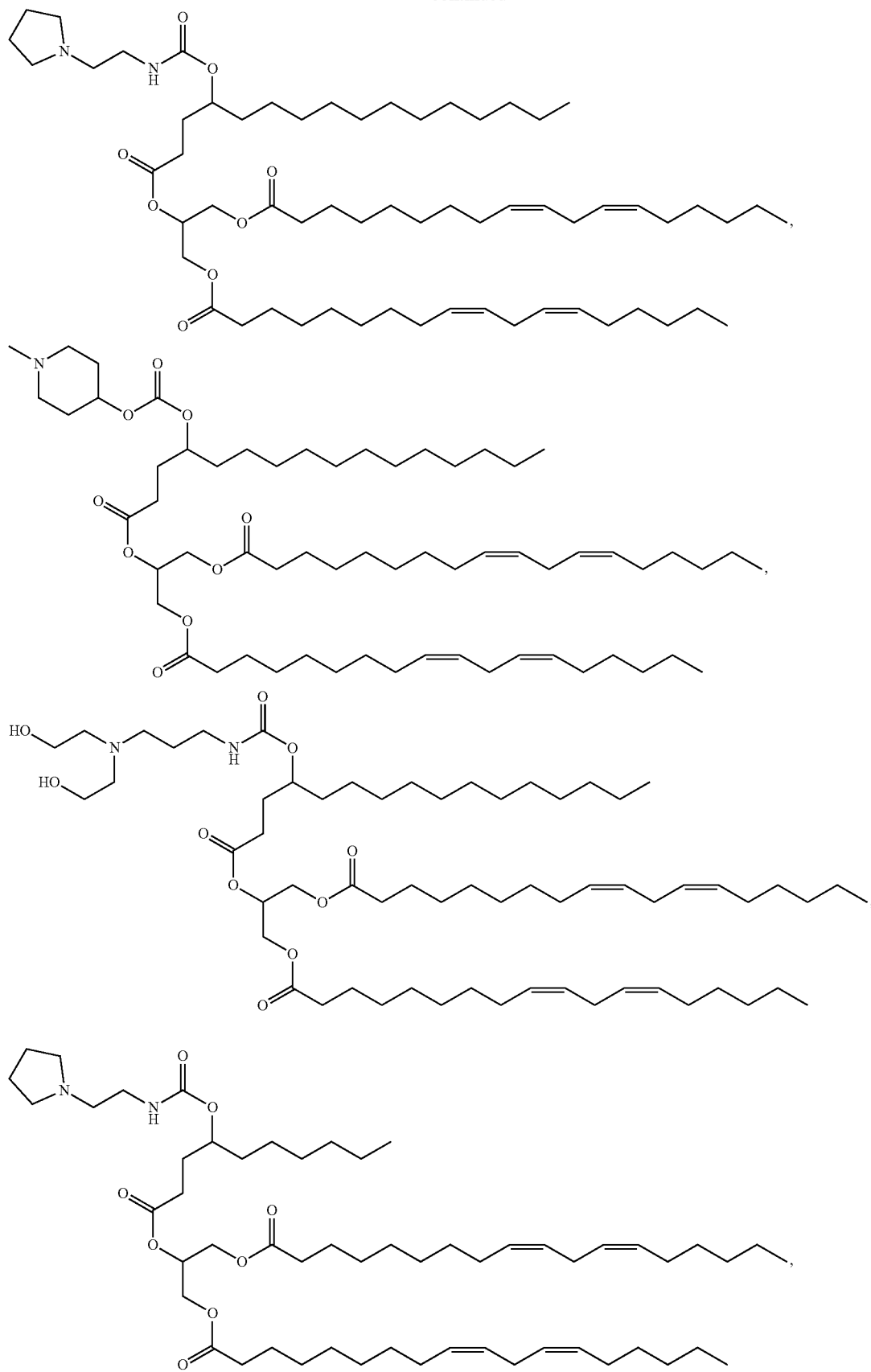

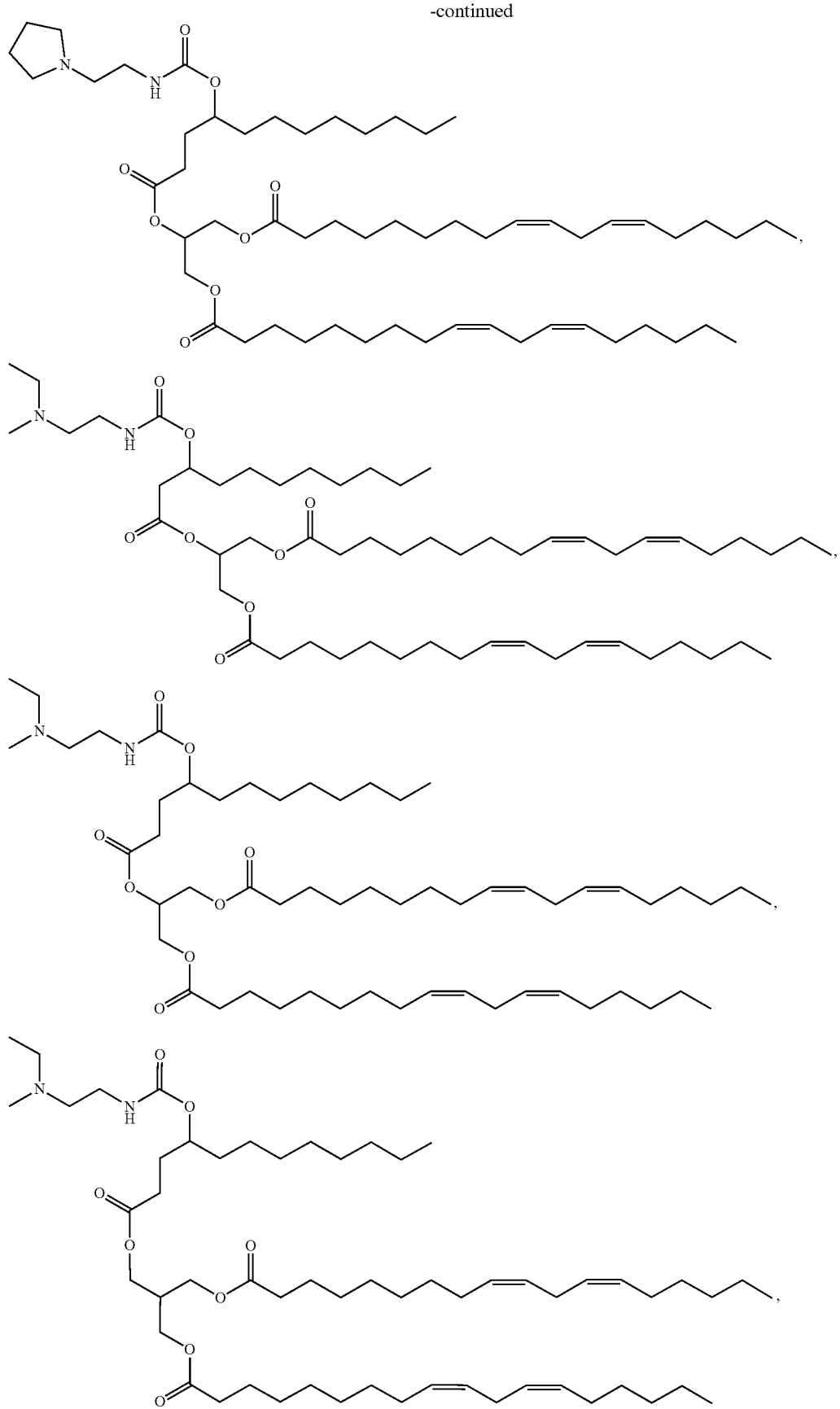

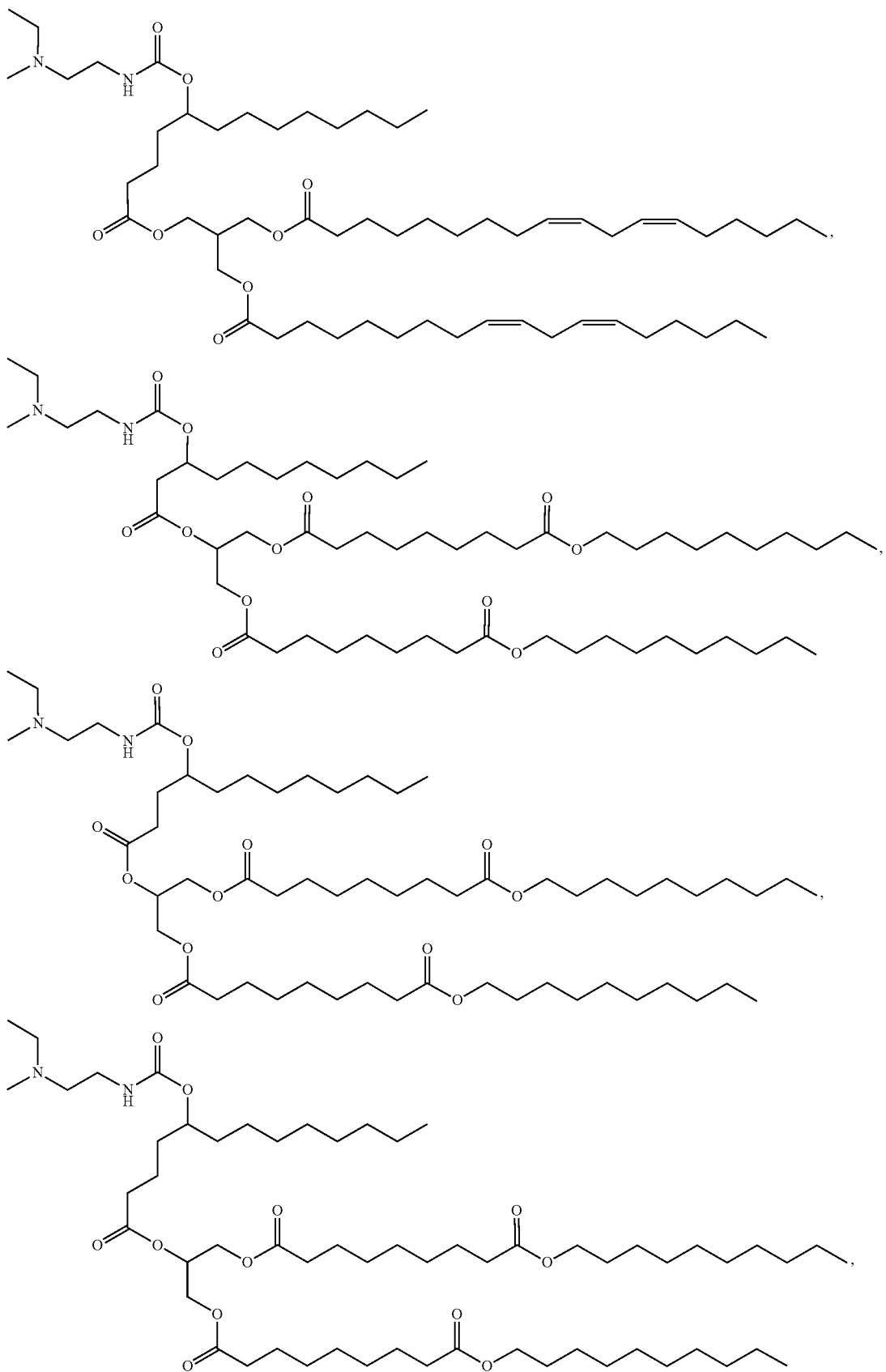

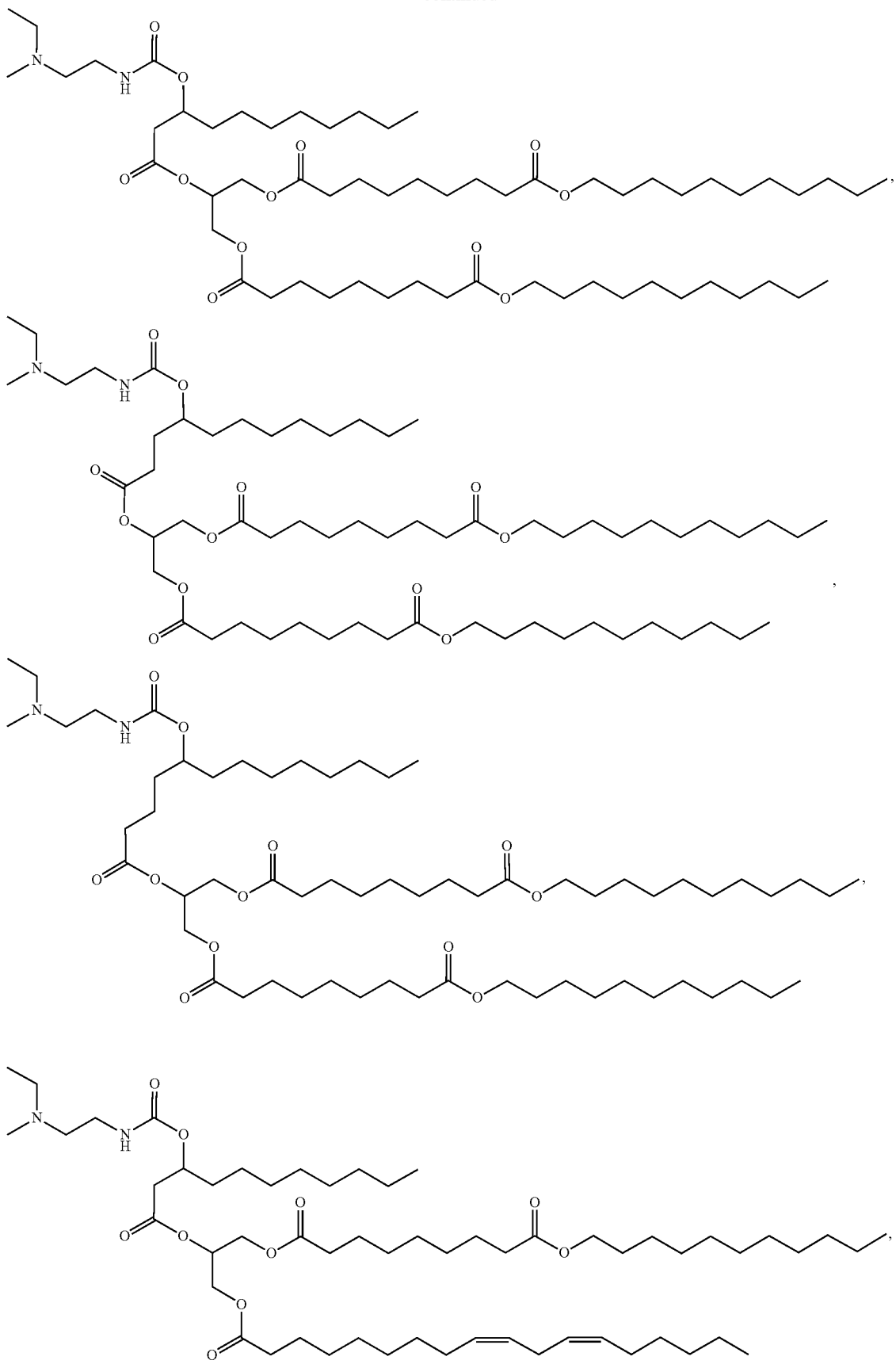

-continued
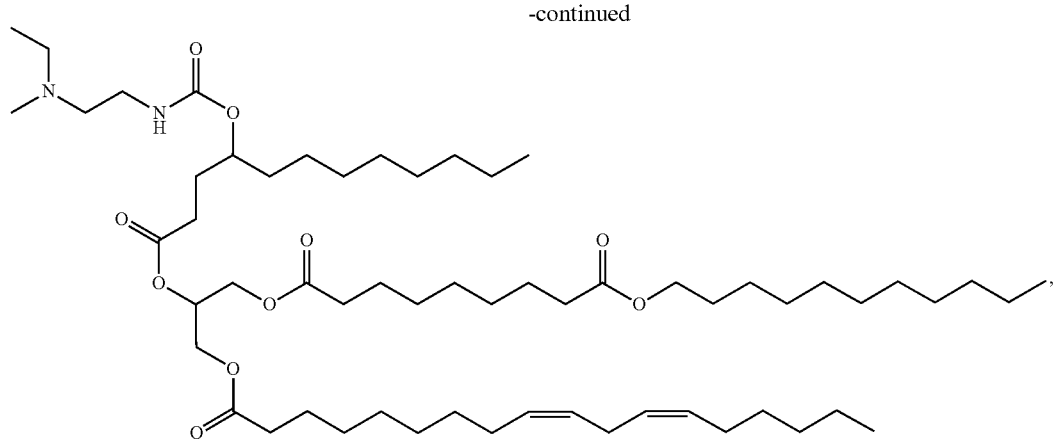
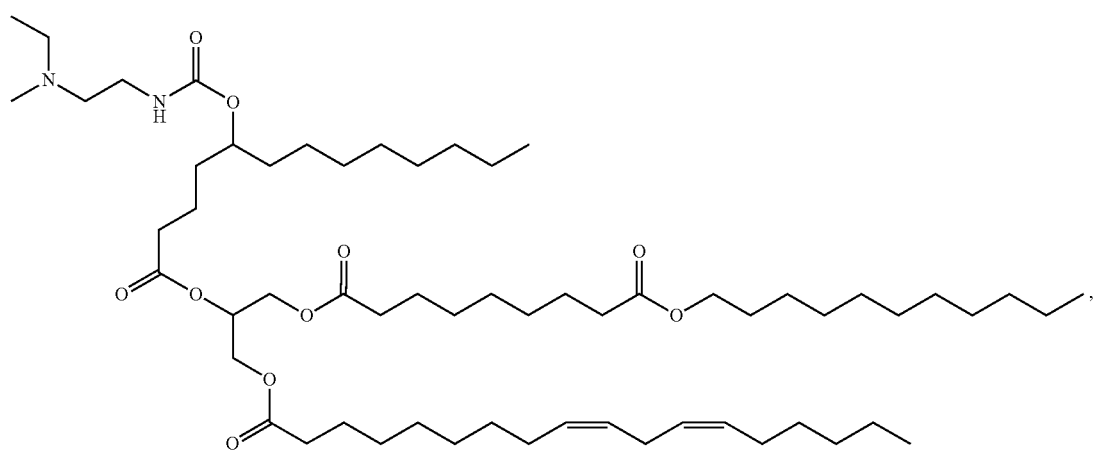
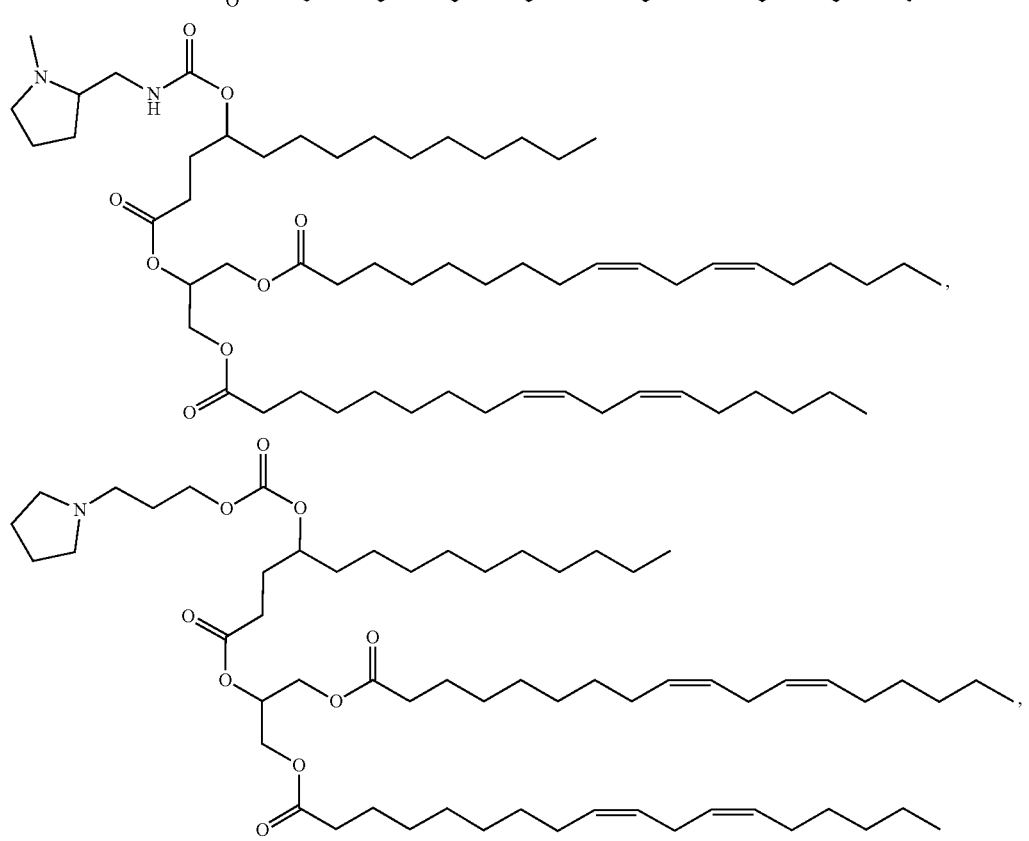

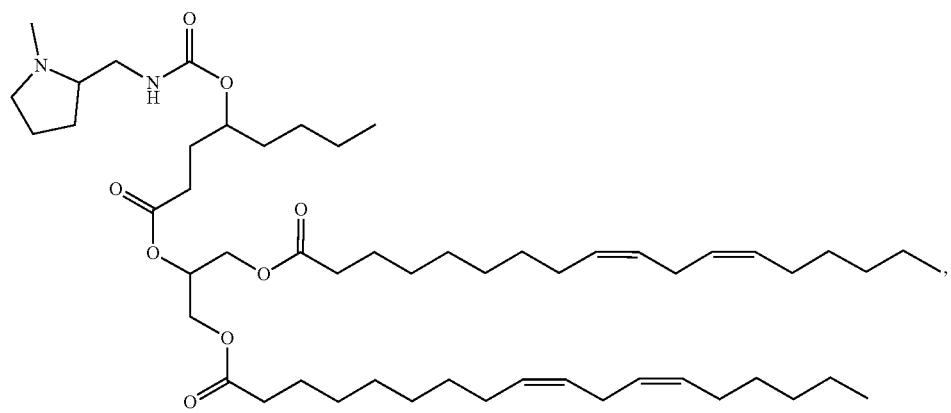
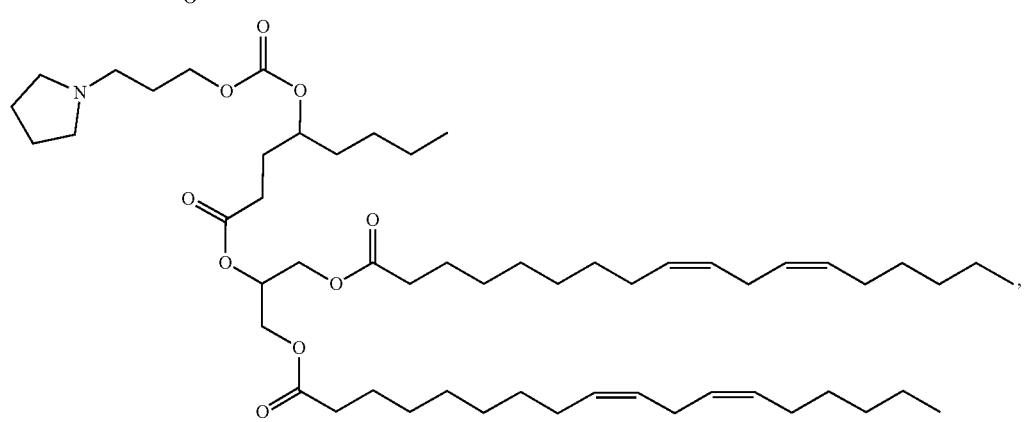
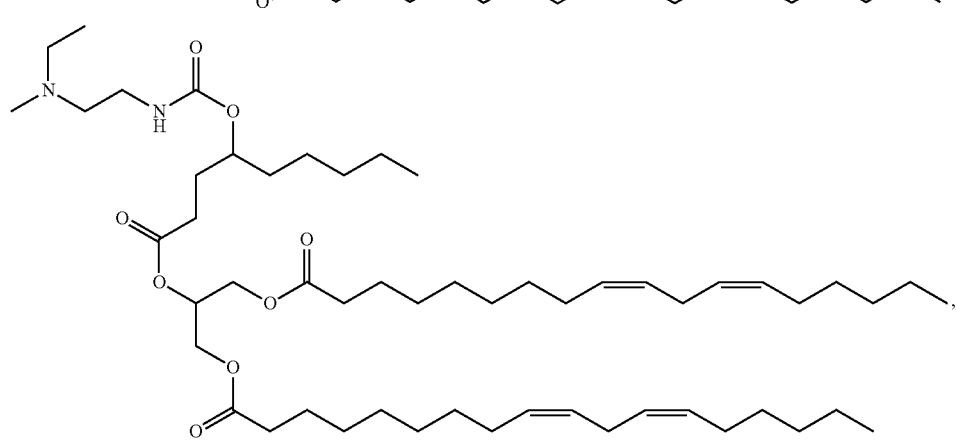
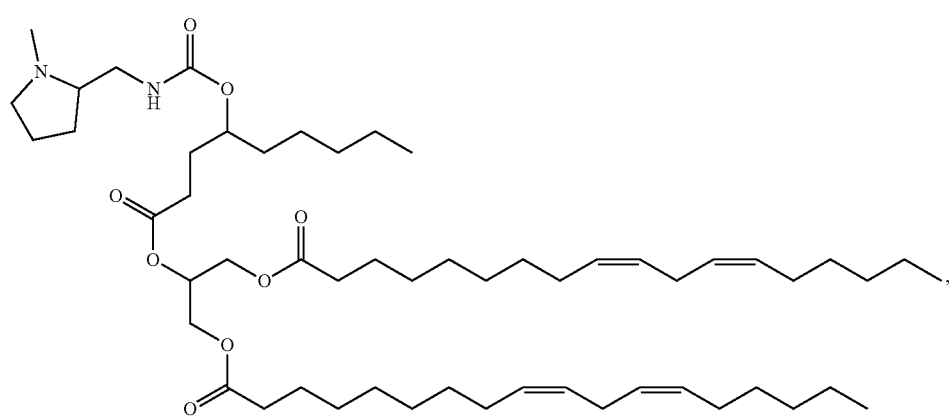

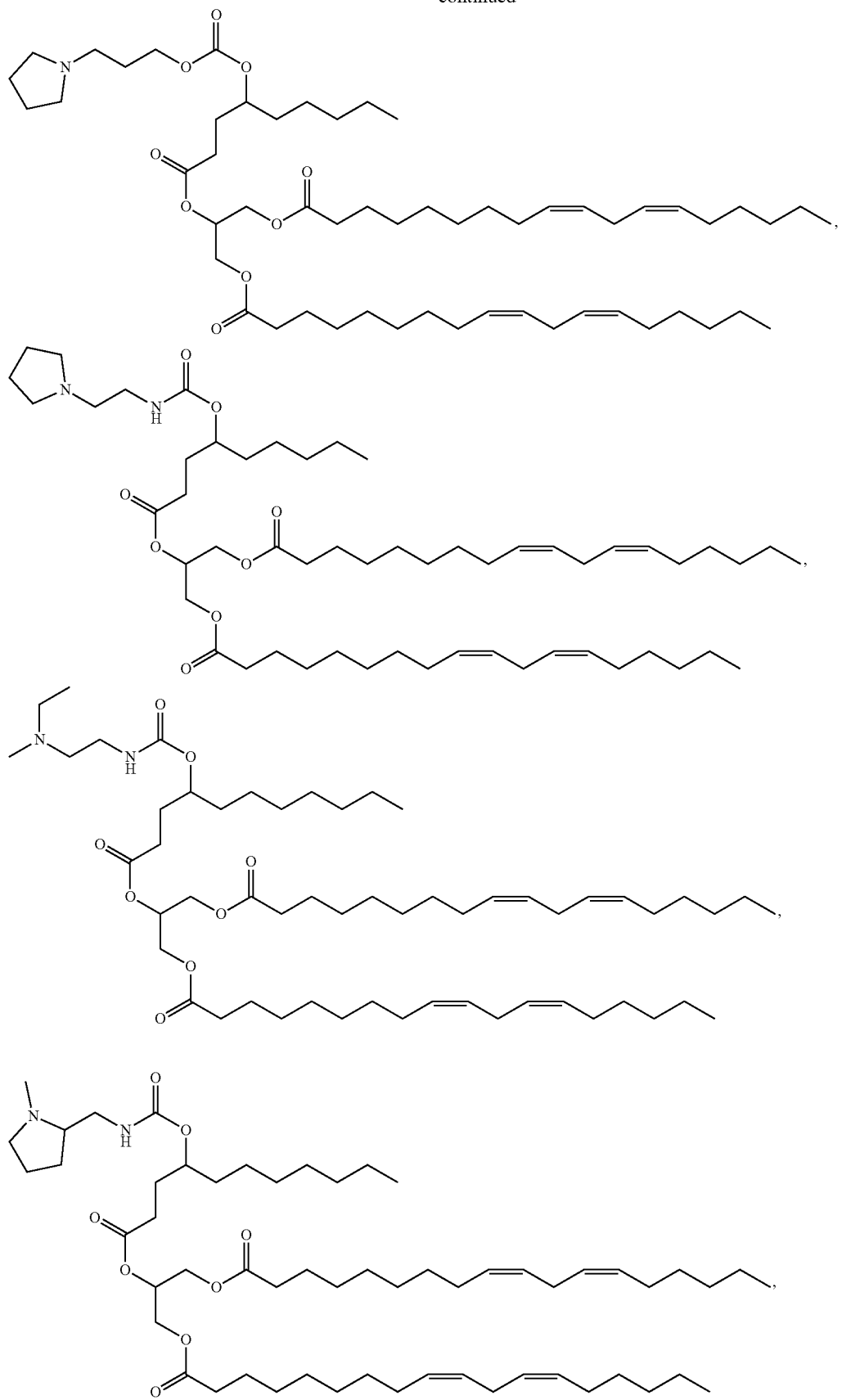

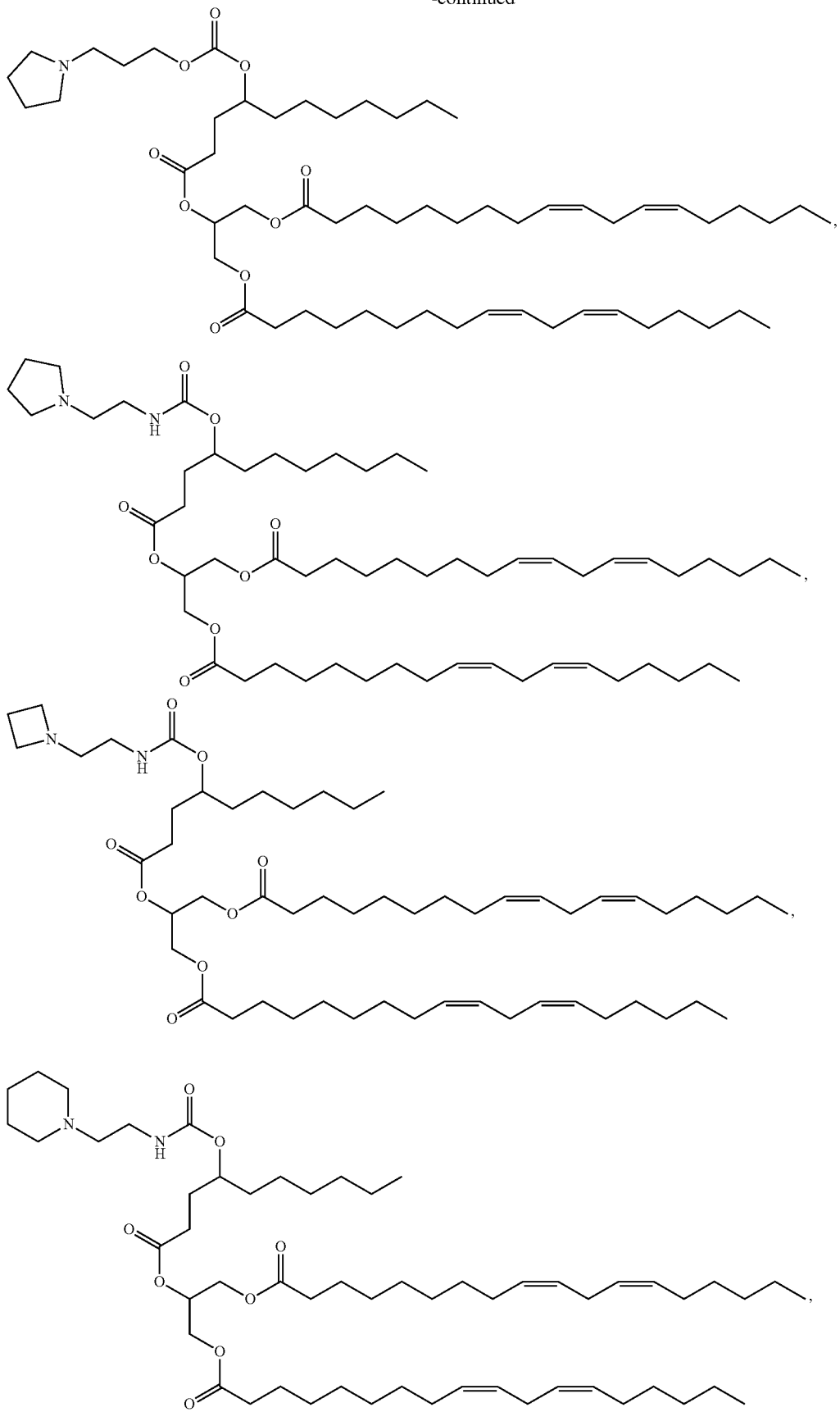

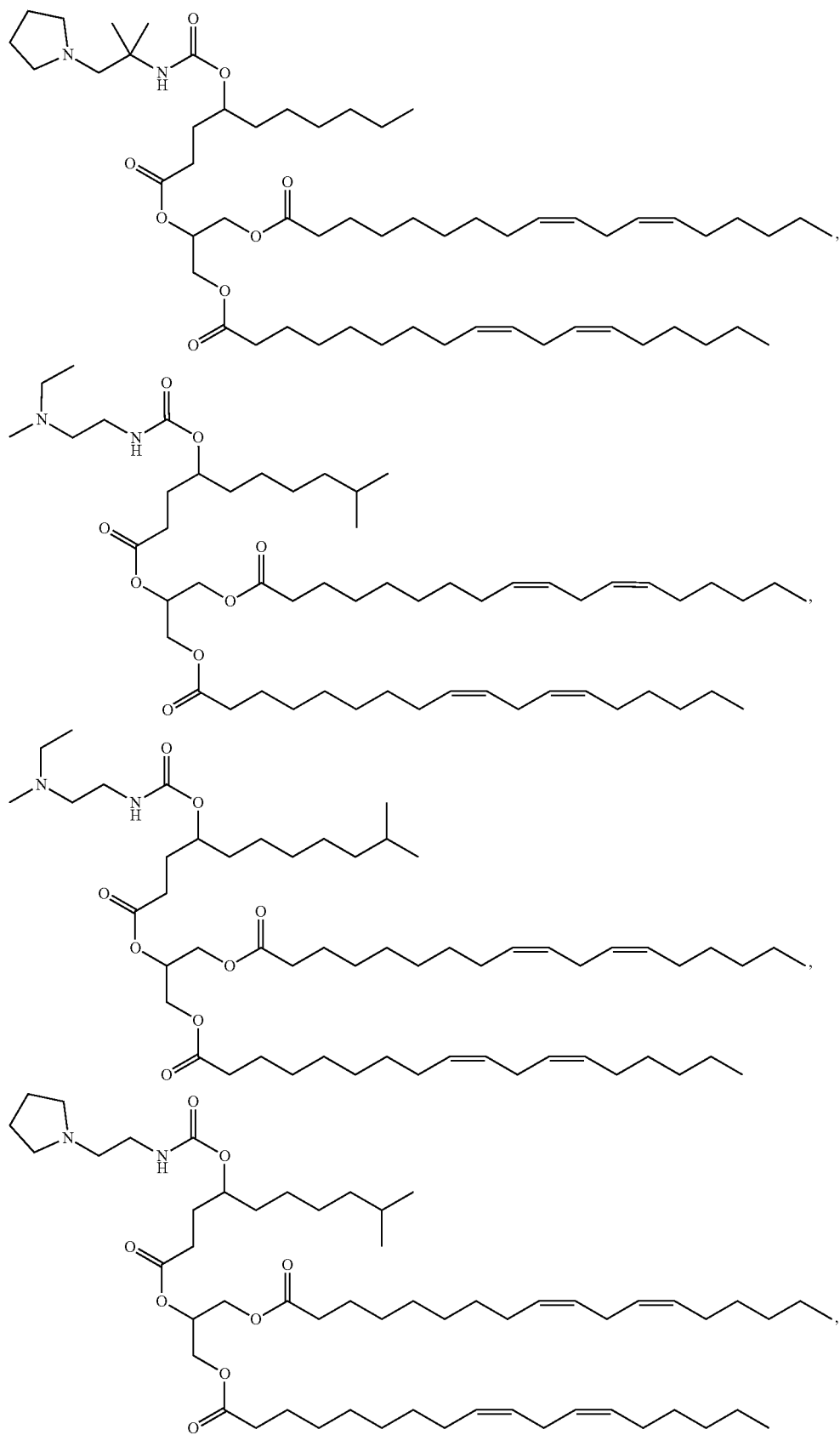

-continued
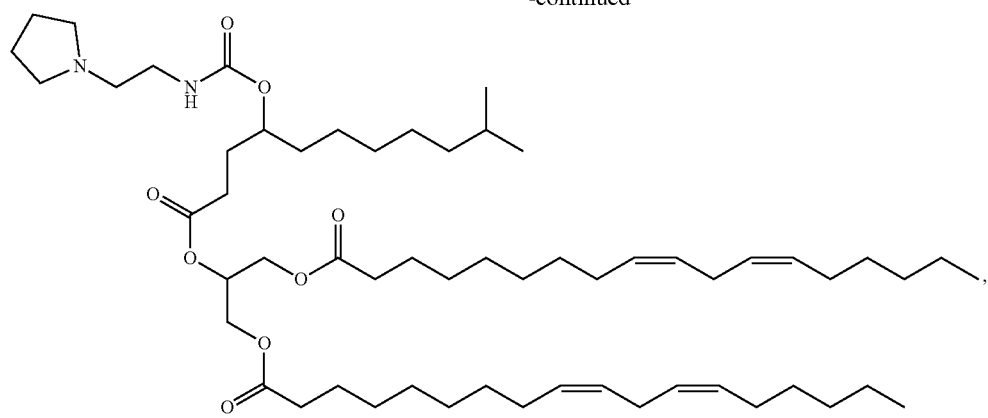
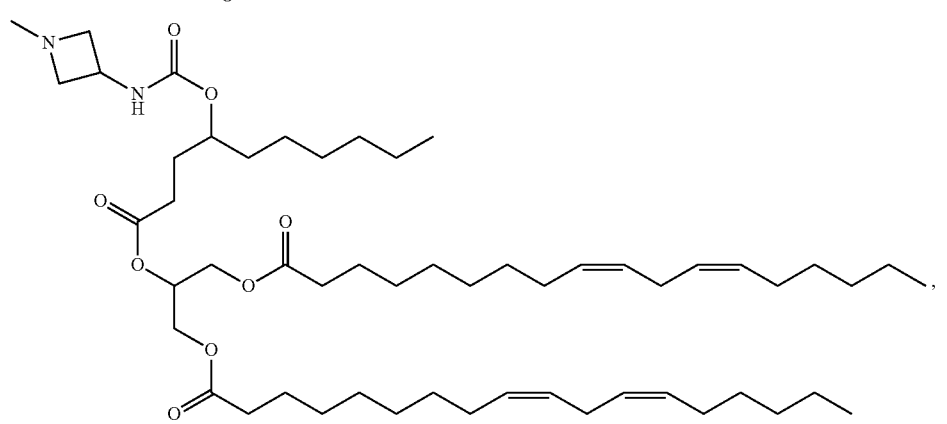
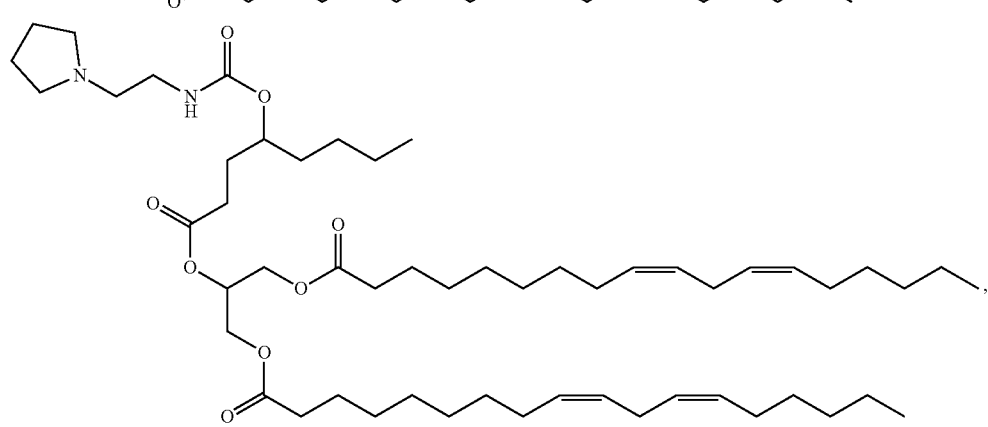
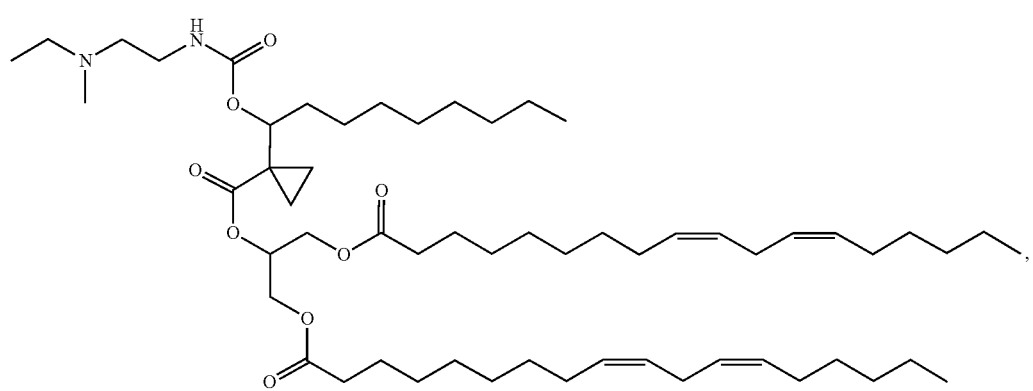

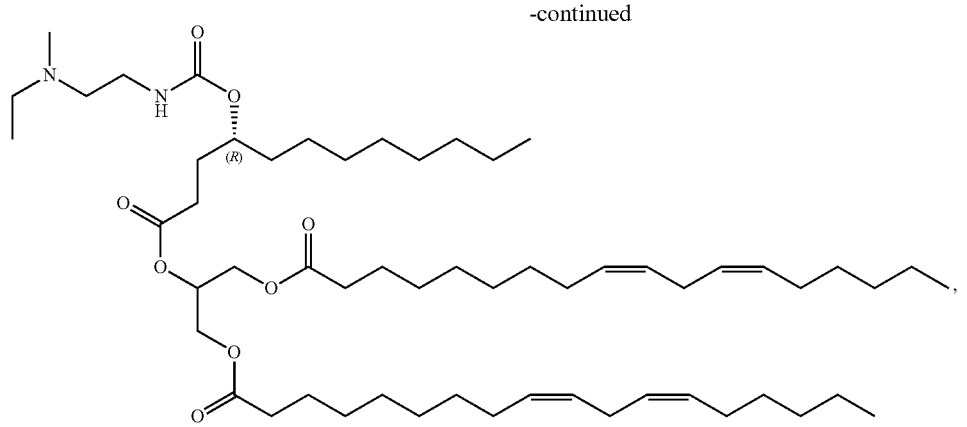
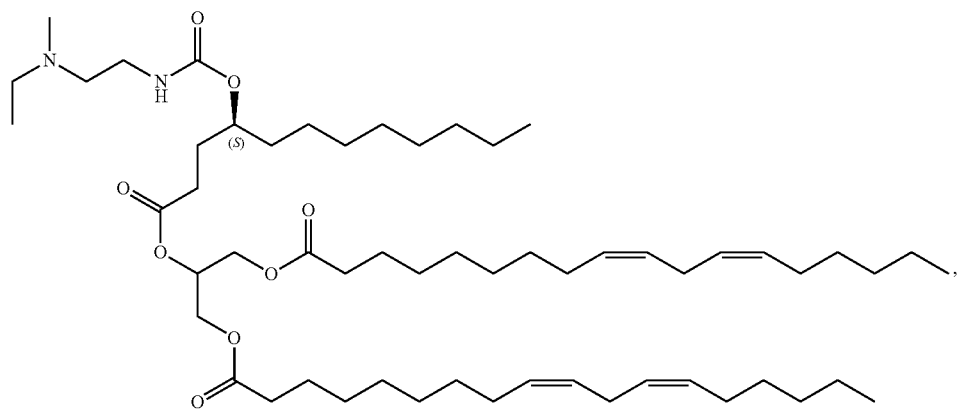
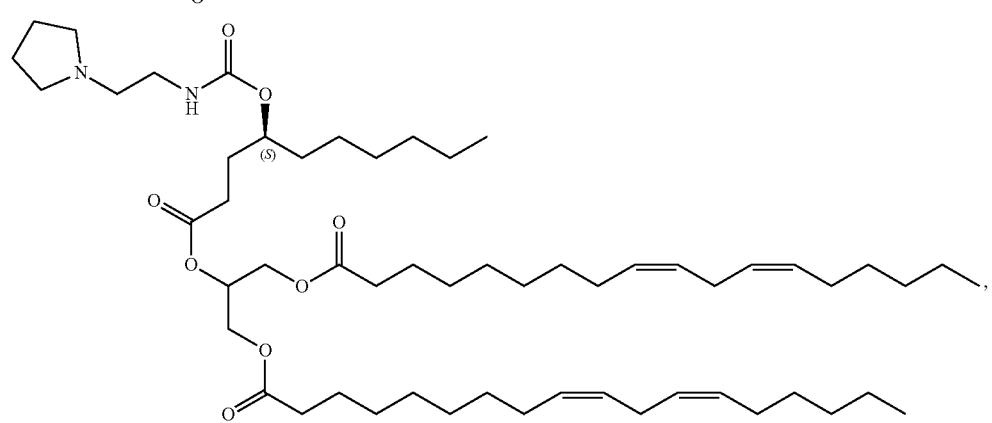
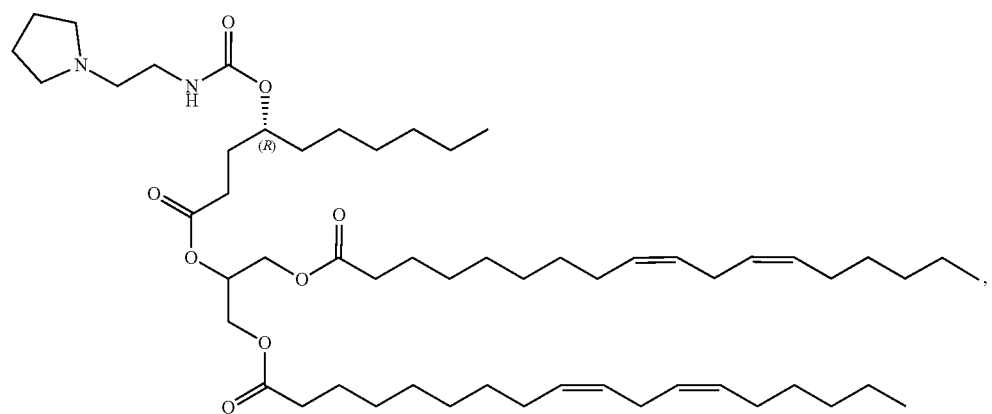

-continued
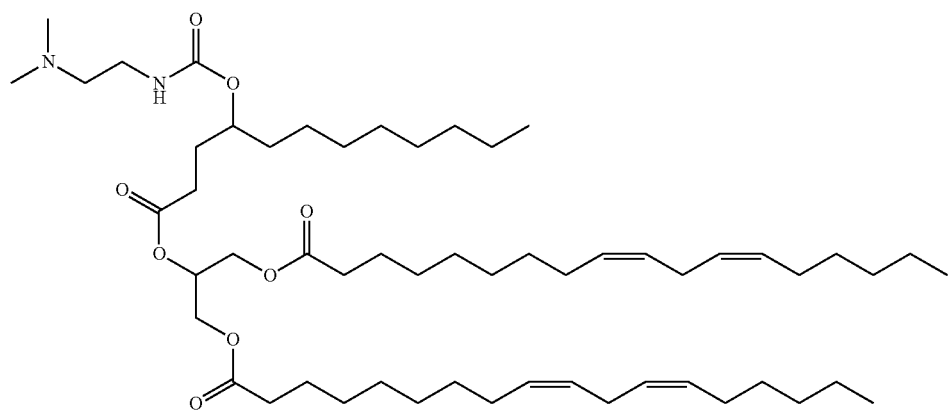
,
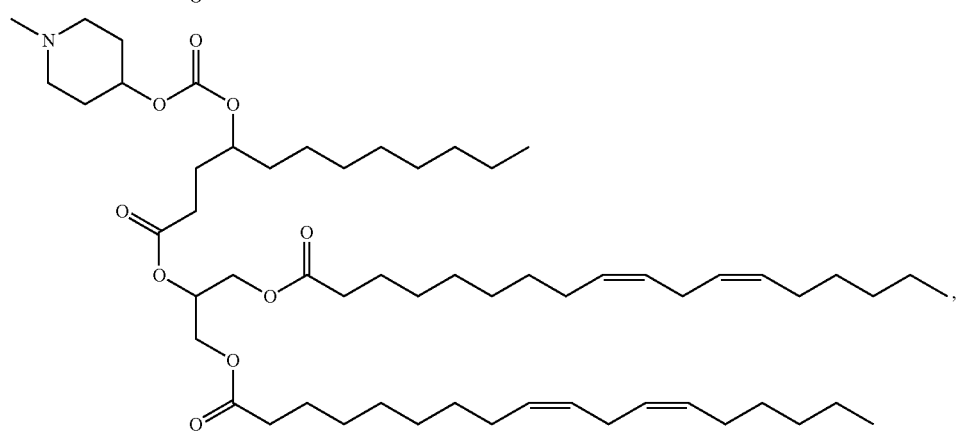
,
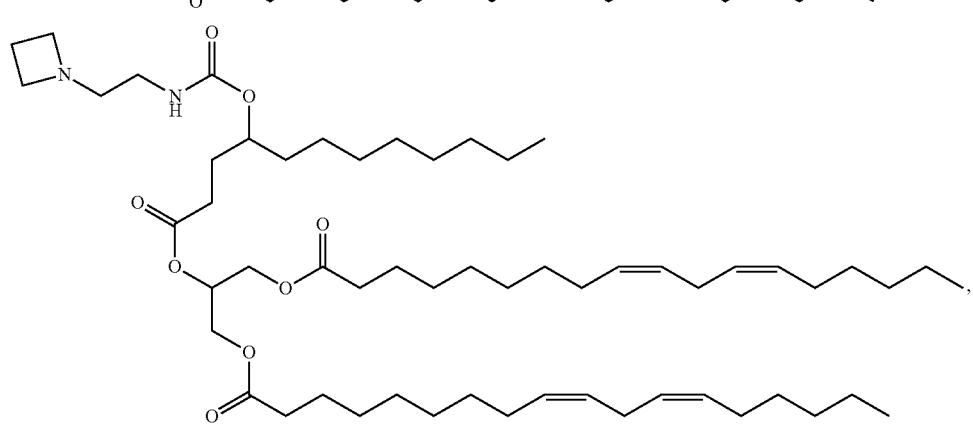
,
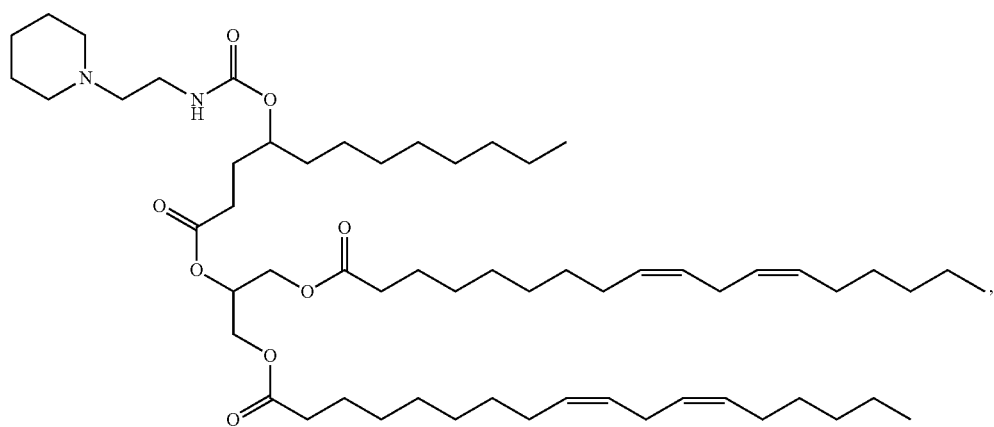
,

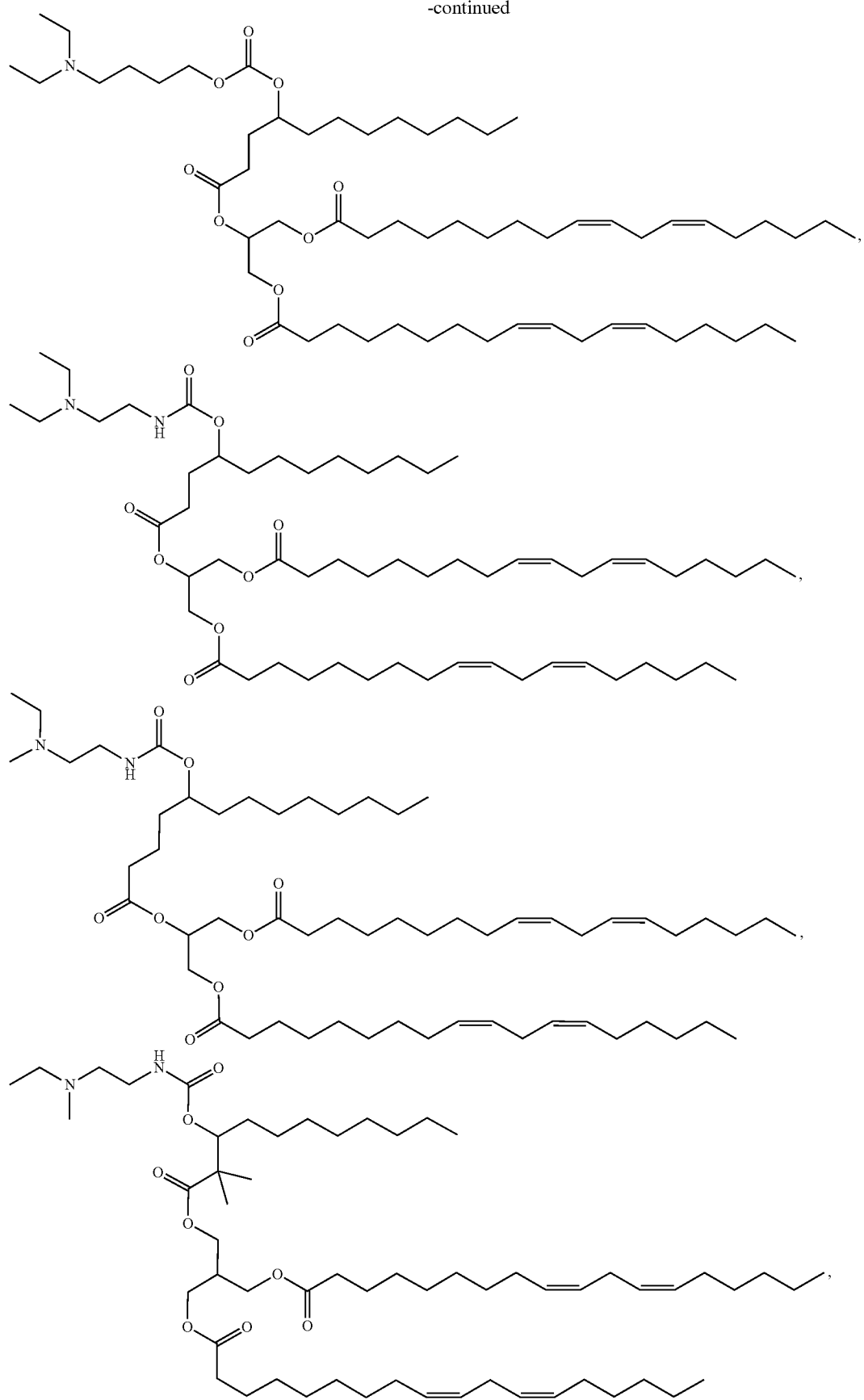

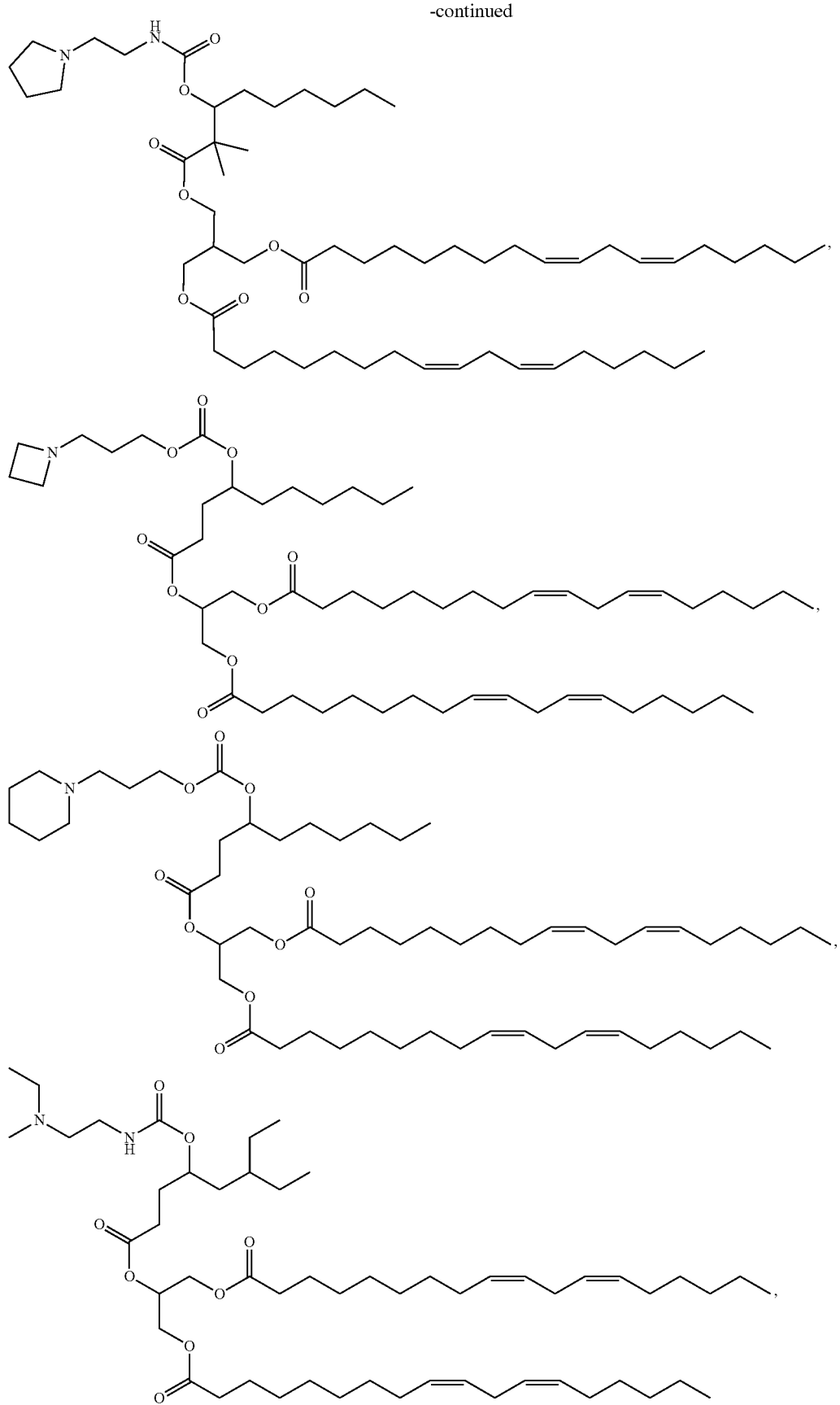

-continued
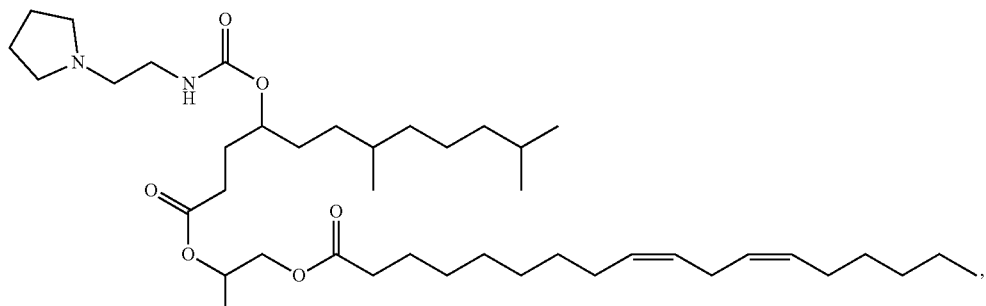
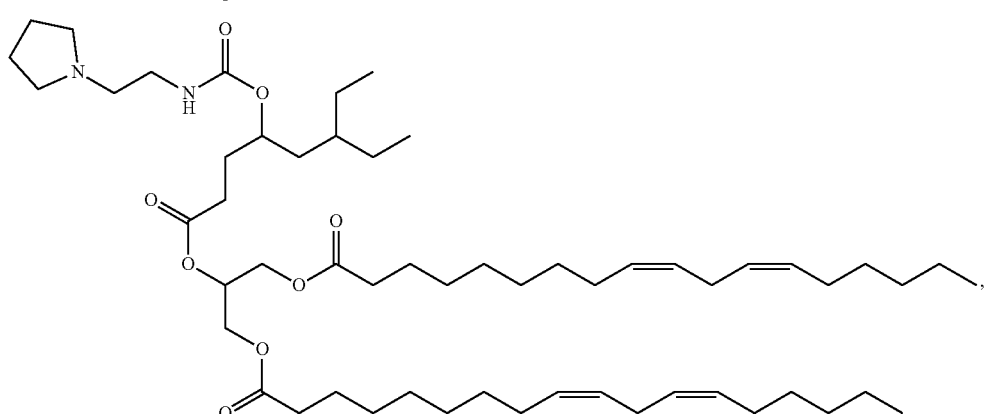
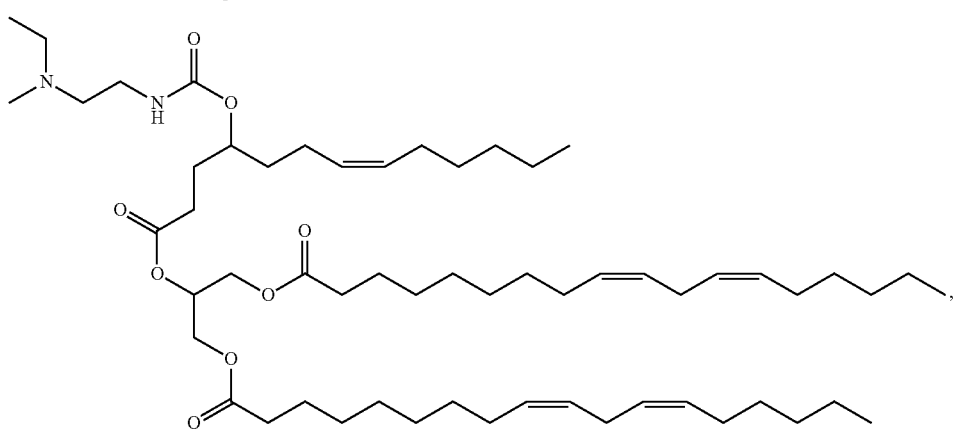
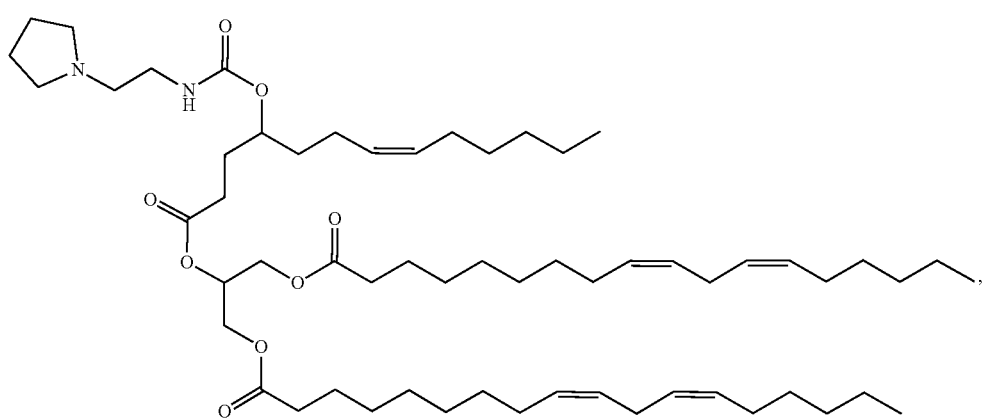

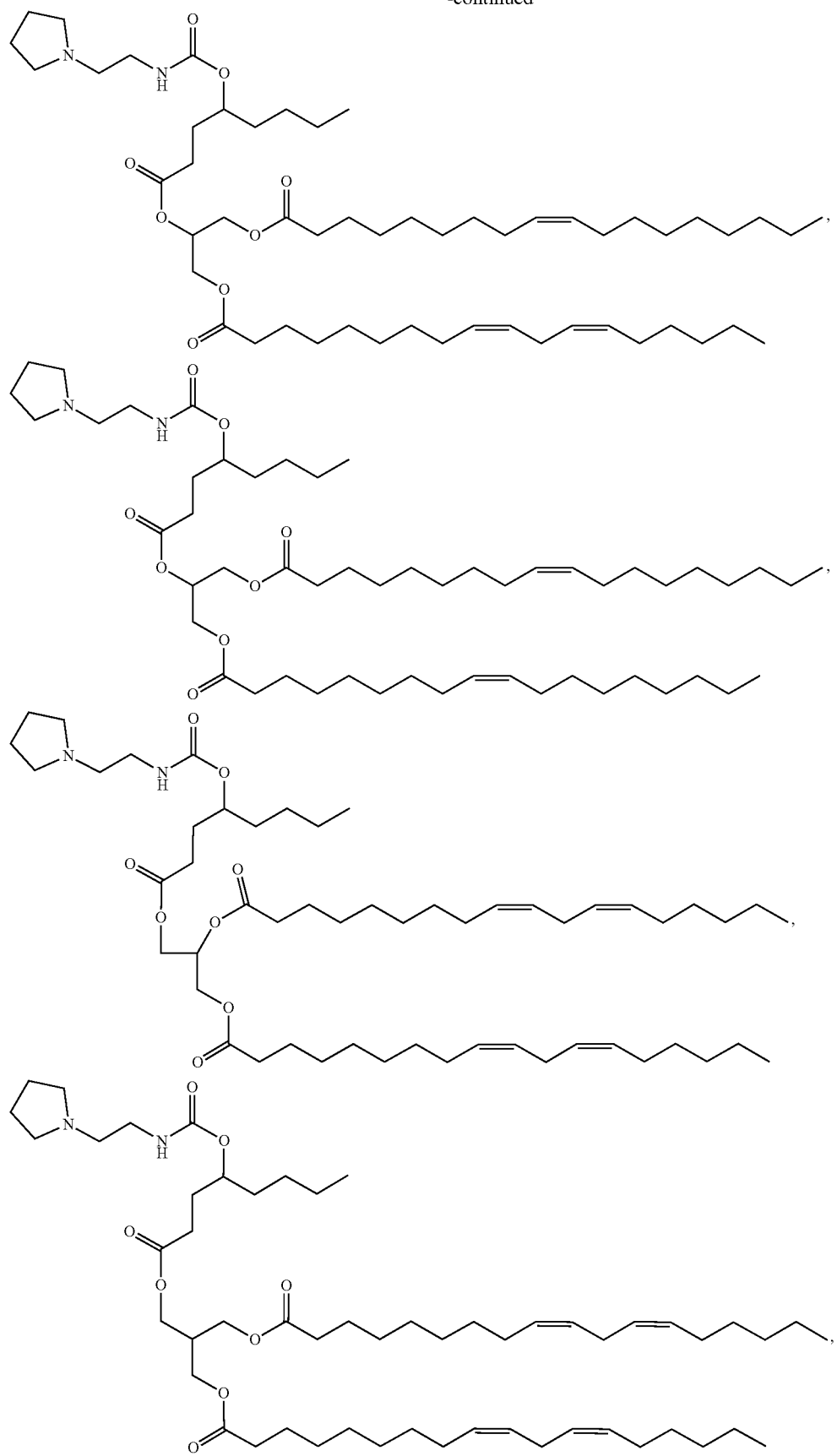

-continued
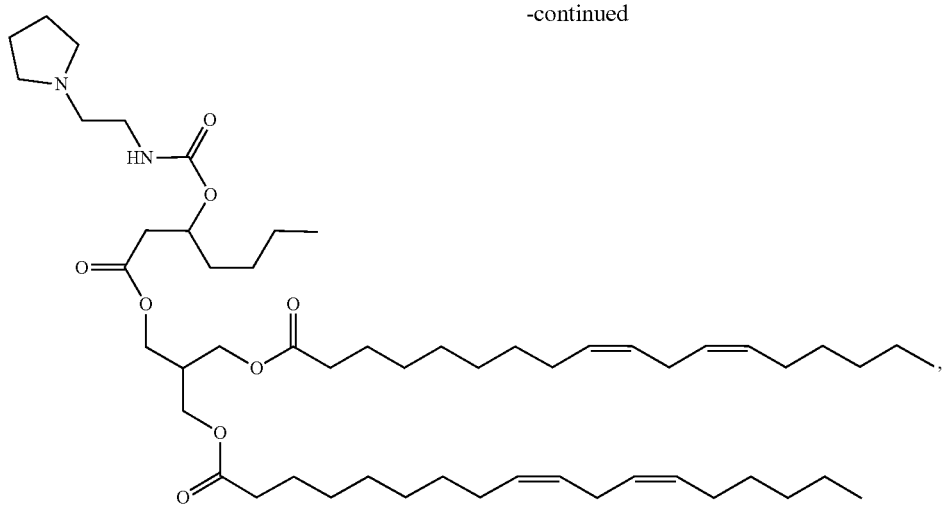
or a salt thereof, preferably a pharmaceutically acceptable salt.
In some embodiments, the compound is selected from
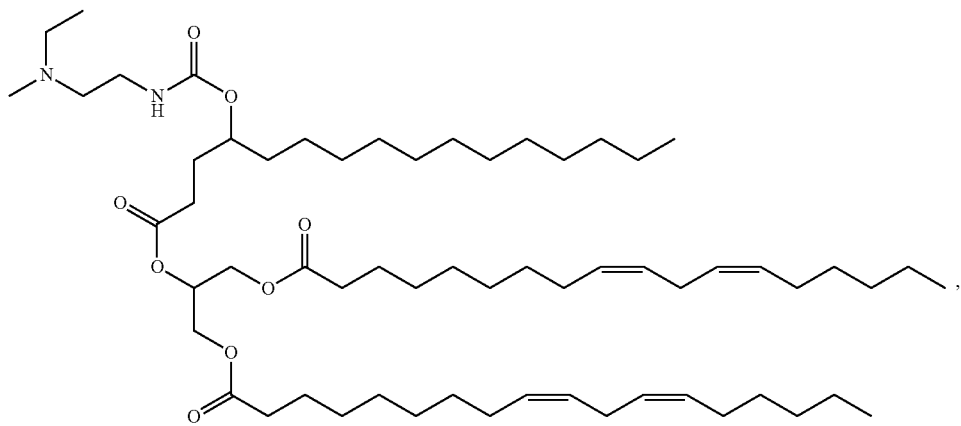
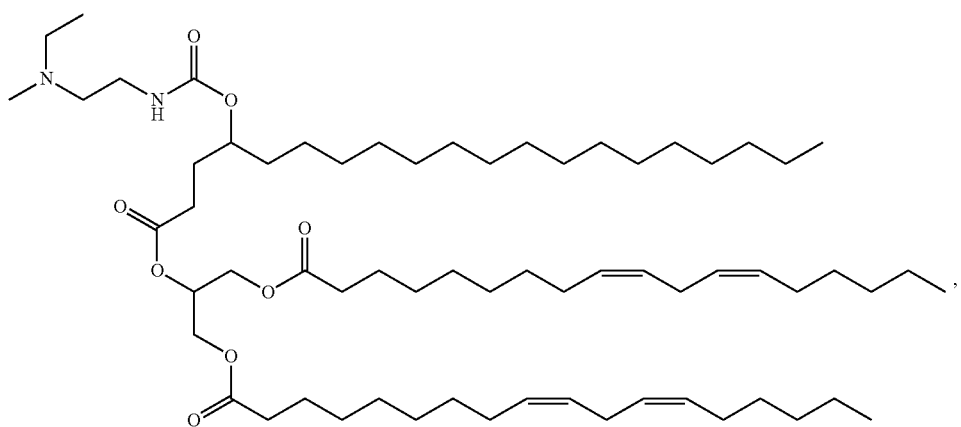

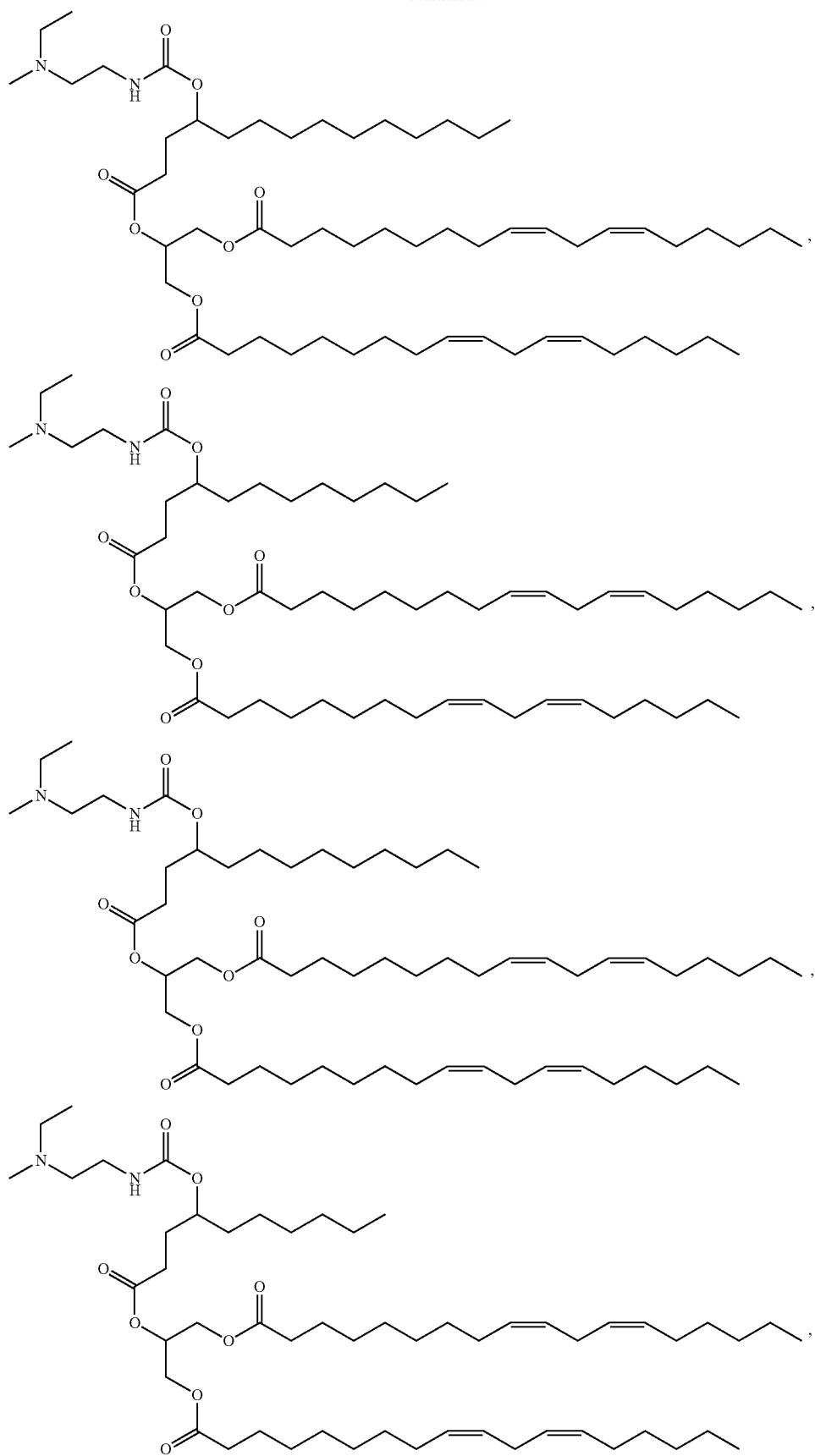

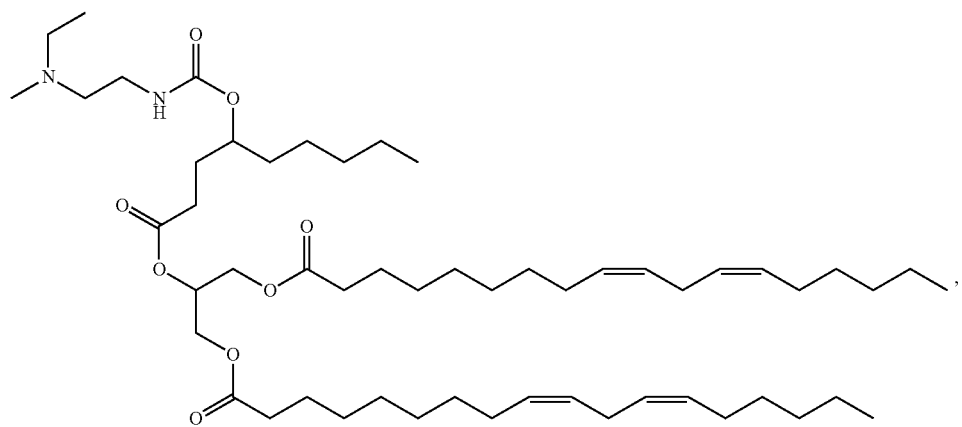
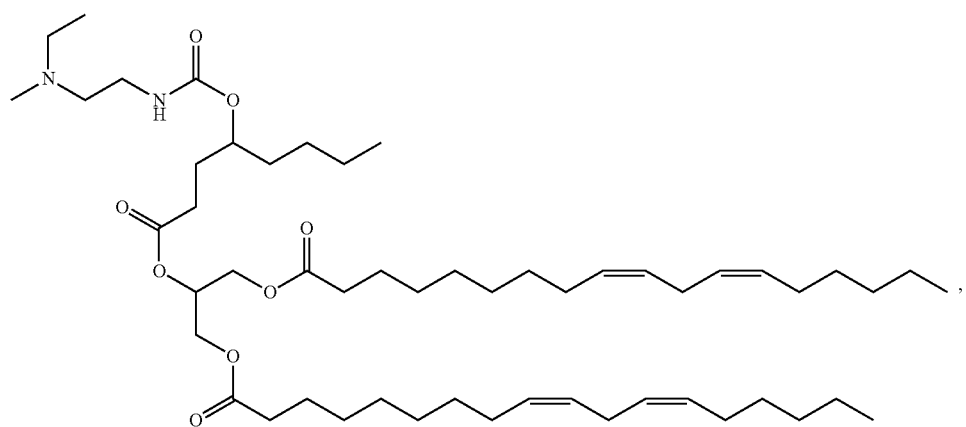
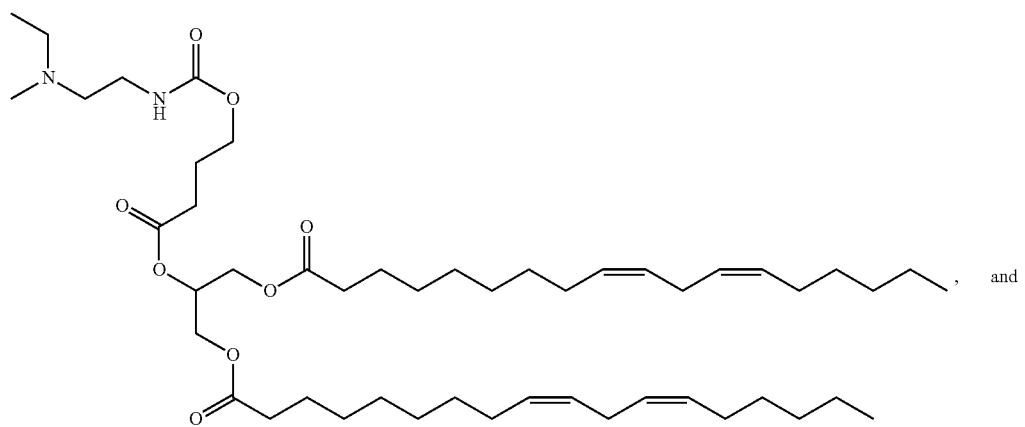

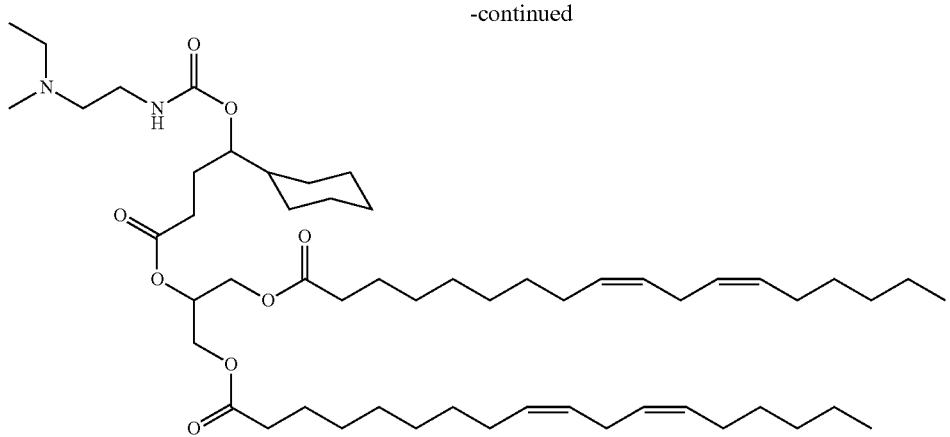
or a salt thereof.
In other embodiments, the compound is selected from
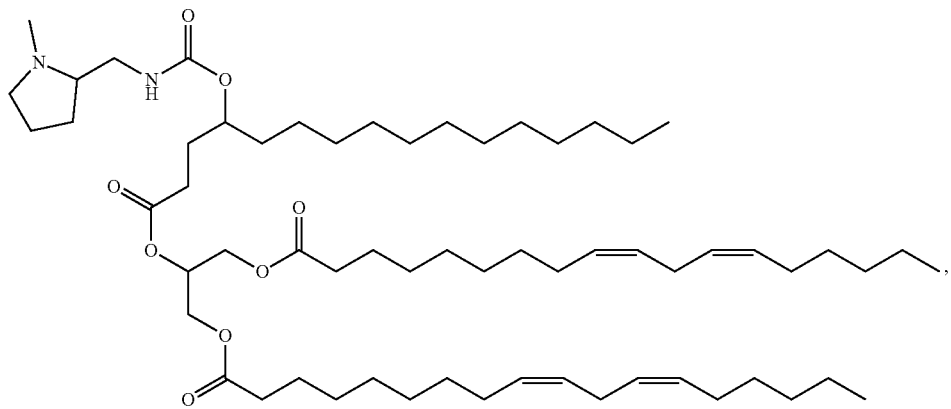
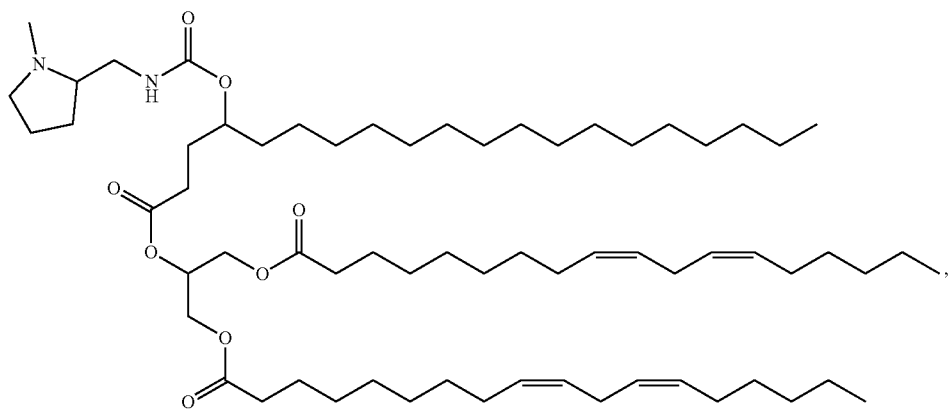

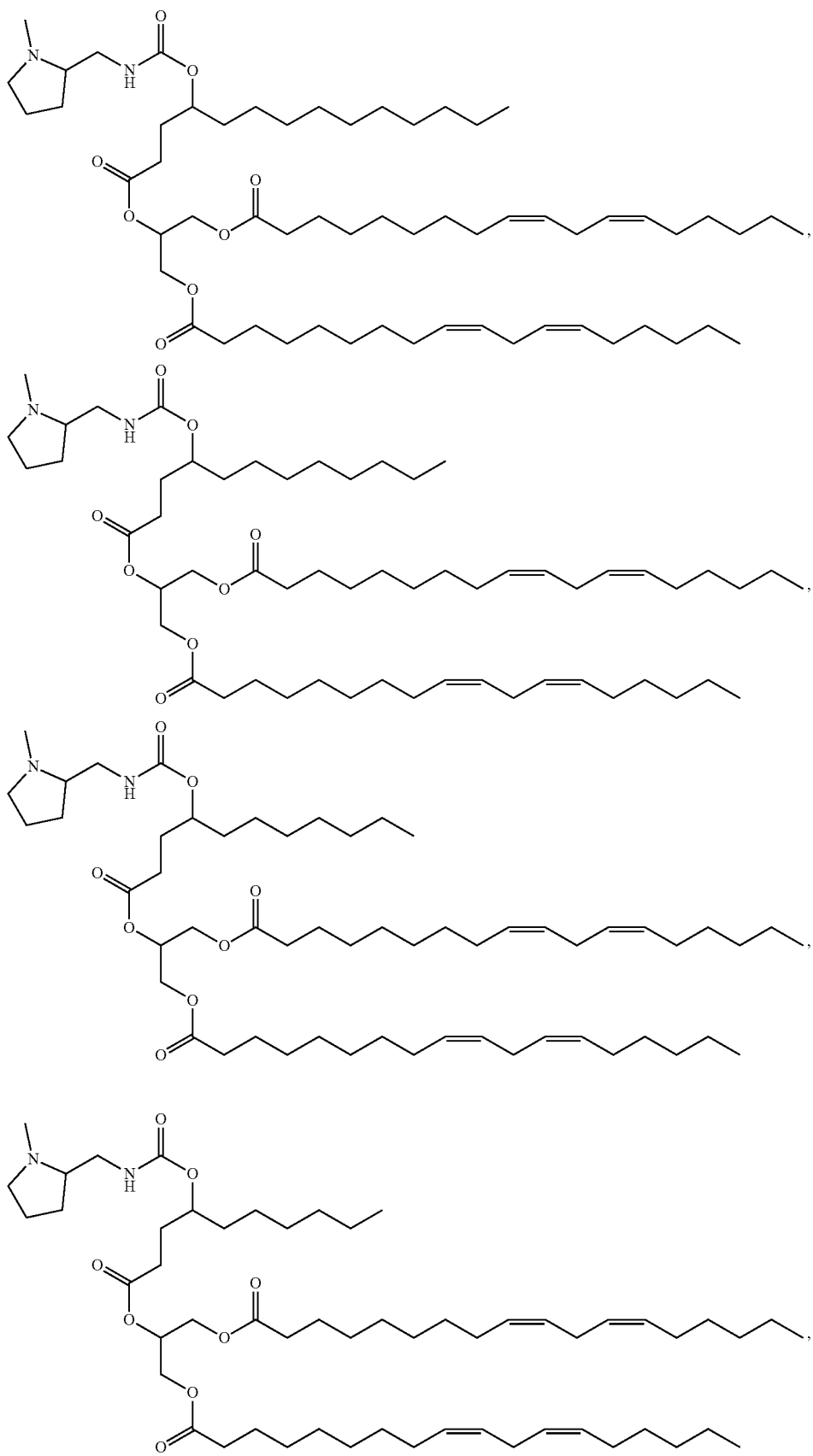

-continued
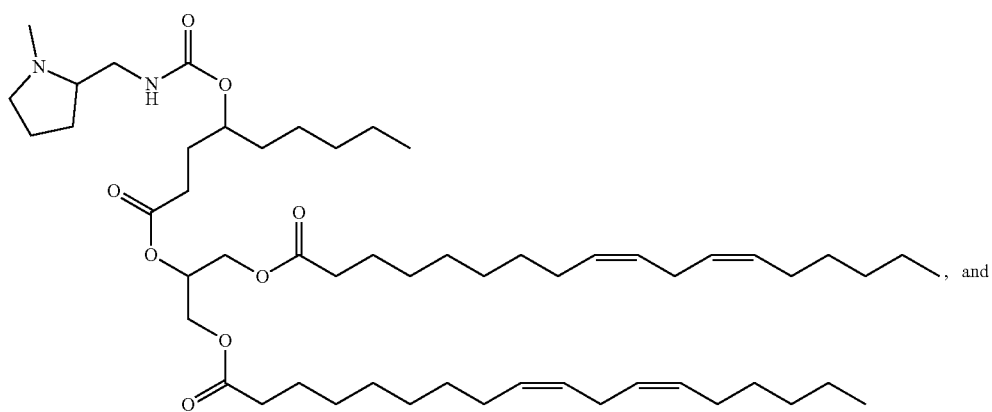
, and
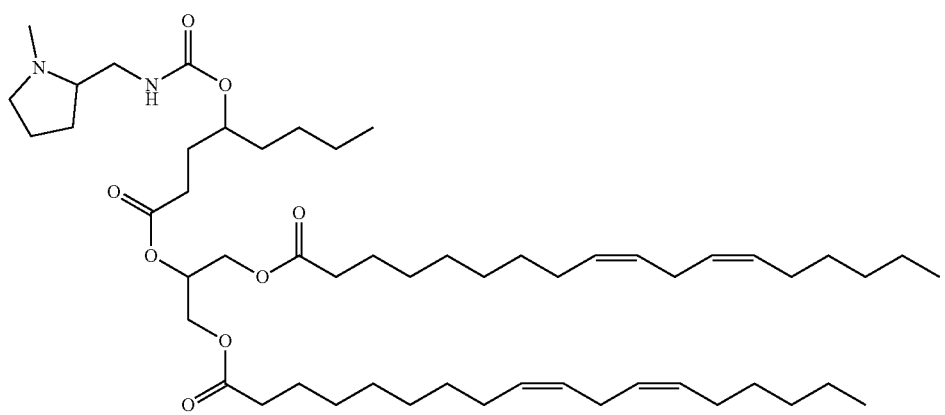
or a salt thereof.
In yet other embodiments, the compound is selected from
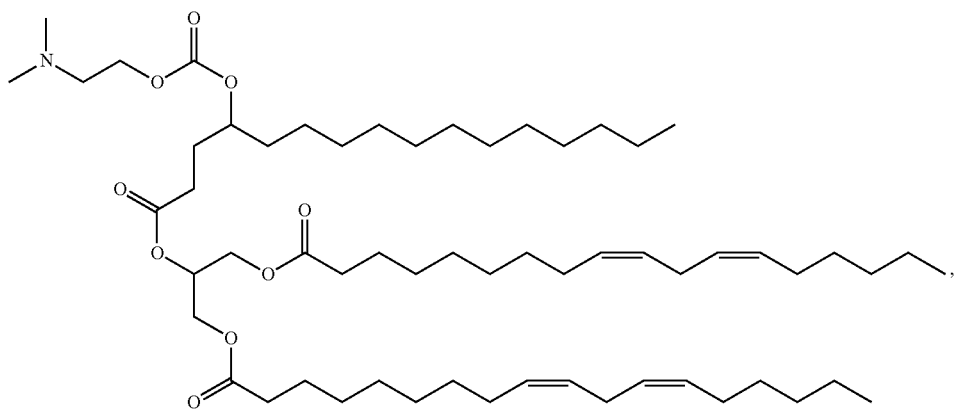
,

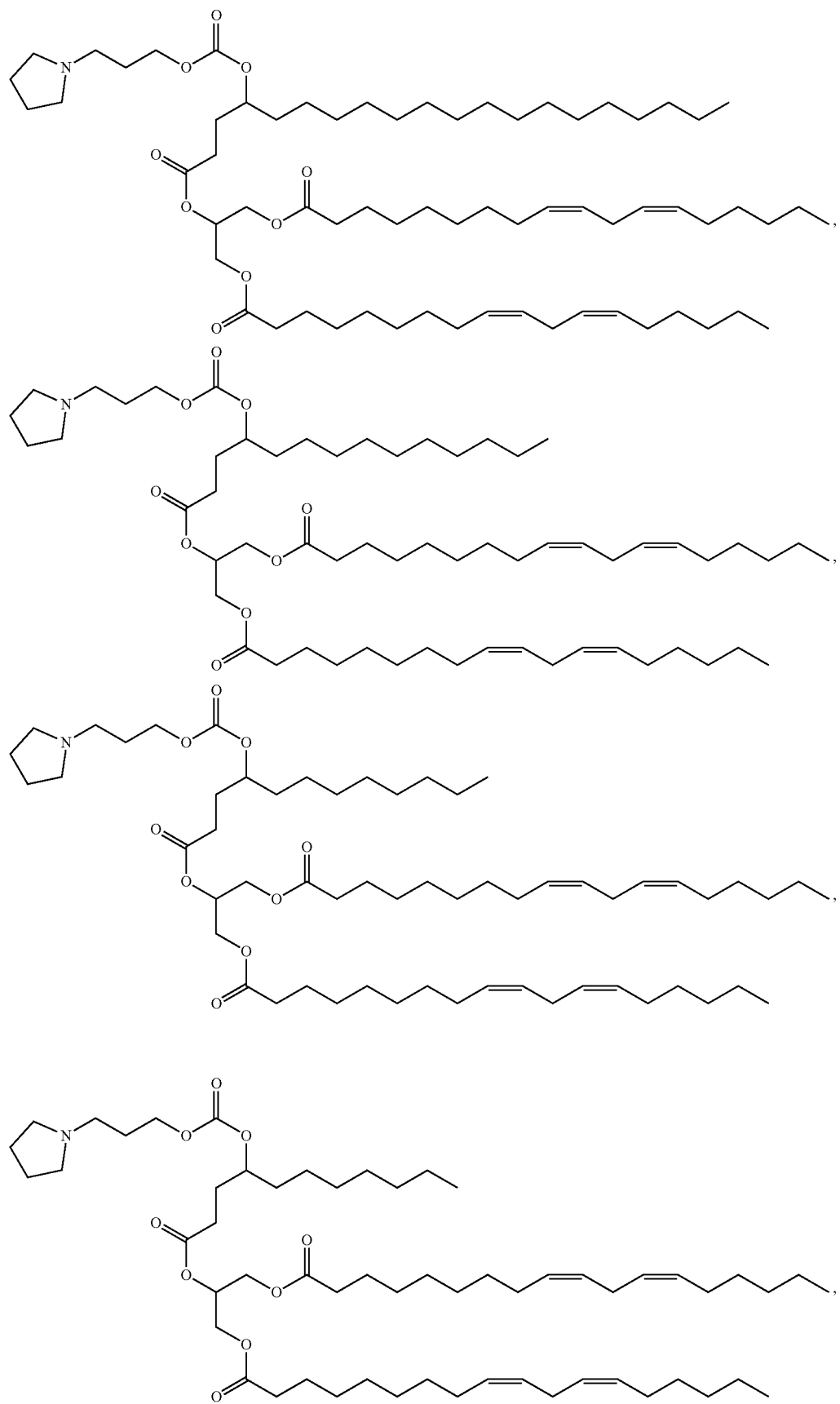

-continued

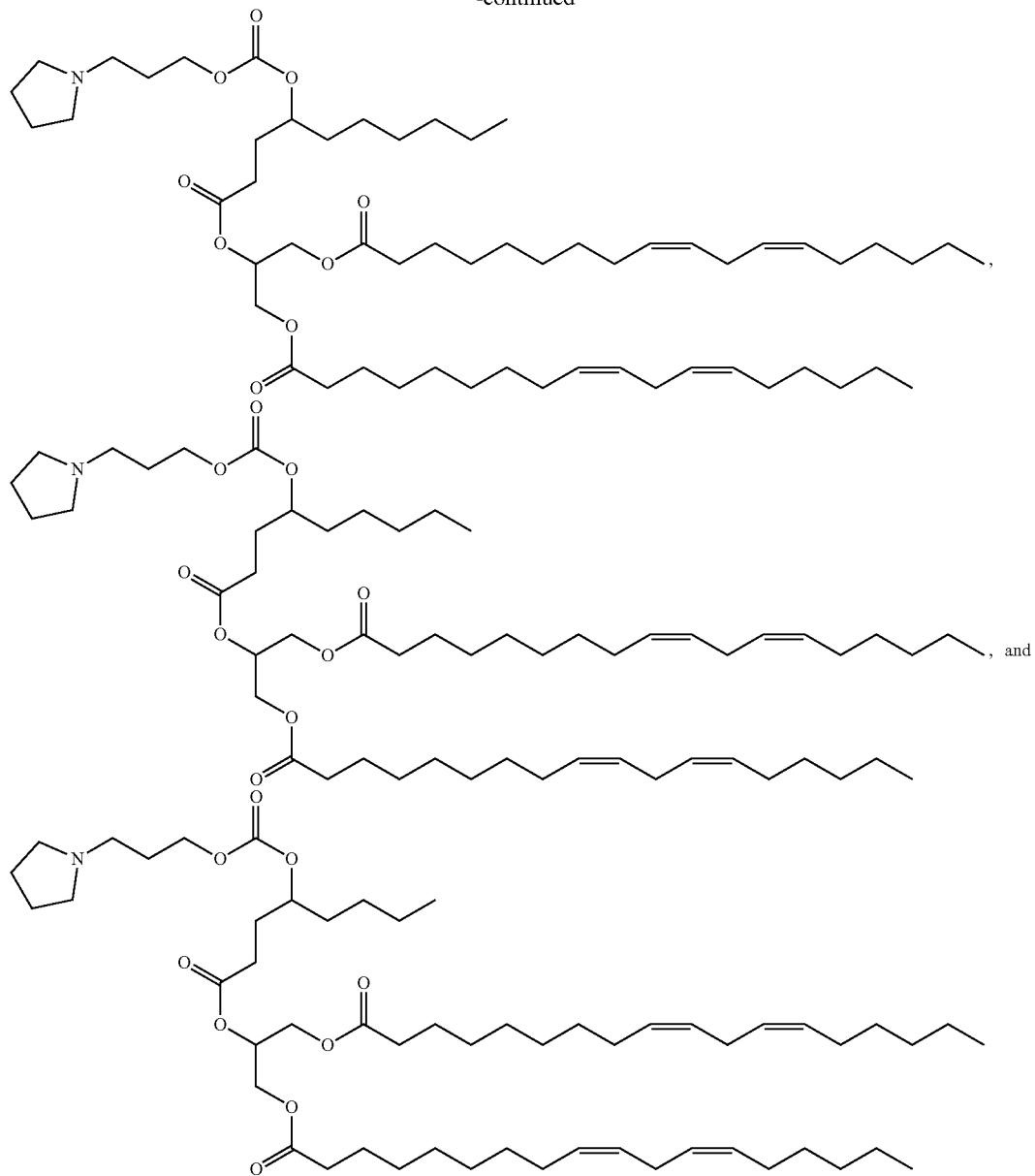

, and or a salt thereof.

In certain embodiments, the disclosure relates to any compound described herein, wherein the pKa of the protonated form of the compound is from about 5.1 to about 8.0, for example, from about 5.6 to about 7.2, from about 5.7 to about 6.5, or from about 5.8 to about 6.2. In some embodiments, the pKa of the protonated form of the compound is from about 5.5 to about 6.0. In certain embodiments, the pKa of the protonated form of the compound is from about 6.1 to about 6.3.

In certain embodiments, the disclosure relates to a composition comprising any compound described herein, In certain embodiments, the disclosure relates to a composition comprising any compound described herein and a lipid component, for example comprising about 50% by weight of a compound described herein and a lipid component, for example, an amine lipid, preferably a compound of Formula (IA), (I), (II), or (III).

In certain embodiments, the disclosure relates to any composition described herein, wherein the composition is an LNP composition. For example, the disclosure relates to an LNP composition comprising any compound described herein and a lipid component. In certain embodiments, the disclosure relates to any LNP composition described herein, wherein the lipid component comprises a helper lipid and a PEG lipid. In certain embodiments, the disclosure relates to any LNP composition described herein, wherein the lipid component comprises a helper lipid, a PEG lipid, and a neutral lipid. In certain embodiments, the disclosure relates to any LNP composition described herein, further comprising a cryoprotectant. In certain embodiments, the disclosure relates to any LNP composition described herein, further comprising a buffer.

In certain embodiments, the disclosure relates to any LNP composition described herein, further comprising a nucleic acid component. In certain embodiments, the disclosure relates to any LNP composition described herein, further comprising an RNA or DNA component. In certain embodiments, the disclosure relates to any LNP composition described herein, wherein the LNP composition has an N/P ratio of about 3-10, for example the N/P ratio is about 6±1, or the N/P ratio is about 6±0.5. In certain embodiments, the disclosure relates to any LNP composition described herein, wherein the LNP composition has an N/P ratio of about 6.

In certain embodiments, the disclosure relates to any LNP composition described herein, wherein the RNA component comprises an mRNA. In certain embodiments, the disclosure relates to any LNP composition described herein, wherein the RNA component comprises an RNA-guided DNA binding agent, for example a Cas nuclease mRNA, such as a Class 2 Cas nuclease mRNA, or a Cas9 nuclease mRNA.

In certain embodiments, the disclosure relates to any LNP composition described herein, wherein the mRNA is a modified mRNA. In certain embodiments, the disclosure relates to any LNP composition described herein, wherein the RNA component comprises a gRNA nucleic acid. In certain embodiments, the disclosure relates to any LNP composition described herein, wherein the gRNA nucleic acid is a gRNA.

In certain embodiments, the disclosure relates to an LNP composition described herein, wherein the RNA component comprises a Class 2 Cas nuclease mRNA and a gRNA. In certain embodiments, the disclosure relates to any LNP composition described herein, wherein the gRNA nucleic acid is or encodes a dual-guide RNA (dgRNA). In certain embodiments, the disclosure relates to any LNP composition described herein, wherein the gRNA nucleic acid is or encodes a single-guide RNA (sgRNA).

In certain embodiments, the disclosure relates to any LNP composition described herein, wherein the gRNA is a modified gRNA. In certain embodiments, the disclosure relates to any LNP composition described herein, wherein the modified gRNA comprises a modification at one or more of the first five nucleotides at a 5' end. In certain embodiments, the disclosure relates to any LNP composition described herein, wherein the modified gRNA comprises a modification at one or more of the last five nucleotides at a 3' end.

In certain embodiments, the disclosure relates to any LNP composition described herein, further comprising at least one template nucleic acid.

In certain embodiments, the disclosure relates to a method of gene editing, comprising contacting a cell with an LNP. In certain embodiments, the disclosure relates to any method of gene editing described herein, comprising cleaving DNA.

In certain embodiments, the disclosure relates to a method of cleaving DNA, comprising contacting a cell with an LNP composition. In certain embodiments, the disclosure relates to any method of cleaving DNA described herein, wherein the cleaving step comprises introducing a single stranded DNA nick. In certain embodiments, the disclosure relates to any method of cleaving DNA described herein, wherein the cleaving step comprises introducing a double-stranded DNA break. In certain embodiments, the disclosure relates to any method of cleaving DNA described herein, wherein the LNP composition comprises a Class 2 Cas mRNA and a guide RNA nucleic acid. In certain embodiments, the disclosure relates to any method of cleaving DNA described herein, further comprising introducing at least one template nucleic acid into the cell. In certain embodiments, the disclosure relates to any method of cleaving DNA described herein, comprising contacting the cell with an LNP composition comprising a template nucleic acid.

In certain embodiments, the disclosure relates to any a method of gene editing described herein, wherein the method comprises administering the LNP composition to an animal, for example a human. In certain embodiments, the disclosure relates to any method of gene editing described herein, wherein the method comprises administering the LNP composition to a cell, such as a eukaryotic cell.

In certain embodiments, the disclosure relates to any method of gene editing described herein, wherein the method comprises administering the mRNA formulated in a first LNP composition and a second LNP composition comprising one or more of an mRNA, a gRNA, a gRNA nucleic acid, and a template nucleic acid. In certain embodiments, the disclosure relates to any method of gene editing described herein, wherein the first and second LNP compositions are administered simultaneously. In certain embodiments, the disclosure relates to any method of gene editing described herein, wherein the first and second LNP compositions are administered sequentially. In certain embodiments, the disclosure relates to any method of gene editing described herein, wherein the method comprises administering the mRNA and the guide RNA nucleic acid formulated in a single LNP composition.

In certain embodiments, the disclosure relates to any method of gene editing described herein, wherein the gene editing results in a gene knockout.

In certain embodiments, the disclosure relates to any method of gene editing described herein, wherein the gene editing results in a gene correction.

BRIEF DESCRIPTION OF DRAWINGS

FIG. 1A illustrates the chemical structures of compounds that are tested. FIG. 1B shows the percentage of editing of TTR in mouse liver cells after delivery. FIG. 1C shows serum TTR levels (μg/mL) after delivery.

FIG. 3A is a graph showing percentage of editing of TTR in mouse liver cells after delivery. FIG. 3B is a graph showing serum TTR (μg/mL) after delivery.

FIG. 4A illustrates the chemical structures of test compounds. FIG. 4B shows the percentage of editing of TTR in mouse liver cells after delivery. FIG. 4C shows serum TTR levels (μg/mL) after delivery.

FIG. 5A illustrates the chemical structures of test compounds. FIG. 5B shows the percentage of editing of TTR in mouse liver cells after delivery. FIG. 5C shows serum TTR levels (μg/mL) after delivery.

FIG. 6A illustrates the chemical structures of test compounds. FIG. 6B shows the percentage of editing of TTR in mouse liver cells after delivery. FIG. 6C shows serum TTR levels (μg/mL) after delivery.

FIG. 7A illustrates the chemical structures of test compounds. FIG. 7B shows the percentage of editing of TTR in mouse liver cells after delivery. FIG. 7C shows serum TTR levels (μg/mL) after delivery.

FIG. 8A illustrates the chemical structures of test compounds where n=1, 2, or 3. FIG. 8B shows the percentage of editing of TTR in mouse liver cells after delivery. FIG. 8C shows serum TTR levels (μg/mL) after delivery.

FIG. 9A illustrates the chemical structures of test compounds. FIG. 9B shows the percentage of editing of TTR in mouse liver cells after delivery. FIG. 9C shows serum TTR levels (μg/mL) after delivery.

FIG. 10A illustrates the chemical structures of test compounds. FIG. 10B shows the percentage of editing of TTR in mouse liver cells after delivery. FIG. 10C shows serum TTR levels (μg/mL) after delivery.

FIG. 11A and FIG. 11B illustrate the chemical structures of test compounds.

FIG. 11C shows the percentage of editing of TTR in mouse liver cells after delivery. FIG. 11D shows serum TTR levels (μg/mL) after delivery.

FIG. 12A shows the percentage of editing of TTR in rat liver cells after delivery. FIG. 12B shows serum TTR levels (μg/mL) after delivery.

FIG. 13A illustrates the chemical structures of test compounds. FIG. 13B shows the percentage of editing of TTR in HUH7 cells after delivery.

DETAILED DESCRIPTION

Figure 1A:
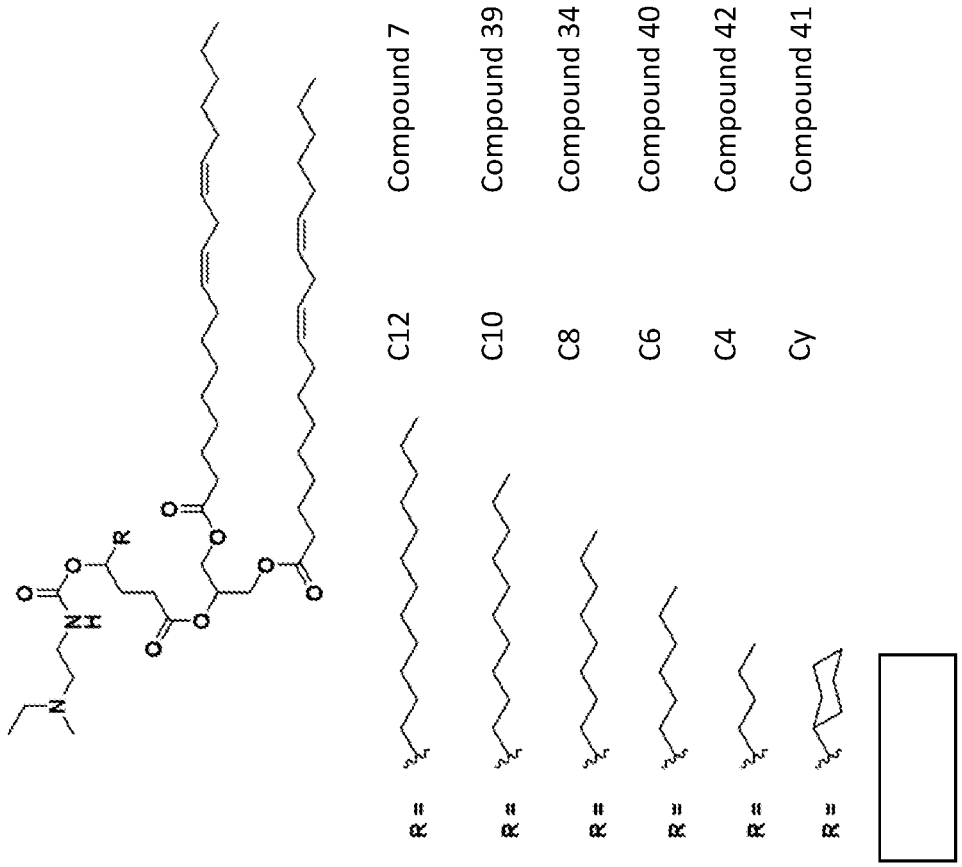
FIGS. 1A-1C show in vivo editing at the TTR locus and the compounds tested in the assay.

The present disclosure provides lipids, particularly ionizable lipids, useful for delivering biologically active agents, including nucleic acids, such as CRISPR/Cas component RNAs (the "cargo"), to a cell, and methods for preparing and using such compositions. The lipids and pharmaceutically acceptable salts thereof are provided, optionally as compositions comprising the lipids, including LNP compositions. In certain embodiments, the LNP composition may comprise a biologically active agent, e.g. an RNA component, and a lipid component that includes a compound of Formula (IA), (I), (II), or (III), as defined herein. In some embodiments, the RNA component comprises a nucleic acid. In some embodiments, the lipids are used to deliver a biologically active agent, e.g. a nucleic acid such as an mRNA to a cell such as a liver cell. In certain embodiments, the RNA component includes a gRNA and optionally an mRNA encoding a Class 2 Cas nuclease and optionally a gRNA or nucleic acids encoding gRNAs. Methods of gene editing and methods of making engineered cells using these compositions are also provided.

Lipid Nanoparticle Compositions

Disclosed herein are various LNP compositions for delivering biologically active agents, such as nucleic acids, e.g., mRNAs and gRNAs, including CRISPR/Cas cargoes. Such LNP compositions include an "ionizable amine lipid", along with a neutral lipid, a PEG lipid, and a helper lipid. "Lipid nanoparticle" or "LNP" refers to, without limiting the meaning, a particle that comprises a plurality of (i.e., more than one) LNP components physically associated with each other by intermolecular forces.

Lipids

The disclosure provides lipids that can be used in LNP compositions.

In certain embodiments, the present disclosure relates to a compound having a structure of Formula (IA):

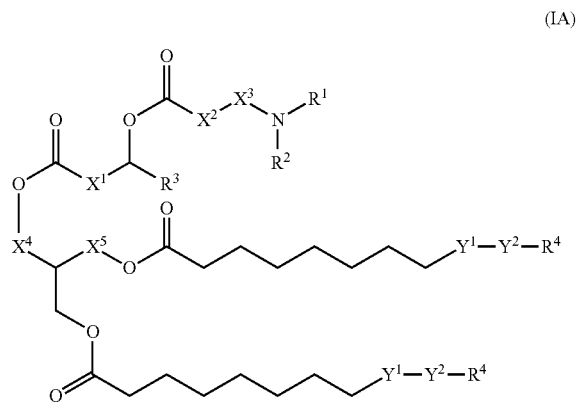

(IA)

wherein, independently for each occurrence,
$X^1$ is $C_{1-3}$ alkylene or

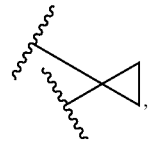

, $X^2$ is selected from O, NH, NMe, and a bond,
$X^3$ is $C_{2-4}$ alkylene,
$X^4$ is $C_1$ alkylene or a bond,
$X^5$ is $C_1$ alkylene or a bond,
$R^1$ is $C_{1-3}$ alkyl,
$R^2$ is $C_{1-3}$ alkyl, or
$R^2$ taken together with the nitrogen atom and either $R^1$ or a carbon atom of $X^3$ form a 4-membered, 5-membered, or 6-membered ring,
each $Y^1$ is independently selected from a bond, —CH=CH—, —(C=O)O—, and —O(C=O)—,
each $Y^2$ is independently selected from —CH$_2$—CH=CH— and $C_3$-$C_4$ alkylene,
$R^3$ is selected from H, $C_{5-7}$ cycloalkyl, $C_8$-$C_{10}$ alkenyl, and $C_{3-18}$ alkyl,
each $R^4$ is independently $C_{4-8}$ alkyl,
or a salt thereof,
with a proviso that when $R^2$ is Me, $R^3$ is linear $C_{12}$ alkyl, $X^1$ is $C_2$ alkylene, $X^2$ is O, $X^3$ is $C_3$ alkylene, $X^4$ is a bond, $X^5$ is $C_1$ alkylene, $Y^1$ is cis —CH=CH—, and —$Y^2$—$R^4$ is cis —CH$_2$—CH=CH—($C_5$-alkyl), then $R^1$ is $C_{2-3}$ alkyl.

In certain embodiments, the compound is a compound of Formula (IA) with a proviso that when $R^2$ is Me, $R^1$ is $C_{2-3}$ alkyl.

In certain embodiments, the compound is a compound of Formula (IA) wherein $R^2$ is not Me.

In certain embodiments, the compound is a compound of Formula (IA) wherein $R^1$ is not Me.

In certain embodiments, the compound is a compound of Formula (IA) wherein $R^3$ is not linear $C_{12}$ alkyl.

In certain embodiments, the compound is a compound of Formula (IA) wherein $X^1$ is not $C_2$ alkylene.

In certain embodiments, the compound is a compound of Formula (IA) wherein $X^2$ is not O.

In certain embodiments, the compound is a compound of Formula (IA) wherein $X^3$ is not $C_3$ alkylene In certain embodiments, the compound is a compound of Formula (IA) wherein $X^4$ is not a bond.

In certain embodiments, the compound is a compound of Formula (IA) wherein $X^5$ is not $C_1$ alkylene.

In certain embodiments, the compound is a compound of Formula (IA) wherein $Y^1$ is not cis —CH=CH—.

In certain embodiments, the compound is a compound of Formula (IA) wherein —$Y^2$—$R^4$ is not cis —$CH_2$—CH=CH—($C_5$-alkyl).

In certain embodiments, the present disclosure relates to a compound of Formula (I):

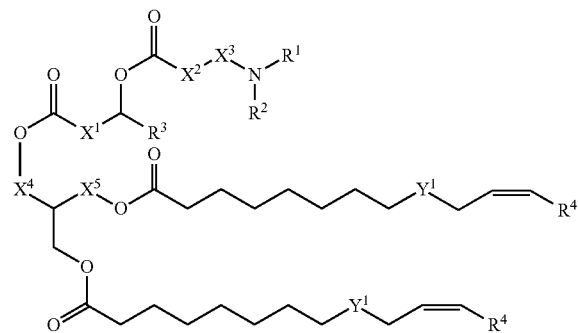

wherein, independently for each occurrence,
$X^1$ is $C_{2-3}$ alkylene,
$X^2$ is selected from O, NH, NMe, and a bond,
$X^3$ is $C_{2-4}$ alkylene,
$X^4$ is $C_1$ alkylene or a bond,
$X^5$ is $C_1$ alkylene or a bond,
$R^1$ is $C_{1-2}$ alkyl,
$R^2$ is $C_{1-2}$ alkyl, or
$R^2$ taken together with the nitrogen atom and either $R^1$ or a carbon atom of
$X^3$ form a 5-membered or a 6-membered ring,
$Y^1$ is selected from —CH=CH—, —(C=O)O—, and —O(C=O)—,
$R^3$ is selected from H, $C_{5-7}$ cycloalkyl, and $C_{3-18}$ alkyl,
$R^4$ is $C_{4-7}$ alkyl,
or a salt thereof,
with a proviso that when $R^2$ is Me, $R^3$ is linear $C_{12}$ alkyl, $X^1$ is $C_2$ alkylene, $X^2$ is O, $X^3$ is $C_3$ alkylene, $X^4$ is a bond, $X^5$ is $C_1$ alkylene, $Y^1$ is cis —CH=CH—, and $R^4$ is $C_5$ alkyl, then $R^1$ is $C_2$ alkyl, or a salt thereof, such as a pharmaceutically acceptable salt thereof.

In certain embodiments, the compound is a compound of Formula (I) with a proviso that when $R^2$ is Me, $R^3$ is linear $C_{12}$ alkyl, $X^1$ is $C_2$ alkylene, $X^2$ is O, $X^3$ is $C_3$ alkylene, $X^4$ is a bond, $X^5$ is $C_1$ alkylene, and $Y^1$ is cis —CH=CH—, then $R^1$ is $C_2$ alkyl.

In certain embodiments, the compound is a compound of Formula (I) with a proviso that when $R^2$ is Me, $R^1$ is $C_2$ alkyl.

In certain embodiments, the compound is a compound of Formula (I) wherein $R^2$ is not Me.

In certain embodiments, the compound is a compound of Formula (I) wherein $R^1$ is not Me.

In certain embodiments, the compound is a compound of Formula (I) wherein $R^3$ is not linear $C_{12}$ alkyl.

In certain embodiments, the compound is a compound of Formula (I) wherein $X^1$ is not $C_2$ alkylene.

In certain embodiments, the compound is a compound of Formula (I) wherein $X^2$ is not O.

In certain embodiments, the compound is a compound of Formula (I) wherein $X^3$ is not $C_3$ alkylene.

In certain embodiments, the compound is a compound of Formula (I) wherein $X^4$ is not a bond.

In certain embodiments, the compound is a compound of Formula (I) wherein $X^5$ is not $C_1$ alkylene.

In certain embodiments, the compound is a compound of Formula (I) wherein $Y^1$ is not cis —CH=CH—.

In some embodiments, the compound is enantiomerically enriched or diastereomerically enriched, for example, the compound is enantiomerically enriched.

In certain embodiments, $X^1$ is linear $C_2$ alkylene. In other embodiments, $X^1$ is $C_1$ alkylene. In some embodiments, $X^1$ is linear $C_3$ alkylene or branched $C_3$ alkylene.

In some other embodiments, $X^2$ is NH or O. In certain preferred embodiments, $X^2$ is O and $X^3$ is $C_{3-4}$ alkylene. In some embodiments, $X^3$ is $C_{2-3}$ alkylene. In certain embodiments, $X^2$ is NMe or a bond.

In certain embodiments, $R^2$ and a carbon atom of $X^3$ taken together form a 4-membered ring. In certain embodiments, $R^2$ and a carbon atom of $X^3$ taken together form a 5-membered ring. In some embodiments, $R^2$ and a carbon atom of $X^3$ taken together form a 6-membered ring. Alternatively, $R^2$ may be $C_2$ alkyl. In some instances, $R^2$ is $C_1$ alkyl. In some embodiments, $R^2$ is substituted, for example, with a hydroxy group, an example of $R^2$ includes hydroxy-substituted $C_2$ alkyl.

In certain embodiments, $R^1$ is $C_1$ alkyl. Alternatively, $R^1$ may be $C_2$ alkyl. In some embodiments, $R^1$ is substituted, for example, with a hydroxy group, an example of $R^1$ includes hydroxy-substituted $C_2$ alkyl. In some embodiments, $R^1$ is unsubstituted. In some embodiments, $R^2$ is unsubstituted. In preferred embodiments, $R^1$ and $R^2$ are both unsubstituted. In other embodiments, $R^1$ and $R^2$ together form a 4-membered ring. In other embodiments, $R^1$ and $R^2$ together form a 5-membered ring. In other embodiments, $R^1$ and $R^2$ together form a 6-membered ring.

In some embodiments, $R^3$ is linear $C_{8-16}$ alkyl, for example linear $C_{7-12}$ alkyl, such as linear $C_{7-9}$ alkyl. Alternatively, $R^3$ can be linear $C_{3-6}$ alkyl. In some embodiments, $R^3$ is branched $C_{6-10}$ alkyl. In other embodiments, $R^3$ is $C_{5-7}$ cycloalkyl, for example $C_6$ cycloalkyl. In some embodiments, $R^3$ is H. In some embodiments, $R^3$ is $C_{8-10}$ alkenyl.

In certain embodiments, $R^4$ is linear $C_{5-6}$ alkyl.

In some embodiments, $X^4$ is a bond.

In certain embodiments, $X^5$ is a $C_1$ alkylene.

In some embodiments, $Y^2$—$R^4$ is —$CH_2$—CH=CH—$R^4$.

In other embodiments, $Y^2$ is linear $C_3$ alkylene.

In some embodiments, $Y^1$ is selected from a bond, —CH=CH—, and —O(C=O)—, for example, —CH=CH— and —O(C=O)—.

In certain embodiments, the compound is a compound of Formula II:

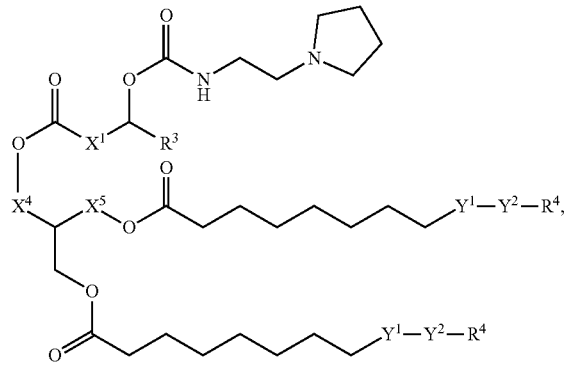

(II)

wherein the variables are defined as for Formula (IA).

In certain embodiments, $X^1$ is linear $C_2$ alkylene. In other embodiments, $X^1$ is $C_1$ alkylene. In some embodiments, $X^1$ is linear $C_3$ alkylene or branched $C_3$ alkylene.

In some embodiments, $R^3$ is linear $C_{8-16}$ alkyl, for example linear $C_{7-12}$ alkyl, such as linear $C_{7-9}$ alkyl. Alternatively, $R^3$ can be linear $C_{3-6}$ alkyl. In some embodiments, $R^3$ is branched $C_{6-10}$ alkyl. In other embodiments, $R^3$ is $C_{5-7}$ cycloalkyl, for example $C_6$ cycloalkyl. In some embodiments, $R^3$ is H. In some embodiments, $R^3$ is $C_{8-10}$ alkenyl.

In certain embodiments, $R^4$ is linear $C_{5-6}$ alkyl.

In some embodiments, $X^4$ is a bond.

In certain embodiments, $X^5$ is a $C_1$ alkylene.

In some embodiments, $Y^2$—$R^4$ is —CH$_2$—CH=CH—$R^4$.

In other embodiments, $Y^2$ is linear $C_3$ alkylene.

In some embodiments, $Y^1$ is selected from a bond, —CH=CH—, and —O(C=O)—, for example, —CH=CH— and —O(C=O)—.

In certain embodiments, the compound is selected from:

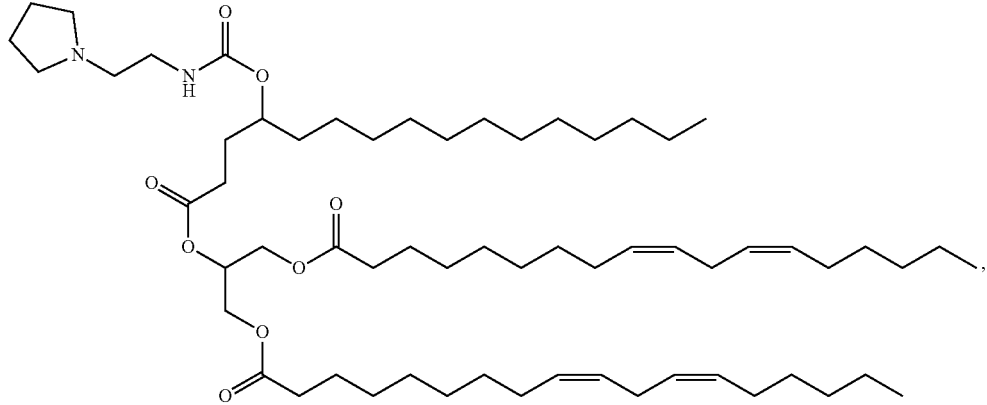

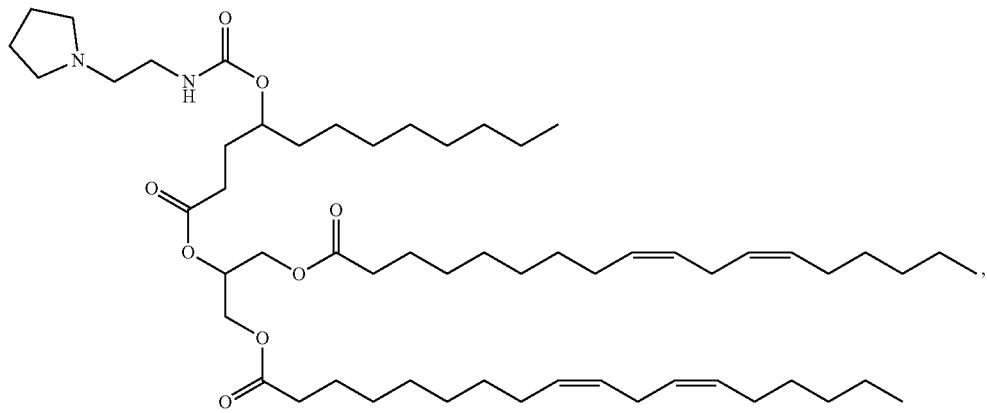

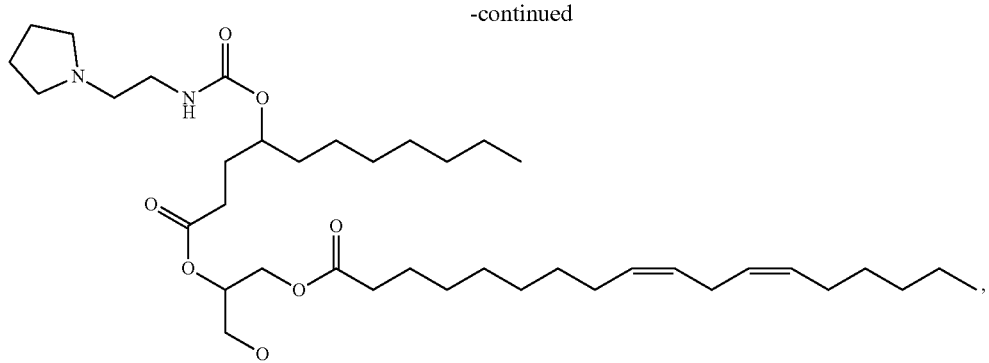,
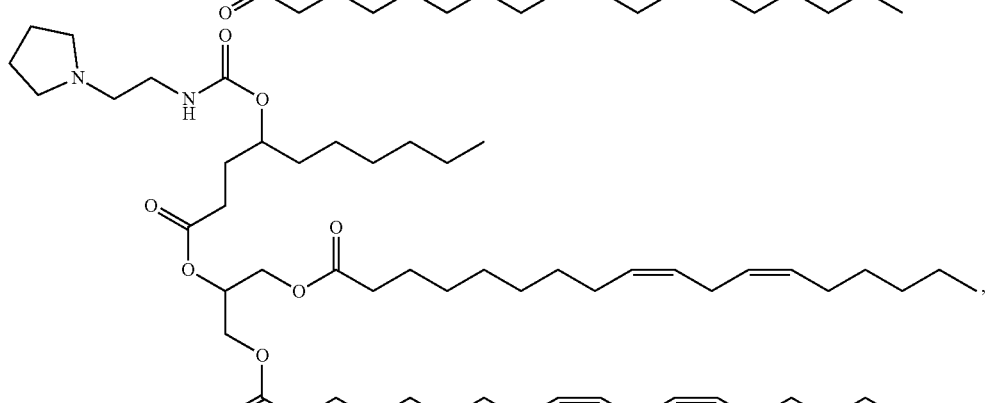,
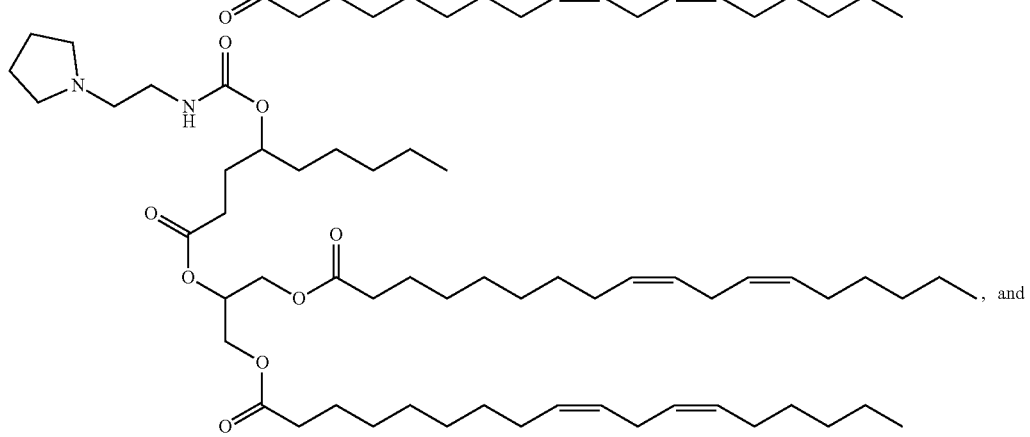, and
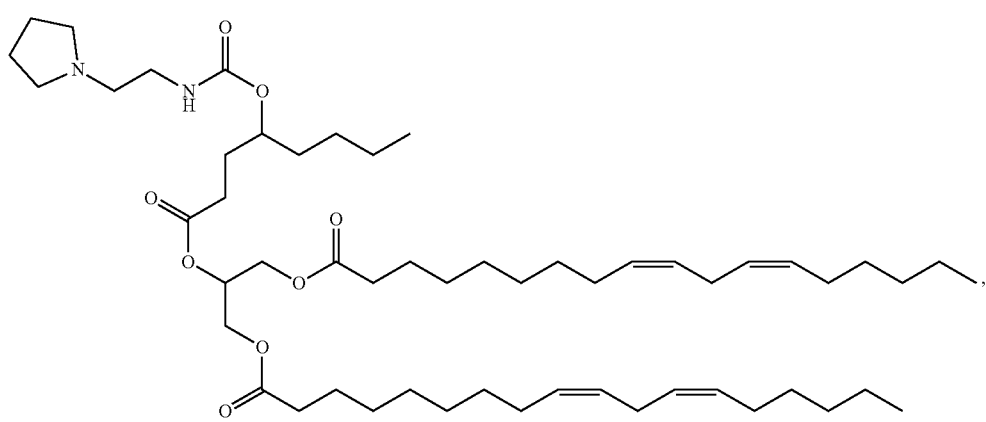,
or a salt thereof.

In certain embodiments, the compound is a compound of Formula III;

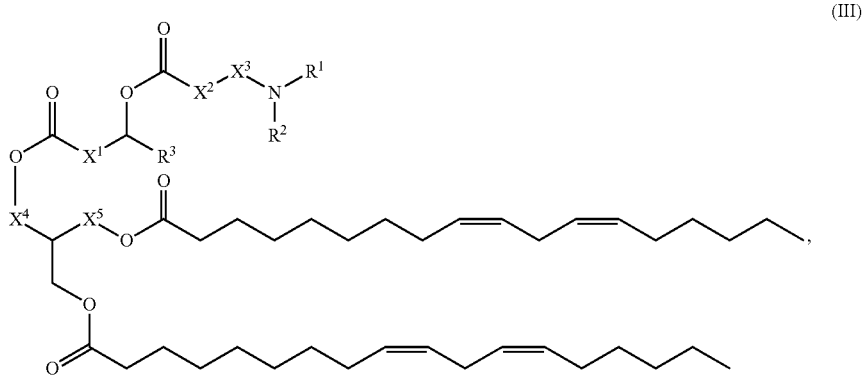

(III)

wherein the variables are defined as for Formula (IA).

In certain embodiments, $X^1$ is linear $C_2$ alkylene. In other embodiments, $X^1$ is $C_1$ alkylene. In some embodiments, $X^1$ is linear $C_3$ alkylene or branched $C_3$ alkylene.

In some other embodiments, $X^2$ is NH or O. In certain preferred embodiments, $X^2$ is O and $X^3$ is $C_{3-4}$ alkylene. In some embodiments, $X^3$ is $C_{2-3}$ alkylene. In certain embodiments, $X^2$ is NMe or a bond.

In certain embodiments, $R^2$ and a carbon atom of $X^3$ taken together form a 4-membered ring. In certain embodiments, $R^2$ and a carbon atom of $X^3$ taken together form a 5-membered ring. In some embodiments, $R^2$ and a carbon atom of $X^3$ taken together form a 6-membered ring. Alternatively, $R^2$ may be $C_2$ alkyl. In some instances, $R^2$ is $C_1$ alkyl. In some embodiments, $R^2$ is substituted, for example, with a hydroxy group, an example of $R^2$ includes hydroxy-substituted $C_2$ alkyl.

In certain embodiments, $R^1$ is $C_1$ alkyl. Alternatively, $R^1$ may be $C_2$ alkyl. In some embodiments, $R^1$ is substituted, for example, with a hydroxy group, an example of $R^1$ includes hydroxy-substituted $C_2$ alkyl. In some embodiments, $R^1$ is unsubstituted. In some embodiments, $R^2$ is unsubstituted. In preferred embodiments, $R^1$ and $R^2$ are both unsubstituted. In other embodiments, $R^1$ and $R^2$ together form a 4-membered ring. In other embodiments, $R^1$ and $R^2$ together form a 5-membered ring. In other embodiments, $R^1$ and $R^2$ together form a 6-membered ring.

In some embodiments, $R^3$ is linear $C_{8-16}$ alkyl, for example linear $C_{7-12}$ alkyl, such as linear $C_{7-9}$ alkyl. Alternatively, $R^3$ can be linear $C_{3-6}$ alkyl. In some embodiments, $R^3$ is branched $C_{6-10}$ alkyl. In other embodiments, $R^3$ is $C_{5-7}$ cycloalkyl, for example $C_6$ cycloalkyl. In some embodiments, $R^3$ is H. In some embodiments, $R^3$ is $C_{8-10}$ alkenyl.

In some embodiments, $X^4$ is a bond.

In certain embodiments, $X^5$ is a $C_1$ alkylene.

Representative compounds of Formula (IA) or (I) include:

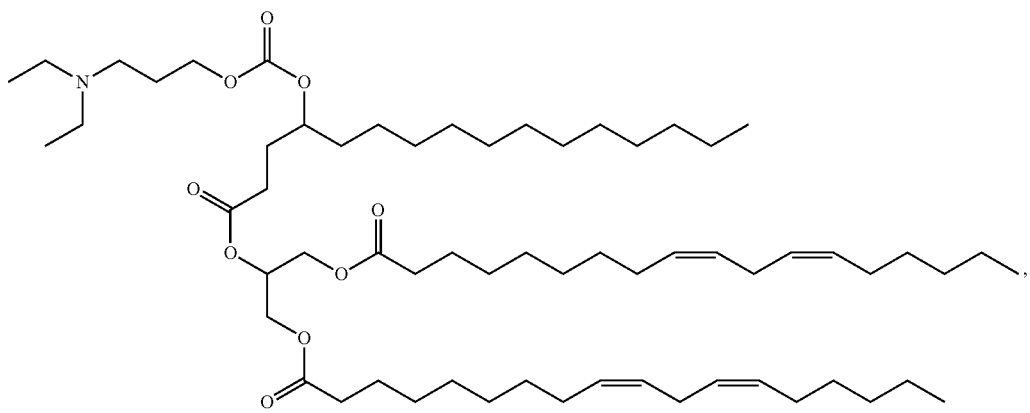

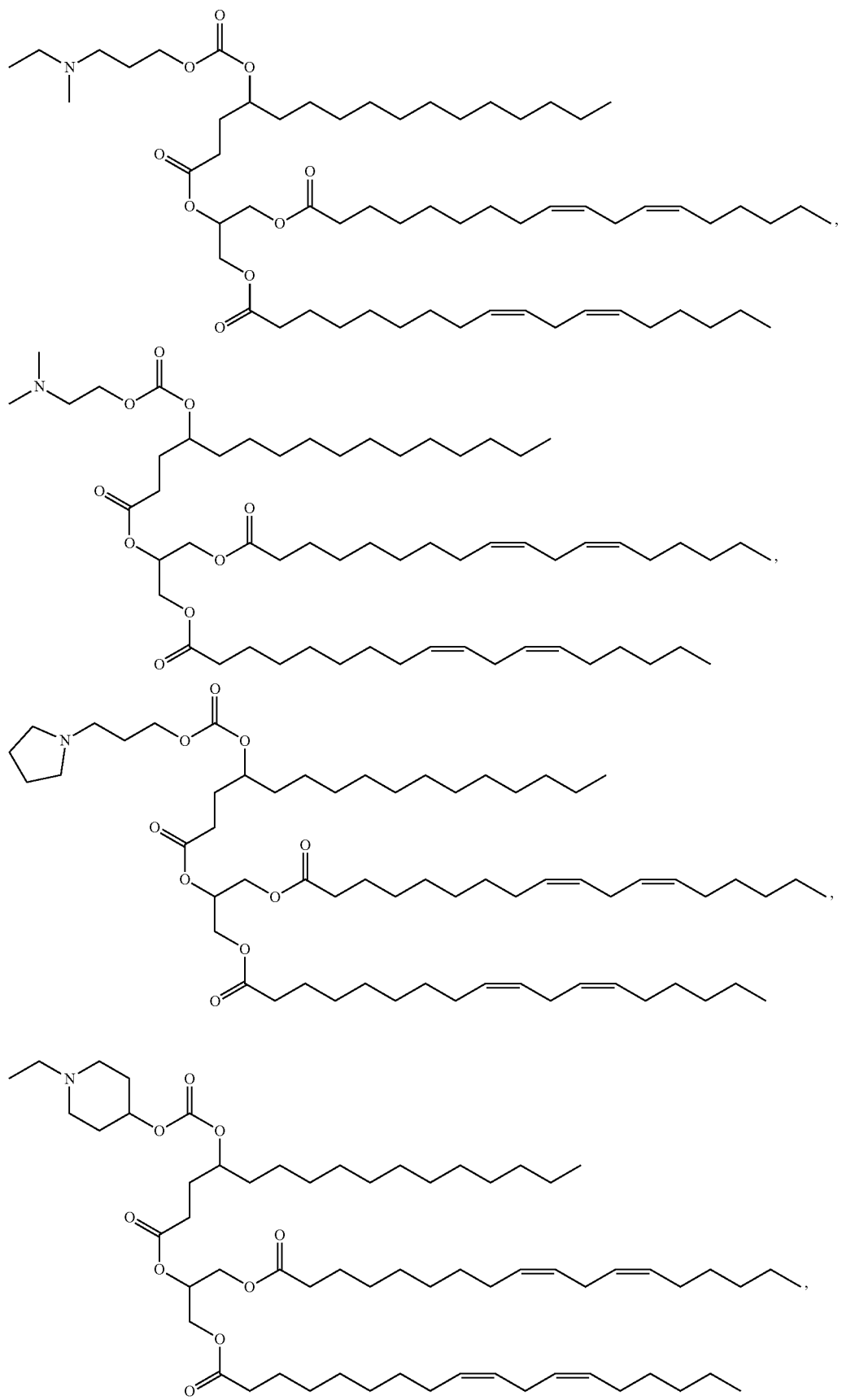

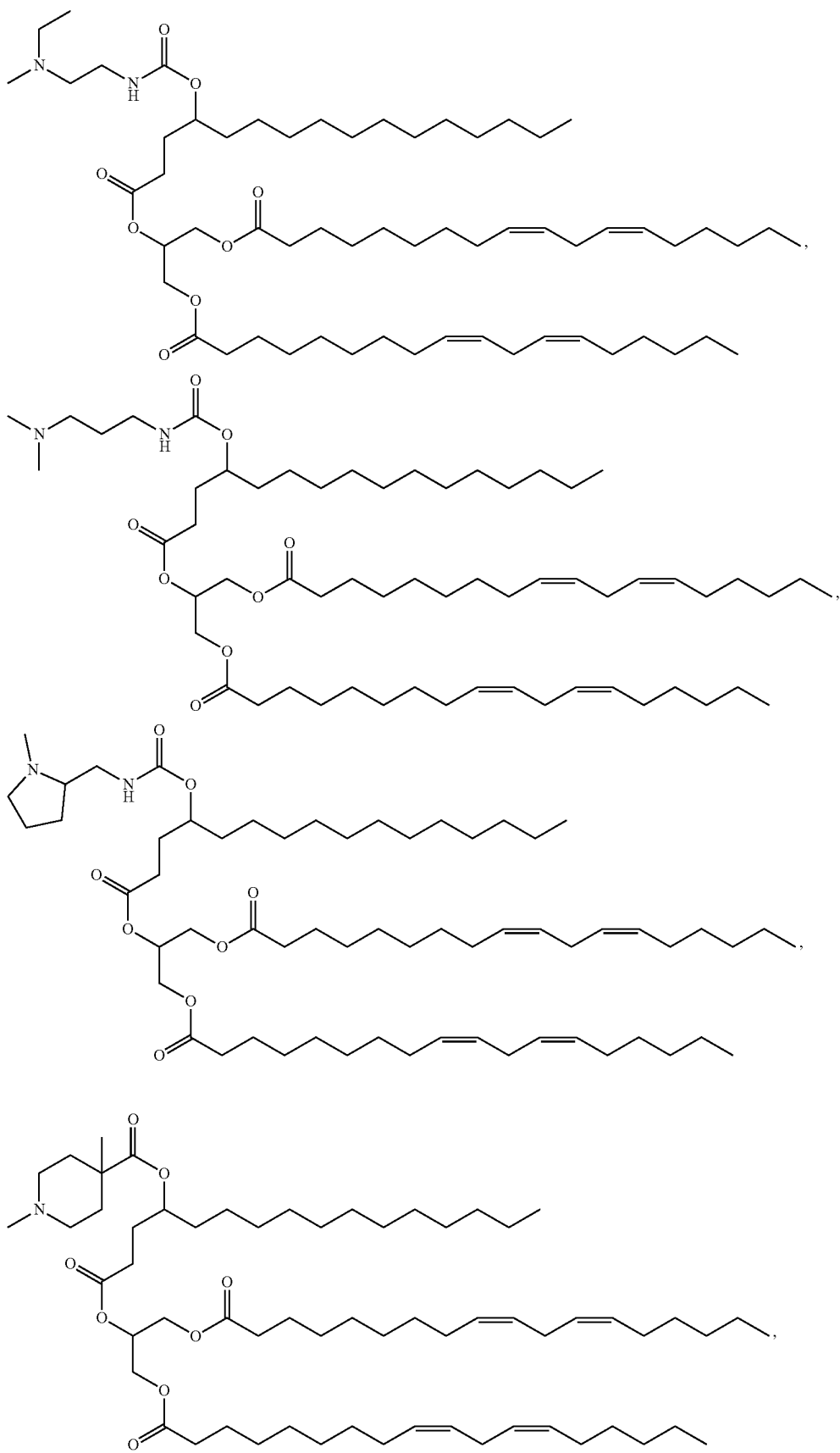

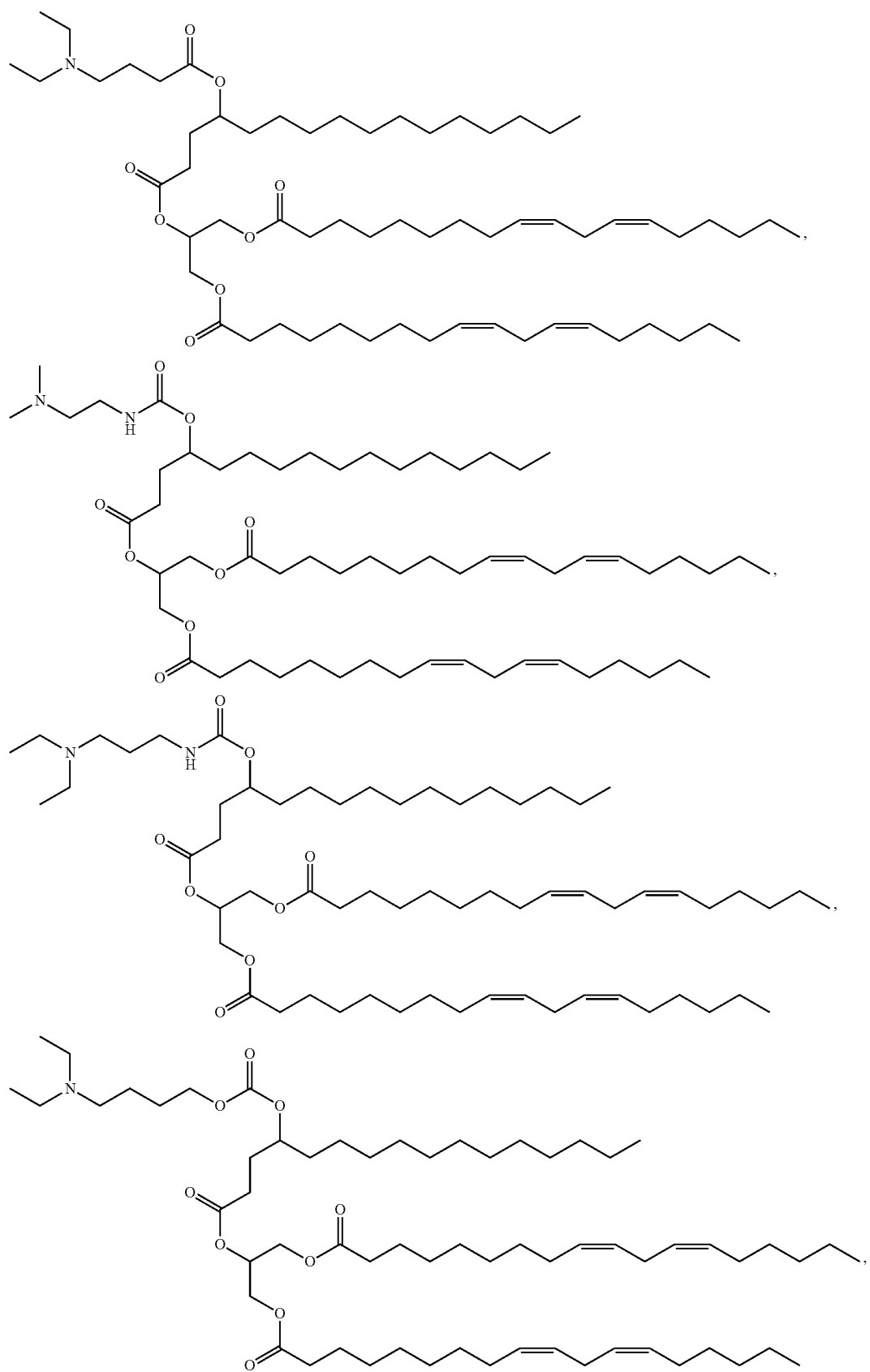

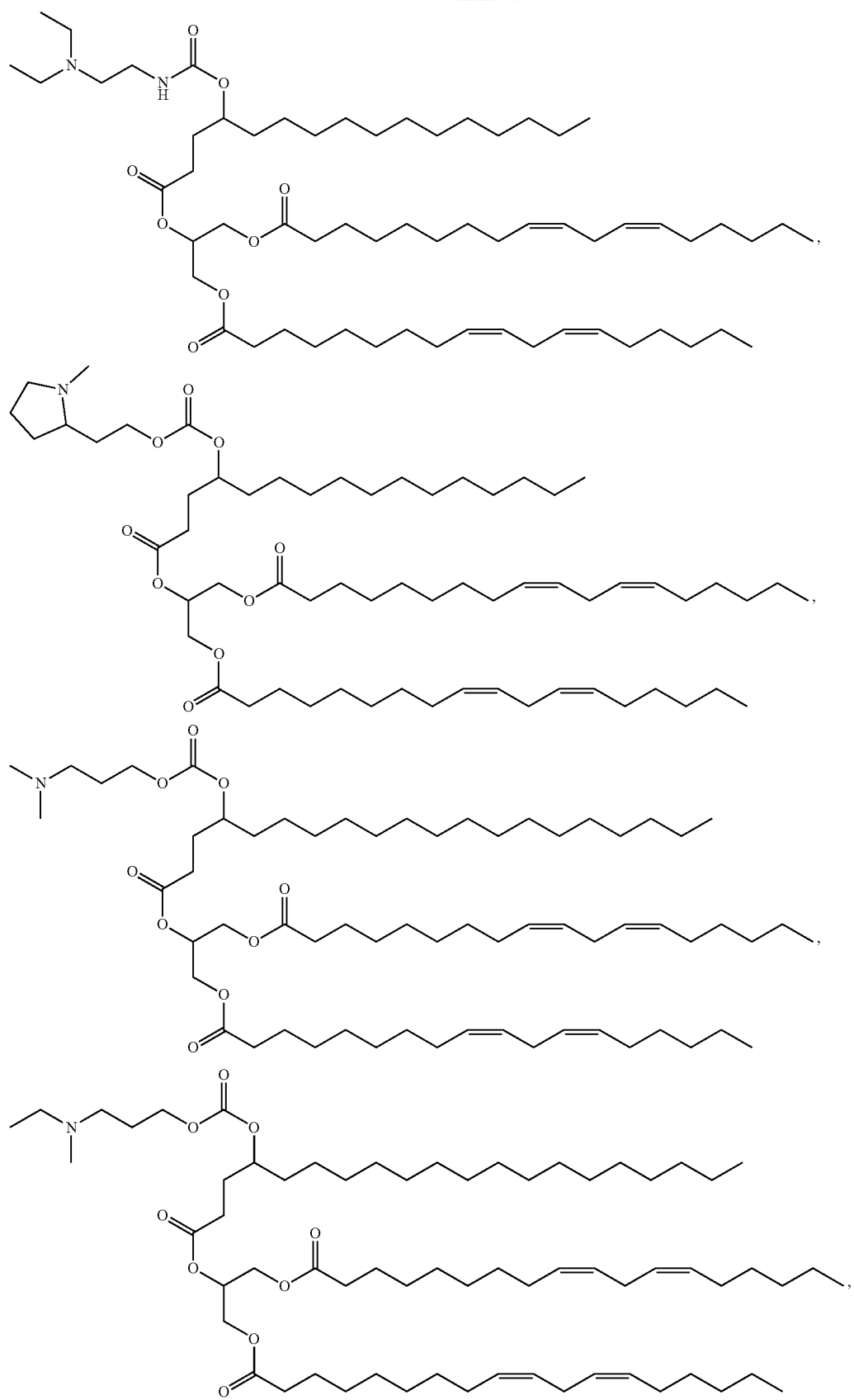

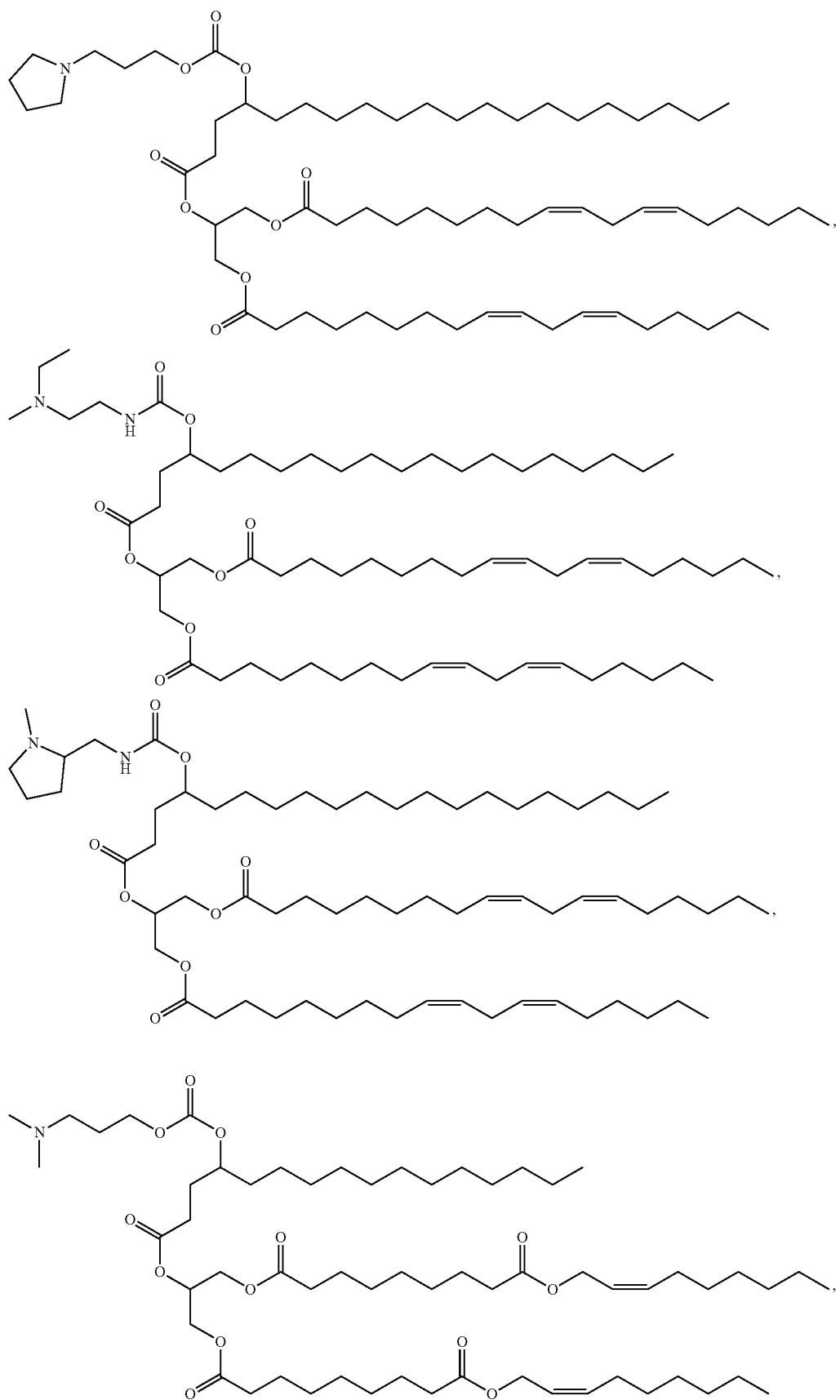

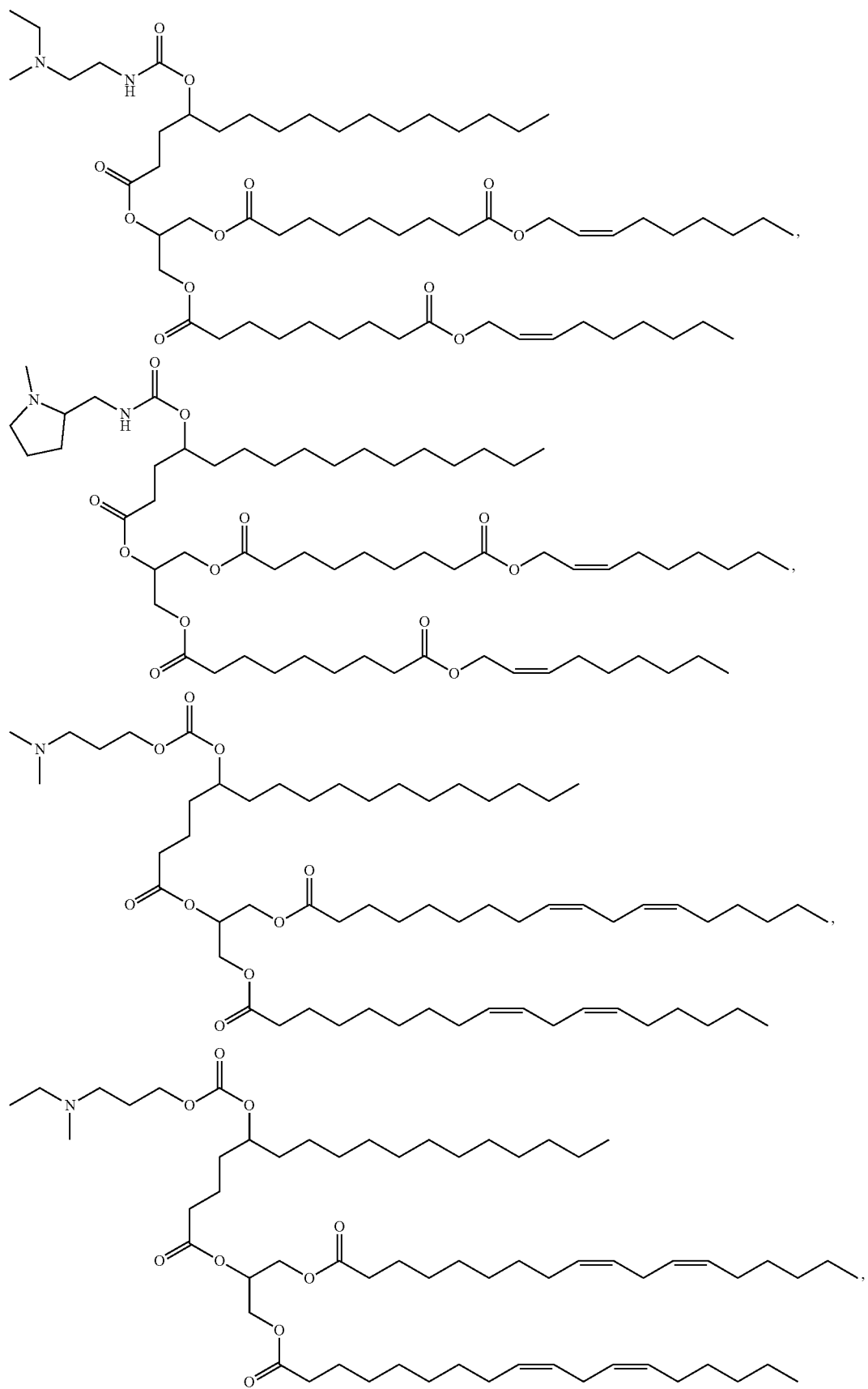

-continued
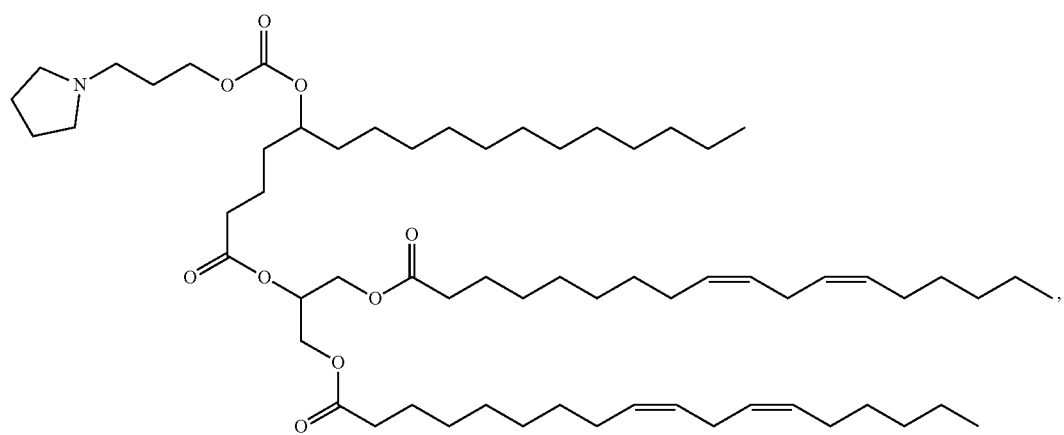
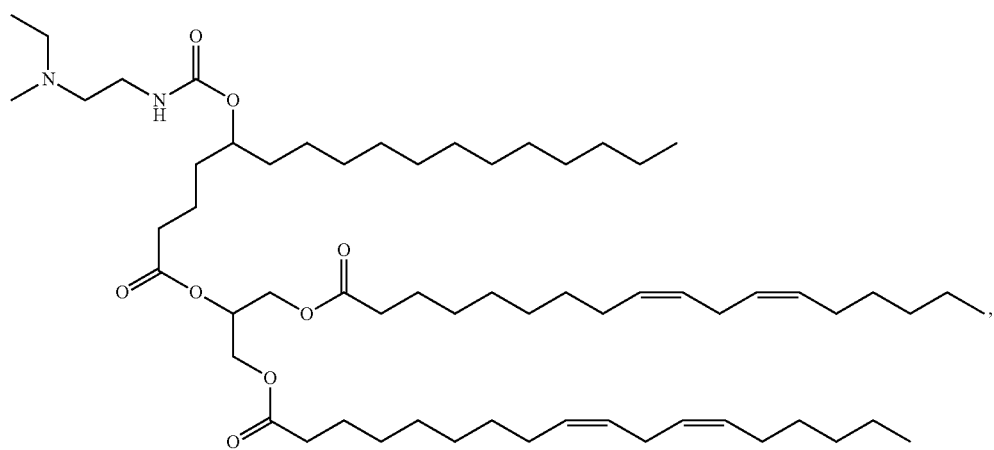
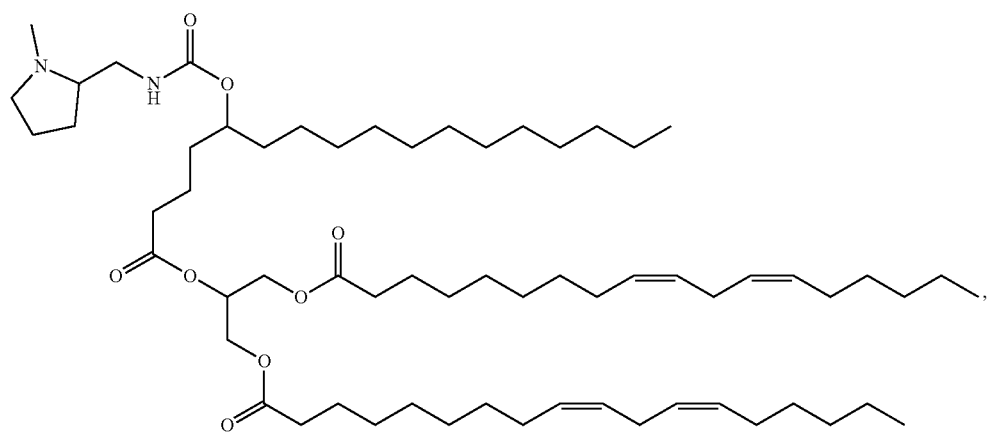

-continued
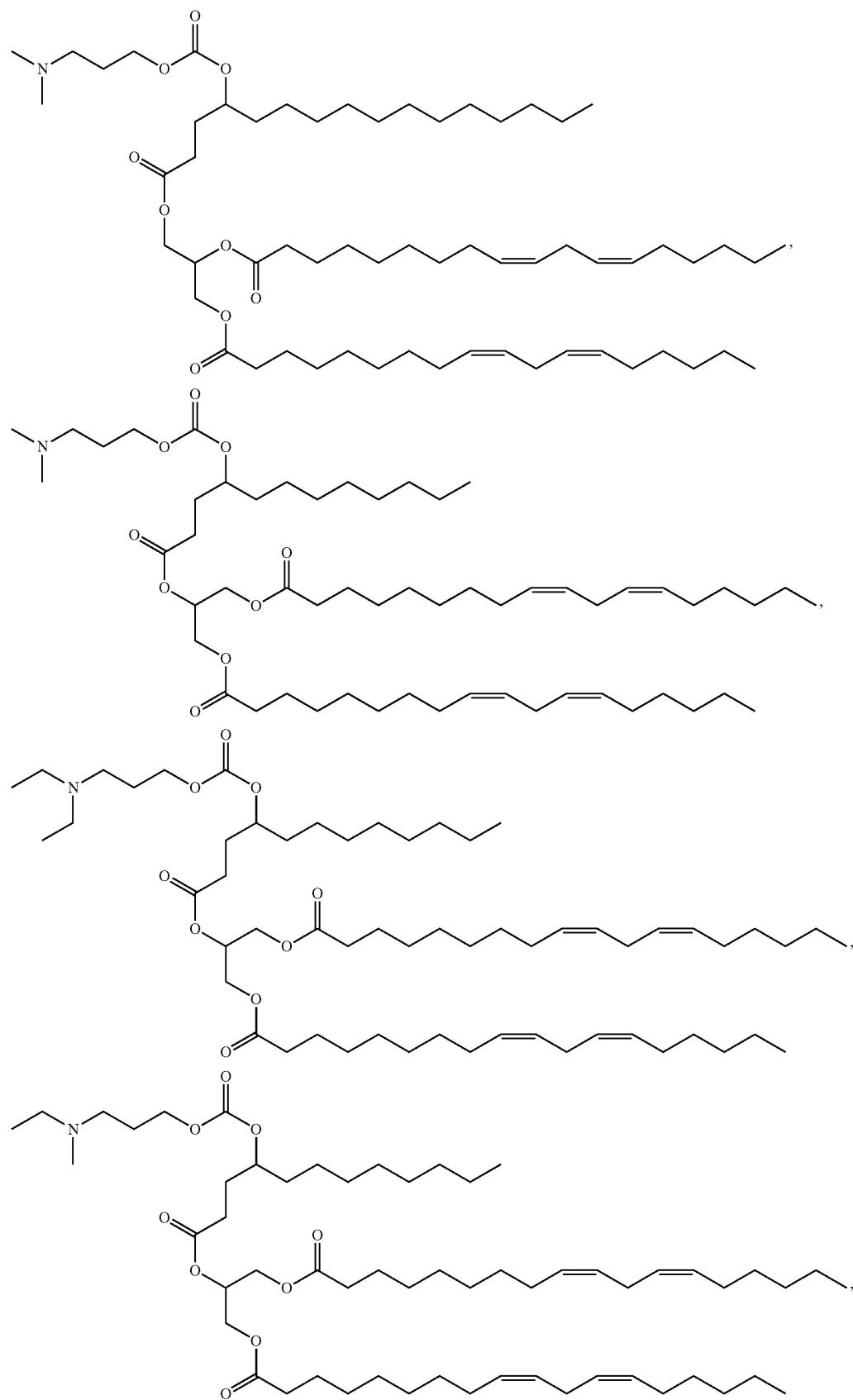

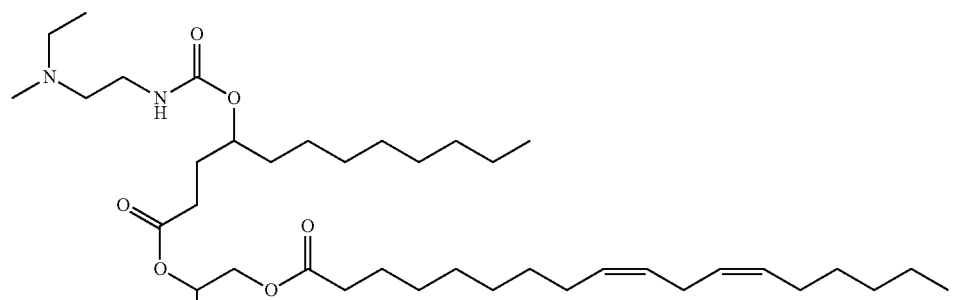
,
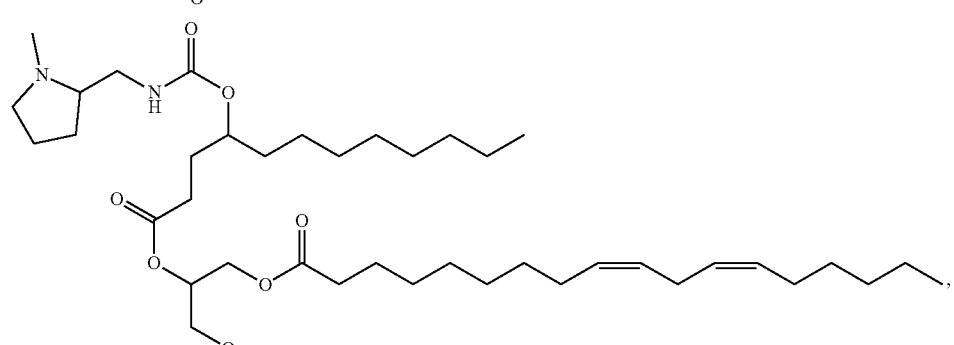
,
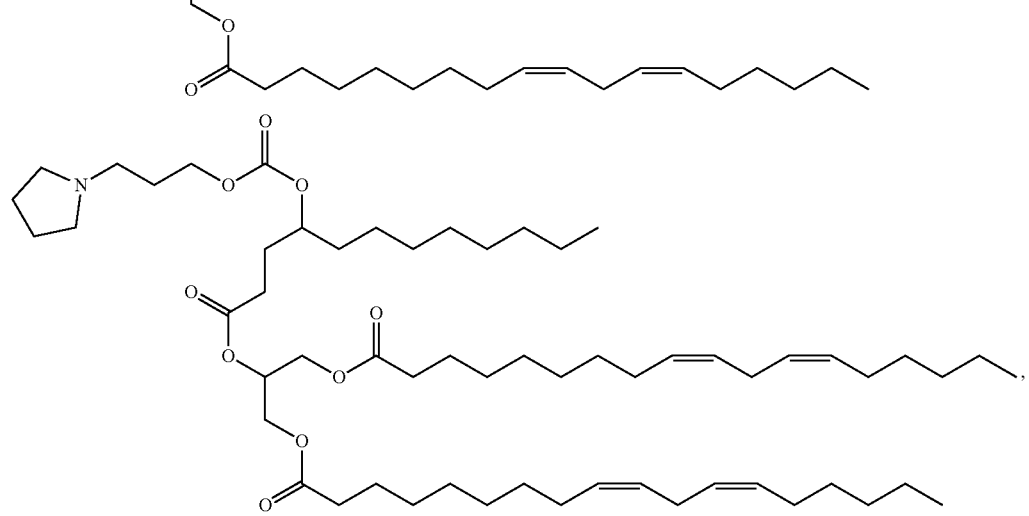
,
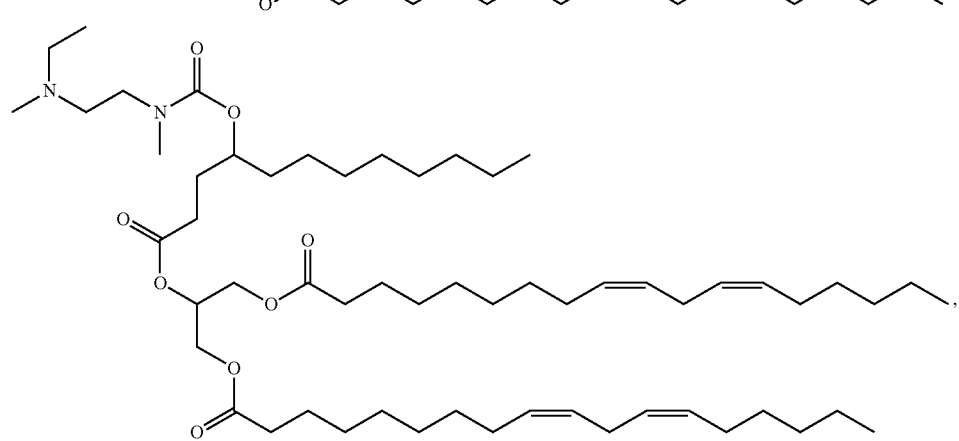
,

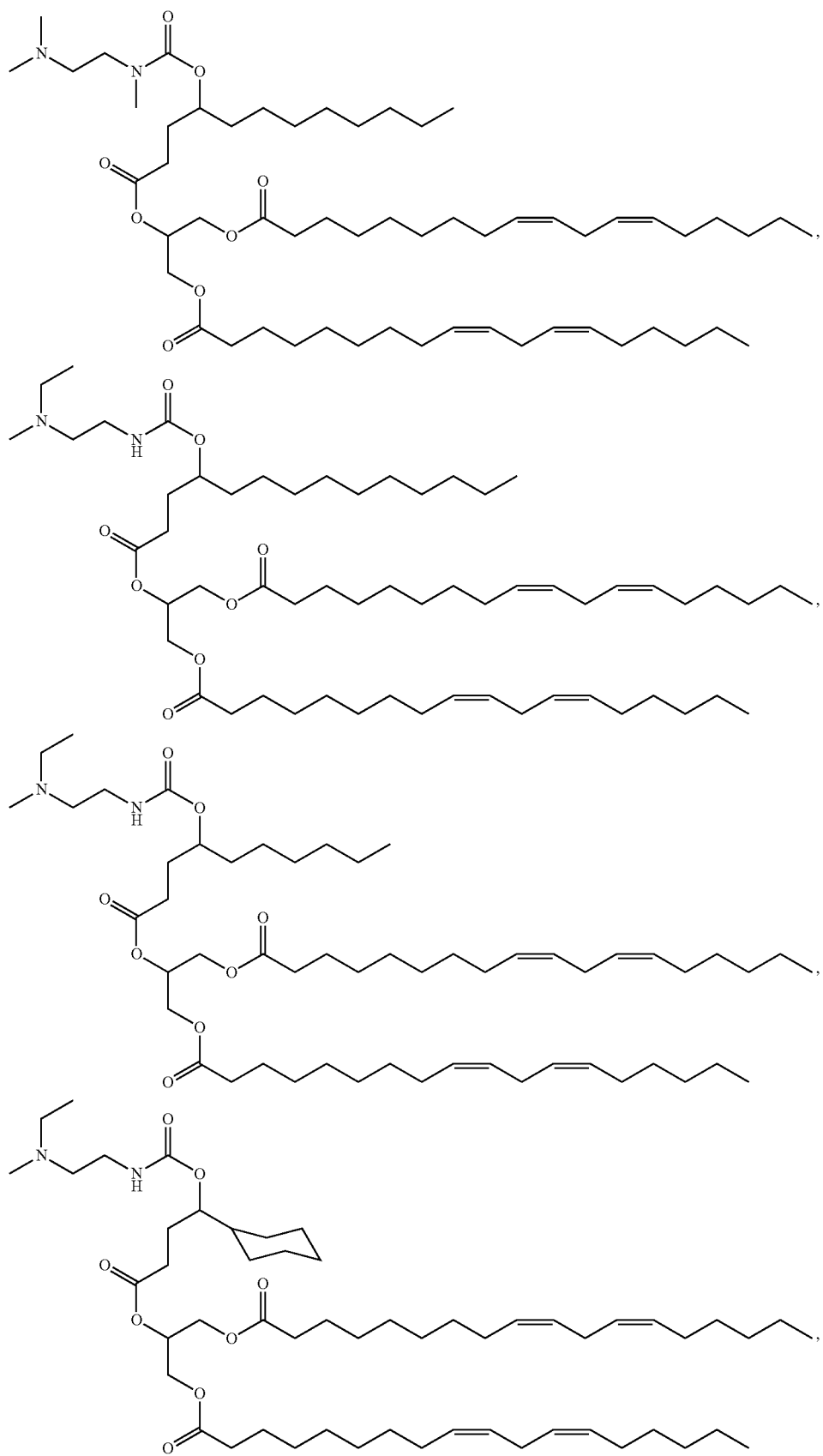

-continued
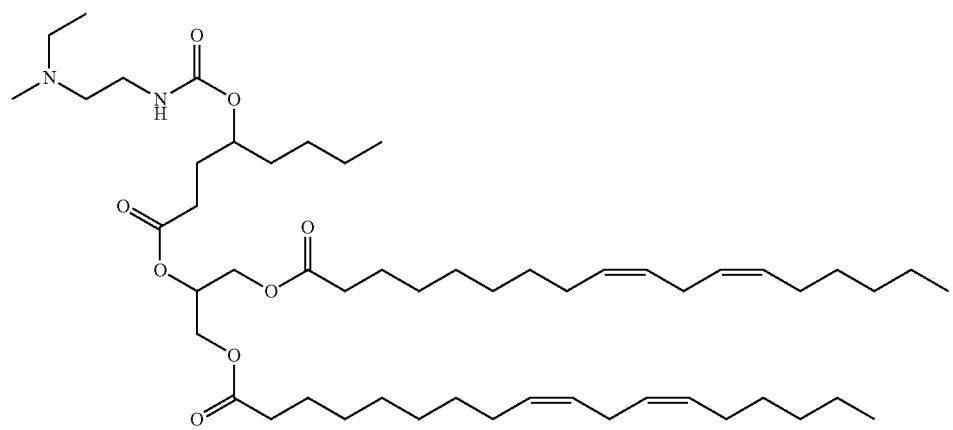
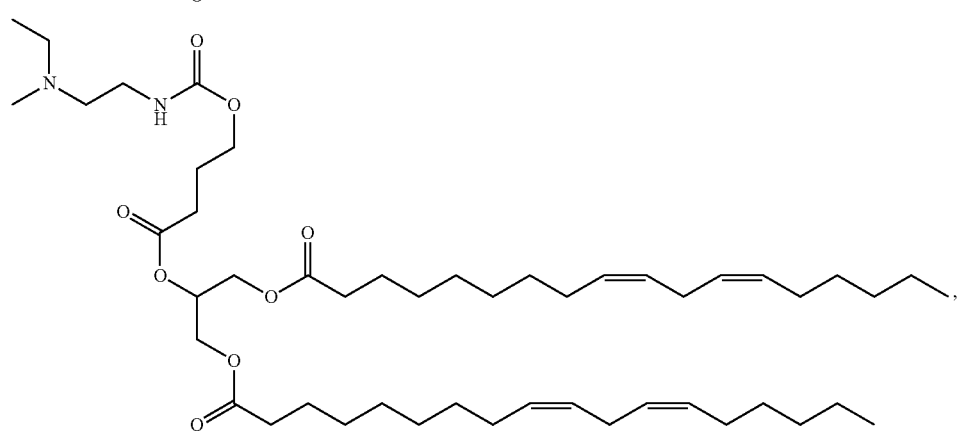
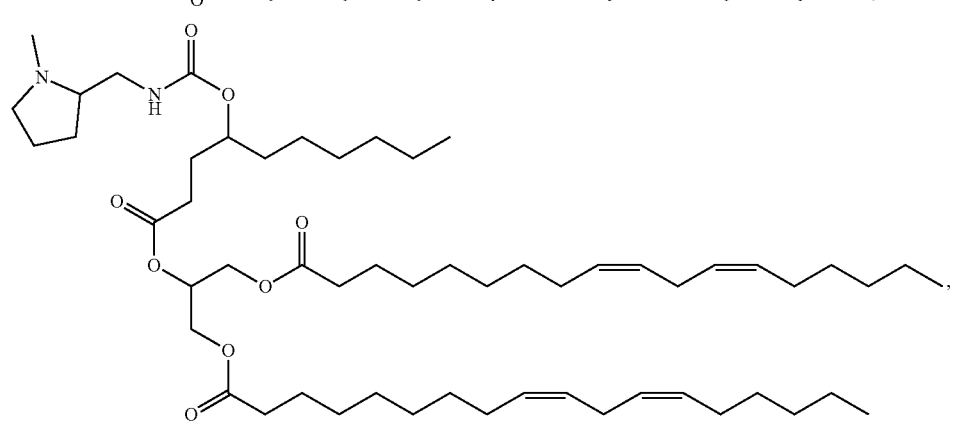
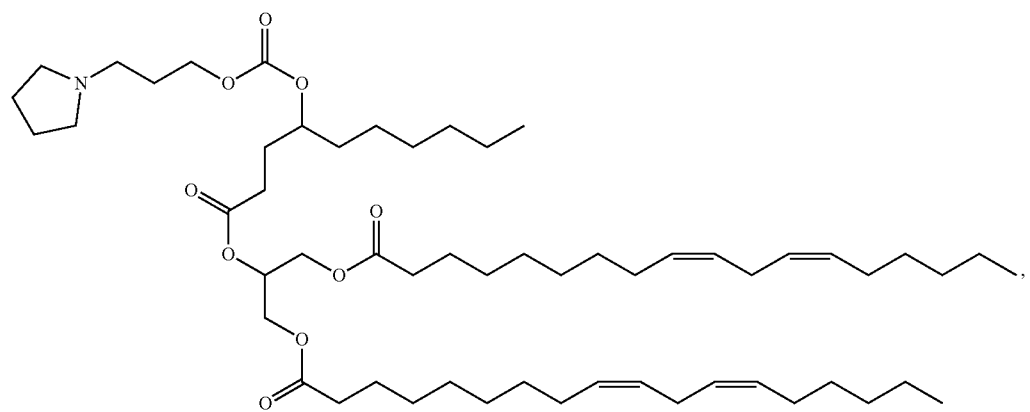

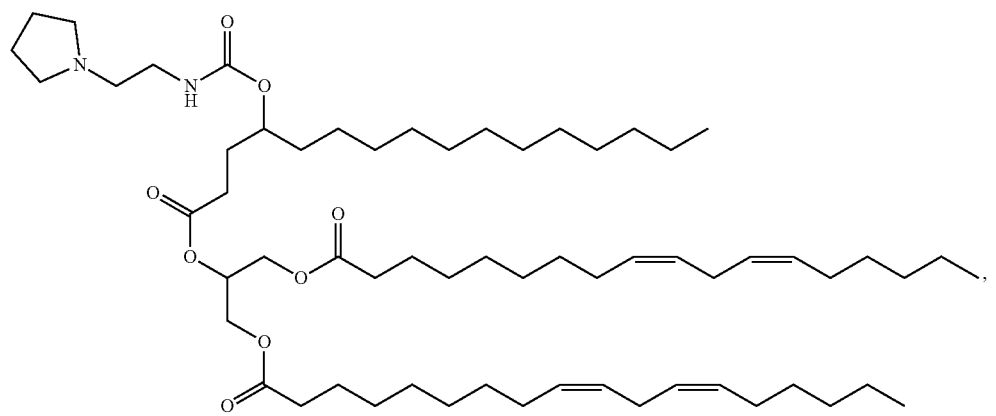,
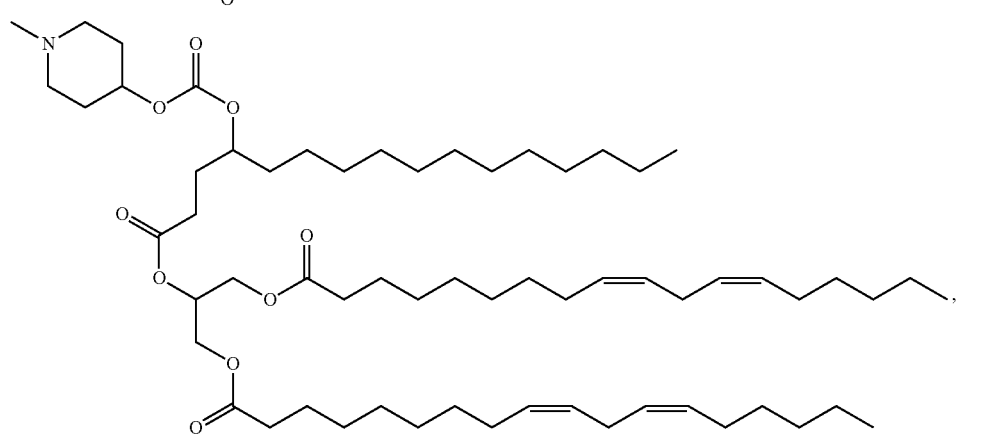,
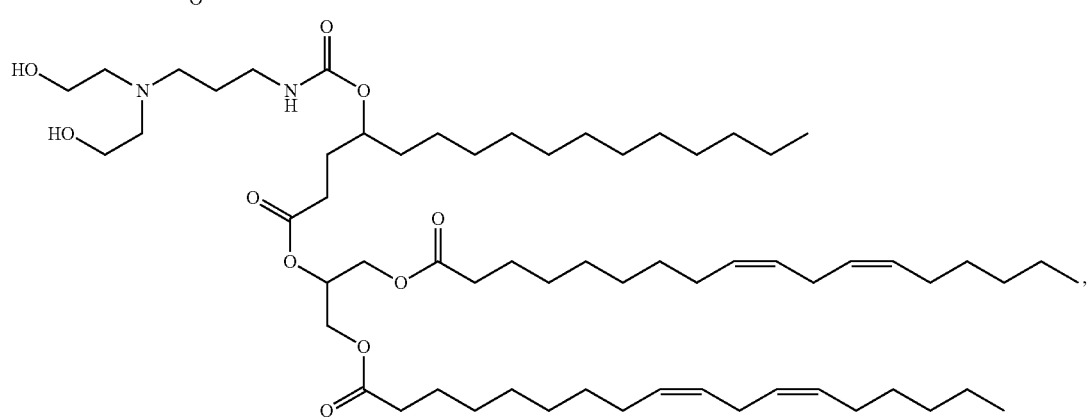,
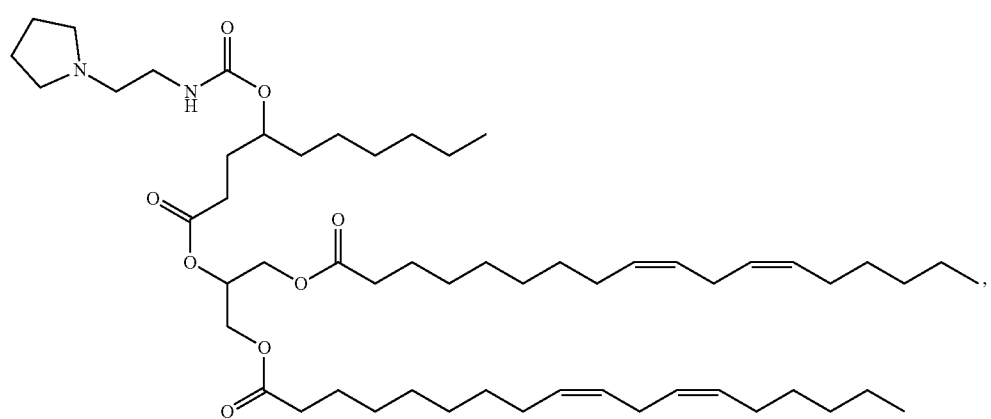,

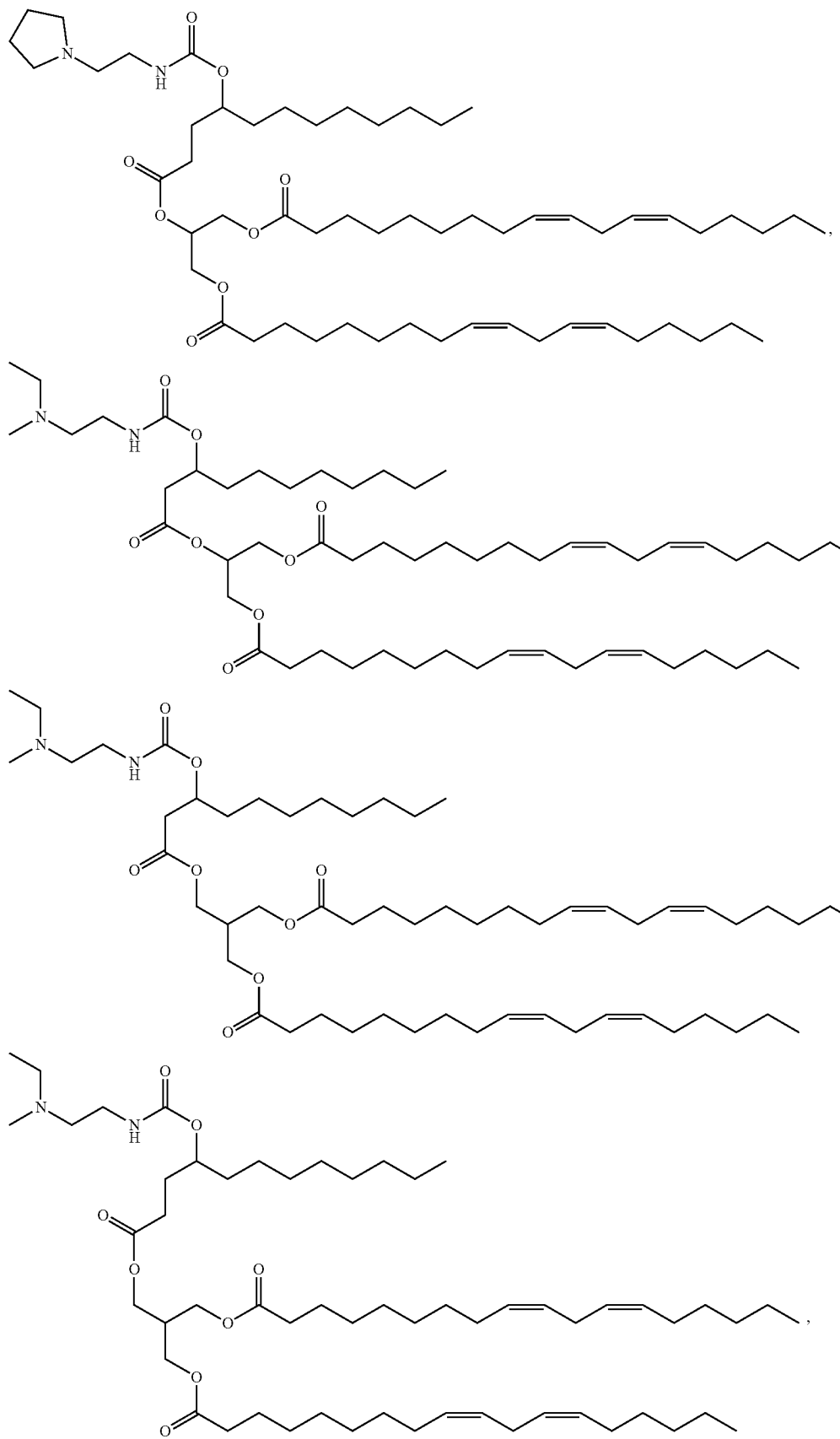

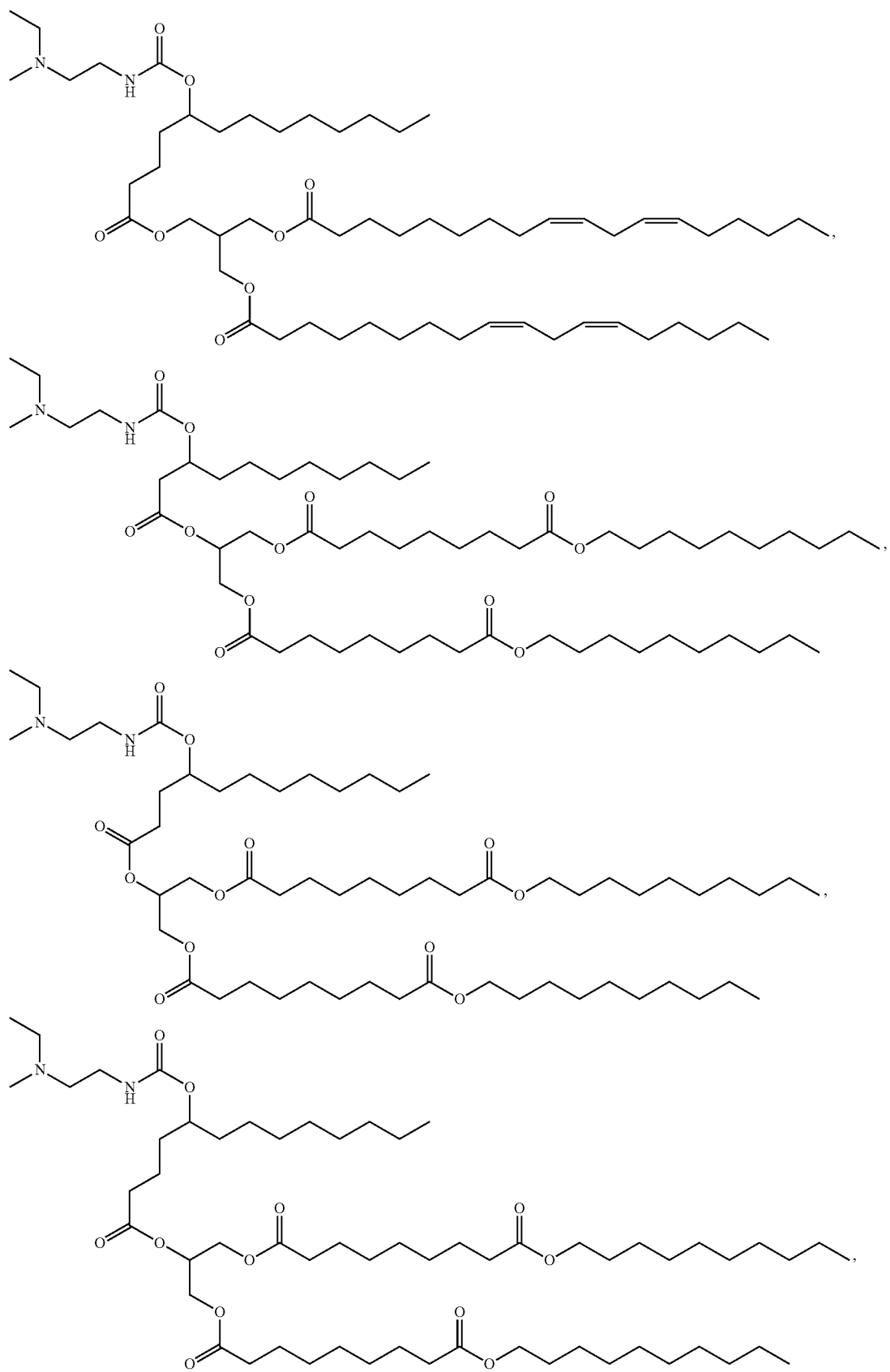

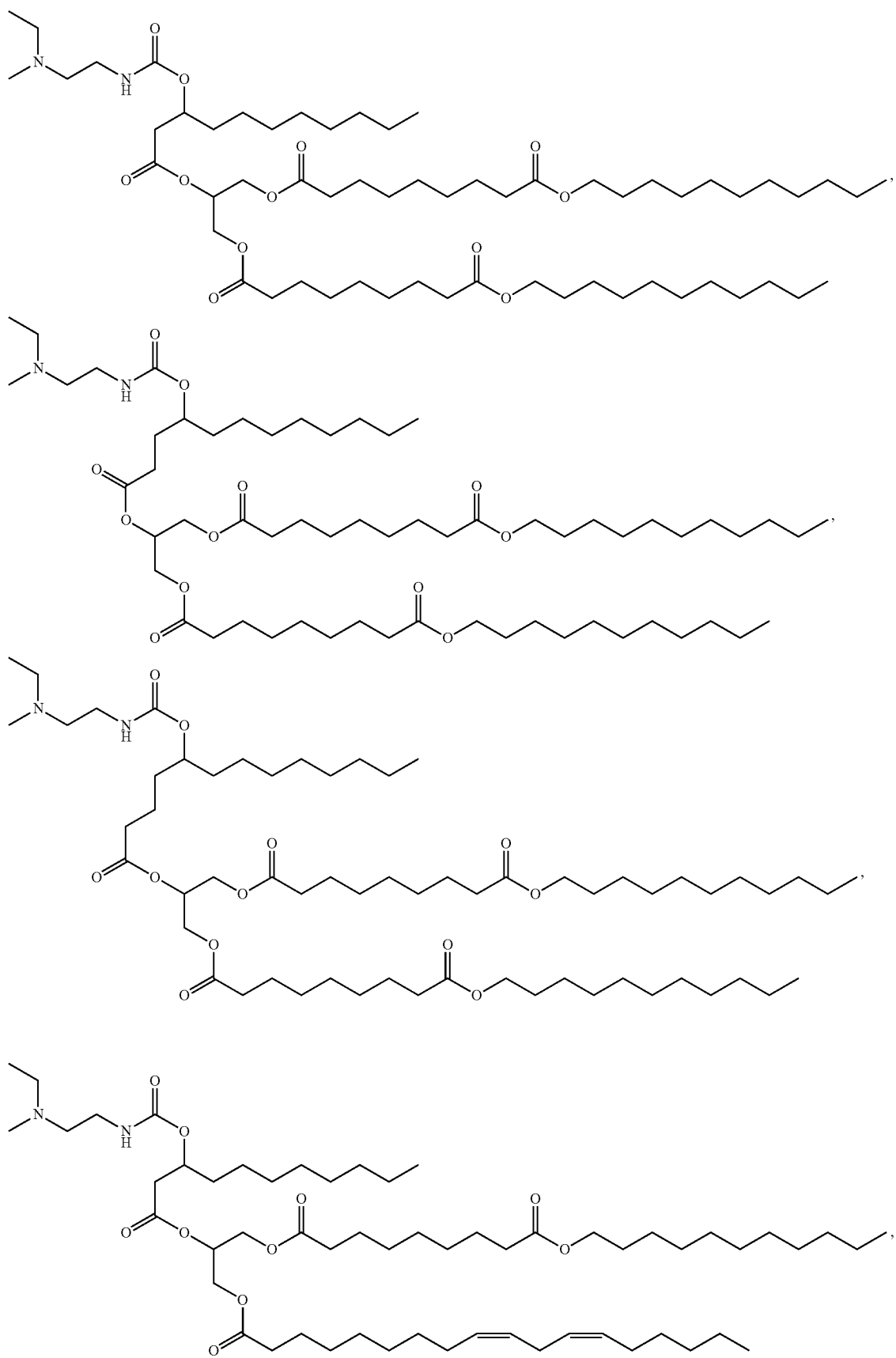

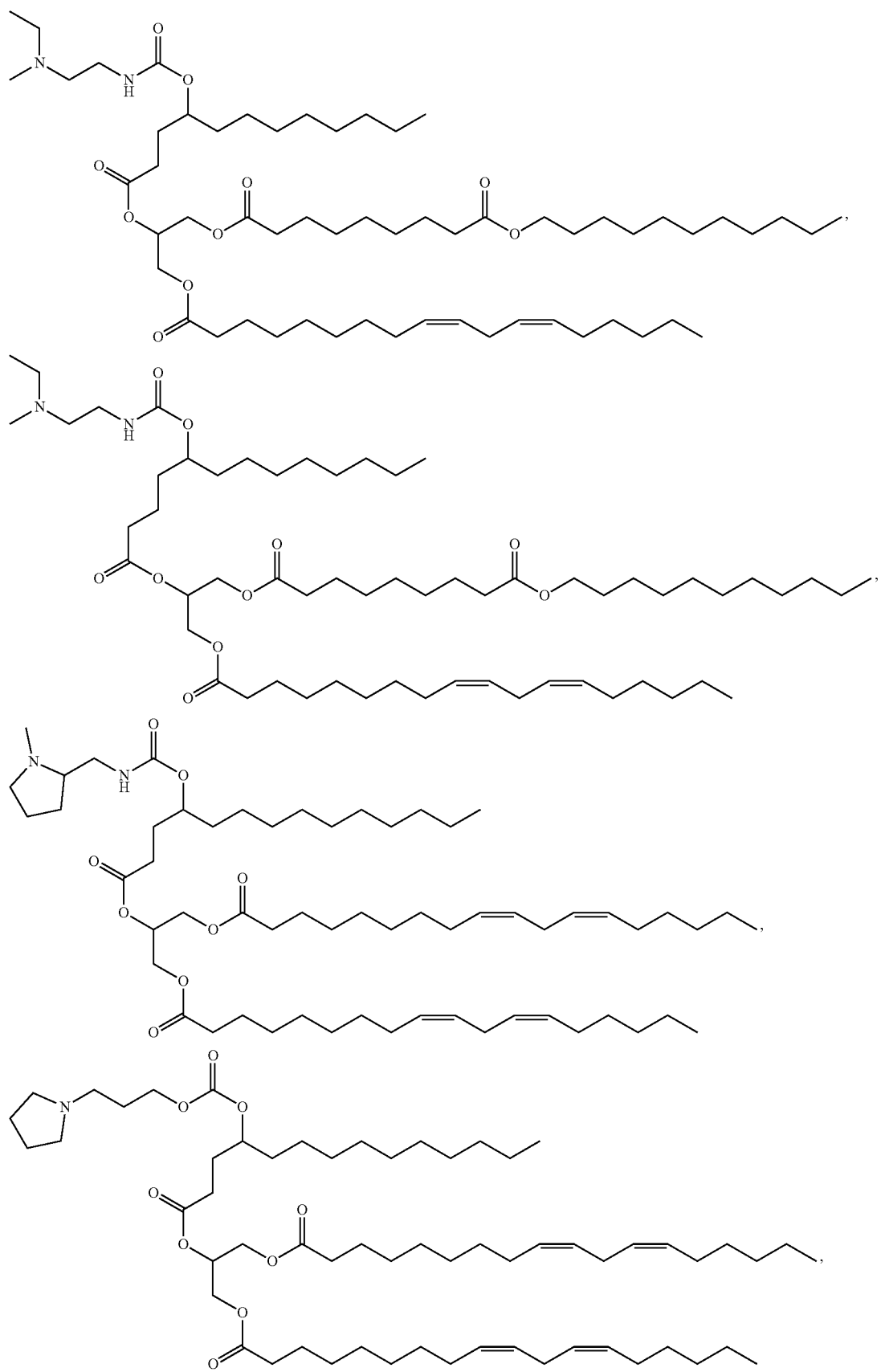

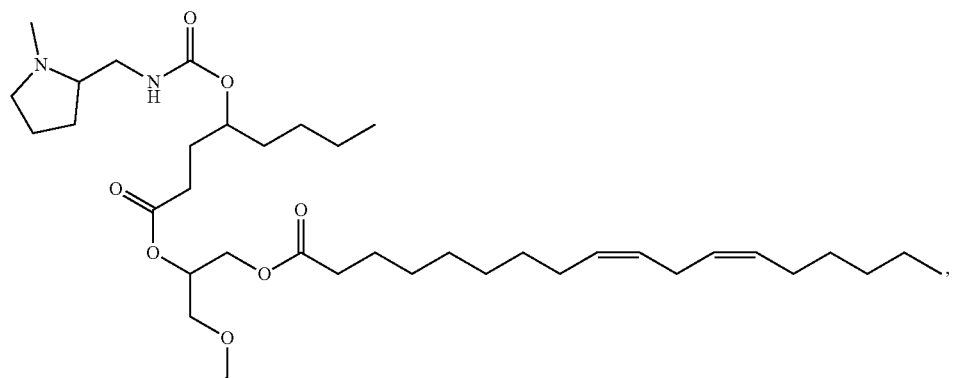
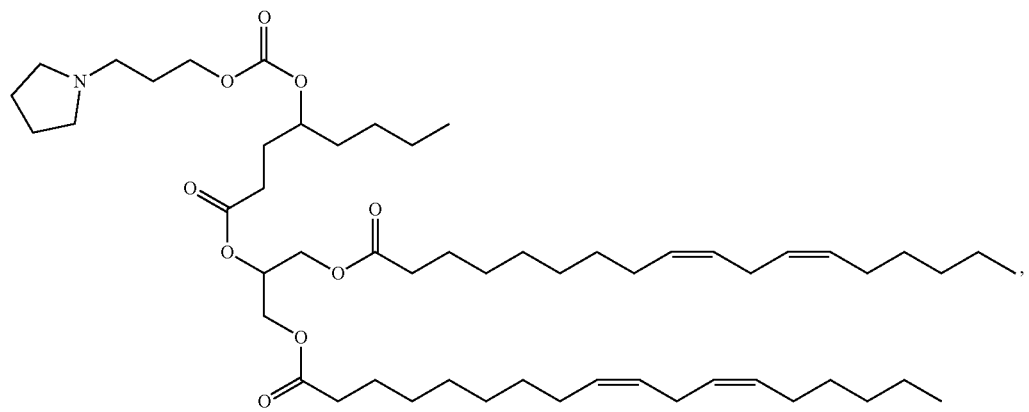
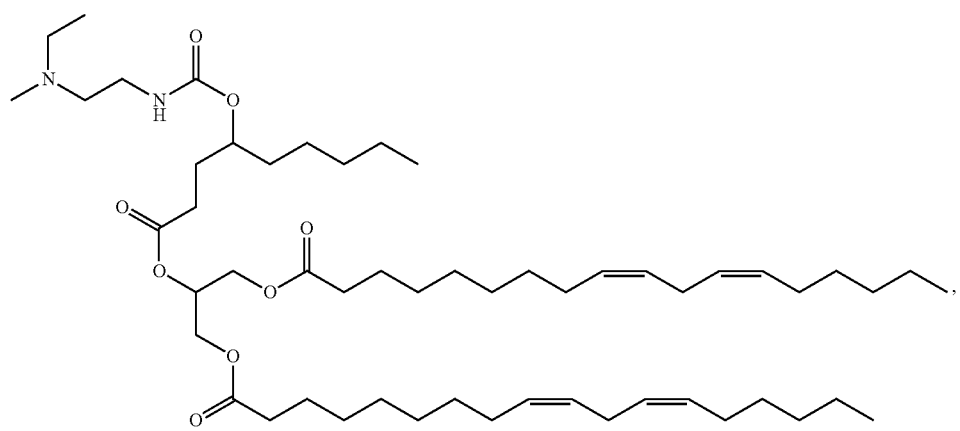
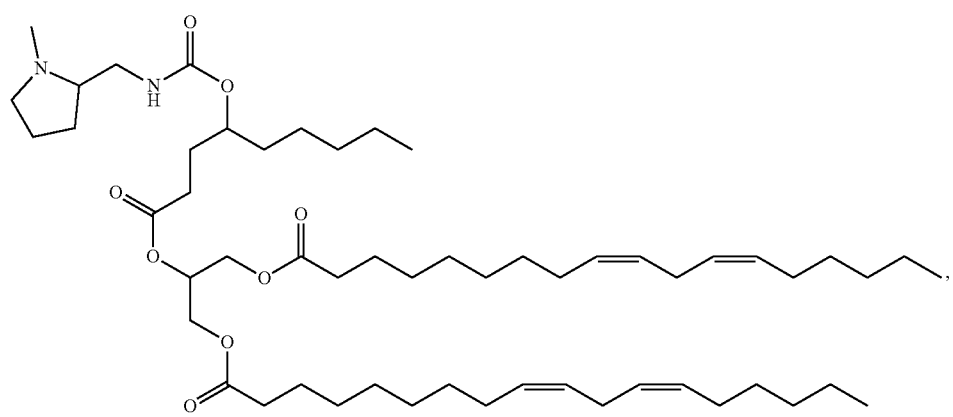

-continued
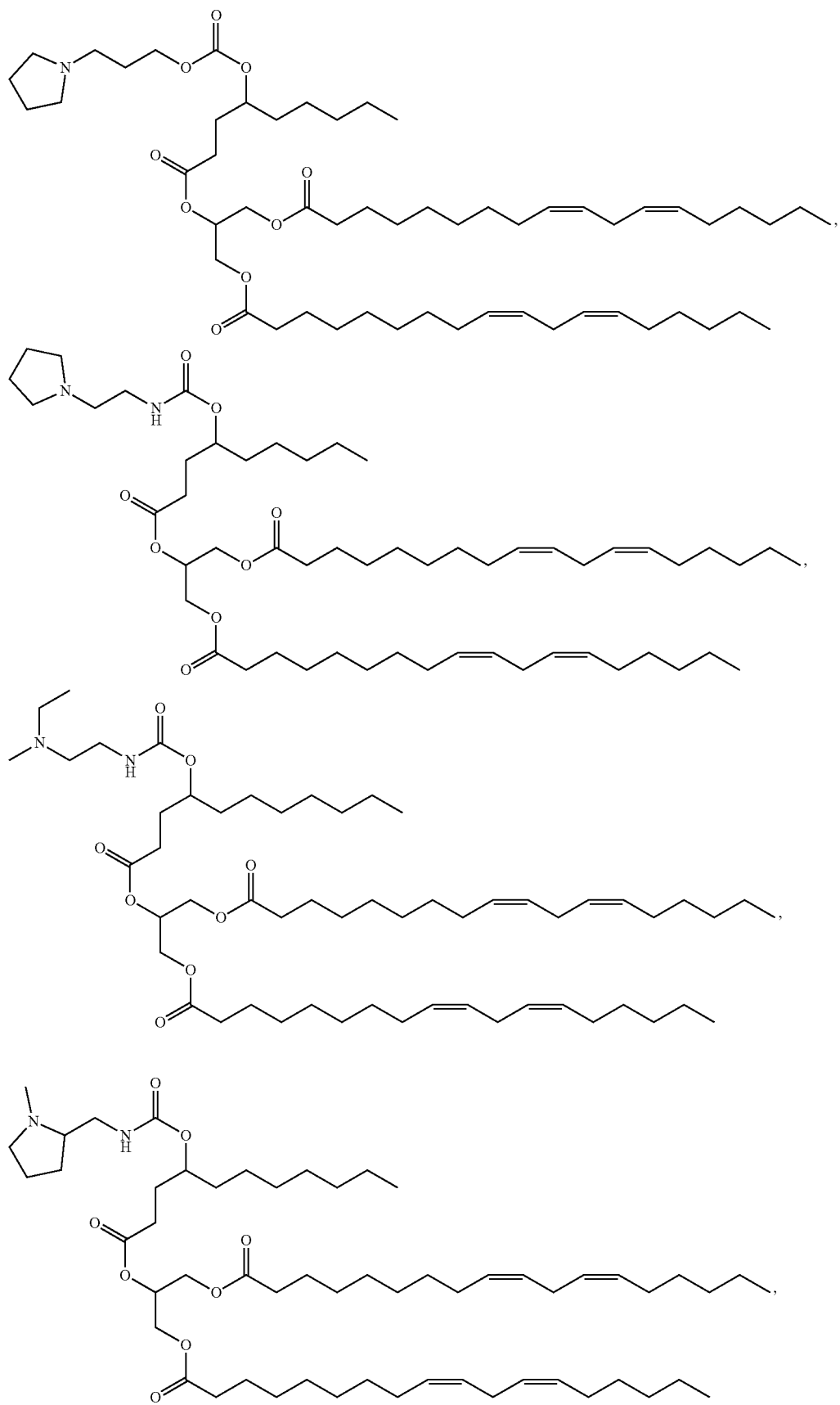

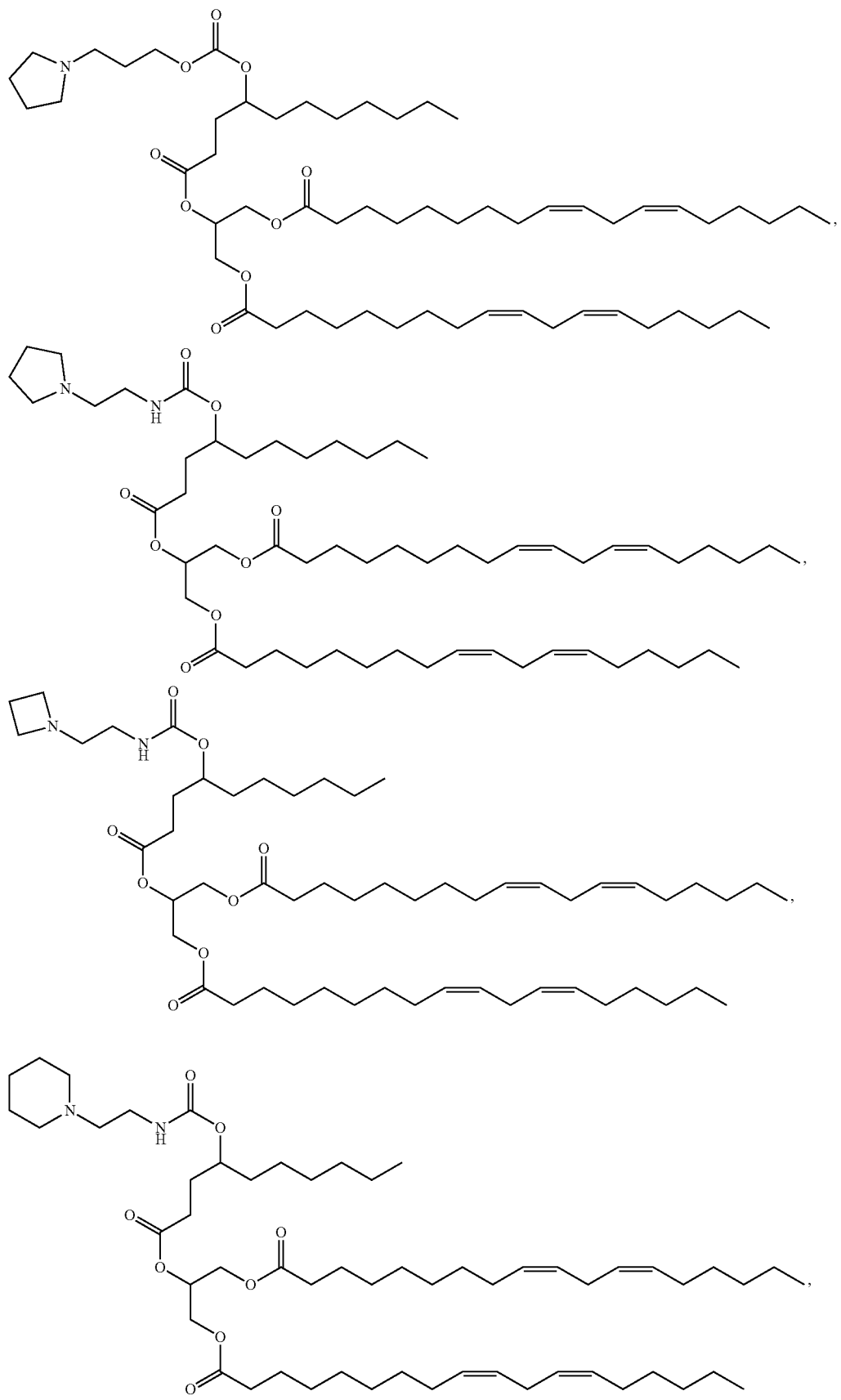

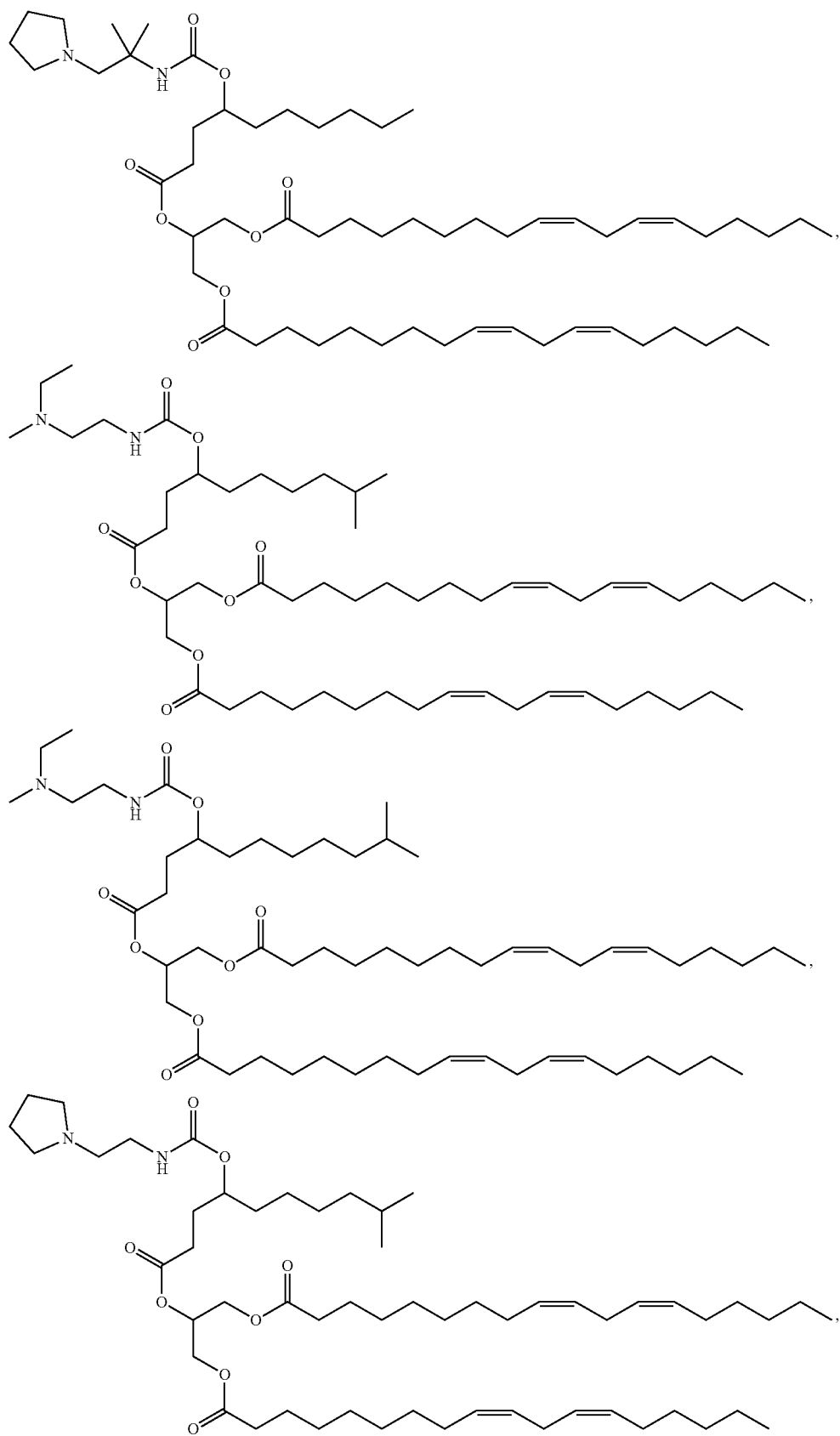

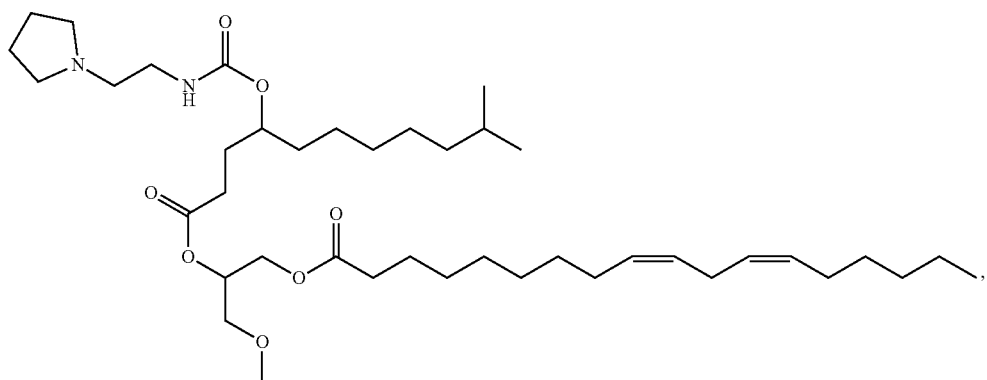,
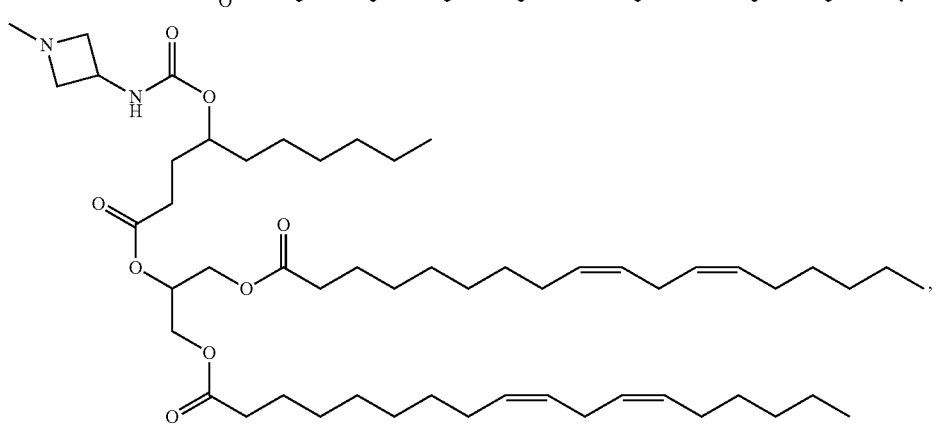,
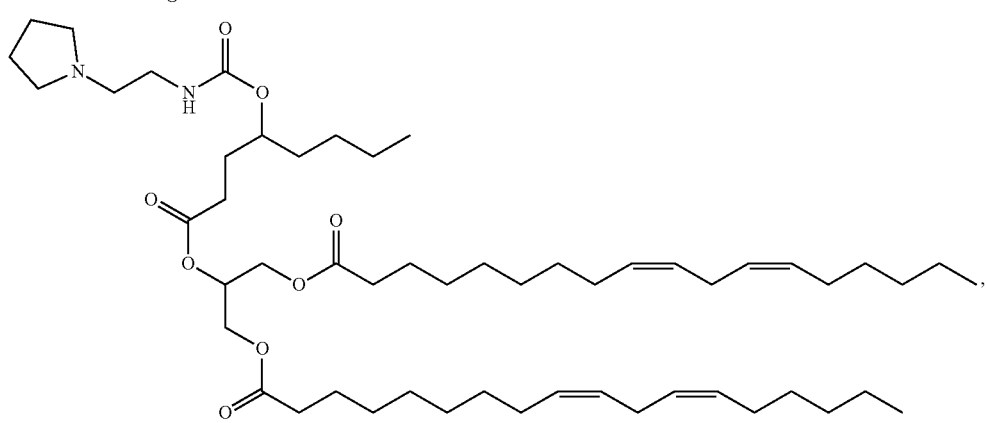,
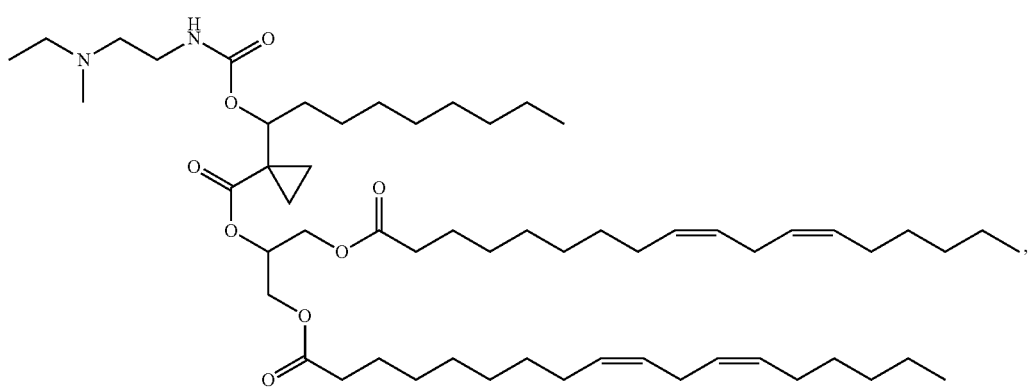,

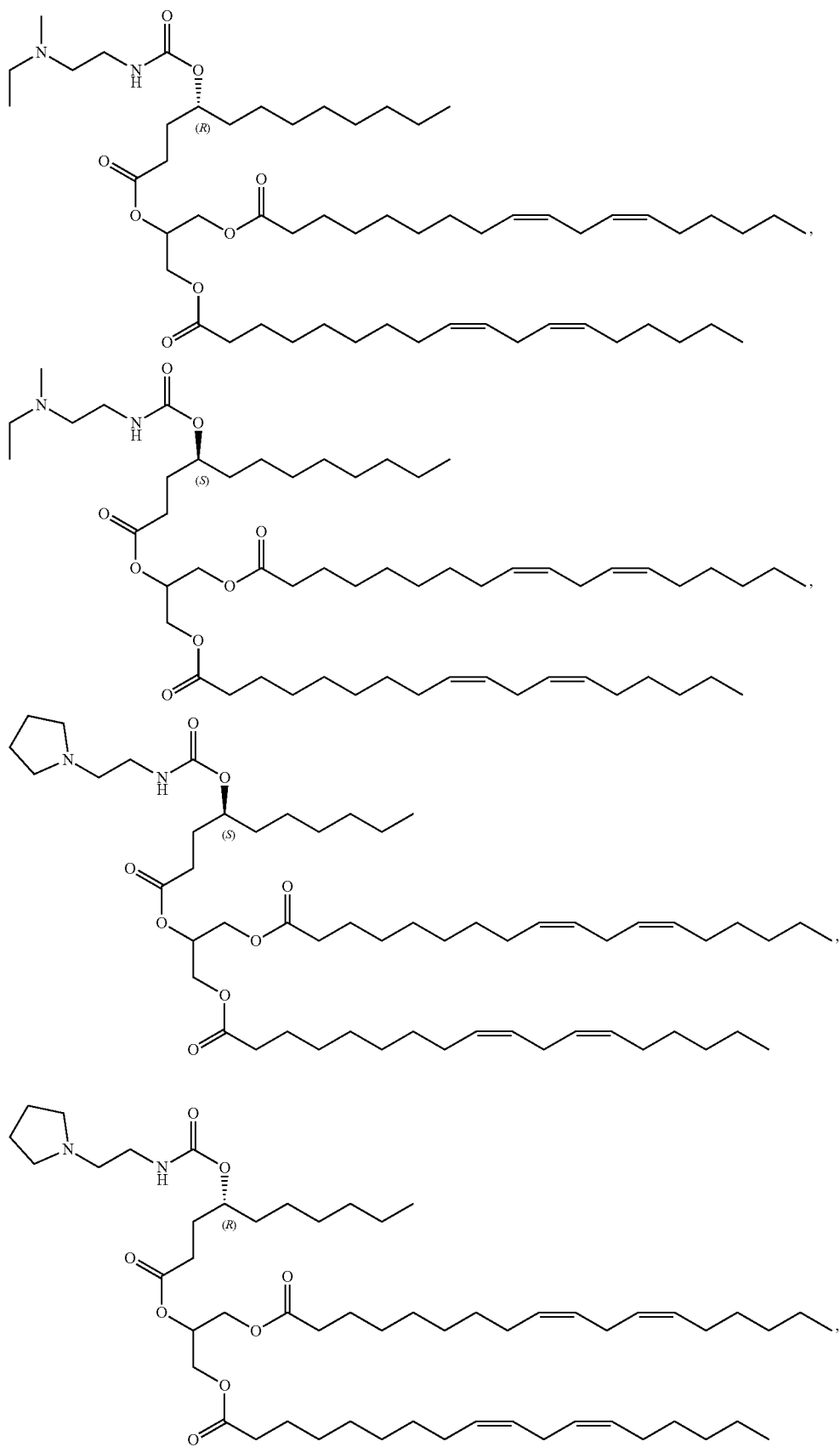

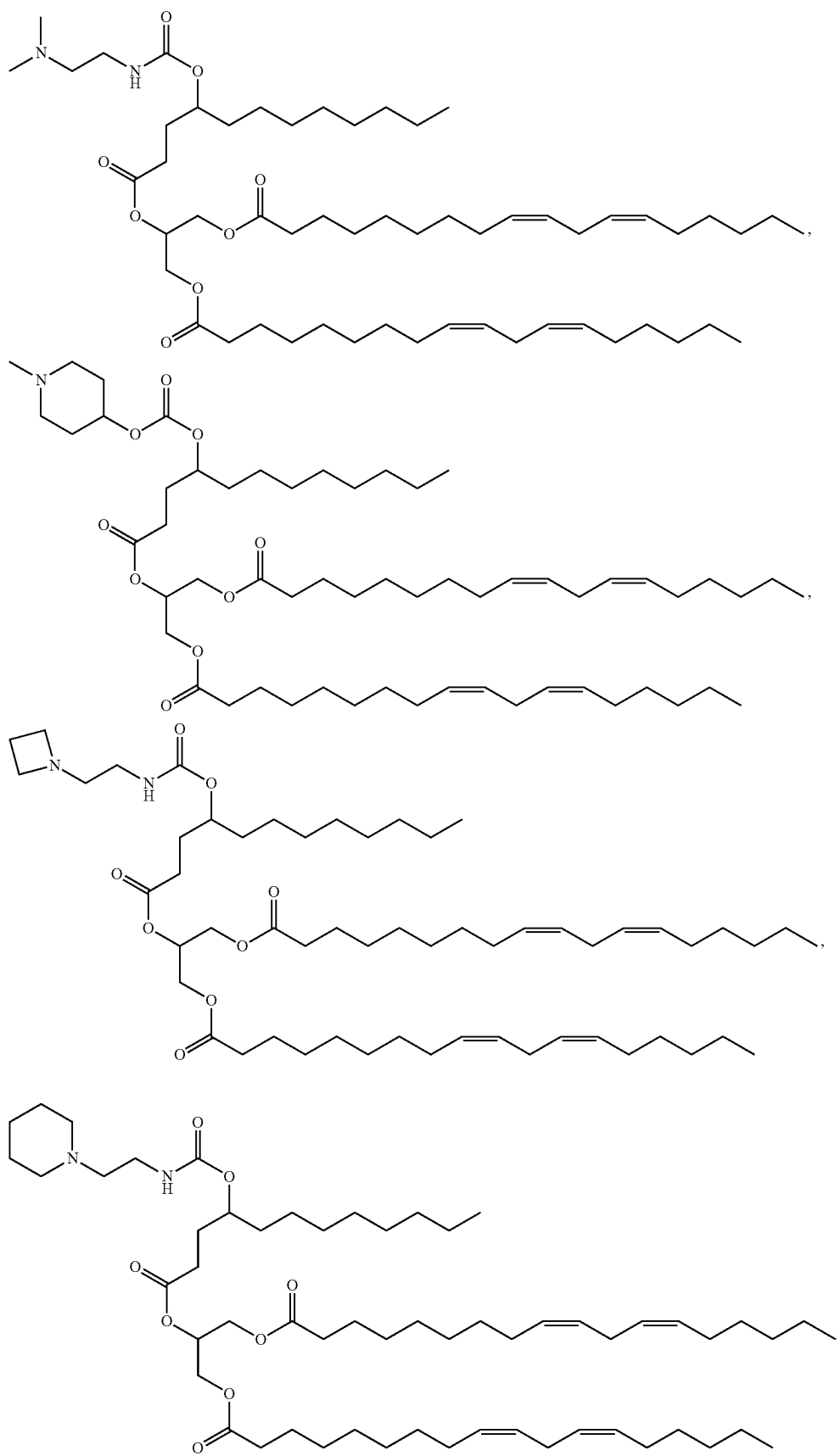

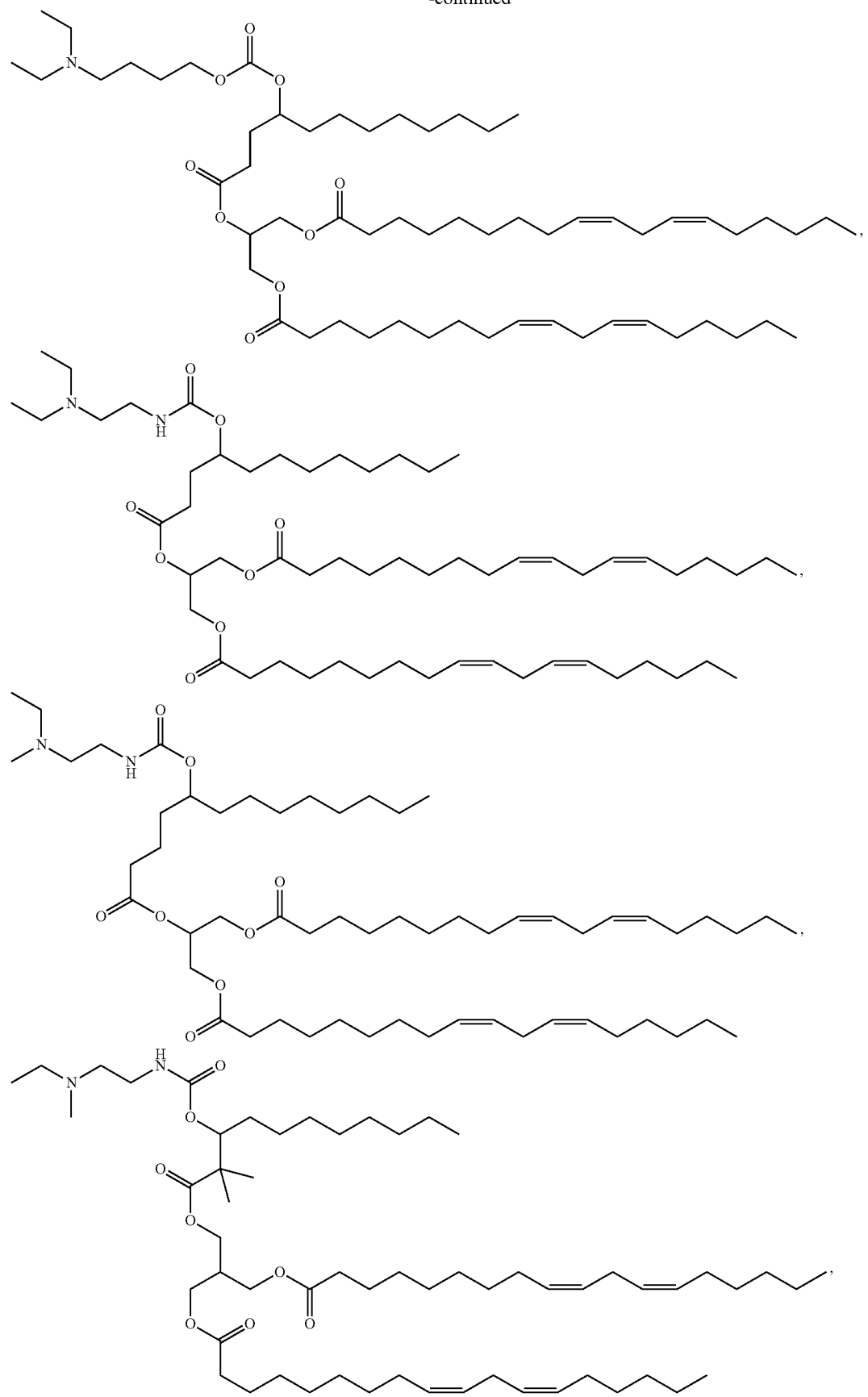

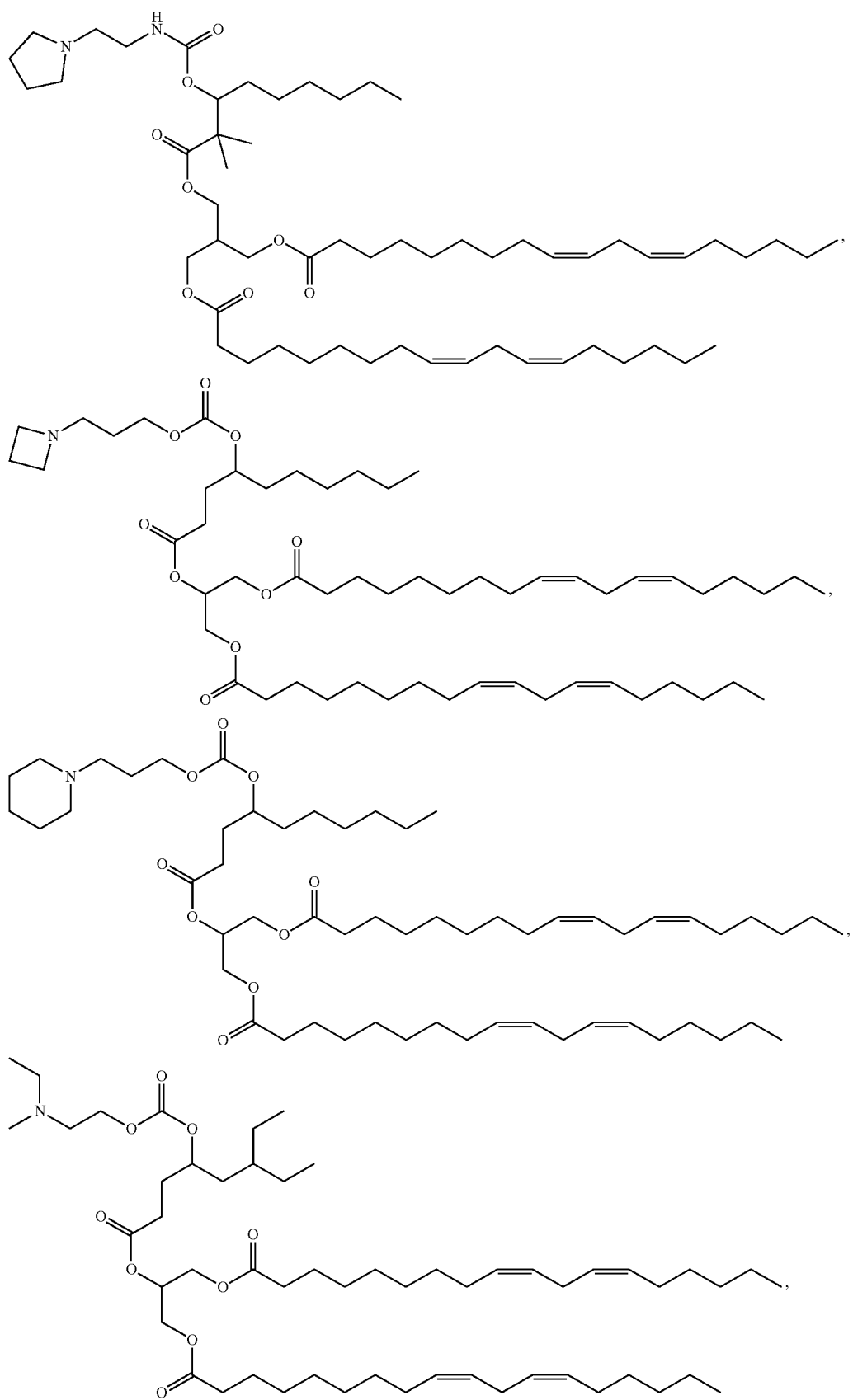

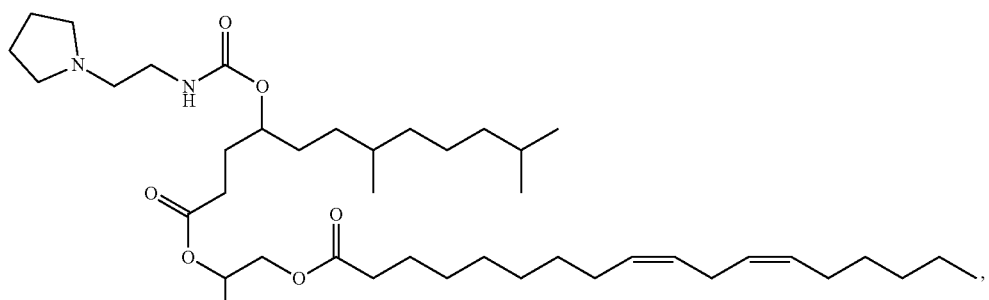
,
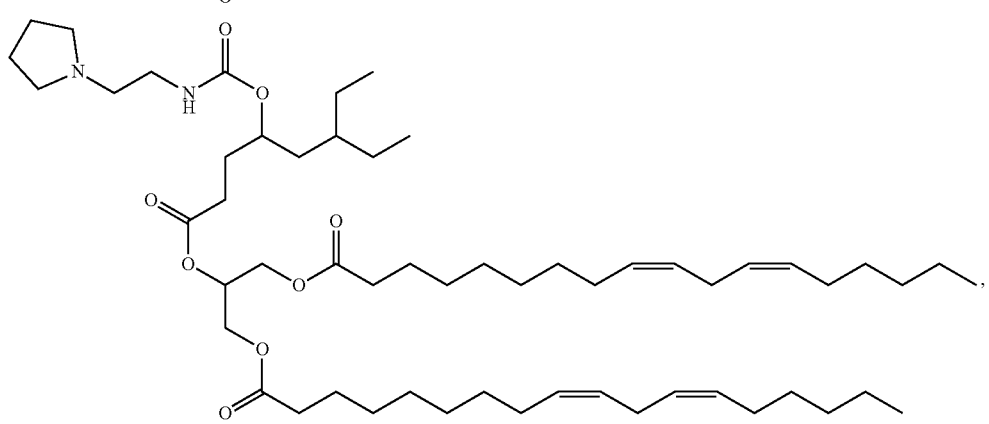
,
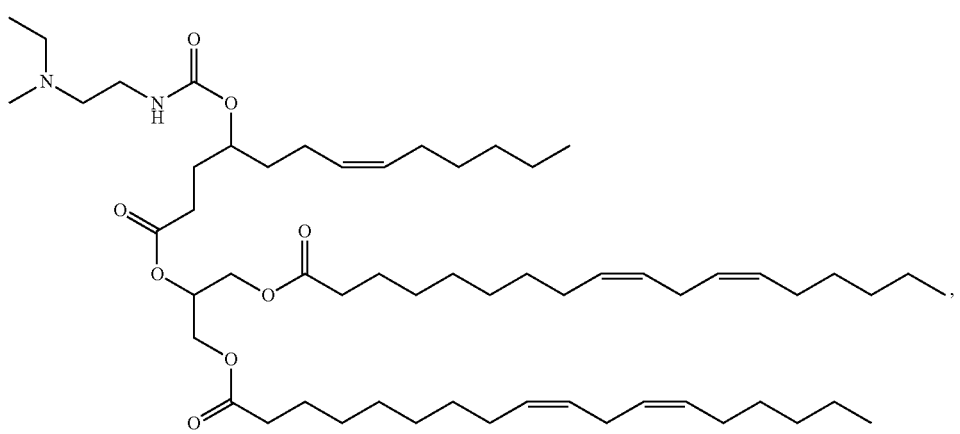
,
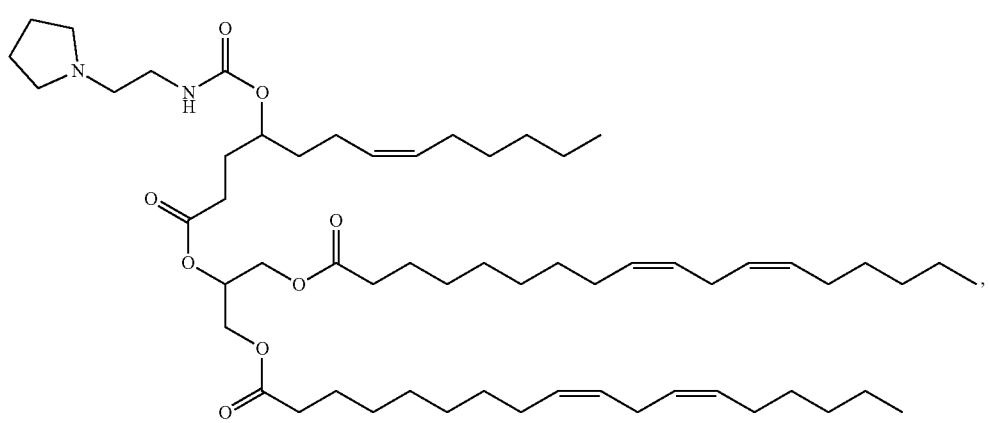
,

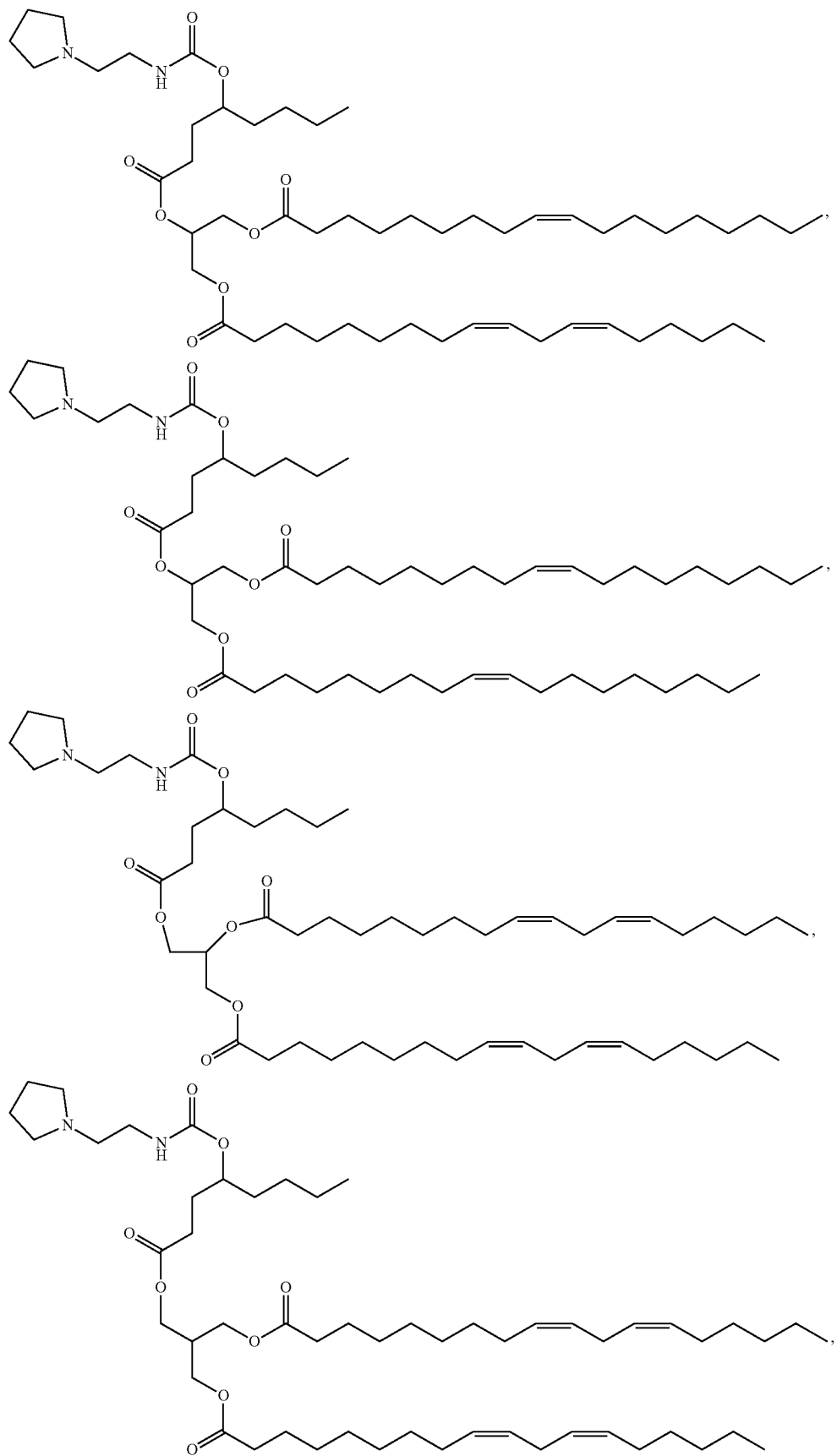

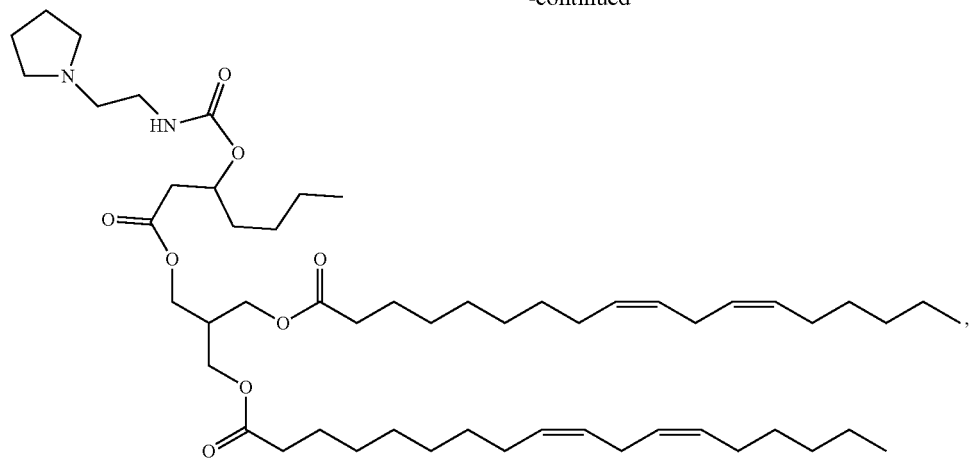
or a salt thereof, such as a pharmaceutically acceptable salt thereof.
Representative compounds of Formula (IA) or (I) include:
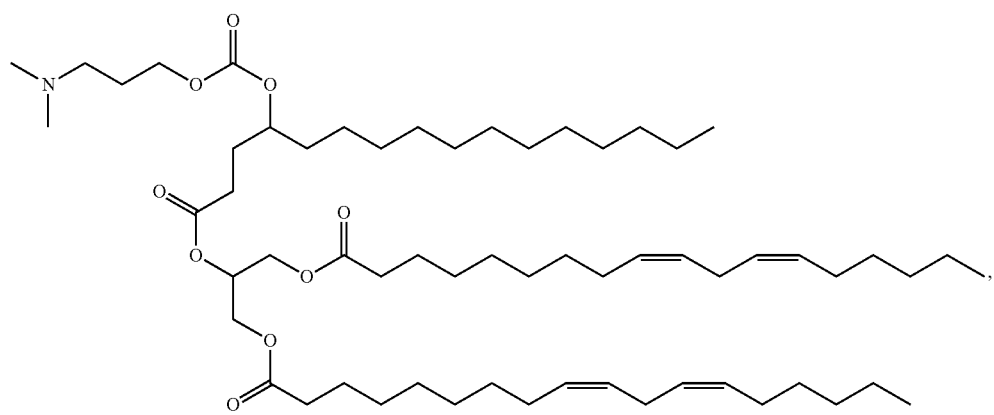
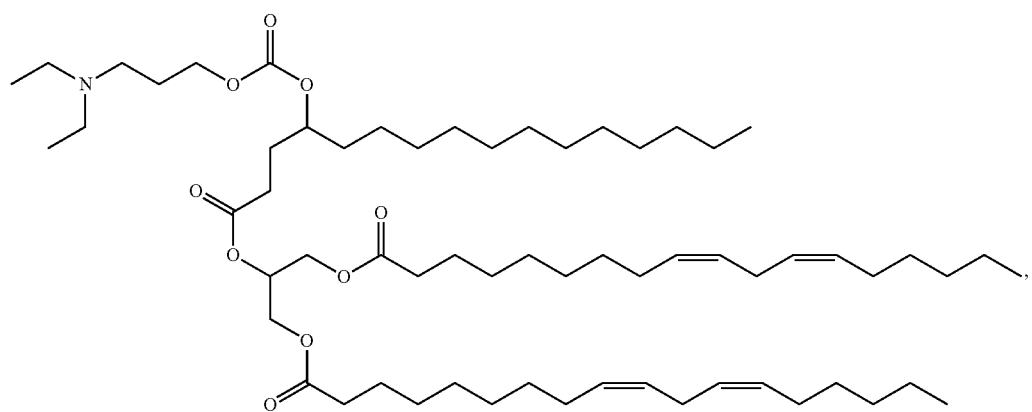

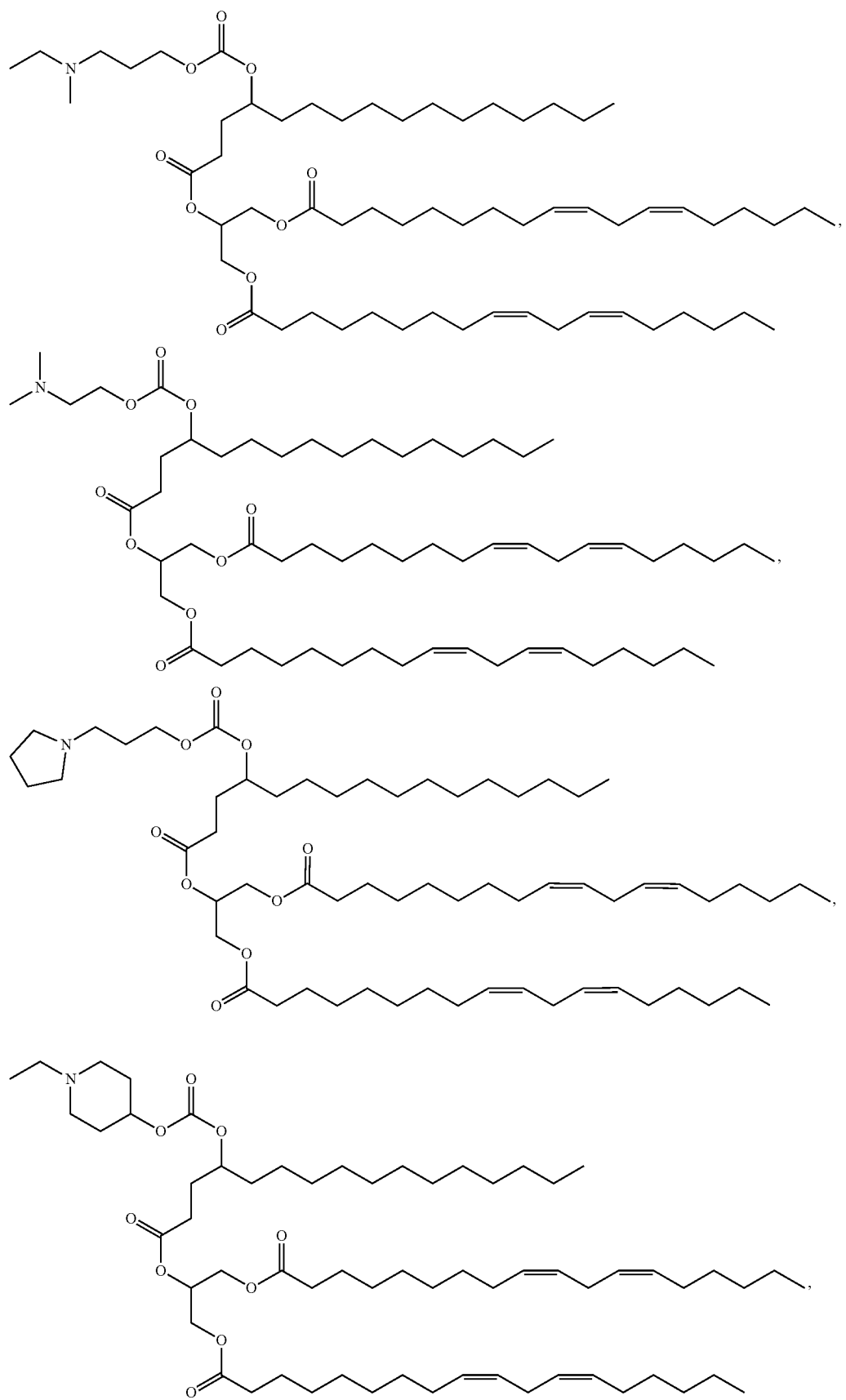

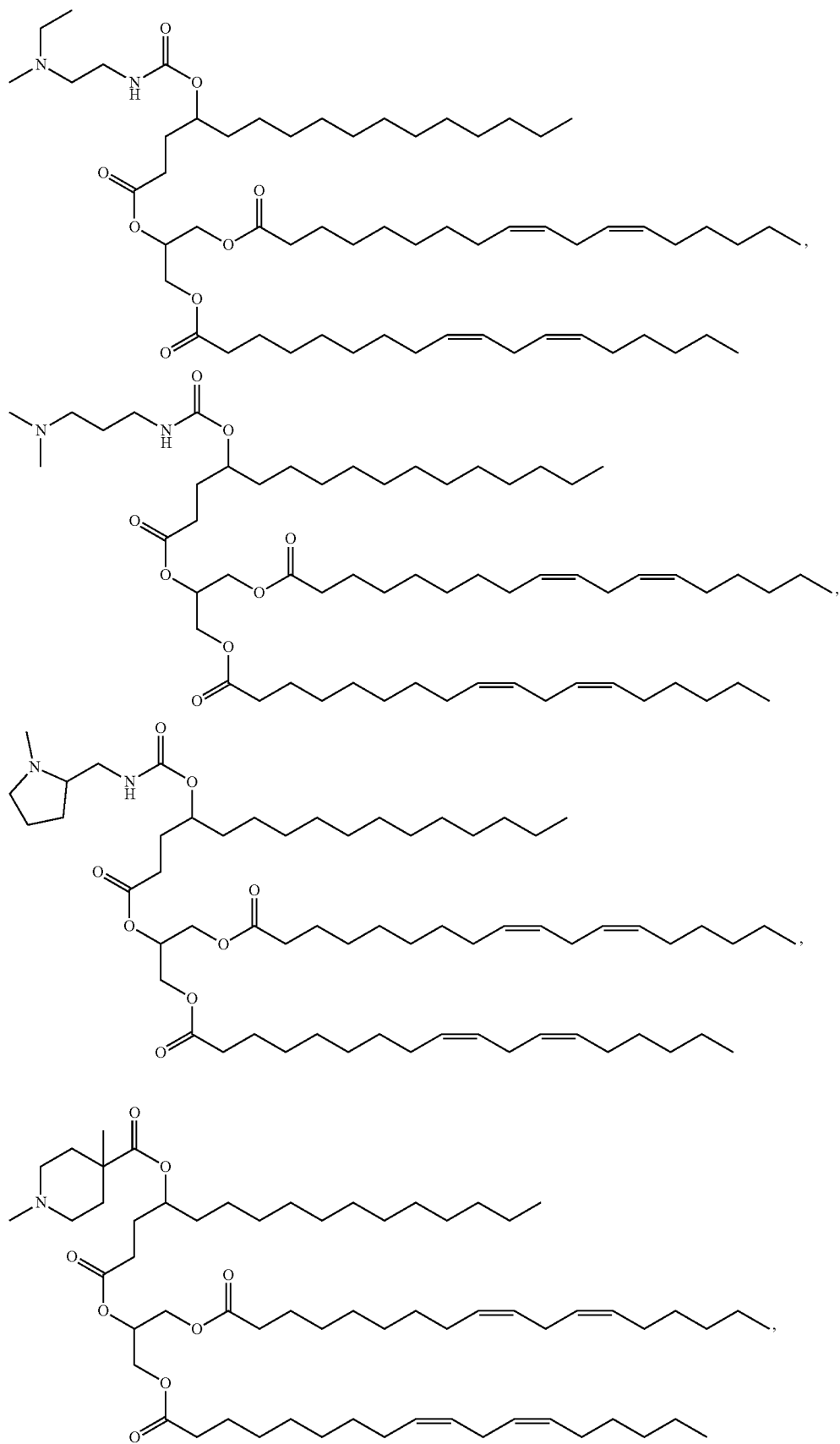

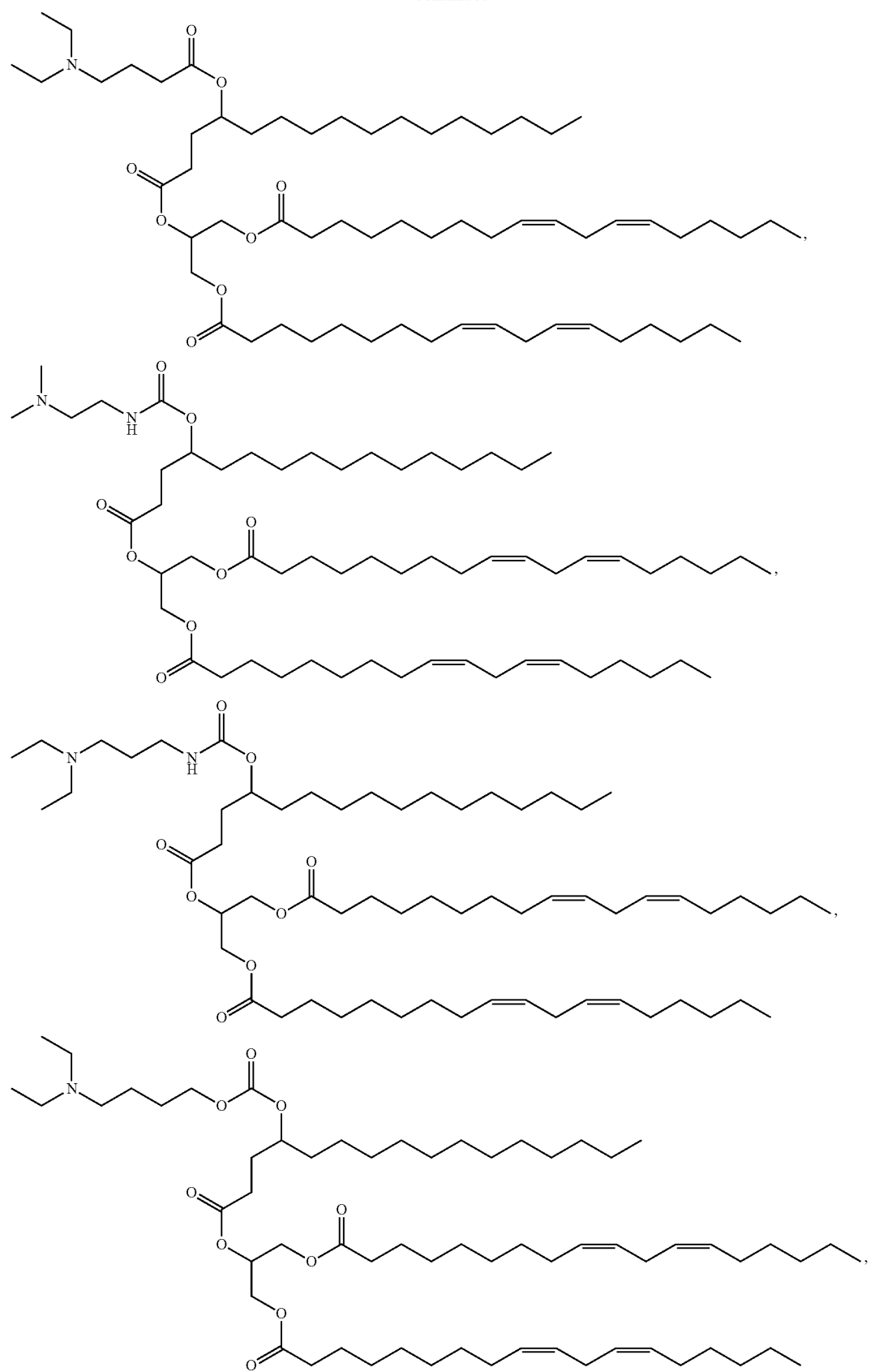

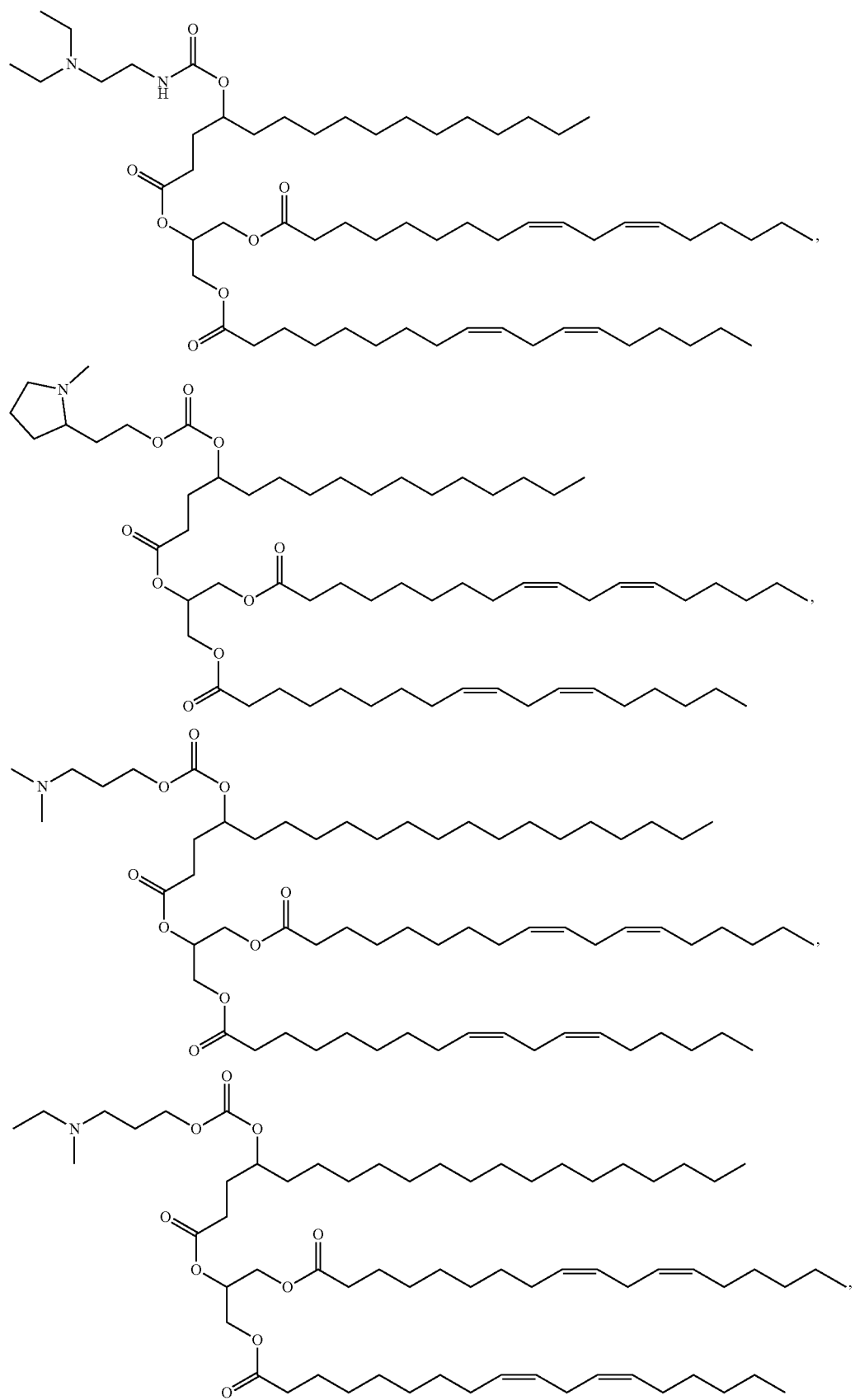

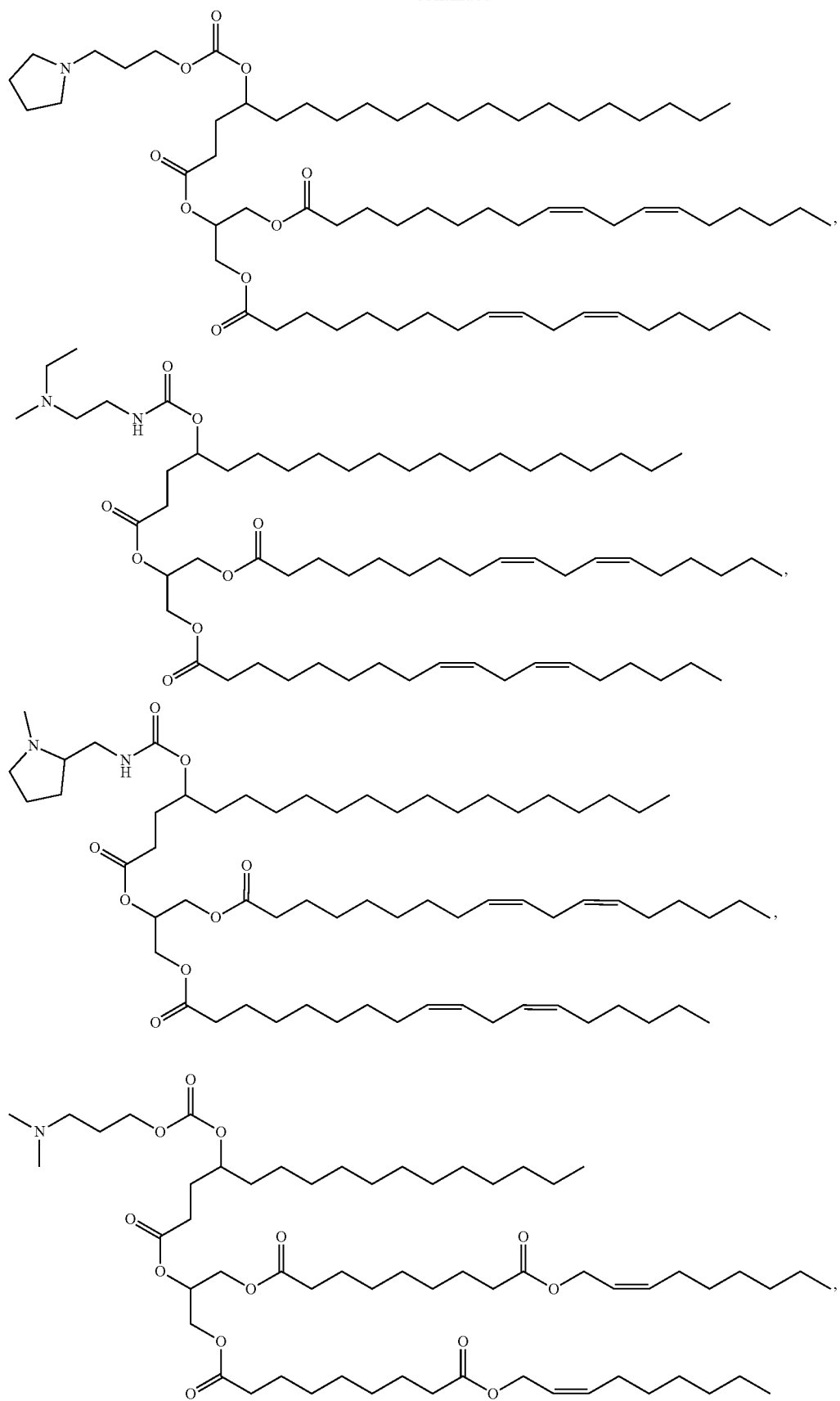

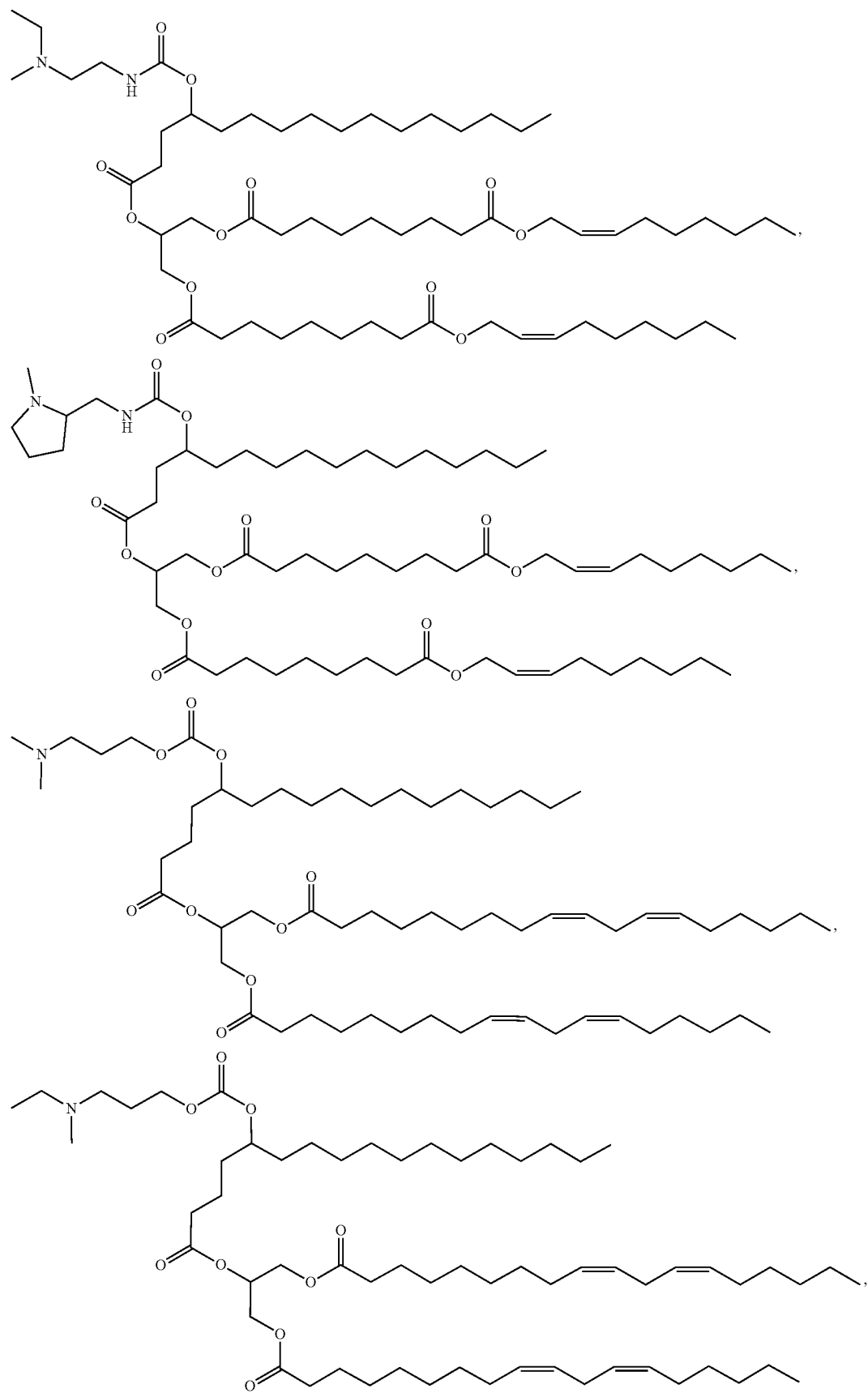

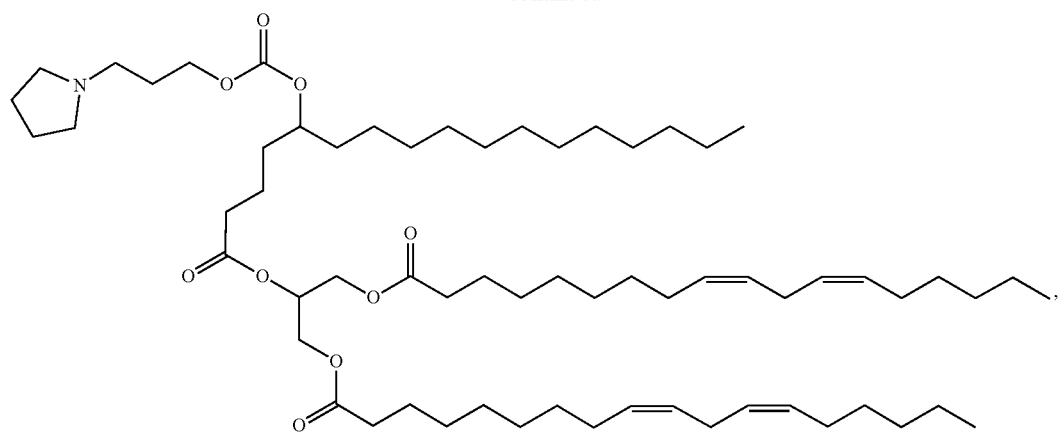
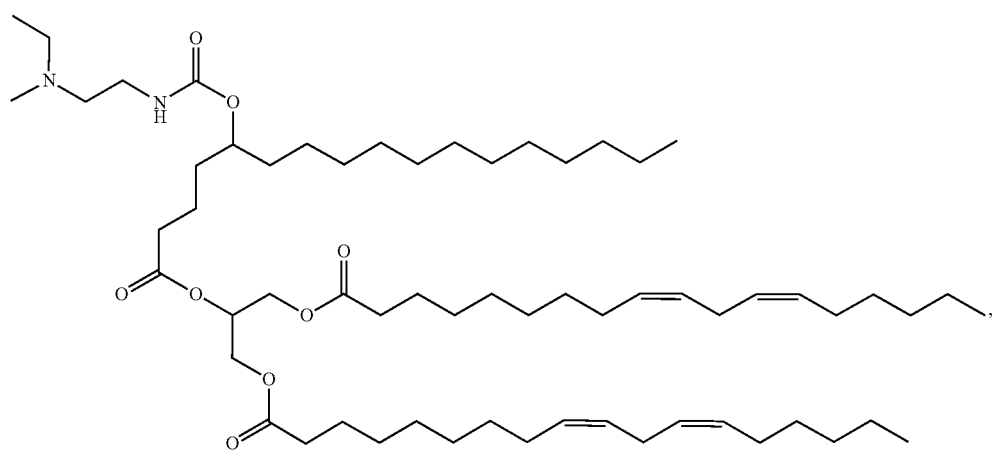
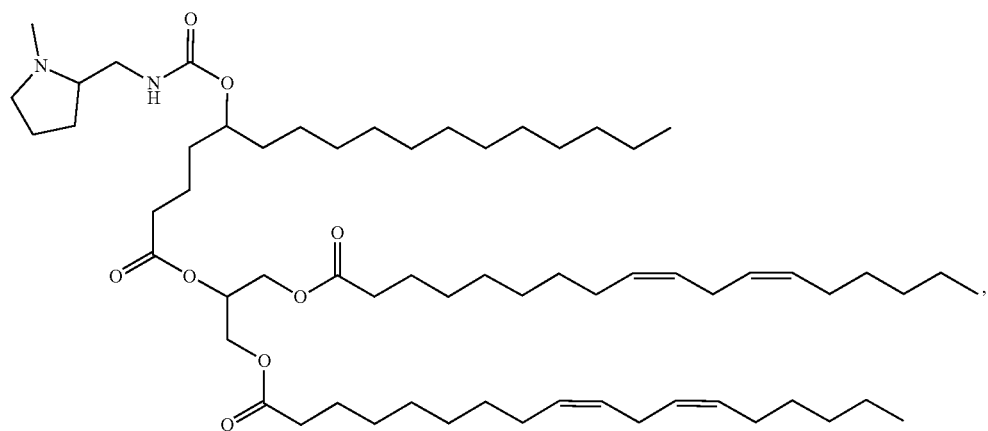

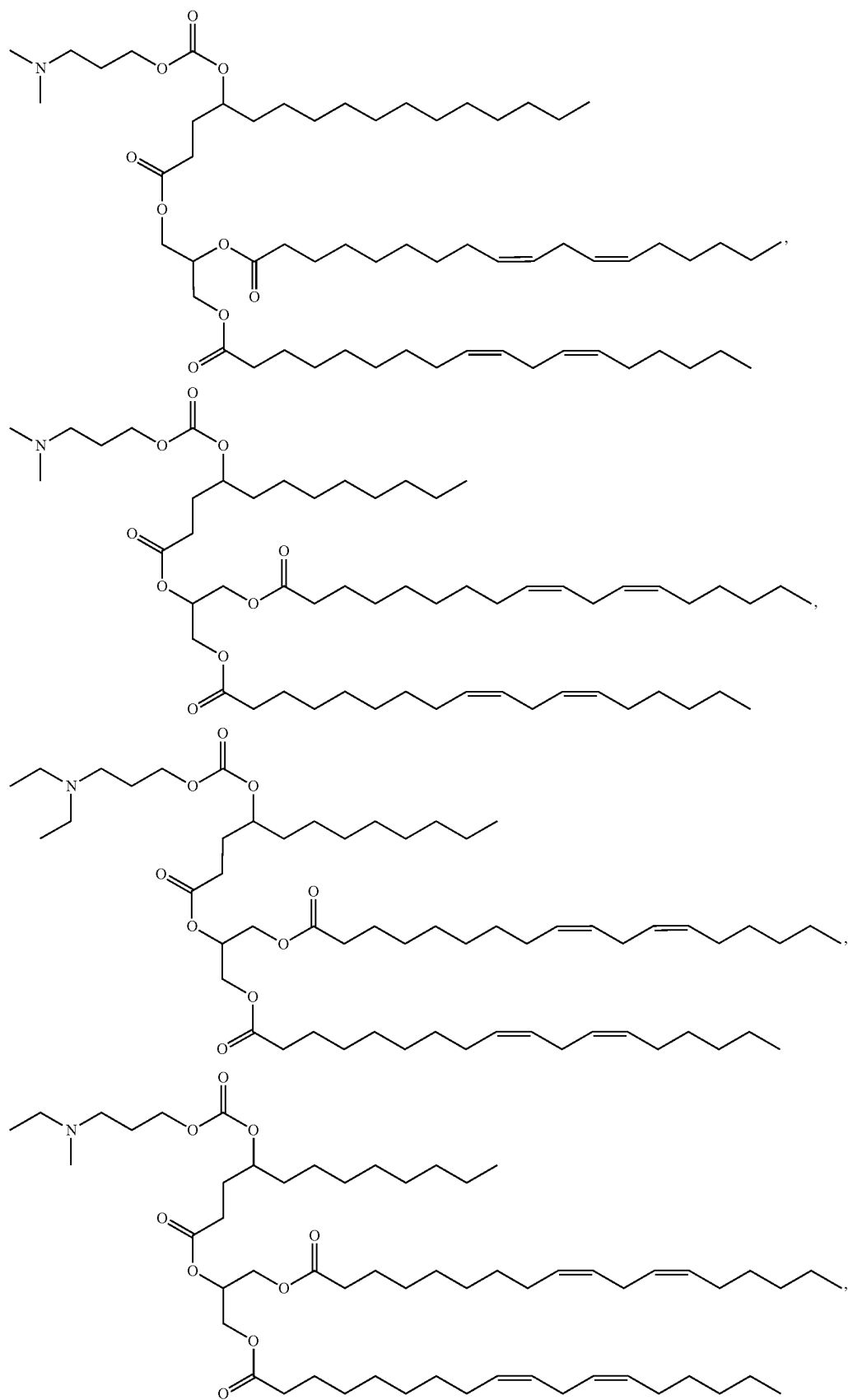

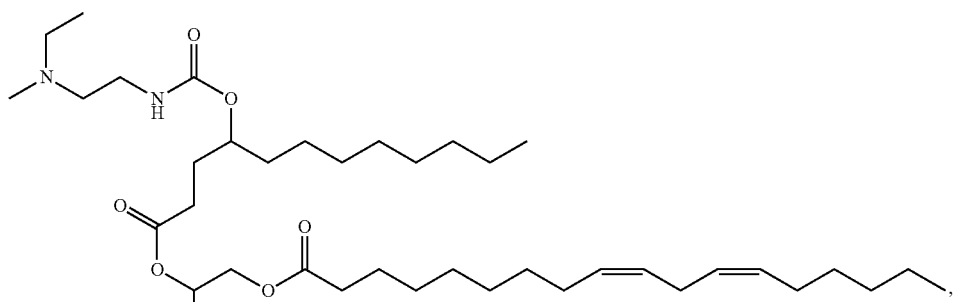
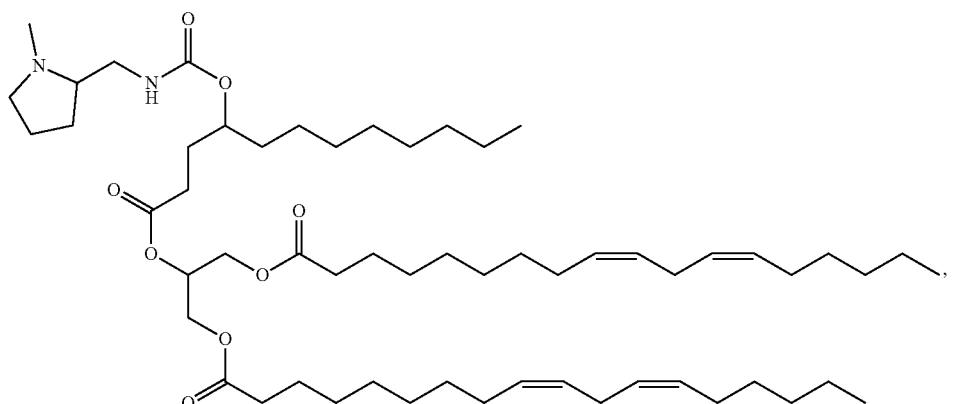
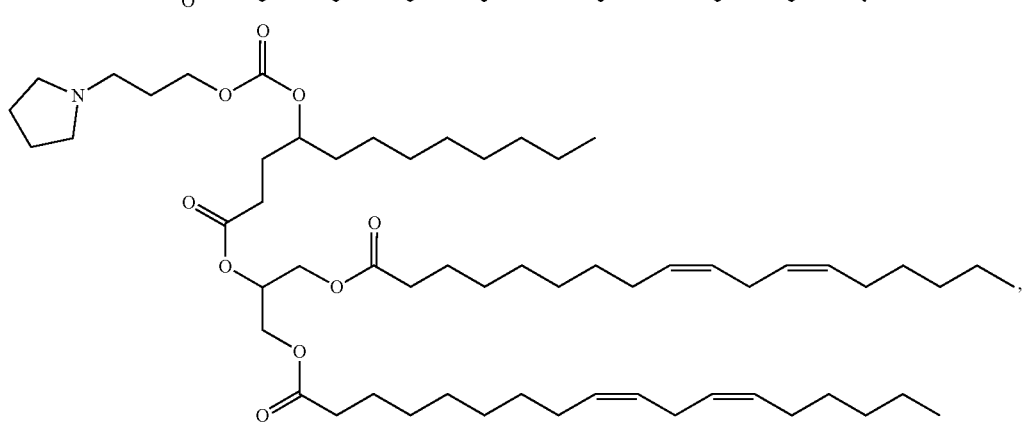
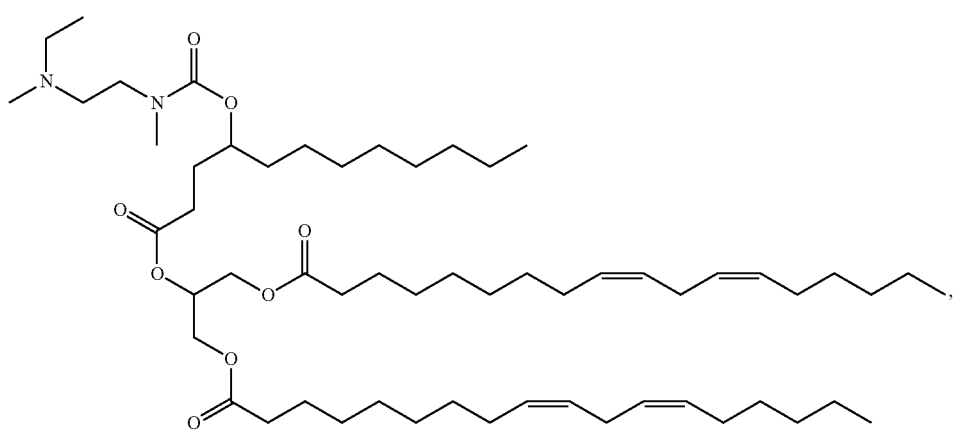

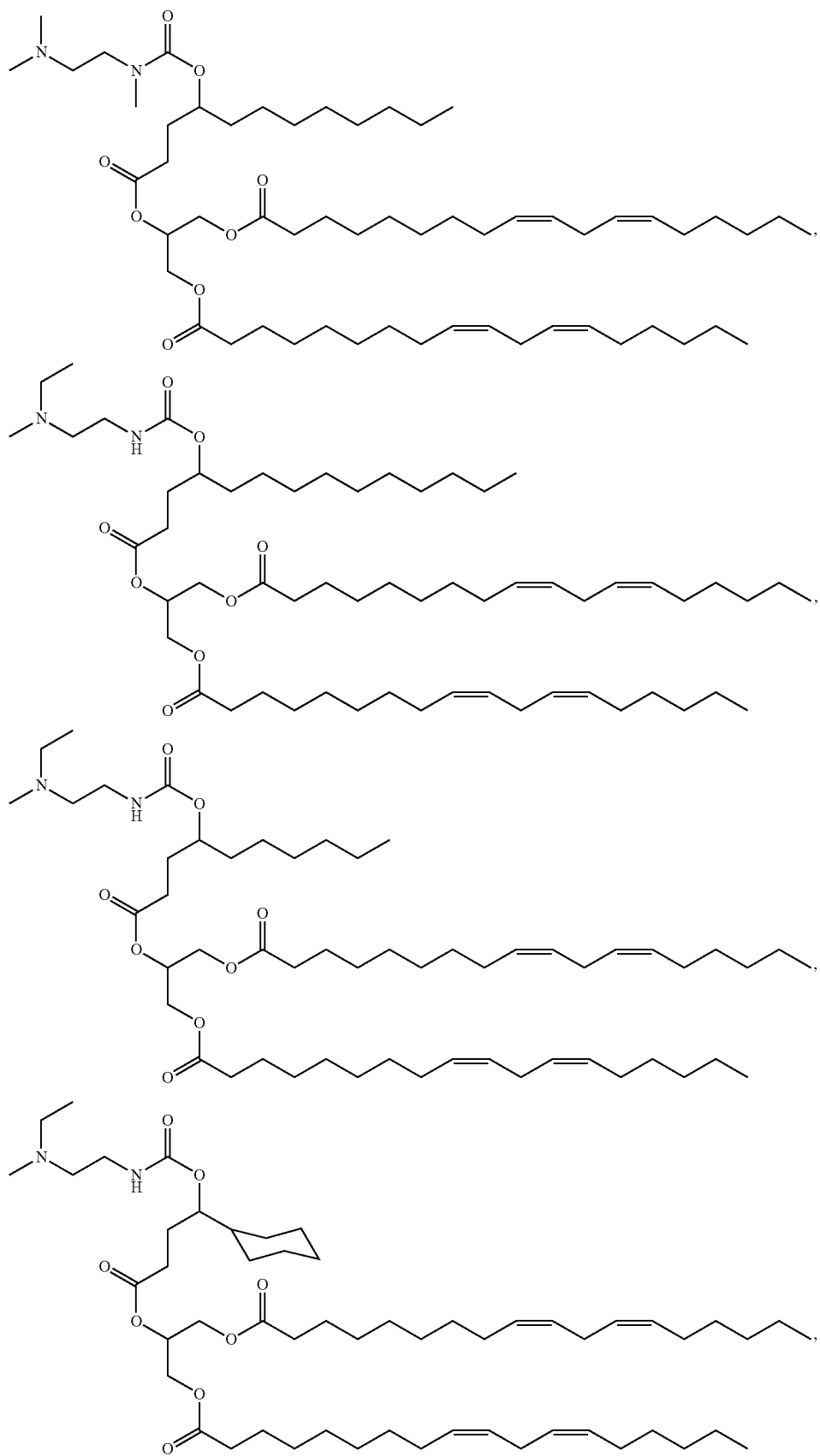

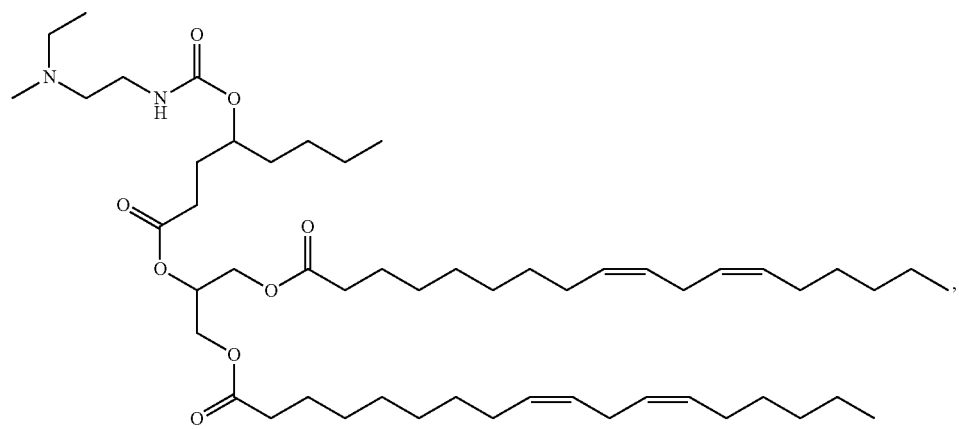
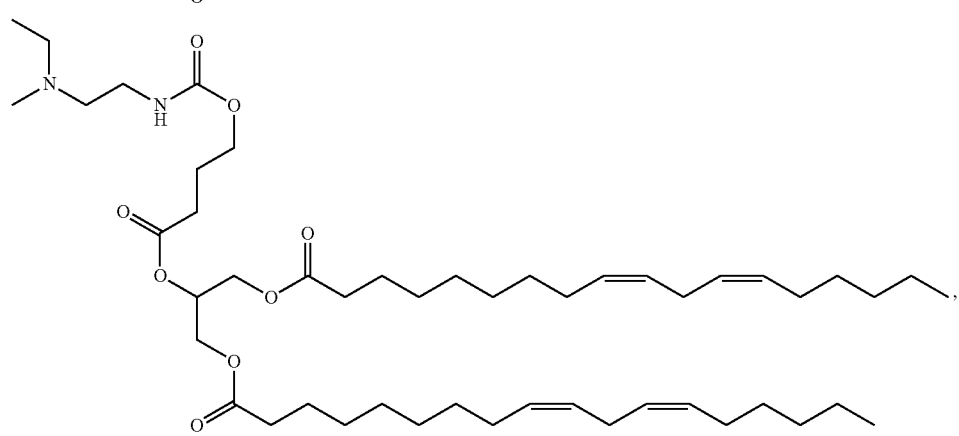
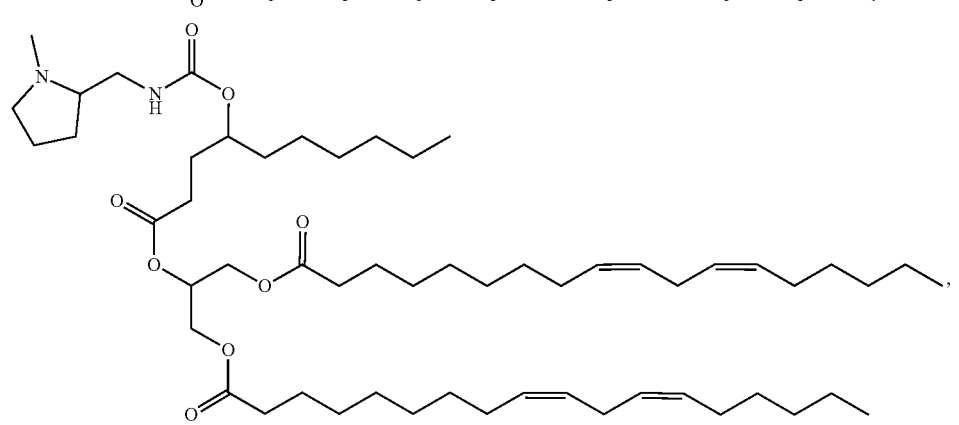
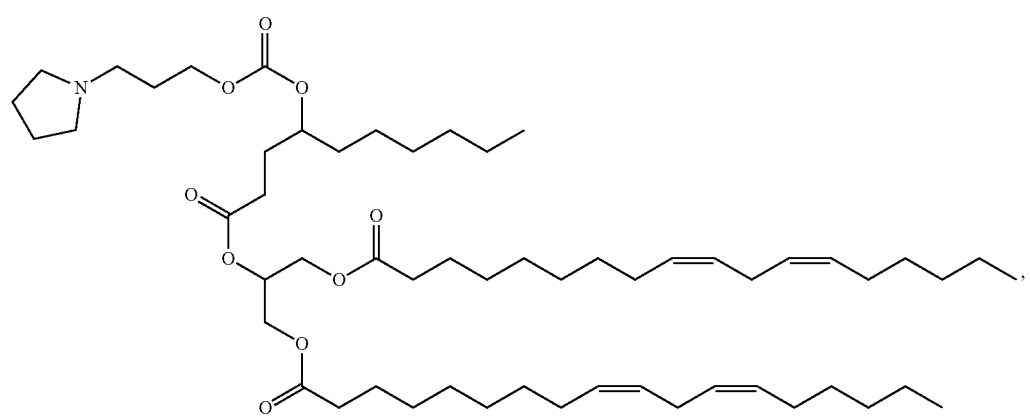

-continued
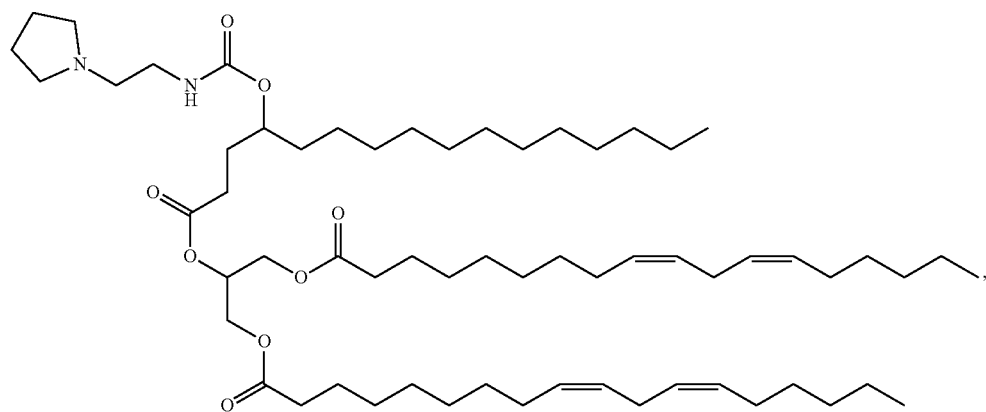
,
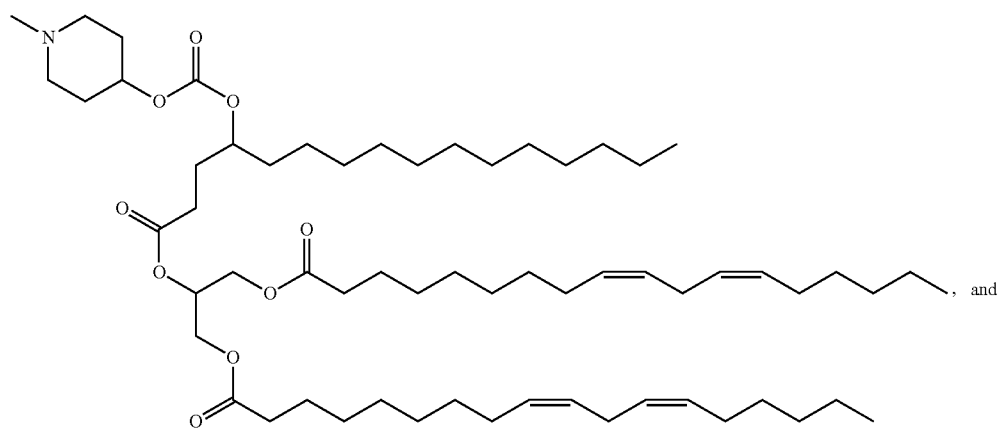
, and
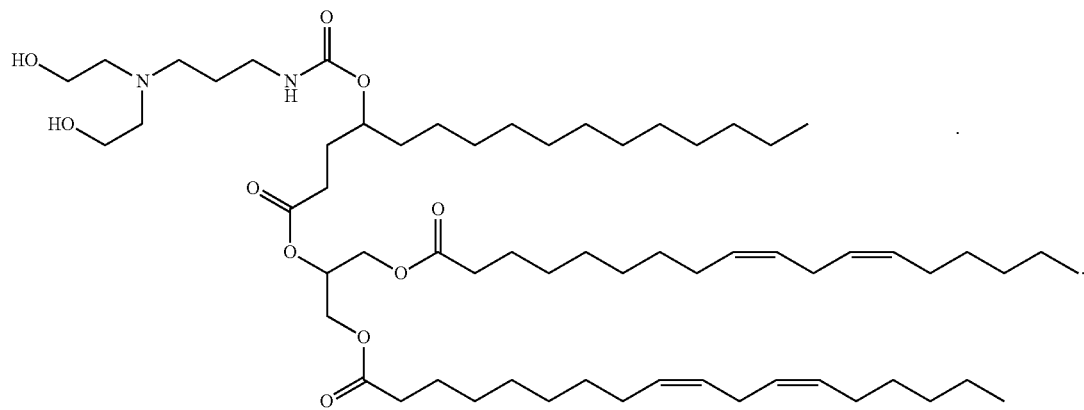
.

In some embodiments, the compound is selected from
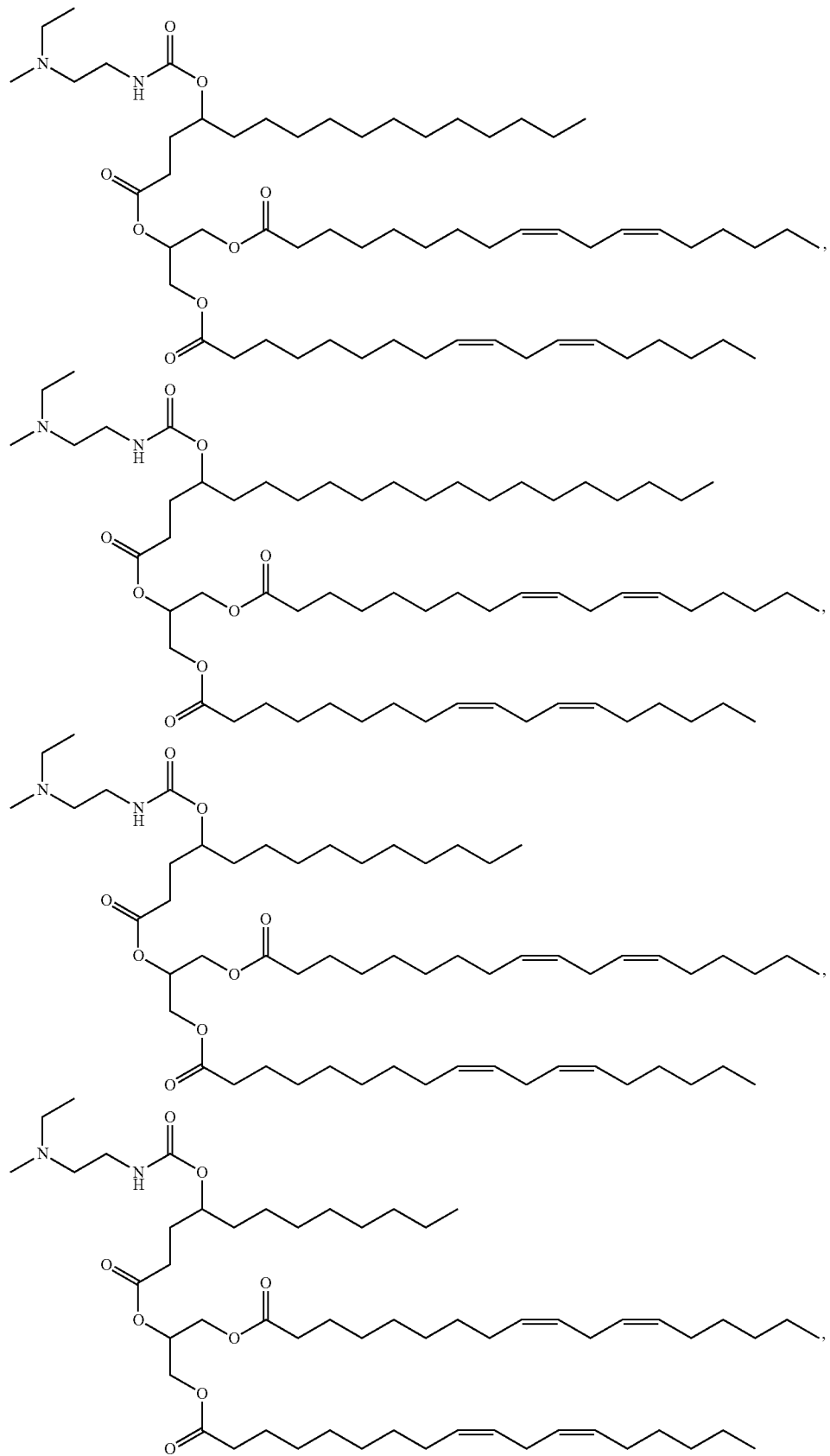

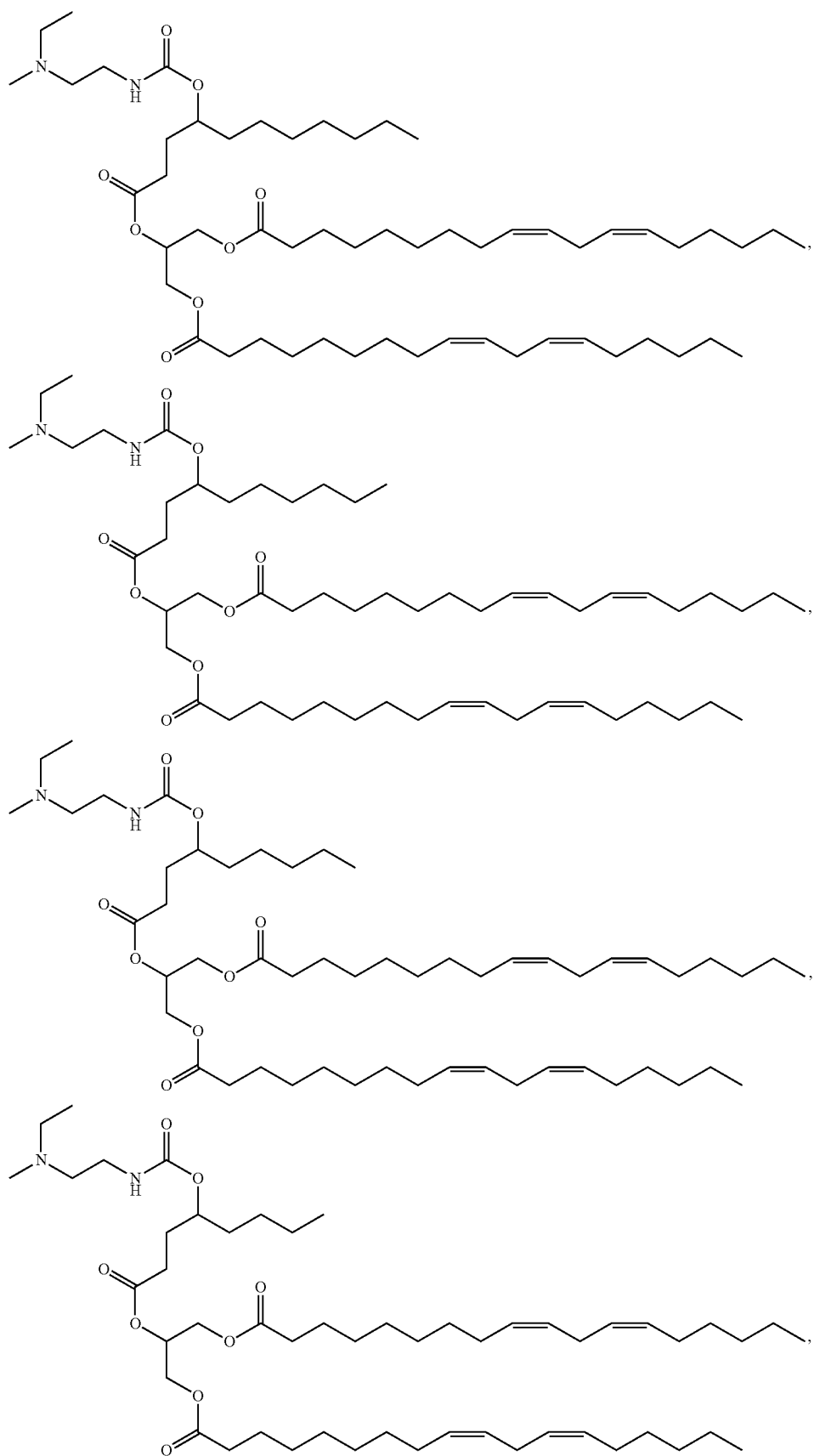

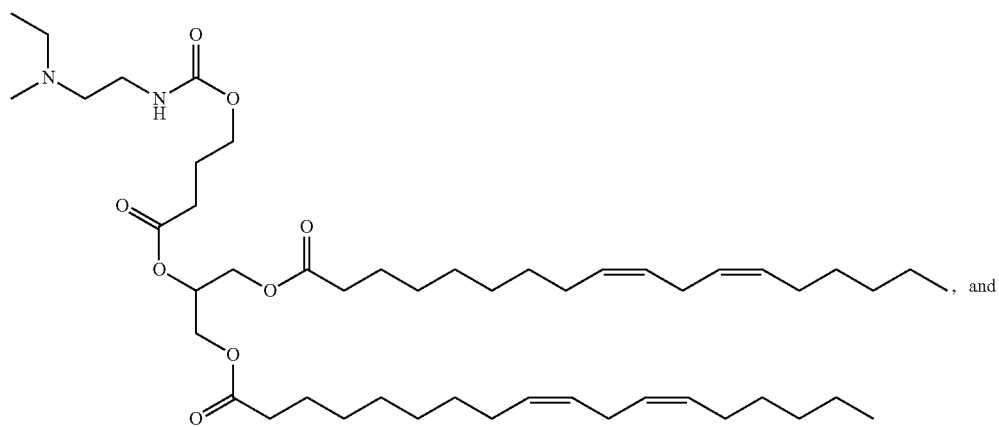
, and
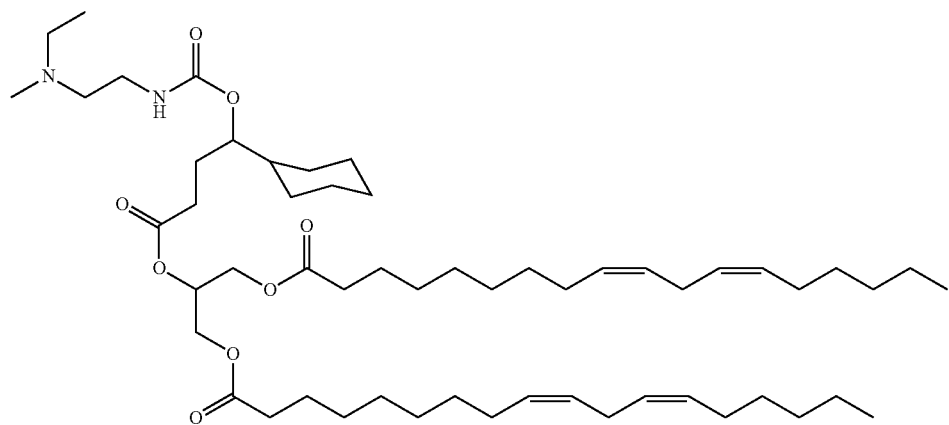
or a salt thereof.
In other embodiments, the compound is selected from
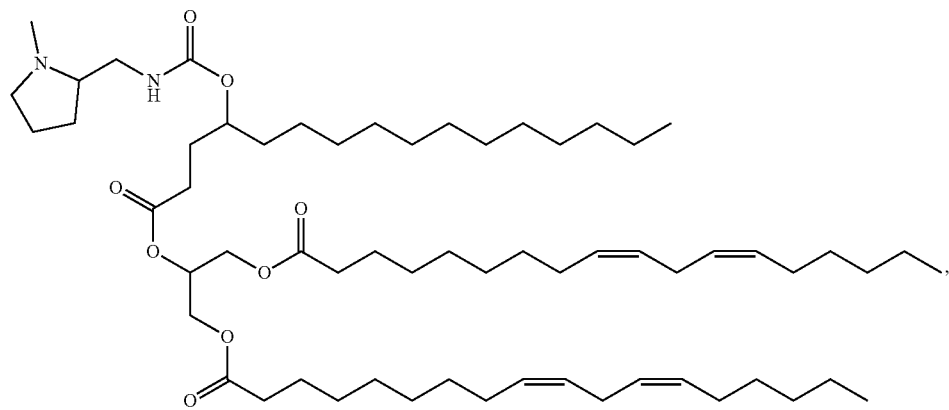
,

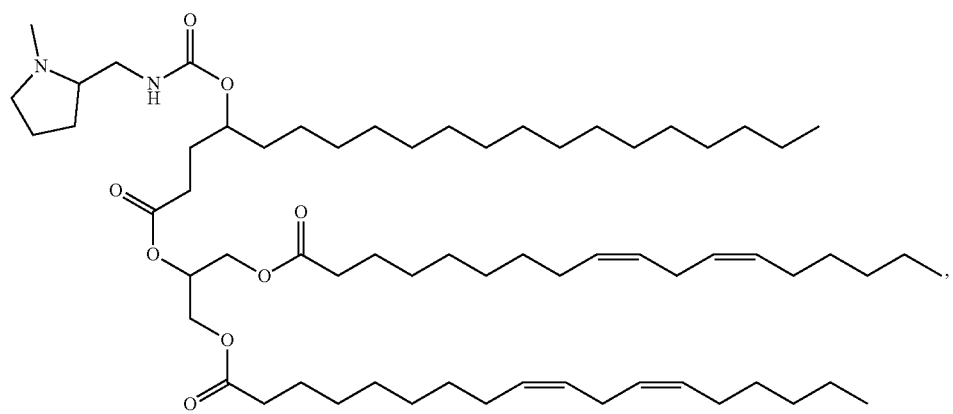,
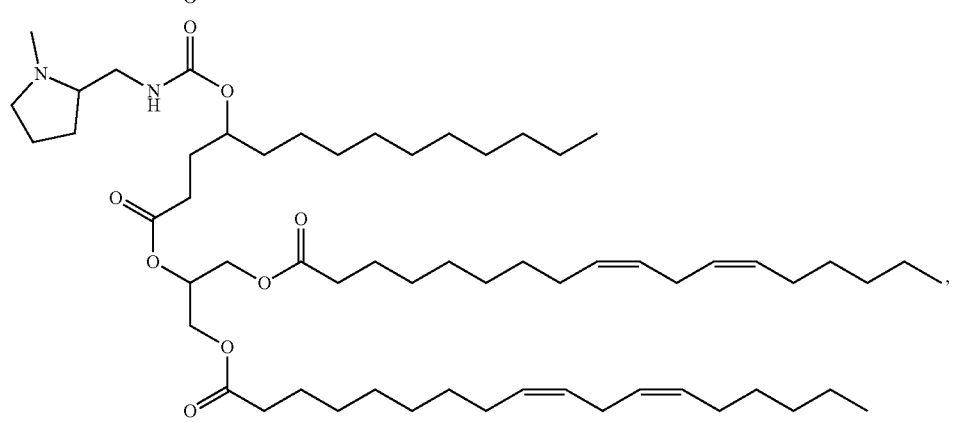,
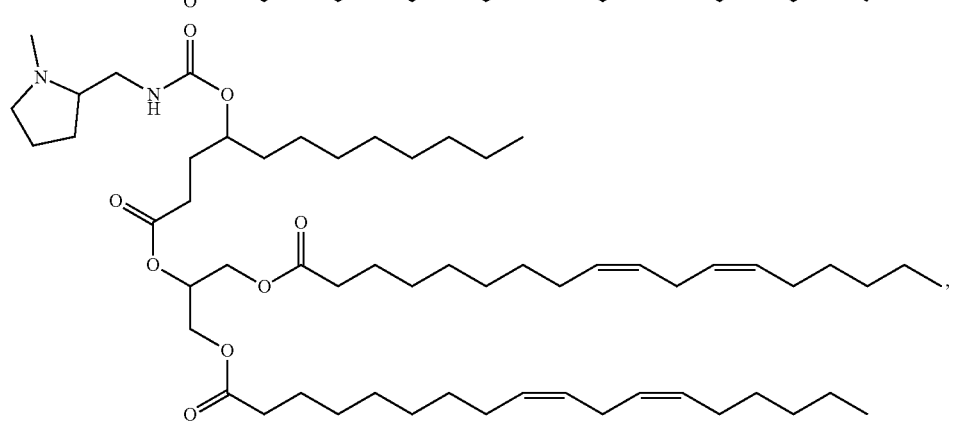,
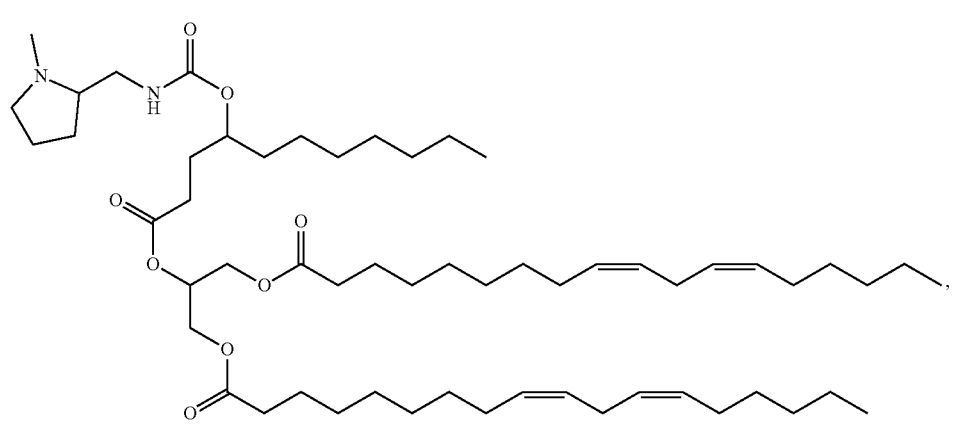;

-continued
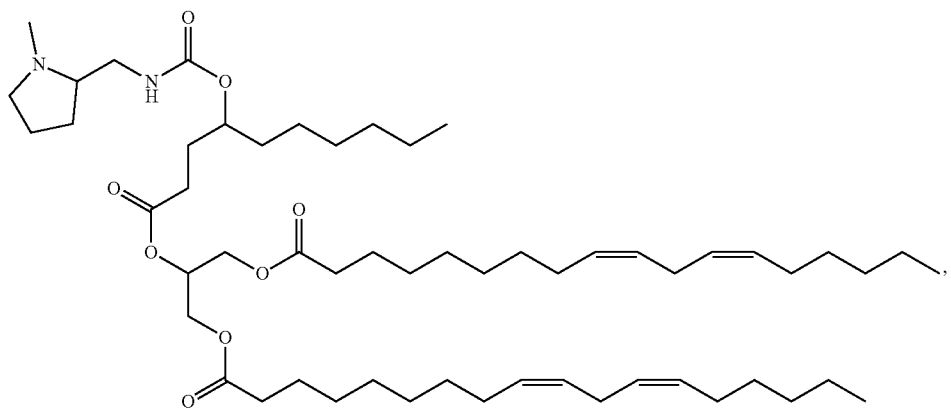
,
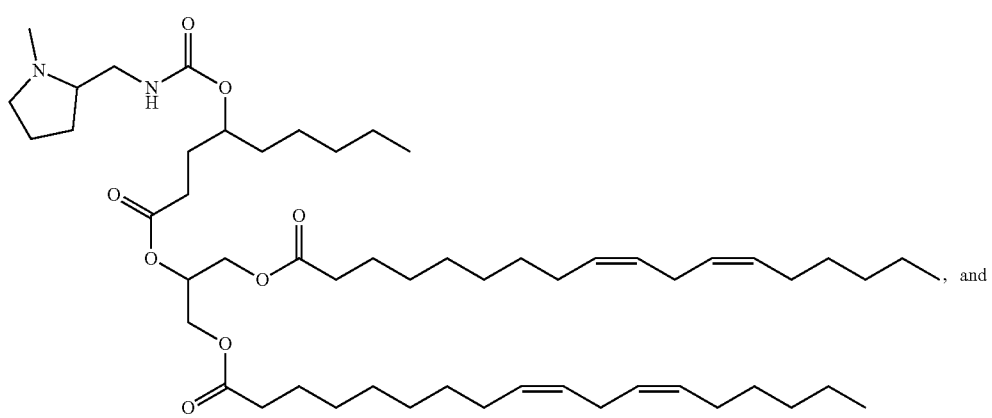
, and
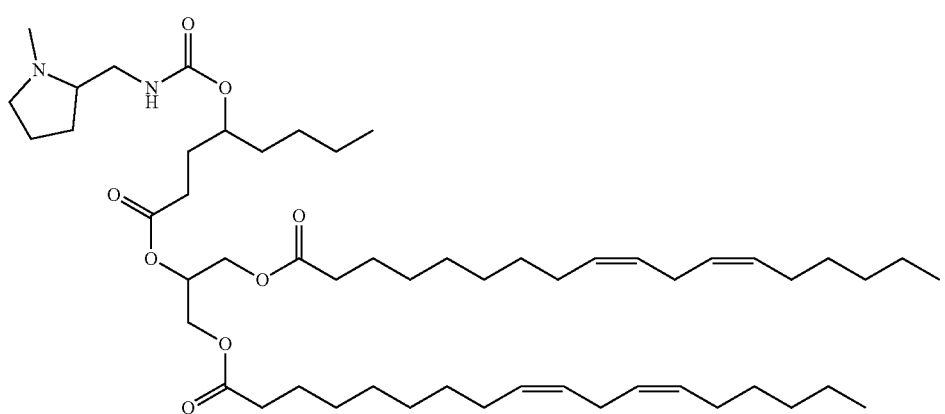
or a salt thereof.

In yet other embodiments, the compound is selected from
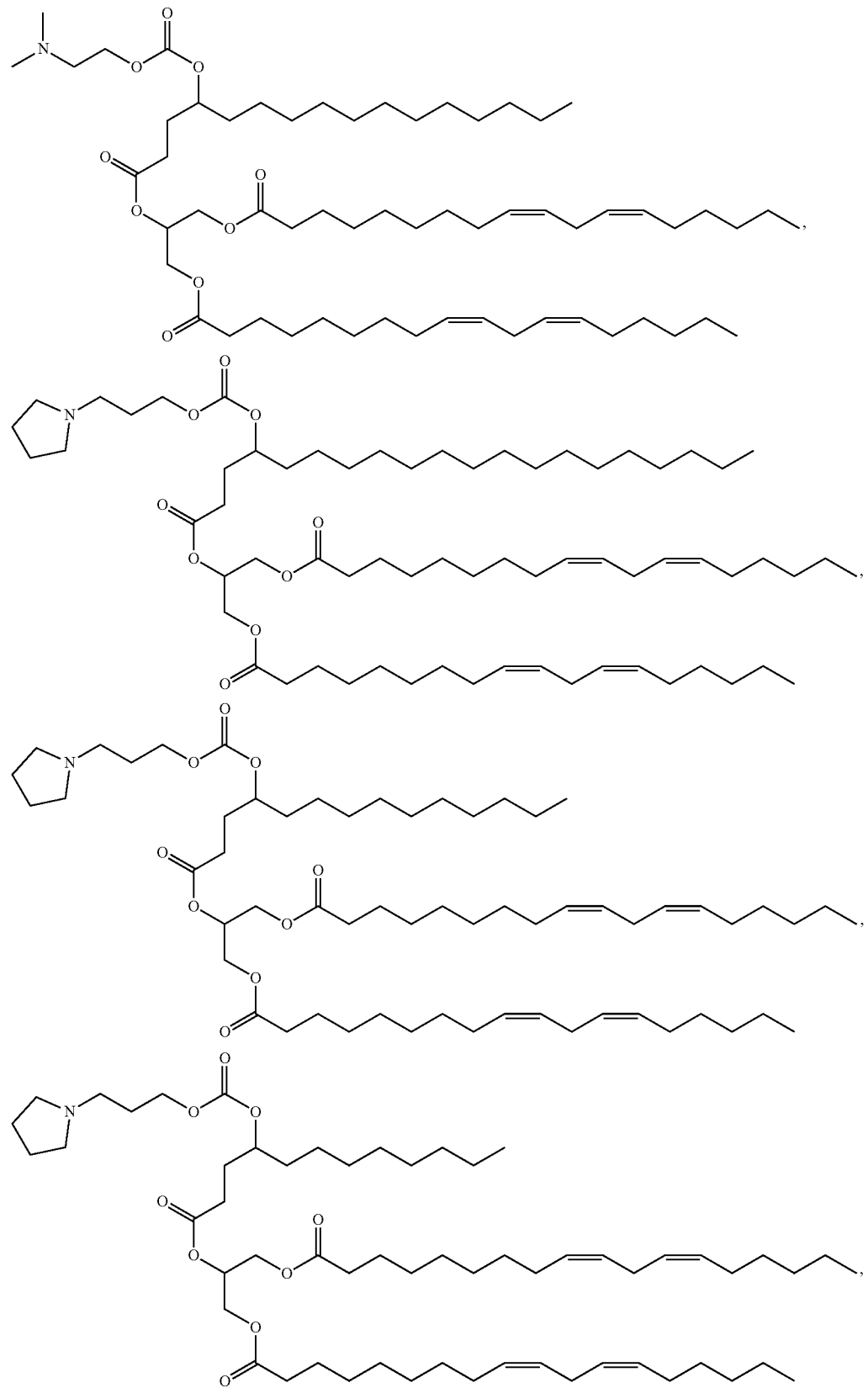

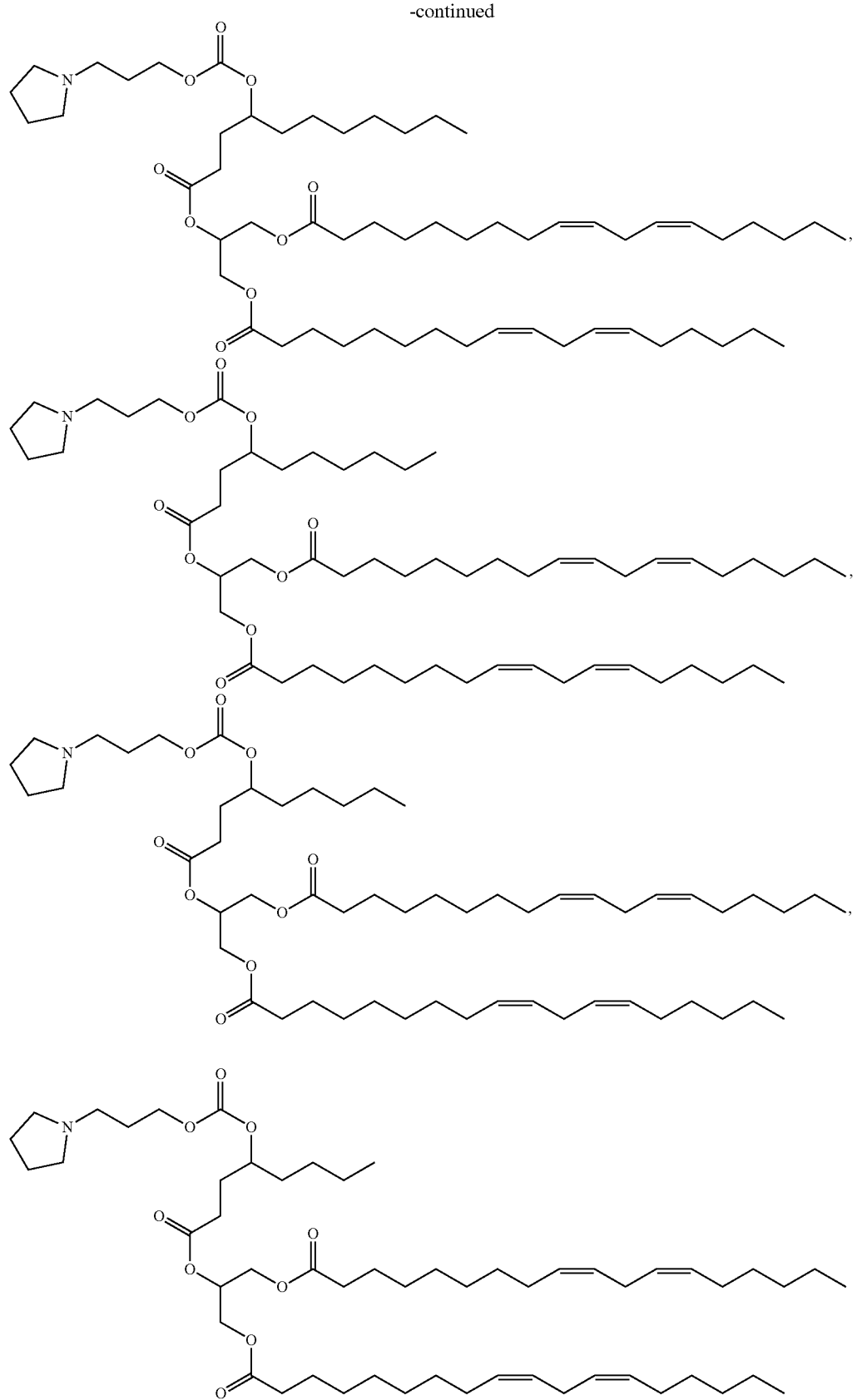
or a salt thereof.

In certain embodiments, at least 75% of the compound of Formula (IA), (I), (II), or (III) of lipid compositions formulated as disclosed herein is cleared from the subject's plasma within 8, 10, 12, 24, or 48 hours, or 3, 4, 5, 6, 7, or 10 days after administration. In certain embodiments, at least 50% of the lipid compositions comprising a compound of Formula (IA), (I), (II), or (III) as disclosed herein are cleared from the subject's plasma within 8, 10, 12, 24, or 48 hours, or 3, 4, 5, 6, 7, or 10 days after administration, which can be determined, for example, by measuring a lipid (e.g. a compound of Formula (IA), (I), (II), or (III)), RNA (e.g. mRNA), or other component in the plasma. In certain embodiments, lipid-encapsulated versus free lipid, RNA, or nucleic acid component of the lipid composition is measured.

Lipid clearance may be measured as described in literature. See Maier, M. A., et al. Biodegradable Lipids Enabling Rapidly Eliminated Lipid Nanoparticles for Systemic Delivery of RNAi Therapeutics. *Mol. Ther.* 2013, 21(8), 1570-78 ("Maier"). For example, in Maier, LNP-siRNA systems containing luciferases-targeting siRNA were administered to six- to eight-week old male C57Bl/6 mice at 0.3 mg/kg by intravenous bolus injection via the lateral tail vein. Blood, liver, and spleen samples were collected at 0.083, 0.25, 0.5, 1, 2, 4, 8, 24, 48, 96, and 168 hours post-dose. Mice were perfused with saline before tissue collection and blood samples were processed to obtain plasma. All samples were processed and analyzed by LC-MS. Further, Maier describes a procedure for assessing toxicity after administration of LNP-siRNA compositions. For example, a luciferase-targeting siRNA was administered at 0, 1, 3, 5, and 10 mg/kg (5 animals/group) via single intravenous bolus injection at a dose volume of 5 mL/kg to male Sprague-Dawley rats. After 24 hours, about 1 mL of blood was obtained from the jugular vein of conscious animals and the serum was isolated. At 72 hours post-dose, all animals were euthanized for necropsy. Assessment of clinical signs, body weight, serum chemistry, organ weights and histopathology was performed. Although Maier describes methods for assessing siRNA-LNP compositions, these methods may be applied to assess clearance, pharmacokinetics, and toxicity of administration of lipid compositions, such as LNP compositions, of the present disclosure.

In certain embodiments, lipid compositions using the compounds of Formula (IA), (I), (II), or (III) disclosed herein exhibit an increased clearance rate relative to alternative ionizable amine lipids. In some such embodiments, the clearance rate is a lipid clearance rate, for example the rate at which a compound of Formula (IA), (I), (II), or (III) is cleared from the blood, serum, or plasma. In some embodiments, the clearance rate is a cargo (e.g. biologically active agent) clearance rate, for example the rate at which a cargo component is cleared from the blood, serum, or plasma. In some embodiments, the clearance rate is an RNA clearance rate, for example the rate at which an mRNA or a gRNA is cleared from the blood, serum, or plasma. In some embodiments, the clearance rate is the rate at which LNP is cleared from the blood, serum, or plasma. In some embodiments, the clearance rate is the rate at which LNP is cleared from a tissue, such as liver tissue or spleen tissue. Desirably, a high rate of clearance can result in a safety profile with no substantial adverse effects, and/or reduced LNP accumulation in circulation and/or in tissues.

The compounds of Formula (IA), (I), (II), or (III) of the present disclosure may form salts depending upon the pH of the medium they are in. For example, in a slightly acidic medium, the compounds of Formula (IA), (I), (II), or (III) may be protonated and thus bear a positive charge. Conversely, in a slightly basic medium, such as, for example, blood where pH is approximately 7.35, the compounds of Formula (IA), (I), (II), or (III) may not be protonated and thus bear no charge. In some embodiments, the compounds of Formula (IA), (I), (II), or (III) of the present disclosure may be predominantly protonated at a pH of at least about 9. In some embodiments, the compounds of Formula (IA), (I), (II), or (III) of the present disclosure may be predominantly protonated at a pH of at least about 10.

The pH at which a compound of Formula (IA), (I), (II), or (III) is predominantly protonated is related to its intrinsic pKa. In preferred embodiments, a salt of a compound of Formula (IA), (I), (II), or (III) of the present disclosure has a pKa in the range of about 5.1 to about 8.0, even more preferably from about 5.5 to about 7.5, for example from about 6.1 to about 6.3. In other preferred embodiments, a salt of a compound of Formula (IA), (I), (II), or (III) of the present disclosure has a pKa in the range of about 5.3 to about 8.0, e.g., from about 5.6 to about 7.2, from about 5.7 to about 6.5. In other embodiments, a salt of a compound of Formula (IA), (I), (II), or (III) of the present disclosure has a pKa in the range of about 5.7 to about 6.4, e.g., from about 5.8 to about 6.2. In other preferred embodiments, a salt of a compound of Formula (IA), (I), (II), or (III) of the present disclosure has a pKa in the range of about 5.7 to about 6.5, e.g., from about 5.8 to about 6.4. Alternatively, a salt of a compound of Formula (IA), (I), (II), or (III) of the present disclosure has a pKa in the range of about 5.8 to about 6.5. In some embodiments, the pKa of the protonated form of the compound of Formula (IA), (I), (II), or (III) is from about 5.5 to about 6.0. A salt of a compound of Formula (IA), (I), (II), or (III) of the present disclosure may have a pKa in the range of about 6.0 to about 8.0, preferably from about 6.0 to about 7.5. The pKa of a salt of a compound of Formula (IA), (I), (II), or (III) can be an important consideration in formulating LNPs, as it has been found that LNPs formulated with certain lipids having a pKa ranging from about 5.5 to about 7.0 are effective for delivery of cargo in vivo, e.g. to the liver. Further, it has been found that LNPs formulated with certain lipids having a pKa ranging from about 5.3 to about 6.4 are effective for delivery in vivo, e.g. to tumors. See, e.g., WO 2014/136086.

In certain embodiments, disclosure relates to a compound of formula (IA), (I), (II), or (III) that is enantioenriched. The level of enantioenrichment of a compound may be expressed as enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R) enantiomer, then the ee of the compound is (98−2)/(98+2), or 96%. In certain embodiments, the compound of formula (IA), (I), (II), or (III) has about 30% ee or greater, 40% ee or greater, 50% ee or greater, 60% ee or greater, 70% ee or greater, about 80% ee, about 85% ee, about 88% ee, about 90% ee, about 91% ee, about 92% ee, about 93% ee, about 94% ee, about 95% ee, about 96% ee, about 97% ee, about 98% ee, about 99% ee, or above about 99% ee, even where this % ee is greater than the % ee of the starting material, such as 0% ee (racemic). In certain embodiments, the compound of formula (IA), (I), (II), or (III) is enantioenriched. In certain embodiments, the compound of formula (IA), (I), (II), or (III) is enantiopure. In embodiments where the compound has more than one stereocenter, that stereocenter may be enriched substantially independently of the stereochemical disposition/enrichment of any other stereocenters of the molecule. For example, a compound described herein may have 30% de or greater, 40% de or greater, 50% de or greater, 60% de or greater, 70% de or greater, 80% de or greater, 90% de or greater, 95% de or greater, or even 98% de or greater at a specific stereocenter.

Additional Lipids

"Neutral lipids" suitable for use in a lipid composition of the disclosure include, for example, a variety of neutral, uncharged or zwitterionic lipids. Examples of neutral phospholipids suitable for use in the present disclosure include, but are not limited to, dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-di-arachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lyso-phosphatidylethanolamine and combinations thereof. In certain embodiments, the neutral phospholipid may be selected from distearoylphosphatidylcholine (DSPC) and dimyristoyl phosphatidyl ethanolamine (DMPE), preferably distearoylphosphatidylcholine (DSPC).

"Helper lipids" include steroids, sterols, and alkyl resorcinols. Helper lipids suitable for use in the present disclosure include, but are not limited to, cholesterol, 5-heptadecylresorcinol, and cholesterol hemisuccinate. In certain embodiments, the helper lipid may be cholesterol or a derivative thereof, such as cholesterol hemisuccinate.

PEG lipids can affect the length of time the nanoparticles can exist in vivo (e.g., in the blood). PEG lipids may assist in the formulation process by, for example, reducing particle aggregation and controlling particle size. PEG lipids used herein may modulate pharmacokinetic properties of the LNPs. Typically, the PEG lipid comprises a lipid moiety and a polymer moiety based on PEG (sometimes referred to as poly(ethylene oxide)) (a PEG moiety). PEG lipids suitable for use in a lipid composition with a compound of Formula (IA), (I), (II), or (III) of the present disclosure and information about the biochemistry of such lipids can be found in Romberg et al., Pharmaceutical Research 25(1), 2008, pp. 55-71 and Hoekstra et al., Biochimica et Biophysica Acta 1660 (2004) 41-52. Additional suitable PEG lipids are disclosed, e.g., in WO 2015/095340 (p. 31, line 14 to p. 37, line 6), WO 2006/007712, and WO 2011/076807 ("stealth lipids").

In some embodiments, the lipid moiety may be derived from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. In some embodiments, the alkyl chain length comprises about C10 to C20. The dialkylglycerol or dialkylglycamide group can further comprise one or more substituted alkyl groups. The chain lengths may be symmetrical or asymmetric.

Unless otherwise indicated, the term "PEG" as used herein means any polyethylene glycol or other polyalkylene ether polymer, such as an optionally substituted linear or branched polymer of ethylene glycol or ethylene oxide. In certain embodiments, the PEG moiety is unsubstituted. Alternatively, the PEG moiety may be substituted, e.g., by one or more alkyl, alkoxy, acyl, hydroxy, or aryl groups. For example, the PEG moiety may comprise a PEG copolymer such as PEG-polyurethane or PEG-polypropylene (see, e.g., J. Milton Harris, Poly(ethylene glycol) chemistry: biotechnical and biomedical applications (1992)); alternatively, the PEG moiety may be a PEG homopolymer. In certain embodiments, the PEG moiety has a molecular weight of about 130 to about 50,000, such as from about 150 to about 30,000, or even from about 150 to about 20,000. Similarly, the PEG moiety may have a molecular weight of about 150 to about 15,000, from about 150 to about 10,000, from about 150 to about 6,000, or even from about 150 to about 5,000. In certain preferred embodiments, the PEG moiety has a molecular weight of about 150 to about 4,000, from about 150 to about 3,000, from about 300 to about 3,000, from about 1,000 to about 3,000, or from about 1,500 to about 2,500.

In certain preferred embodiments, the PEG moiety is a "PEG-2K," also termed "PEG 2000," which has an average molecular weight of about 2,000 daltons. PEG-2K is represented herein by the following formula (II), wherein n is 45, meaning that the number averaged degree of polymerization comprises about 45 subunits

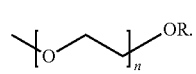

(II)

However, other PEG embodiments known in the art may be used, including, e.g., those where the number-averaged degree of polymerization comprises about 23 subunits (n=23), and/or 68 subunits (n=68). In some embodiments, n may range from about 30 to about 60. In some embodiments, n may range from about 35 to about 55. In some embodiments, n may range from about 40 to about 50. In some embodiments, n may range from about 42 to about 48. In some embodiments, n may be 45. In some embodiments, R may be selected from H, substituted alkyl, and unsubstituted alkyl. In some embodiments, R may be unsubstituted alkyl, such as methyl.

In any of the embodiments described herein, the PEG lipid may be selected from PEG-dilauroylglycerol, PEG-dimyristoylglycerol (PEG-DMG) (catalog #GM-020 from NOF, Tokyo, Japan), PEG-dipalmitoylglycerol, PEG-distearoylglycerol (PEG-DSPE) (catalog #DSPE-020CN, NOF, Tokyo, Japan), PEG-dilaurylglycamide, PEG-dimyristylglycamide, PEG-dipalmitoylglycamide, and PEG-distearoylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG) (cat. #880150P from Avanti Polar Lipids, Alabaster, Alabama, USA), 1,2-distearoyl-sn-glycero-3-phosphoethanolamine-N-[methoxy(polyethylene glycol)-2000] (PEG2k-

DSPE) (cat. #880120C from Avanti Polar Lipids, Alabaster, Alabama, USA), 1,2-distearoyl-sn-glycerol, methoxypolyethylene glycol (PEG2k-DSG; GS-020, NOF Tokyo, Japan), poly(ethylene glycol)-2000-dimethacrylate (PEG2k-DMA), and 1,2-distearyloxypropyl-3-amine-N-[methoxy(polyethylene glycol)-2000] (PEG2k-DSA). In certain such embodiments, the PEG lipid may be PEG2k-DMG. In some embodiments, the PEG lipid may be PEG2k-DSG. In other embodiments, the PEG lipid may be PEG2k-DSPE. In some embodiments, the PEG lipid may be PEG2k-DMA. In yet other embodiments, the PEG lipid may be PEG2k-C-DMA. In certain embodiments, the PEG lipid may be compound S027, disclosed in WO2016/010840 (paragraphs [00240] to [00244]). In some embodiments, the PEG lipid may be PEG2k-DSA. In other embodiments, the PEG lipid may be PEG2k-C11. In some embodiments, the PEG lipid may be PEG2k-C14. In some embodiments, the PEG lipid may be PEG2k-C16. In some embodiments, the PEG lipid may be PEG2k-C18.

Cationic lipids suitable for use in a lipid composition of the disclosure include, but are not limited to, N,N-dioleyl-N,N-dimethylammonium chloride (DODAC),N,N-distearyl-N,N-dimethylammonium bromide (DDAB), N-(1-(2,3-dioleoyloxy)propyl)-N,N,N-trimethylammonium chloride (DOTAP), 1,2-Dioleoyl-3-Dimethylammonium-propane (DODAP), N-(1-(2,3-dioleyloxy)propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl(C12:0) trimethyl ammonium propane (DLTAP), Dioctadecylamidoglycyl spermine (DOGS), DC-Choi, Dioleoyloxy-N-[2-(sperminecarboxamido)ethyl]-N,N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy)propylamine (DODMA), 2-[5'-(cholest-5-en-3[beta]-oxy)-3'-oxapentoxy)-3-dimethyl-1-(cis,cis-9',1-2'-octadecadienoxy) propane (CpLinDMA), N,N-Dimethyl-3,4-dioleyloxybenzylamine (DMOBA), and 1,2-N,N'-Dioleylcarbamyl-3-dimethylaminopropane (DOcarbDAP). In one embodiment the cationic lipid is DOTAP or DLTAP.

Anionic lipids suitable for use in the present disclosure include, but are not limited to, phosphatidylglycerol, cardiolipin, diacylphosphatidylserine, diacylphosphatidic acid, N-dodecanoyl phosphatidyl ethanolamine, N-succinyl phosphatidylethanolamine, N-glutaryl phosphatidylethanolamine cholesterol hemisuccinate (CHEMS), and lysylphosphatidylglycerol.

Lipid Compositions

The present disclosure provides a lipid composition comprising at least one compound of Formula (IA), (I), (II), or (III) or a salt thereof (e.g., a pharmaceutically acceptable salt thereof) and at least one other lipid component. Such compositions can also contain a biologically active agent, optionally in combination with one or more other lipid components. In some embodiments, the lipid compositions comprise a lipid component and an aqueous component comprising a biologically active agent.

In one embodiment, the lipid composition comprises a compound of Formula (IA), (I), (II), or (III), or a pharmaceutically acceptable salt thereof, and at least one other lipid component. In another embodiment, the lipid composition further comprises a biologically active agent, optionally in combination with one or more other lipid components. In another embodiment the lipid composition is in the form of a liposome. In another embodiment the lipid composition is in the form of a lipid nanoparticle (LNP). In another embodiment the lipid composition is suitable for delivery to the liver.

In one embodiment, the lipid composition comprises a compound of Formula (IA), (I), (II), or (III), or a pharmaceutically acceptable salt thereof, and another lipid component. Such other lipid components include, but are not limited to, neutral lipids, helper lipids, PEG lipids, cationic lipids, and anionic lipids. In certain embodiments, the lipid composition comprises a compound of Formula (IA), (I), (II), or (III), or a pharmaceutically acceptable salt thereof, and a neutral lipid, e.g. DSPC, optionally with one or more additional lipid components. In another embodiment, the lipid composition comprises a compound of Formula (IA), (I), (II), or (III), or a pharmaceutically acceptable salt thereof, and a helper lipid, e.g. cholesterol, optionally with one or more additional lipid components. In further embodiment, the lipid composition comprises a compound of Formula (IA), (I), (II), or (III), or a pharmaceutically acceptable salt thereof, and a PEG lipid, optionally with one or more additional lipid components. In further embodiment, the lipid composition comprises a compound of Formula (IA), (I), (II), or (III), or a pharmaceutically acceptable salt thereof, and a cationic lipid, optionally with one or more additional lipid components. In further embodiment, the lipid composition comprises a compound of Formula (IA), (I), (II), or (III), or a pharmaceutically acceptable salt thereof, and an anionic lipid, optionally with one or more additional lipid components. In a sub-embodiment, the lipid composition comprises a compound of Formula (IA), (I), (II), or (III), or a pharmaceutically acceptable salt thereof, a helper lipid, and a PEG lipid, optionally with a neutral lipid. In a further sub-embodiment, the lipid composition comprises a compound of Formula (IA), (I), (II), or (III), or a pharmaceutically acceptable salt thereof, a helper lipid, a PEG lipid, and a neutral lipid.

Compositions containing lipids of Formula (IA), (I), (II), or (III), or a pharmaceutically acceptable salt thereof, or lipid compositions thereof may be in various forms, including, but not limited to, particle forming delivery agents including microparticles, nanoparticles and transfection agents that are useful for delivering various molecules to cells. Specific compositions are effective at transfecting or delivering biologically active agents. Preferred biologically active agents are RNAs and DNAs. In further embodiments, the biologically active agent is chosen from mRNA, gRNA, and DNA. The gRNA may be a dgRNA or an sgRNA. In certain embodiments, the cargo includes an mRNA encoding an RNA-guided DNA binding agent (e.g. a Cas nuclease, a Class 2 Cas nuclease, or Cas9), a gRNA or a nucleic acid encoding a gRNA, or a combination of mRNA and gRNA.

Exemplary compounds of Formula (IA), (I), (II), or (III) for use in the above lipid compositions are given in Examples 2-48, 50-97, 99-103, and 105-113.

In certain embodiments, the compound of Formula (IA) is Compound 2. In certain embodiments, the compound of Formula (IA) is Compound 3. In certain embodiments, the compound of Formula (IA) is Compound 4. In certain embodiments, the compound of Formula (IA) is Compound 5. In certain embodiments, the compound of Formula (IA) is Compound 6. In certain embodiments, the compound of Formula (IA) is Compound 7. In certain embodiments, the compound of Formula (IA) is Compound 8. In certain embodiments, the compound of Formula (IA) is Compound 9. In certain embodiments, the compound of Formula (IA) is Compound 10.

In certain embodiments, the compound of Formula (IA) is Compound 11. In certain embodiments, the compound of Formula (IA) is Compound 12. In certain embodiments, the compound of Formula (IA) is Compound 13. In certain embodiments, the compound of Formula (IA) is Compound 14. In certain embodiments, the compound of Formula (IA) is Compound 15. In certain embodiments, the compound of Formula (IA) is Compound 16. In certain embodiments, the compound of Formula (IA) is Compound 17. In certain embodiments, the compound of Formula (IA) is Compound 18. In certain embodiments, the compound of Formula (IA) is Compound 19. In certain embodiments, the compound of Formula (IA) is Compound 20.

In certain embodiments, the compound of Formula (IA) is Compound 21. In certain embodiments, the compound of Formula (IA) is Compound 22. In certain embodiments, the compound of Formula (IA) is Compound 23. In certain embodiments, the compound of Formula (IA) is Compound 24. In certain embodiments, the compound of Formula (IA) is Compound 25. In certain embodiments, the compound of Formula (IA) is Compound 26. In certain embodiments, the compound of Formula (IA) is Compound 27. In certain embodiments, the compound of Formula (IA) is Compound 28. In certain embodiments, the compound of Formula (IA) is Compound 29. In certain embodiments, the compound of Formula (IA) is Compound 30.

In certain embodiments, the compound of Formula (IA) is Compound 31. In certain embodiments, the compound of Formula (IA) is Compound 32. In certain embodiments, the compound of Formula (IA) is Compound 33. In certain embodiments, the compound of Formula (IA) is Compound 34. In certain embodiments, the compound of Formula (IA) is Compound 35. In certain embodiments, the compound of Formula (IA) is Compound 36. In certain embodiments, the compound of Formula (IA) is Compound 37. In certain embodiments, the compound of Formula (IA) is Compound 38. In certain embodiments, the compound of Formula (IA) is Compound 39. In certain embodiments, the compound of Formula (IA) is Compound 40.

In certain embodiments, the compound of Formula (IA) is Compound 41. In certain embodiments, the compound of Formula (IA) is Compound 42. In certain embodiments, the compound of Formula (IA) is Compound 43. In certain embodiments, the compound of Formula (IA) is Compound 44. In certain embodiments, the compound of Formula (IA) is Compound 45. In certain embodiments, the compound of Formula (IA) is Compound 46. In certain embodiments, the compound of Formula (IA) is Compound 47. In certain embodiments, the compound of Formula (IA) is Compound 48. In certain embodiments, the compound of Formula (IA) is Compound 50.

In certain embodiments, the compound of Formula (IA) is Compound 51. In certain embodiments, the compound of Formula (IA) is Compound 52. In certain embodiments, the compound of Formula (IA) is Compound 53. In certain embodiments, the compound of Formula (IA) is Compound 54. In certain embodiments, the compound of Formula (IA) is Compound 55. In certain embodiments, the compound of Formula (IA) is Compound 56. In certain embodiments, the compound of Formula (IA) is Compound 57. In certain embodiments, the compound of Formula (IA) is Compound 58. In certain embodiments, the compound of Formula (IA) is Compound 59. In certain embodiments, the compound of Formula (IA) is Compound 60.

In certain embodiments, the compound of Formula (IA) is Compound 61. In certain embodiments, the compound of Formula (IA) is Compound 62. In certain embodiments, the compound of Formula (IA) is Compound 63. In certain embodiments, the compound of Formula (IA) is Compound 64. In certain embodiments, the compound of Formula (IA) is Compound 65. In certain embodiments, the compound of Formula (IA) is Compound 66. In certain embodiments, the compound of Formula (IA) is Compound 67. In certain embodiments, the compound of Formula (IA) is Compound 68. In certain embodiments, the compound of Formula (IA) is Compound 69. In certain embodiments, the compound of Formula (IA) is Compound 70.

In certain embodiments, the compound of Formula (IA) is Compound 71. In certain embodiments, the compound of Formula (IA) is Compound 72. In certain embodiments, the compound of Formula (IA) is Compound 73. In certain embodiments, the compound of Formula (IA) is Compound 74. In certain embodiments, the compound of Formula (IA) is Compound 75. In certain embodiments, the compound of Formula (IA) is Compound 76. In certain embodiments, the compound of Formula (IA) is Compound 77. In certain embodiments, the compound of Formula (IA) is Compound 78. In certain embodiments, the compound of Formula (IA) is Compound 79. In certain embodiments, the compound of Formula (IA) is Compound 80.

In certain embodiments, the compound of Formula (IA) is Compound 81. In certain embodiments, the compound of Formula (IA) is Compound 82. In certain embodiments, the compound of Formula (IA) is Compound 83. In certain embodiments, the compound of Formula (IA) is Compound 84. In certain embodiments, the compound of Formula (IA) is Compound 85. In certain embodiments, the compound of Formula (IA) is Compound 86. In certain embodiments, the compound of Formula (IA) is Compound 87. In certain embodiments, the compound of Formula (IA) is Compound 88. In certain embodiments, the compound of Formula (IA) is Compound 89. In certain embodiments, the compound of Formula (IA) is Compound 90.

In certain embodiments, the compound of Formula (IA) is Compound 91. In certain embodiments, the compound of Formula (IA) is Compound 92. In certain embodiments, the compound of Formula (IA) is Compound 93. In certain embodiments, the compound of Formula (IA) is Compound 94. In certain embodiments, the compound of Formula (IA) is Compound 95. In certain embodiments, the compound of Formula (IA) is Compound 96. In certain embodiments, the compound of Formula (IA) is Compound 97. In certain embodiments, the compound of Formula (IA) is Compound 99. In certain embodiments, the compound of Formula (IA) is Compound 100.

In certain embodiments, the compound of Formula (IA) is Compound 101. In certain embodiments, the compound of Formula (IA) is Compound 102. In certain embodiments, the compound of Formula (IA) is Compound 103. In certain embodiments, the compound of Formula (IA) is Compound 105. In certain embodiments, the compound of Formula (IA) is Compound 106. In certain embodiments, the compound of Formula (IA) is Compound 107. In certain embodiments, the compound of Formula (IA) is Compound 108. In certain embodiments, the compound of Formula (IA) is Compound 109. In certain embodiments, the compound of Formula (IA) is Compound 110.

In certain embodiments, the compound of Formula (IA) is Compound 111. In certain embodiments, the compound of Formula (IA) is Compound 112. In certain embodiments, the compound of Formula (IA) is Compound 113.

In certain embodiments, the compound is not Compound 1. In certain embodiments, the compound is not Compound 49. In certain embodiments, the compound is not Compound 114.

LNP Compositions

The lipid compositions may be provided as LNP compositions. Lipid nanoparticles may be, e.g., microspheres (including unilamellar and multilamellar vesicles, e.g. "liposomes"-lamellar phase lipid bilayers that, in some embodiments are substantially spherical, and, in more particular embodiments can comprise an aqueous core, e.g., comprising a substantial portion of RNA molecules), a dispersed phase in an emulsion, micelles or an internal phase in a suspension.

The LNPs have a size of about 1 to about 1,000 nm, about 10 to about 500 nm, about 20 to about 500 nm, in a sub-embodiment about 50 to about 400 nm, in a sub-embodiment about 50 to about 300 nm, in a sub-embodiment about 50 to about 200 nm, and in a sub-embodiment about 50 to about 150 nm, and in another sub-embodiment about 60 to about 120 nm. Preferably, the LNPs have a size from about 60 nm to about 100 nm. The average sizes (diameters) of the fully formed LNP, may be measured by dynamic light scattering on a Malvern Zetasizer. The LNP sample is diluted in phosphate buffered saline (PBS) so that the count rate is approximately 200-400 kcps. The data is presented as a weighted average of the intensity measure.

Embodiments of the present disclosure provide lipid compositions described according to the respective molar ratios of the component lipids in the composition. All mol-% numbers are given as a fraction of the lipid component of the lipid composition or, more specifically, the LNP compositions. In certain embodiments, the mol-% of the compound of Formula (IA), (I), (II), or (III) may be from about 30 mol-% to about 70 mol-%. In certain embodiments, the mol-% of the compound of Formula (IA), (I), (II), or (III) may be at least 30 mol-%, at least 40 mol-%, at least 50 mol-%, or at least 60 mol-%.

In certain embodiments, the mol-% of the neutral lipid may be from about 0 mol-% to about 30 mol-%. In certain embodiments, the mol-% of the neutral lipid may be from about 0 mol-% to about 20 mol-%. In certain embodiments, the mol-% of the neutral lipid may be about 10 mol-%. In certain embodiments, the mol-% of the neutral lipid may be about 9 mol-%.

In certain embodiments, the mol-% of the helper lipid may be from about 0 mol-% to about 80 mol-%. In certain embodiments, the mol-% of the helper lipid may be from about 20 mol-% to about 60 mol-%. In certain embodiments, the mol-% of the helper lipid may be from about 30 mol-% to about 50 mol-%. In certain embodiments, the mol-% of the helper lipid may be from 30 mol-% to about 40 mol-% or from about 35% mol-% to about 45 mol-%. In certain embodiments, the mol-% of the helper lipid is adjusted based on compound of Formula (IA), (I), (II), or (III), neutral lipid, and/or PEG lipid concentrations to bring the lipid component to 100 mol-%.

In certain embodiments, the mol-% of the PEG lipid may be from about 1 mol-% to about 10 mol-%. In certain embodiments, the mol-% of the PEG lipid may be from about 1 mol-% to about 4 mol-%. In certain embodiments, the mol-% of the PEG lipid may be about 1 mol-% to about 2 mol-%. In certain embodiments, the mol-% of the PEG lipid may be about 1.5 mol-%.

In various embodiments, an LNP composition comprises a compound of Formula (IA), (I), (II), or (III) or a salt thereof (such as a pharmaceutically acceptable salt thereof (e.g., as disclosed herein)), a neutral lipid (e.g., DSPC), a helper lipid (e.g., cholesterol), and a PEG lipid (e.g., PEG2k-DMG). In some embodiments, an LNP composition comprises a compound of Formula (IA), (I), (II), or (III) or a pharmaceutically acceptable salt thereof (e.g., as disclosed herein), DSPC, cholesterol, and a PEG lipid. In some such embodiments, the LNP composition comprises a PEG lipid comprising DMG, such as PEG2k-DMG. In certain preferred embodiments, an LNP composition comprises a compound of Formula (IA), (I), (II), or (III) or a pharmaceutically acceptable salt thereof, cholesterol, DSPC, and PEG2k-DMG.

In certain embodiments, the lipid compositions, such as LNP compositions, comprise a lipid component and a nucleic acid component, e.g. an RNA component and the molar ratio of compound of Formula (IA), (I), (II), or (III) to nucleic acid can be measured. Embodiments of the present disclosure also provide lipid compositions having a defined molar ratio between the positively charged amine groups of pharmaceutically acceptable salts of the compounds of Formula (IA), (I), (II), or (III) (N) and the negatively charged phosphate groups (P) of the nucleic acid to be encapsulated. This may be mathematically represented by the equation N/P. In some embodiments, a lipid composition, such as an LNP composition, may comprise a lipid component that comprises a compound of Formula (IA), (I), (II), or (III) or a pharmaceutically acceptable salt thereof; and a nucleic acid component, wherein the N/P ratio is about 3 to 10. In some embodiments, an LNP composition may comprise a lipid component that comprises a compound of Formula (IA), (I), (II), or (III) or a pharmaceutically acceptable salt thereof; and an RNA component, wherein the N/P ratio is about 3 to 10. For example, the N/P ratio may be about 4-7. Alternatively, the N/P ratio may about 6, e.g., 6±1, or 6±0.5.

In some embodiments, the aqueous component comprises a biologically active agent. In some embodiments, the aqueous component comprises a polypeptide, optionally in combination with a nucleic acid. In some embodiments, the aqueous component comprises a nucleic acid, such as an RNA. In some embodiments, the aqueous component is a nucleic acid component. In some embodiments, the nucleic acid component comprises DNA and it can be called a DNA component. In some embodiments, the nucleic acid component comprises RNA and it can be called an RNA component. In some embodiments, the aqueous component, such as an RNA component may comprise an mRNA, such as an mRNA encoding an RNA-guided DNA binding agent. In some embodiments, the RNA-guided DNA binding agent is a Cas nuclease. In certain embodiments, aqueous component may comprise an mRNA that encodes Cas9. In certain embodiments, the aqueous component may comprise a gRNA. In some compositions comprising an mRNA encoding an RNA-guided DNA binding agent, the composition further comprises a gRNA nucleic acid, such as a gRNA. In some embodiments, the aqueous component comprises an RNA-guided DNA binding agent and a gRNA. In some embodiments, the aqueous component comprises a Cas nuclease mRNA and a gRNA. In some embodiments, the aqueous component comprises a Class 2 Cas nuclease mRNA and a gRNA.

In certain embodiments, a lipid composition, such as an LNP composition, may comprise an mRNA encoding a Cas nuclease such as a Class 2 Cas nuclease, a compound of Formula (IA), (I), (II), or (III) or a pharmaceutically acceptable salt thereof, a helper lipid, optionally a neutral lipid, and a PEG lipid. In certain compositions comprising an mRNA encoding a Cas nuclease such as a Class 2 Cas nuclease, the helper lipid is cholesterol. In other compositions comprising an mRNA encoding a Cas nuclease such as a Class 2 Cas nuclease, the neutral lipid is DSPC. In additional embodiments comprising an mRNA encoding a Cas nuclease such as a Class 2 Cas nuclease, e.g. Cas9, the PEG lipid is PEG2k-DMG. In specific compositions comprising an mRNA encoding a Cas nuclease such as a Class 2 Cas nuclease, and a compound of Formula (IA), (I), (II), or (III) or a pharmaceutically acceptable salt thereof. In certain compositions, the composition further comprises a gRNA, such as a dgRNA or an sgRNA.

In some embodiments, a lipid composition, such as an LNP composition, may comprise a gRNA. In certain embodiments, a composition may comprise a compound of Formula (IA), (I), (II), or (III) or a pharmaceutically acceptable salt thereof, a gRNA, a helper lipid, optionally a neutral lipid, and a PEG lipid. In certain LNP compositions comprising a gRNA, the helper lipid is cholesterol. In some compositions comprising a gRNA, the neutral lipid is DSPC. In additional embodiments comprising a gRNA, the PEG lipid is PEG2k-DMG. In certain compositions, the gRNA is selected from dgRNA and sgRNA.

In certain embodiments, a lipid composition, such as an LNP composition, comprises an mRNA encoding an RNA-guided DNA binding agent and a gRNA, which may be an sgRNA, in an aqueous component and a compound of Formula (IA), (I), (II), or (III) in a lipid component. For example, an LNP composition may comprise a compound of Formula (IA), (I), (II), or (III) or a pharmaceutically acceptable salt thereof, an mRNA encoding a Cas nuclease, a gRNA, a helper lipid, a neutral lipid, and a PEG lipid. In certain compositions comprising an mRNA encoding a Cas nuclease and a gRNA, the helper lipid is cholesterol. In some compositions comprising an mRNA encoding a Cas nuclease and a gRNA, the neutral lipid is DSPC. In additional embodiments comprising an mRNA encoding a Cas nuclease and a gRNA, the PEG lipid is PEG2k-DMG.

In certain embodiments, the lipid compositions, such as LNP compositions include an RNA-guided DNA binding agent, such as a Class 2 Cas mRNA and at least one gRNA. In certain embodiments, the LNP composition includes a ratio of gRNA to RNA-guided DNA binding agent mRNA, such as Class 2 Cas nuclease mRNA of about 1:1 or about 1:2. In some embodiments, the ratio is from about 25:1 to about 1:25, from about 10:1 to about 1:10, from about 8:1 to about 1:8, from about 4:1 to about 1:4, or from about 2:1 to about 1:2.

The lipid compositions disclosed herein, such as LNP compositions, may include a template nucleic acid, e.g. a DNA template. The template nucleic acid may be delivered with, or separately from the lipid compositions comprising a compound of Formula (IA), (I), (II), or (III) or a pharmaceutically acceptable salt thereof, including as LNP compositions. In some embodiments, the template nucleic acid may be single- or double-stranded, depending on the desired repair mechanism. The template may have regions of homology to the target DNA, e.g. within the target DNA sequence, and/or to sequences adjacent to the target DNA.

In some embodiments, LNPs are formed by mixing an aqueous RNA solution with an organic solvent-based lipid solution. Suitable solutions or solvents include or may contain: water, PBS, Tris buffer, NaCl, citrate buffer, acetate buffer, ethanol, chloroform, diethylether, cyclohexane, tetrahydrofuran, methanol, isopropanol. For example, the organic solvent may be 100% ethanol. A pharmaceutically acceptable buffer, e.g., for in vivo administration of LNPs, may be used. In certain embodiments, a buffer is used to maintain the pH of the composition comprising LNPs at or above pH 6.5. In certain embodiments, a buffer is used to maintain the pH of the composition comprising LNPs at or above pH 7.0. In certain embodiments, the composition has a pH ranging from about 7.2 to about 7.7. In additional embodiments, the composition has a pH ranging from about 7.3 to about 7.7 or ranging from about 7.4 to about 7.6. In further embodiments, the composition has a pH of about 7.2, 7.3, 7.4, 7.5, 7.6, or 7.7. The pH of a composition may be measured with a micro pH probe. In certain embodiments, a cryoprotectant is included in the composition. Non-limiting examples of cryoprotectants include sucrose, trehalose, glycerol, DMSO, and ethylene glycol. Exemplary compositions may include up to 10% cryoprotectant, such as, for example, sucrose. In certain embodiments, the composition may comprise tris saline sucrose (TSS). In certain embodiments, the LNP composition may include about 1, 2, 3, 4, 5, 6, 7, 8, 9, or 10% cryoprotectant. In certain embodiments, the LNP composition may include about 1, 2, 3, 4, 5, 6, 7, 8, 9, or 10% sucrose. In some embodiments, the LNP composition may include a buffer. In some embodiments, the buffer may comprise a phosphate buffer (PBS), a Tris buffer, a citrate buffer, and mixtures thereof. In certain exemplary embodiments, the buffer comprises NaCl. In certain embodiments, the buffer lacks NaCl. Exemplary amounts of NaCl may range from about 20 mM to about 45 mM. Exemplary amounts of NaCl may range from about 40 mM to about 50 mM. In some embodiments, the amount of NaCl is about 45 mM. In some embodiments, the buffer is a Tris buffer. Exemplary amounts of Tris may range from about 20 mM to about 60 mM. Exemplary amounts of Tris may range from about 40 mM to about 60 mM.

In some embodiments, the amount of Tris is about 50 mM. In some embodiments, the buffer comprises NaCl and Tris. Certain exemplary embodiments of the LNP compositions contain 5% sucrose and 45 mM NaCl in Tris buffer. In other exemplary embodiments, compositions contain sucrose in an amount of about 5% w/v, about 45 mM NaCl, and about 50 mM Tris at pH 7.5. The salt, buffer, and cryoprotectant amounts may be varied such that the osmolality of the overall composition is maintained. For example, the final osmolality may be maintained at less than 450 mOsm/L. In further embodiments, the osmolality is between 350 and 250 mOsm/L. Certain embodiments have a final osmolality of 300+/−20 mOsm/L or 310+/−40 mOsm/L.

In some embodiments, microfluidic mixing, T-mixing, or cross-mixing of the aqueous RNA solution and the lipid solution in an organic solvent is used. In certain aspects, flow rates, junction size, junction geometry, junction shape, tube diameter, solutions, and/or RNA and lipid concentrations may be varied. LNPs or LNP compositions may be concentrated or purified, e.g., via dialysis, centrifugal filter, tangential flow filtration, or chromatography. The LNPs may be stored as a suspension, an emulsion, or a lyophilized powder, for example. In some embodiments, an LNP composition is stored at 2-8° C., in certain aspects, the LNP compositions are stored at room temperature. In additional embodiments, an LNP composition is stored frozen, for example at −20° C. or −80° C. In other embodiments, an LNP composition is stored at a temperature ranging from about 0° C. to about −80° C. Frozen LNP compositions may be thawed before use, for example on ice, at room temperature, or at 25° C.

The LNPs may be, e.g., microspheres (including unilamellar and multilamellar vesicles, e.g., "liposomes"—lamellar phase lipid bilayers that, in some embodiments, are substantially spherical—and, in more particular embodiments, can comprise an aqueous core, e.g., comprising a substantial portion of RNA molecules), a dispersed phase in an emulsion, micelles, or an internal phase in a suspension.

Preferred lipid compositions, such as LNP compositions, are biodegradable, in that they do not accumulate to cytotoxic levels in vivo at a therapeutically effective dose. In some embodiments, the compositions do not cause an innate immune response that leads to substantial adverse effects at a therapeutic dose level. In some embodiments, the compositions provided herein do not cause toxicity at a therapeutic dose level.

In some embodiments, the LNPs disclosed herein have a polydispersity index (PDI) that may range from about 0.005 to about 0.75. In some embodiments, the LNP have a PDI that may range from about 0.01 to about 0.5. In some embodiments, the LNP have a PDI that may range from about zero to about 0.4. In some embodiments, the LNP have a PDI that may range from about zero to about 0.35. In some embodiments, the LNP have a PDI that may range from about zero to about 0.35. In some embodiments, the LNP PDI may range from about zero to about 0.3. In some embodiments, the LNP have a PDI that may range from about zero to about 0.25. In some embodiments, the LNP PDI may range from about zero to about 0.2. In some embodiments, the LNP have a PDI that may be less than about 0.08, 0.1, 0.15, 0.2, or 0.4.

The LNPs disclosed herein have a size (e.g. Z-average diameter) of about 1 to about 250 nm. In some embodiments, the LNPs have a size of about 10 to about 200 nm. In further embodiments, the LNPs have a size of about 20 to about 150 nm. In some embodiments, the LNPs have a size of about 50 to about 150 nm. In some embodiments, the LNPs have a size of about 50 to about 100 nm. In some embodiments, the LNPs have a size of about 50 to about 120 nm. In some embodiments, the LNPs have a size of about 60 to about 100 nm. In some embodiments, the LNPs have a size of about 75 to about 150 nm.

In some embodiments, the LNPs have a size of about 75 to about 120 nm. In some embodiments, the LNPs have a size of about 75 to about 100 nm. Unless indicated otherwise, all sizes referred to herein are the average sizes (diameters) of the fully formed nanoparticles, as measured by dynamic light scattering on a Malvern Zetasizer. The nanoparticle sample is diluted in phosphate buffered saline (PBS) so that the count rate is approximately 200-400 kcps. The data is presented as a weighted-average of the intensity measure (Z-average diameter).

In some embodiments, the LNPs are formed with an average encapsulation efficiency ranging from about 50% to about 100%. In some embodiments, the LNPs are formed with an average encapsulation efficiency ranging from about 50% to about 95%. In some embodiments, the LNPs are formed with an average encapsulation efficiency ranging from about 70% to about 90%. In some embodiments, the LNPs are formed with an average encapsulation efficiency ranging from about 90% to about 100%. In some embodiments, the LNPs are formed with an average encapsulation efficiency ranging from about 75% to about 95%.

Cargo

The cargo delivered via LNP composition may be a biologically active agent. In certain embodiments, the cargo is or comprises one or more biologically active agent, such as mRNA, guide RNA, nucleic acid, expression vector, template nucleic acid, RNA-guided DNA binding agent, antibody (e.g., monoclonal, chimeric, humanized, nanobody, and fragments thereof etc.), cholesterol, hormone, peptide, protein, chemotherapeutic and other types of antineoplastic agent, low molecular weight drug, vitamin, cofactor, nucleoside, nucleotide, oligonucleotide, enzymatic nucleic acid, antisense nucleic acid, triplex forming oligonucleotide, antisense DNA or RNA composition, chimeric DNA:RNA composition, allozyme, aptamer, ribozyme, decoys and analogs thereof, plasmid and other types of vectors, and small nucleic acid molecule, RNAi agent, short interfering nucleic acid (siNA), short interfering RNA (siRNA), double-stranded RNA (dsRNA), micro-RNA (miRNA), short hairpin RNA (shRNA) and "self-replicating RNA" (encoding a replicase enzyme activity and capable of directing its own replication or amplification in vivo) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), and iRNA (asymmetrical interfering RNA). The above list of biologically active agents is exemplary only, and is not intended to be limiting. Such compounds may be purified or partially purified, and may be naturally occurring or synthetic, and may be chemically modified.

The cargo delivered via LNP composition may be an RNA, such as an mRNA molecule encoding a protein of interest. For example, an mRNA for expressing a protein such as green fluorescent protein (GFP), an RNA-guided DNA binding agent, or a Cas nuclease is included. LNP compositions that include a Cas nuclease mRNA, for example a Class 2 Cas nuclease mRNA that allows for expression in a cell of a Class 2 Cas nuclease such as a Cas9 or Cpf1 protein are provided. Further, the cargo may contain one or more guide RNAs or nucleic acids encoding guide RNAs. A template nucleic acid, e.g., for repair or recombination, may also be included in the composition or a template nucleic acid may be used in the methods described herein. In a sub-embodiment, the cargo comprises an mRNA that encodes a *Streptococcus pyogenes* Cas9, optionally and an *S. pyogenes* gRNA. In a further sub-embodiment, the cargo comprises an mRNA that encodes a *Neisseria meningitidis* Cas9, optionally and an nme gRNA.

"mRNA" refers to a polynucleotide and comprises an open reading frame that can be translated into a polypeptide (i.e., can serve as a substrate for translation by a ribosome and amino-acylated tRNAs). mRNA can comprise a phosphate-sugar backbone including ribose residues or analogs thereof, e.g., 2'-methoxy ribose residues. In some embodiments, the sugars of an mRNA phosphate-sugar backbone consist essentially of ribose residues, 2'-methoxy ribose residues, or a combination thereof. In general, mRNAs do not contain a substantial quantity of thymidine residues (e.g., 0 residues or fewer than 30, 20, 10, 5, 4, 3, or 2 thymidine residues; or less than 10%, 9%, 8%, 7%, 6%, 5%, 4%, 4%, 3%, 2%, 1%, 0.5%, 0.2%, or 0.1% thymidine content). An mRNA can contain modified uridines at some or all of its uridine positions.

CRISPR/Cas Cargo

In certain embodiments, the disclosed compositions comprise an mRNA encoding an RNA-guided DNA binding agent, such as a Cas nuclease. In particular embodiments, the disclosed compositions comprise an mRNA encoding a Class 2 Cas nuclease, such as *S. pyogenes* Cas9.

As used herein, an "RNA-guided DNA binding agent" means a polypeptide or complex of polypeptides having RNA and DNA binding activity, or a DNA-binding subunit of such a complex, wherein the DNA binding activity is sequence-specific and depends on the sequence of the RNA. Exemplary RNA-guided DNA binding agents include Cas cleavases/nickases and inactivated forms thereof ("dCas DNA binding agents"). "Cas nuclease", as used herein, encompasses Cas cleavases, Cas nickases, and dCas DNA binding agents. Cas cleavases/nickases and dCas DNA binding agents include a Csm or Cmr complex of a type III CRISPR system, the Cas10, Csm1, or Cmr2 subunit thereof, a Cascade complex of a type I CRISPR system, the Cas3 subunit thereof, and Class 2 Cas nucleases. As used herein, a "Class 2 Cas nuclease" is a single-chain polypeptide with RNA-guided DNA binding activity. Class 2 Cas nucleases include Class 2 Cas cleavases/nickases (e.g., H840A, D10A, or N863A variants), which further have RNA-guided DNA cleavases or nickase activity, and Class 2 dCas DNA binding agents, in which cleavase/nickase activity is inactivated. Class 2 Cas nucleases include, for example, Cas9, Cpf1, C2c1, C2c2, C2c3, HF Cas9 (e.g., N497A, R661A, Q695A, Q926A variants), HypaCas9 (e.g., N692A, M694A, Q695A, H698A variants), eSPCas9(1.0) (e.g, K810A, K1003A, R1060A variants), and eSPCas9(1.1) (e.g., K848A, K1003A, R1060A variants) proteins and modifications thereof. Cpf1 protein, Zetsche et al., Cell, 163: 1-13 (2015), is homologous to Cas9, and contains a RuvC-like nuclease domain. Cpf1 sequences of Zetsche are incorporated by reference in their entirety. See, e.g., Zetsche, Tables Si and S3. See, e.g., Makarova et al., *Nat Rev Microbiol*, 13(11): 722-36 (2015); Shmakov et al., *Molecular Cell*, 60:385-397 (2015).

As used herein, "ribonucleoprotein" (RNP) or "RNP complex" refers to a guide RNA together with an RNA-guided DNA binding agent, such as a Cas nuclease, e.g., a Cas cleavase, Cas nickase, or dCas DNA binding agent (e.g., Cas9). In some embodiments, the guide RNA guides the RNA-guided DNA binding agent such as Cas9 to a target sequence, and the guide RNA hybridizes with and the agent binds to the target sequence; in cases where the agent is a cleavase or nickase, binding can be followed by cleaving or nicking.

In some embodiments of the present disclosure, the cargo for the LNP composition includes at least one guide RNA comprising guide sequences that direct an RNA-guided DNA binding agent, which can be a nuclease (e.g., a Cas nuclease such as Cas9), to a target DNA. The gRNA may guide the Cas nuclease or Class 2 Cas nuclease to a target sequence on a target nucleic acid molecule. In some embodiments, a gRNA binds with and provides specificity of cleavage by a Class 2 Cas nuclease. In some embodiments, the gRNA and the Cas nuclease may form a ribonucleoprotein (RNP), e.g., a CRISPR/Cas complex such as a CRISPR/Cas9 complex. In some embodiments, the CRISPR/Cas complex may be a Type-II CRISPR/Cas9 complex. In some embodiments, the CRISPR/Cas complex may be a Type-V CRISPR/Cas complex, such as a Cpf1/guide RNA complex. Cas nucleases and cognate gRNAs may be paired. The gRNA scaffold structures that pair with each Class 2 Cas nuclease vary with the specific CRISPR/Cas system.

"Guide RNA", "gRNA", and simply "guide" are used herein interchangeably to refer to a cognate guide nucleic acid for an RNA-guided DNA binding agent. A gRNA may be either a crRNA (also known as CRISPR RNA), or the combination of a crRNA and a trRNA (also known as tracrRNA). Guide RNAs can include modified RNAs as described herein. The crRNA and trRNA may be associated as a single RNA molecule (single guide RNA, sgRNA) or in two separate RNA molecules (dual guide RNA, dgRNA). "Guide RNA" or "gRNA" refers to each type. The trRNA may be a naturally-occurring sequence, or a trRNA sequence with modifications or variations compared to naturally-occurring sequences.

As used herein, a "guide sequence" refers to a sequence within a guide RNA that is complementary to a target sequence and functions to direct a guide RNA to a target sequence for binding or modification (e.g., cleavage) by an RNA-guided DNA binding agent. A "guide sequence" may also be referred to as a "targeting sequence," or a "spacer sequence." A guide sequence can be 20 base pairs in length, e.g., in the case of *Streptococcus pyogenes* (i.e., Spy Cas9) and related Cas9 homologs/orthologs. Shorter or longer sequences can also be used as guides, e.g., 15-, 16-, 17-, 18-, 19-, 21-, 22-, 23-, 24-, or 25-nucleotides in length. In some embodiments, the target sequence is in a gene or on a chromosome, for example, and is complementary to the guide sequence. In some embodiments, the degree of complementarity or identity between a guide sequence and its corresponding target sequence may be about or at least 75%, 80%, 85%, 90%, 95%, 96%, 97%, 98%, 99%, or 100%. In some embodiments, the guide sequence and the target region may be 100% complementary or identical over a region of at least 15, 16, 17, 18, 19, or 20 contiguous nucleotides. In other embodiments, the guide sequence and the target region may contain at least one mismatch. For example, the guide sequence and the target sequence may contain 1, 2, 3, or 4 mismatches, where the total length of the target sequence is at least 17, 18, 19, 20 or more base pairs. In some embodiments, the guide sequence and the target region may contain 1-4 mismatches where the guide sequence comprises at least 17, 18, 19, 20 or more nucleotides. In some embodiments, the guide sequence and the target region may contain 1, 2, 3, or 4 mismatches where the guide sequence comprises 20 nucleotides.

Target sequences for RNA-guided DNA binding proteins such as Cas proteins include both the positive and negative strands of genomic DNA (i.e., the sequence given and the sequence's reverse compliment), as a nucleic acid substrate for a Cas protein is a double stranded nucleic acid. Accordingly, where a guide sequence is said to be "complementary to a target sequence", it is to be understood that the guide sequence may direct a gRNA to bind to the reverse complement of a target sequence. Thus, in some embodiments, where the guide sequence binds the reverse complement of a target sequence, the guide sequence is identical to certain nucleotides of the target sequence (e.g., the target sequence not including the PAM) except for the substitution of U for T in the guide sequence.

The length of the targeting sequence may depend on the CRISPR/Cas system and components used. For example, different Class 2 Cas nucleases from different bacterial species have varying optimal targeting sequence lengths. Accordingly, the targeting sequence may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the targeting sequence length is 0, 1, 2, 3, 4, or 5 nucleotides longer or shorter than the guide sequence of a naturally-occurring CRISPR/Cas system. In certain embodiments, the Cas nuclease and gRNA scaffold will be derived from the same CRISPR/Cas system. In some embodiments, the targeting sequence may comprise or consist of 18-24 nucleotides. In some embodiments, the targeting sequence may comprise or consist of 19-21 nucleotides. In some embodiments, the targeting sequence may comprise or consist of 20 nucleotides.

In some embodiments, the sgRNA is a "Cas9 sgRNA" capable of mediating RNA-guided DNA cleavage by a Cas9 protein. In some embodiments, the sgRNA is a "Cpf1 sgRNA" capable of mediating RNA-guided DNA cleavage by a Cpf1 protein. In certain embodiments, the gRNA comprises a crRNA and tracr RNA sufficient for forming an active complex with a Cas9 protein and mediating RNA-guided DNA cleavage. In certain embodiments, the gRNA comprises a crRNA sufficient for forming an active complex with a Cpf1 protein and mediating RNA-guided DNA cleavage. See Zetsche 2015.

Certain embodiments of the disclosure also provide nucleic acids, e.g., expression cassettes, encoding the gRNA described herein. A "guide RNA nucleic acid" is used herein to refer to a guide RNA (e.g. an sgRNA or a dgRNA) and a guide RNA expression cassette, which is a nucleic acid that encodes one or more guide RNAs.

Modified RNAs

In certain embodiments, the lipid compositions, such as LNP compositions comprise modified nucleic acids, including modified RNAs.

Modified nucleosides or nucleotides can be present in an RNA, for example a gRNA or mRNA. A gRNA or mRNA comprising one or more modified nucleosides or nucleotides, for example, is called a "modified" RNA to describe the presence of one or more non-naturally and/or naturally occurring components or configurations that are used instead of or in addition to the canonical A, G, C, and U residues. In some embodiments, a modified RNA is synthesized with a non-canonical nucleoside or nucleotide, here called "modified."

Modified nucleosides and nucleotides can include one or more of: (i) alteration, e.g., replacement, of one or both of the non-linking phosphate oxygens and/or of one or more of the linking phosphate oxygens in the phosphodiester backbone linkage (an exemplary backbone modification); (ii) alteration, e.g., replacement, of a constituent of the ribose sugar, e.g., of the 2' hydroxyl on the ribose sugar (an exemplary sugar modification); (iii) wholesale replacement of the phosphate moiety with "dephospho" linkers (an exemplary backbone modification); (iv) modification or replacement of a naturally occurring nucleobase, including with a non-canonical nucleobase (an exemplary base modification); (v) replacement or modification of the ribose-phosphate backbone (an exemplary backbone modification); (vi) modification of the 3' end or 5' end of the oligonucleotide, e.g., removal, modification or replacement of a terminal phosphate group or conjugation of a moiety, cap or linker (such 3' or 5' cap modifications may comprise a sugar and/or backbone modification); and (vii) modification or replacement of the sugar (an exemplary sugar modification).

Certain embodiments comprise a modification to an mRNA, gRNA, or nucleic acid. Certain embodiments comprise a 5' end modification to an mRNA, gRNA, or nucleic acid. Certain embodiments comprise a 3' end modification to an mRNA, gRNA, or nucleic acid. A modified RNA can contain 5' end and 3' end modifications. A modified RNA can contain one or more modified residues at non-terminal locations. In certain embodiments, a gRNA includes at least one modified residue. In certain embodiments, an mRNA includes at least one modified residue.

Unmodified nucleic acids can be prone to degradation by, e.g., intracellular nucleases or those found in serum. For example, nucleases can hydrolyze nucleic acid phosphodiester bonds. Accordingly, in one aspect the RNAs (e.g. mRNAs, gRNAs) described herein can contain one or more modified nucleosides or nucleotides, e.g., to introduce stability toward intracellular or serum-based nucleases. In some embodiments, the modified gRNA molecules described herein can exhibit a reduced innate immune response when introduced into a population of cells, both in vivo and ex vivo. The term "innate immune response" includes a cellular response to exogenous nucleic acids, including single stranded nucleic acids, which involves the induction of cytokine expression and release, particularly the interferons, and cell death.

Accordingly, in some embodiments, the RNA or nucleic acid in the disclosed LNP compositions comprises at least one modification which confers increased or enhanced stability to the nucleic acid, including, for example, improved resistance to nuclease digestion in vivo. As used herein, the terms "modification" and "modified" as such terms relate to the nucleic acids provided herein, include at least one alteration which preferably enhances stability and renders the RNA or nucleic acid more stable (e.g., resistant to nuclease digestion) than the wild-type or naturally occurring version of the RNA or nucleic acid. As used herein, the terms "stable" and "stability" as such terms relate to the nucleic acids of the present disclosure, and particularly with respect to the RNA, refer to increased or enhanced resistance to degradation by, for example nucleases (i.e., endonucleases or exonucleases) which are normally capable of degrading such RNA. Increased stability can include, for example, less sensitivity to hydrolysis or other destruction by endogenous enzymes (e.g., endonucleases or exonucleases) or conditions within the target cell or tissue, thereby increasing or enhancing the residence of such RNA or nucleic acid in the target cell, tissue, subject and/or cytoplasm. The stabilized RNA or nucleic acid molecules provided herein demonstrate longer half-lives relative to their naturally occurring, unmodified counterparts (e.g. the wild-type version of the mRNA). Also contemplated by the terms "modification" and "modified" as such terms related to the mRNA of the LNP compositions disclosed herein are alterations which improve or enhance translation of mRNA nucleic acids, including for example, the inclusion of sequences which function in the initiation of protein translation (e.g., the Kozak consensus sequence). (Kozak, M., Nucleic Acids Res 15 (20): 8125-48 (1987)).

In some embodiments, an RNA or nucleic acid of the LNP compositions disclosed herein has undergone a chemical or biological modification to render it more stable. Exemplary modifications to an RNA, such as an mRNA, include the depletion of a base (e.g., by deletion or by the substitution of one nucleotide for another) or modification of a base, for example, the chemical modification of a base. The phrase "chemical modifications" as used herein, includes modifications which introduce chemistries which differ from those seen in naturally occurring RNA or nucleic acids, for example, covalent modifications such as the introduction of modified nucleotides, (e.g., nucleotide analogs, or the inclusion of pendant groups which are not naturally found in such RNA or nucleic acid molecules).

In some embodiments of a backbone modification, the phosphate group of a modified residue can be modified by replacing one or more of the oxygens with a different substituent. Further, the modified residue, e.g., modified residue present in a modified nucleic acid, can include the wholesale replacement of an unmodified phosphate moiety with a modified phosphate group as described herein. In some embodiments, the backbone modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. The phosphorous atom in an unmodified phosphate group is achiral. However, replacement of one of the non-bridging oxygens with one of the above atoms or groups of atoms can render the phosphorous atom chiral. The stereogenic phosphorous atom can possess either the "R" configuration (herein Rp) or the "S" configuration (herein Sp). The backbone can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens. The phosphate group can be replaced by non-phosphorus containing connectors in certain backbone modifications. In some embodiments, the charged phosphate group can be replaced by a neutral moiety. Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

mRNA

In some embodiments, a composition or formulation disclosed herein comprises an mRNA comprising an open reading frame (ORF) encoding an RNA-guided DNA binding agent, such as a Cas nuclease, or Class 2 Cas nuclease as described herein. In some embodiments, an mRNA comprising an ORF encoding an RNA-guided DNA binding agent, such as a Cas nuclease or Class 2 Cas nuclease, is provided, used, or administered. An mRNA may comprise one or more of a 5' cap, a 5' untranslated region (UTR), a 3' UTRs, and a polyadenine tail. The mRNA may comprise a modified open reading frame, for example to encode a nuclear localization sequence or to use alternate codons to encode the protein.

The mRNA in the disclosed LNP compositions may encode, for example, a secreted hormone, enzyme, receptor, polypeptide, peptide or other protein of interest that is normally secreted. In one embodiment, the mRNA may optionally have chemical or biological modifications which, for example, improve the stability and/or half-life of such mRNA or which improve or otherwise facilitate protein production.

In addition, suitable modifications include alterations in one or more nucleotides of a codon such that the codon encodes the same amino acid but is more stable than the codon found in the wild-type version of the mRNA. For example, an inverse relationship between the stability of RNA and a higher number cytidines (C's) and/or uridines (U's) residues has been demonstrated, and RNA devoid of C and U residues have been found to be stable to most RNases (Heidenreich, et al. J Biol Chem 269, 2131-8 (1994)). In some embodiments, the number of C and/or U residues in an mRNA sequence is reduced. In another embodiment, the number of C and/or U residues is reduced by substitution of one codon encoding a particular amino acid for another codon encoding the same or a related amino acid. Contemplated modifications to the mRNA nucleic acids also include the incorporation of pseudouridines. The incorporation of pseudouridines into the mRNA nucleic may enhance stability and translational capacity, as well as diminishing immunogenicity in vivo. See, e.g., Karikó, K., et al., Molecular Therapy 16 (11): 1833-1840 (2008). Substitutions and modifications to the mRNA may be performed by methods readily known to one or ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible).

The term modification also includes, for example, the incorporation of non-nucleotide linkages or modified nucleotides into the mRNA sequences (e.g., modifications to one or both the 3' and 5' ends of an mRNA molecule encoding a functional secreted protein or enzyme). Such modifications include the addition of bases to an mRNA sequence (e.g., the inclusion of a poly A tail or a longer poly A tail), the alteration of the 3' UTR or the 5' UTR, complexing the mRNA with an agent (e.g., a protein or a complementary nucleic acid molecule), and inclusion of elements which change the structure of an mRNA molecule (e.g., which form secondary structures).

The poly A tail is thought to stabilize natural messengers. Therefore, in one embodiment a long poly A tail can be added to an mRNA molecule thus rendering the mRNA more stable. Poly A tails can be added using a variety of art-recognized techniques. For example, long poly A tails can be added to synthetic or in vitro transcribed mRNA using poly A polymerase (Yokoe, et al. Nature Biotechnology. 1996; 14: 1252-1256). A transcription vector can also encode long poly A tails. In addition, poly A tails can be added by transcription directly from PCR products. In one embodiment, the length of the poly A tail is at least about 90, 200, 300, 400 at least 500 nucleotides. In one embodiment, the length of the poly A tail is adjusted to control the stability of a modified mRNA molecule and, thus, the transcription of protein. For example, since the length of the poly A tail can influence the half-life of an mRNA molecule, the length of the poly A tail can be adjusted to modify the level of resistance of the mRNA to nucleases and thereby control the time course of protein expression in a cell. In one embodiment, the stabilized mRNA molecules are sufficiently resistant to in vivo degradation (e.g., by nucleases), such that they may be delivered to the target cell without a transfer vehicle.

In one embodiment, an mRNA can be modified by the incorporation 3' and/or 5' untranslated (UTR) sequences which are not naturally found in the wild-type mRNA. In one embodiment, 3' and/or 5' flanking sequence which naturally flanks an mRNA and encodes a second, unrelated protein can be incorporated into the nucleotide sequence of an mRNA molecule encoding a therapeutic or functional protein in order to modify it. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA nucleic acid molecule to increase the stability of the sense mRNA molecule. See, e.g., US2003/0083272.

More detailed descriptions of the mRNA modifications can be found in US2017/0210698A1, at pages 57-68, which content is incorporated herein.

Template Nucleic Acid

The compositions and methods disclosed herein may include a template nucleic acid. The template may be used to alter or insert a nucleic acid sequence at or near a target site for an RNA-guided DNA binding protein such as a Cas nuclease, e.g., a Class 2 Cas nuclease. In some embodiments, the methods comprise introducing a template to the cell. In some embodiments, a single template may be provided. In other embodiments, two or more templates may be provided such that editing may occur at two or more target sites. For example, different templates may be provided to edit a single gene in a cell, or two different genes in a cell.

In some embodiments, the template may be used in homologous recombination. In some embodiments, the homologous recombination may result in the integration of the template sequence or a portion of the template sequence into the target nucleic acid molecule. In other embodiments, the template may be used in homology-directed repair, which involves DNA strand invasion at the site of the cleavage in the nucleic acid. In some embodiments, the homology-directed repair may result in including the template sequence in the edited target nucleic acid molecule. In yet other embodiments, the template may be used in gene editing mediated by non-homologous end joining. In some embodiments, the template sequence has no similarity to the nucleic acid sequence near the cleavage site. In some embodiments, the template or a portion of the template sequence is incorporated. In some embodiments, the template includes flanking inverted terminal repeat (ITR) sequences.

In some embodiments, the template sequence may correspond to, comprise, or consist of an endogenous sequence of a target cell. It may also or alternatively correspond to, comprise, or consist of an exogenous sequence of a target cell. As used herein, the term "endogenous sequence" refers to a sequence that is native to the cell. The term "exogenous sequence" refers to a sequence that is not native to a cell, or a sequence whose native location in the genome of the cell is in a different location. In some embodiments, the endogenous sequence may be a genomic sequence of the cell. In some embodiments, the endogenous sequence may be a chromosomal or extrachromosomal sequence. In some embodiments, the endogenous sequence may be a plasmid sequence of the cell.

In some embodiments, the template contains ssDNA or dsDNA containing flanking invert-terminal repeat (ITR) sequences. In some embodiments, the template is provided as a vector, plasmid, minicircle, nanocircle, or PCR product.

In some embodiments, the nucleic acid is purified. In some embodiments, the nucleic acid is purified using a precipitation method (e.g., LiCl precipitation, alcohol precipitation, or an equivalent method, e.g., as described herein). In some embodiments, the nucleic acid is purified using a chromatography-based method, such as an HPLC-based method or an equivalent method (e.g., as described herein). In some embodiments, the nucleic acid is purified using both a precipitation method (e.g., LiCl precipitation) and an HPLC-based method. In some embodiments, the nucleic acid is purified by tangential flow filtration (TFF).

The compounds or compositions will generally, but not necessarily, include one or more pharmaceutically acceptable excipients. The term "excipient" includes any ingredient other than the compound(s) of the disclosure, the other lipid component(s) and the biologically active agent. An excipient may impart either a functional (e.g. drug release rate controlling) and/or a non-functional (e.g. processing aid or diluent) characteristic to the compositions. The choice of excipient will to a large extent depend on factors such as the particular mode of administration, the effect of the excipient on solubility and stability, and the nature of the dosage form.

Parenteral formulations are typically aqueous or oily solutions or suspensions. Where the formulation is aqueous, excipients such as sugars (including but not restricted to glucose, mannitol, sorbitol, etc.) salts, carbohydrates and buffering agents (preferably to a pH of 3 to 9), but, for some applications, they may be more suitably formulated with a sterile non-aqueous solution or as a dried form to be used in conjunction with a suitable vehicle such as sterile, pyrogen-free water (WFI).

While the inventions are described in conjunction with the illustrated embodiments, it is understood that they are not intended to limit the inventions to those embodiments. On the contrary, the inventions are intended to cover all alternatives, modifications, and equivalents, including equivalents of specific features, which may be included within the inventions as defined by the appended claims.

Both the foregoing general description and detailed description, as well as the following examples, are exemplary and explanatory only and are not restrictive of the teachings. The section headings used herein are for organizational purposes only and are not to be construed as limiting the desired subject matter in any way. In the event that any literature incorporated by reference contradicts any term defined in this specification, this specification controls. All ranges given in the application encompass the endpoints unless stated otherwise.

Definitions

It should be noted that, as used in this application, the singular form "a", "an" and "the" include plural references unless the context clearly dictates otherwise. Thus, for example, reference to "a composition" includes a plurality of compositions and reference to "a cell" includes a plurality of cells and the like. The use of "or" is inclusive and means "and/or" unless stated otherwise.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; embodiments in the specification that recite "about" various components are also contemplated as "at" the recited components; and embodiments in the specification that recite "consisting essentially of" various components are also contemplated as "consisting of" or "comprising" the recited components (this interchangeability does not apply to the use of these terms in the claims).

Numeric ranges are inclusive of the numbers defining the range. Measured and measureable values are understood to be approximate, taking into account significant digits and the error associated with the measurement. As used in this application, the terms "about" and "approximately" have their art-understood meanings; use of one vs the other does not necessarily imply different scope. Unless otherwise indicated, numerals used in this application, with or without a modifying term such as "about" or "approximately", should be understood to encompass normal divergence and/or fluctuations as would be appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated reference value unless otherwise stated or otherwise evident from the context (except where such number would exceed 100% of a possible value).

As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of nanoparticle compositions. Moreover, more than one mammalian cell may be contacted by a nanoparticle composition.

As used herein, the term "delivering" means providing an entity to a destination. For example, delivering a therapeutic and/or prophylactic to a subject may involve administering a nanoparticle composition including the therapeutic and/or prophylactic to the subject (e.g., by an intravenous, intramuscular, intradermal, or subcutaneous route). Administration of a nanoparticle composition to a mammal or mammalian cell may involve contacting one or more cells with the nanoparticle composition.

As used herein, "encapsulation efficiency" refers to the amount of a therapeutic and/or prophylactic that becomes part of a nanoparticle composition, relative to the initial total amount of therapeutic and/or prophylactic used in the preparation of a nanoparticle composition. For example, if 97 mg of therapeutic and/or prophylactic are encapsulated in a nanoparticle composition out of a total 100 mg of therapeutic and/or prophylactic initially provided to the composition, the encapsulation efficiency may be given as 97%. As used herein, "encapsulation" may refer to complete, substantial, or partial enclosure, confinement, surrounding, or encasement.

As used herein, the term "biodegradable" is used to refer to materials that, when introduced into cells, are broken down by cellular machinery (e.g., enzymatic degradation) or by hydrolysis into components that cells can either reuse or dispose of without significant toxic effect(s) on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis.

As used herein, the "N/P ratio" is the molar ratio of ionizable (in the physiological pH range) nitrogen atoms in a lipid (e.g. Compound of Formula I) to phosphate groups in an RNA, e.g., in a nanoparticle composition including a lipid component and an RNA.

Compositions may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, the "polydispersity index" is a ratio that describes the homogeneity of the particle size distribution of a system. A small value, e.g., less than 0.3, indicates a narrow particle size distribution. In some embodiments, the polydispersity index may be less than 0.1.

As used herein, "transfection" refers to the introduction of a species (e.g., an RNA) into a cell. Transfection may occur, for example, in vitro, ex vivo, or in vivo.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched (i.e., linear). The alkyl group can also be substituted or unsubstituted (preferably unsubstituted). For example, the alkyl group can be substituted with one or more groups including, but not limited to, alkyl, cycloalkyl, alkoxy, amino, ether, halide, hydroxy, nitro, silyl, sulfoxo, sulfonate, carboxylate, or thiol, as described herein. A "lower alkyl" group is an alkyl group containing from one to six (e.g., from one to four) carbon atoms.

The term "alkenyl", as used herein, refers to an aliphatic group containing at least one carbon-carbon double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, an alkenyl group may be substituted by one or more alkyl, carbocyclyl, aryl, heterocyclyl, or heteroaryl groups is contemplated. Exemplary alkenyl groups include, but are not limited to, vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

An "alkylene" group refers to a divalent alkyl radical, which may be branched or unbranched (i.e., linear). Any of the above mentioned monovalent alkyl groups may be converted to an alkylene by abstraction of a second hydrogen atom from the alkyl. Representative alkylenes include C$_{2-4}$ alkylene and C$_{2-3}$ alkylene. Typical alkylene groups include, but are not limited to —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like. The alkylene group can also be substituted or unsubstituted. For example, the alkylene group can be substituted with one or more groups including, but not limited to, alkyl, aryl, heteroaryl, cycloalkyl, alkoxy, amino, ether, halide, hydroxy, nitro, silyl, sulfoxo, sulfonate, sulfonamide, urea, amide, carbamate, ester, carboxylate, or thiol, as described herein.

The term "alkenylene" includes divalent, straight or branched, unsaturated, acyclic hydrocarbyl groups having at least one carbon-carbon double bond and, in one embodiment, no carbon-carbon triple bonds. Any of the above-mentioned monovalent alkenyl groups may be converted to an alkenylene by abstraction of a second hydrogen atom from the alkenyl. Representative alkenylenes include C$_{2-6}$alkenylenes. The term "C$_{x-y}$" when used in conjunction with a chemical moiety, such as alkyl or alkylene, is meant to include groups that contain from x to y carbons in the chain. For example, the term "C$_{x-y}$ alkyl" refers to substituted or unsubstituted saturated hydrocarbon groups, including straight-chain and branched-chain alkyl and alkylene groups that contain from x to y carbons in the chain.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicant reserves the right to physically incorporate into this application any and all materials and information from any such articles, patents, patent applications, or other physical and electronic documents.

EXAMPLES

General Information

All reagents and solvents were purchased and used as received from commercial vendors or synthesized according to cited procedures. All intermediates and final compounds were purified using flash column chromatography on silica gel. NMR spectra were recorded on a Bruker or Varian 400 MHz spectrometer, and NMR data were collected in CDCl$_3$ at ambient temperature. Chemical shifts are reported in parts per million (ppm) relative to CDCl$_3$ (7.26). Data for $^1$H NMR are reported as follows: chemical shift, multiplicity (br=broad, s=singlet, d=doublet, t=triplet, dd=doublet of doublets, dt=doublet of triplets, q=quartet, m=multiplet, ddd=doublet of doublet of doublets, td=triplet of doublets, tt=triplet of triplets, tdd=triplet of doublet of doublets, dddd=doublet of doublet of doublet of doublets), coupling constant, and integration. MS data were recorded on a Waters SQD2 mass spectrometer with an electrospray ionization (ESI) source. Purity of the final compounds was determined by UPLC-MS-ELS using a Waters Acquity H-Class liquid chromatography instrument equipped with SQD2 mass spectrometer with photodiode array (PDA) and evaporative light scattering (ELS) detectors.

The pKa of each amine lipid was determined according to the method in Jayaraman, et al. (Angewandte Chemie, 2012) with the following adaptations. The pKa was determined for unformulated amine lipid in ethanol. Lipid stock solutions (2.94 mM) were diluted into Sodium Phosphate Buffers (0.1 M, Boston Bioproducts) of different pH (pH-range: 4.5-9.0) yielding a final lipid concentration of approx. 100 µM. The test samples were supplemented with TNS {6-(p-Toluidino)-2-naphthalenesulfonic acid sodium salt}, incubated and the fluorescence intensity was measured using excitation and emission wavelengths of 321 nm and 448 nm, respectively. The recorded data were normalized and the respective pKa values were derived from sigmoidal fitting.

TABLE 1

Compounds

| Compound (pKa) | Structure |
| --- | --- |
| 1 (6.35) | 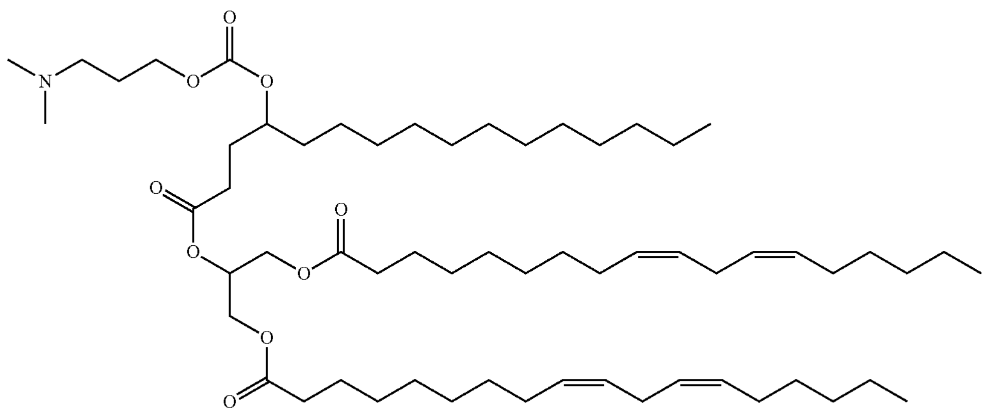 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C] |
| 2 (5.28) | 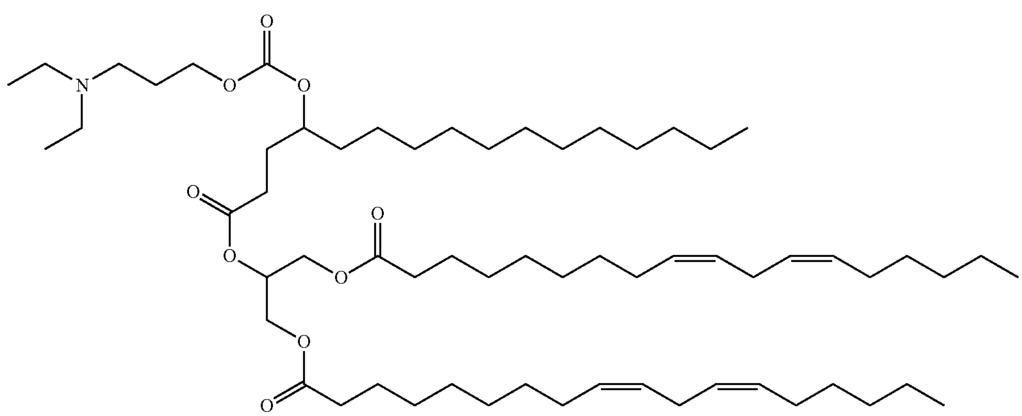 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(CC)CC] |
| 3 (5.89) | 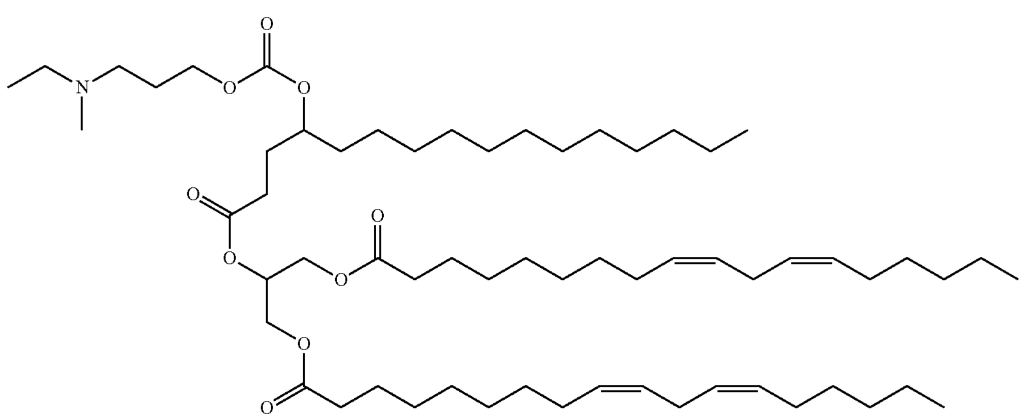 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)CC] |

TABLE 1-continued

Compounds

| Compound (pKa) | Structure |
|---|---|
| 4 (<5) | 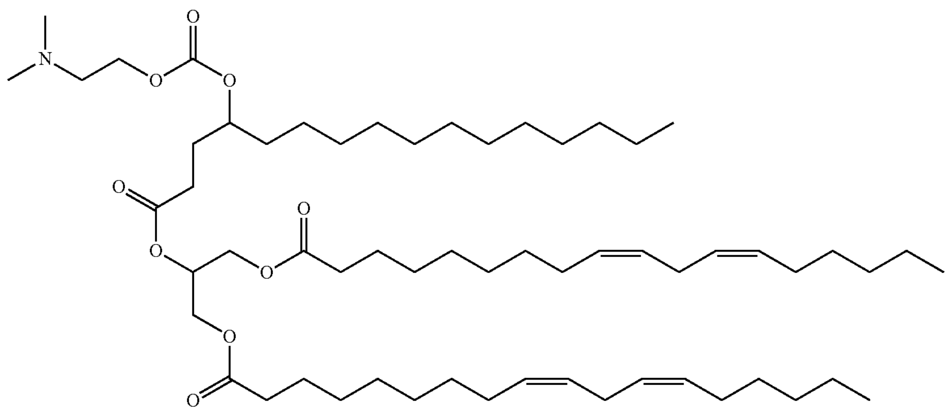 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCN(C)C] |
| 5 (6.25) | 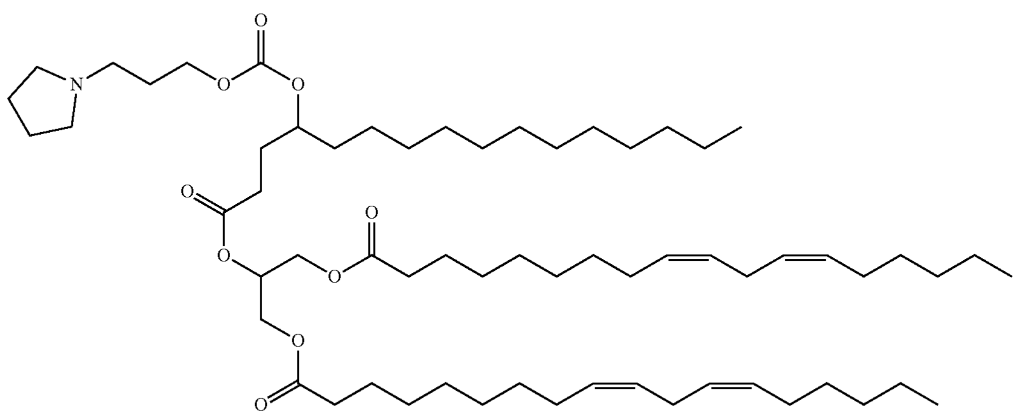 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN1CCCC1] |
| 6 (5.37) | 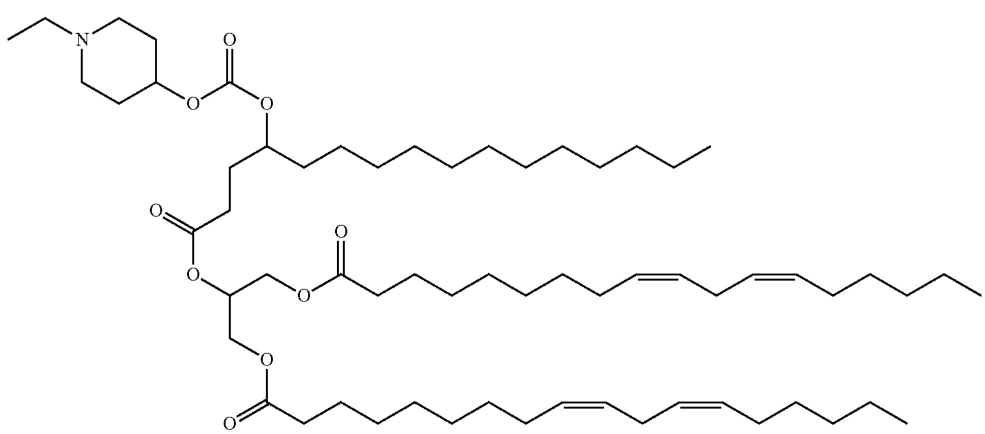 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OC1CCN(CC)CC1] |

TABLE 1-continued

Compounds

| Compound (pKa) | Structure |
| --- | --- |
| 7 (6.36) | 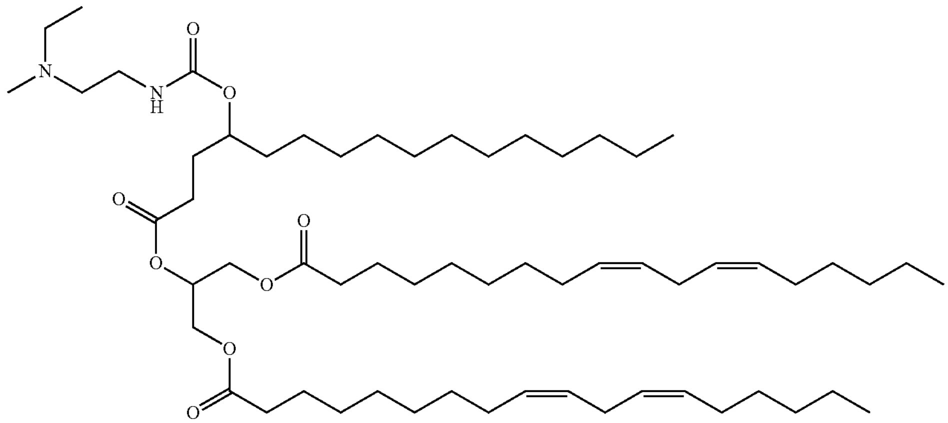 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCN(C)CC] |
| 8 (7.54) | 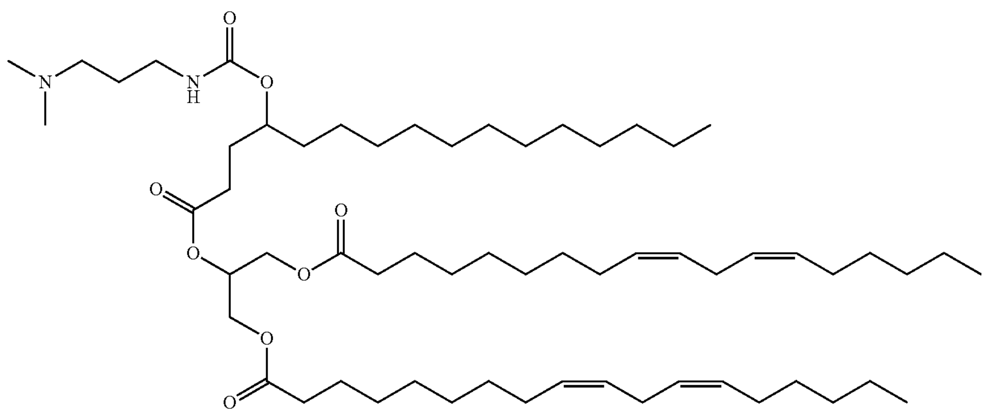 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCCN(C)C] |
| 9 (6.32) | 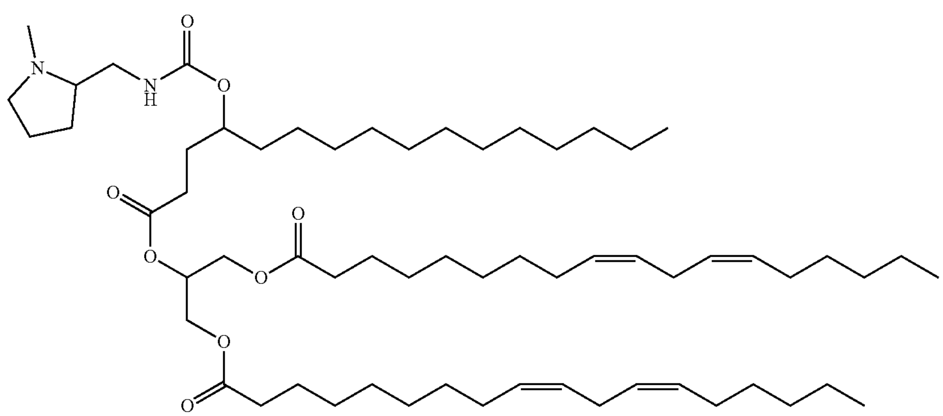 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCC1CCCN1C] |

TABLE 1-continued

Compounds

| Compound (pKa) | Structure |
| --- | --- |
| 10 (6.05) | 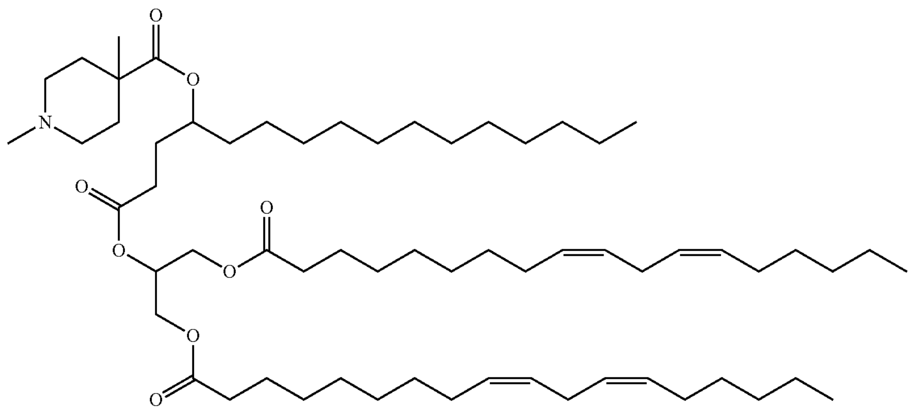 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)C1(C)CCN(C)CC1] |
| 11 (5.60) | 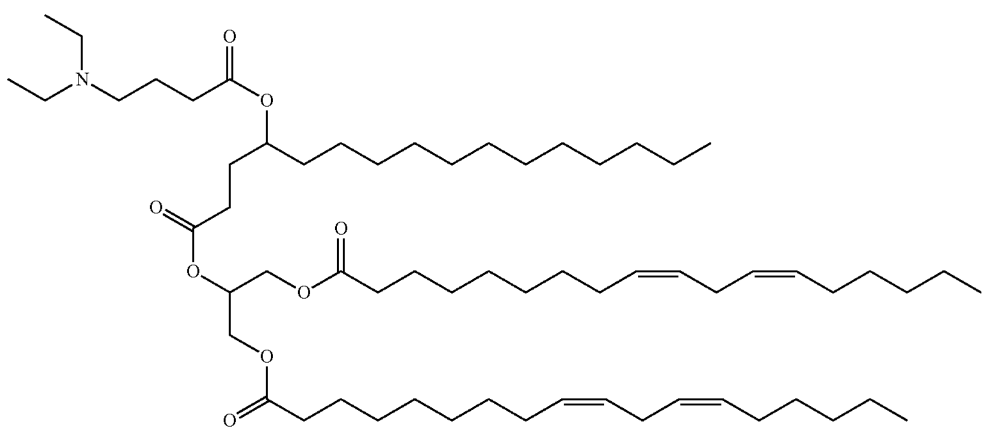 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)CCCN(CC)CC] |
| 12 (6.82) | 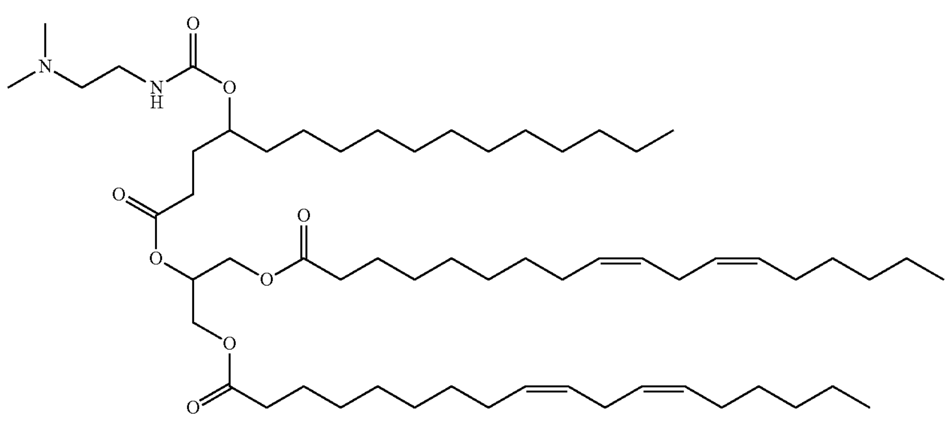 |

TABLE 1-continued

| Compound (pKa) | Structure |
| --- | --- |
| 13 (7.20) | [chemical structure] |
| 14 (5.91) | [chemical structure] |
| 15 (5.90) | [chemical structure] |

TABLE 1-continued

| Compound (pKa) | Structure |
| --- | --- |
| 16 (5.72) | 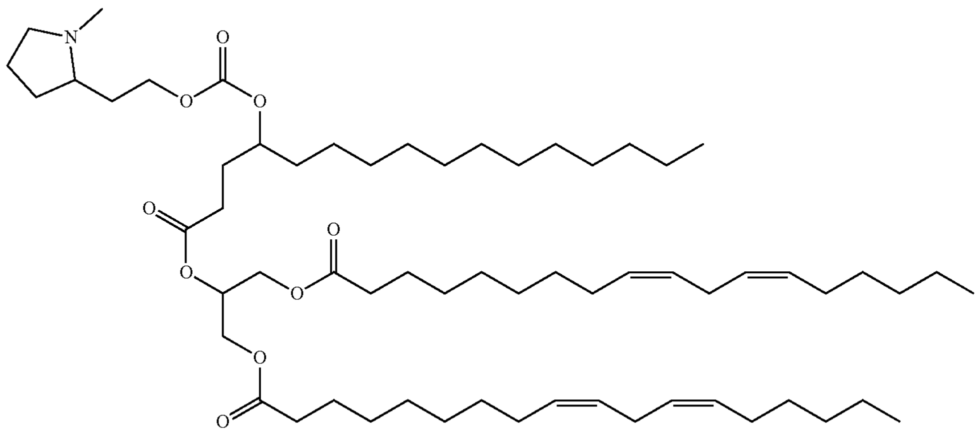 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCC1CCCN1C] |
| 17 (6.18) | 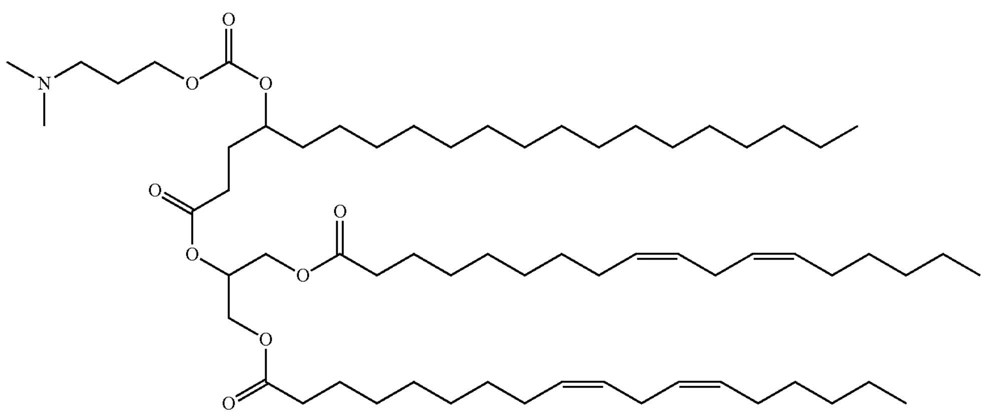 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)OCCCN(C)C] |
| 18 (5.83) | 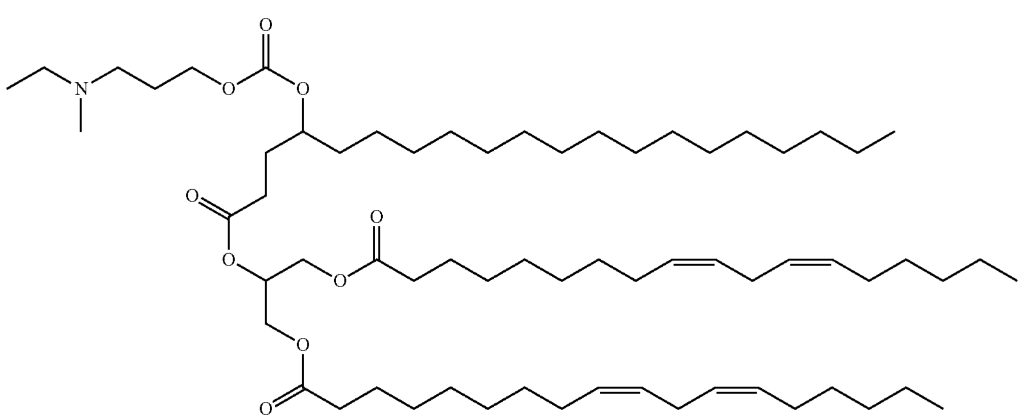 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)OCCCN(C)CC] |

TABLE 1-continued

Compounds

| Compound (pKa) | Structure |
| --- | --- |
| 19 (5.99) | 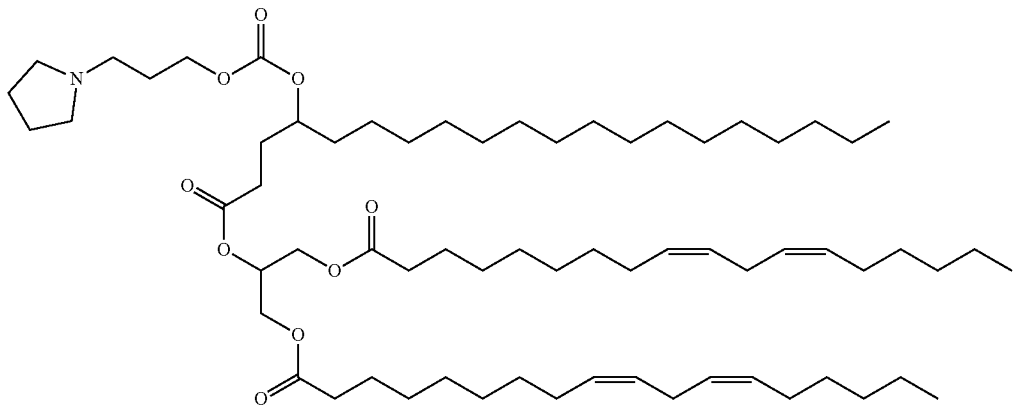 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)OCCCN1CCCC1] |
| 20 (6.17) | 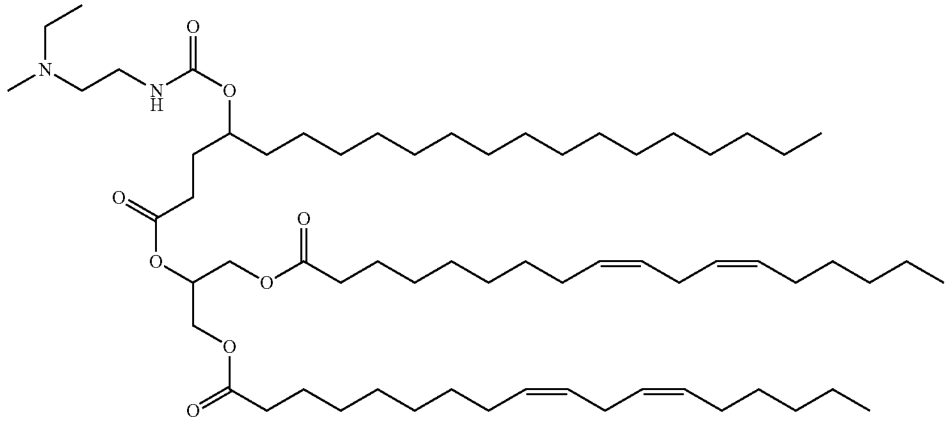 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)NCCN(C)CC] |
| 21 (6.12) | 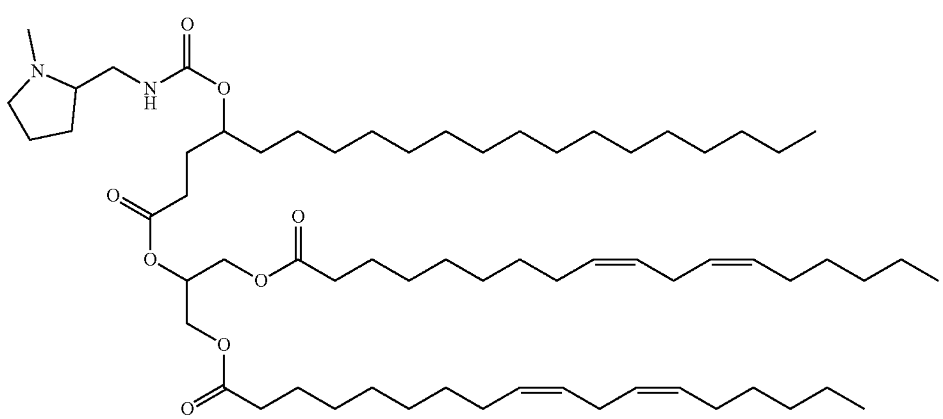 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)NCC1CCCN1C] |

TABLE 1-continued

Compounds

| Compound (pKa) | Structure |
|---|---|
| 22 (6.06) | 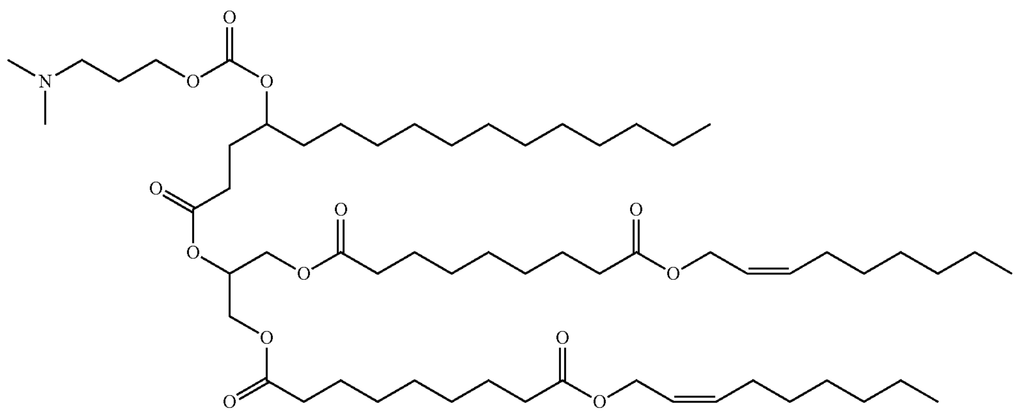 [SMILES: CCCCCC/C=C\COC(=O)CCCCCCCC(=O)OCC(COC(=O)CCCCCCCC(=O)OC/C=C\CCCCCC)OC(=O)CCC(CCCCCCCCCCCC)OC(=O)OCCCN(C)C] |
| 23 (6.19) | 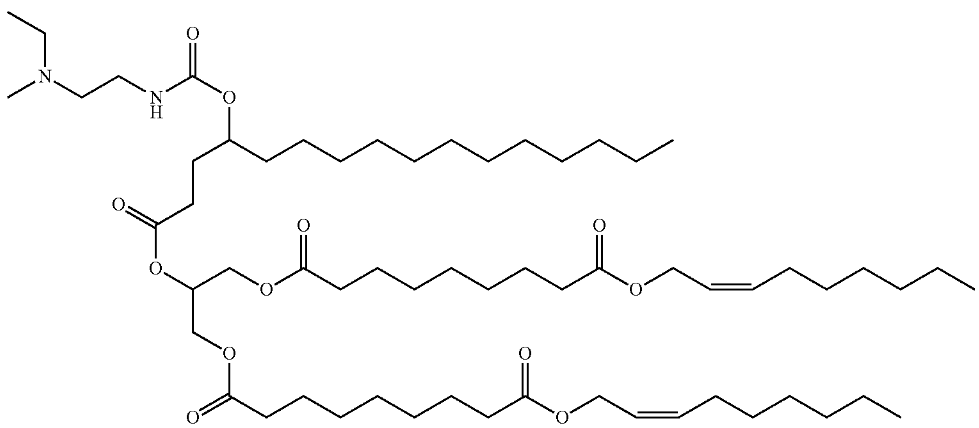 [SMILES: CCCCCC/C=C\COC(=O)CCCCCCCC(=O)OCC(COC(=O)CCCCCCCC(=O)OC/C=C\CCCCCC)OC(=O)CCC(CCCCCCCCCCCC)OC(=O)NCCN(C)CC] |
| 24 (6.10) | 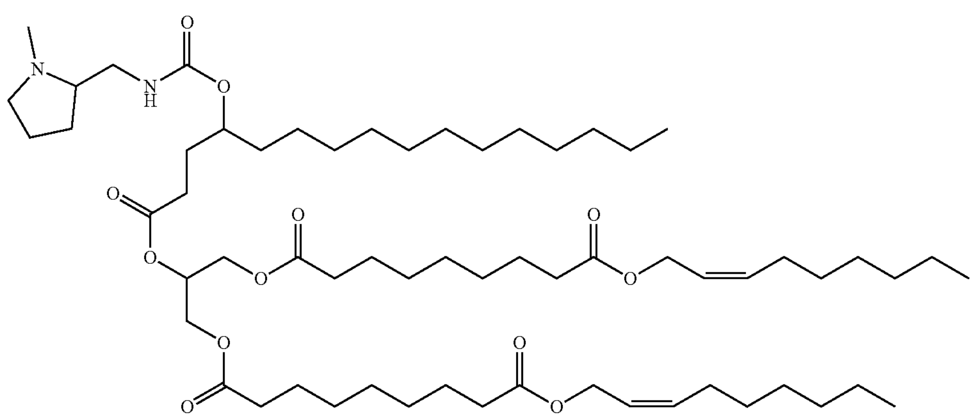 [SMILES: CCCCCC/C=C\COC(=O)CCCCCCCC(=O)OCC(COC(=O)CCCCCCCC(=O)OC/C=C\CCCCCC)OC(=O)CCC(CCCCCCCCCCCC)OC(=O)NCC1CCCN1C] |

TABLE 1-continued

| Compounds | |
|---|---|
| Compound (pKa) | Structure |

25
(6.12)

26
(5.82)

27
(5.97)

TABLE 1-continued
Compounds
| Compound (pKa) | Structure |
|---|---|
| 28 (6.06) | 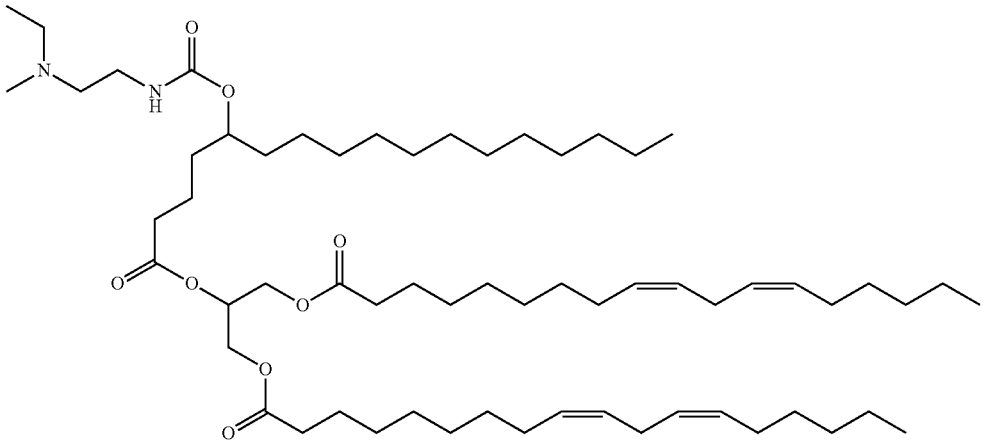 [SMILES: CCCCC/C=C\C/C=C\CCCCCCCC(=O)OCC(COC(=O)CCCCCCC/C=C\C/C=C\CCCCC)OC(=O)CCCC(CCCCCCCCCCCC)OC(=O)NCCN(C)CC] |
| 29 (6.05) | 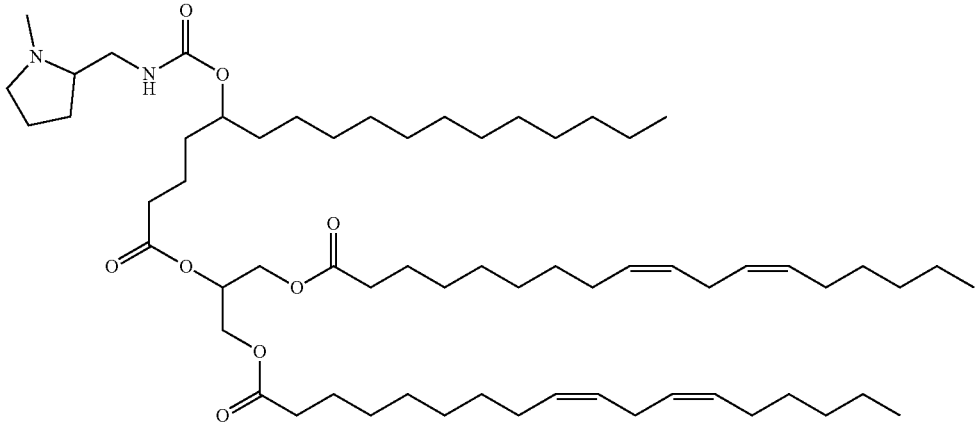 [SMILES: CCCCC/C=C\C/C=C\CCCCCCCC(=O)OCC(COC(=O)CCCCCCC/C=C\C/C=C\CCCCC)OC(=O)CCCC(CCCCCCCCCCCC)OC(=O)NCC1CCCN1C] |
| 30 (6.53) | 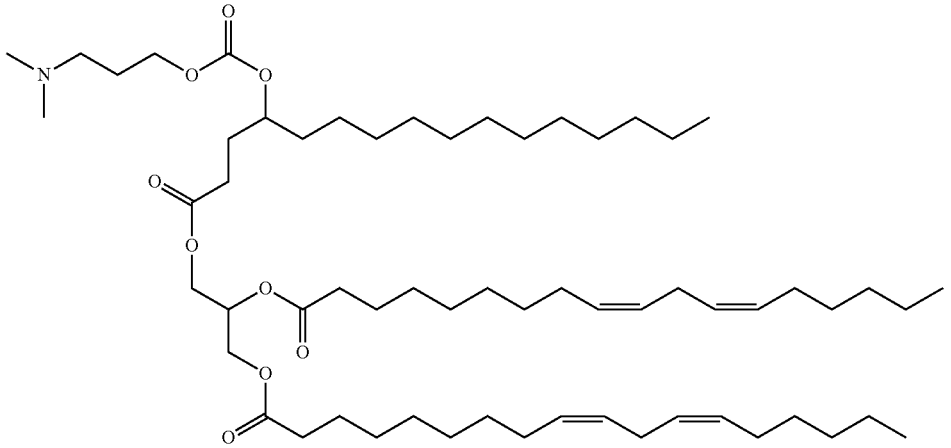 [SMILES: CCCCC/C=C\C/C=C\CCCCCCCC(=O)OCC(COC(=O)CCC(CCCCCCCCCCCC)OC(=O)OCCCN(C)C)OC(=O)CCCCCCC/C=C\C/C=C\CCCCC] |

TABLE 1-continued

| Compound (pKa) | Structure |
|---|---|
| 31 Compound 31 (6.28) | 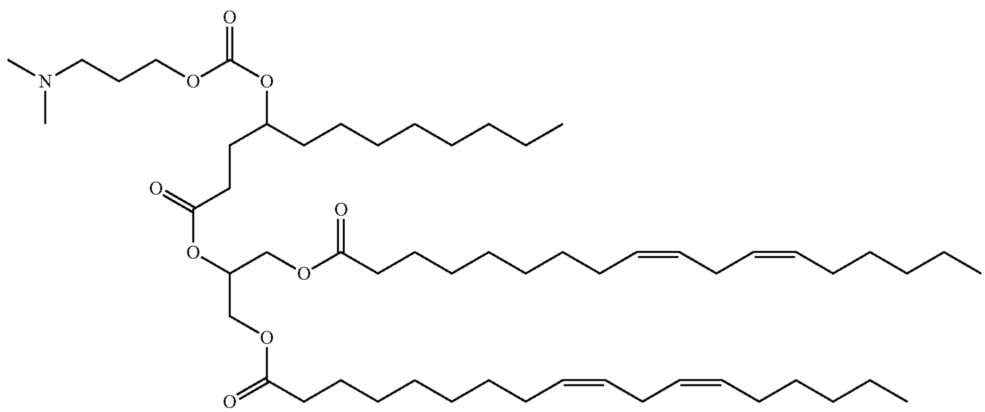 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OCCCN(C)C] |
| 32 (5.64) | 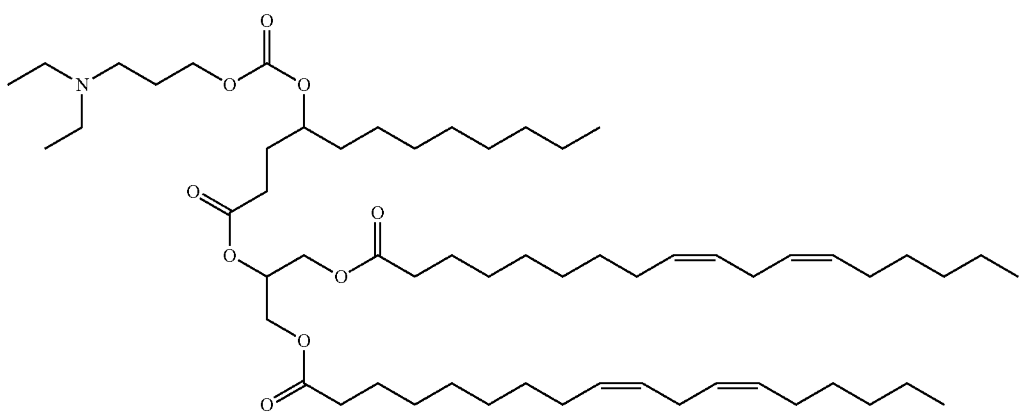 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OCCCN(CC)CC] |
| 33 (5.95) | 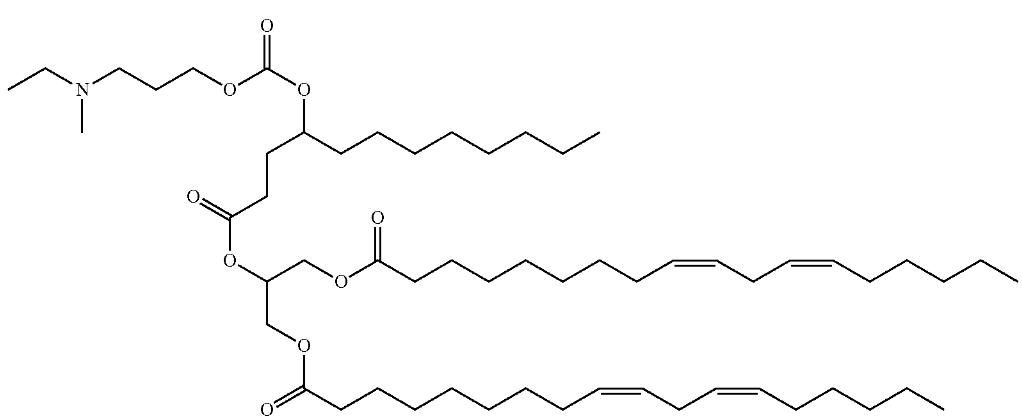 |

TABLE 1-continued

Compounds

| Compound (pKa) | Structure |
| --- | --- |
| 34 (6.36) | 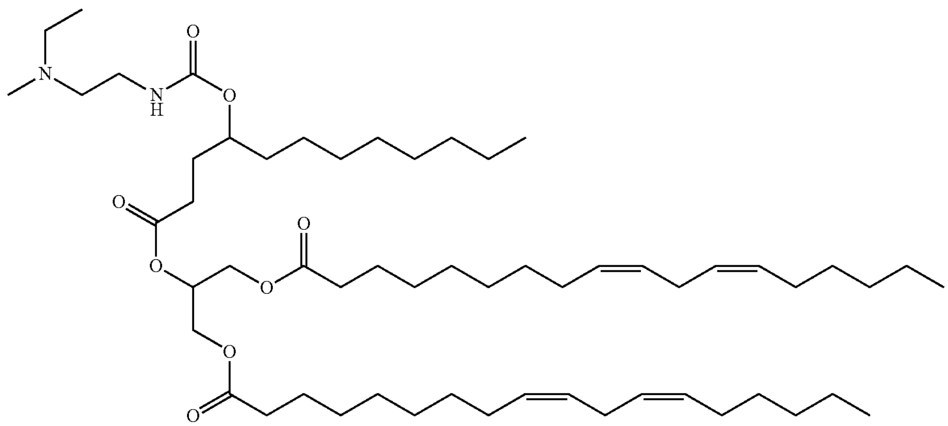 |
| 35 (6.35) | 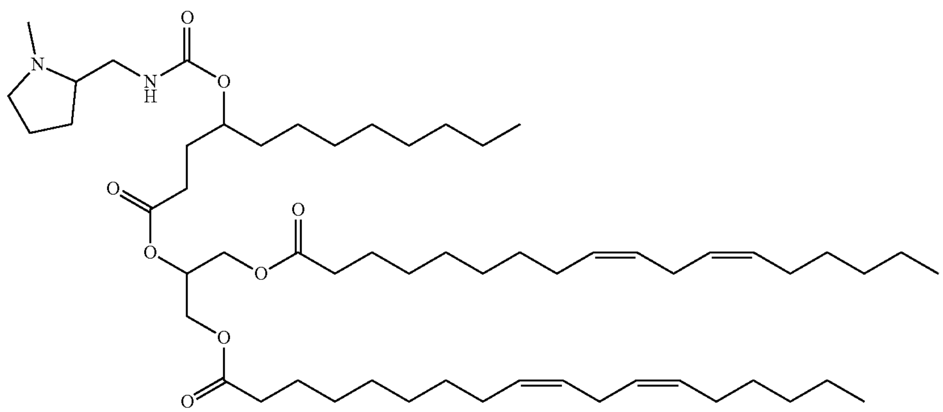 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCC1CCCN1C] |
| 36 (6.13) | 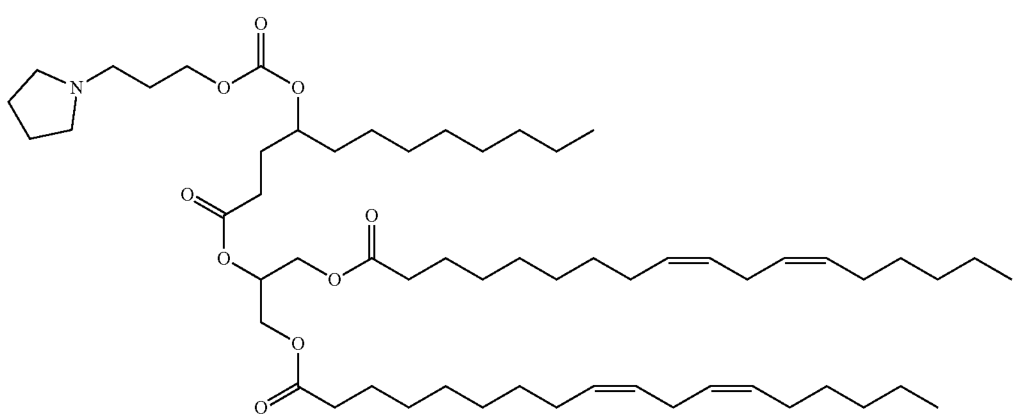 |

TABLE 1-continued

Compounds

| Compound (pKa) | Structure |
| --- | --- |
| 37 (5.36) | 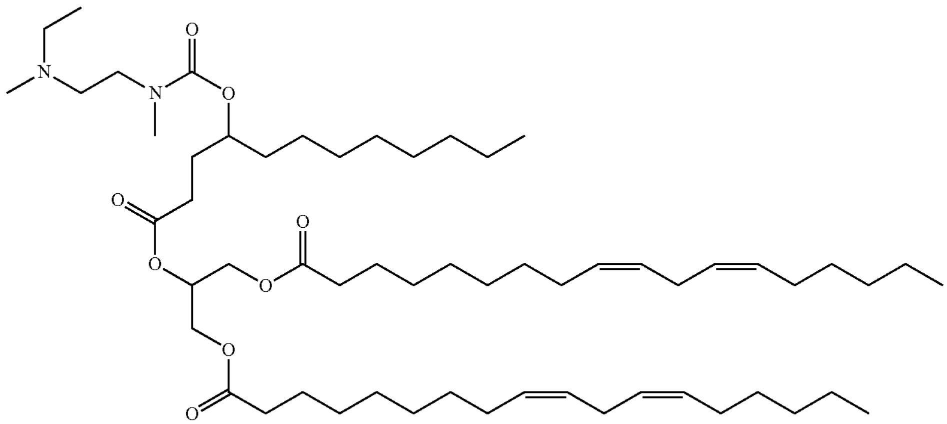 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)N(C)CCN(C)CC] |
| 38 (5.62) | 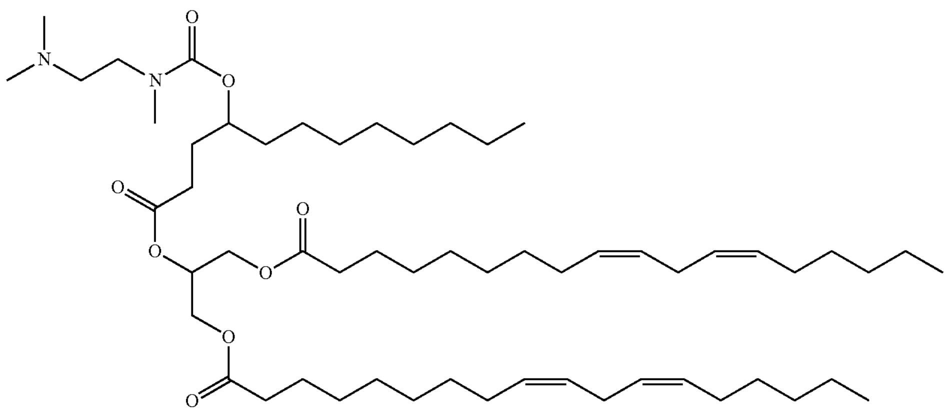 |
| 39 (6.32) | 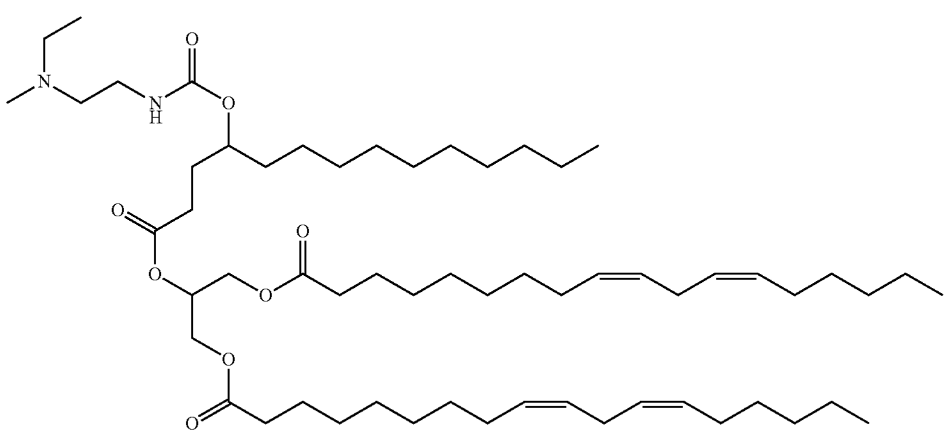 [SMILES: CCCCC/C=C\C/C=C\CCCCCCCC(=O)OCC(COC(=O)CCCCCCC/C=C\C/C=C\CCCCC)OC(=O)CCC(CCCCCCCCCC)OC(=O)NCCN(C)CC] |

TABLE 1-continued

Compounds

| Compound (pKa) | Structure |
| --- | --- |
| 40 (6.34) | 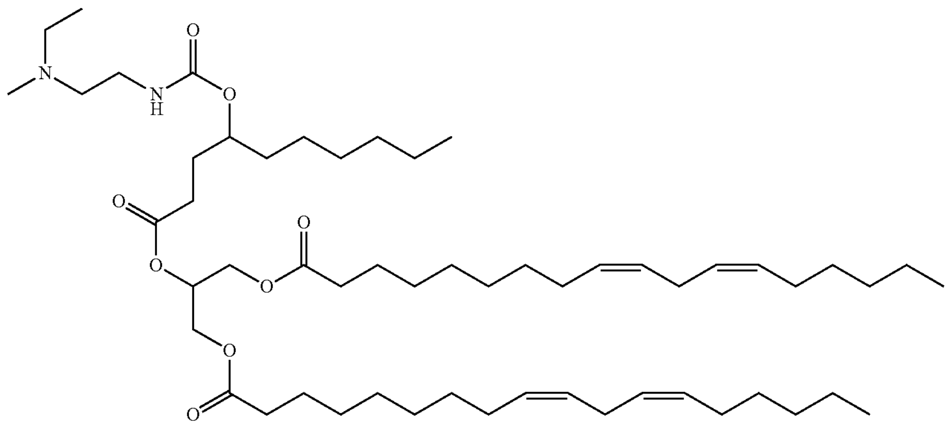 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NCCN(C)CC] |
| 41 (6.51) | 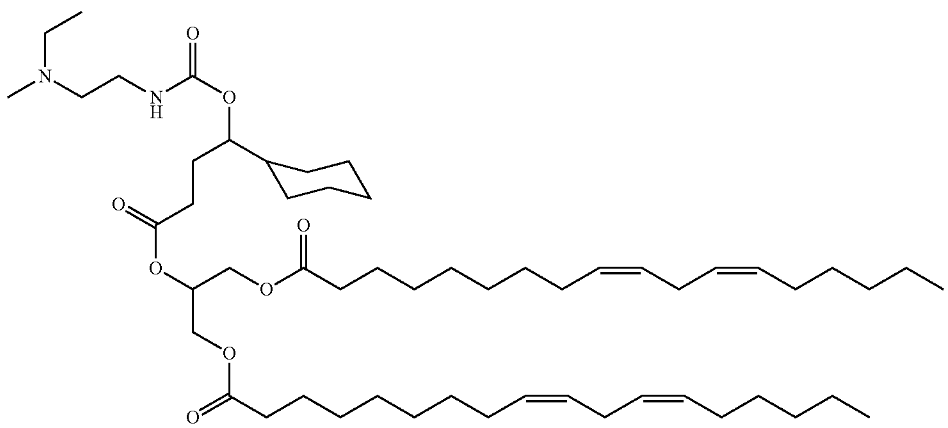 [SMILES: CCCCC/C=C\C/C=C\CCCCCCCC(=O)OCC(COC(=O)CCCCCCC/C=C\C/C=C\CCCCC)OC(=O)CCC(OC(=O)NCCN(C)CC)C1CCCCC1] |
| 42 (6.52) | 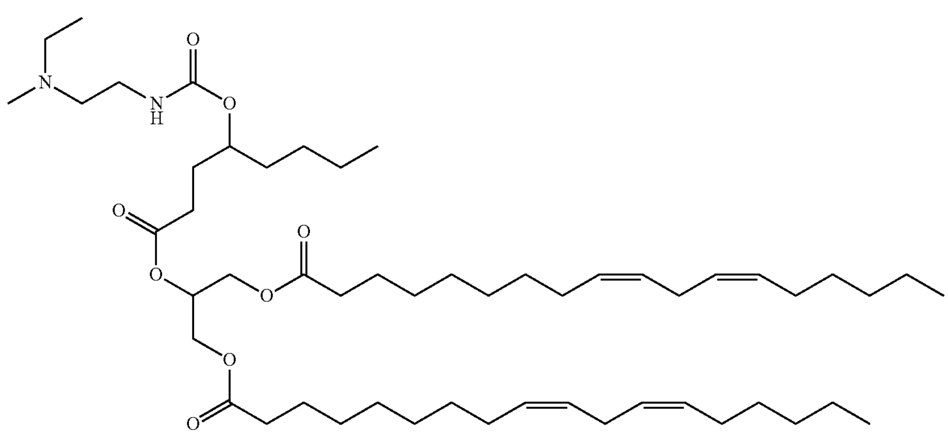 [SMILES: CCCCC/C=C\C/C=C\CCCCCCCC(=O)OCC(COC(=O)CCCCCCC/C=C\C/C=C\CCCCC)OC(=O)CCC(CCCC)OC(=O)NCCN(C)CC] |

TABLE 1-continued

Compounds

| Compound (pKa) | Structure |
|---|---|
| 43 (7.33) | 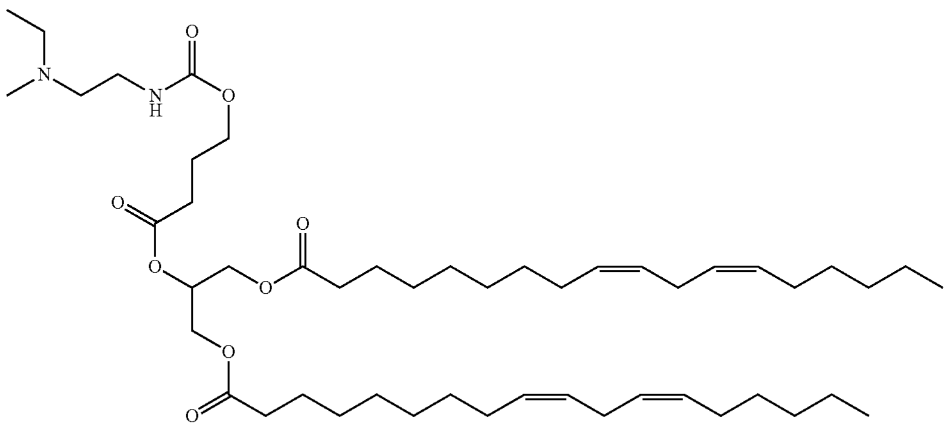 [SMILES: CCCCC/C=C\C/C=C\CCCCCCCC(=O)OCC(COC(=O)CCCCCCC/C=C\C/C=C\CCCCC)OC(=O)CCCOC(=O)NCCN(C)CC] |
| 44 (6.45) | 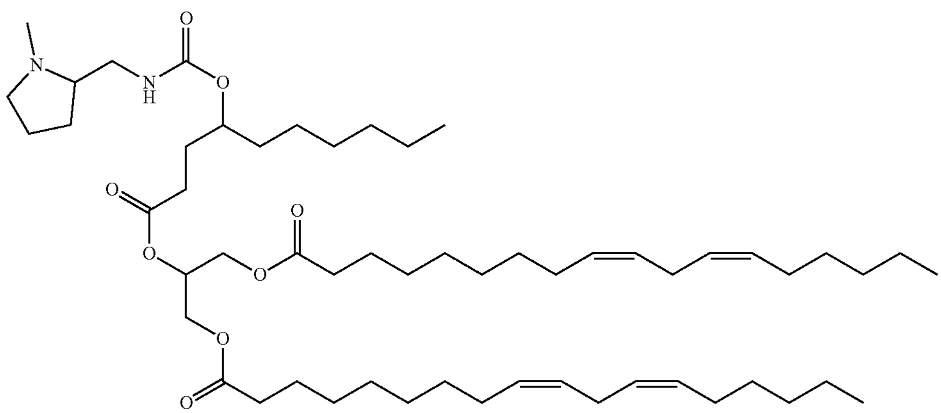 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NCC1CCCN1C] |
| 45 (5.79) | 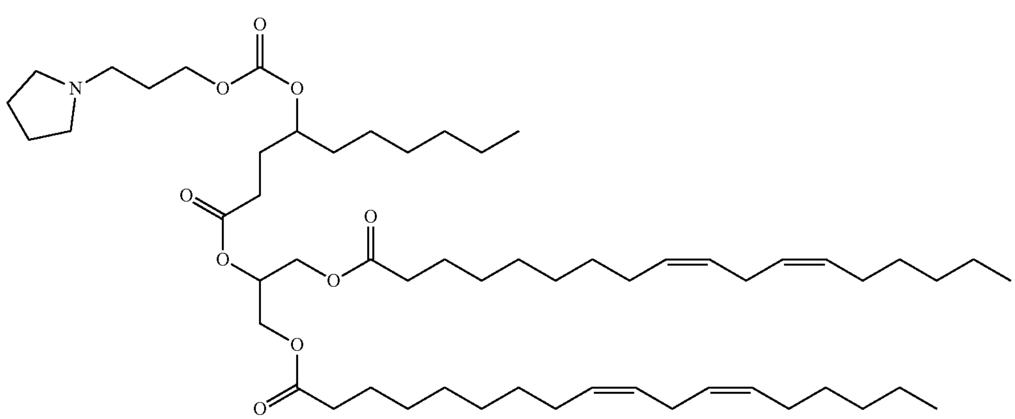 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)OCCCN1CCCC1] |

TABLE 1-continued

Compounds

| Compound (pKa) | Structure |
| --- | --- |
| 46 (6.16) | 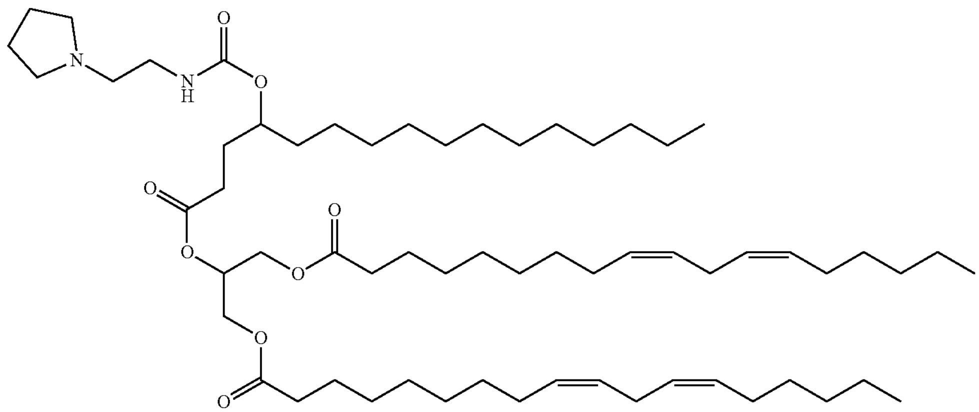 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCN1CCCC1] |
| f47 (5.99) | 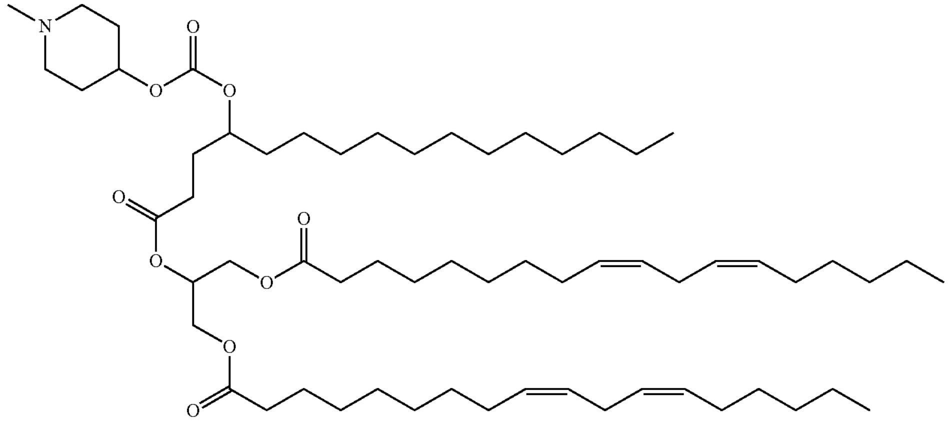 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OC1CCN(C)CC1] |
| 48 (ND) | 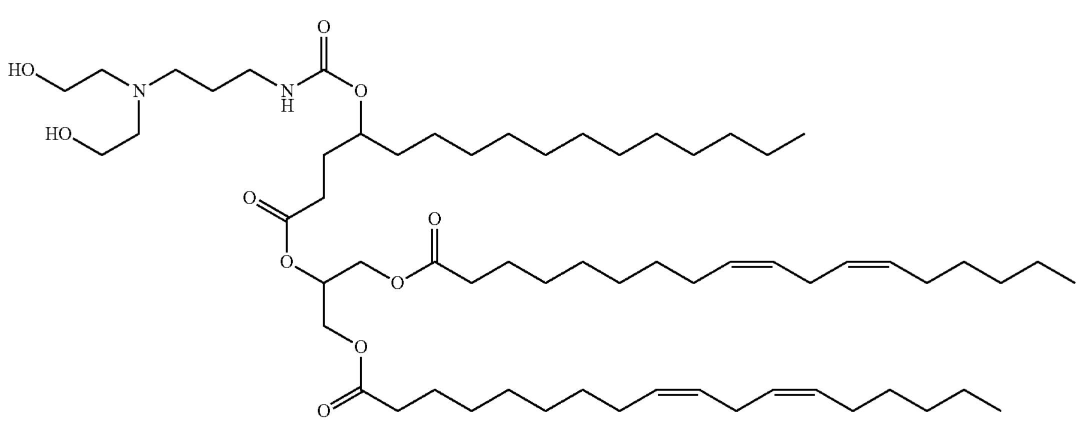 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCCN(CCO)CCO] |

TABLE 1-continued
| Compound (pKa) | Structure |
|---|---|
| 49 | 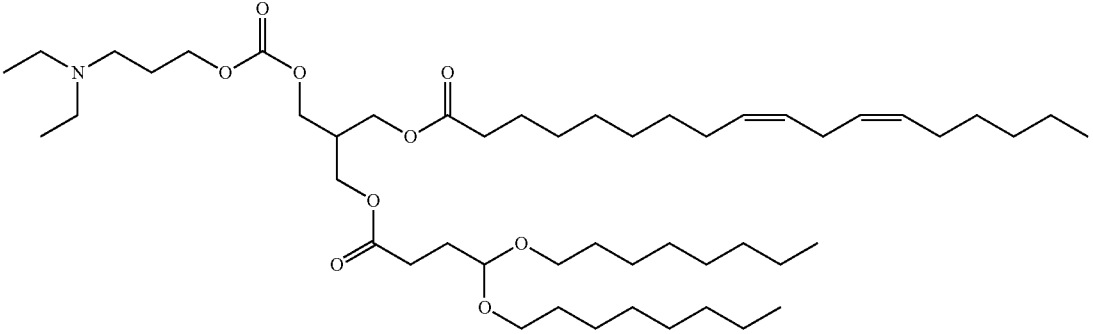 [SMILES: CCCCC/C=C\C/C=C\CCCCCCCC(=O)OCC(COC(=O)CCC(OCCCCCCCC)OCCCCCCCC)COC(=O)OCCCN(CC)CC] |
| 50 (6.50) | 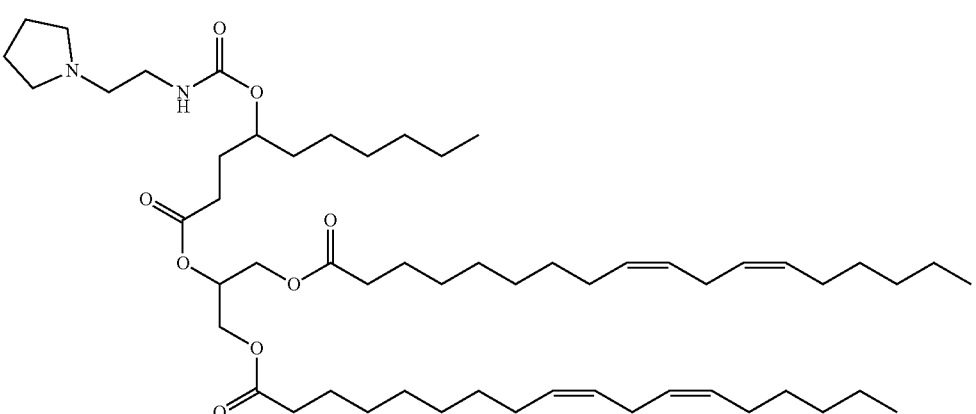 |
| 51 (6.37) | 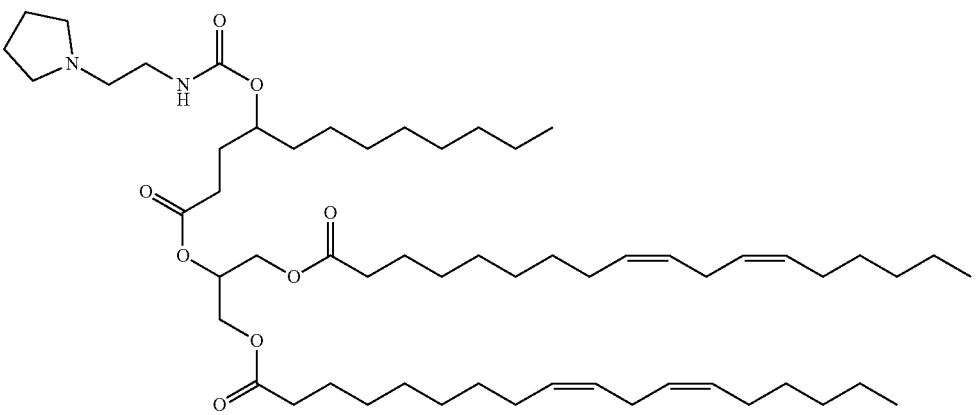 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCCN1CCCC1] |

TABLE 1-continued

Compounds

| Compound (pKa) | Structure |
| --- | --- |
| 52 (6.26) | 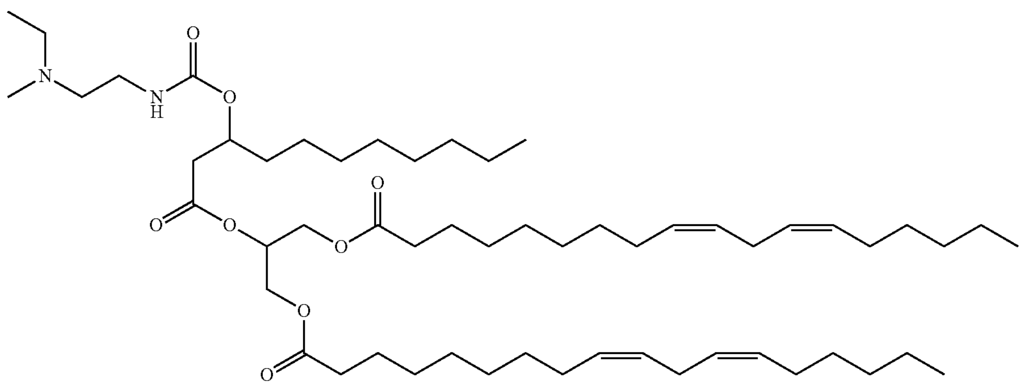 [SMILES: CCCCC/C=C\C/C=C\CCCCCCCC(=O)OCC(COC(=O)CCCCCCC/C=C\C/C=C\CCCCC)OC(=O)CC(CCCCCCCC)OC(=O)NCCN(C)CC] |
| 53 (6.29) | 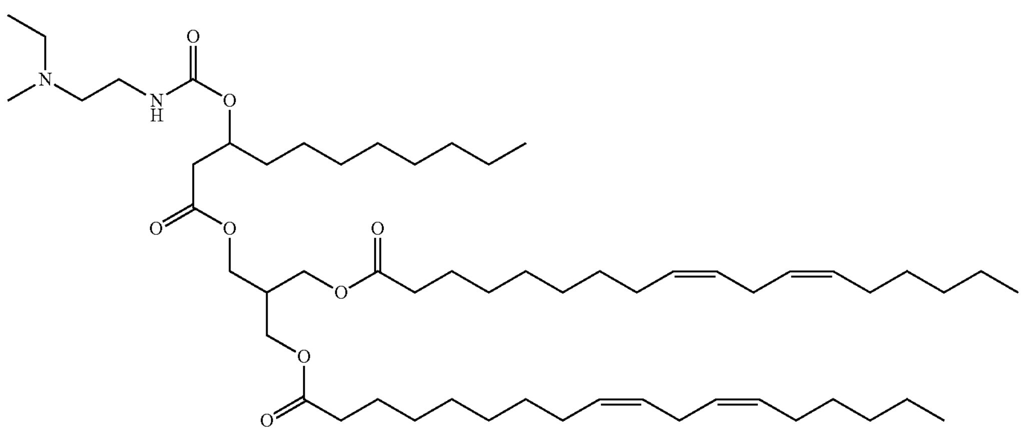 [SMILES: CCCCC/C=C\C/C=C\CCCCCCCC(=O)OCC(COC(=O)CCCCCCC/C=C\C/C=C\CCCCC)COC(=O)CC(CCCCCCCC)OC(=O)NCCN(C)CC] |
| 54 (6.25) | 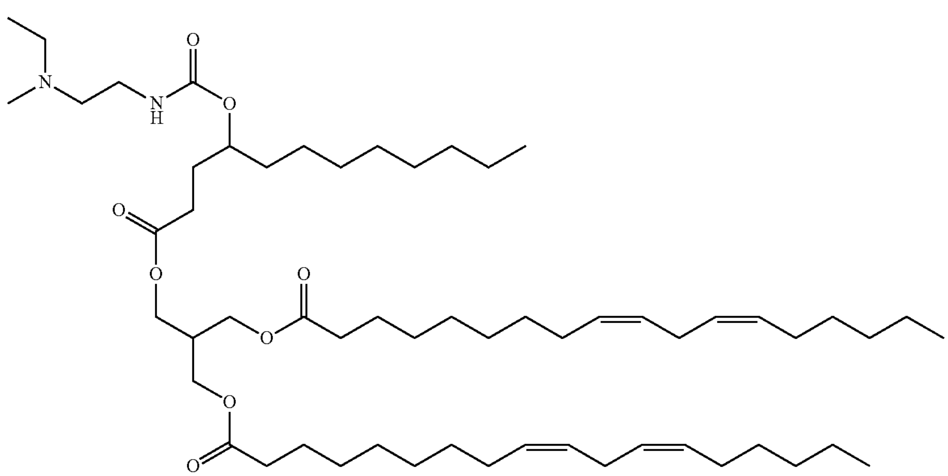 [SMILES: CCCCC/C=C\C/C=C\CCCCCCCC(=O)OCC(COC(=O)CCCCCCC/C=C\C/C=C\CCCCC)COC(=O)CCC(CCCCCCCC)OC(=O)NCCN(C)CC] |

TABLE 1-continued

Compounds

| Compound (pKa) | Structure |
| --- | --- |
| 55 (6.43) | 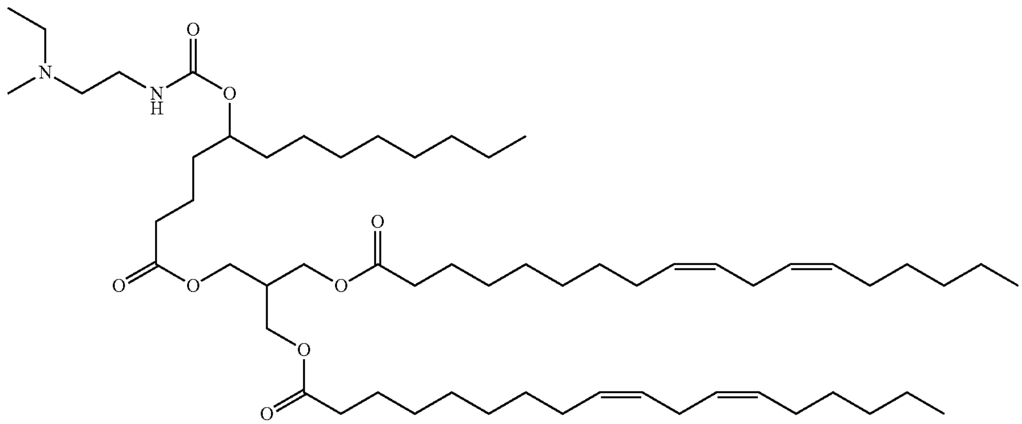 [SMILES: CCCCC/C=C\C/C=C\CCCCCCCC(=O)OCC(COC(=O)CCCCCCC/C=C\C/C=C\CCCCC)COC(=O)CCCC(CCCCCCCC)OC(=O)NCCN(C)CC] |
| 56 (6.28) | 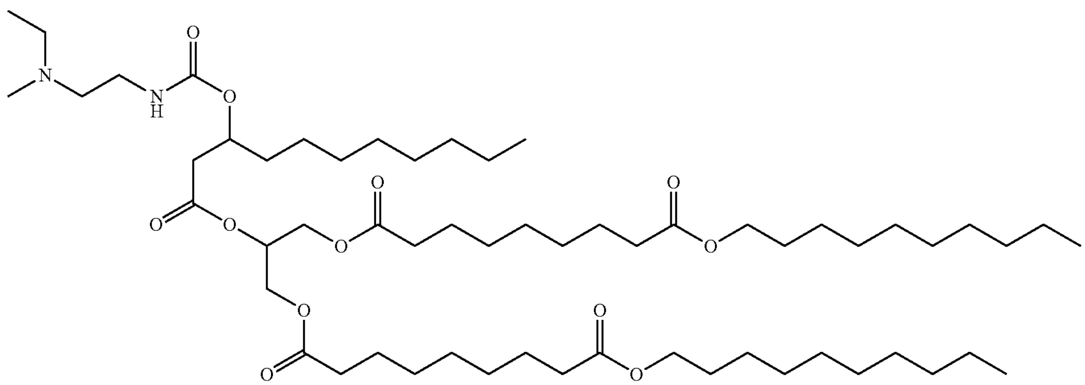 [SMILES: CCCCCCCCCCOC(=O)CCCCCCCC(=O)OCC(COC(=O)CCCCCCCC(=O)OCCCCCCCCCC)OC(=O)CC(CCCCCCCC)OC(=O)NCCN(C)CC] |
| 57 (6.18) | 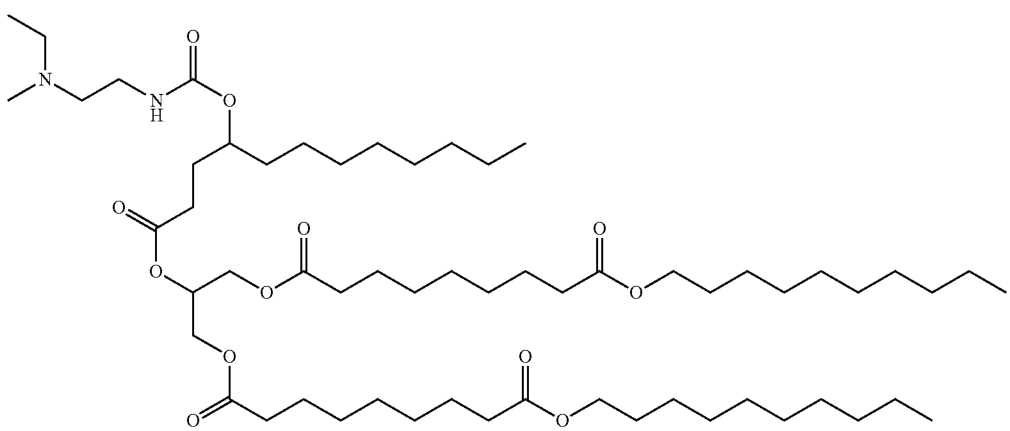 [SMILES: CCCCCCCCCCOC(=O)CCCCCCCC(=O)OCC(COC(=O)CCCCCCCC(=O)OCCCCCCCCCC)OC(=O)CCC(CCCCCCCC)OC(=O)NCCN(C)CC] |

TABLE 1-continued

Compounds

| Compound (pKa) | Structure |
| --- | --- |
| 58 (6.32) | 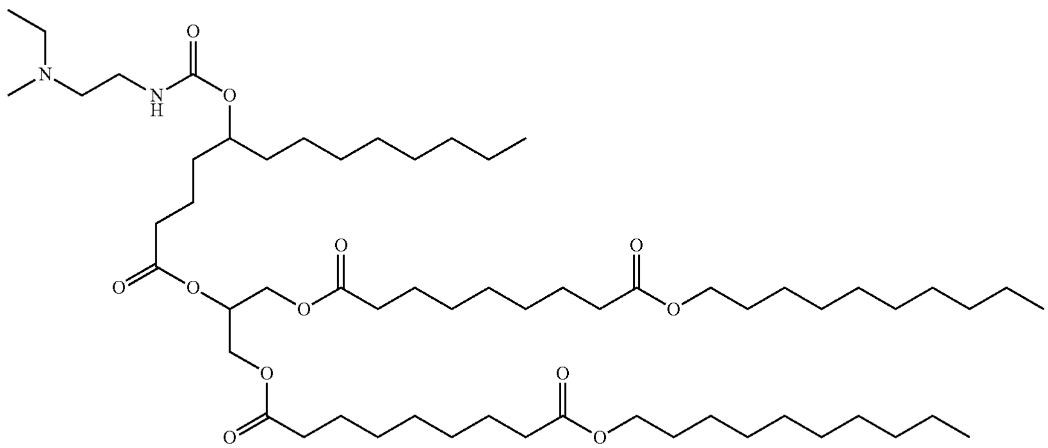 [SMILES: CCCCCCCCCCOC(=O)CCCCCCCC(=O)OCC(COC(=O)CCCCCCCC(=O)OCCCCCCCCCC)OC(=O)CCCC(CCCCCCCC)OC(=O)NCCN(C)CC] |
| 59 (6.34) | 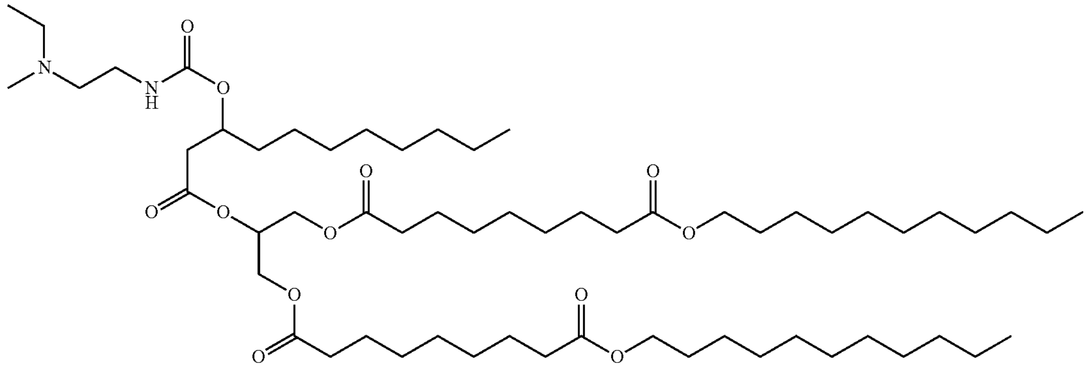 [SMILES: CCCCCCCCCCCOC(=O)CCCCCCCC(=O)OCC(COC(=O)CCCCCCCC(=O)OCCCCCCCCCCC)OC(=O)CC(CCCCCCCC)OC(=O)NCCN(C)CC] |
| 60 (6.22) | 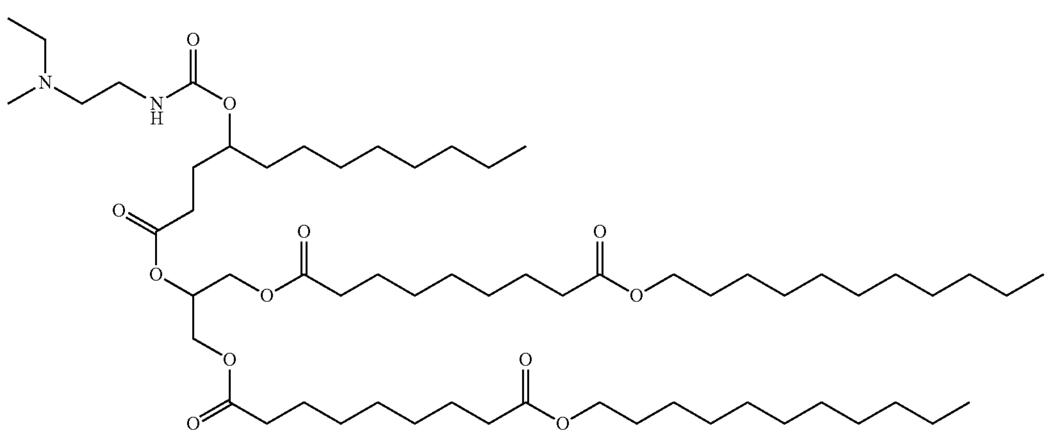 [SMILES: CCCCCCCCCCCOC(=O)CCCCCCCC(=O)OCC(COC(=O)CCCCCCCC(=O)OCCCCCCCCCCC)OC(=O)CCC(CCCCCCCC)OC(=O)NCCN(C)CC] |

TABLE 1-continued

Compounds

| Compound (pKa) | Structure |
| --- | --- |
| 61 (6.29) | 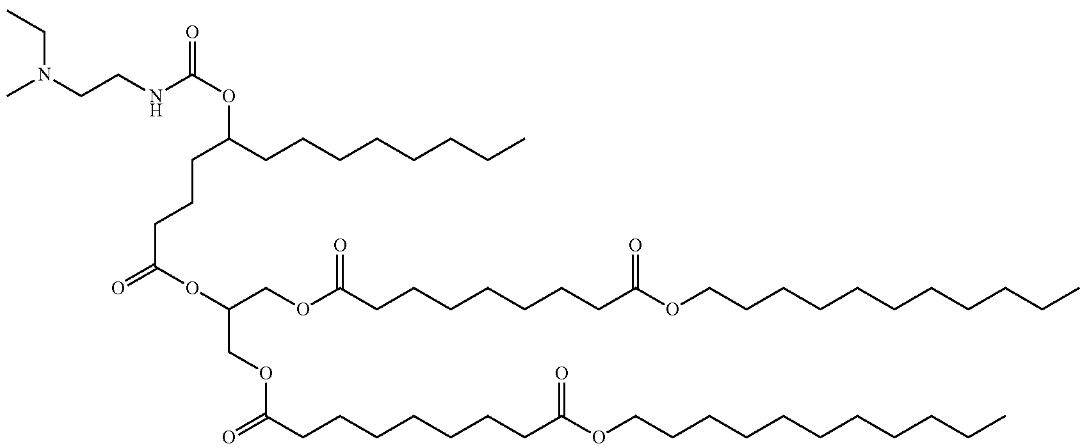 [SMILES: CCCCCCCCCCCOC(=O)CCCCCCCC(=O)OCC(COC(=O)CCCCCCCC(=O)OCCCCCCCCCCC)OC(=O)CCCC(CCCCCCCC)OC(=O)NCCN(C)CC] |
| 62 (6.32) | 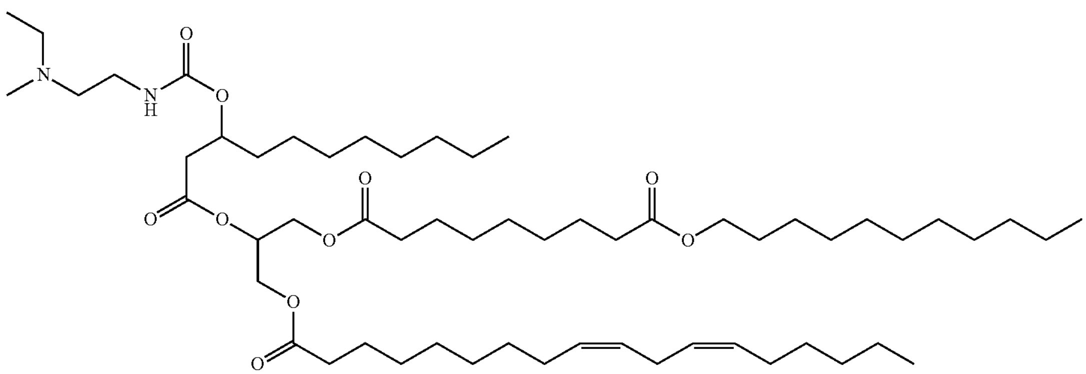 [SMILES: CCCCC/C=C\C/C=C\CCCCCCCC(=O)OCC(COC(=O)CCCCCCCC(=O)OCCCCCCCCCCC)OC(=O)CC(CCCCCCCC)OC(=O)NCCN(C)CC] |
| 63 (6.32) | 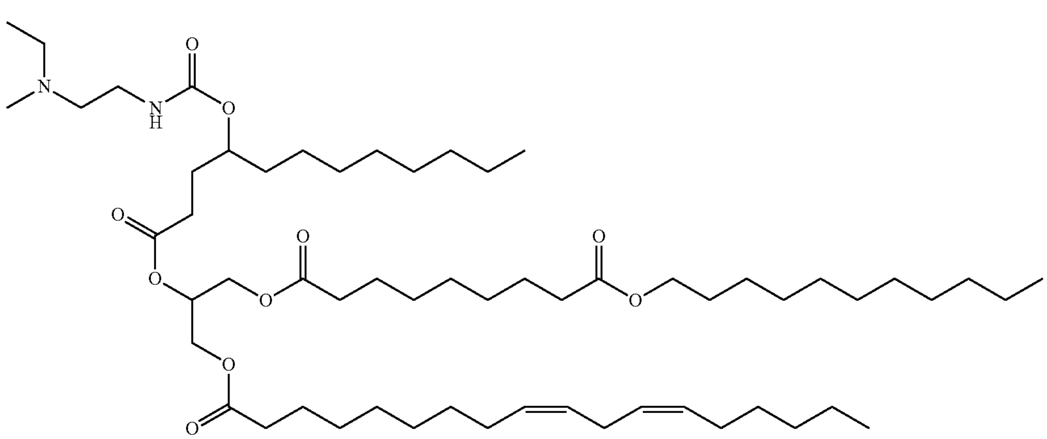 [SMILES: CCCCC/C=C\C/C=C\CCCCCCCC(=O)OCC(COC(=O)CCCCCCCC(=O)OCCCCCCCCCCC)OC(=O)CCC(CCCCCCCC)OC(=O)NCCN(C)CC] |

TABLE 1-continued

Compounds

| Compound (pKa) | Structure |
|---|---|
| 64 (6.30) | 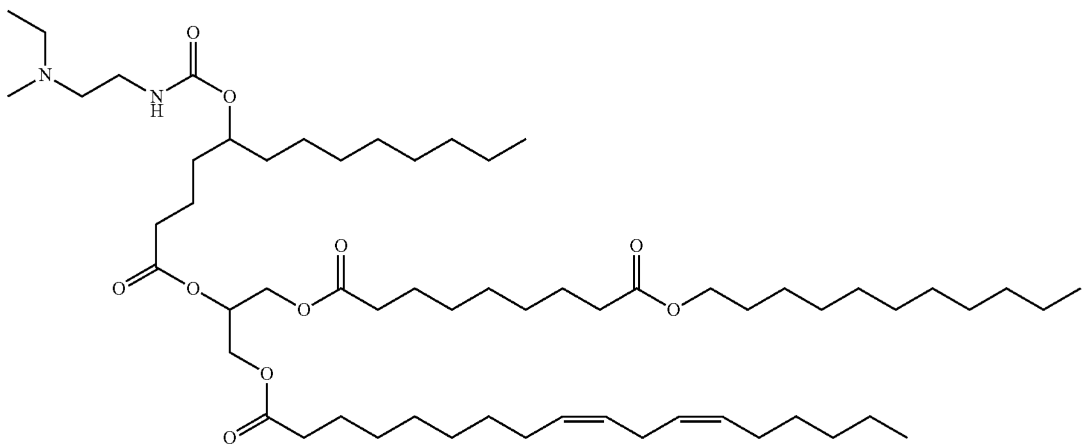 [SMILES: CCCCC/C=C\C/C=C\CCCCCCCC(=O)OCC(COC(=O)CCCCCCCC(=O)OCCCCCCCCCCC)OC(=O)CCCC(CCCCCCCC)OC(=O)NCCN(C)CC] |
| 65 (6.37) | 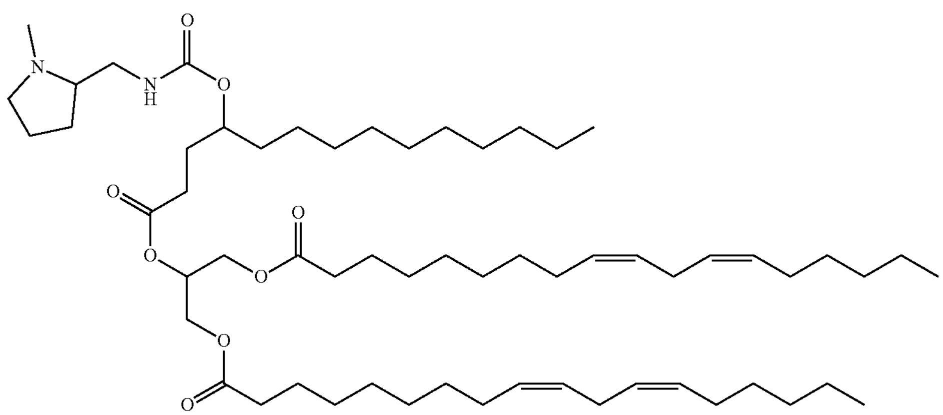 [SMILES: CCCCC/C=C\C/C=C\CCCCCCCC(=O)OCC(COC(=O)CCCCCCC/C=C\C/C=C\CCCCC)OC(=O)CCC(CCCCCCCCCC)OC(=O)NCC1CCCN1C] |
| 66 (6.15) | 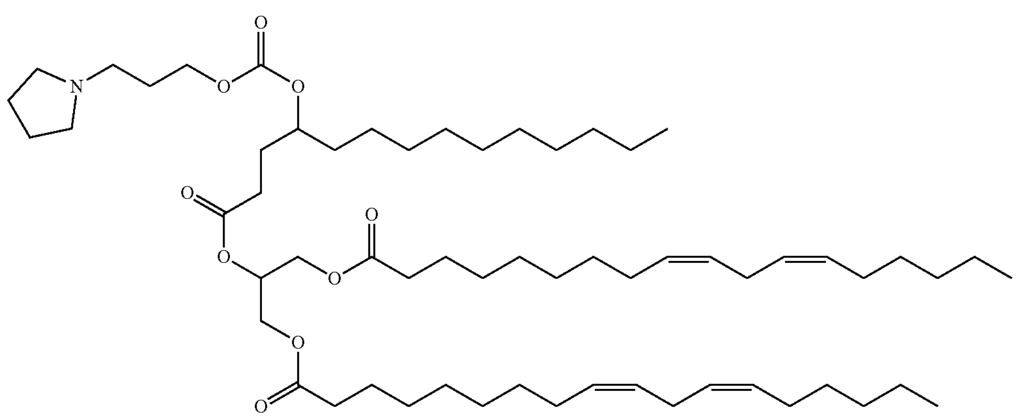 [SMILES: CCCCC/C=C\C/C=C\CCCCCCCC(=O)OCC(COC(=O)CCCCCCC/C=C\C/C=C\CCCCC)OC(=O)CCC(CCCCCCCCCC)OC(=O)OCCCN1CCCC1] |

TABLE 1-continued

Compounds

| Compound (pKa) | Structure |
|---|---|
| 67 (6.43) | 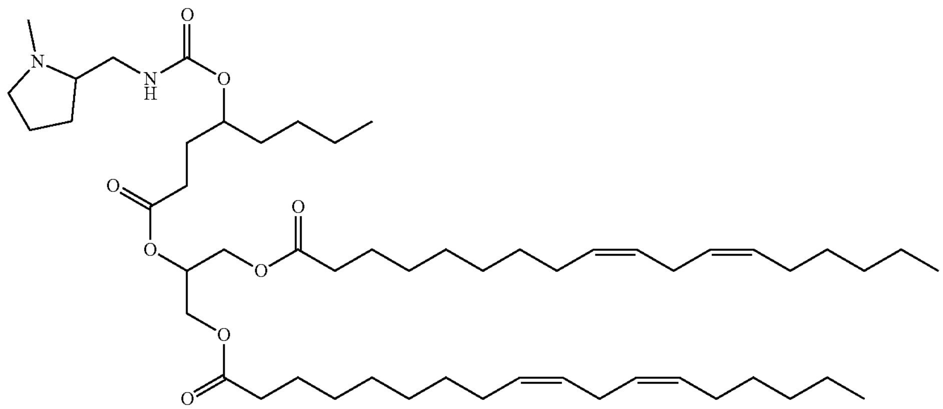 [SMILES: CCCCC/C=C\C/C=C\CCCCCCCC(=O)OCC(COC(=O)CCCCCCC/C=C\C/C=C\CCCCC)OC(=O)CCC(CCCC)OC(=O)NCC1CCCN1C] |
| 68 (6.32) | 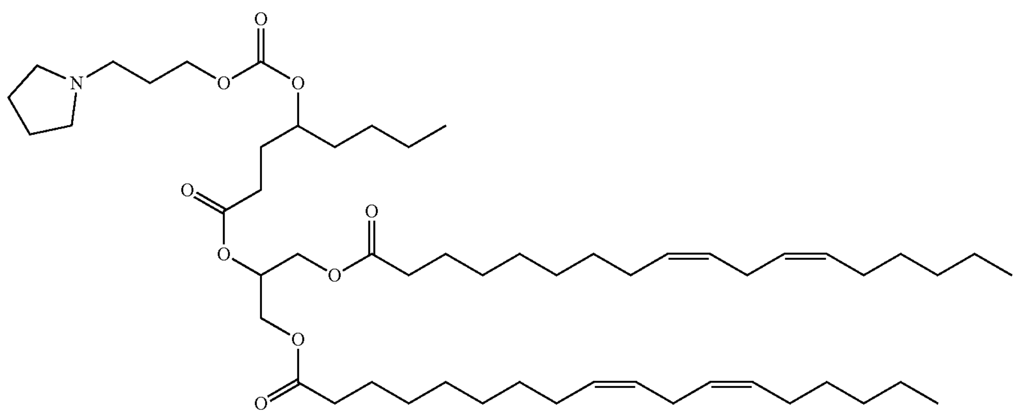 [SMILES: CCCCC/C=C\C/C=C\CCCCCCCC(=O)OCC(COC(=O)CCCCCCC/C=C\C/C=C\CCCCC)OC(=O)CCC(CCCC)OC(=O)OCCCN1CCCC1] |
| 69 (6.44) | 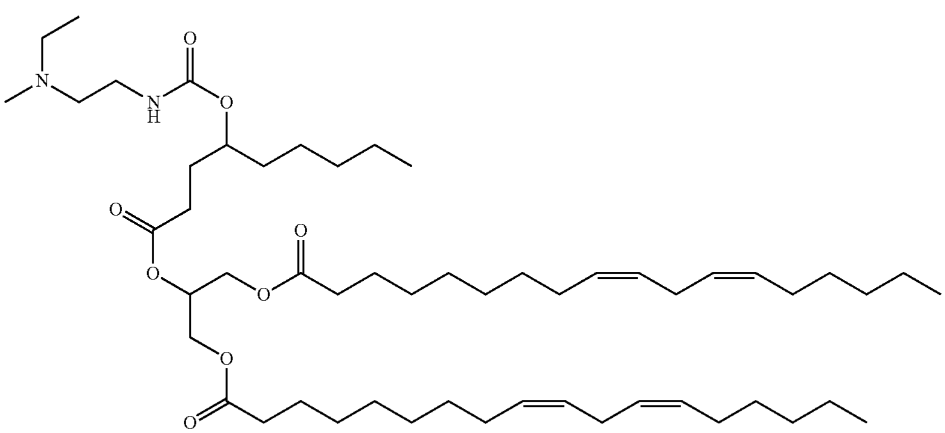 [SMILES: CCCCC/C=C\C/C=C\CCCCCCCC(=O)OCC(COC(=O)CCCCCCC/C=C\C/C=C\CCCCC)OC(=O)CCC(CCCCC)OC(=O)NCCN(C)CC] |

TABLE 1-continued
Compounds
| Compound (pKa) | Structure |
|---|---|
| 70 (6.61) | 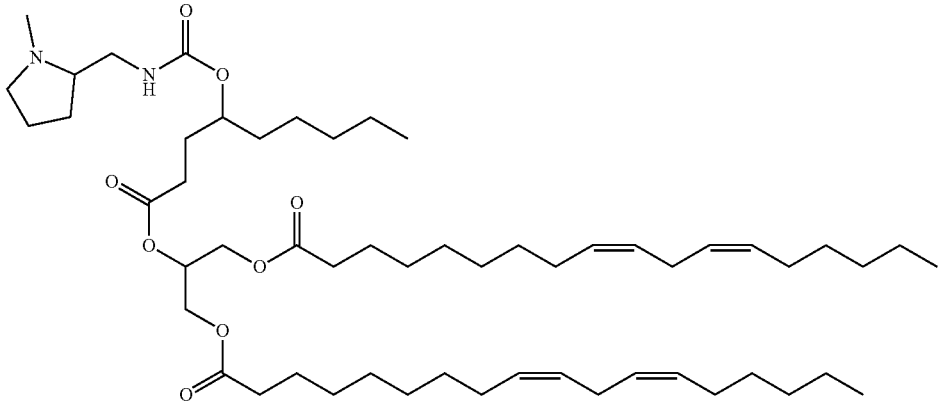 [SMILES: CCCCC/C=C\C/C=C\CCCCCCCC(=O)OCC(COC(=O)CCCCCCC/C=C\C/C=C\CCCCC)OC(=O)CCC(CCCCC)OC(=O)NCC1CCCN1C] |
| 71 (6.28) | 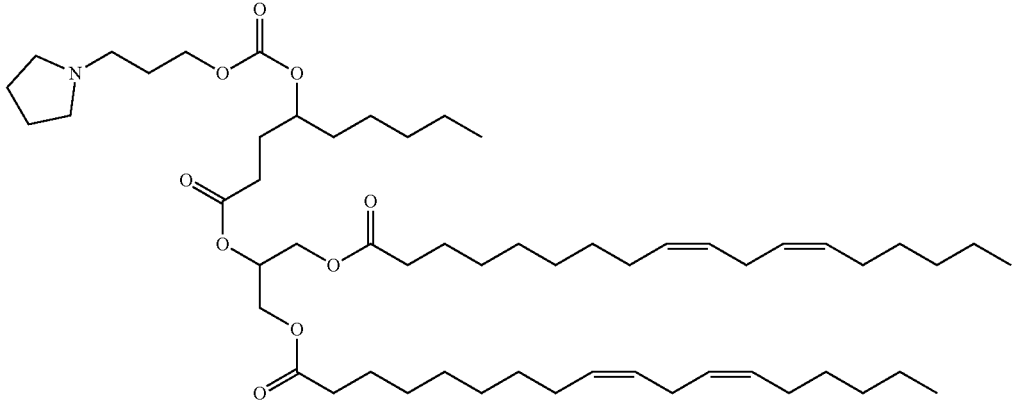 [SMILES: CCCCC/C=C\C/C=C\CCCCCCCC(=O)OCC(COC(=O)CCCCCCC/C=C\C/C=C\CCCCC)OC(=O)CCC(CCCCC)OC(=O)OCCCN1CCCC1] |
| 72 (7.01) | 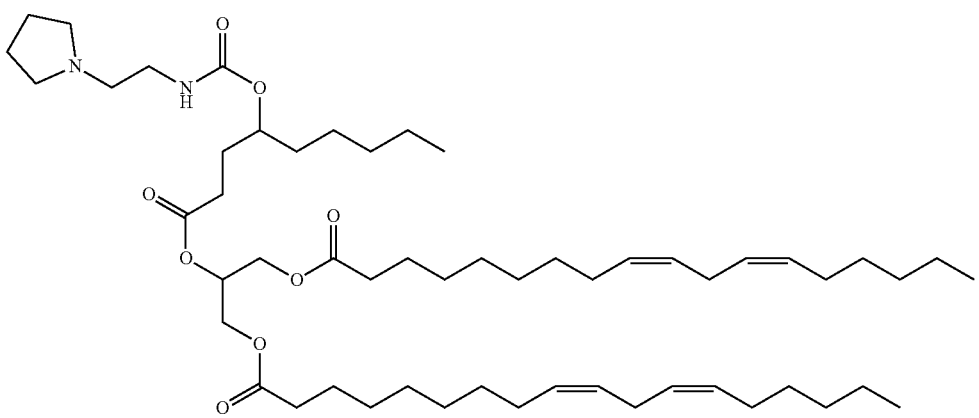 |

TABLE 1-continued

Compounds

| Compound (pKa) | Structure |
|---|---|
| 73 (6.41) | 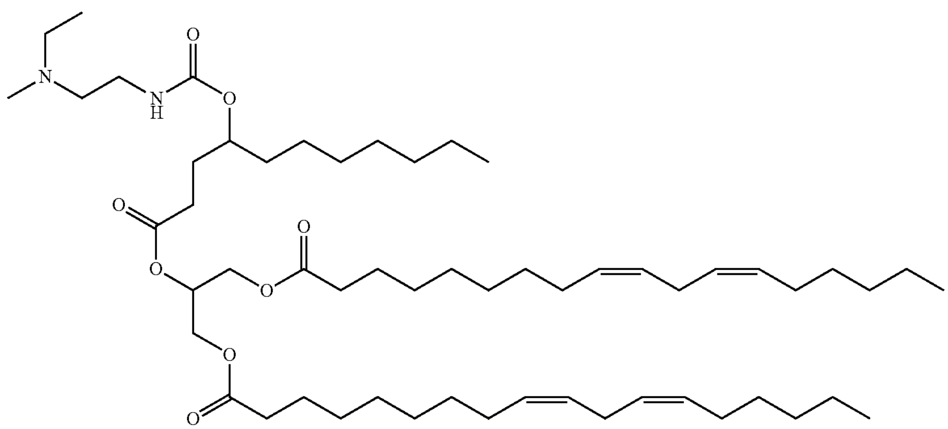 |
| 74 (6.44) | 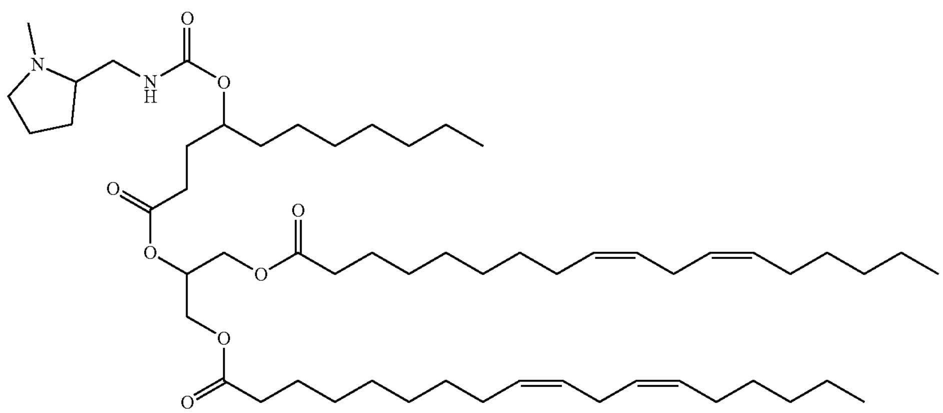 [SMILES: CCCCC/C=C\C/C=C\CCCCCCCC(=O)OCC(COC(=O)CCCCCCC/C=C\C/C=C\CCCCC)OC(=O)CCC(CCCCCCC)OC(=O)NCC1CCCN1C] |
| 75 (6.17) | 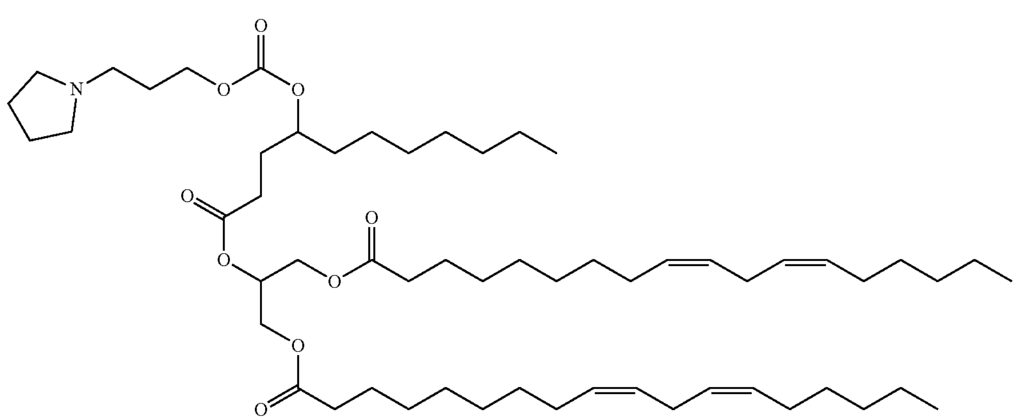 [SMILES: CCCCC/C=C\C/C=C\CCCCCCCC(=O)OCC(COC(=O)CCCCCCC/C=C\C/C=C\CCCCC)OC(=O)CCC(CCCCCCC)OC(=O)OCCCN1CCCC1] |

TABLE 1-continued
Compounds
| Compound (pKa) | Structure |
| --- | --- |
| 76 (6.74) | 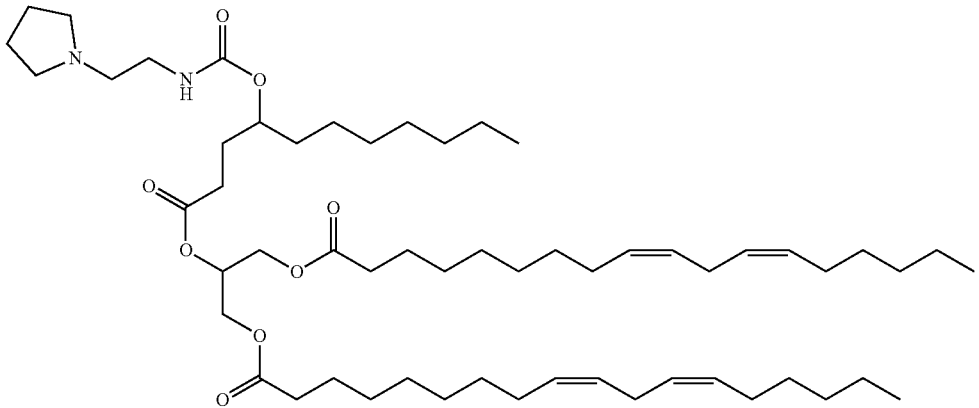 [SMILES: CCCCC/C=C\C/C=C\CCCCCCCC(=O)OCC(COC(=O)CCCCCCC/C=C\C/C=C\CCCCC)OC(=O)CCC(CCCCCCC)OC(=O)NCCN1CCCC1] |
| 77 (7.23) | 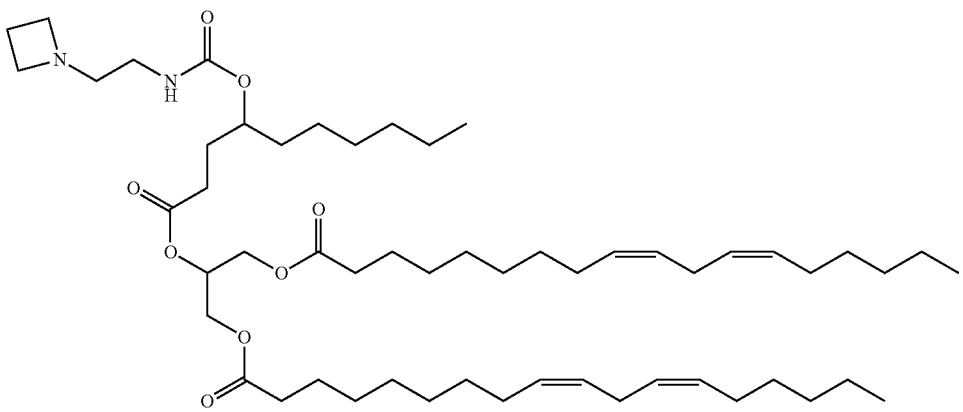 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NCCN1CCC1] |
| 78 (5.93) | 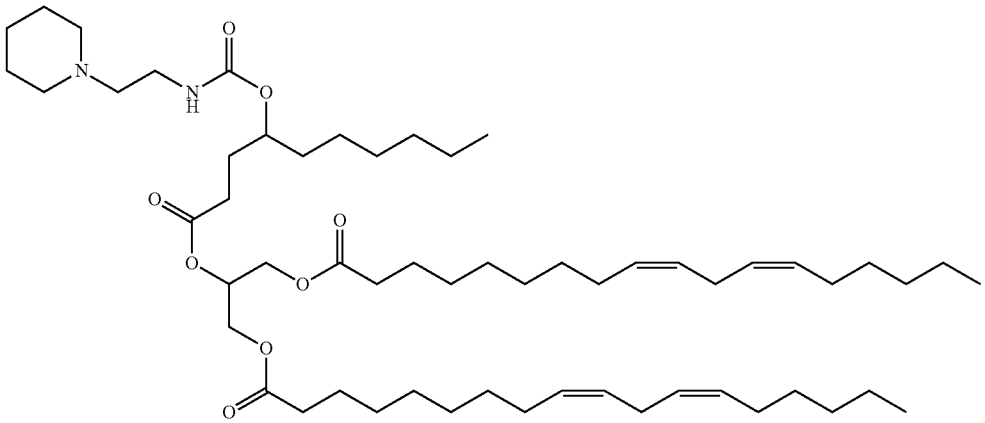 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NCCN1CCCCC1] |

TABLE 1-continued
Compounds
| Compound (pKa) | Structure |
|---|---|
| 79 (4.96) | 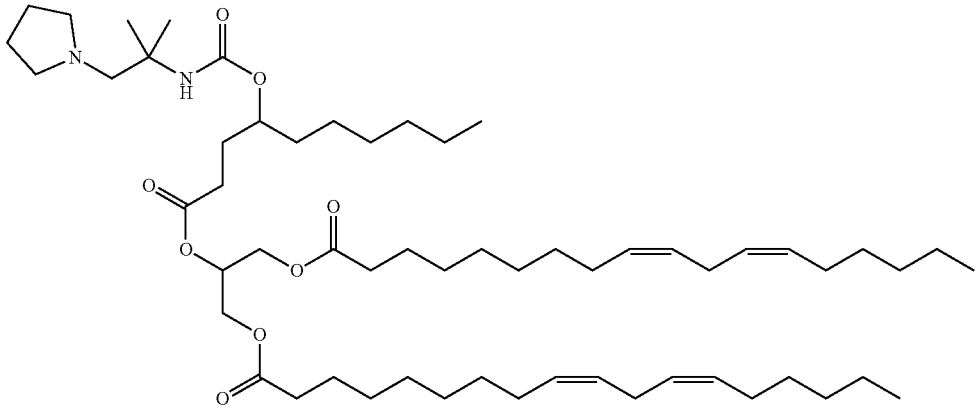 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NC(C)(C)CN1CCCC1] |
| 80 (6.41) | 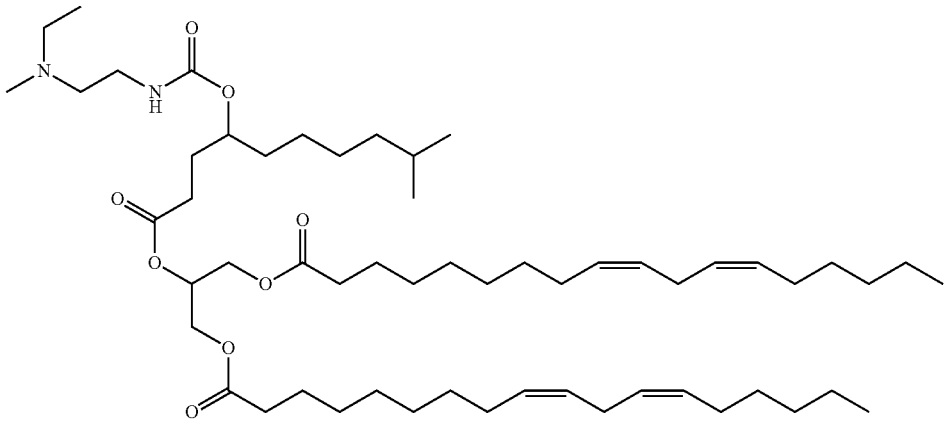 [SMILES: CCCCC/C=C\C/C=C\CCCCCCCC(=O)OCC(COC(=O)CCCCCCC/C=C\C/C=C\CCCCC)OC(=O)CCC(CCCCC(C)C)OC(=O)NCCN(C)CC] |
| 81 (6.42) | 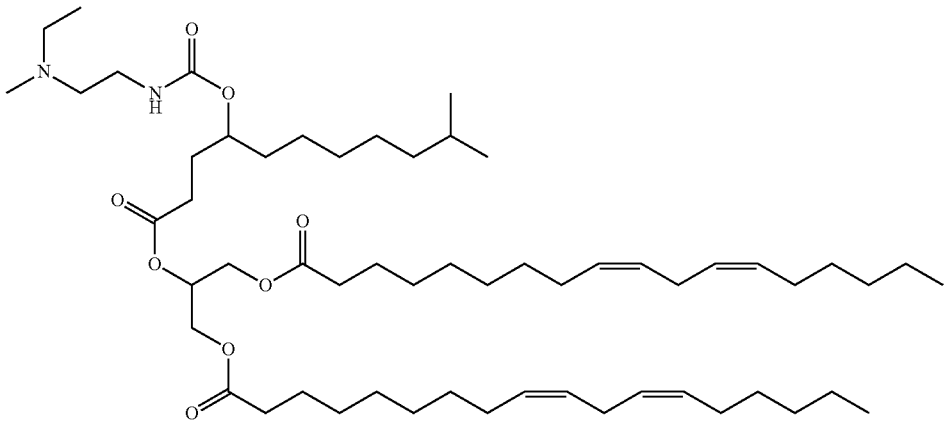 [SMILES: CCCCC/C=C\C/C=C\CCCCCCCC(=O)OCC(COC(=O)CCCCCCC/C=C\C/C=C\CCCCC)OC(=O)CCC(CCCCCC(C)C)OC(=O)NCCN(C)CC] |

TABLE 1-continued
Compounds
| Compound (pKa) | Structure |
|---|---|
| 82 (6.71) | 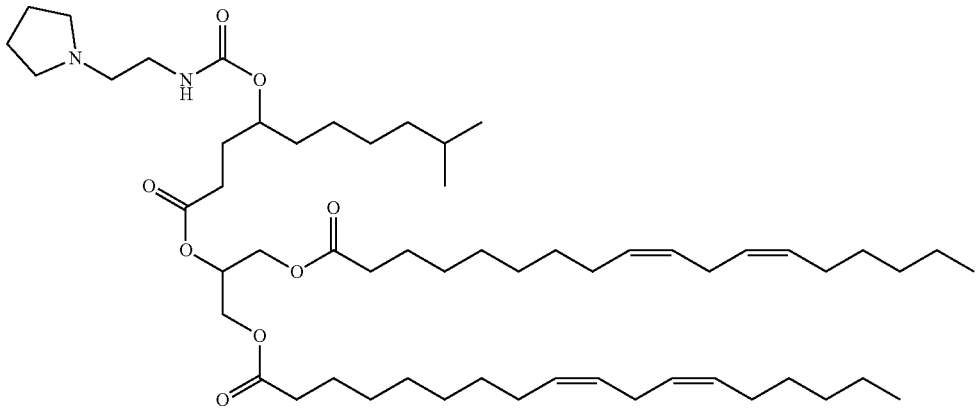 |
| 83 (6.61) | 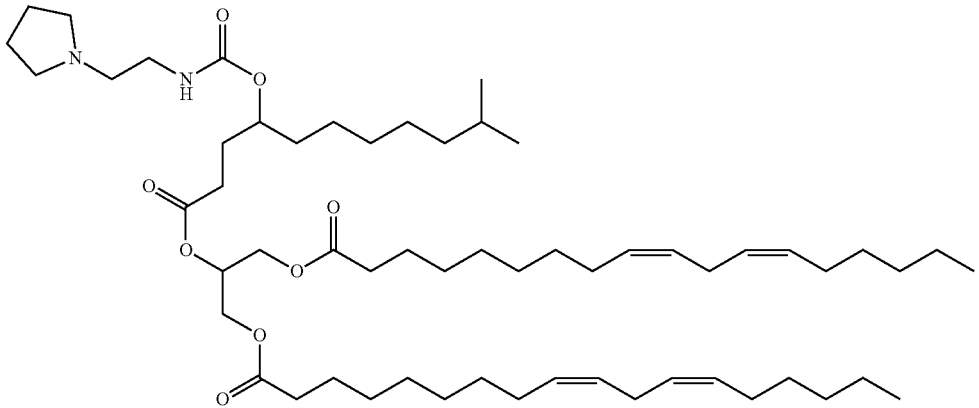 [SMILES: CCCCC/C=C\C/C=C\CCCCCCCC(=O)OCC(COC(=O)CCCCCCC/C=C\C/C=C\CCCCC)OC(=O)CCC(CCCCCC(C)C)OC(=O)NCCN1CCCC1] |
| 84 (7.39) | 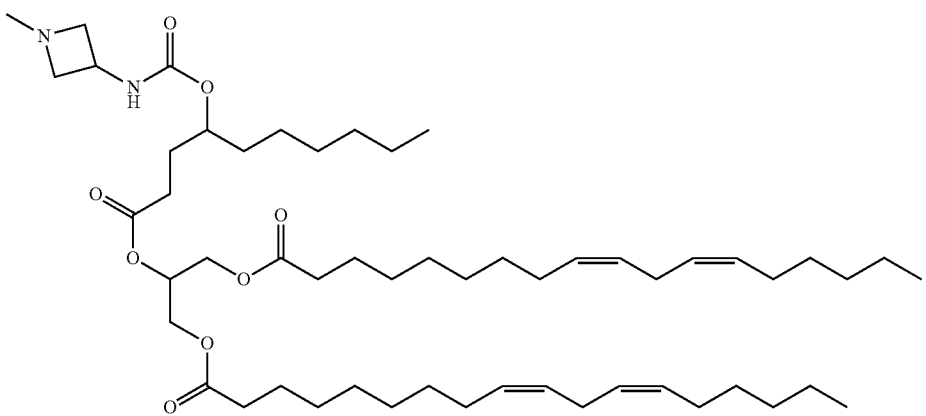 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NC1CN(C)C1] |

TABLE 1-continued
Compounds
| Compound (pKa) | Structure |
|---|---|
| 85 (7.02) | 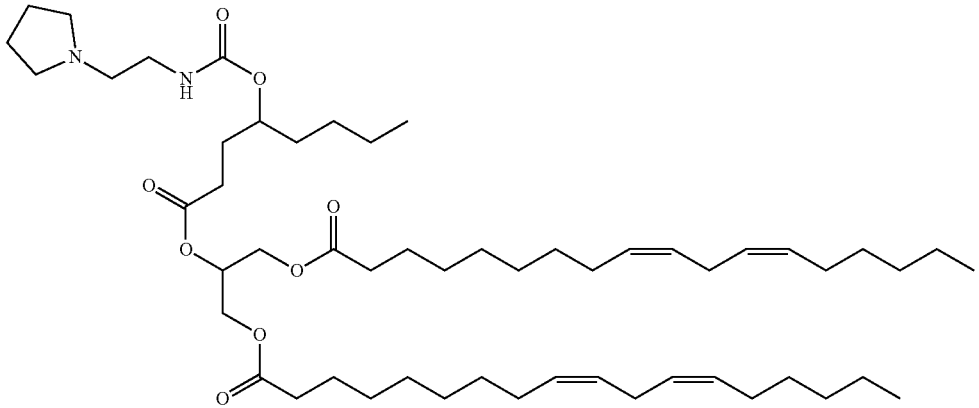 [SMILES: CCCCC/C=C\C/C=C\CCCCCCCC(=O)OCC(COC(=O)CCCCCCC/C=C\C/C=C\CCCCC)OC(=O)CCC(CCCC)OC(=O)NCCN1CCCC1] |
| 86 (6.23) | 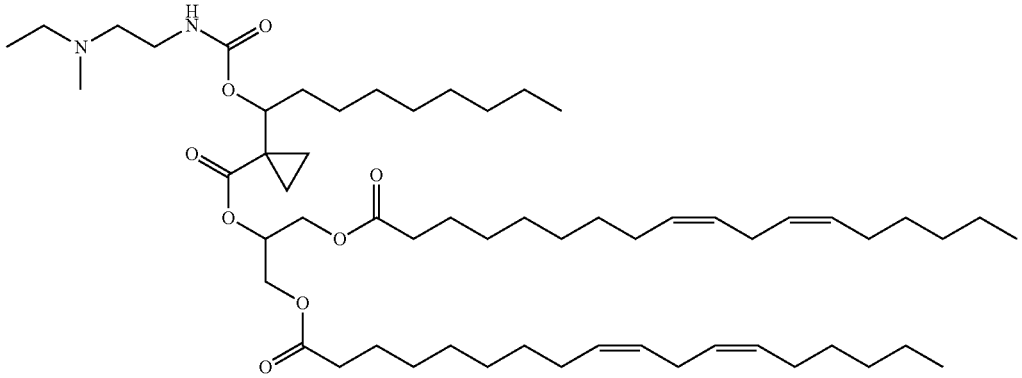 [SMILES: CCCCC/C=C\C/C=C\CCCCCCCC(=O)OCC(COC(=O)CCCCCCC/C=C\C/C=C\CCCCC)OC(=O)C1(C(CCCCCCCC)OC(=O)NCCN(C)CC)CC1] |
| 87 (ND) | 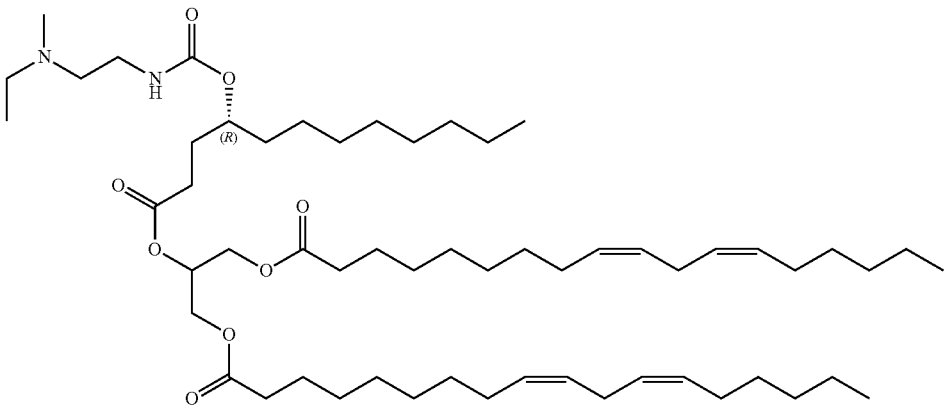 |

TABLE 1-continued

Compounds

| Compound (pKa) | Structure |
|---|---|
| 88 (ND) | 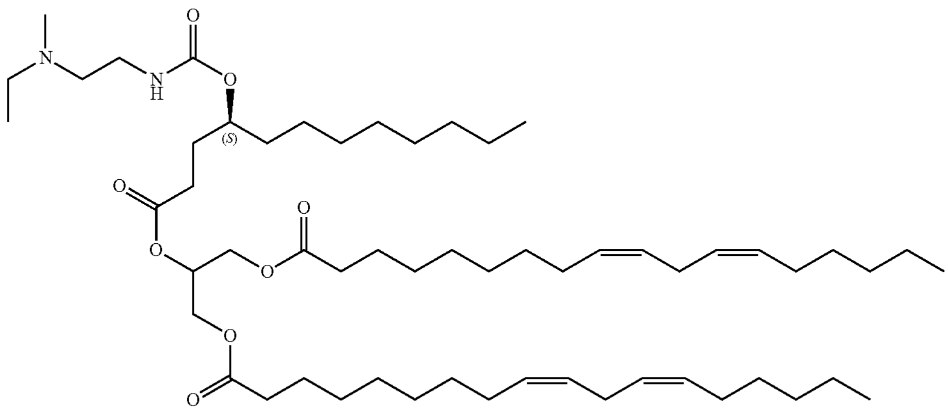 |
| 89 (6.76) | 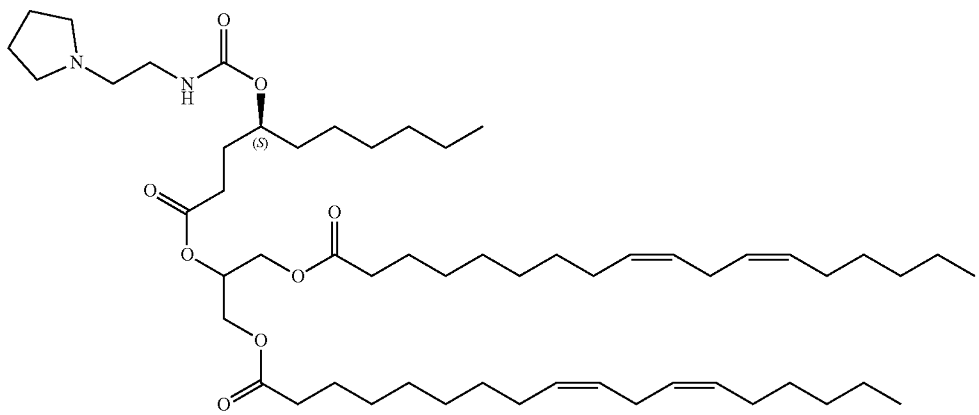 |
| 90 (6.80) | 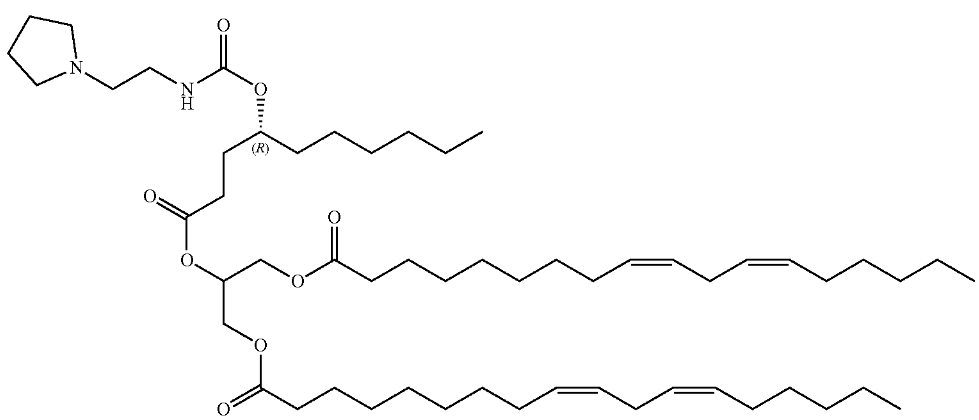 |

TABLE 1-continued

Compounds

| Compound (pKa) | Structure |
| --- | --- |
| 91 (6.48) | 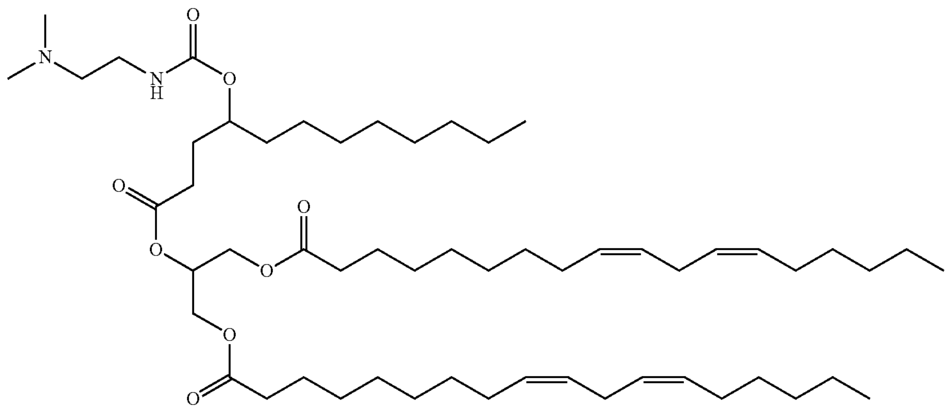 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCCN(C)C] |
| 92 (5.96) | 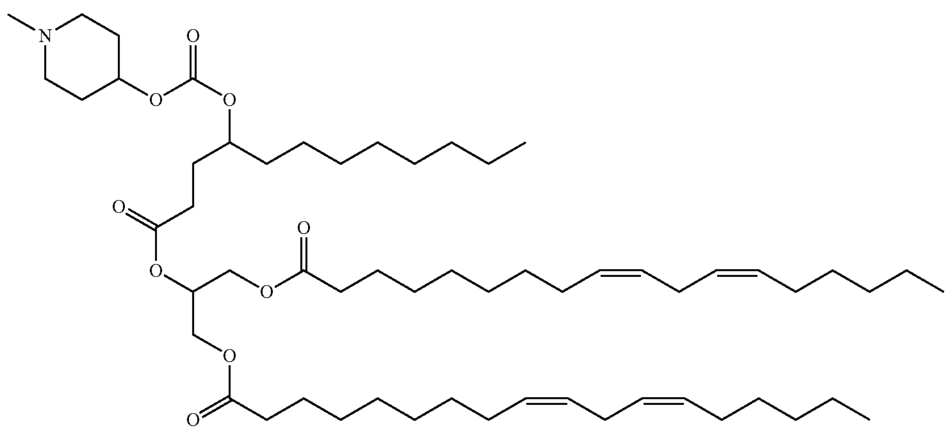 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OC1CCN(C)CC1] |
| 93 (6.96) | 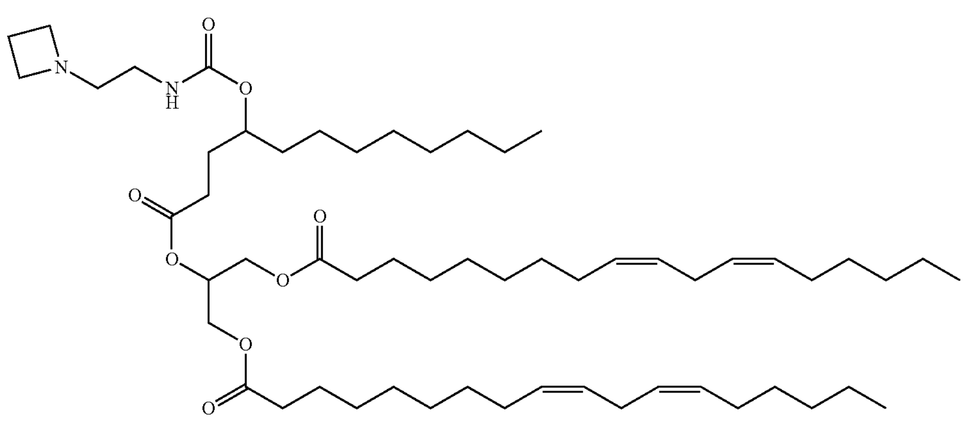 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCCN1CCC1] |

TABLE 1-continued

Compounds

| Compound (pKa) | Structure |
| --- | --- |
| 94 (5.80) | 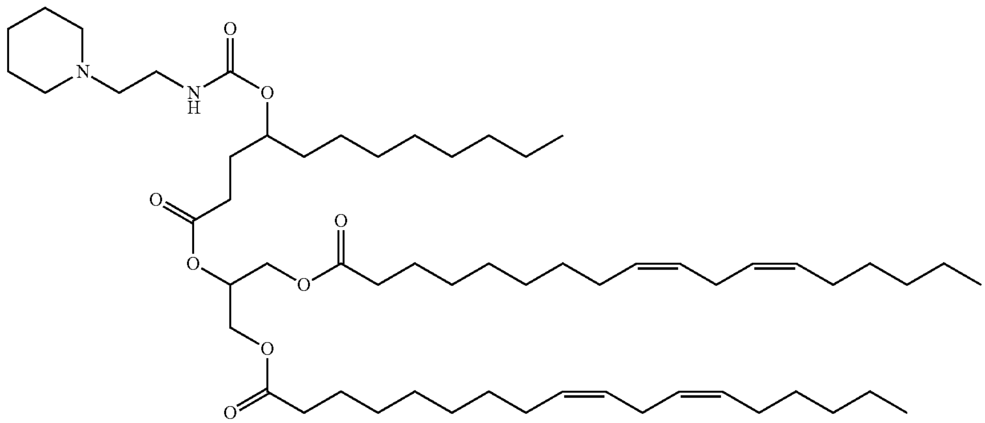 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCCN1CCCCC1] |
| 95 (6.15) | 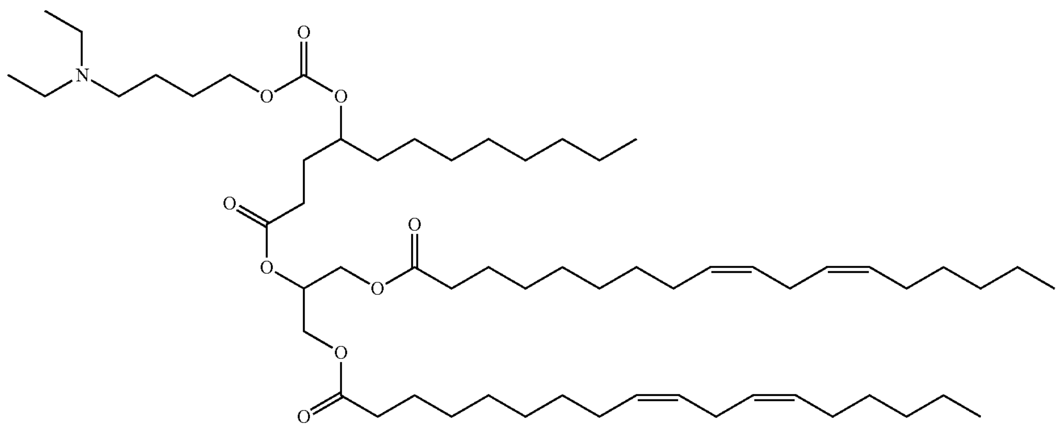 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OCCCCN(CC)CC] |
| 96 (6.14) | 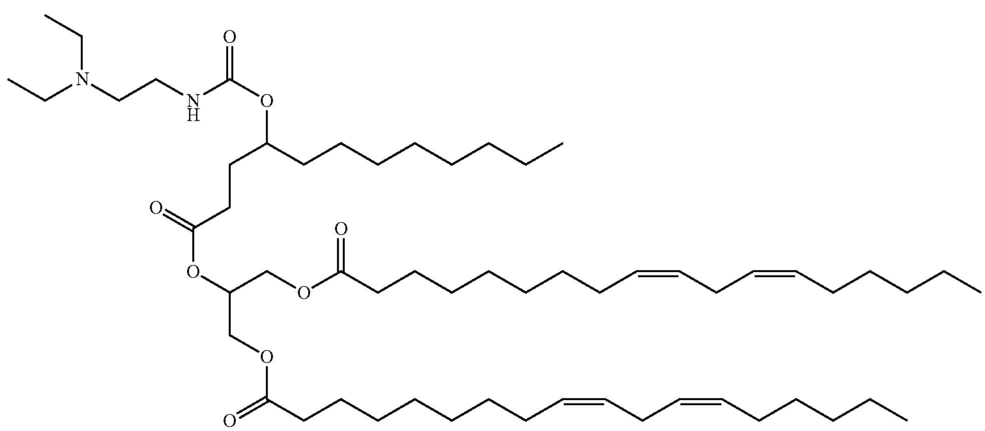 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCCN(CC)CC] |

TABLE 1-continued

Compounds

| Compound (pKa) | Structure |
| --- | --- |
| 97 (6.38) | 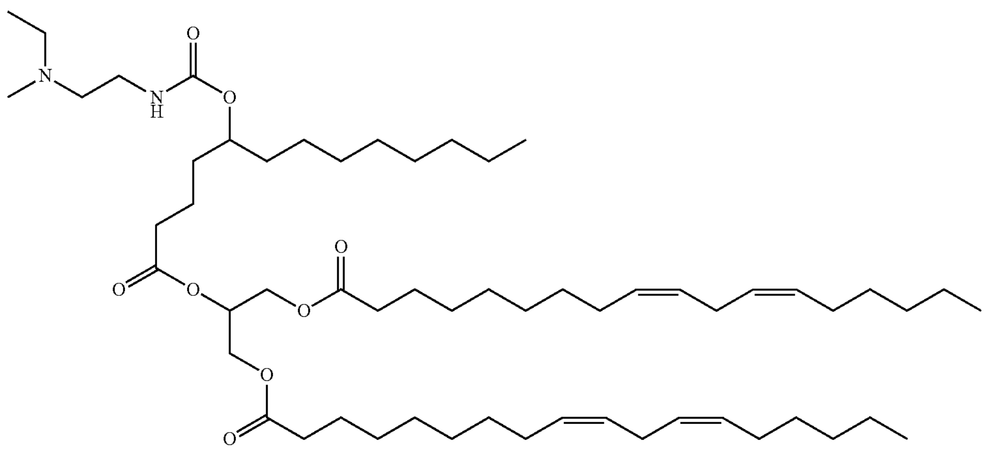 [SMILES: CCCCC/C=C\C/C=C\CCCCCCCC(=O)OCC(COC(=O)CCCCCCC/C=C\C/C=C\CCCCC)OC(=O)CCCC(CCCCCCCC)OC(=O)NCCN(C)CC] |
| 99 (5.96) | 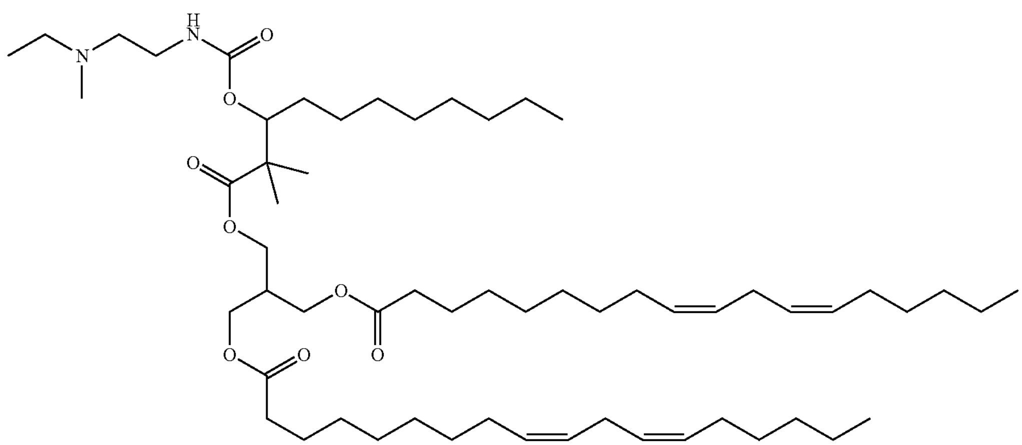 [SMILES: CCCCC/C=C\C/C=C\CCCCCCCC(=O)OCC(COC(=O)CCCCCCC/C=C\C/C=C\CCCCC)COC(=O)C(C)(C)C(CCCCCCCC)OC(=O)NCCN(C)CC] |
| 100 (6.60) | 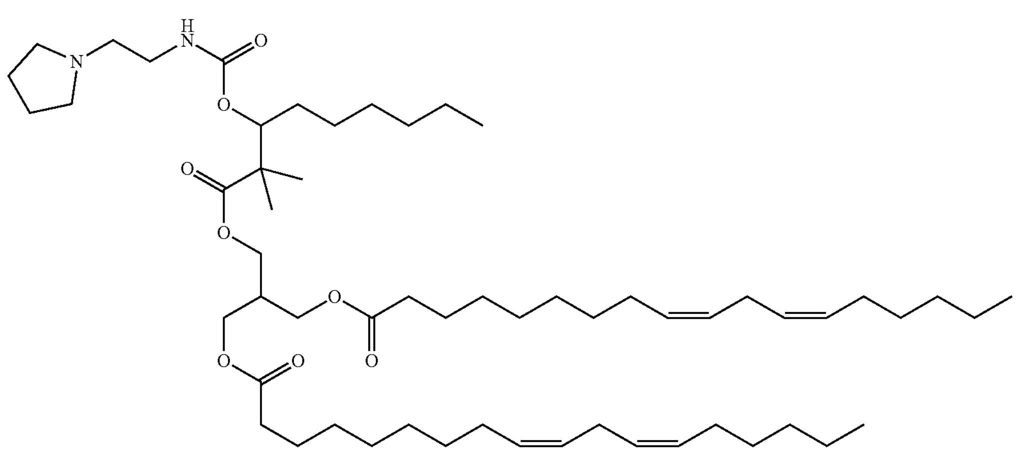 [SMILES: CCCCC/C=C\C/C=C\CCCCCCCC(=O)OCC(COC(=O)CCCCCCC/C=C\C/C=C\CCCCC)COC(=O)C(C)(C)C(CCCCCC)OC(=O)NCCN1CCCC1] |

TABLE 1-continued

Compounds

| Compound (pKa) | Structure |
| --- | --- |
| 101 (6.75) | 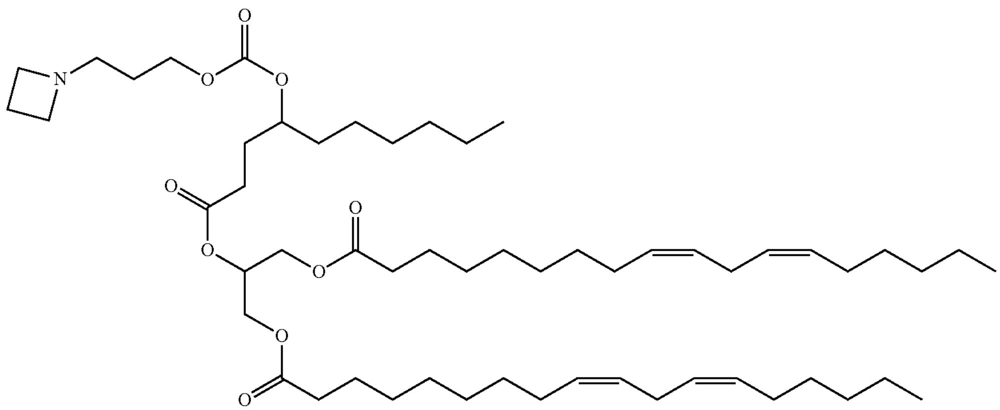 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)OCCCN1CCC1] |
| 102 (5.16) | 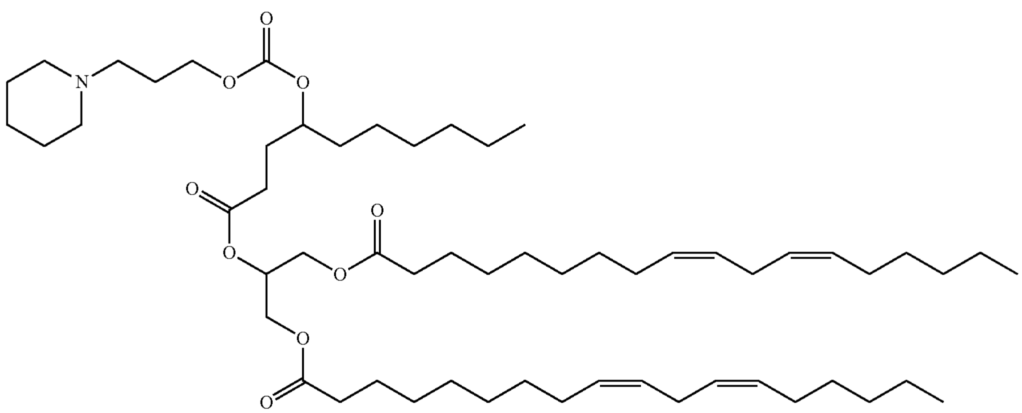 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)OCCCN1CCCCC1] |
| 103 (6.09) | 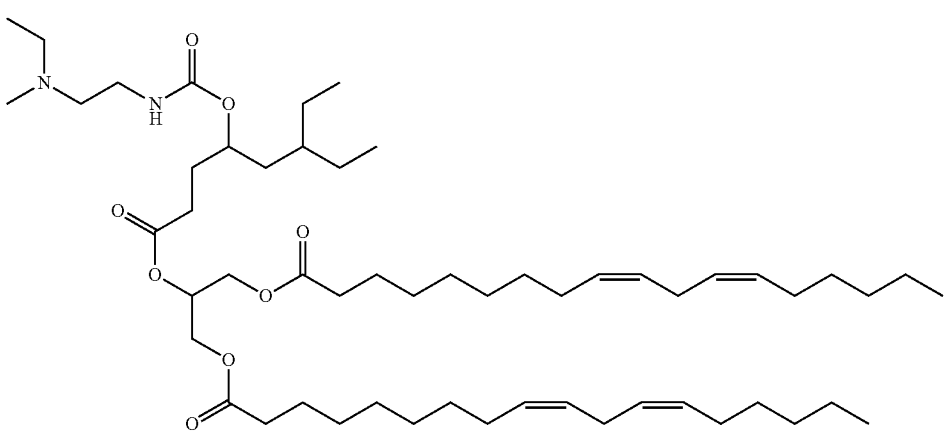 [SMILES: CCCCC/C=C\C/C=C\CCCCCCCC(=O)OCC(COC(=O)CCCCCCC/C=C\C/C=C\CCCCC)OC(=O)CCC(CC(CC)CC)OC(=O)NCCN(C)CC] |

TABLE 1-continued
Compounds
| Compound (pKa) | Structure |
|---|---|
| 105 (6.53) | 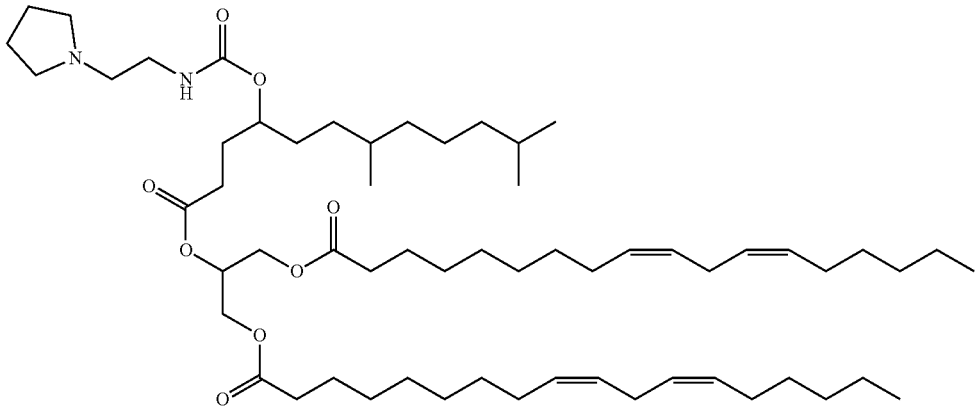 [SMILES: CCCCC/C=C\C/C=C\CCCCCCCC(=O)OCC(COC(=O)CCCCCCC/C=C\C/C=C\CCCCC)OC(=O)CCC(CCC(C)CCCC(C)C)OC(=O)NCCN1CCCC1] |
| 106 (6.80) | 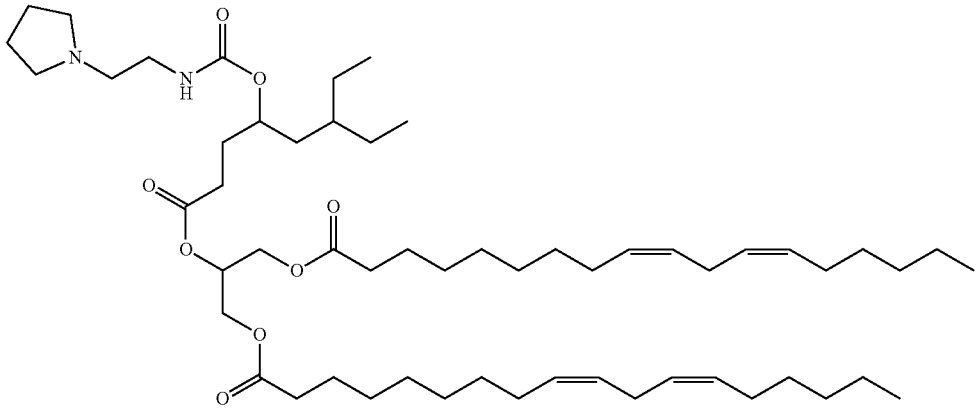 [SMILES: CCCCC/C=C\C/C=C\CCCCCCCC(=O)OCC(COC(=O)CCCCCCC/C=C\C/C=C\CCCCC)OC(=O)CCC(CC(CC)CC)OC(=O)NCCN1CCCC1] |
| 107 (6.35) | 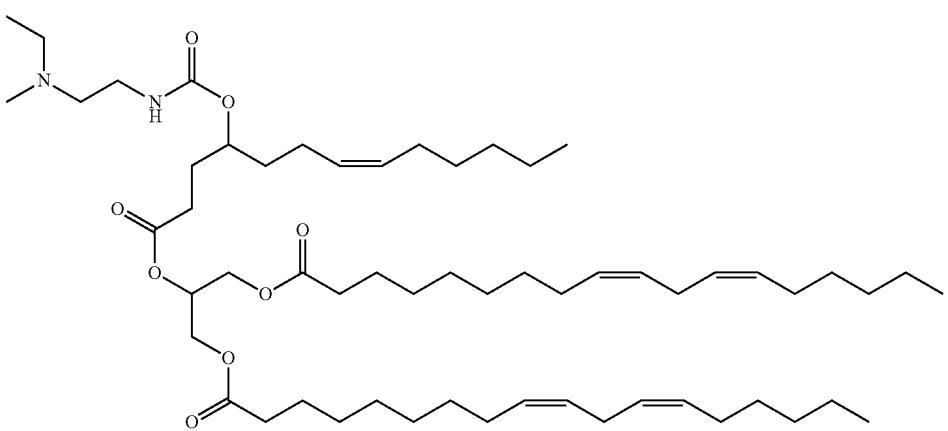 [SMILES: CCCCC/C=C\C/C=C\CCCCCCCC(=O)OCC(COC(=O)CCCCCCC/C=C\C/C=C\CCCCC)OC(=O)CCC(CC/C=C\CCCCC)OC(=O)NCCN(C)CC] |

TABLE 1-continued
Compounds
Compound
(pKa)  Structure
108
(6.52)
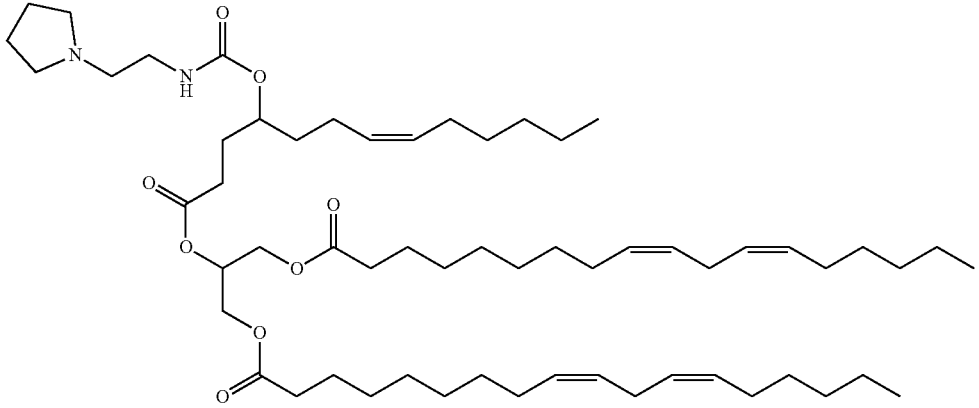 [SMILES: CCCCC/C=C\C/C=C\CCCCCCCC(=O)OCC(COC(=O)CCCCCCC/C=C\C/C=C\CCCCC)OC(=O)CCC(CC/C=C\CCCCC)OC(=O)NCCN1CCCC1]
109
(6.91)
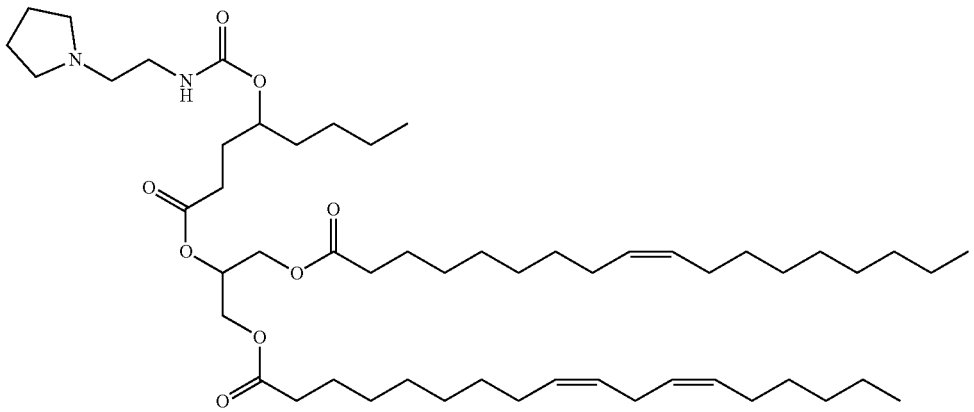 [SMILES: CCCCC/C=C\C/C=C\CCCCCCCC(=O)OCC(COC(=O)CCCCCCC/C=C\CCCCCCCC)OC(=O)CCC(CCCC)OC(=O)NCCN1CCCC1]
110
(7.01)
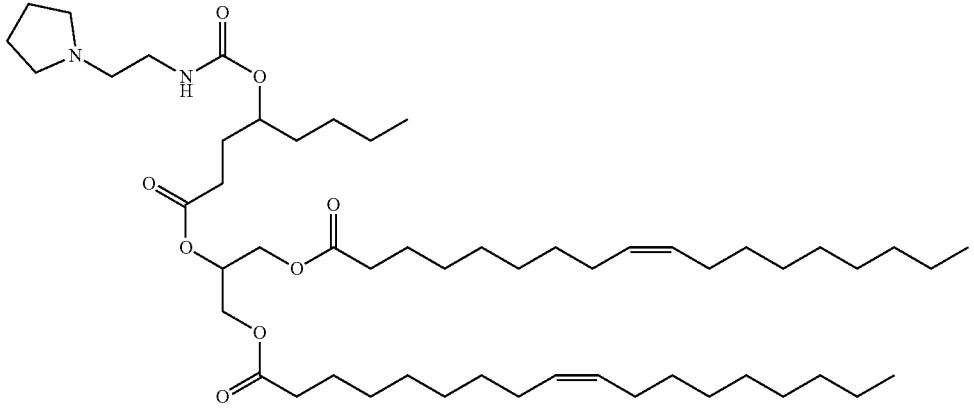 [SMILES: CCCCCCCC/C=C\CCCCCCCC(=O)OCC(COC(=O)CCCCCCC/C=C\CCCCCCCC)OC(=O)CCC(CCCC)OC(=O)NCCN1CCCC1]

TABLE 1-continued

Compounds

| Compound (pKa) | Structure |
| --- | --- |
| 111 (7.02) | 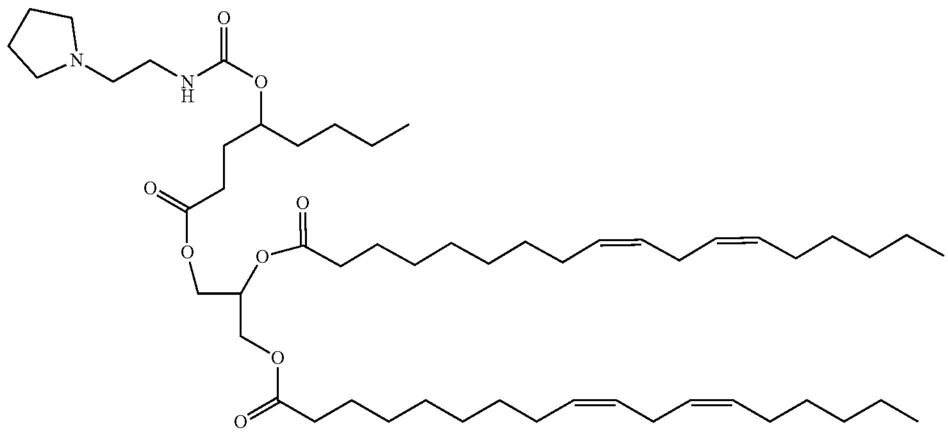 [SMILES: CCCCC/C=C\C/C=C\CCCCCCCC(=O)OCC(COC(=O)CCC(CCCC)OC(=O)NCCN1CCCC1)OC(=O)CCCCCCC/C=C\C/C=C\CCCCC] |
| 112 (7.02) | 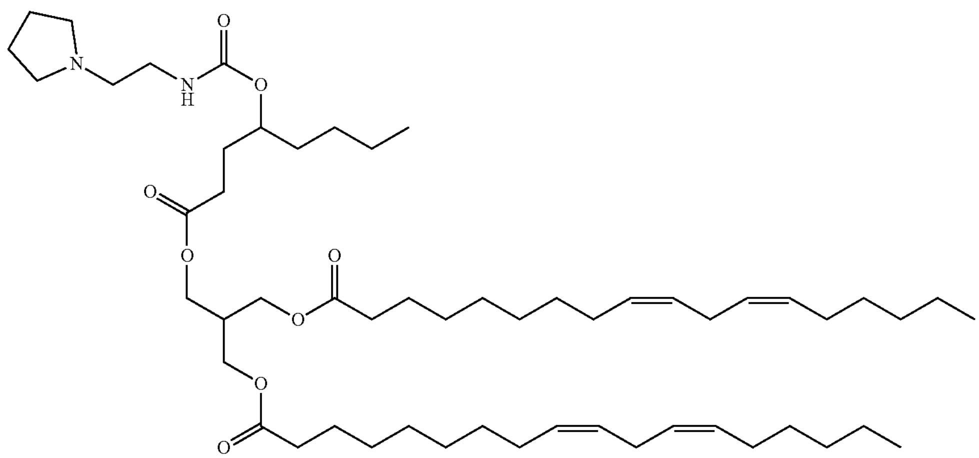 [SMILES: CCCCC/C=C\C/C=C\CCCCCCCC(=O)OCC(COC(=O)CCCCCCC/C=C\C/C=C\CCCCC)COC(=O)CCC(CCCC)OC(=O)NCCN1CCCC1] |
| 113 (7.02) | 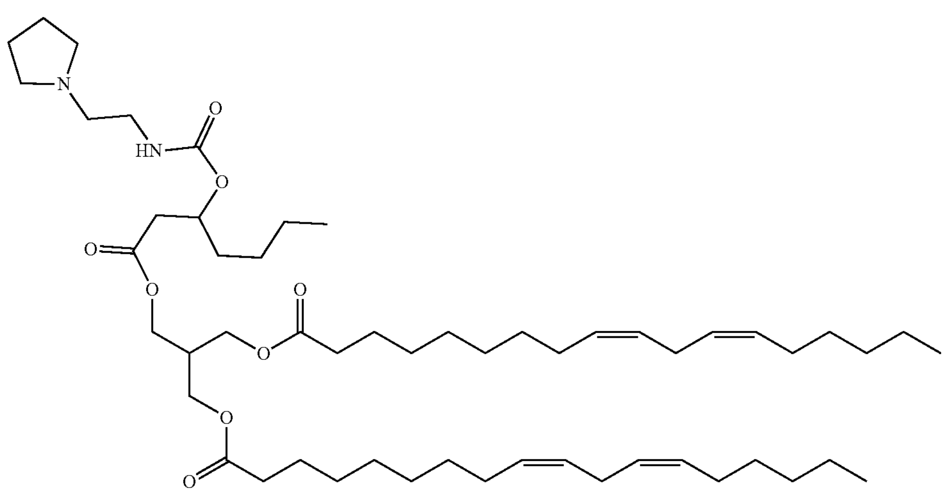 [SMILES: CCCCC/C=C\C/C=C\CCCCCCCC(=O)OCC(COC(=O)CCCCCCC/C=C\C/C=C\CCCCC)COC(=O)CC(CCCC)OC(=O)NCCN1CCCC1] |

TABLE 1-continued

Compounds

| Compound (pKa) | Structure |
|---|---|
| 114 (6.93) | (structure shown) |

Example 1—Comparative Compound 1

Intermediate 1a: 4-oxohexadecanoic acid

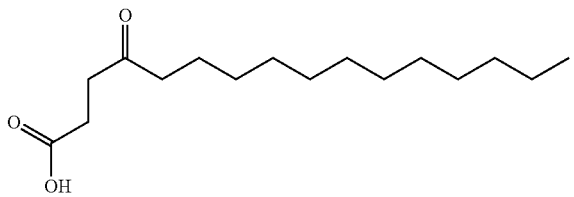 [SMILES: CCCCCCCCCCCCC(=O)CCC(=O)O]

A solution of succinic anhydride (3.0 g, 1.0 equiv) in THF (0.1 M) was cooled to −78° C., followed by the addition of dodecyl magnesium bromide (1.0 M solution in hexanes, 0.5 equiv) dropwise over 5 min. The reaction was maintained at −78° C. for at least 18 h before being quenched by the addition of water and 1 M HCl. The reaction mixture was concentrated in vacuo, and the resulting aqueous layer was extracted 3× with DCM. The combined DCM layers were then extracted 2× with 2 M NaOH, and the combined aqueous layers were acidified to pH=1 using concentrated HCl. The mixture was then extracted 3× with DCM. The combined DCM layers were dried over $Na_2SO_4$, filtered, and concentrated in vacuo to afford crude material. The crude material was triturated 3× with hexanes, and the resulting precipitate was filtered to afford product as a white solid (1.31 g, 33%). $^1$H NMR (400 MHz, $CDCl_3$) δ 2.72 (ddd, J=7.0, 5.8, 1.1 Hz, 2H), 2.67-2.60 (m, 2H), 2.44 (t, J=7.5 Hz, 2H), 1.59 (q, J=7.4 Hz, 2H), 1.26 (d, J=2.7 Hz, 18H), 0.91-0.85 (m, 3H).

Intermediate 1b: 2-oxopropane-1,3-diyl (9Z,9′Z, 12Z,12′Z)-bis(octadeca-9,12-dienoate)

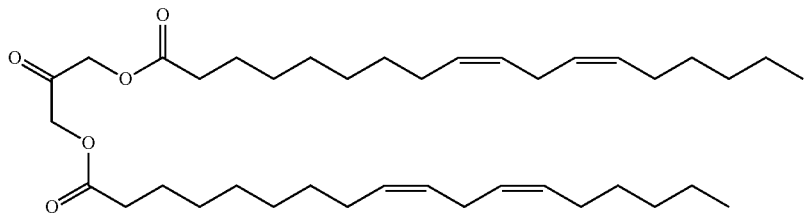 [SMILES: CCCCC/C=C\C/C=C\CCCCCCCC(=O)OCC(=O)COC(=O)CCCCCCC/C=C\C/C=C\CCCCC]

To a solution of dihydroxyacetone (1.55 g, 1.0 equiv) in DCM (0.1 M) was added linoleic acid (2.05 equiv), DMAP (0.2 equiv), DIPEA (2.4 equiv), and EDCI (2.4 equiv). The reaction was stirred at room temperature for at least 18 h. Upon completion, the mixture was quenched by the addition of water, and the organic layer was washed 1× with 1 M HCl and 1× with 5% NaHCO₃. The organic layer was then dried over Na₂SO₄, filtered, and concentrated in vacuo. Crude material was purified by column chromatography (EtOAc/hexanes) to product as a colorless oil (8.0 g, 75%). ¹H NMR (400 MHz, CDCl₃) δ 5.44-5.28 (m, 8H), 4.75 (s, 4H), 2.82-2.74 (m, 4H), 2.42 (t, J=7.5 Hz, 4H), 2.05 (q, J=6.7 Hz, 8H), 1.67 (q, J=7.4 Hz, 4H), 1.40-1.24 (m, 28H), 0.95-0.86 (m, 6H).

Intermediate 1c: 2-hydroxy-3-[(9Z,12Z)-octadeca-9,12-dienoyloxy]propyl (9Z,12Z)-octadeca-9,12-dienoate

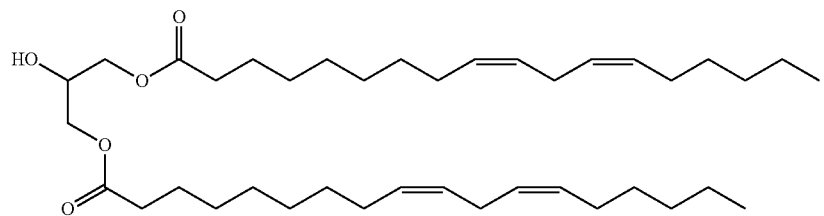 [SMILES: CCCCC/C=C\C/C=C\CCCCCCCC(=O)OCC(O)COC(=O)CCCCCCC/C=C\C/C=C\CCCCC]

A solution of Intermediate 1b (8.1 g, 1.0 equiv) in 4:2:1 THF/water/toluene (0.05-0.1 M) was cooled to 0-5° C., followed by the addition of NaBH₄ (1.7 equiv). The reaction was stirred for at least 1 h at 0-25° C. Upon completion, the mixture was quenched by the addition of water and EtOAc, and the mixture was extracted 3× with EtOAc. The combined organic layers were dried over Na₂SO₄, filtered, and concentrated in vacuo. Crude material was purified by column chromatography (EtOAc/hexanes) to afford product as a colorless oil (5.9 g, 73%). ¹H NMR (400 MHz, CDCl₃) δ 5.46-5.26 (m, 8H), 4.23-4.10 (m, 4H), 2.81-2.73 (m, 4H), 2.42 (d, J=4.8 Hz, 1H), 2.38-2.31 (m, 4H), 2.05 (q, J=6.7 Hz, 8H), 1.68-1.57 (m, 4H), 1.42-1.23 (m, 29H), 0.93-0.85 (m, 6H).

Intermediate 1d: 2-((4-oxohexadecanoyl)oxy)propane-1,3-diyl (9Z,9'Z,12Z,12'Z)-bis(octadeca-9,12-dienoate)

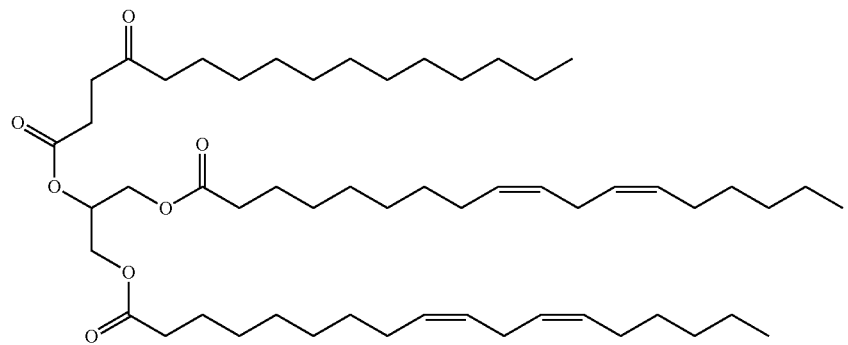 [SMILES: CCCCC/C=C\C/C=C\CCCCCCCC(=O)OCC(COC(=O)CCCCCCC/C=C\C/C=C\CCCCC)OC(=O)CCC(=O)CCCCCCCCCCCC]

To a solution of Intermediate 1c (1.0 equiv) in DCM (0.2 M) was added Intermediate 1a (1.0-1.2 equiv), Et₃N or DIPEA (1.5-4.5 equiv), DMAP (0.1-0.2 equiv), and EDCI (1-2 equiv). The reaction was stirred at room temperature for at least 12 h before being quenched by the addition of water. The mixture was washed 1× with 1 M HCl and 1× with 5% NaHCO₃. The organic layer was then dried over Na₂SO₄, filtered, and concentrated in vacuo. Crude material was purified by column chromatography (EtOAc/hexanes) to afford product as a colorless oil (780 mg, 79%). ¹H NMR (400 MHz, CDCl₃) δ 5.45-5.28 (m, 8H), 5.24 (tt, J=5.9, 4.3 Hz, 1H), 4.29 (dd, J=11.9, 4.3 Hz, 2H), 4.15 (dd, J=11.9, 5.8 Hz, 2H), 2.84-2.74 (m, 4H), 2.71 (t, J=6.8 Hz, 2H), 2.59 (t, J=6.3 Hz, 2H), 2.43 (t, J=7.5 Hz, 2H), 2.32 (t, J=7.6 Hz, 4H), 2.05 (q, J=6.8 Hz, 8H), 1.60 (dd, J=14.7, 7.3 Hz, 6H), 1.44-1.20 (m, 49H), 0.88 (td, J=6.9, 4.3 Hz, 9H).

Intermediate 1e: 2-((4-oxohexadecanoyl)oxy)propane-1,3-diyl (9Z,9'Z,12Z,12'Z)-bis(octadeca-9,12-dienoate)

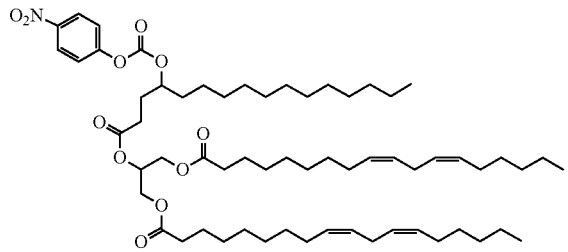 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)Oc1ccc([N+](=O)[O-])cc1]

A solution of Intermediate 1d (1.43 g, 1.0 equiv) in 4:2:1 THF/water/toluene (0.05-0.1 M) was cooled to 0-5° C., followed by the addition of NaBH₄ (5.0 equiv). The reaction was maintained at 0-25° C. for at least 2 h. The reaction was then diluted with water and EtOAc, and the resulting biphasic mixture was extracted 3× with EtOAc. The combined organic layers were dried over Na$_2$SO$_4$, filtered, and concentrated in vacuo. Crude material was purified by column chromatography (EtOAc/hexanes) to afford an intermediate alcohol as a colorless oil.

The resulting alcohol was immediately resolubilized in DCM (0.1 M), followed by the addition of pyridine (2-3 equiv) and 4-nitrophenyl chloroformate (1-1.5 equiv). The reaction was stirred for at least 1 h at room temperature. The mixture was quenched by the addition of water and extracted 3× with DCM. The combined DCM layers were dried over Na$_2$SO$_4$, filtered, and concentrated in vacuo. Crude material was purified by column chromatography (EtOAc/hexanes) to afford product as a colorless oil (910 mg, 54%). $^1$H NMR (400 MHz, CDCl$_3$) δ 8.37-8.25 (m, 2H), 7.48-7.40 (m, 2H), 5.49-5.25 (m, 9H), 4.96-4.84 (m, 1H), 4.34 (dd, J=12.0, 4.3 Hz, 2H), 4.18 (dd, J=11.9, 5.7 Hz, 2H), 2.79 (t, J=6.4 Hz, 4H), 2.49 (dd, J=8.4, 6.7 Hz, 2H), 2.33 (tt, J=7.6, 4.2 Hz, 4H), 2.16-1.95 (m, 10H), 1.81-1.71 (m, 1H), 1.65 (ddq, J=15.2, 7.5, 4.8, 4.2 Hz, 6H), 1.50-1.13 (m, 50H), 0.90 (td, J=6.8, 3.7 Hz, 9H).

Compound 1: 2-((4-(((3-(dimethylamino)propoxy) carbonyl)oxy)hexadecanoyl)oxy)propane-1,3-diyl (9Z,9'Z,12Z,12'Z)-bis(octadeca-9,12-dienoate)

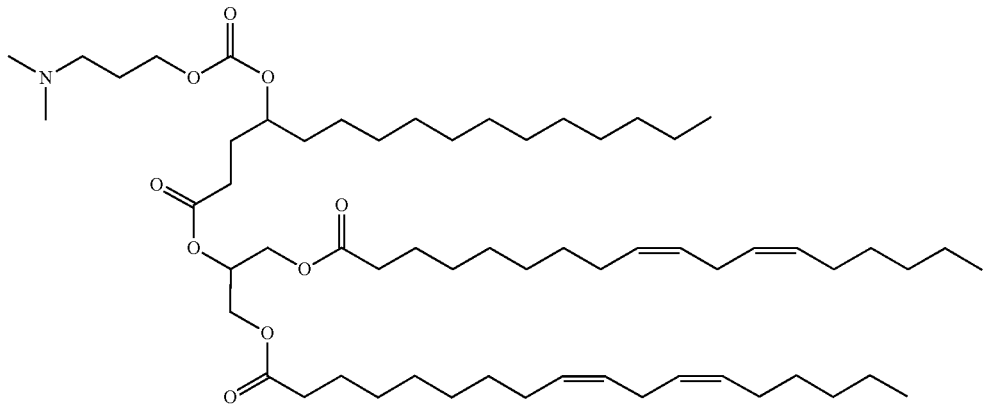

To a solution of Intermediate 1e (250 mg, 1.0 equiv) in MeCN (0.1 M) was added pyridine (3.0 equiv), 3-(dimethylamino)propan-1-ol (1.5-3.0 equiv), and DMAP (1.0 equiv). The reaction was stirred for at least 2 hours at room temperature. Heptane (0.1 M) was then added to the reaction mixture, and the heptane layer was washed 3× with MeCN. The combined MeCN layers were back-extracted three times with heptane, and the combined heptane layers were washed one final time with MeCN. Heptane was then removed in vacuo, and crude material was purified by column chromatography (MeOH/DCM) to afford product as a colorless oil (100 mg, 41%). $^1$H NMR (400 MHz, CDCl$_3$) δ 5.46-5.22 (m, 9H), 4.72 (tdd, J=7.5, 5.3, 4.0 Hz, 1H), 4.29 (dd, J=12.0, 4.4 Hz, 2H), 4.23-4.10 (m, 4H), 2.84-2.73 (m, 4H), 2.62-2.27 (m, 13H), 2.05 (q, J=6.9 Hz, 8H), 2.01-1.84 (m, 4H), 1.68-1.50 (m, 7H), 1.43-1.21 (m, 50H), 0.88 (td, J=6.9, 4.1 Hz, 9H). MS: 1001.2 m/z [M+H].

Example 2—Compound 2

Compound 2: 2-((4-(((3-(diethylamino)propoxy) carbonyl)oxy)hexadecanoyl)oxy)propane-1,3-diyl (9Z,9'Z,12Z,12'Z)-bis(octadeca-9,12-dienoate)

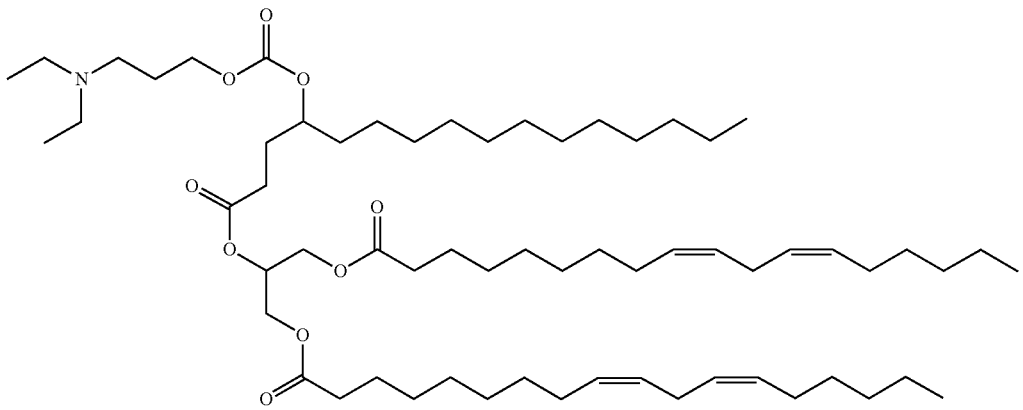 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(CC)CC]

Compound 2 was synthesized in 64% yield from Intermediate 1e and 3-(diethylamino)propan-1-ol using the method employed for Example 1. H NMR (400 MHz, CDCl₃) δ 5.43-5.20 (m, 9H), 4.72 (tdd, J=7.5, 5.3, 4.0 Hz, 1H), 4.29 (dd, J=11.9, 4.4 Hz, 2H), 4.23-4.10 (m, 4H), 2.81-2.73 (m, 4H), 2.57-2.36 (m, 8H), 2.31 (td, J=7.6, 1.3 Hz, 4H), 2.05 (q, J=6.8 Hz, 8H), 1.97-1.77 (m, 4H), 1.61 (t, J=7.4 Hz, 6H), 1.40-1.21 (m, 49H), 1.01 (t, J=7.1 Hz, 6H), 0.88 (td, J=6.9, 4.1 Hz, 9H). MS: 1029.7 m/z [M+H].

Example 3—Compound 3

Compound 3: 2-((4-(((3-(ethyl(methyl)amino)propoxy)carbonyl)oxy)hexadecanoyl)oxy)propane-1,3-diyl (9Z,9'Z,12Z,12'Z)-bis(octadeca-9,12-dienoate)

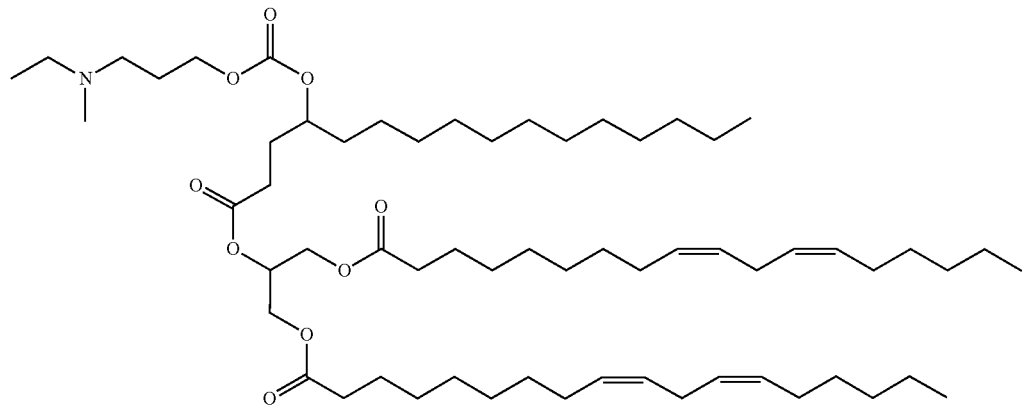 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)CC]

Compound 3 was synthesized in 79% yield from Intermediate 1e and 3-((methyl)ethylamino)propan-1-ol using the method employed for Example 1. ¹H NMR (400 MHz, CDCl₃) δ 5.49-5.20 (m, 9H), 4.77-4.67 (m, 1H), 4.29 (dd, J=11.9, 4.4 Hz, 2H), 4.16 (tdd, J=11.9, 6.2, 2.5 Hz, 4H), 2.77 (t, J=6.4 Hz, 4H), 2.70-2.37 (m, 7H), 2.37-2.25 (m, 7H), 2.13-1.82 (m, 12H), 1.69-1.48 (m, 7H), 1.42-1.20 (m, 46H), 1.14 (s, 2H), 0.88 (td, J=6.8, 3.9 Hz, 7H). MS: 1015.7 m/z [M+H].

Example 4—Compound 4

Compound 4: 2-((4-(((2-(dimethylamino)ethoxy)carbonyl)oxy)hexadecanoyl)oxy)propane-1,3-diyl (9Z,9'Z,12Z,12'Z)-bis(octadeca-9,12-dienoate)

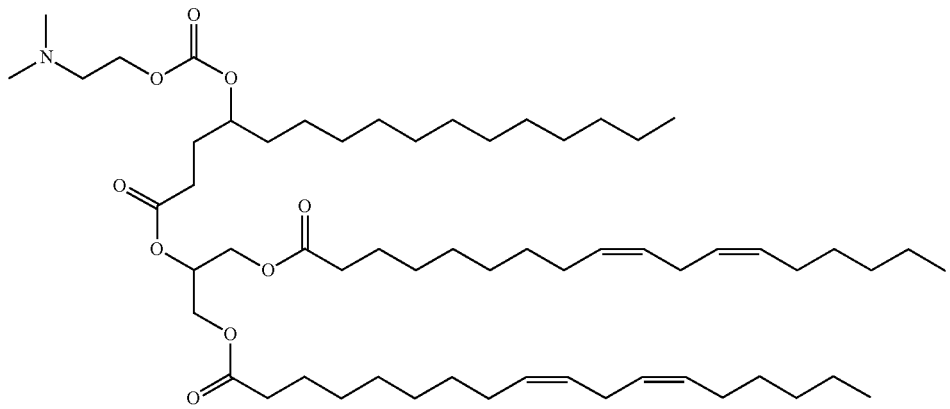 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCN(C)C]

Compound 4 was synthesized in 93% yield from Intermediate 1e and 2-dimethylaminoethan-1-ol using the method employed for Example 1. $^1$H NMR (400 MHz, CDCl$_3$) δ 5.42-5.31 (m, 8H), 5.25 (tt, J=5.8, 4.3 Hz, 1H), 4.73 (tdd, J=7.6, 5.5, 4.0 Hz, 1H), 4.29 (dd, J=11.9, 4.4 Hz, 4H), 4.14 (ddd, J=11.9, 5.8, 3.4 Hz, 2H), 2.77 (td, J=6.0, 1.1 Hz, 4H), 2.70 (d, J=16.4 Hz, 1H), 2.49-2.29 (m, 11H), 2.05 (q, J=6.8 Hz, 8H), 1.99-1.81 (m, 2H), 1.67-1.50 (m, 8H), 1.40-1.21 (m, 48H), 0.88 (td, J=7.0, 4.2 Hz, 9H). MS: 987.6 m/z [M+H].

Example 5—Compound 5

Compound 5: 2-((4-(((3-(pyrrolidin-1-yl)propoxy)carbonyl)oxy)hexadecanoyl)oxy)propane-1,3-diyl (9Z,9'Z,12Z,12'Z)-bis(octadeca-9,12-dienoate)

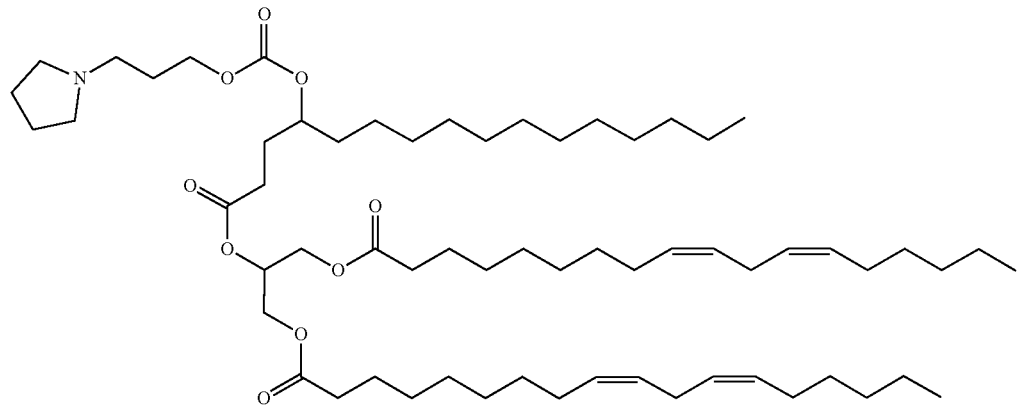 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN1CCCC1]

Compound 5 was synthesized in 54% yield from Intermediate 1e and 3-(pyrrolidin-1-yl)propan-1-ol using the method employed for Example 1. $^1$H NMR (400 MHz, CDCl$_3$) δ 5.45-5.21 (m, 9H), 4.72 (tdd, J=7.3, 5.5, 4.2 Hz, 1H), 4.29 (dd, J=11.9, 4.4 Hz, 2H), 4.17 (dddd, J=15.3, 9.1, 7.3, 3.7 Hz, 4H), 2.77 (td, J=6.0, 1.1 Hz, 4H), 2.57 (d, J=8.8 Hz, 6H), 2.40 (dt, J=8.7, 6.5 Hz, 2H), 2.31 (td, J=7.6, 1.2 Hz, 4H), 2.05 (q, J=6.8 Hz, 8H), 1.98-1.83 (m, 5H), 1.80 (p, J=3.2 Hz, 4H), 1.68-1.50 (m, 7H), 1.41-1.18 (m, 48H), 0.96-0.81 (m, 9H). MS: 1027.6 m/z [M+H].

Example 6—Compound 6

Example 6: 2-((4-((((1-ethylpiperidin-4-yl)oxy)carbonyl)oxy)hexadecanoyl)oxy)propane-1,3-diyl (9Z,9'Z,12Z,12'Z)-bis(octadeca-9,12-dienoate)

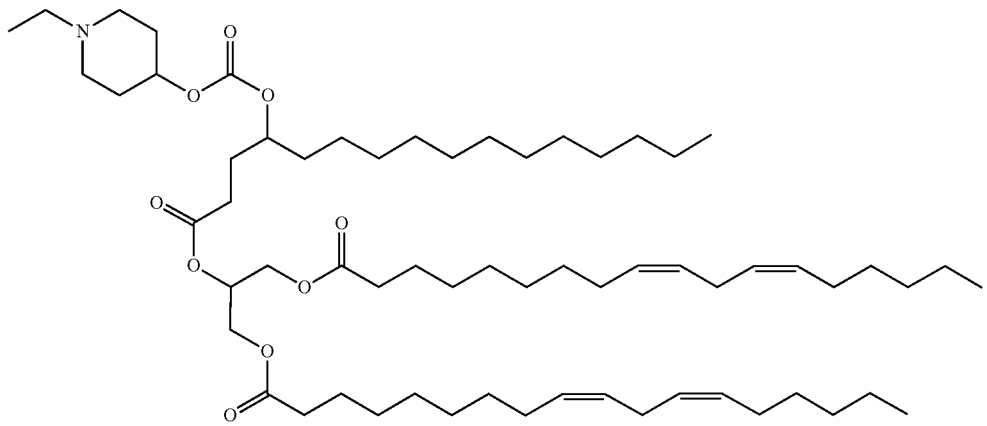 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OC1CCN(CC)CC1]

Compound 6 was synthesized in 53% yield from Intermediate 1e and 1-ethylpiperidin-4-ol using the method employed for Example 1. $^1$H NMR (400 MHz, CDCl$_3$) δ 5.42-5.21 (m, 9H), 4.72 (tdd, J=7.6, 5.3, 4.0 Hz, 1H), 4.64 (d, J=5.1 Hz, 1H), 4.29 (dd, J=11.9, 4.4 Hz, 2H), 4.14 (ddd, J=11.9, 5.8, 4.1 Hz, 2H), 2.84-2.70 (m, 6H), 2.51-2.36 (m, 4H), 2.31 (td, J=7.6, 1.4 Hz, 4H), 2.24 (d, J=23.1 Hz, 2H), 2.11-1.93 (m, 11H), 1.92-1.73 (m, 4H), 1.70-1.52 (m, 8H), 1.43-1.21 (m, 48H), 1.09 (t, J=7.2 Hz, 3H), 0.88 (td, J=7.0, 4.2 Hz, 9H). MS: 1028.2 m/z [M+H].

Example 7—Compound 7

Compound 7: 2-((4-(((2-(ethyl(methyl)amino)ethyl)carbamoyl)oxy)hexadecanoyl)oxy)propane-1,3-diyl (9Z,9′Z,12Z,12′Z)-bis(octadeca-9,12-dienoate)

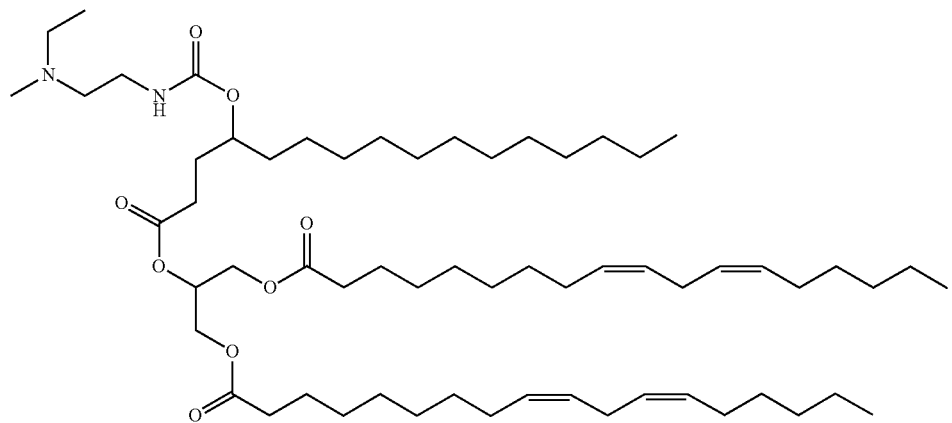 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCN(C)CC]

Compound 7 was synthesized in 66% yield from Intermediate 1e and N1-ethyl-N1-methylethane-1,2-diamine using the method employed for Example 1. $^1$H NMR (400 MHz, CDCl$_3$) δ 5.47-5.08 (m, 10H), 4.76 (s, 1H), 4.28 (ddd, J=11.9, 4.4, 1.4 Hz, 2H), 4.15 (ddd, J=11.9, 5.9, 3.3 Hz, 2H), 3.24 (q, J=6.0 Hz, 2H), 2.82-2.74 (m, 4H), 2.53-2.26 (m, 10H), 2.21 (s, 3H), 2.05 (q, J=6.8 Hz, 8H), 1.98-1.74 (m, 2H), 1.68-1.41 (m, 8H), 1.41-1.19 (m, 49H), 1.04 (t, J=7.2 Hz, 3H), 0.95-0.82 (m, 9H). MS: 1001.1 m/z [M+H].

Example 8—Compound 8

Compound 8: 2-((4-(((3-(dimethylamino)propyl)carbamoyl)oxy)hexadecanoyl)oxy)propane-1,3-diyl

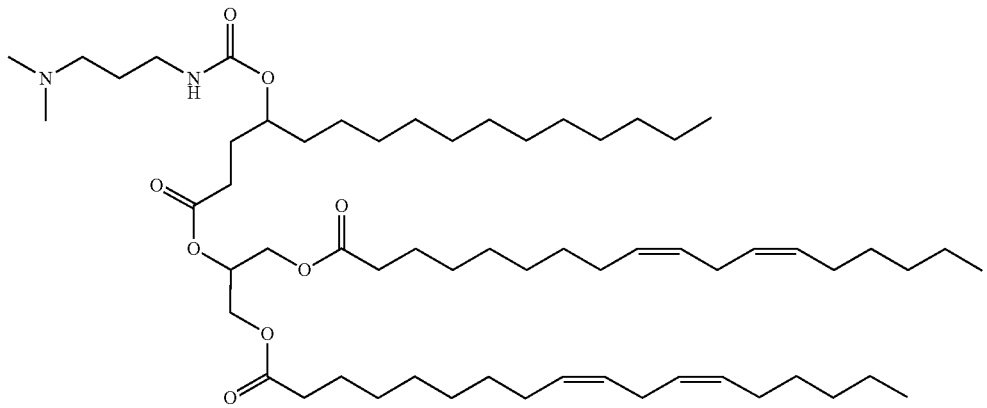 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCCN(C)C]

Compound 8 was synthesized in 55% yield from Intermediate 1e and N1,N1-dimethylpropane-1,3-diamine using the method employed for Example 1. ¹H NMR (400 MHz, CDCl₃) δ 5.46 (t, J=5.8 Hz, 1H), 5.43-5.28 (m, 8H), 5.24 (tt, J=5.8, 4.4 Hz, 1H), 4.75 (s, 1H), 4.28 (ddd, J=11.9, 4.5, 2.2 Hz, 2H), 4.15 (ddd, J=11.9, 5.8, 1.6 Hz, 2H), 3.23 (h, J=6.4 Hz, 2H), 2.82-2.73 (m, 4H), 2.48-2.20 (m, 14H), 2.05 (q, J=6.8 Hz, 8H), 1.97-1.42 (m, 12H), 1.42-1.20 (m, 48H), 0.88 (td, J=6.9, 4.1 Hz, 9H). MS: 1000.6 m/z [M+H].

Example 9—Compound 9

Compound 9: 2-((4-((((1-methylpyrrolidin-2-yl)methyl)carbamoyl)oxy)hexadecanoyl)oxy) propane-1,3-diyl (9Z,9'Z,12Z,12'Z)-bis(octadeca-9,12-dienoate)

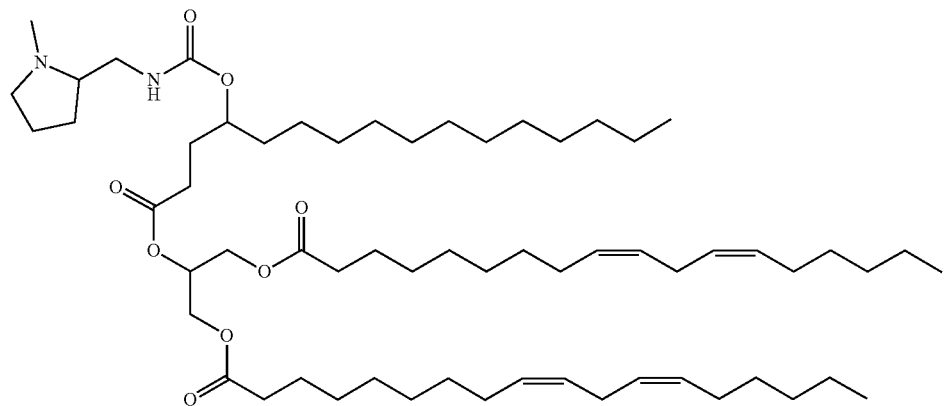 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCC1CCCN1C]

Compound 9 was synthesized in 65% yield from Intermediate 1e and (1-methylpyrrolidin-2-yl)methanamine using the method employed for Example 1. ¹H NMR (400 MHz, Chloroform-d) δ 5.45-5.28 (m, 8H), 5.25 (ddd, J=10.2, 5.8, 4.4 Hz, 1H), 5.19-5.11 (m, 1H), 4.76 (s, 1H), 4.28 (dd, J=11.9, 4.4 Hz, 2H), 4.14 (ddd, J=11.9, 5.9, 3.0 Hz, 2H), 3.44-3.31 (m, 1H), 3.19-3.02 (m, 2H), 2.84-2.72 (m, 4H), 2.46-2.16 (m, 12H), 2.05 (q, J=6.9 Hz, 8H), 1.97-1.66 (m, 6H), 1.66-1.42 (m, 8H), 1.42-1.20 (m, 49H), 0.88 (td, J=7.0, 4.2 Hz, 9H). MS: 1013.1 m/z [M+H].

Example 10—Compound 10

Compound 10: 2-((4-((1,4-dimethylpiperidine-4-carbonyl)oxy)hexadecanoyl)oxy)propane-1,3-diyl (9Z,9'Z,12Z,12'Z)-bis(octadeca-9,12-dienoate)

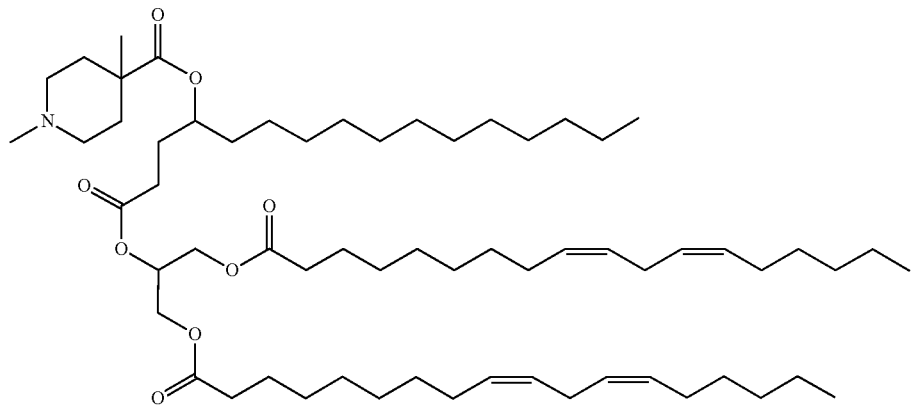 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)C1(C)CCN(C)CC1]

A solution of Intermediate 1d (360 mg, 1.0 equiv) in 4:2:1 THF/water/toluene (0.05 M) was cooled to 0° C., followed by the addition of NaBH$_4$ (5.0 equiv). The reaction was maintained at 0° C. for 18 h. The reaction was then diluted with water and EtOAc, and the resulting biphasic mixture was extracted 3× with EtOAc. The combined organic layers were dried over Na$_2$SO$_4$, filtered, and concentrated in vacuo. Crude material was purified by column chromatography (EtOAc/hexanes) to afford intermediate alcohol as a colorless oil.

The resulting crude alcohol was immediately resolubilized in DCM (0.1 M), followed by the addition of 1,4-dimethylpiperidine-4-carboxylic acid (1.0 equiv), DMAP (0.1 equiv), DIPEA (4.0 equiv), and EDCI (1.5 equiv). The reaction was stirred at room temperature. After 16 h, additional 1,4-dimethylpiperidine-4-carboxylic acid (1.0 equiv), DMAP (0.05 equiv), DIPEA (2.0 equiv), and EDCI (1.5 equiv) were added to the reaction, and the reaction was heated to 40° C. After an additional two hours, the reaction was quenched by the addition of water and DCM, and the organic layer was washed 1× with 1 M HCl, 1× with 5% NaHCO$_3$, and 1× with brine. The resulting organic layer was dried over Na$_2$SO$_4$, filtered, and concentrated in vacuo. Crude material was purified by column chromatography (MeOH/DCM) to afford product as a pink oil (94 mg, 22%). $^1$H NMR (400 MHz, CDCl$_3$) δ 5.46-5.22 (m, 9H), 4.92 (ddd, J=11.6, 7.5, 4.7 Hz, 1H), 4.30 (dd, J=11.9, 4.4 Hz, 2H), 4.14 (ddd, J=12.0, 5.8, 1.9 Hz, 2H), 2.82-2.74 (m, 4H), 2.67 (s, 2H), 2.41-2.25 (m, 9H), 2.14 (d, J=14.2 Hz, 4H), 2.05 (q, J=6.8 Hz, 8H), 1.98-1.78 (m, 3H), 1.66-1.49 (m, 9H), 1.43-1.18 (m, 50H), 0.88 (td, J=6.9, 4.3 Hz, 9H).

Example 11—Compound 11

Compound 11: 2-((4-((4-(diethylamino)butanoyl)oxy)hexadecanoyl)oxy)propane-1,3-diyl (9Z,9'Z,12Z,12'Z)-bis(octadeca-9,12-dienoate)

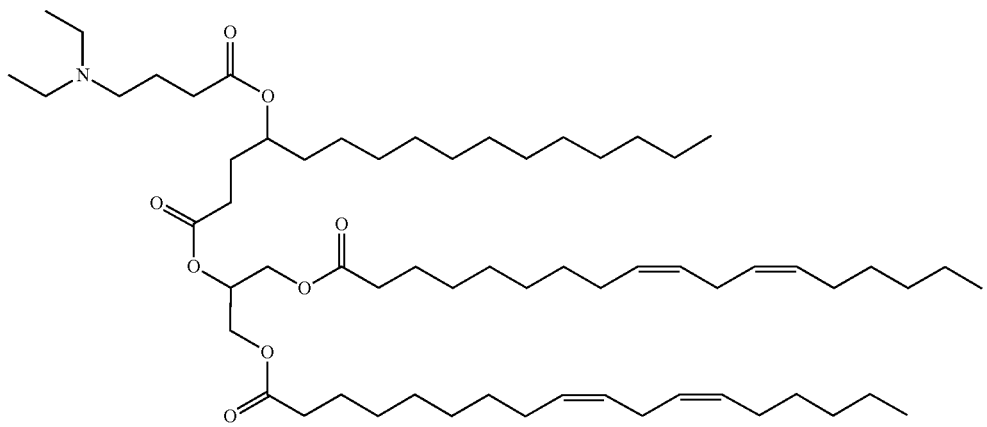 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)CCCN(CC)CC]

Compound 11 was synthesized in 17% yield from Intermediate 1d and 3-(diethylamino)butanoic acid using the method employed for Example 10. $^1$H NMR (400 MHz, CDCl$_3$) δ 5.46 (t, J=5.8 Hz, 1H), 5.43-5.28 (m, 8H), 5.24 (tt, J=5.8, 4.4 Hz, 1H), 4.75 (s, 1H), 4.28 (ddd, J=11.9, 4.5, 2.2 Hz, 2H), 4.15 (ddd, J=11.9, 5.8, 1.6 Hz, 2H), 3.23 (h, J=6.4 Hz, 2H), 2.82-2.73 (m, 4H), 2.48-2.20 (m, 14H), 2.05 (q, J=6.8 Hz, 8H), 1.97-1.42 (m, 12H), 1.42-1.20 (m, 48H), 0.88 (td, J=6.9, 4.1 Hz, 9H). MS: 1013.9 m/z [M+H].

Example 12—Compound 12

Compound 12: 2-((4-(((2-(dimethylamino)ethyl)carbamoyl)oxy)hexadecanoyl)oxy)propane-1,3-diyl (9Z,9'Z,12Z,12'Z)-bis(octadeca-9,12-dienoate)

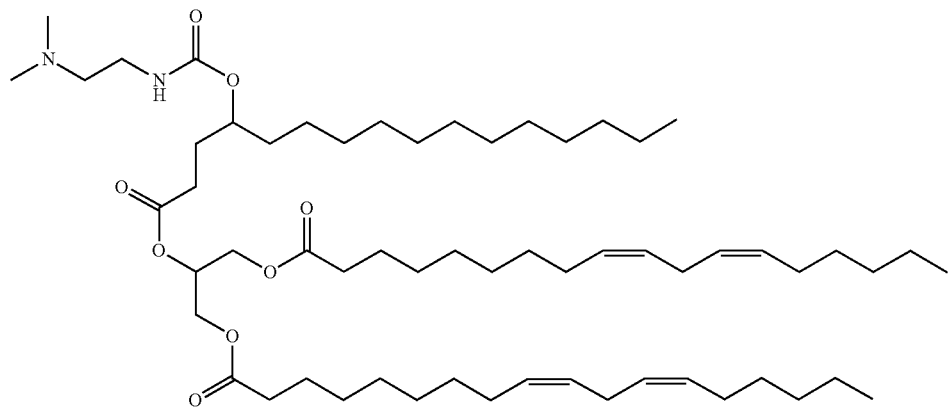 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCN(C)C]

Compound 12 was synthesized in 67% yield from Intermediate 1e and N1,N1-dimethylethane-1,2-diamine using the method employed for Example 1. ¹H NMR (400 MHz, CDCl₃) δ 5.44-5.29 (m, 8H), 5.29-5.18 (m, 2H), 4.75 (s, 1H), 4.34-4.24 (m, 2H), 4.15 (ddd, J=11.9, 5.8, 3.6 Hz, 2H), 3.25 (q, J=5.8 Hz, 2H), 2.77 (td, J=6.2, 1.2 Hz, 4H), 2.47-2.35 (m, 4H), 2.35-2.28 (m, 4H), 2.24 (s, 6H), 2.05 (q, J=7.1 Hz, 8H), 1.98-1.73 (m, 4H), 1.65-1.42 (m, 7H), 1.40-1.20 (m, 48H), 0.88 (td, J=7.0, 4.3 Hz, 9H). MS: 987.2 m/z [M+H].

Example 13—Compound 13

Compound 13: 2-((4-(((3-(diethylamino)propyl) carbamoyl)oxy)hexadecanoyl)oxy)propane-1,3-diyl (9Z,9'Z,12Z,12'Z)-bis(octadeca-9,12-dienoate)

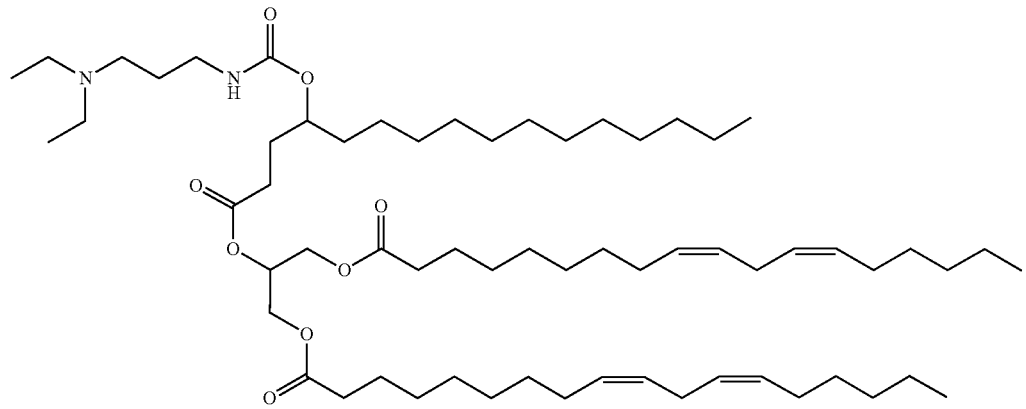

Compound 13 was synthesized in 62% yield from Intermediate 1e and N1,N1-diethylpropane-1,3-diamine using the method employed for Example 1. ¹H NMR (400 MHz, CDCl₃) δ 5.93 (s, 1H), 5.44-5.28 (m, 8H), 5.24 (ddd, J=5.8, 4.5, 1.3 Hz, 1H), 4.74 (s, 1H), 4.28 (ddd, J=11.9, 4.5, 2.7 Hz, 2H), 4.14 (ddd, J=11.9, 5.8, 1.2 Hz, 2H), 3.24 (tt, J=13.2, 6.6 Hz, 2H), 2.81-2.71 (m, 4H), 2.57 (d, J=7.7 Hz, 6H), 2.38 (ddd, J=8.9, 6.8, 3.2 Hz, 2H), 2.35-2.28 (m, 4H), 2.05 (q, J=6.6 Hz, 8H), 1.94-1.85 (m, 2H), 1.79 (dq, J=14.8, 8.1 Hz, 2H), 1.73-1.56 (m, 7H), 1.56-1.43 (m, 3H), 1.40-1.20 (m, 47H), 1.06 (t, J=7.1 Hz, 6H), 0.88 (td, J=7.0, 4.3 Hz, 9H). MS: 1029.2 m/z [M+H].

Example 14—Compound 14

Compound 14: 2-((4-(((4-(diethylamino)butoxy) carbonyl)oxy)hexadecanoyl)oxy)propane-1,3-diyl (9Z,9'Z,12Z,12'Z)-bis(octadeca-9,12-dienoate)

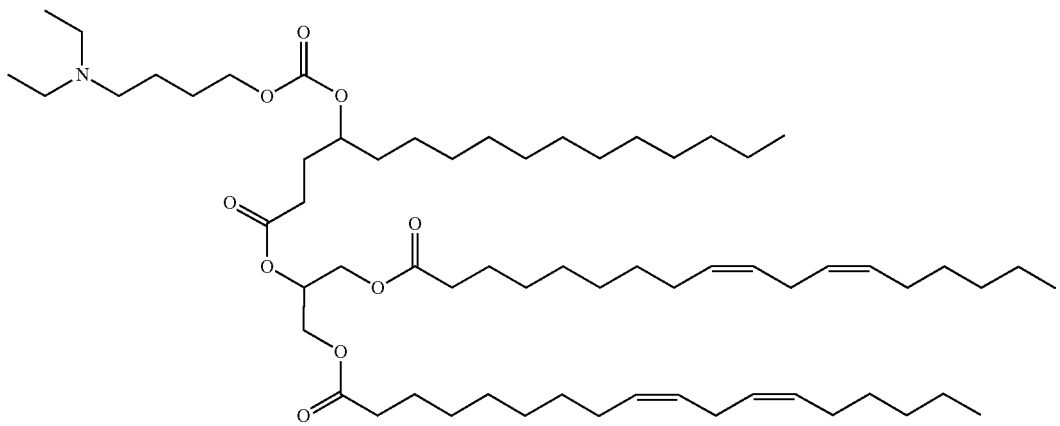 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCCN(CC)CC]

Compound 14 was synthesized in 60% yield from Intermediate 1e and N1,N1-dimethylethane-1,2-diamine using the method employed for Example 1. $^1$H NMR (400 MHz, CDCl$_3$) δ 5.45-5.30 (m, 9H), 5.28 (tt, J=5.8, 4.3 Hz, 1H), 4.78-4.69 (m, 1H), 4.31 (dd, J=11.9, 4.4 Hz, 2H), 4.22-4.09 (m, 4H), 2.79 (td, J=6.1, 1.1 Hz, 4H), 2.63 (q, J=7.2 Hz, 4H), 2.55 (t, J=7.6 Hz, 2H), 2.47-2.38 (m, 2H), 2.38-2.30 (m, 4H), 2.07 (q, J=7.1 Hz, 8H), 2.02-1.85 (m, 2H), 1.76-1.51 (m, 11H), 1.45-1.21 (m, 49H), 1.08 (t, J=7.2 Hz, 6H), 0.95-0.82 (m, 9H). MS: 1044.1 m/z [M+H].

Example 15—Compound 15

Compound 15: 2-((4-(((2-(diethylamino)ethyl)carbamoyl)oxy)hexadecanoyl)oxy)propane-1,3-diyl (9Z,9'Z,12Z,12'Z)-bis(octadeca-9,12-dienoate)

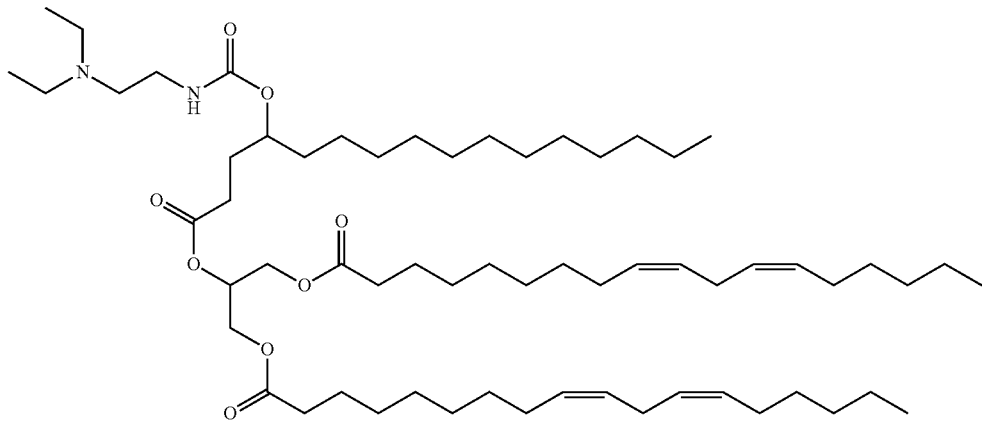

Compound 15 was synthesized in 75% yield from Intermediate 1e and N1,N1-diethylethane-1,2-diamine using the method employed for Example 1. $^1$H NMR (400 MHz, CDCl$_3$) δ 5.44-5.29 (m, 9H), 5.25 (ddd, J=5.8, 4.4, 1.4 Hz, 1H), 4.75 (s, 1H), 4.28 (ddd, J=11.9, 4.4, 1.2 Hz, 2H), 4.14 (ddd, J=11.9, 5.8, 3.0 Hz, 2H), 3.23 (q, J=5.7 Hz, 2H), 2.80-2.73 (m, 4H), 2.57 (q, J=7.0 Hz, 6H), 2.38 (ddd, J=9.0, 6.6, 4.7 Hz, 2H), 2.34-2.28 (m, 4H), 2.05 (q, J=6.8 Hz, 8H), 1.90 (h, J=9.0, 7.9 Hz, 1H), 1.80 (p, J=7.3, 6.5 Hz, 1H), 1.66-1.44 (m, 7H), 1.40-1.20 (m, 53H), 1.03 (t, J=7.1 Hz, 6H), 0.88 (td, J=6.9, 4.3 Hz, 9H). MS: 1014.9 m/z [M+H].

Example 16—Compound 16

Compound 16: 2-((4-(((2-(1-methylpyrrolidin-2-yl)ethoxy)carbonyl)oxy)hexadecanoyl)oxy) propane-1,3-diyl (9Z,9'Z,12Z,12'Z)-bis(octadeca-9,12-dienoate)

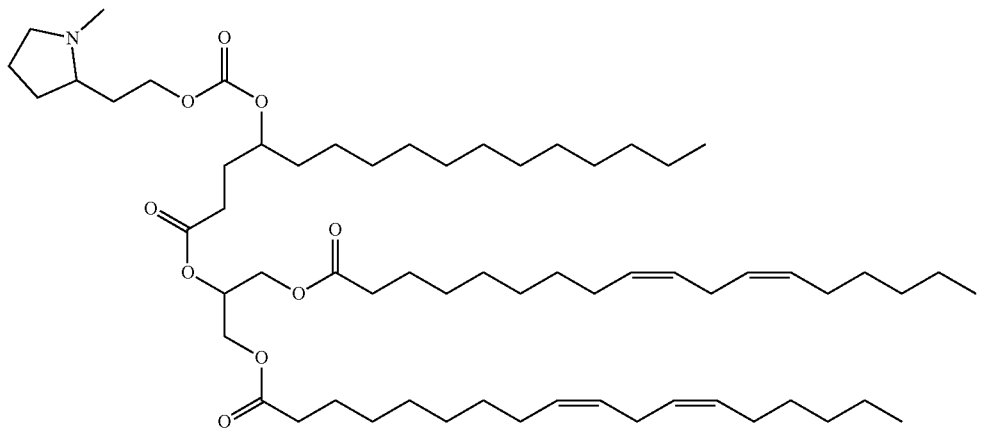 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCC1CCCN1C]

Compound 16 was synthesized in 78% yield from Intermediate 1e and 2-(1-methylpyrrolidin-2-yl)ethan-1-ol using the method employed for Example 1. ¹H NMR (400 MHz, CDCl₃) δ 5.43-5.28 (m, 9H), 5.25 (tt, J=5.8, 4.3 Hz, 1H), 4.72 (qd, J=7.6, 4.6 Hz, 1H), 4.29 (dd, J=11.9, 4.4 Hz, 2H), 4.26-4.09 (m, 4H), 3.14 (t, J=8.8 Hz, 1H), 2.82-2.74 (m, 4H), 2.45-2.28 (m, 9H), 2.22 (td, J=11.5, 10.9, 6.0 Hz, 2H), 2.15-1.91 (m, 12H), 1.69-1.48 (m, 9H), 1.42-1.20 (m, 50H), 0.88 (td, J=6.9, 4.1 Hz, 9H). MS: 1027.9 m/z [M+H].

Example 17—Compound 17

Intermediate 17a: Hexadecylmagnesium Bromide

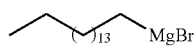

To a solution of Mg (15.92 g, 2 equiv) in THF (300 mL) was added 12 (0.01 equiv), then 1-bromohexadecane (1.0 equiv) in THF (100 mL) was added to the above drop wise at 80° C. The mixture was stirred for 6 h at 80° C. Product was obtained in quantitative yield as brown liquid and used immediately in next step.

Intermediate 17b: 4-oxoicosanoic acid

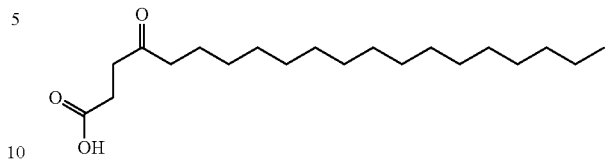

A solution of succinic anhydride (54 g, 1.0 equiv) in THF (1.2 M) was cooled to −78° C., followed by the addition of Intermediate 17a. The reaction was maintained at −78° C. for 12 h before being poured into sat. NH₄Cl and extracted 3× with EtOAc. The combined organic phases were washed with brine, dried with Na₂SO₄, filtered, and concentrated. Purification by column chromatography afforded product as a white solid (4 g, 2%). ¹H NMR (400 MHz, CDCl₃) δ 4.11 (t, J=6.7 Hz, 1H), 2.80-2.62 (m, 4H), 2.46 (t, J=7.5 Hz, 1H), 1.63 (dq, J=14.7, 7.1 Hz, 2H), 1.49-1.20 (m, 27H), 0.90 (t, J=6.7 Hz, 3H).

Intermediate 17c: 2-((4-oxoicosanoyl)oxy)propane-1,3-diyl (9Z,9'Z,12Z,12'Z)-bis(octadeca-9,12-dienoate)

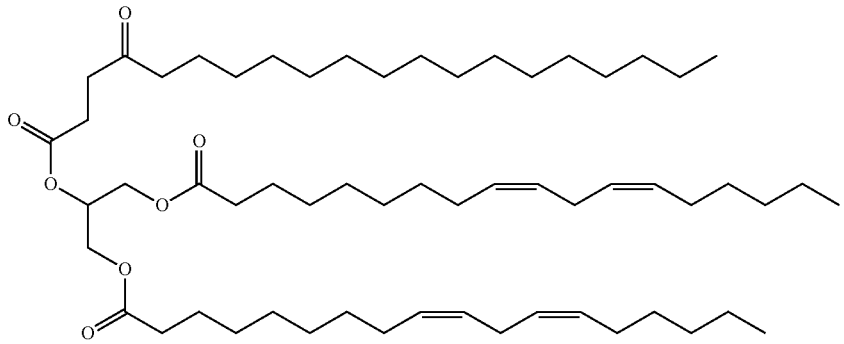 [SMILES: CCCCC/C=C\C/C=C\CCCCCCCC(=O)OCC(COC(=O)CCCCCCC/C=C\C/C=C\CCCCC)OC(=O)CCC(=O)CCCCCCCCCCCCCCCC]

Intermediate 17c was synthesized in 53% yield from Intermediate 17b and Intermediate 1c using the method employed for Intermediate 1d. ¹H NMR (400 MHz, CDCl₃) δ 5.43-5.21 (m, 9H), 4.29 (dt, J=11.9, 4.1 Hz, 2H), 4.14 (dd, J=11.9, 5.9 Hz, 2H), 4.06 (t, J=6.8 Hz, 1H), 2.73 (dt, J=22.5, 6.5 Hz, 6H), 2.67-2.54 (m, 4H), 2.42 (t, J=7.5 Hz, 2H), 2.31 (t, J=7.6 Hz, 4H), 2.04 (q, J=6.9 Hz, 9H), 1.61 (q, J=7.9, 7.3 Hz, 8H), 1.42-1.15 (m, 55H), 0.88 (td, J=6.7, 4.0 Hz, 9H).

Intermediate 17d: 2-((4-(((4-nitrophenoxy)carbonyl)oxy)icosanoyl)oxy)propane-1,3-diyl (9Z,9'Z,12Z,12'Z)-bis(octadeca-9,12-dienoate)

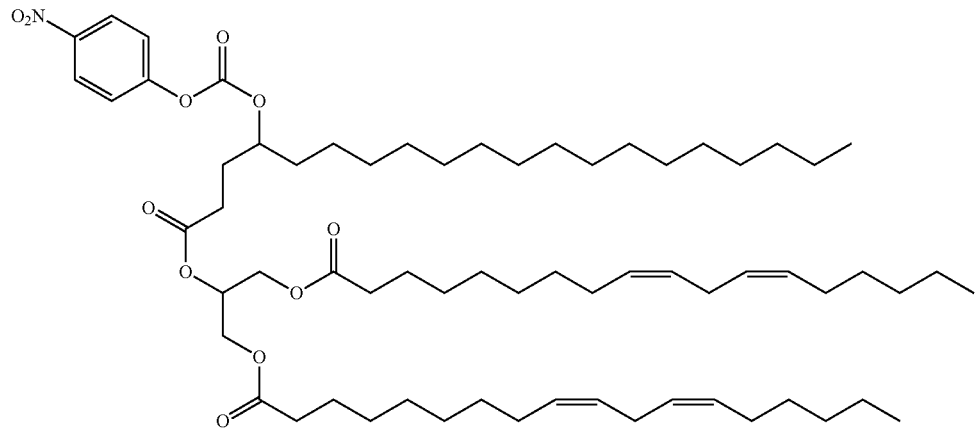 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)Oc1ccc([N+](=O)[O-])cc1]

Intermediate 17d was synthesized in 29% yield from Intermediate 17c using the method employed for Intermediate 1e. $^1$H NMR (400 MHz, CDCl$_3$) δ 8.33-8.24 (m, 2H), 7.43-7.34 (m, 2H), 5.45-5.23 (m, 8H), 4.92-4.82 (m, 1H), 4.31 (dd, J=12.0, 4.3 Hz, 2H), 4.20-4.09 (m, 2H), 2.76 (t, J=6.3 Hz, 4H), 2.47 (dd, J=8.3, 6.7 Hz, 2H), 2.30 (td, J=7.6, 4.2 Hz, 4H), 2.04 (q, J=7.2 Hz, 9H), 1.61 (ddt, J=11.5, 7.4, 3.7 Hz, 4H), 1.43-1.22 (m, 49H), 0.88 (td, J=6.9, 3.8 Hz, 9H).

Compound 17: 2-((4-(((3-(dimethylamino)propoxy)carbonyl)oxy)icosanoyl)oxy)propane-1,3-diyl (9Z,9'Z,12Z,12'Z)-bis(octadeca-9,12-dienoate)

Compound 17 was synthesized in 74% yield from Intermediate 17d and 3-(dimethylamino)propan-1-ol using the method employed for Example 1. $^1$H NMR (400 MHz, CDCl$_3$), 5.42-5.22 (m, 10H), 4.72 (tdd, J=7.5, 5.4, 4.0 Hz, 1H), 4.36-4.25 (m, 2H), 4.23-4.08 (m, 4H), 2.82-2.71 (m, 4H), 2.50-2.28 (m, 9H), 2.25 (s, 6H), 2.09-1.97 (m, 9H), 1.91-1.80 (m, 3H), 1.70-1.47 (m, 7H), 1.40-1.20 (m, 57H), 0.96-0.82 (m, 9H). MS: 1058.1 m/z [M+H].

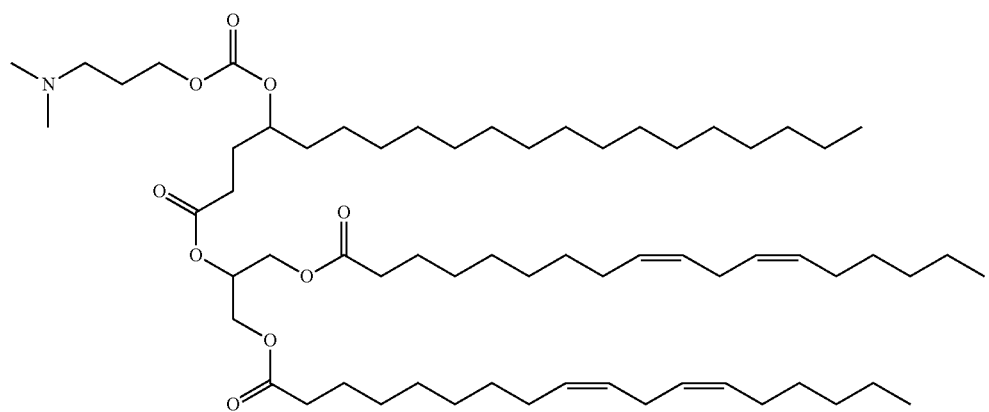 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)OCCCN(C)C]

Example 18—Compound 18

Compound 18: 2-((4-(((3-(ethyl(methyl)amino)
propoxy)carbonyl)oxy)icosanoyl)oxy)propane-1,3-
diyl (9Z,9'Z,12Z,12'Z)-bis(octadeca-9,12-dienoate)

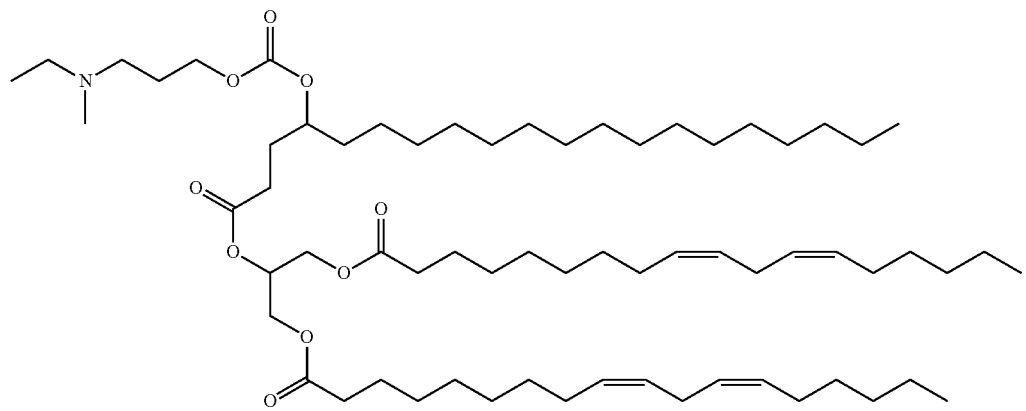 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)OCCCN(C)CC]

Compound 18 was synthesized in 77% yield from Intermediate 17d and 3-((methyl)ethylamino)propan-1-ol using the method employed for Example 1. H NMR (400 MHz, CDCl$_3$) δ 5.45-5.22 (m, 10H), 4.72 (qd, J=7.7, 4.7 Hz, 1H), 4.29 (dd, J=12.0, 4.4 Hz, 2H), 4.20-4.10 (m, 4H), 2.83-2.73 (m, 4H), 2.51-2.36 (m, 6H), 2.35-2.28 (m, 4H), 2.24 (s, 3H), 2.10-1.99 (m, 9H), 1.91-1.82 (m, 3H), 1.66-1.52 (m, 6H), 1.42-1.19 (m, 60H), 1.06 (t, J=7.1 Hz, 3H), 0.88 (td, J=6.9, 4.1 Hz, 9H). MS: 1072.3 m/z [M+H].

Example 19—Compound 19

Compound 19: 2-((4-(((3-(pyrrolidin-1-yl)propoxy)
carbonyl)oxy)icosanoyl)oxy)propane-1,3-diyl (9Z,
9'Z,12Z,12'Z)-bis(octadeca-9,12-dienoate)

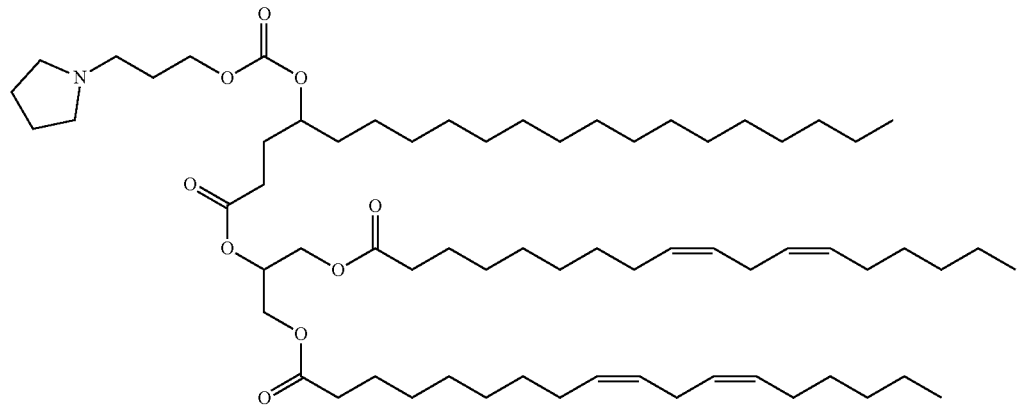 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)OCCCN1CCCC1]

Compound 19 was synthesized in 67% yield from Intermediate 17d and 3-(pyrrolidin-1-yl)propan-1-ol using the method employed for Example 1. $^1$H NMR (400 MHz, CDCl$_3$) δ 5.44-5.22 (m, 9H), 4.72 (tt, J=7.5, 4.5 Hz, 1H), 4.29 (dd, J=11.9, 4.4 Hz, 2H), 4.24-4.10 (m, 4H), 2.83-2.72 (m, 4H), 2.57 (d, J=8.3 Hz, 6H), 2.40 (dt, J=8.6, 6.7 Hz, 2H), 2.31 (td, J=7.6, 1.2 Hz, 4H), 2.04 (dd, J=8.5, 5.3 Hz, 8H), 2.00-1.86 (m, 4H), 1.86-1.78 (m, 4H), 1.53 (ddt, J=14.1, 8.3, 4.7 Hz, 7H), 1.44-1.20 (m, 56H), 0.88 (td, J=6.9, 4.2 Hz, 9H). MS: 1084.2 m/z [M+H].

Example 20—Compound 20

Compound 20: 2-((4-(((2-(ethyl(methyl)amino)ethyl)carbamoyl)oxy)icosanoyl)oxy)propane-1,3-diyl (9Z,9'Z,12Z,12'Z)-bis(octadeca-9,12-dienoate)

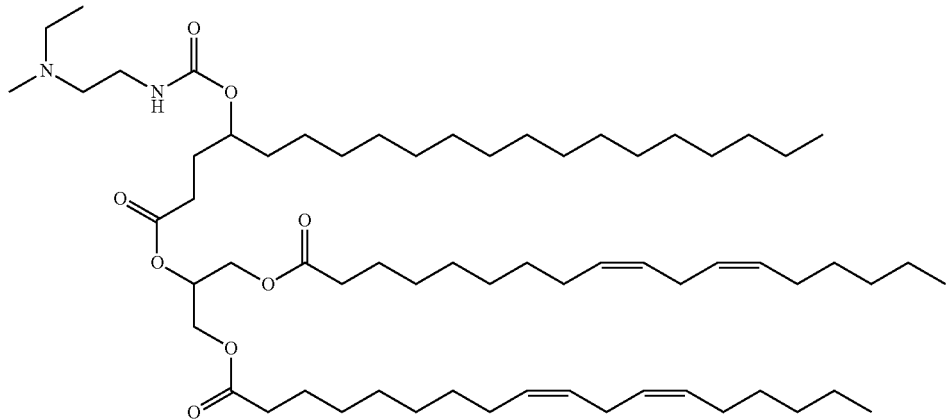 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)NCCN(C)CC]

Compound 20 was synthesized in 73% yield from Intermediate 17d and 3-(pyrrolidin-1-yl)propan-1-ol using the method employed for Example 1. $^1$H NMR (400 MHz, CDCl$_3$) δ 5.44-5.17 (m, 10H), 4.75 (s, 1H), 4.28 (ddd, J=11.9, 4.4, 1.3 Hz, 2H), 4.15 (ddd, J=11.9, 5.8, 3.4 Hz, 2H), 3.25 (d, J=6.2 Hz, 2H), 2.81-2.73 (m, 4H), 2.50-2.36 (m, 6H), 2.36-2.28 (m, 4H), 2.22 (s, 3H), 2.05 (q, J=6.8 Hz, 8H), 1.94-1.71 (m, 4H), 1.66-1.20 (m, 63H), 1.05 (t, J=7.1 Hz, 3H), 0.88 (td, J=6.9, 4.2 Hz, 9H). MS: 1056.6 m/z [M+H].

Example 21—Compound 21

Compound 21: 2-((4-((((1-methylpyrrolidin-2-yl)methyl)carbamoyl)oxy)icosanoyl)oxy)propane-1,3-diyl (9Z,9'Z,12Z,12'Z)-bis(octadeca-9,12-dienoate)

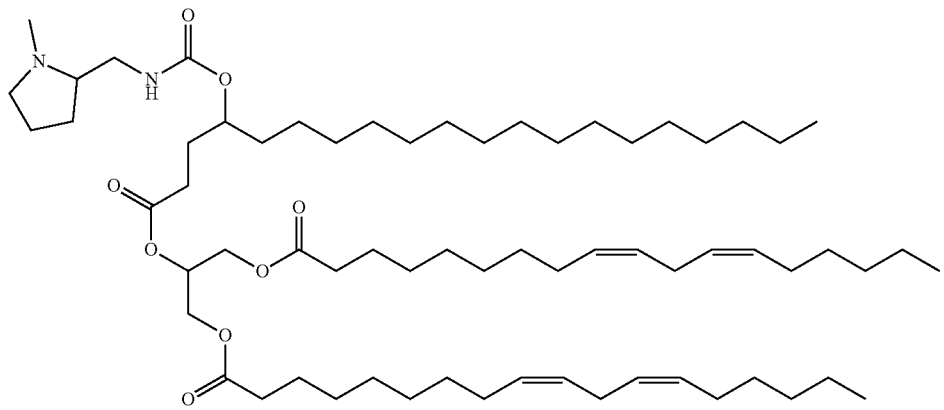 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCCCCCC)OC(=O)NCC1CCCN1C]

Compound 21 was synthesized in 85% yield from Intermediate 17d (1-methylpyrrolidin-2-yl)methanamine using the method employed for Example 1. $^1$H NMR (400 MHz, CDCl$_3$) δ 5.43-5.30 (m, 8H), 5.29-5.18 (m, 2H), 4.76 (s, 1H), 4.28 (dd, J=11.9, 4.4 Hz, 2H), 4.21-4.07 (m, 2H), 3.46-3.30 (m, 1H), 3.11 (ddt, J=22.3, 8.9, 4.3 Hz, 2H), 2.80-2.72 (m, 4H), 2.45-2.15 (m, 12H), 2.04 (dd, J=8.5, 5.3 Hz, 9H), 1.96-1.77 (m, 4H), 1.71 (tq, J=8.4, 5.1, 4.0 Hz, 2H), 1.65-1.45 (m, 8H), 1.39-1.20 (m, 60H), 0.88 (td, J=6.9, 4.4 Hz, 9H). MS: 1068.8 m/z [M+H].

Example 22—Compound 22

Intermediate 22a: (Z)-9-(non-2-en-1-yloxy)-9-oxononanoic acid

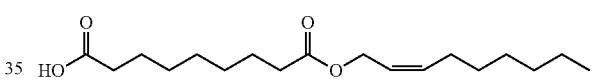

To a solution of nonanedioic acid (25 g, 1.3 equiv) in THF (100 mL) at 0° C. was added oxalyl chloride (1.0 equiv) dropwise over one minute. Next, DMF (0.1 equiv) was added dropwise over one minute. The reaction mixture was stirred at 0° C. for 10 min, followed by room temperature for 10 min. Then, the reaction was cooled back to 0° C., followed by the addition of cis-2-nonen-1-ol (1.0 equiv) in THF (100 mL). The reaction was stirred at 0° C. for 5 min, then stirred at room temperature for 16 h. Upon completion, the reaction was concentrated in vacuo, slurried with DCM, and filtered. The filtrate was concentrated and purified by column chromatography (80 g, MeOH/DCM) to afford product as a pale yellow oil (15 g, 47%) that was used directly in subsequent steps.

Intermediate 22b: 9,9'-di((Z)-non-2-en-1-yl) O'1, O1-(2-oxopropane-1,3-diyl) di(nonanedioate)

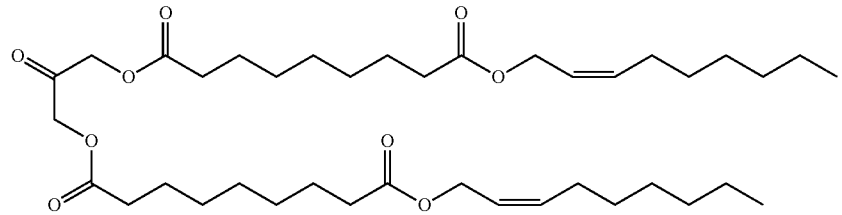 [SMILES: CCCCCC/C=C\COC(=O)CCCCCCCC(=O)OCC(=O)COC(=O)CCCCCCCC(=O)OC/C=C\CCCCCC]

Intermediate 22b was synthesized in 73% yield by combining dihydroxyacetone and Intermediate 22a using the method employed for Intermediate 1b.

Intermediate 22c: O'1,O1-(2-hydroxypropane-1,3-diyl) 9,9'-di((Z)-non-2-en-1-yl) di(nonanedioate)

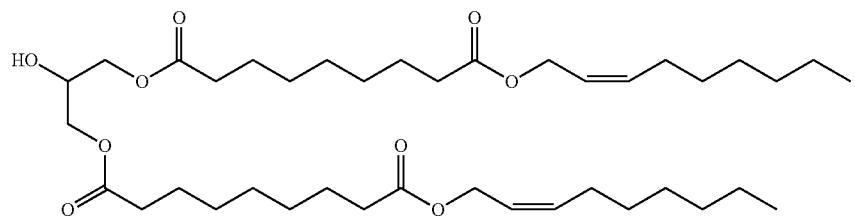 [SMILES: CCCCCC/C=C\COC(=O)CCCCCCCC(=O)OCC(O)COC(=O)CCCCCCCC(=O)OC/C=C\CCCCCC]

Intermediate 22c was synthesized in 71% yield from Intermediate 22b using the method employed for Intermediate 1c, except that the reaction was completed after 45 min. $^1$H NMR (400 MHz, CDCl$_3$) δ 5.64 (dtt, J=11.0, 7.3, 1.3 Hz, 2H), 5.52 (dtt, J=10.9, 6.8, 1.5 Hz, 2H), 4.67-4.58 (m, 4H), 4.23-4.05 (m, 5H), 2.51 (d, J=4.6 Hz, 1H), 2.32 (dt, J=18.1, 7.6 Hz, 8H), 2.15-2.00 (m, 4H), 1.61 (td, J=10.0, 2.7 Hz, 8H), 1.42-1.20 (m, 28H), 0.93-0.83 (m, 6H).

Intermediate 22d: 9,9'-di((Z)-non-2-en-1-yl) O'1, O1-(2-((4-oxohexadecanoyl)oxy)propane-1,3-diyl) di(nonanedioate)

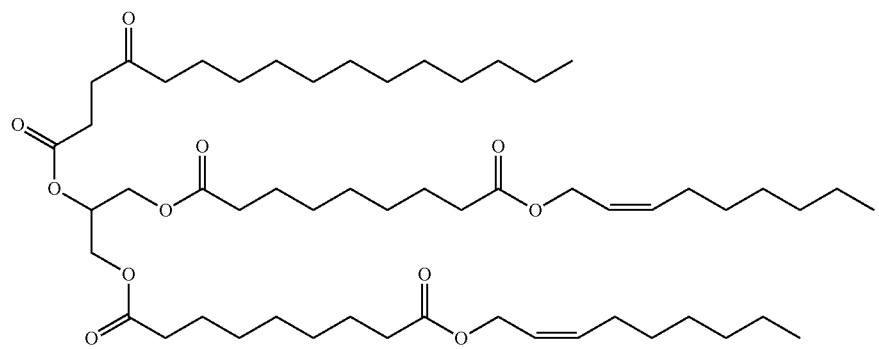 [SMILES: CCCCCC/C=C\COC(=O)CCCCCCCC(=O)OCC(COC(=O)CCCCCCCC(=O)OC/C=C\CCCCCC)OC(=O)CCC(=O)CCCCCCCCCCCC]

Intermediate 22d was synthesized in 38% yield from Intermediate 22c and Intermediate 1a using the method employed for Intermediate 1d. ¹H NMR (400 MHz, CDCl₃) δ 5.66 (dtt, J=11.0, 7.3, 1.3 Hz, 2H), 5.54 (dtt, J=11.0, 6.9, 1.5 Hz, 2H), 5.26 (tt, J=5.9, 4.3 Hz, 1H), 4.64 (dd, J=6.9, 1.3 Hz, 4H), 4.31 (dd, J=11.9, 4.3 Hz, 2H), 4.17 (dd, J=11.9, 5.9 Hz, 2H), 2.74 (t, J=6.7 Hz, 2H), 2.68-2.56 (m, 2H), 2.45 (t, J=7.5 Hz, 2H), 2.33 (td, J=7.6, 6.0 Hz, 8H), 2.19-2.07 (m, 4H), 1.70-1.57 (m, 12H), 1.43-1.23 (m, 46H), 0.98-0.84 (m, 9H).

Intermediate 22e: O'1,O1-(2-((4-(((4-nitrophenoxy) carbonyl)oxy)hexadecanoyl)oxy)propane-1,3-diyl) 9,9'-di((Z)-non-2-en-1-yl) di(nonanedioate)

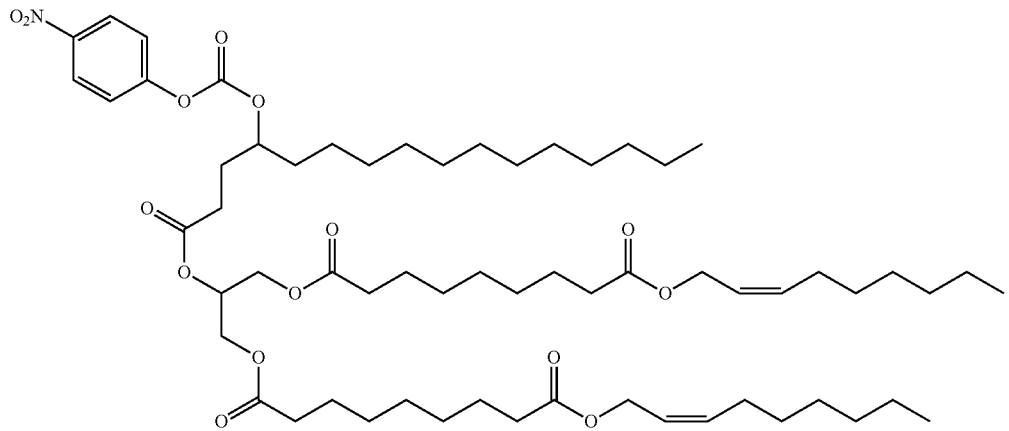 [SMILES: CCCCCC/C=C\COC(=O)CCCCCCCC(=O)OCC(COC(=O)CCCCCCCC(=O)OC/C=C\CCCCCC)OC(=O)CCC(CCCCCCCCCCCC)OC(=O)Oc1ccc([N+](=O)[O-])cc1]

Intermediate 22e was synthesized in 51% yield from Intermediate 22d using the method employed for Intermediate 1e. ¹H NMR (400 MHz, CDCl₃) δ 8.38-8.31 (m, 1H), 8.31-8.24 (m, 2H), 7.54-7.47 (m, 1H), 7.44-7.36 (m, 2H), 5.64 (dtt, J=11.0, 7.3, 1.3 Hz, 2H), 5.51 (dtt, J=11.0, 6.8, 1.5 Hz, 2H), 5.26 (tt, J=5.8, 4.3 Hz, 1H), 4.86 (ddd, J=11.8, 7.5, 4.8 Hz, 1H), 4.65-4.57 (m, 4H), 4.36-4.25 (m, 2H), 4.21-4.10 (m, 2H), 2.50-2.44 (m, 2H), 2.30 (td, J=7.5, 4.5 Hz, 8H), 2.13-2.05 (m, 4H), 1.62 (d, J=37.2 Hz, 9H), 1.46-1.18 (m, 49H), 0.94-0.80 (m, 9H).

Compound 22: O'1,O1-(2-((4-(((3-(dimethylamino) propoxy)carbonyl)oxy)hexadecanoyl)oxy) propane-1,3-diyl) 9,9'-di((Z)-non-2-en-1-yl) di(nonanedioate)

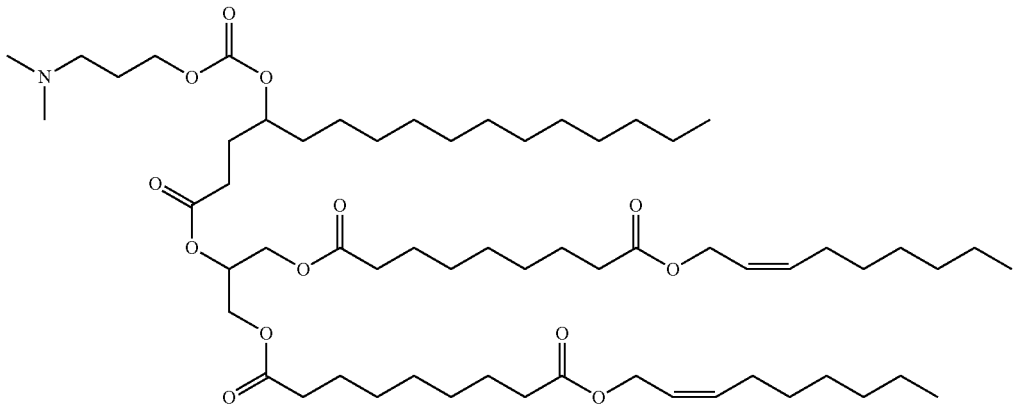 [SMILES: CCCCCC/C=C\COC(=O)CCCCCCCC(=O)OCC(COC(=O)CCCCCCCC(=O)OC/C=C\CCCCCC)OC(=O)CCC(CCCCCCCCCCCC)OC(=O)OCCCN(C)C]

Compound 22 was synthesized in 54% yield from Intermediate 22e and 3-(dimethylamino)propan-1-ol using the method employed for Example 1. ¹H NMR (400 MHz, CDCl₃) δ 5.71-5.58 (m, 2H), 5.52 (dtt, J=10.9, 6.8, 1.5 Hz, 2H), 5.25 (tt, J=5.7, 4.4 Hz, 1H), 4.72 (ddd, J=11.7, 7.4, 4.5 Hz, 1H), 4.62 (dd, J=6.8, 1.3 Hz, 4H), 4.34-4.25 (m, 2H), 4.25-4.08 (m, 4H), 2.39 (ddd, J=12.9, 8.4, 6.4 Hz, 4H), 2.34-2.21 (m, 13H), 2.09 (tdd, J=7.4, 5.7, 1.5 Hz, 4H), 2.02-1.67 (m, 7H), 1.69-1.51 (m, 11H), 1.42-1.19 (m, 45H), 0.97-0.78 (m, 8H). MS: 1065.7 m/z [M+H].

Example 23—Compound 23

Compound 23: O'1,O1-(2-((4-(((2-(ethyl(methyl)amino)ethyl)carbamoyl)oxy)hexadecanoyl)oxy) propane-1,3-diyl) 9,9'-di((Z)-non-2-en-1-yl) di(nonanedioate)

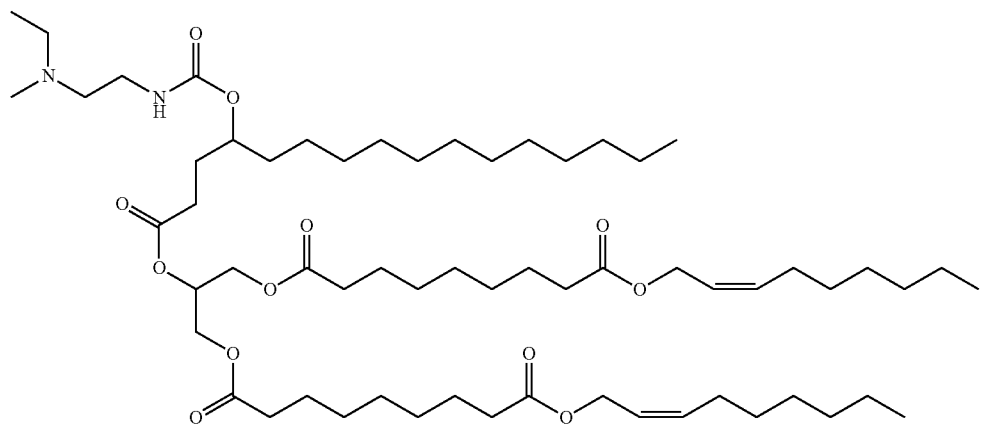 [SMILES: CCCCCC/C=C\COC(=O)CCCCCCCC(=O)OCC(COC(=O)CCCCCCCC(=O)OC/C=C\CCCCCC)OC(=O)CCC(CCCCCCCCCCCC)OC(=O)NCCN(C)CC]

Compound 23 was synthesized in 59% yield from Intermediate 22e and N1-ethyl-N1-methylethane-1,2-diamine using the method employed in Example 1. ¹H NMR (400 MHz, CDCl₃) δ 5.72-5.59 (m, 2H), 5.52 (dtt, J=11.0, 6.8, 1.5 Hz, 2H), 5.36-5.18 (m, 2H), 4.75 (s, 1H), 4.62 (dd, J=6.9, 1.2 Hz, 4H), 4.28 (dd, J=11.9, 4.4 Hz, 2H), 4.14 (ddd, J=11.9, 5.8, 3.5 Hz, 2H), 3.35-3.20 (m, 2H), 2.56-2.43 (m, 4H), 2.38 (ddd, J=8.7, 6.6, 4.1 Hz, 2H), 2.34-2.19 (m, 11H), 2.10 (qd, J=7.4, 1.5 Hz, 4H), 1.96-1.72 (m, 3H), 1.63 (d, J=6.9 Hz, 11H), 1.41-1.18 (m, 48H), 1.07 (t, J=7.1 Hz, 3H), 0.93-0.81 (m, 9H). MS: 1065.2 m/z [M+H].

Example 24—Compound 24

Compound 24: O'1,O1-(2-((4-((((1-methylpyrrolidin-2-yl)methyl)carbamoyl)oxy)hexadecanoyl) oxy) propane-1,3-diyl)9,9'-di((Z)-non-2-en-1-yl) di(nonanedioate)

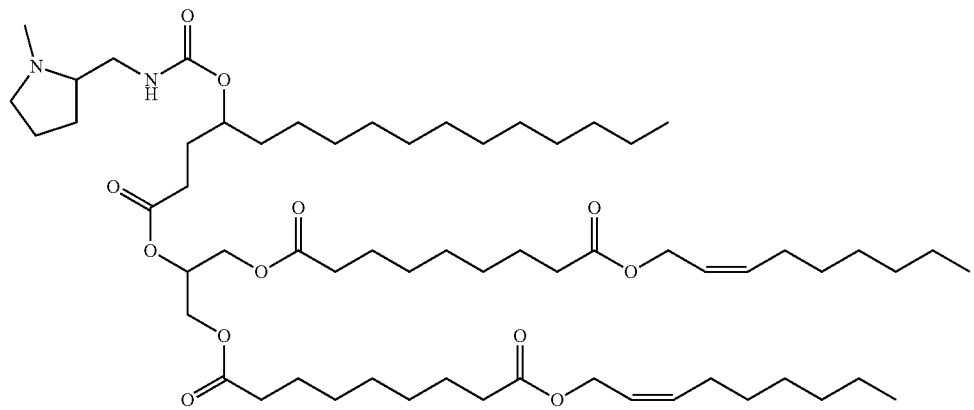 [SMILES: CCCCCC/C=C\COC(=O)CCCCCCCC(=O)OCC(COC(=O)CCCCCCCC(=O)OC/C=C\CCCCCC)OC(=O)CCC(CCCCCCCCCCCC)OC(=O)NCC1CCCN1C]

Compound 24 was synthesized from Intermediate 22e and (1-methylpyrrolidin-2-yl)methanamine using the method employed in Example 1. $^1$H NMR (400 MHz, CDCl$_3$) δ 5.71-5.59 (m, 2H), 5.52 (dtt, J=10.9, 6.8, 1.5 Hz, 2H), 5.24 (ddd, J=8.8, 5.8, 4.4 Hz, 2H), 4.76 (s, 1H), 4.62 (dd, J=6.9, 1.3 Hz, 4H), 4.28 (dd, J=11.9, 4.4 Hz, 2H), 4.14 (ddd, J=11.9, 5.8, 3.2 Hz, 2H), 3.39 (q, J=11.2, 10.1 Hz, 1H), 3.10 (t, J=14.0 Hz, 2H), 2.50-2.20 (m, 15H), 2.10 (qd, J=7.4, 1.5 Hz, 4H), 1.97-1.67 (m, 6H), 1.61 (d, J=7.3 Hz, 12H), 1.41-1.18 (m, 47H), 0.97-0.79 (m, 9H). MS: 1076.7 m/z [M+H].

Example 25—Compound 25

Intermediate 25a: 5-oxoheptadecanoic acid

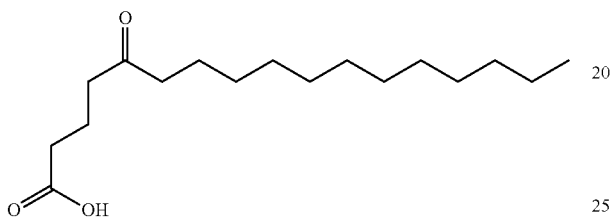

Intermediate 25a was synthesized in 64% yield from glutaric anhydride and dodecylmagnesium bromide solution using the method employed in Intermediate 1a. $^1$H NMR (400 MHz, CDCl$_3$) δ 2.75 (t, J=6.7 Hz, 1H), 2.49 (t, J=7.2 Hz, 2H), 2.44-2.35 (m, 4H), 1.90 (p, J=7.2 Hz, 2H), 1.56 (t, J=7.3 Hz, 2H), 1.26 (d, J=4.0 Hz, 19H), 0.88 (t, J=6.7 Hz, 3H).

Intermediate 25b: 2-((5-oxoheptadecanoyl)oxy)propane-1,3-diyl (9Z,9'Z,12Z,12'Z)-bis(octadeca-9,12-dienoate)

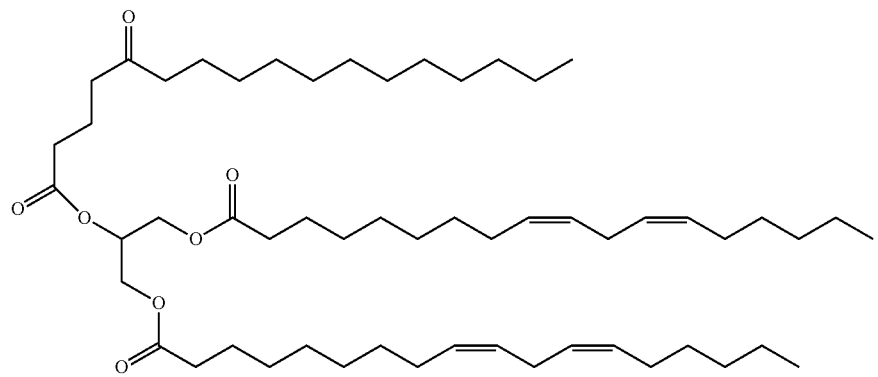 [SMILES: CCCCC/C=C\C/C=C\CCCCCCCC(=O)OCC(COC(=O)CCCCCCC/C=C\C/C=C\CCCCC)OC(=O)CCCC(=O)CCCCCCCCCCCC]

Intermediate 25b was synthesized in 55% yield from Intermediate 25a and Intermediate 1c using the method employed for Intermediate 1d. $^1$H NMR (400 MHz, CDCl$_3$) δ 5.45-5.19 (m, 9H), 4.30 (dd, J=11.9, 4.3 Hz, 2H), 4.12 (dd, J=11.9, 5.8 Hz, 2H), 2.76 (t, J=6.4 Hz, 4H), 2.46 (t, J=7.2 Hz, 2H), 2.42-2.24 (m, 8H), 2.04 (q, J=6.8 Hz, 8H), 1.88 (p, J=7.2 Hz, 2H), 1.57 (dp, J=21.3, 7.2 Hz, 6H), 1.43-1.18 (m, 41H), 0.87 (td, J=6.8, 4.1 Hz, 8H).

Intermediate 25c: 2-((5-(((4-nitrophenoxy)carbonyl)oxy)heptadecanoyl)oxy)propane-1,3-diyl (9Z,9'Z,12Z,12'Z)-bis(octadeca-9,12-dienoate)

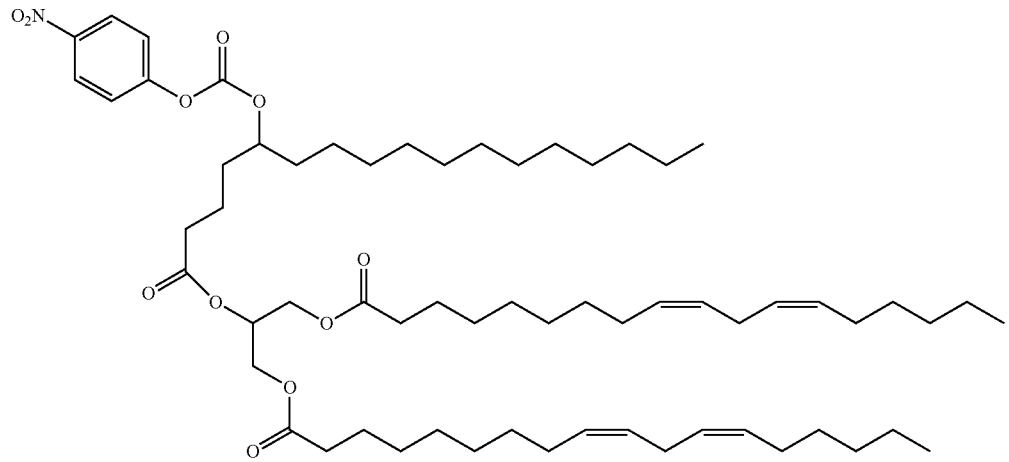 [SMILES: CCCCC/C=C\C/C=C\CCCCCCCC(=O)OCC(COC(=O)CCCCCCC/C=C\C/C=C\CCCCC)OC(=O)CCCC(CCCCCCCCCCCC)OC(=O)Oc1ccc([N+](=O)[O-])cc1]

Intermediate 25c was synthesized in 23% yield from Intermediate 25b using the method employed for Intermediate 1e. $^1$H NMR (400 MHz, CDCl$_3$) δ 8.31-8.24 (m, 2H), 7.42-7.35 (m, 2H), 5.44-5.19 (m, 9H), 4.83 (q, J=5.7 Hz, 1H), 4.31 (ddd, J=12.0, 4.4, 2.9 Hz, 2H), 4.14 (ddd, J=11.9, 5.8, 2.1 Hz, 2H), 2.76 (t, J=6.3 Hz, 4H), 2.34 (dt, J=30.7, 7.0 Hz, 6H), 2.04 (q, J=6.9 Hz, 8H), 1.80-1.52 (m, 14H), 1.29 (dd, J=19.3, 12.3 Hz, 44H), 0.88 (td, J=6.8, 3.7 Hz, 9H).

Compound 25: 2-((5-(((3-(dimethylamino)propoxy)carbonyl)oxy)heptadecanoyl)oxy)propane-1,3-diyl (9Z,9'Z,12Z,12'Z)-bis(octadeca-9,12-dienoate)

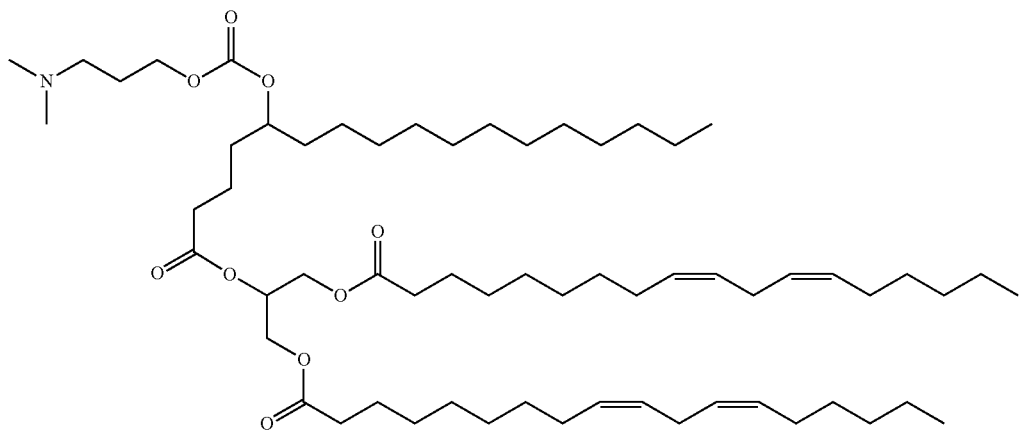 [SMILES: CCCCC/C=C\C/C=C\CCCCCCCC(=O)OCC(COC(=O)CCCCCCC/C=C\C/C=C\CCCCC)OC(=O)CCCC(CCCCCCCCCCCC)OC(=O)OCCCN(C)C]

Compound 25 was synthesized in 94% yield from Intermediate 25c and 3-(dimethylamino)propan-1-ol using the method employed for Example 1. $^1$H NMR (400 MHz, CDCl$_3$) δ 5.46-5.19 (m, 9H), 4.74-4.65 (m, 1H), 4.29 (ddd, J=11.9, 4.4, 1.7 Hz, 2H), 4.25-4.07 (m, 4H), 2.82-2.72 (m, 4H), 2.39-2.28 (m, 8H), 2.22 (s, 6H), 2.05 (q, J=6.8 Hz, 8H), 1.84 (dq, J=8.2, 6.7 Hz, 2H), 1.73-1.50 (m, 14H), 1.41-1.18 (m, 50H), 0.88 (td, J=7.0, 4.2 Hz, 9H). MS: 1016.11 m/z [M+H].

Example 26—Compound 26

Compound 26: 2-((5-(((3-(ethyl(methyl)amino) propoxy)carbonyl)oxy)heptadecanoyl)oxy) propane-1,3-diyl (9Z,9'Z,12Z,12'Z)-bis(octadeca-9,12-dienoate)

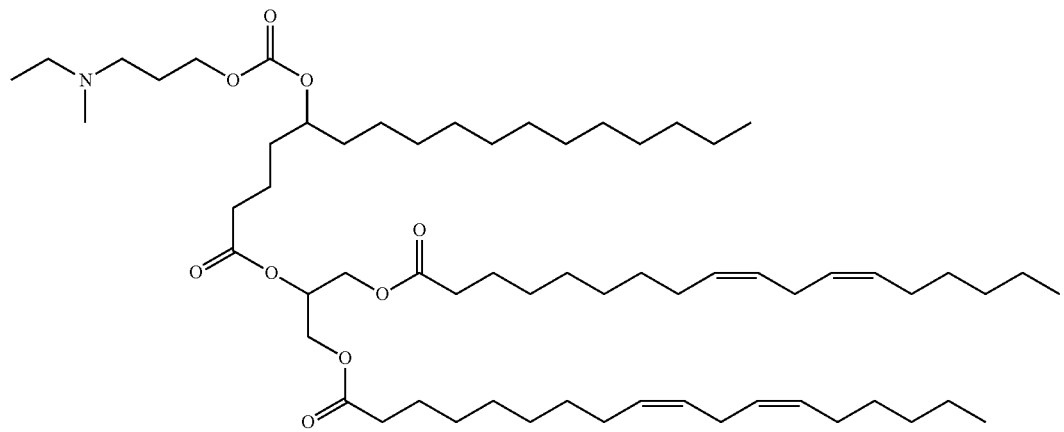 [SMILES: CCCCC/C=C\C/C=C\CCCCCCCC(=O)OCC(COC(=O)CCCCCCC/C=C\C/C=C\CCCCC)OC(=O)CCCC(CCCCCCCCCCCC)OC(=O)OCCCN(C)CC]

Compound 26 was synthesized in 84% yield from Intermediate 25c and 3-((methyl)ethylamino)propan-1-ol using the method employed for Example 1. H NMR (400 MHz, CDCl$_3$) δ 5.46-5.20 (m, 10H), 4.69 (dq, J=7.5, 5.5 Hz, 1H), 4.29 (ddd, J=11.9, 4.4, 1.6 Hz, 2H), 4.25-4.10 (m, 4H), 2.83-2.72 (m, 4H), 2.45-2.38 (m, 4H), 2.37-2.28 (m, 6H), 2.21 (s, 3H), 2.05 (q, J=6.8 Hz, 8H), 1.88-1.79 (m, 2H), 1.74-1.52 (m, 13H), 1.44-1.22 (m, 51H), 1.04 (t, J=7.2 Hz, 3H), 0.88 (td, J=6.9, 4.1 Hz, 9H). MS: 1030.1 m/z [M+H].

Example 27—Compound 27

Compound 27: 2-((5-(((3-(pyrrolidin-1-yl)propoxy) carbonyl)oxy)heptadecanoyl)oxy)propane-1,3-diyl (9Z,9'Z,12Z,12'Z)-bis(octadeca-9,12-dienoate)

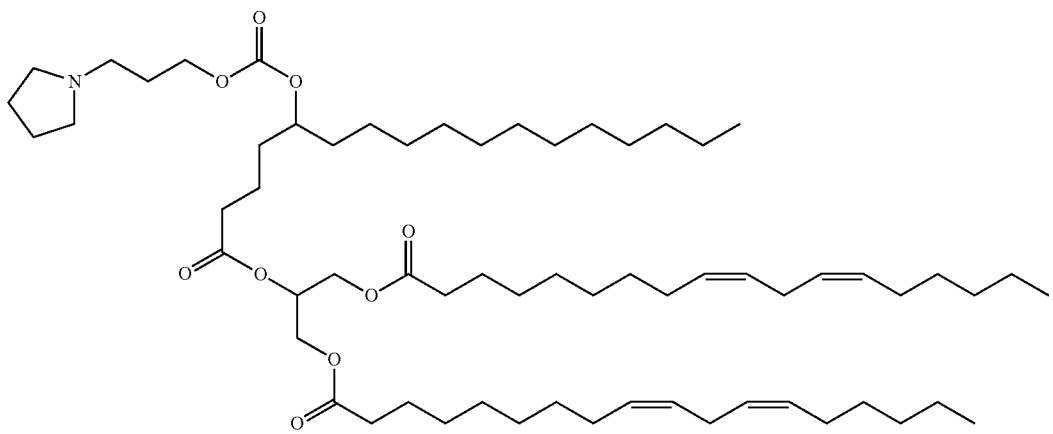 [SMILES: CCCCC/C=C\C/C=C\CCCCCCCC(=O)OCC(COC(=O)CCCCCCC/C=C\C/C=C\CCCCC)OC(=O)CCCC(CCCCCCCCCCCC)OC(=O)OCCCN1CCCC1]

Compound 27 was synthesized in 79% yield from Intermediate 25c and 3-(pyrrolidin-1-yl)propan-1-ol using the method employed for Example 1. $^1$H NMR (400 MHz, CDCl$_3$) δ 5.44-5.21 (m, 10H), 4.69 (dt, J=7.1, 5.3 Hz, 1H), 4.29 (ddd, J=11.9, 4.3, 1.6 Hz, 2H), 4.25-4.10 (m, 4H), 2.81-2.73 (m, 4H), 2.52 (dd, J=14.8, 7.1 Hz, 6H), 2.33 (dt, J=13.4, 7.2 Hz, 6H), 2.05 (q, J=6.8 Hz, 8H), 1.89 (dq, J=10.8, 6.8 Hz, 2H), 1.82-1.74 (m, J=3.8, 3.3 Hz, 4H), 1.71-1.53 (m, 13H), 1.40-1.21 (m, 49H), 0.88 (td, J=6.9, 4.2 Hz, 9H). MS: 1041.8 m/z [M+H].

Example 28—Compound 28

Compound 28: 2-((5-(((2-(ethyl(methyl)amino)ethyl)carbamoyl)oxy)heptadecanoyl)oxy) propane-1,3-diyl (9Z,9'Z,12Z,12'Z)-bis(octadeca-9,12-dienoate)

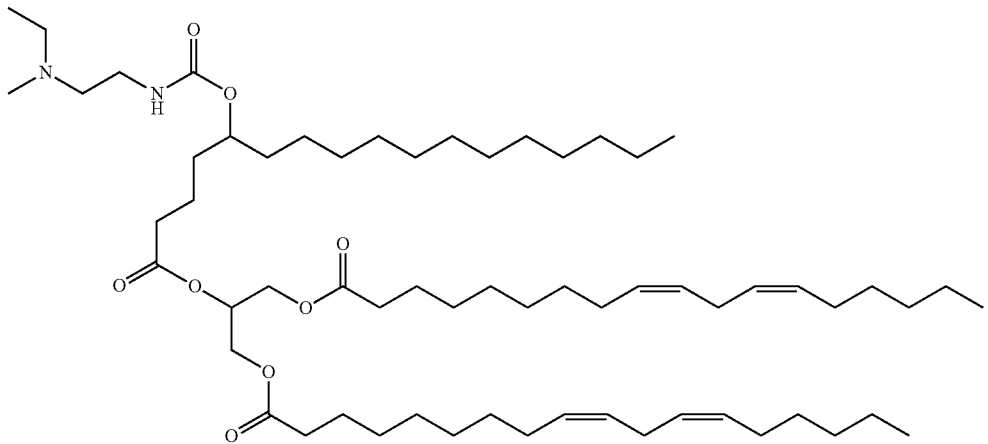 [SMILES: CCCCC/C=C\C/C=C\CCCCCCCC(=O)OCC(COC(=O)CCCCCCC/C=C\C/C=C\CCCCC)OC(=O)CCCC(CCCCCCCCCCCC)OC(=O)NCCN(C)CC]

Compound 28 was synthesized in 87% yield from Intermediate 25c and N1-ethyl-N1-methylethane-1,2-diamine using the method employed for Example 1. $^1$H NMR (400 MHz, CDCl$_3$) δ 5.43-5.21 (m, 10H), 5.12 (s, 1H), 4.80-4.65 (m, 1H), 4.29 (dt, J=11.9, 4.5 Hz, 2H), 4.19-4.09 (m, 2H), 3.24 (d, J=4.8 Hz, 2H), 2.83-2.72 (m, 4H), 2.44 (dt, J=14.6, 6.6 Hz, 4H), 2.38-2.27 (m, 6H), 2.20 (s, 3H), 2.04 (dd, J=7.8, 5.7 Hz, 8H), 1.74-1.42 (m, 15H), 1.42-1.19 (m, 50H), 1.04 (t, J=7.1 Hz, 3H), 0.88 (td, J=7.0, 4.4 Hz, 9H). MS: 1014.1 m/z [M+H].

Example 29—Compound 29

Compound 29: 2-((5-((((1-methylpyrrolidin-2-yl)methyl)carbamoyl)oxy)heptadecanoyl)oxy) propane-1,3-diyl (9Z,9'Z,12Z,12'Z)-bis(octadeca-9,12-dienoate)

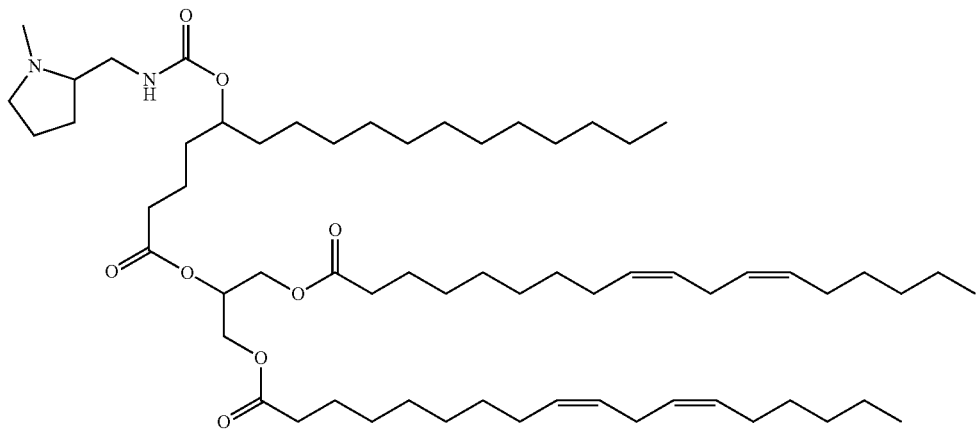 [SMILES: CCCCC/C=C\C/C=C\CCCCCCCC(=O)OCC(COC(=O)CCCCCCC/C=C\C/C=C\CCCCC)OC(=O)CCCC(CCCCCCCCCCCC)OC(=O)NCC1CCCN1C]

le;2qCompound 29 was synthesized in 93% yield from Intermediate 25c and (1-methylpyrrolidin-2-yl)methanamine using the method employed for Example 1. $^1$H NMR (400 MHz, CDCl$_3$) δ 5.43-5.21 (m, 11H), 5.08 (d, J=8.8 Hz, 1H), 4.74 (s, 1H), 4.29 (dt, J=11.9, 4.6 Hz, 2H), 4.13 (ddd, J=11.9, 5.8, 4.5 Hz, 2H), 3.39 (q, J=11.3, 10.6 Hz, 1H), 3.08 (d, J=25.9 Hz, 2H), 2.82-2.73 (m, 4H), 2.39-2.18 (m, 12H), 2.05 (q, J=6.8 Hz, 9H), 1.91-1.82 (m, 1H), 1.62 (dddd, J=27.4, 20.2, 13.2, 6.7 Hz, 18H), 1.42-1.20 (m, 52H), 0.88 (td, J=6.9, 4.4 Hz, 9H). MS: 1026.8 m/z [M+H].

Example 30—Compound 30

Intermediate 30a: 3-hydroxypropane-1,2-diyl (9Z, 9'Z,12Z,12'Z)-bis(octadeca-9,12-dienoate)

le;2q

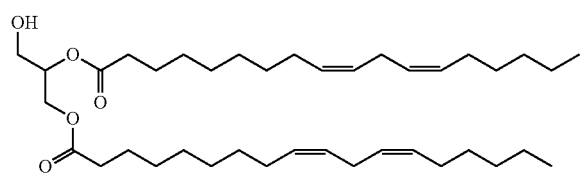 [SMILES: CCCCC/C=C\C/C=C\CCCCCCCC(=O)OCC(CO)OC(=O)CCCCCCC/C=C\C/C=C\CCCCC]

le;2qTo a solution of glycerol (1.59 g, 1.0 equiv) in DCM (0.1 M) was added linoleic acid (2.05 equiv), DMAP (0.2 equiv), DIPEA (2.4 equiv), EDCI (2.4 equiv), and 1 mL of DMF in sequence. The reaction was stirred at room temperature for 65 h. Upon completion, the mixture was quenched by the addition of water, and the organic layer was washed 1× with 1 M HCl and 1× with 5% NaHCO$_3$. The organic layer was then dried over Na$_2$SO$_4$, filtered, and concentrated in vacuo. Crude material was purified by column chromatography (EtOAc/hexanes) to product as a colorless oil. $^1$H NMR (400 MHz, CDCl$_3$) δ 5.43-5.28 (m, 8H), 5.13-5.04 (m, 1H), 4.32 (dd, J=11.9, 4.6 Hz, 1H), 4.23 (dd, J=11.9, 5.6 Hz, 1H), 3.73 (ddd, J=6.5, 5.0, 1.3 Hz, 2H), 2.82-2.73 (m, 4H), 2.33 (dt, J=8.8, 7.5 Hz, 4H), 2.03 (dq, J=13.1, 6.6 Hz, 9H), 1.69-1.57 (m, 4H), 1.44-1.23 (m, 29H), 0.96-0.83 (m, 6H).

Intermediate 30b: 3-((4-oxohexadecanoyl)oxy)propane-1,2-diyl (9Z,9'Z,12Z,12'Z)-bis(octadeca-9,12-dienoate)

le;2q le;2qIntermediate 30b was synthesized in 66% yield from Intermediate 30a and Intermediate 1a using the method employed in Intermediate 1d. $^1$H NMR (400 MHz, CDCl$_3$) δ 5.43-5.26 (m, 9H), 4.29 (ddd, J=11.8, 4.3, 2.1 Hz, 2H), 4.15 (ddd, J=11.9, 7.7, 6.0 Hz, 2H), 2.82-2.74 (m, 4H), 2.71 (td, J=6.3, 5.6, 2.4 Hz, 2H), 2.62-2.55 (m, 2H), 2.43 (t, J=7.5 Hz, 2H), 2.31 (td, J=7.6, 5.4 Hz, 4H), 2.05 (q, J=6.9 Hz, 8H), 1.66-1.54 (m, 8H), 1.41-1.19 (m, 47H), 0.88 (td, J=7.0, 4.4 Hz, 9H).

Intermediate 30c: 3-((4-(((4-nitrophenoxy)carbonyl)oxy)hexadecanoyl)oxy)propane-1,2-diyl (9Z,9'Z,12Z,12'Z)-bis(octadeca-9,12-dienoate)

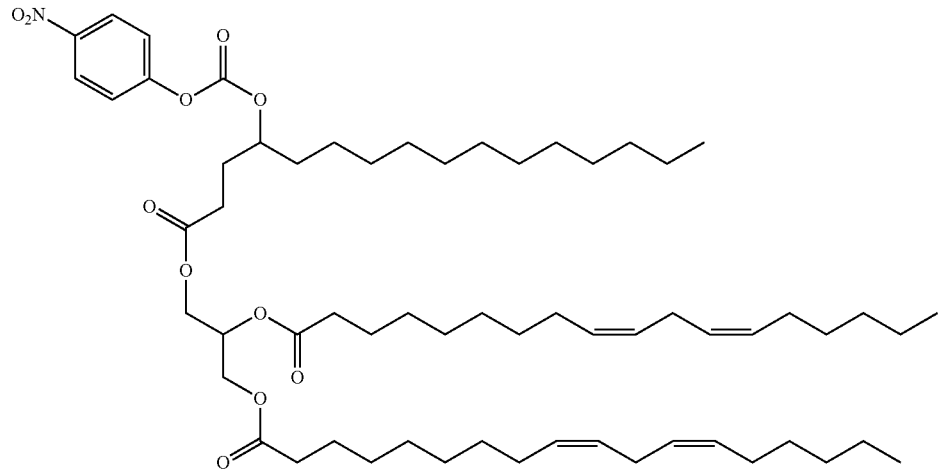 [SMILES: CCCCC/C=C\C/C=C\CCCCCCCC(=O)OCC(COC(=O)CCC(CCCCCCCCCCCC)OC(=O)Oc1ccc([N+](=O)[O-])cc1)OC(=O)CCCCCCC/C=C\C/C=C\CCCCC]

Intermediate 30c was synthesized in 40% yield from Intermediate 30b using the method employed in Intermediate 1e.

Compound 30: 9-dodecyl-2-methyl-7,12-dioxo-6,8,13-trioxa-2-azahexadecane-15,16-diyl (9Z,9'Z,12Z,12'Z)-bis(octadeca-9,12-dienoate)

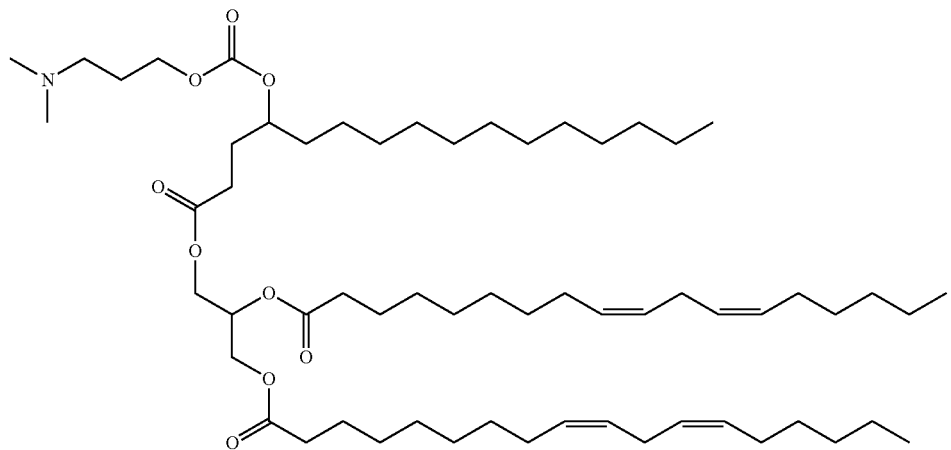 [SMILES: CCCCC/C=C\C/C=C\CCCCCCCC(=O)OCC(COC(=O)CCC(CCCCCCCCCCCC)OC(=O)OCCCN(C)C)OC(=O)CCCCCCC/C=C\C/C=C\CCCCC]

Compound 30 was synthesized in 84% yield from Intermediate 30c and 3-((methyl)ethylamino)propan-1-ol using the method employed in Example 1. $^1$H NMR (500 MHz, CDCl$_3$) δ 5.44-5.20 (m, 8H), 4.76-4.67 (m, 1H), 4.29 (ddd, J=11.9, 4.3, 1.7 Hz, 2H), 4.22-4.11 (m, 4H), 2.77 (t, J=6.7 Hz, 4H), 2.45-2.28 (m, 8H), 2.22 (s, 6H), 2.05 (q, J=6.9 Hz, 8H), 2.00-1.79 (m, 4H), 1.69-1.51 (m, 6H), 1.40-1.17 (m, 48H), 0.88 (td, J=6.9, 4.8 Hz, 8H). MS: 1002.2 m/z [M+H].

Example 31—Compound 31

Intermediate 31a: 4-oxododecanoic acid

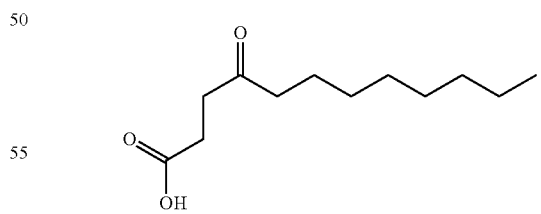

Intermediate 31a was synthesized in 9% yield from succinic anhydride and octylmagnesium bromide solution using the method employed in Intermediate 1a. $^1$H NMR (400 MHz, CDCl$_3$) δ 2.71 (t, J=6.4 Hz, 2H), 2.62 (t, J=6.7 Hz, 2H), 2.43 (t, J=7.5 Hz, 2H), 1.57 (p, J=7.1 Hz, 2H), 1.26 (d, J=3.6 Hz, 10H), 0.87 (t, J=6.7 Hz, 3H).

Intermediate 31b: 2-((4-oxododecanoyl)oxy)propane-1,3-diyl (9Z,9'Z,12Z,12'Z)-bis(octadeca-9,12-dienoate)

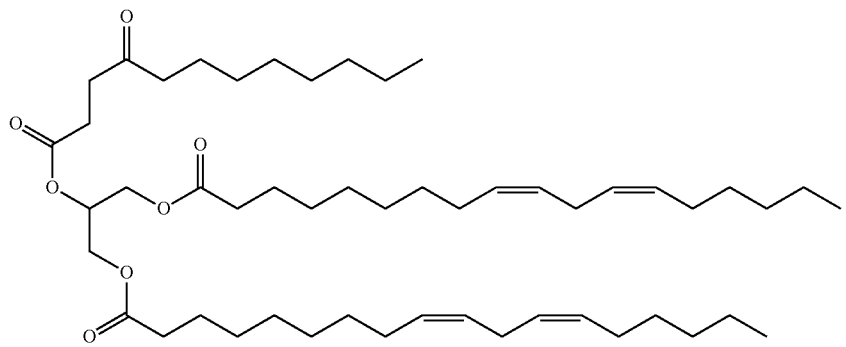 [SMILES: CCCCC/C=C\C/C=C\CCCCCCCC(=O)OCC(COC(=O)CCCCCCC/C=C\C/C=C\CCCCC)OC(=O)CCC(=O)CCCCCCCC]

Intermediate 31b was synthesized in 38% yield from Intermediate 31a and Intermediate 1c using the method employed in Intermediate 1d. $^1$H NMR (400 MHz, CDCl$_3$) δ 5.47-5.19 (m, 8H), 4.28 (dd, J=11.9, 4.3 Hz, 2H), 4.15 (dd, J=11.9, 5.9 Hz, 2H), 2.77 (t, J=6.4 Hz, 4H), 2.71 (t, J=6.5 Hz, 2H), 2.59 (t, J=6.5 Hz, 2H), 2.43 (t, J=7.5 Hz, 2H), 2.32 (t, J=7.6 Hz, 4H), 2.04 (q, J=6.9 Hz, 8H), 1.67-1.53 (m, 6H), 1.40-1.20 (m, 37H), 0.88 (td, J=6.8, 5.0 Hz, 9H).

Intermediate 31c: 2-((4-(((4-nitrophenoxy)carbonyl)oxy)dodecanoyl)oxy)propane-1,3-diyl (9Z,9'Z,12Z,12'Z)-bis(octadeca-9,12-dienoate)

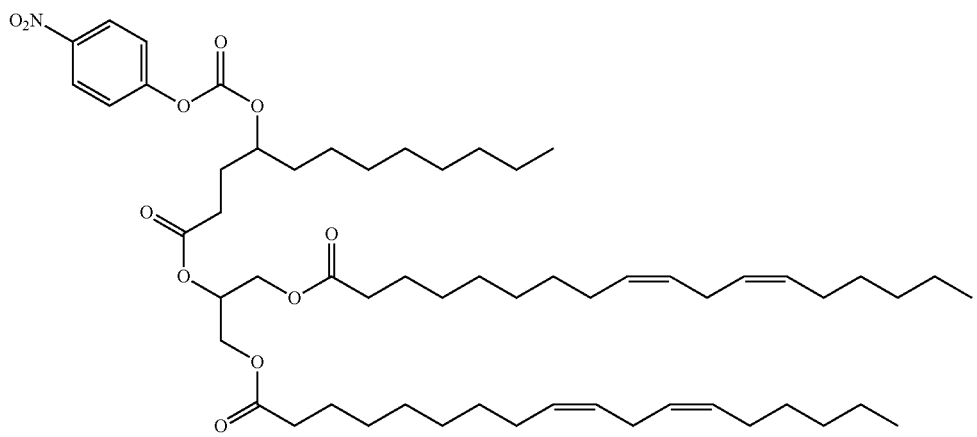 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)Oc1ccc([N+](=O)[O-])cc1]

Intermediate 31c was synthesized in 68% yield using the method employed in Intermediate 1e. $^1$H NMR (400 MHz, CDCl$_3$) δ 8.26-8.16 (m, 2H), 7.40-7.30 (m, 2H), 5.39-5.05 (m, 9H), 4.80 (tdd, J=7.5, 5.4, 4.0 Hz, 1H), 4.49-4.04 (m, 4H), 2.77-2.63 (m, 4H), 2.45-2.18 (m, 6H), 2.08-1.85 (m, 10H), 1.74-1.46 (m, 6H), 1.41-1.11 (m, 40H), 0.81 (td, J=6.9, 2.4 Hz, 9H).

Compound 31: 2-((4-(((3-(dimethylamino)propoxy)carbonyl)oxy)dodecanoyl)oxy)propane-1,3-diyl (9Z,9'Z,12Z,12'Z)-bis(octadeca-9,12-dienoate)

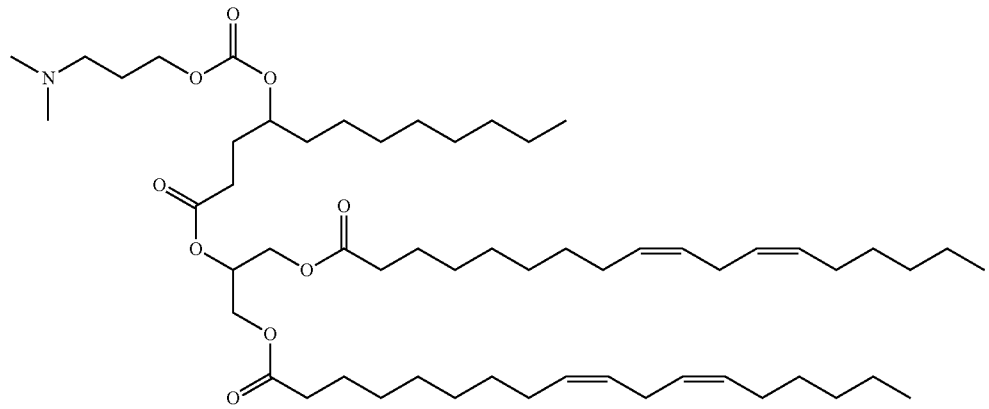 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OCCCN(C)C]

Compound 31 was synthesized in 71% yield from Intermediate 31c and 3-(dimethylamino)propan-1-ol using the method employed in Example 1. $^1$H NMR (400 MHz, CDCl$_3$) δ 5.42-5.22 (m, 9H), 4.72 (tdd, J=7.4, 5.3, 4.0 Hz, 1H), 4.34-4.26 (m, 2H), 4.23-4.10 (m, 4H), 2.82-2.72 (m, 4H), 2.45-2.36 (m, 4H), 2.31 (ddd, J=8.0, 7.1, 1.2 Hz, 4H), 2.25 (s, 6H), 2.05 (q, J=6.6 Hz, 8H), 1.99-1.91 (m, 1H), 1.91-1.82 (m, 3H), 1.67-1.53 (m, 6H), 1.40-1.21 (m, 41H), 0.94-0.82 (m, 9H). MS: 945.6 m/z [M+H].

Example 32—Compound 32

Compound 32: 2-((4-(((3-(diethylamino)propoxy)carbonyl)oxy)dodecanoyl)oxy)propane-1,3-diyl (9Z,9'Z,12Z,12'Z)-bis(octadeca-9,12-dienoate)

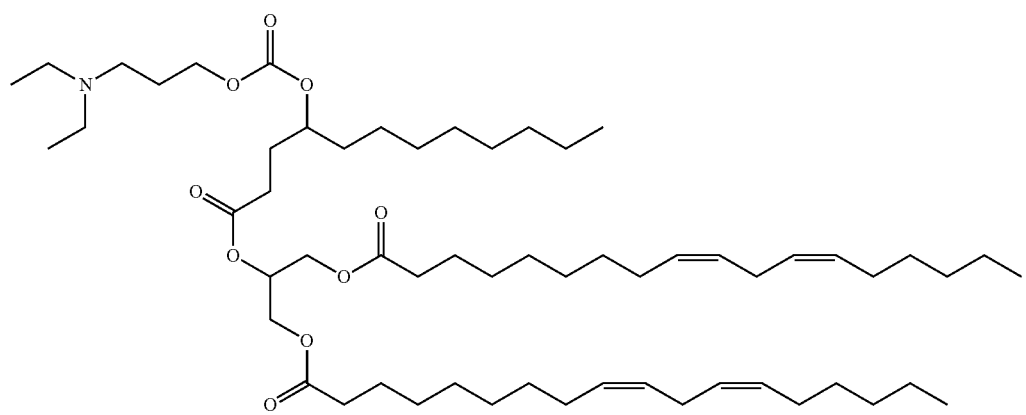 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OCCCN(CC)CC]

Compound 32 was synthesized in 71% yield from Intermediate 31c and 3-(diethyl amino)propan-1-ol using the method employed in Example 1. $^1$H NMR (400 MHz, CDCl$_3$) δ 5.43-5.28 (m, 9H), 5.25 (ddd, J=5.8, 4.4, 1.5 Hz, 1H), 4.72 (tdd, J=7.6, 5.4, 4.0 Hz, 1H), 4.29 (dd, J=11.9, 4.4 Hz, 2H), 4.25-4.08 (m, 5H), 2.77 (td, J=6.1, 1.1 Hz, 4H), 2.64-2.53 (m, 6H), 2.40 (dt, J=8.7, 6.8 Hz, 2H), 2.31 (ddd, J=8.0, 7.2, 1.1 Hz, 4H), 2.10-2.01 (m, 10H), 1.95 (dddd, J=11.1, 9.2, 6.9, 3.5 Hz, 1H), 1.91-1.81 (m, 3H), 1.69-1.49 (m, 7H), 1.39-1.20 (m, 42H), 1.05 (t, J=7.2 Hz, 6H), 0.88 (td, J=7.0, 4.9 Hz, 9H). MS: 974.0 m/z [M+H].

Example 33—Compound 33

Compound 33: 2-((4-(((3-(ethyl(methyl)amino)propoxy)carbonyl)oxy)dodecanoyl)oxy)propane-1,3-diyl (9Z,9'Z, 12Z, 12'Z)-bis(octadeca-9,12-dienoate)

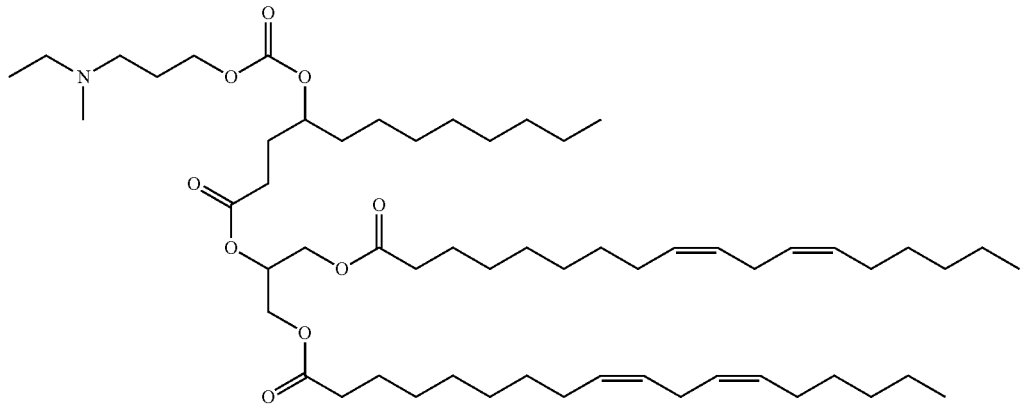 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OCCCN(C)CC]

Compound 33 was synthesized in 79% yield from Intermediate 31c and 3-((methyl)ethylamino)propan-1-ol using the method employed in Example 1. $^1$H NMR (400 MHz, CDCl$_3$) δ 5.45-5.21 (m, 10H), 4.72 (tdd, J=9.5, 6.7, 4.1 Hz, 1H), 4.38-4.25 (m, 2H), 4.25-4.10 (m, 4H), 2.77 (td, J=6.2, 1.1 Hz, 4H), 2.51-2.38 (m, 6H), 2.37-2.27 (m, 5H), 2.24 (d, J=2.4 Hz, 3H), 2.05 (q, J=7.1 Hz, 8H), 1.97-1.83 (m, 4H), 1.70-1.50 (m, 7H), 1.39-1.21 (m, 41H), 1.06 (t, J=7.2 Hz, 3H), 0.94-0.84 (m, 9H). 960.1 m/z [M+H].

Example 34—Compound 34

Compound 34: 2-((4-(((2-(ethyl(methyl)amino)ethyl)carbamoyl)oxy)dodecanoyl)oxy)propane-1,3-diyl (9Z,9'Z,12Z,12'Z)-bis(octadeca-9,12-dienoate)

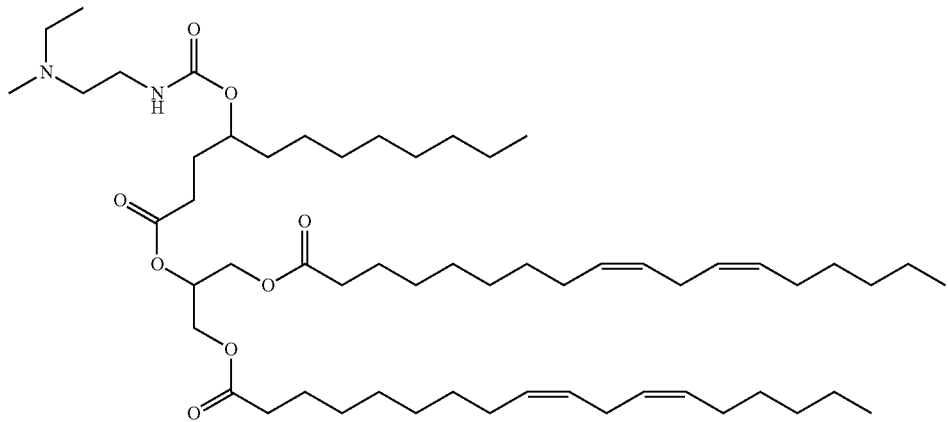

Compound 34 was synthesized in 59% yield from Intermediate 31c and N1-ethyl-N1-methyl ethane-1,2-diamine using the method employed in Example 1. $^1$H NMR (400 MHz, CDCl$_3$) δ 5.44-5.13 (m, 10H), 4.75 (s, 1H), 4.28 (ddd, J=11.9, 4.4, 1.4 Hz, 2H), 4.15 (ddd, J=11.9, 5.8, 3.3 Hz, 2H), 3.25 (q, J=5.7 Hz, 2H), 2.83-2.73 (m, 4H), 2.53-2.35 (m, 6H), 2.35-2.27 (m, 4H), 2.21 (d, J=3.3 Hz, 3H), 2.05 (q, J=6.8 Hz, 8H), 1.96-1.74 (m, 3H), 1.66-1.43 (m, 7H), 1.41-1.21 (m, 41H), 1.05 (t, J=7.1 Hz, 3H), 0.88 (td, J=6.9, 5.6 Hz, 9H). 944.7 m/z [M+H].

Example 35—Compound 35

Compound 35: 2-((4-((((1-methylpyrrolidin-2-yl)methyl)carbamoyl)oxy)dodecanoyl)oxy) propane-1,3-diyl (9Z,9'Z,12Z,12'Z)-bis(octadeca-9,12-dienoate)

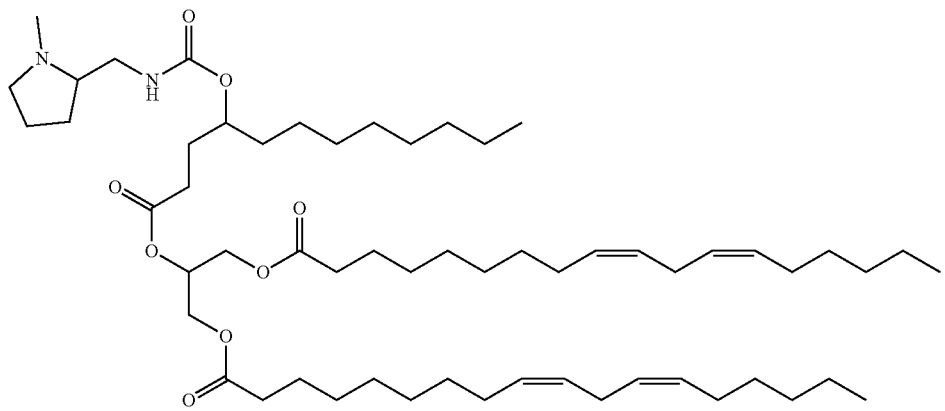 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCC1CCCN1C]

Compound 35 was synthesized in 71% yield from Intermediate 31c and (1-methylpyrrolidin-2-yl)methanamine using the method employed in Example 1. $^1$H NMR (400 MHz, CDCl$_3$) δ 5.44-5.21 (m, 10H), 4.86-4.66 (m, 1H), 4.28 (dd, J=11.9, 4.4 Hz, 2H), 4.14 (ddd, J=11.9, 5.8, 3.1 Hz, 2H), 3.48-3.35 (m, 1H), 3.22-3.00 (m, 2H), 2.83-2.71 (m, 4H), 2.47-2.19 (m, 12H), 2.04 (q, J=6.9 Hz, 8H), 1.96-1.67 (m, 6H), 1.67-1.42 (m, 8H), 1.41-1.19 (m, 41H), 0.95-0.84 (m, 9H). 956.5 m/z [M+H].

Example 36—Compound 36

Compound 36: 2-((4-(((3-(pyrrolidin-1-yl)propoxy)carbonyl)oxy)dodecanoyl)oxy)propane-1,3-diyl (9Z,9'Z,12Z,12'Z)-bis(octadeca-9,12-dienoate)

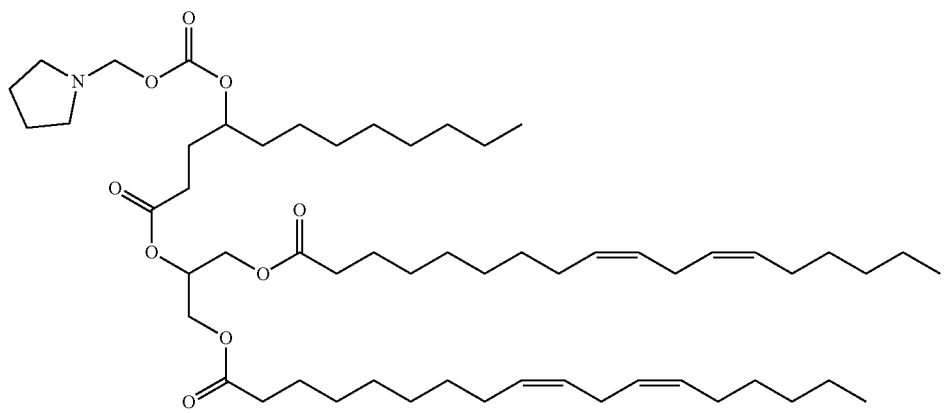 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OCN1CCCC1]

Compound 36 was synthesized in 34% yield from Intermediate 31c and 3-(pyrrolidin-1-yl)propan-1-ol using the method employed in Example 1. H NMR (400 MHz, CDCl$_3$) δ 5.43-5.22 (m, 9H), 4.72 (tdd, J=7.4, 5.4, 4.0 Hz, 1H), 4.29 (dd, J=11.9, 4.3 Hz, 2H), 4.25-4.08 (m, 4H), 2.82-2.72 (m, 4H), 2.67 (t, J=7.6 Hz, 5H), 2.47-2.27 (m, 6H), 2.09-1.91 (m, 11H), 1.91-1.80 (m, 4H), 1.68-1.47 (m, 7H), 1.47-1.19 (m, 42H), 0.88 (td, J=7.0, 4.8 Hz, 9H). 971.3 m/z [M+H].

Example 37—Compound 37

Compound 37: 2-((4-(((2-(ethyl(methyl)amino)ethyl)(methyl)carbamoyl)oxy)dodecanoyl)oxy) propane-1,3-diyl (9Z,9'Z,12Z,12'Z)-bis(octadeca-9,12-dienoate)

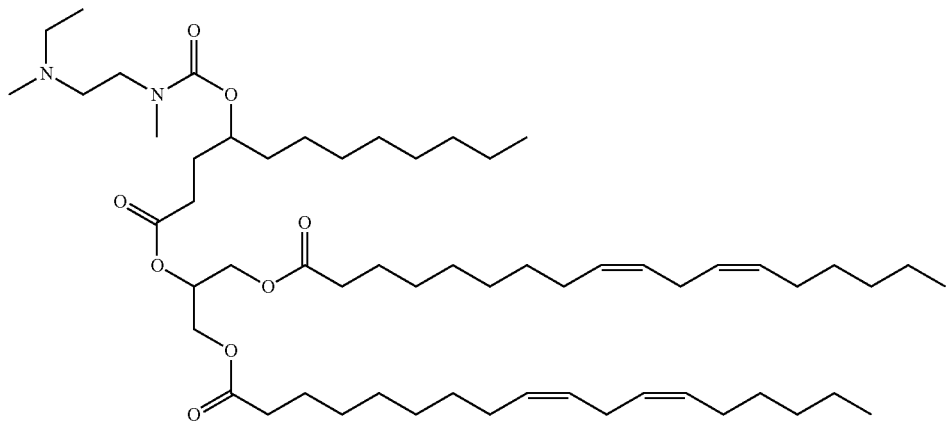 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)N(C)CCN(C)CC]

Compound 37 was synthesized in 67% yield from Intermediate 31c and N1-ethyl-N1,N2-dimethylethane-1,2-diamine using the method employed in Example 1. $^1$H NMR (400 MHz, CDCl$_3$) δ 5.44-5.18 (m, 8H), 4.78 (s, 1H), 4.28 (dt, J=11.9, 4.3 Hz, 2H), 4.14 (dd, J=11.9, 5.8 Hz, 2H), 3.44-3.24 (m, 2H), 2.91 (d, J=8.1 Hz, 3H), 2.81-2.71 (m, 4H), 2.60-2.21 (m, 12H), 2.05 (q, J=6.9 Hz, 7H), 1.98-1.46 (m, 14H), 1.43-1.19 (m, 37H), 1.14-1.00 (m, 3H), 0.88 (td, J=7.0, 5.3 Hz, 8H). 958.6 m/z [M+H].

Example 38—Compound 38

Compound 38: 2-((4-(((2-(dimethylamino)ethyl)(methyl)carbamoyl)oxy)dodecanoyl)oxy) propane-1,3-diyl (9Z,9'Z,12Z,12'Z)-bis(octadeca-9,12-dienoate)

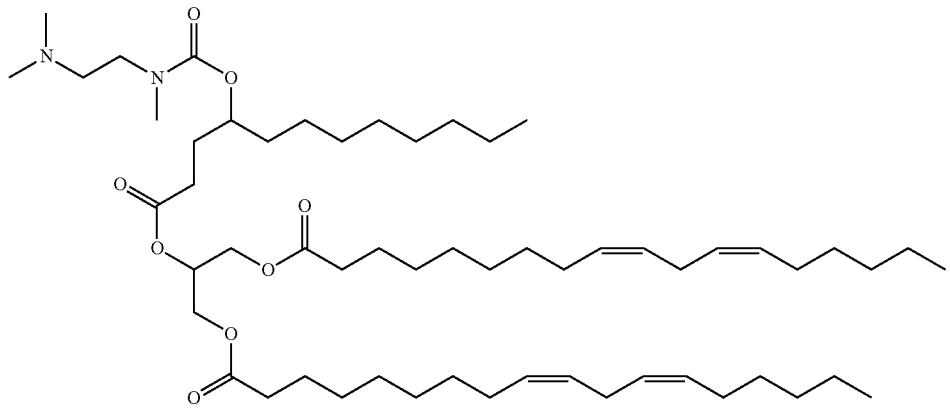 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)N(C)CCN(C)C]

Compound 38 was synthesized in 83% yield from Intermediate 31c and N1,N1,N2-trimethylethane-1,2-diamine using the method employed in Example 1. $^1$H NMR (400 MHz, CDCl$_3$) δ 5.43-5.19 (m, 8H), 4.78 (s, 1H), 4.28 (dt, J=11.9, 4.1 Hz, 2H), 4.14 (dd, J=11.9, 5.8 Hz, 2H), 3.37 (d, J=23.8 Hz, 2H), 2.91 (d, J=6.8 Hz, 3H), 2.82-2.72 (m, 4H), 2.54-2.21 (m, 13H), 2.04 (q, J=6.7 Hz, 7H), 1.95-1.44 (m, 14H), 1.42-1.21 (m, 37H), 0.88 (td, J=7.0, 5.3 Hz, 8H). 944.5 m/z [M+H].

Example 39—Compound 39

Intermediate 39a: decylmagnesium bromide

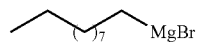

To a solution of Mg (10.99 g, 2 equiv) and I2 (0.0001 eq) in THF (250 mL) was added drop wise 1-bromodecane (1.0 equiv) at 80° C. over 2 hr. After addition, the mixture was stirred at this temperature for 2 h. The crude product decylmagnesium bromide was obtained as black brown solution that was immediately used into the next step without further purification.

Intermediate 39b: 4-oxotetradecanoic acid

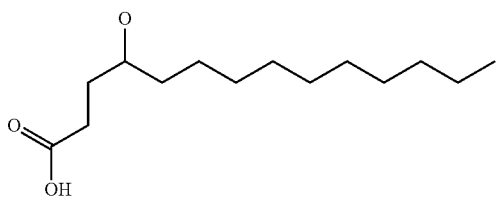 [SMILES: CCCCCCCCCCC(O)CCC(=O)O]

A solution of succinic anhydride (45 g, 1.0 equiv) in THF (1.1 M) was cooled to −78° C., followed by the addition of Intermediate 39a. The reaction was maintained at −78° C. for 2 h before being stirred at 15° C. for 16 h. The reaction was then quenched by the addition of sat. NH$_4$Cl, diluted with H$_2$O, and extracted with EtOAc. The combined organic layers were washed with brine, dried over Na$_2$SO$_4$, filtered, and concentrated. Purification by column chromatography afforded product as a white solid (7.8 g, 7%). $^1$H NMR (400 MHz, CDCl$_3$) δ 2.74 (dd, J=6.9, 5.2 Hz, 2H), 2.70-2.63 (m, 2H), 2.46 (t, J=7.5 Hz, 2H), 1.67-1.54 (m, 2H), 1.29 (d, J=5.2 Hz, 14H), 0.90 (t, J=6.8 Hz, 3H).

Intermediate 39c: 2-((4-oxotetradecanoyl)oxy)propane-1,3-diyl (9Z,9'12Z,12'Z)-bis(octadeca-9,12-dienoate)

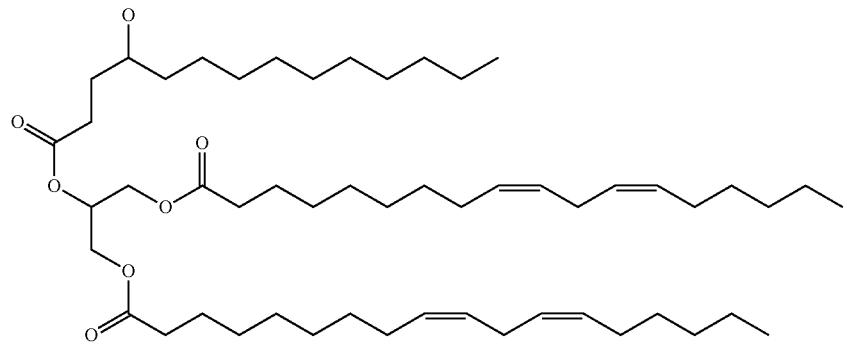 [SMILES: CCCCC/C=C\C/C=C\CCCCCCCC(=O)OCC(COC(=O)CCCCCCC/C=C\C/C=C\CCCCC)OC(=O)CCC(O)CCCCCCCCCC]

Intermediate 39c was prepared from Intermediates 39b and Intermediate 1c using the method employed for Intermediate 1d. $^1$H NMR (400 MHz, CDCl$_3$) δ 5.42-5.18 (m, 9H), 4.28 (dd, J=11.9, 4.3 Hz, 2H), 4.14 (dd, J=11.9, 5.9 Hz, 2H), 2.74 (dt, J=22.1, 6.8 Hz, 6H), 2.66-2.56 (m, 2H), 2.43 (t, J=7.5 Hz, 2H), 2.31 (t, J=7.6 Hz, 4H), 2.04 (q, J=6.8 Hz, 8H), 1.59 (tq, J=14.2, 7.5 Hz, 7H), 1.41-1.18 (m, 44H), 0.88 (td, J=6.9, 4.6 Hz, 9H).

Intermediate 39d: 2-((4-(((4-nitrophenoxy)carbonyl)oxy)tetradecanoyl)oxy)propane-1,3-diyl (9Z,9'Z,12Z,12'Z)-bis(octadeca-9,12-dienoate)

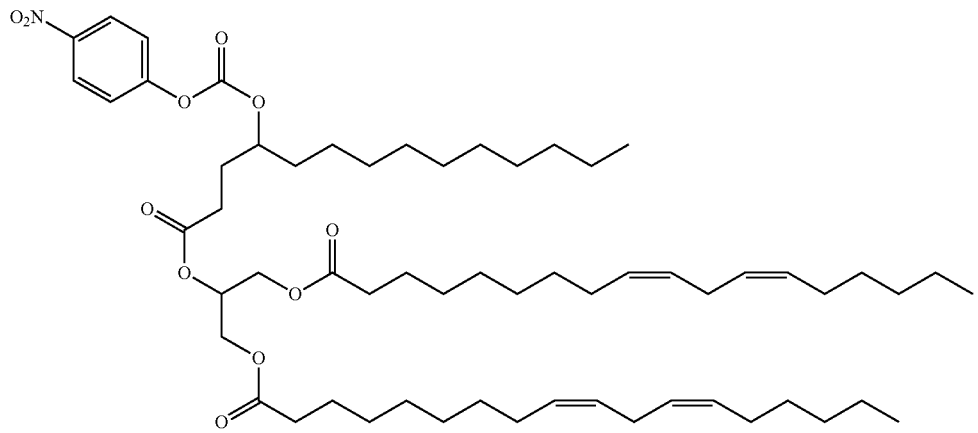 [SMILES: CCCCC/C=C\C/C=C\CCCCCCCC(=O)OCC(COC(=O)CCCCCCC/C=C\C/C=C\CCCCC)OC(=O)CCC(CCCCCCCCCC)OC(=O)Oc1ccc([N+](=O)[O-])cc1]

To a solution of Intermediate 39c in MeOH (0.13 M) was added NaBH₄ (2.5 eq) slowly at 5° C. The mixture was stirred at this temperature for 2 h. The reaction mixture was quenched by addition H₂O and then extracted 2× with EtOAc. The combined organic layers were washed with brine, dried over Na₂SO₄, filtered and concentrated under reduced pressure to give a residue. The residue was purified by column chromatography to afford a colorless oil that was immediately reconstituted in DCM (1 M), followed by the addition of 4-nitrophenylchloroformate (1.5 equiv) and pyridine (2 equiv) at 0° C. The mixture was stirred at 20° C. for 12 h, after which point the reaction mixture was concentrated under reduced pressure to give a residue. The residue was purified by column chromatography to afford Intermediate 39d in 31% yield. ¹H NMR (400 MHz, CDCl₃) δ 8.33-8.22 (m, 2H), 7.46-7.33 (m, 2H), 5.43-5.23 (m, 9H), 4.31 (dd, J=12.0, 4.3 Hz, 2H), 4.15 (dd, J=12.0, 5.8 Hz, 2H), 2.76 (t, J=6.3 Hz, 4H), 2.47 (t, J=7.5 Hz, 2H), 2.30 (td, J=7.6, 4.2 Hz, 4H), 2.04 (q, J=7.3 Hz, 10H), 1.67 (dt, J=47.7, 6.1 Hz, 7H), 1.30 (tq, J=14.3, 4.9, 3.0 Hz, 53H), 0.88 (td, J=6.8, 3.5 Hz, 10H).

Compound 39: 2-((4-(((2-(ethyl(methyl)amino)ethyl)carbamoyl)oxy)tetradecanoyl)oxy)propane-1,3-diyl (9Z,9'Z,12Z,12'Z)-bis(octadeca-9,12-dienoate)

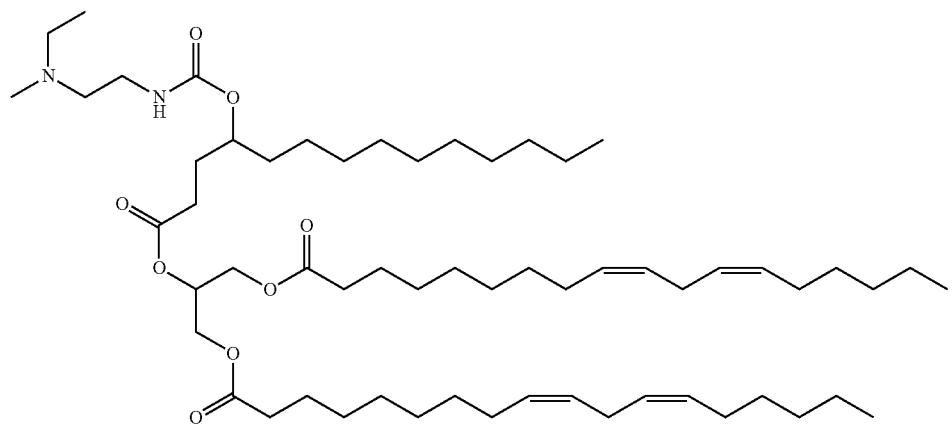 [SMILES: CCCCC/C=C\C/C=C\CCCCCCCC(=O)OCC(COC(=O)CCCCCCC/C=C\C/C=C\CCCCC)OC(=O)CCC(CCCCCCCCCC)OC(=O)NCCN(C)CC]

Compound 39 was synthesized in 78% yield from Intermediate 39d and N1-ethyl-N1-methylethane-1,2-diamine using the method employed for Example 1. ¹H NMR (400 MHz, CDCl₃) δ 5.49-5.17 (m, 9H), 4.75 (s, 1H), 4.28 (dd, J=11.9, 4.4 Hz, 2H), 4.15 (ddd, J=11.9, 5.9, 3.3 Hz, 2H), 3.26 (q, J=6.0 Hz, 2H), 2.77 (t, J=6.4 Hz, 4H), 2.52-2.27 (m, 10H), 2.23 (s, 3H), 2.05 (q, J=6.8 Hz, 8H), 1.95-1.42 (m, 14H), 1.42-1.18 (m, 40H), 1.05 (t, J=7.1 Hz, 3H), 0.88 (td, J=6.8, 4.5 Hz, 7H). 972.9 m/z [M+H].

Example 40—Compound 40

Intermediate 40a: 4-hydroxydecanoic acid

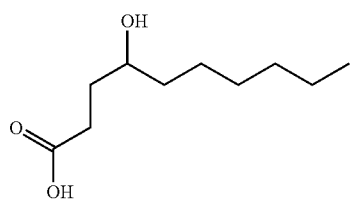

To a solution of 5-hexyltetrahydrofuran-2-one (15 g, 1.0 equiv) in EtOH (240 mL) and H₂O (80 mL) was added NaOH (2.0 equiv). The reaction was stirred at 25° C. for 12 h. The mixture was concentrated to remove EtOH. Then it was adjusted pH to 5 by aq. 1 N HCl and extracted 3× with EtOAc. The combined organic phase was washed with brine, dried over Na₂SO₄, filtered and concentrated in vacuo. The residue was purified by silica gel chromatography (EtOAc/hexanes) to afford product as a white solid (48%).

Intermediate 40b: 4-oxodecanoic acid

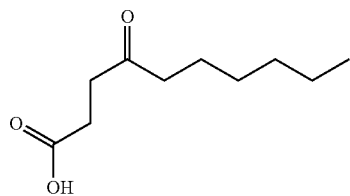

To a solution of NaH$_2$PO$_4$ (17 equiv) and Na$_2$HPO$_4$ (2.4 equiv) in H$_2$O (1000 mL) was added Intermediate 40a (10 g, 1.0 equiv). Then NaClO (200 mL, 6~8% Cl) was added to the solution. The reaction mixture was stirred at 25° C. for 12 h. To the mixture was then added H$_3$PO$_4$ (200 mL, 85%) and silica gel (300 g). The mixture was dried under reduced pressure and washed 3× with EtOAc. The organic layer was concentrated under reduced pressure to afford the crude product. Crude product was purified by silica gel chromatography (EtoAc/hexanes) to afford product as a white solid (80%). $^1$H NMR (400 MHz, CDCl$_3$) δ 2.70 (dd, J=7.0, 5.3 Hz, 2H), 2.63-2.58 (m, 2H), 2.43 (t, J=7.5 Hz, 2H), 1.58 (q, J=7.4 Hz, 2H), 1.33-1.19 (m, 6H), 0.90-0.83 (m, 3H).

Intermediate 40c: 2-((4-oxodecanoyl)oxy)propane-1,3-diyl (9Z,9'Z,12Z,12'Z)-bis(octadeca-9,12-dienoate)

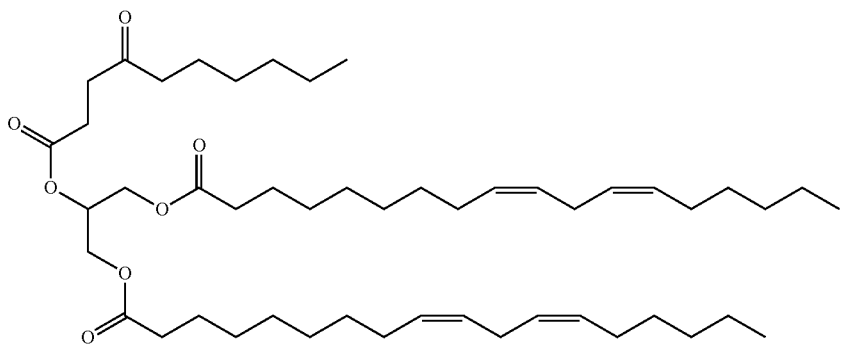 [SMILES: CCCCC/C=C\C/C=C\CCCCCCCC(=O)OCC(COC(=O)CCCCCCC/C=C\C/C=C\CCCCC)OC(=O)CCC(=O)CCCCCC]

Intermediate 40c was synthesized in 40% yield from Intermediate 40b and Intermediate 1c using the method employed for Example 1. $^1$H NMR (400 MHz, CDCl$_3$) δ 5.42-5.28 (m, 8H), 5.24 (tt, J=5.9, 4.3 Hz, 1H), 4.28 (dd, J=11.9, 4.3 Hz, 2H), 4.14 (dd, J=11.9, 5.9 Hz, 2H), 2.73 (dt, J=22.4, 6.7 Hz, 7H), 2.58 (t, J=6.5 Hz, 2H), 2.43 (t, J=7.5 Hz, 2H), 2.31 (t, J=7.6 Hz, 4H), 2.04 (q, J=6.9 Hz, 8H), 1.59 (q, J=6.7 Hz, 7H), 1.40-1.22 (m, 35H), 0.88 (td, J=6.8, 4.0 Hz, 9H).

Intermediate 40d: 2-((4-(((4-nitrophenoxy)carbonyl)oxy)decanoyl)oxy)propane-1,3-diyl (9Z,9'Z,12Z,12'Z)-bis(octadeca-9,12-dienoate)

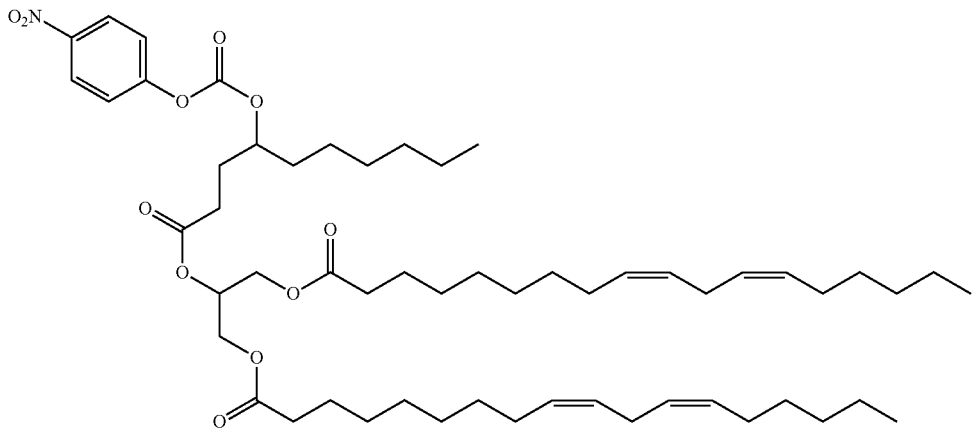

Intermediate 40d was synthesized in 31% yield from Intermediate 40c using the method employed for Intermediate 1e. $^1$H NMR (400 MHz, CDCl$_3$) δ 8.37-8.27 (m, 2H), 7.43 (dd, J=9.1, 5.9 Hz, 2H), 5.45-5.24 (m, 9H), 4.34 (dd, J=12.0, 4.3 Hz, 2H), 4.18 (dd, J=11.9, 6.0 Hz, 2H), 2.79 (t, J=6.3 Hz, 4H), 2.49 (t, J=7.5 Hz, 2H), 2.41-2.30 (m, 4H), 2.07 (q, J=6.9 Hz, 9H), 1.83-1.58 (m, 7H), 1.48-1.12 (m, 37H), 1.00-0.82 (m, 9H).

Compound 40: 2-((4-(((2-(ethyl(methyl)amino)ethyl)carbamoyl)oxy)decanoyl)oxy)propane-1,3-diyl (9Z,9'Z,12Z,12'Z)-bis(octadeca-9,12-dienoate)

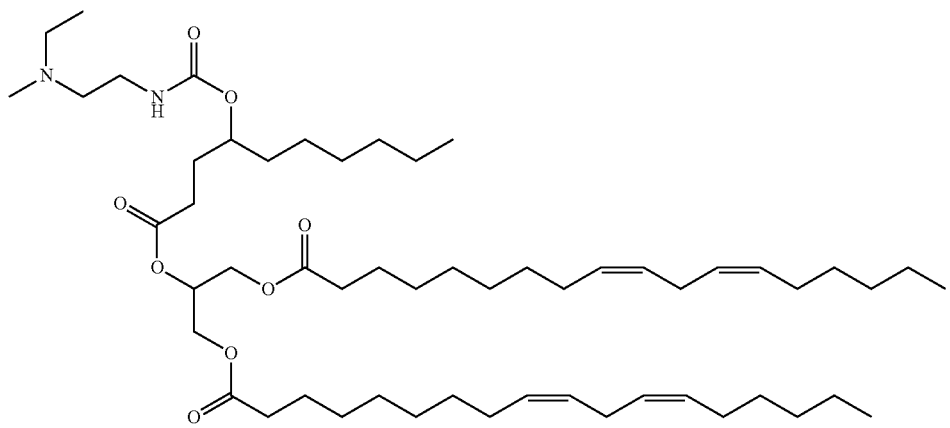 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NCCN(C)CC]

Compound 40 was synthesized in 53% yield from Intermediate 40d and N1-ethyl-N1-methylethane-1,2-diamine using the method employed for Example 1. $^1$H NMR (400 MHz, CDCl$_3$) δ 5.44-5.19 (m, 9H), 4.76 (s, 1H), 4.32-4.22 (m, 2H), 4.15 (ddd, J=11.9, 5.9, 3.4 Hz, 2H), 3.26 (s, 2H), 2.77 (t, J=6.5 Hz, 4H), 2.57-2.36 (m, 6H), 2.36-2.27 (m, 4H), 2.23 (s, 3H), 2.05 (q, J=6.6 Hz, 8H), 1.98-1.42 (m, 15H), 1.41-1.19 (m, 35H), 1.06 (t, J=7.2 Hz, 3H), 0.88 (td, J=9.7, 8.2, 4.2 Hz, 9H). MS: 916.7 m/z [M+H].

Example 41—Compound 41

Intermediate 41a: 4-cyclohexyl-4-oxobutanoic acid

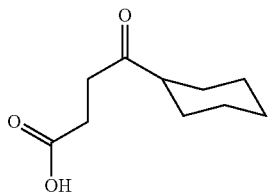 [SMILES: O=C(O)CCC(=O)C1CCCCC1]

To a solution of succinic anhydride (30 g, 1.0 equiv) in Et$_2$O (300 mL) was added CuI (0.1 equiv). The mixture was cooled to −20° C. Then, cyclohexyl magnesium bromide (1.0 equiv) was added to the mixture. The reaction was warmed to 25° C. and stirred for 14 h. The reaction was quenched with the addition of 1 M aq. HCl and stirred for 15 min. The reaction was then filtered, and the filtrate was extracted 3× with DCM. The combined organic layers were dried over Na$_2$SO$_4$, filtered, and concentrated. The crude residue was purified by column chromatography (EtOAc/hexanes) to afford product as a pale pink solid (13%). $^1$H NMR (400 MHz, CDCl$_3$) δ 10.09 (s, 1H), 2.66 (dt, J=55.4, 6.5 Hz, 4H), 2.35 (td, J=10.8, 9.3, 5.2 Hz, 1H), 1.75 (ddd, J=43.2, 36.6, 11.9 Hz, 5H), 1.46-1.09 (m, 5H).

Intermediate 41b: 2-((4-cyclohexyl-4-oxobutanoyl)oxy)propane-1,3-diyl (9Z,9'Z,12Z,12'Z)-bis(octadeca-9,12-dienoate)

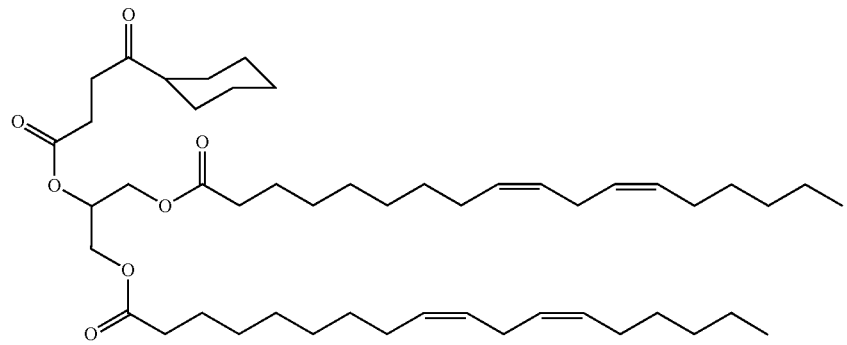 [SMILES: CCCCC/C=C\C/C=C\CCCCCCCC(=O)OCC(COC(=O)CCCCCCC/C=C\C/C=C\CCCCC)OC(=O)CCC(=O)C1CCCCC1]

Intermediate 41b was synthesized in 34% yield from Intermediate 41a and Intermediate 1c using the method employed for Example 1. $^1$H NMR (400 MHz, CDCl$^3$) δ 5.42-5.28 (m, 8H), 5.24 (ddd, J=10.2, 5.6, 4.2 Hz, 1H), 4.28 (dt, J=11.9, 4.6 Hz, 2H), 4.14 (ddd, J=11.9, 5.8, 2.3 Hz, 2H), 2.81-2.70 (m, 6H), 2.64-2.54 (m, 3H), 2.38-2.27 (m, 5H), 2.04 (q, J=6.8 Hz, 8H), 1.89-1.55 (m, 11H), 1.40-1.20 (m, 34H), 0.88 (t, J=6.8 Hz, 6H).

Intermediate 41c: 2-((4-cyclohexyl-4-(((4-nitrophenoxy)carbonyl)oxy)butanoyl)oxy)propane-1,3-diyl (9Z,9'Z,12Z,12'Z)-bis(octadeca-9,12-dienoate)

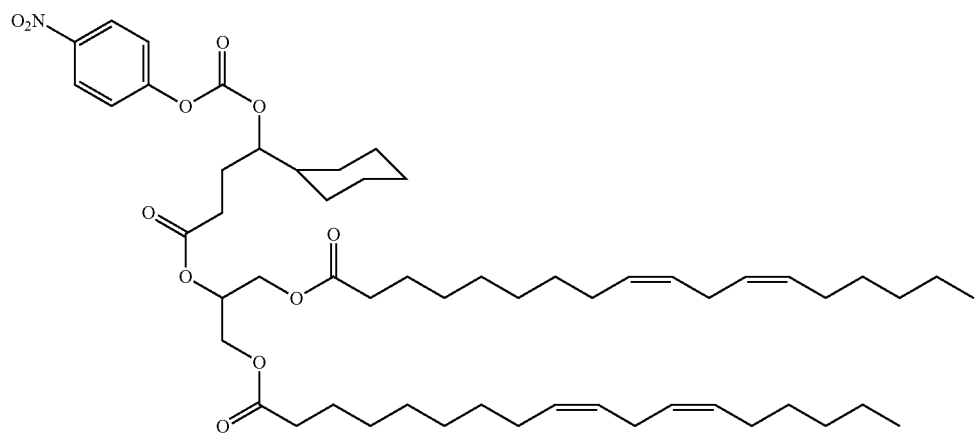 [SMILES: CCCCC/C=C\C/C=C\CCCCCCCC(=O)OCC(COC(=O)CCCCCCC/C=C\C/C=C\CCCCC)OC(=O)CCC(OC(=O)Oc1ccc([N+](=O)[O-])cc1)C1CCCCC1]

Intermediate 41c was synthesized in 14% yield from Intermediate 41b using the method employed for Example 1. $^1$H NMR (400 MHz, CDCl$_3$) δ 8.33-8.21 (m, 2H), 7.45-7.34 (m, 2H), 5.44-5.13 (m, 9H), 4.70 (ddd, J=9.3, 6.1, 3.4 Hz, 1H), 4.50 (dd, J=12.3, 3.9 Hz, 1H), 4.35-4.10 (m, 4H), 2.76 (t, J=6.4 Hz, 4H), 2.50-2.40 (m, 2H), 2.38-2.22 (m, 4H), 2.04 (q, J=6.9 Hz, 10H), 1.85-1.52 (m, 10H), 1.49-1.00 (m, 31H), 0.88 (t, J=6.8 Hz, 6H).

Compound 41: 2-((4-cyclohexyl-4-(((2-(ethyl(methyl)amino)ethyl)carbamoyl)oxy)butanoyl)oxy)propane-1,3-diyl (9Z,9'Z,12Z,12'Z)-bis(octadeca-9,12-dienoate)

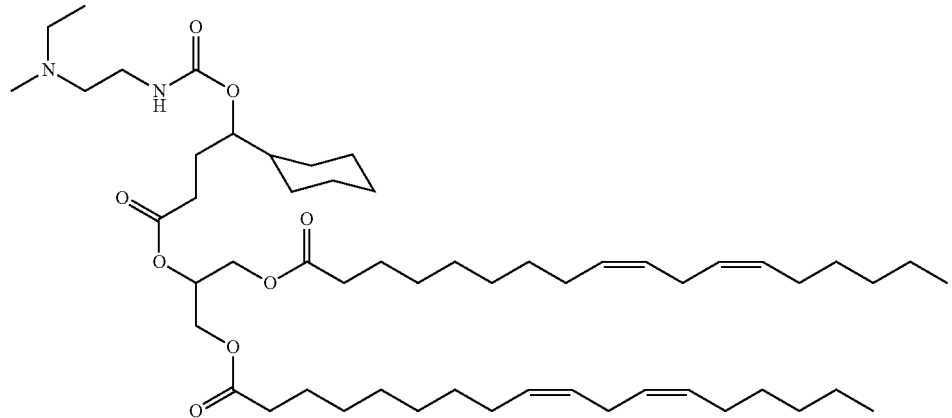 [SMILES: CCCCC/C=C\C/C=C\CCCCCCCC(=O)OCC(COC(=O)CCCCCCC/C=C\C/C=C\CCCCC)OC(=O)CCC(OC(=O)NCCN(C)CC)C1CCCCC1]

Compound 41 was synthesized in 60% yield from Intermediate 41d and N1-ethyl-N1-methylethane-1,2-diamine using the method employed for Intermediate 1e. $^1$H NMR (400 MHz, CDCl$_3$) δ 5.45-5.09 (m, 9H), 4.60 (s, 1H), 4.28 (ddd, J=11.9, 4.5, 1.6 Hz, 2H), 4.15 (ddd, J=11.9, 5.8, 2.9 Hz, 2H), 3.25 (s, 2H), 2.77 (t, J=6.5 Hz, 4H), 2.54-2.15 (m, 12H), 2.05 (q, J=6.7 Hz, 8H), 1.99-0.95 (m, 50H), 0.93-0.80 (m, 6H). MS: 914.5 m/z [M+H].

Example 42—Compound 42

Intermediate 42a: 4-hydroxyoctanoic acid

Intermediate 42a was synthesized in 53% yield from 5-butyltetrahydrofuran-2-one using the method employed for Intermediate 39b.

Intermediate 42b: 4-oxooctanoic acid

Intermediate 42b was synthesized in 61% yield from Intermediate 42a using the method employed for Intermediate 38b. $^1$H NMR (400 MHz, CDCl$_3$) δ 2.65 (ddd, J=7.0, 5.8, 1.1 Hz, 2H), 2.56 (ddd, J=7.1, 6.0, 1.2 Hz, 2H), 2.38 (t, J=7.5 Hz, 2H), 1.56-1.44 (m, 2H), 1.30-1.17 (m, 2H), 0.84 (t, J=7.3 Hz, 3H).

Intermediate 42c: 2-((4-oxooctanoyl)oxy)propane-1,3-diyl (9Z,9'Z,12Z,12'Z)-bis(octadeca-9,12-dienoate)

Intermediate 42c was synthesized in 29% yield from Intermediate 42b and Intermediate 1c using the method employed for Example 1. $^1$H NMR (400 MHz, CDCl$_3$) δ 5.35 (tq, J=18.2, 9.4, 7.6 Hz, 8H), 5.24 (t, J=5.3 Hz, 1H), 4.28 (dd, J=12.0, 3.9 Hz, 2H), 4.14 (dd, J=12.1, 5.8 Hz, 2H), 2.74 (dt, J=20.9, 6.7 Hz, 6H), 2.59 (d, J=6.6 Hz, 2H), 2.43 (t, J=7.6 Hz, 2H), 2.31 (t, J=7.7 Hz, 4H), 2.04 (q, J=7.0 Hz, 8H), 1.60 (t, J=7.5 Hz, 8H), 1.31 (d, J=14.1 Hz, 29H), 0.88 (t, J=6.9 Hz, 9H).

Intermediate 42d: 2-((4-(((4-nitrophenoxy)carbonyl)oxy)octanoyl)oxy)propane-1,3-diyl (9Z,9'Z,12Z,12'Z)-bis(octadeca-9,12-dienoate)

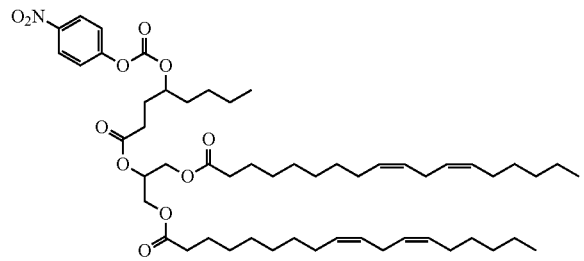 [SMILES: CCCCC/C=C\C/C=C\CCCCCCCC(=O)OCC(COC(=O)CCCCCCC/C=C\C/C=C\CCCCC)OC(=O)CCC(CCCC)OC(=O)Oc1ccc([N+](=O)[O-])cc1]

Intermediate 42d was synthesized in 51% yield from Intermediate 40c using the method employed for Intermediate 1e. $^1$H NMR (400 MHz, CDCl$_3$) δ 8.28 (dd, J=7.8, 4.7 Hz, 2H), 7.47-7.36 (m, 2H), 5.32 (dp, J=19.8, 9.2 Hz, 8H), 5.17 (s, 1H), 4.87 (d, J=7.3 Hz, 1H), 4.49 (d, J=12.2 Hz, 1H), 4.36-4.09 (m, 4H), 2.75 (d, J=6.7 Hz, 4H), 2.49 (dt, J=23.8, 7.9 Hz, 2H), 2.42-2.14 (m, 5H), 2.03 (q, J=7.2 Hz, 10H), 1.73 (s, 1H), 1.61 (dd, J=23.8, 11.9 Hz, 6H), 1.31 (d, J=14.4 Hz, 30H), 0.89 (tt, J=9.5, 7.0, 2.7 Hz, 9H).

Compound 42: 2-((4-(((2-(ethyl(methyl)amino)ethyl)carbamoyl)oxy)octanoyl)oxy)propane-1,3-diyl (9Z,9'Z,12Z,12'Z)-bis(octadeca-9,12-dienoate)

Compound 42 was synthesized in 93% yield from Intermediate 42d and N1-ethyl-N1-methylethane-1,2-diamine using the method employed for Example 1. $^1$H NMR (400 MHz, CDCl$_3$) δ 5.43-5.10 (m, 11H), 4.76 (s, 1H), 4.28 (ddd, J=11.9, 4.5, 1.3 Hz, 2H), 4.15 (ddd, J=11.8, 5.8, 3.3 Hz, 2H), 3.25 (s, 2H), 2.77 (t, J=6.5 Hz, 4H), 2.39 (ddd, J=8.7, 6.6, 4.3 Hz, 6H), 2.35-2.28 (m, 4H), 2.22 (s, 3H), 2.05 (q, J=6.7 Hz, 8H), 1.96-1.74 (m, 3H), 1.61 (s, 11H), 1.42-1.22 (m, 34H), 1.10-0.99 (m, 3H), 0.95-0.83 (m, 9H).

Example 43—Compound 43

Intermediate 43a: sodium 4-hydroxybutanoate

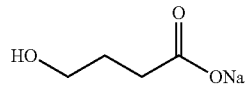

To a mixture of tetrahydrofuran-2-one (10 g, 1.0 equiv) in H$_2$O (100 mL) was added NaOH (4.0 equiv), and the mixture was degassed and purged 3× with N$_2$. The mixture was stirred at 25° C. for 24 hr under N$_2$ atmosphere. The reaction mixture was then concentrated under reduced pressure to afford the crude residue was a colorless oil that was used in the next step without further purification (12 g, crude).

Intermediate 43b: benzyl 4-hydroxybutanoate

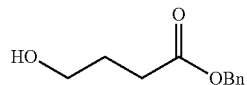 [SMILES: O=C(CCCO)OCc1ccccc1]

To a mixture of Intermediate 43a (12 g, 1.0 equiv) in acetone (100 mL) was added TBAB (0.05 equiv) and benzyl

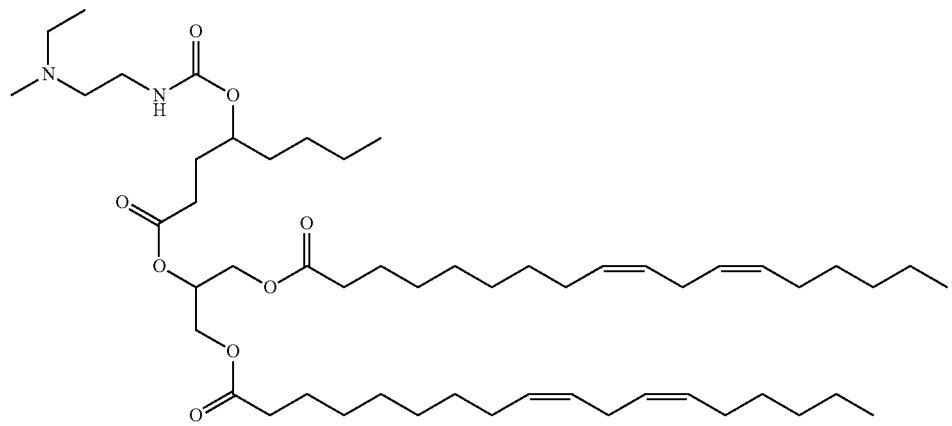

bromide (1.2 equiv), and the mixture was degassed and purged 3× with $N_2$. The mixture was stirred at 60° C. for 12 hr under $N_2$ atmosphere. The reaction mixture was then concentrated under reduced pressure, and the resulting residue was diluted with EtOAc and washed 1× each with 1 N $NaHSO_4$, $NaHCO_3$ and $H_2O$. The organic layer was dried over $Na_2SO_4$, filtered and concentrated, and the crude residue was purified by column chromatography (EtOAc/hexanes) to afford product as a colorless oil (43%).

Intermediate 43c: benzyl 4-(((4-nitrophenoxy)carbonyl)oxy)butanoate

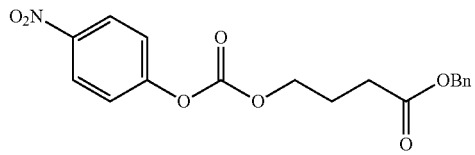 [SMILES: O=C(CCCOC(=O)Oc1ccc([N+](=O)[O-])cc1)OCc1ccccc1]

To a mixture of Intermediate 43b (5 g, 1.0 equiv) in DCM (150 mL) was added 4-nitrophenyl chloroformate (1.0 equiv), and the mixture was degassed and purged 3× with $N_2$. The reaction was cooled to 0° C. followed by the addition of pyridine (2.0 equiv). The reaction was stirred for 25° C. for 5 h under $N_2$ atmosphere. The reaction mixture was then concentrated under reduced pressure, diluted with hexanes, and filtered. The filtrate was washed 10× with $H_2O$, and the combined organic layers were washed with brine, dried over $Na_2SO_4$, filtered, and concentrated. Crude material was purified by column chromatography to afford product as a yellow oil (32%).

Intermediate 43d: benzyl 4-(((2-(ethyl(methyl)amino)ethyl)carbamoyl)oxy)butanoate

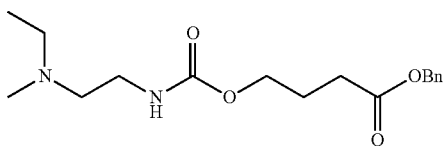 [SMILES: CCN(C)CCNC(=O)OCCCC(=O)OCc1ccccc1]

To a mixture of Intermediate 43c (3 g, 1.0 equiv) in MeCN (50 mL) was added N1-ethyl-N1-methylethane-1,2-diamine (2.5 equiv), pyridine (3.0 equiv), and DMAP (1.0 equiv). The mixture was degassed and purged 3× with $N_2$, and the mixture was stirred at 70° C. for 12 h under $N_2$. The reaction mixture was then concentrated under reduced pressure, and the crude residue was purified by column chromatography to afford product as a yellow oil (56%). $^1H$ NMR (400 MHz, $CDCl_3$) δ 7.33-7.23 (m, 4H), 5.24 (d, J=12.8 Hz, 1H), 5.05 (s, 2H), 4.04 (dt, J=12.9, 6.7 Hz, 2H), 3.19 (q, J=5.8 Hz, 2H), 3.00 (s, 1H), 2.39 (dt, J=10.4, 6.6 Hz, 6H), 2.13 (s, 3H), 1.89 (p, J=6.9 Hz, 2H), 0.98 (t, J=7.1 Hz, 3H).

Intermediate 43e: 4-(((2-(ethyl(methyl)amino)ethyl)carbamoyl)oxy)butanoic acid

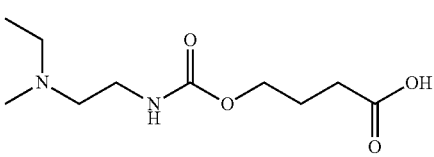 [SMILES: CCN(C)CCNC(=O)OCCCC(=O)O]

A mixture of Intermediate 43d (1.5 g, 1.0 equiv) in MeOH (30 mL) was added Pd/C (10% wt, 0.05 equiv), and the mixture was degassed and purged 3× with H2. The reaction mixture was stirred at 25° C. for 1 h under H2 atmosphere, after which point the filtrate was concentrated to afford a crude residue that was used in the next step without further purification. $^1H$ NMR (400 MHz, $CD_3OD$) δ 4.11 (t, J=6.3 Hz, 2H), 3.49 (t, J=6.0 Hz, 2H), 3.29-3.21 (m, 5H), 2.89 (s, 3H), 2.38 (t, J=7.2 Hz, 2H), 1.92 (p, J=6.7 Hz, 2H), 1.34 (t, J=7.3 Hz, 3H).

Compound 43: 2-((4-(((2-(ethyl(methyl)amino)ethyl)carbamoyl)oxy)butanoyl)oxy)propane-1,3-diyl (9Z,9'Z,12Z,12'Z)-bis(octadeca-9,12-dienoate)

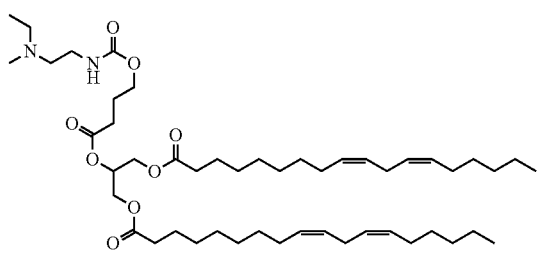 [SMILES: CCCCC/C=C\C/C=C\CCCCCCCC(=O)OCC(COC(=O)CCCCCCC/C=C\C/C=C\CCCCC)OC(=O)CCCOC(=O)NCCN(C)CC]

Compound 43 was synthesized in 45% yield from Intermediate 43d and Intermediate 1c using the method employed for Intermediate 1d. $^1H$ NMR (400 MHz, $CDCl_3$) δ 5.43-5.22 (m, 9H), 4.29 (dd, J=11.9, 4.4 Hz, 2H), 4.18-4.06 (m, 4H), 3.25 (q, J=5.8 Hz, 2H), 2.76 (t, J=6.4 Hz, 4H), 2.43 (dt, J=10.5, 7.3 Hz, 6H), 2.31 (t, J=7.6 Hz, 4H), 2.20 (s, 3H), 2.04 (q, J=6.9 Hz, 8H), 1.95 (q, J=6.9 Hz, 2H), 1.59 (d, J=7.1 Hz, 7H), 1.40-1.22 (m, 26H), 1.04 (t, J=7.1 Hz, 3H), 0.88 (t, J=6.8 Hz, 6H).

Example 44—Compound 44

Compound 44: 2-((4-((((1-methylpyrrolidin-2-yl)methyl)carbamoyl)oxy)decanoyl)oxy)propane-1,3-diyl (9Z,9'Z,12Z,12'Z)-bis(octadeca-9,12-dienoate)

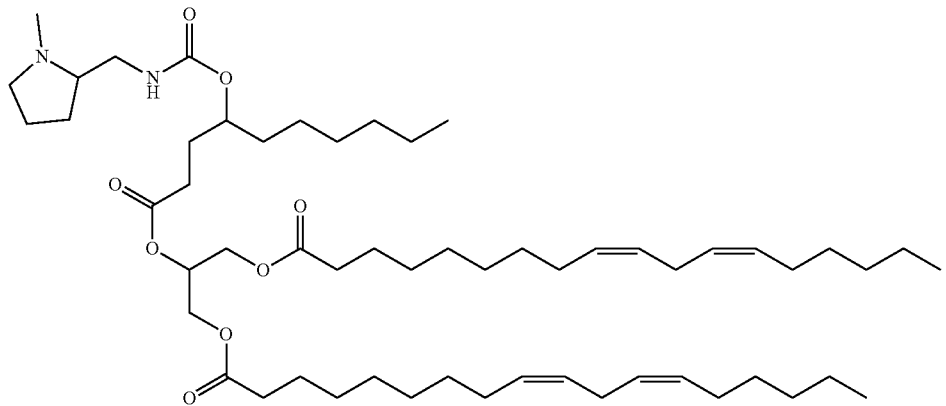 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NCC1CCCN1C]

Compound 44 was synthesized in 35% yield from Intermediate 40d and (1-methylpyrrolidin-2-yl)methanamine using the method employed for Intermediate 1e. $^1$H NMR (400 MHz, CDCl$_3$) δ 5.44-5.20 (m, 9H), 5.16 (s, 1H), 4.76 (s, 1H), 4.28 (dd, J=11.9, 4.4 Hz, 2H), 4.15 (ddd, J=11.9, 5.8, 3.0 Hz, 2H), 3.39 (s, 1H), 3.10 (d, J=27.2 Hz, 2H), 2.81-2.73 (m, 4H), 2.43-2.18 (m, 11H), 2.05 (q, J=6.7 Hz, 8H), 1.96-1.42 (m, 17H), 1.30 (dqt, J=12.8, 8.8, 5.4 Hz, 36H), 0.92-0.83 (m, 9H). MS: 928.9 m/z [M+H].

Example 45—Compound 45

Compound 45: 2-((4-(((3-(pyrrolidin-1-yl)propoxy)carbonyl)oxy)decanoyl)oxy)propane-1,3-diyl (9Z,9'Z,12Z,12'Z)-bis(octadeca-9,12-dienoate)

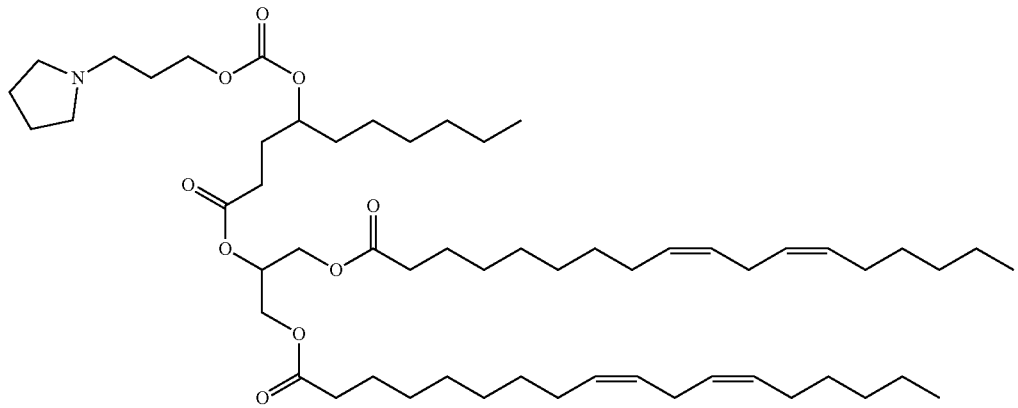 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)OCCCN1CCCC1]

Compound 45 was synthesized in 52% yield from Intermediate 40d and 3-(pyrrolidin-1-yl)propan-1-ol using the method employed for Example 1. $^1$H NMR (400 MHz, CDCl$_3$) δ 5.44-5.21 (m, 9H), 4.72 (ddd, J=11.3, 8.8, 5.7 Hz, 1H), 4.29 (dd, J=11.9, 4.3 Hz, 2H), 4.25-4.10 (m, 4H), 2.81-2.74 (m, 4H), 2.59 (s, 5H), 2.40 (dt, J=8.6, 6.4 Hz, 2H), 2.36-2.27 (m, 4H), 2.05 (q, J=6.7 Hz, 8H), 1.98-1.78 (m, 9H), 1.67-1.51 (m, 7H), 1.41-1.21 (m, 36H), 0.88 (td, J=7.0, 5.0 Hz, 9H). MS: 943.8 m/z [M+H].

Example 46—Compound 46

Compound 46: 2-((4-(((2-(pyrrolidin-1l-yl)ethyl)carbamoyl)oxy)hexadecanoyl)oxy)propane-1,3-diyl (9Z,9'Z,12Z,12'Z)-bis(octadeca-9,12-dienoate)

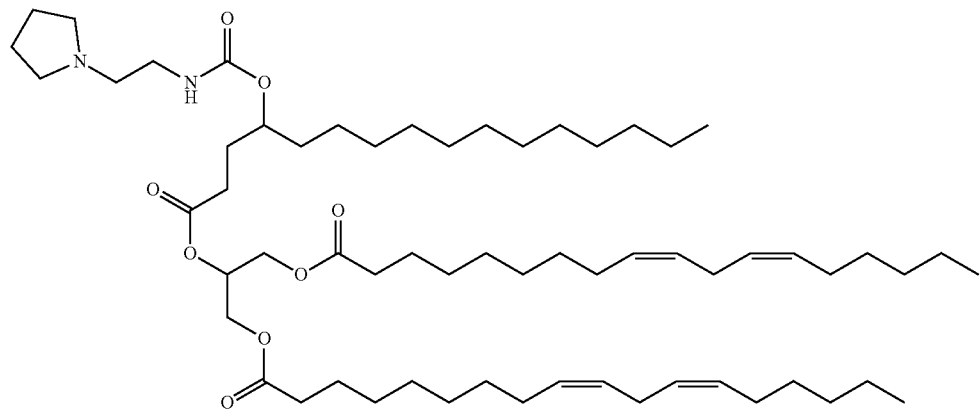 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCN1CCCC1]

Compound 46 was synthesized in 53% yield from Intermediate 1e and 2-(pyrrolidin-1-yl)ethan-1-amine using the method employed for Example 1. $^1$H NMR (400 MHz, CDCl$_3$) δ 5.55 (s, 1H), 5.46-5.21 (m, 9H), 4.75 (s, 1H), 4.28 (dd, J=11.9, 4.4 Hz, 2H), 4.15 (ddd, J=11.9, 5.8, 3.6 Hz, 2H), 3.35 (d, J=6.0 Hz, 2H), 2.81-2.60 (m, 9H), 2.39 (ddd, J=8.6, 6.7, 3.8 Hz, 2H), 2.31 (t, J=7.6 Hz, 4H), 2.05 (q, J=6.8 Hz, 8H), 1.84 (s, 7H), 1.66-1.19 (m, 55H), 0.88 (td, J=7.0, 4.3 Hz, 9H). MS: 1012.5 m/z [M+H].

Example 47—Compound 47

Compound 47: 2-((4-((((1-methylpiperidin-4-yl)oxy)carbonyl)oxy)hexadecanoyl)oxy)propane-1,3-diyl (9Z,9'Z,12Z,12'Z)-bis(octadeca-9,12-dienoate)

To a solution of Intermediate 1e (250 mg, 1.0 equiv) in MeCN (0.1 M) was added pyridine (3.0 equiv), 1-methylpiperidin-4-ol (1.5 equiv), and DMAP (1.0 equiv). The reaction was stirred for 18 h at room temperature. An additional portion of 1-methylpiperidin-4-ol (3.0 equiv) was added, and the mixture was heated to 50° C. After 2 h, an additional portion of DMAP (1.0 equiv) was added, and the reaction was maintained for another 2 h. Upon completion, heptane (0.1 M) was then added to the reaction mixture, and the heptane layer was washed 3× with MeCN. The combined MeCN layers were back-extracted three times with heptane, and the combined heptane layers were washed one final time with MeCN. Heptane was then removed in vacuo, and crude material was purified by column chromatography (MeOH/DCM) to afford product as a colorless oil (62 mg, 32%). $^1$H NMR (400 MHz, CDCl$_3$) δ 5.44-5.20 (m, 9H), 4.77-4.60 (m, 2H), 4.29 (dd, J=11.9, 4.4 Hz, 2H), 4.14 (ddd, J=11.9, 5.8, 3.6 Hz, 2H), 2.83-2.66 (m, 6H), 2.46-2.26 (m, 11H), 2.08-1.71 (m, 18H), 1.71-1.47 (m, 8H), 1.40-1.21 (m, 47H), 0.88 (td, J=7.0, 4.2 Hz, 9H). MS: 1013.7 m/z [M+H].

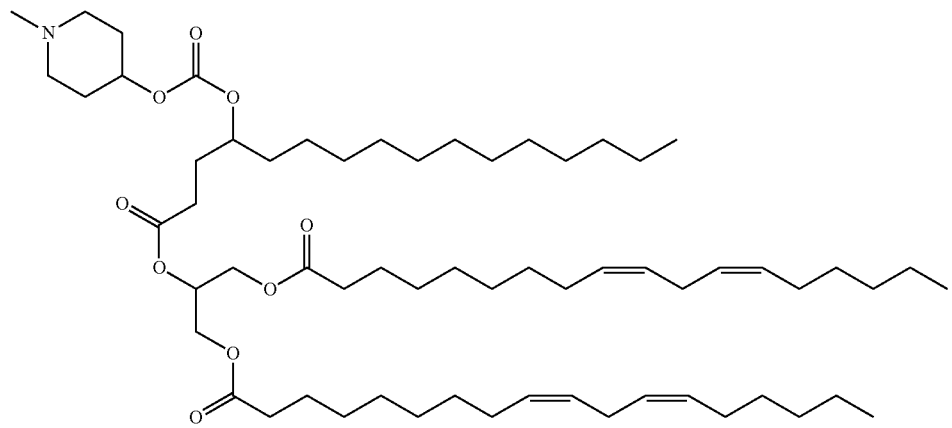 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OC1CCN(C)CC1]

Example 48—Compound 48

Compound 48: 2-((4-(((3-(bis(2-hydroxyethyl)amino)propyl)carbamoyl)oxy)hexadecanoyl)oxy)propane-1,3-diyl (9Z,9'Z,12Z,12'Z)-bis(octadeca-9,12-dienoate)

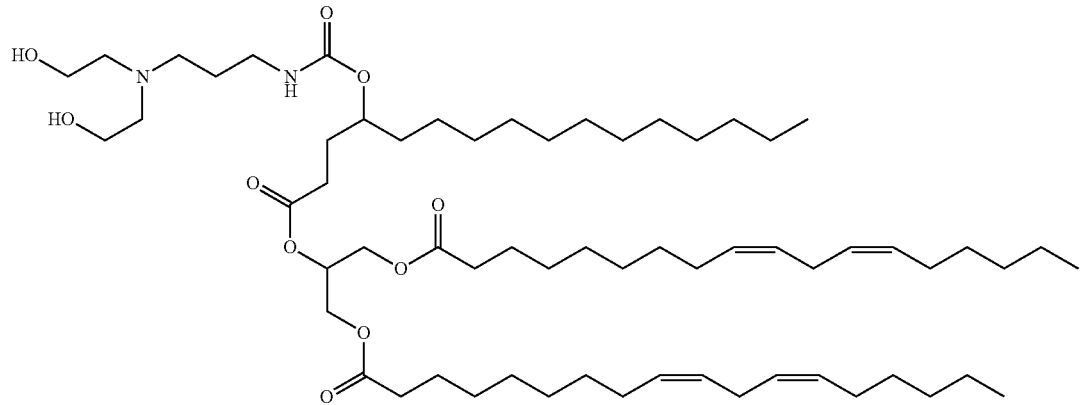 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCCN(CCO)CCO]

To a solution of Intermediate 1e (250 mg, 1.0 equiv) in MeCN (0.1 M) was added pyridine (3.0 equiv) and 2-[(3-aminopropyl)(2-hydroxyethyl)amino]ethan-1-ol (1.5 equiv). The reaction was stirred for 2 h at room temperature. Upon completion, heptane (0.1 M) was then added to the reaction mixture, and the heptane layer was washed 3× with MeCN. The combined MeCN layers were back-extracted three times with heptane, and the combined heptane layers were washed one final time with MeCN. Heptane was then removed in vacuo, and crude material was purified by column chromatography (MeOH/DCM) to afford product as a colorless oil (97 mg, 48%). $^1$H NMR (400 MHz, CDCl$_3$) δ 5.43-5.20 (m, 9H), 4.76 (s, 1H), 4.29 (ddd, J=11.9, 4.6, 1.8 Hz, 2H), 4.16 (dd, J=11.9, 5.8 Hz, 2H), 3.72 (t, J=5.0 Hz, 4H), 3.35-3.22 (m, 2H), 2.98-2.46 (m, 14H), 2.41-2.28 (m, 6H), 2.09-1.86 (m, 9H), 1.80 (dd, J=14.2, 7.2 Hz, 3H), 1.67-1.42 (m, 7H), 1.42-1.18 (m, 46H), 0.88 (td, J=7.0, 4.3 Hz, 9H). MS: 1060.6 m/z [M+H].

Example 49—Comparative Compound 49

Compound 49: 3-((4,4-bis(octyloxy)butanoyl)oxy)-2-((((3-(diethylamino)propoxy)carbonyl)oxy)methyl)propyl (9Z,12Z)-octadeca-9,12-dienoate

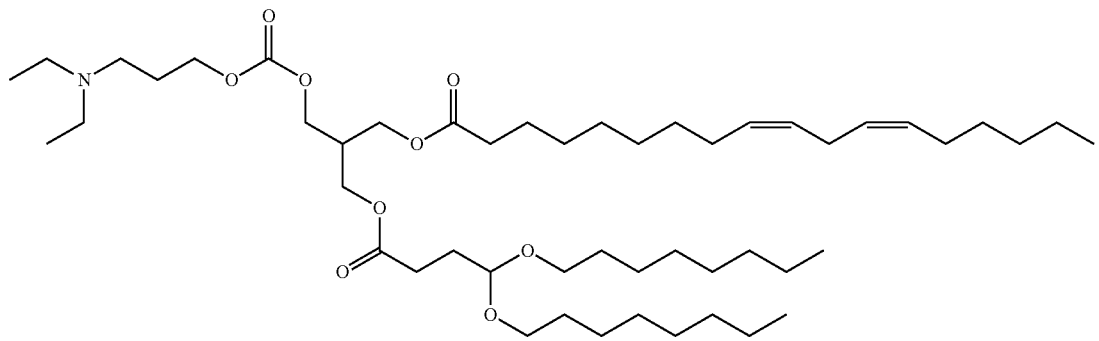 [SMILES: CCCCC/C=C\C/C=C\CCCCCCCC(=O)OCC(COC(=O)CCC(OCCCCCCCC)OCCCCCCCC)COC(=O)OCCCN(CC)CC]

Compound 49 was synthesized according to methods described in WO 2015/095340 A1 (Example 13). 1H NMR (CDCl$_3$, 400 MHz) δ 5.35 (m, 4H), 4.48 (t, J=5.6 Hz, 1H), 4.17 (m, 8H), 3.56 (m, 2H), 3.40 (m, 2H), 2.77 (t, J=6.6 Hz, 2H), 2.55 (q, J=7.2 Hz, 6H), 2.40 (m, 3H), 2.30 (t, J=7.6 Hz, 2H), 2.05 (q, J=6.8 Hz, 4H), 1.92 (m, 2H), 1.84 (m, 2H), 1.57 (m, 6H), 1.30 (m, 34H), 1.03 (t, J=7.2 Hz, 6H), 0.88 (m, 9H) ppm; MS: 853 m/z [M+H].

Example 50—Compound 50

Compound 50: 2-((4-(((2-(pyrrolidin-1-yl)ethyl)carbamoyl)oxy)decanoyl)oxy)propane-1,3-diyl (9Z, 9′Z,12Z,12′Z)-bis(octadeca-9,12-dienoate)

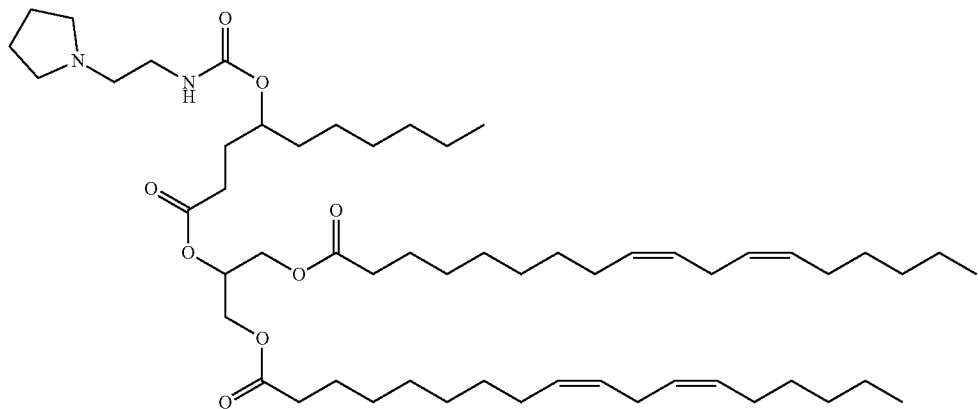 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NCCN1CCCC1]

Compound 50 was synthesized in 36% yield from Intermediate 40d and 2-(pyrrolidin-1-yl)ethan-1-amine using the method employed for Example 1. $^1$H NMR (400 MHz, CDCl$_3$) δ 5.49-5.29 (m, 8H), 5.27-5.20 (m, 1H), 4.76 (s, 1H), 4.28 (dd, J=11.9, 4.4 Hz, 2H), 4.15 (ddd, J=11.9, 5.8, 3.8 Hz, 2H), 3.35 (s, 2H), 2.83-2.44 (m, 10H), 2.39 (ddd, J=8.4, 6.7, 3.3 Hz, 2H), 2.36-2.25 (m, 4H), 2.05 (q, J=6.8 Hz, 8H), 1.98-1.43 (m, 15H), 1.42-1.20 (m, 33H), 0.89 (td, J=6.1, 5.4, 0.9 Hz, 9H). MS: 928.6 m/z [M+H].

Example 51—Compound 51

Compound 51: 2-((4-(((2-(pyrrolidin-1-yl)ethyl)carbamoyl)oxy)dodecanoyl)oxy)propane-1,3-diyl (9Z,9′Z,12Z,12′Z)-bis(octadeca-9,12-dienoate)

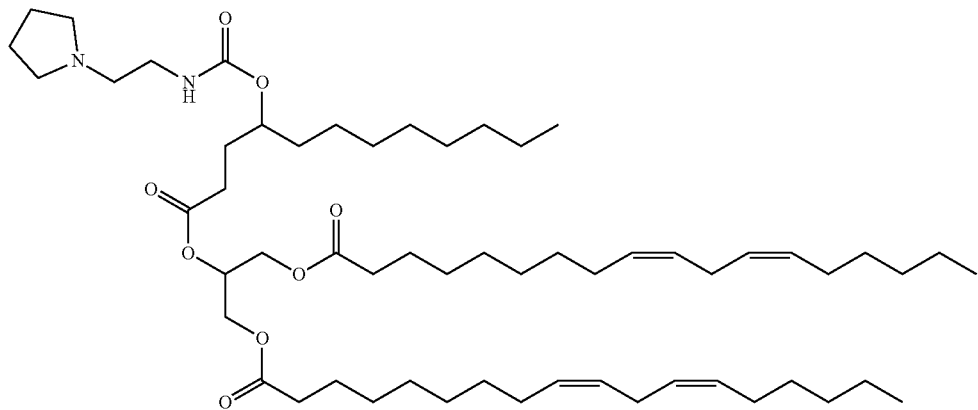 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCCN1CCCC1]

Compound 51 was synthesized in 27% yield from Intermediate 31c and 2-(pyrrolidin-1-yl)ethan-1-amine using the method employed for Example 1. $^1$H NMR (400 MHz, CDCl$_3$) δ 5.55 (s, 1H), 5.44-5.28 (m, 8H), 5.28-5.22 (m, 1H), 4.76 (s, 1H), 4.28 (dd, J=11.9, 4.4 Hz, 2H), 4.15 (ddd, J=11.9, 5.8, 3.9 Hz, 2H), 3.37 (s, 2H), 2.83-2.51 (m, 10H), 2.39 (ddd, J=8.4, 6.8, 3.1 Hz, 2H), 2.35-2.27 (m, 4H), 2.05 (q, J=6.7 Hz, 8H), 1.97-1.41 (m, 17H), 1.41-1.20 (m, 40H), 0.94-0.84 (m, 9H). MS: 957.0 m/z [M+H].

Example 52—Compound 52

Intermediate 52a: benzyl 3-hydroxyundecanoate

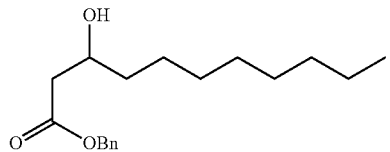 [SMILES: CCCCCCCCC(O)CC(=O)OCc1ccccc1]

To a solution of THF (150 mL) at 66° C. under N$_2$ was added Zn (22.99 g, 1.0 equiv.) and nonanal (25 g, 1.0 equiv.) dropwise. Next, benzyl 2-bromoacetate (50.00 g, 1.24 eq) was added to the reaction mixture dropwise slowly and carefully. Upon compete addition of benzyl 2-bromoacetate, the mixture was cooled and stirred at 20° C. for 2 h. The reaction mixture was then concentrated under reduced pressure to remove THF, and the resulting residue was diluted with water and extracted 3× with EtOAc. The combined organic layers were concentrated under reduced pressure and purified by column chromatography to afford product as a yellow oil (25 g, 49%). $^1$H NMR (400 MHz, CDCl$_3$) δ 7.33-7.24 (m, 5H), 5.09 (s, 2H), 3.95 (tt, J=7.7, 3.8 Hz, 1H), 2.75 (d, J=3.9 Hz, 1H), 2.56-2.35 (m, 2H), 1.54-1.11 (m, 18H), 0.81 (t, J=6.7 Hz, 3H).

Intermediate 52b: benzyl 3-(((4-nitrophenoxy)carbonyl)oxy)undecanoate

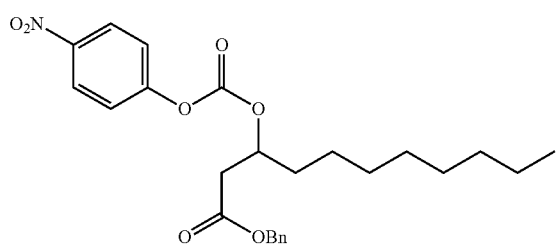 [SMILES: CCCCCCCCC(CC(=O)OCc1ccccc1)OC(=O)Oc1ccc([N+](=O)[O-])cc1]

To a solution of Intermediate 52a (25 g, 1.0 equiv.) in DCM (250 mL) was added (4-nitrophenyl) carbonochloridate (17.23 g, 1.0 equiv.) and pyridine (13.80 mL, 2.0 equiv.) under N$_2$ atmosphere. The mixture was stirred at 20° C. for 2 h. Upon completion, the reaction mixture was concentrated under reduced pressure to remove DCM, and the resulting residue was diluted with water and extracted 3× with EtOAc. The combined organic layers were concentrated under reduced pressure and purified by column chromatography to afford product as a colorless oil (12 g, 31%). $^1$H NMR (400 MHz, CDCl$_3$) δ 8.31-8.01 (m, 4H), 7.28 (s, 5H), 5.22-5.14 (m, 2H), 5.13-5.01 (m, 4H), 2.68 (dd, J=14.8, 6.4 Hz, 3H), 1.75-1.64 (m, 2H), 1.30-1.19 (m, 18H), 0.80 (t, J=6.6 Hz, 3H).

Intermediate 52c: benzyl 3-(((2-(ethyl(methyl)amino)ethyl)carbamoyl)oxy)undecanoate

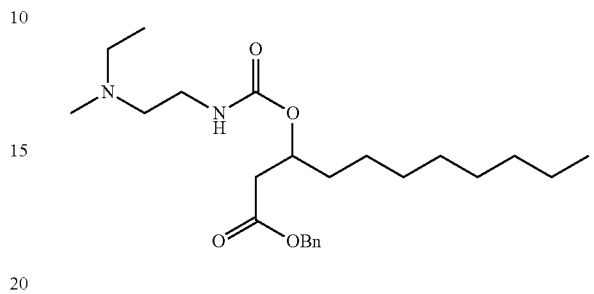

To a solution of Intermediate 52b (14 g, 1.0 equiv.) and N'-ethyl-N'-methyl-ethane-1,2-diamine (6.25 g, 2.0 equiv.) in MeCN (400 mL) was added pyridine (7.41 mL, 3.0 equiv.) and DMAP (3.74 g, 1.0 equiv.). The mixture was stirred at 20° C. for 12 h. Upon completion, the reaction mixture was concentrated under reduced pressure to remove MeCN, and the resulting residue was diluted with water and extracted 3× with EtOAc. The combined organic layers were concentrated under reduced pressure and purified by column chromatography to afford product as a colorless oil (6 g, 47%). $^1$H NMR (400 MHz, CDCl$_3$) δ 7.39-7.28 (m, 5H), 5.11 (s, 4H), 3.21 (h, J=6.8 Hz, 2H), 2.62 (td, J=14.4, 13.6, 6.4 Hz, 2H), 2.50-2.39 (m, 4H), 1.59 (h, J=8.2 Hz, 2H), 1.25 (d, J=16.1 Hz, 14H), 1.03 (t, J=7.2 Hz, 3H), 0.86 (t, J=6.7 Hz, 3H).

Intermediate 52d: 3-(((2-(ethyl(methyl)amino)ethyl)carbamoyl)oxy)undecanoic acid

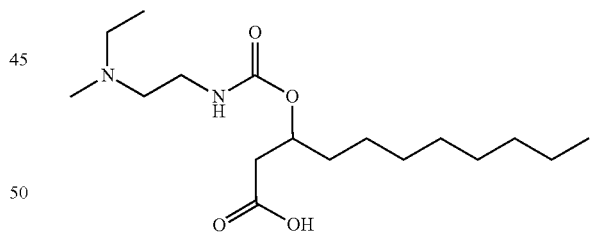

To a solution of Intermediate 52c (6 g, 1.0 equiv) in MeOH (60 mL) was added Pd/C (2 g, 10% w/w). The mixture was stirred at 20° C. for 2 h under H2. The reaction mixture was then filtered, and the filtrate was concentrated under reduced pressure to give a residue. The residue was purified by column chromatography to afford product as a brown oil. $^1$H NMR (400 MHz, CDCl$_3$) δ 12.76 (s, 1H), 6.28 (t, J=5.8 Hz, 1H), 5.01 (p, J=6.1, 5.6 Hz, 1H), 3.30 (qq, J=13.8, 6.0 Hz, 2H), 2.70 (hd, J=12.1, 11.0, 5.4 Hz, 3H), 2.37 (d, J=14.1 Hz, 4H), 1.51 (ddq, J=21.6, 14.2, 6.71 Hz, 2H), 1.34-1.14 (m, 11H), 1.10 (t, J=7.1 Hz, 3H), 0.80 (t, J=6.7 Hz, 3H).

Compound 52: 2-((3-(((2-(ethyl(methyl)amino)ethyl)carbamoyl)oxy)undecanoyl)oxy)propane-1,3-diyl (9Z,9'Z,12Z,12'Z)-bis(octadeca-9,12-dienoate)

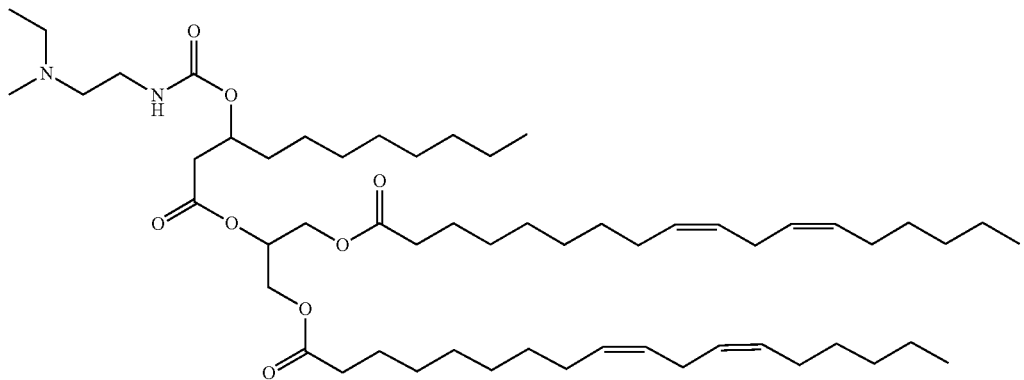 [SMILES: CCCCC/C=C\C/C=C\CCCCCCCC(=O)OCC(COC(=O)CCCCCCC/C=C\C/C=C\CCCCC)OC(=O)CC(CCCCCCCC)OC(=O)NCCN(C)CC]

To a solution of Intermediate 52d (1.0-1.1 equiv.) and Intermediate 1c (1.0-1.1 equiv.) in DCM (0.1-0.25 equiv.) was added DMAP (0.25 equiv.), DIPEA (3.5 equiv.), and EDCI (1.5 equiv.) in sequence. The reaction was stirred at 23° C. for at least 16 h. Additional DMAP (0.25 equiv.) was added to the reaction, and the reaction was stirred at 23° C. for another 6 h. The reaction was then quenched by the addition of water, washed 1× with 1 M HCl and 1× with 5% NaHCO$_3$. The organic layer was dried over Na$_2$SO$_4$, filtered, and concentrated. Purification by column chromatography afforded product as a colorless oil (28%). $^1$H NMR (400 MHz, CDCl$_3$) δ 5.53-5.28 (m, 8H), 5.24 (s, 1H), 5.08 (s, 1H), 4.28 (ddd, J=15.9, 11.9, 4.5 Hz, 2H), 4.15 (dt, J=13.4, 6.8 Hz, 2H), 2.77 (t, J=6.5 Hz, 4H), 2.59 (tt, J=15.9, 9.0 Hz, 6H), 2.37-2.14 (m, 6H), 2.05 (q, J=6.8 Hz, 7H), 1.59 (d, J=14.2 Hz, 12H), 1.46-0.97 (m, 42H), 0.96-0.81 (m, 9H). MS: 930.8 m/z [M+H].

Example 53—Compound 53

Intermediate 53a: 2-(hydroxymethyl)propane-1,3-diyl (9Z,9'Z,12Z,12'Z)-bis(octadeca-9,12-dienoate)

To a solution of linoleic acid (20 g, 1.0 equiv.) and 2-(hydroxymethyl)propane-1,3-diol (7.57 g, 1.0 equiv.) in DCM (200 mL) was added EDCI (13.67 g, 1.0 equiv.), DMAP (1.39 g, 0.16 equiv.) and DIPEA (37.27 mL, 3.0 equiv.). The mixture was stirred at 20° C. for 2 hr. Upon completion, the reaction mixture was concentrated under reduced pressure to remove DCM, and the resulting residue was diluted with water and extracted 3× with EtOAc. The combined organic layers were washed with brine, dried over Na$_2$SO$_4$, filtered, and concentrated in vacuo. The crude residue was purified by column chromatography (EtOAc/hexanes) to afford product as a colorless oil (6.3 g, 11%). $^1$H NMR (400 MHz, CD$_3$OD) δ 5.44-5.30 (m, 8H), 4.17 (qd, J=11.1, 6.0 Hz, 4H), 3.63 (d, J=6.0 Hz, 2H), 2.80 (t, J=6.1 Hz, 4H), 2.35 (t, J=7.4 Hz, 4H), 2.21 (h, J=6.0 Hz, 1H), 2.14-2.03 (m, 8H), 1.64 (p, J=7.4 Hz, 4H), 1.46-1.28 (m, 27H), 0.93 (t, J=6.7 Hz, 6H).

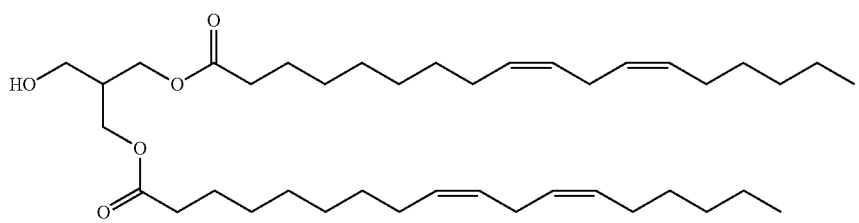 [SMILES: CCCCC/C=C\C/C=C\CCCCCCCC(=O)OCC(CO)COC(=O)CCCCCCC/C=C\C/C=C\CCCCC]

Compound 53: 2-(11-methyl-5-octyl-3,7-dioxo-2,6-dioxa-8,11-diazatridecyl)propane-1,3-diyl (9Z,9'Z, 12Z,12'Z)-bis(octadeca-9,12-dienoate)

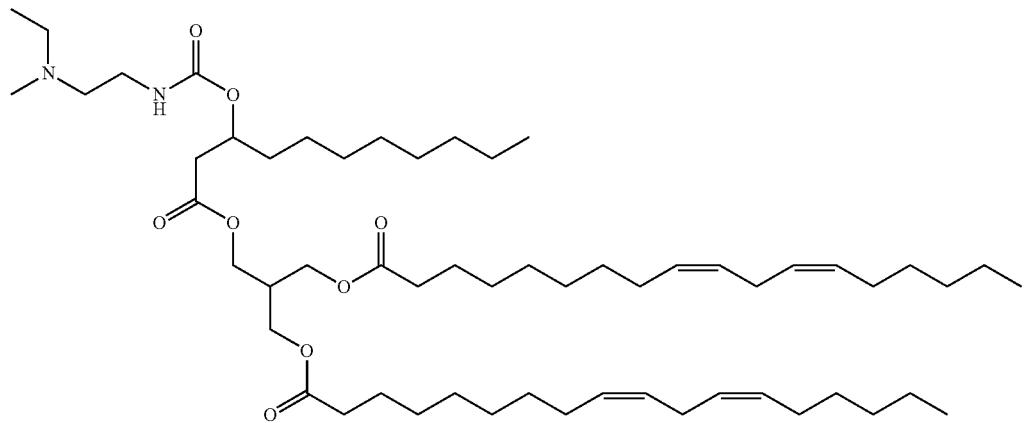 [SMILES: CCCCC/C=C\C/C=C\CCCCCCCC(=O)OCC(COC(=O)CCCCCCC/C=C\C/C=C\CCCCC)COC(=O)CC(CCCCCCCC)OC(=O)NCCN(C)CC]

Compound 53 was synthesized in 45% yield from Intermediate 52d and Intermediate 53a using the method employed for Compound 52. $^1$H NMR (400 MHz, CDCl$_3$) δ 5.48-5.24 (m, 8H), 5.07 (t, J=6.5 Hz, 1H), 4.20-4.07 (m, 6H), 2.77 (t, J=6.5 Hz, 4H), 2.62-2.46 (m, 4H), 2.45-2.37 (m, 2H), 2.34-2.15 (m, 6H), 2.05 (q, J=6.8 Hz, 8H), 1.43-0.97 (m, 43H), 0.95-0.83 (m, 9H). MS: 944.8 m/z [M+H].

Example 54—Compound 54

Intermediate 54a: benzyl 4-hydroxydodecanoate

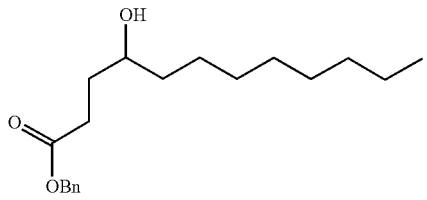 [SMILES: CCCCCCCCC(O)CCC(=O)OCc1ccccc1]

To a solution of 5-octyltetrahydrofuran-2-one (20 g, 1.0 equiv.) in water (200-250 mL) was added NaOH (1.1 equiv.). The mixture was stirred at 20° C. for 24 hr under N$_2$ atmosphere. Next, the reaction mixture was concentrated under reduced pressure to remove solvent water. The resulting crude material was reconstituted in acetone (200 mL) followed by the addition of TBAB (0.05 equiv.) and BnBr (1.2-1.5 equiv.). The mixture was heated to 60° C. and stirred for 12 h under N$_2$ atmosphere. Upon completion, the mixture was concentrated under reduced pressure, and the resulting residue was poured into sat. NaHCO$_3$ solution. The product was extracted 3× with EtOAc, and the combined organic layers were washed with brine, dried over Na$_2$SO$_4$, filtered, and concentrated in vacuo. The crude residue was purified by column chromatography (EtOAc/hexanes) to afford product as a colorless oil (20 g, 39%). $^1$H NMR (400 MHz, CDCl$_3$) δ 7.45-7.29 (m, 5H), 5.12 (s, 2H), 3.65-3.57 (m, 1H), 2.51 (td, J=7.2, 2.7 Hz, 2H), 1.86 (dtd, J=14.6, 7.4, 3.5 Hz, 1H), 1.71 (ddd, J=14.2, 8.6, 7.1 Hz, 1H), 1.61 (d, J=5.0 Hz, 1H), 1.52-1.17 (m, 17H), 0.88 (t, J=6.7 Hz, 3H).

Intermediate 54b: benzyl 4-(((4-nitrophenoxy)carbonyl)oxy)dodecanoate

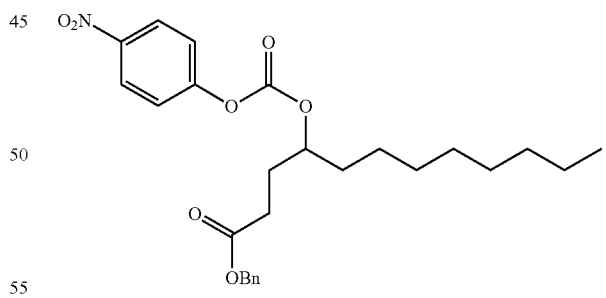

To a solution of Intermediate 54a (10 g, 1.0 equiv.) in DCM (80-100 mL) was added (4-nitrophenyl) carbonochloridate (1.5 equiv.). The reaction was degassed and purged 3× with N$_2$ and cooled to 0° C. before the addition of pyridine (2.0 equiv.). The reaction mixture was stirred at 20° C. for 5 h under N$_2$ atmosphere. Upon completion, the mixture was concentrated under reduced pressure and the resulting residue was reconstituted in hexanes and filtered. The resulting filtrate was washed 3× with water, and the organic layer was washed with brine, dried over Na$_2$SO$_4$, filtered, and concentrated in vacuo. The crude residue was purified by column chromatography (EtOAc/hexanes) to afford product as a colorless oil (9 g, 29%). ¹H NMR (400 MHz, CDCl₃) δ 8.27 (dd, J=9.8, 7.8 Hz, 2H), 7.50-7.30 (m, 8H), 5.12 (d, J=8.3 Hz, 2H), 4.87 (ddt, J=12.2, 7.3, 4.1 Hz, 1H), 2.50 (t, J=7.5 Hz, 2H), 2.16-2.06 (m, 1H), 1.99 (dq, J=14.8, 7.5 Hz, 1H), 1.73 (ddd, J=14.0, 12.0, 7.0 Hz, 1H), 1.63 (tt, J=8.6, 4.5 Hz, 1H), 1.45-1.19 (m, 12H), 0.94-0.84 (m, 3H).

Intermediate 54c: benzyl 4-(((2-(ethyl(methyl)amino)ethyl)carbamoyl)oxy)dodecanoate

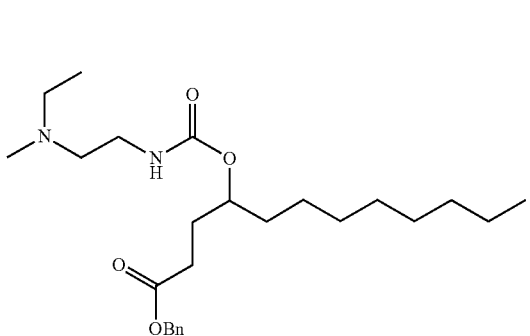 [SMILES: CCCCCCCCC(CCC(=O)O)OC(=O)NCCN(C)CC]

To a solution of Intermediate 54b (9 g, 1.0 equiv.) in MeCN (45-90 mL) was added N'-ethyl-N'-methyl-ethane-1,2-diamine (1.5-2.5 equiv.), pyridine (3-4 equiv.), and DMAP (2.33 g, 1.0 equiv.), and the resulting mixture was degassed and purged 3× with N₂. The reaction heated to 70° C. and stirred for 2 h under N₂ atmosphere. Upon completion, the mixture was concentrated to remove solvent, and the resulting residue was diluted with EtOAc, washed 3× with sat. NaHCO₃, and 3× with water. The organic layer was then dried over Na₂SO₄, filtered, and concentrated in vacuo. The crude residue was purified by column chromatography (EtOAc/hexanes) to afford product as a pale yellow oil (5 g, 60%). ¹H NMR (400 MHz, CDCl₃) δ 7.38-7.22 (m, 5H), 5.04 (s, 2H), 4.69 (s, 1H), 3.16 (q, J=6.0 Hz, 2H), 2.45-2.27 (m, 6H), 2.13 (s, 3H), 1.95-1.71 (m, 2H), 1.40 (d, J=7.3 Hz, 2H), 1.34-1.09 (m, 13H), 0.96 (t, J=7.1 Hz, 3H), 0.80 (t, J=6.7 Hz, 3H).

Intermediate 54d: 4-(((2-(ethyl(methyl)amino)ethyl)carbamoyl)oxy)dodecanoic acid

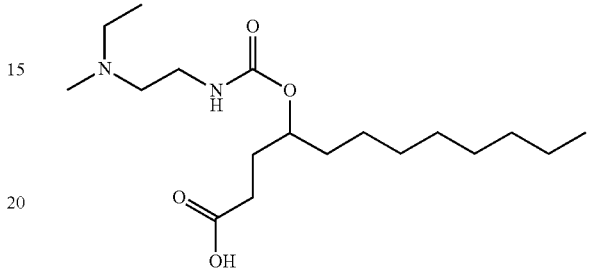

To a solution of Intermediate 54c (6 g, 1.0 equiv) in MeOH (60 mL) was added Pd/C (1.8 g, 10% w/w). The mixture was stirred at 20° C. for 5 h under H2. The reaction mixture was then filtered, and the filtrate was concentrated under reduced pressure to give a residue. The residue was purified by column chromatography to afford product as a brown oil (3.2 g, 67%). ¹H NMR (400 MHz, CD₃OD) δ 4.76 (dp, J=8.1, 4.1 Hz, 1H), 3.65 (dt, J=14.0, 7.0 Hz, 1H), 3.28-3.10 (m, 4H), 3.07 (ddd, J=11.3, 7.5, 2.1 Hz, 1H), 2.79 (s, 3H), 2.27 (ddd, J=14.0, 8.2, 4.4 Hz, 1H), 2.20-1.99 (m, 2H), 1.86-1.74 (m, 1H), 1.71-1.56 (m, 1H), 1.48 (dq, J=13.7, 7.6, 6.8 Hz, 1H), 1.31 (dd, J=14.1, 7.0 Hz, 14H), 0.94-0.83 (m, 3H).

Compound 54: 2-(12-methyl-6-octyl-3,8-dioxo-2,7-dioxa-9,12-diazatetradecyl)propane-1,3-diyl (9Z,9'Z,12Z,12'Z)-bis(octadeca-9,12-dienoate)

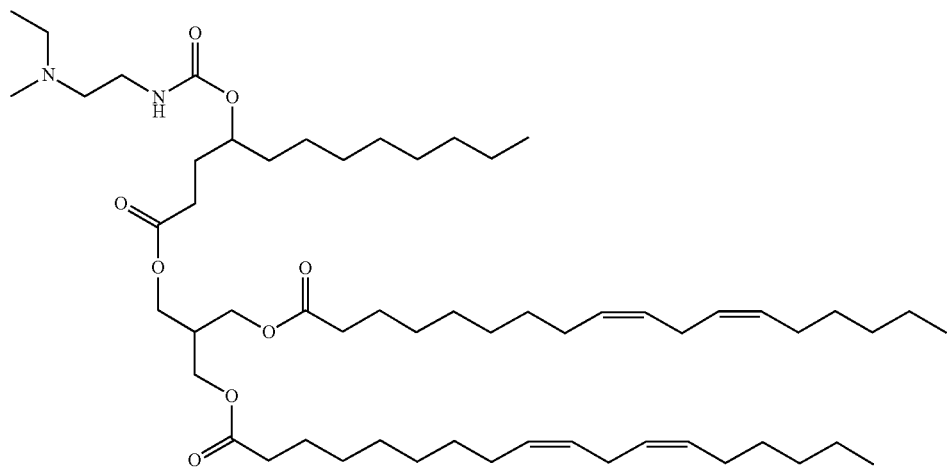 [SMILES: CCCCC/C=C\C/C=C\CCCCCCCC(=O)OCC(COC(=O)CCCCCCC/C=C\C/C=C\CCCCC)COC(=O)CCC(CCCCCCCC)OC(=O)NCCN(C)CC]

Compound 54 was synthesized in 47% yield from Intermediate 54d and Intermediate 53a using the method employed for Compound 52. $^1$H NMR (400 MHz, CDCl$_3$) δ 5.44-5.26 (m, 8H), 4.75 (s, 1H), 4.12 (d, J=6.0 Hz, 6H), 2.77 (t, J=6.5 Hz, 4H), 2.55-2.34 (m, 6H), 2.34-2.19 (m, 6H), 2.05 (q, J=6.8 Hz, 8H), 1.97-1.70 (m, 4H), 1.61 (t, J=7.2 Hz, 10H), 1.41-1.00 (m, 43H), 0.94-0.82 (m, 9H). MS: 959.1 m/z [M+H].

Example 55—Compound 55

Intermediate 55a: benzyl 5-hydroxytridecanoate

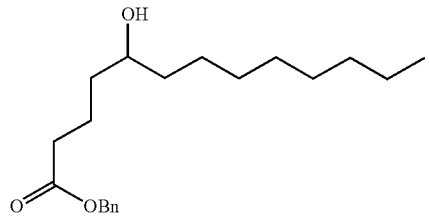 [SMILES: CCCCCCCCC(O)CCCC(=O)OCc1ccccc1]

Intermediate 55a was prepared in 25% yield from 6-octyltetrahydropyran-2-one using the method employed for Intermediate 54a. $^1$H NMR (400 MHz, CDCl$_3$) δ 7.34 (qt, J=9.5, 4.5 Hz, 5H), 5.11 (s, 2H), 3.57 (s, 1H), 2.39 (t, J=7.3 Hz, 2H), 1.85-1.65 (m, 2H), 1.60-1.11 (m, 18H), 0.98-0.80 (m, 3H).

Intermediate 55b: benzyl 5-(((4-nitrophenoxy)carbonyl)oxy)tridecanoate

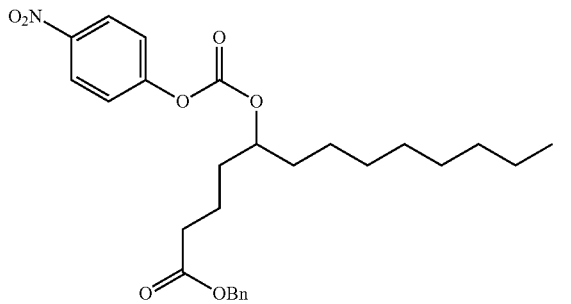 [SMILES: CCCCCCCCC(CCCC(=O)OCc1ccccc1)OC(=O)Oc1ccc([N+](=O)[O-])cc1]

Intermediate 55b was prepared in 37% yield from Intermediate 55a using the method employed for Intermediate 54b. $^1$H NMR (400 MHz, CDCl$_3$) δ 8.32-8.24 (m, 3H), 7.39 (dddd, J=20.3, 9.9, 5.7, 1.9 Hz, 8H), 5.12 (s, 2H), 4.87-4.75 (m, 1H), 2.41 (t, J=6.8 Hz, 2H), 1.69 (dddt, J=33.5, 23.3, 14.2, 6.0 Hz, 6H), 1.51-1.01 (m, 13H), 0.87 (t, J=6.6 Hz, 3H).

Intermediate 55c: benzyl 5-(((2-(ethyl(methyl)amino)ethyl)carbamoyl)oxy)tridecanoate

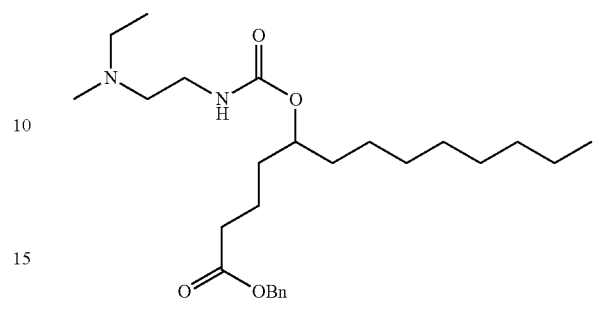

Intermediate 55c was prepared in 53% yield from Intermediate 55b using the method employed for Intermediate 54c. $^1$H NMR (400 MHz, CDCl$_3$) δ 7.41-7.18 (m, 5H), 5.04 (s, 2H), 4.65 (p, J=6.5 Hz, 1H), 3.19 (q, J=6.4, 5.9 Hz, 2H), 2.49-2.23 (m, 6H), 2.16 (d, J=29.0 Hz, 3H), 1.69-1.54 (m, J=6.7 Hz, 2H), 1.44 (tt, J=13.6, 7.1 Hz, 4H), 1.37-1.05 (m, 14H), 0.98 (t, J=7.1 Hz, 3H), 0.80 (t, J=6.6 Hz, 3H).

Intermediate 55d: 5-(((2-(ethyl(methyl)amino)ethyl)carbamoyl)oxy)tridecanoic acid

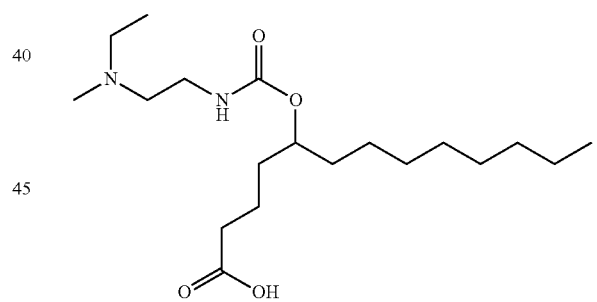

To a solution of Intermediate 55c (2.2 g, 1.0 equiv) in THF (20 mL) was added Pd/C (2.5 g, 10% w/w). The mixture was stirred at 20° C. for 5 h under H2. The reaction mixture was then filtered, and the filtrate was concentrated under reduced pressure to give a residue. The residue was purified by column chromatography to afford product as a brown oil (1 g, 58%). $^1$H NMR (400 MHz, CDCl$_3$) δ 12.81 (s, 1H), 5.93-5.72 (m, 1H), 4.61 (q, J=7.1 Hz, 1H), 3.68-3.47 (m, 1H), 3.29-3.04 (m, 1H), 2.76 (tt, J=17.2, 9.1 Hz, 3H), 2.40 (s, 3H), 2.34-2.06 (m, 2H), 1.85-0.87 (m, 22H), 0.80 (t, J=6.4 Hz, 3H).

Compound 55: 2-(13-methyl-7-octyl-3,9-dioxo-2,8-dioxa-10,13-diazapentadecyl)propane-1,3-diyl (9Z,9'Z,12Z,12'Z)-bis(octadeca-9,12-dienoate)

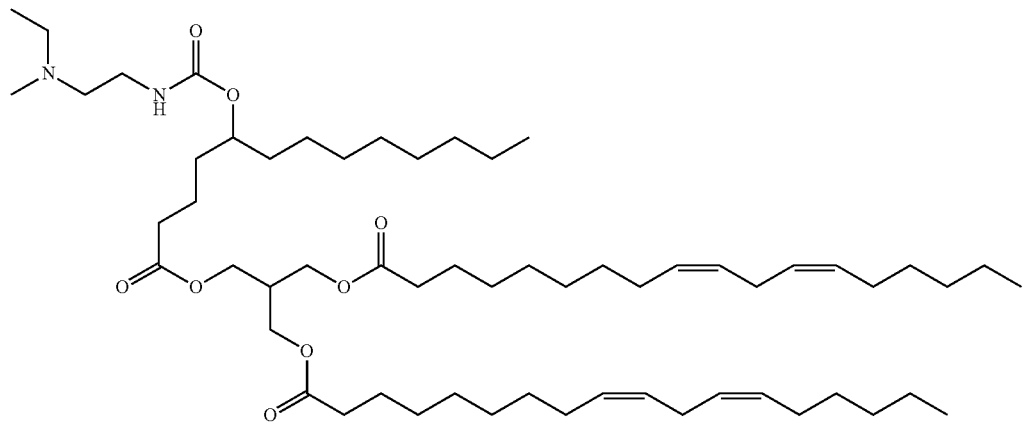 [SMILES: CCCCC/C=C\C/C=C\CCCCCCCC(=O)OCC(COC(=O)CCCCCCC/C=C\C/C=C\CCCCC)COC(=O)CCCC(CCCCCCCC)OC(=O)NCCN(C)CC]

Compound 55 was prepared in 58% yield from Intermediate 53a and Intermediate 55d using the method employed for Compound 52. $^1$H NMR (400 MHz, CDCl$_3$) δ 5.44-5.27 (m, 8H), 4.73 (s, 1H), 4.12 (d, J=6.0 Hz, 6H), 3.32 (s, 2H), 2.81-2.73 (m, 4H), 2.49 (d, J=45.9 Hz, 4H), 2.43-2.22 (m, 10H), 2.05 (q, J=6.8 Hz, 8H), 1.75-1.42 (m, 13H), 1.42-1.21 (m, 40H), 1.11 (s, 3H), 0.95-0.82 (m, 9H). MS: 972.8 m/z [M+H].

Example 56—Compound 56

Intermediate 56a: 9-(decyloxy)-9-oxononanoic acid

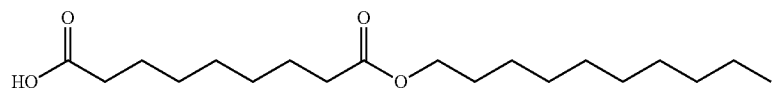 [SMILES: CCCCCCCCCCOC(=O)CCCCCCCC(=O)O]

To a mixture of nonanedioic acid (90 g, 1.0 equiv.) in THF (300-900 mL) at 0° C. was added DMF (0.1-0.2 equiv.) and (COCl)$_2$ (1.0 equiv.) dropwise. The mixture was degassed and purged 3× with N$_2$, and then the mixture was stirred at 20° C. for 2 h under N$_2$ atmosphere. Decan-1-ol (1.0 equiv.) was added to the reaction mixture dropwise at 0° C. and stirred at 20° C. for 2 h under N$_2$ atmosphere. The reaction mixture was concentrated under reduced pressure to remove solvent, and the resulting solution was poured into water and extracted 3× with EtOAc. The combined organic layers were washed with brine, then dried over Na$_2$SO$_4$, filtered, and concentrated in vacuo. The crude residue was purified by column chromatography (EtOAc/hexanes) to afford product as a white solid (20 g, 6%). $^1$H NMR (400 MHz, CDCl$_3$) δ 4.05 (t, J=6.7 Hz, 2H), 2.34 (t, J=7.5 Hz, 2H), 2.29 (t, J=7.5 Hz, 2H), 1.62 (q, J=7.3 Hz, 6H), 1.41-1.15 (m, 19H), 0.88 (t, J=6.7 Hz, 3H).

Intermediate 56b: 9,9'-didecyl O'1,O1-(2-oxopropane-1,3-diyl) di(nonanedioate)

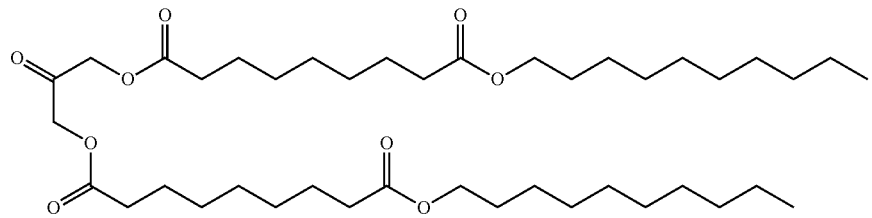 [SMILES: CCCCCCCCCCOC(=O)CCCCCCCC(=O)OCC(=O)COC(=O)CCCCCCCC(=O)OCCCCCCCCCC]

To a mixture of 1,3-dihydroxypropan-2-one (1.37 g, 0.5 equiv.), EDCI (1.0 equiv.) and DMAP (1.0 equiv.) in DCM (100-200 mL) was added Intermediate 56a (1.0 equiv.) portionwise at 0° C., and the mixture was degassed and purged 3× with $N_2$. The mixture was stirred at 20° C. for 5 r under $N_2$ atmosphere. The reaction mixture was concentrated under reduced pressure to remove solvent, and the resulting solution was poured into water and extracted 3× with EtOAc. The combined organic layers were washed with brine, then dried over $Na_2SO_4$, filtered, and concentrated in vacuo. The crude residue was purified by column chromatography (EtOAc/hexanes) to afford product as a white solid (10 g, 46%). $^1$H NMR (400 MHz, $CDCl_3$) δ 4.74 (d, J=2.1 Hz, 4H), 4.05 (t, J=6.8 Hz, 4H), 2.41 (t, J=7.5 Hz, 4H), 2.28 (t, J=7.5 Hz, 4H), 1.62 (d, J=8.8 Hz, 12H), 1.39-1.19 (m, 39H), 0.87 (t, J=6.7 Hz, 6H).

Intermediate 56c: 9,9'-didecyl O'1,O1-(2-hydroxypropane-1,3-diyl) di(nonanedioate)

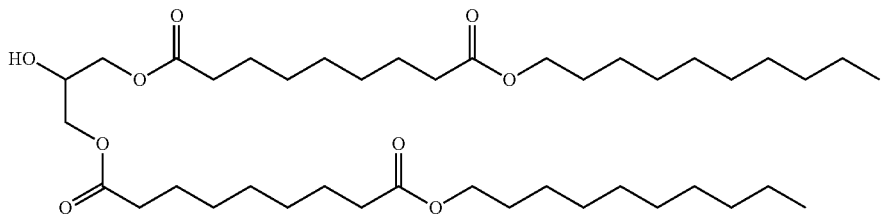 [SMILES: CCCCCCCCCCOC(=O)CCCCCCCC(=O)OCC(O)COC(=O)CCCCCCCC(=O)OCCCCCCCCCC]

To a solution of Intermediate 56b (13.4 g, 1.0 equiv.) in THF/toluene/water (4:1:2, 0.4 M) at 0° C. under $N_2$ was added $NaBH_4$ (1.5 equiv.). The mixture was stirred at 15-20° C. for 5 h under $N_2$. Upon completion, the reaction mixture was diluted with water and extracted 3× with EtOAc. The combined organic layers were washed with brine, then dried over $Na_2SO_4$, filtered, and concentrated in vacuo. The crude residue was purified by column chromatography (EtOAc/hexanes) to afford product as a white solid (5.1 g, 38%). $^1$H NMR (400 MHz, $CDCl_3$) δ 4.15-4.03 (m, 5H), 3.98 (t, J=6.8 Hz, 4H), 2.44 (d, J=4.8 Hz, 1H), 2.25 (dt, J=24.2, 7.5 Hz, 8H), 1.55 (q, J=7.1 Hz, 12H), 1.22 (d, J=22.7 Hz, 38H), 0.81 (t, J=6.7 Hz, 6H).

Compound 56: 9,9'-didecyl O'1,O1-(2-((3-(((2-(ethyl(methyl)amino)ethyl)carbamoyl)oxy)undecanoyl)oxy)propane-1,3-diyl) di(nonanedioate)

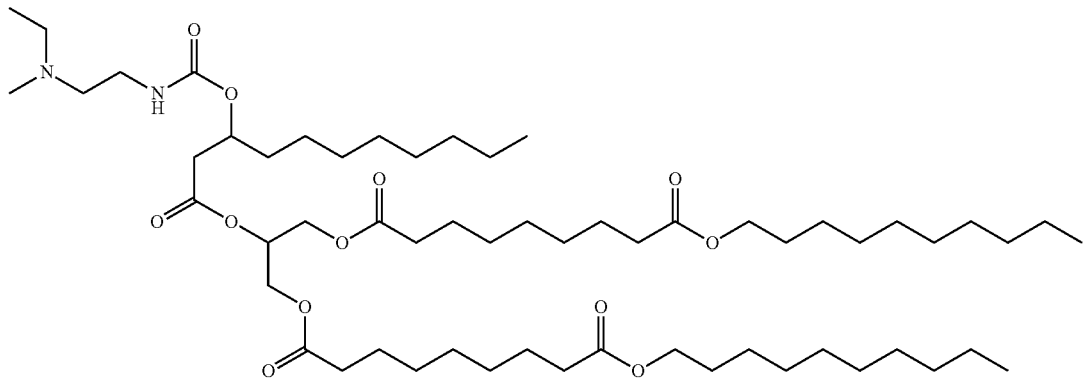 [SMILES: CCCCCCCCCCOC(=O)CCCCCCCC(=O)OCC(COC(=O)CCCCCCCC(=O)OCCCCCCCCCC)OC(=O)CC(CCCCCCCC)OC(=O)NCCN(C)CC]

Compound 56 was prepared in 36% yield from Intermediate 52d and Intermediate 56c using the method employed for Compound 52. $^1$H NMR (400 MHz, CDCl$_3$) δ 5.24 (t, J=5.2 Hz, 1H), 5.13-5.04 (m, 1H), 4.28 (ddd, J=14.5, 11.9, 4.5 Hz, 2H), 4.14 (ddd, J=11.9, 8.3, 5.8 Hz, 2H), 4.05 (t, J=6.8 Hz, 4H), 3.31 (s, 2H), 2.58 (qd, J=15.3, 6.4 Hz, 6H), 2.30 (dt, J=10.3, 7.6 Hz, 10H), 1.61 (dd, J=10.1, 4.1 Hz, 16H), 1.29 (dt, J=17.6, 3.3 Hz, 54H), 0.88 (td, J=6.9, 1.9 Hz, 9H). MS: 1027.2 m/z [M+H].

Example 57—Compound 57

Compound 57: 9,9'-didecyl O'1,O1-(2-((4-(((2-(ethyl(methyl)amino)ethyl)carbamoyl)oxy)dodecanoyl)oxy)propane-1,3-diyl) di(nonanedioate)

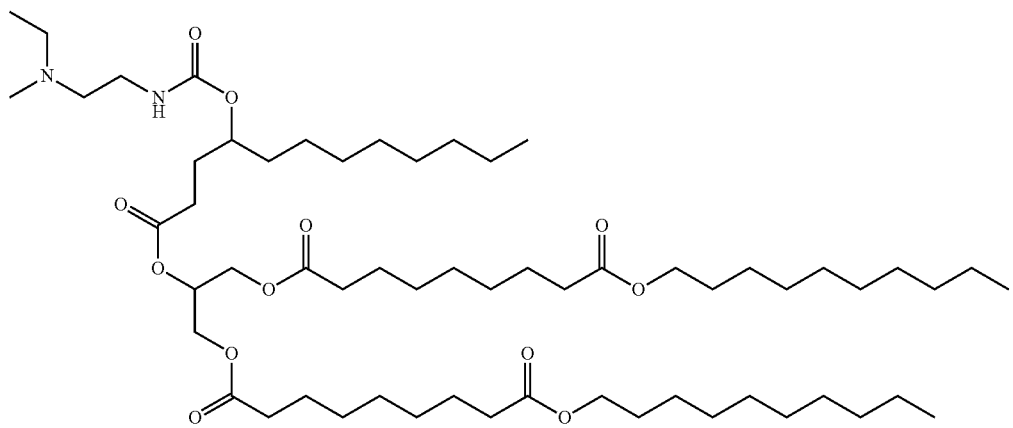 [SMILES: CCCCCCCCCCOC(=O)CCCCCCCC(=O)OCC(COC(=O)CCCCCCCC(=O)OCCCCCCCCCC)OC(=O)CCC(CCCCCCCC)OC(=O)NCCN(C)CC]

Compound 57 was prepared in 55% yield from Intermediate 54d and Intermediate 56c using the method employed for Compound 52. $^1$H NMR (400 MHz, CDCl$_3$) δ 5.28-5.21 (m, 1H), 4.76 (s, 1H), 4.28 (ddd, J=11.8, 4.4, 1.2 Hz, 2H), 4.15 (ddd, J=11.9, 5.9, 4.6 Hz, 2H), 4.05 (t, J=6.8 Hz, 4H), 3.29 (s, 2H), 2.38 (ddd, J=8.6, 6.9, 2.7 Hz, 5H), 2.35-2.12 (m, 10H), 1.98-1.73 (m, 3H), 1.68-1.37 (m, 17H), 1.29 (dt, J=19.5, 4.1 Hz, 54H), 0.88 (td, J=6.9, 1.9 Hz, 9H). MS: 1040.8 m/z [M+H].

Example 58—Compound 58

Compound 58: 9,9'-didecyl O'1,O1-(2-((5-(((2-(ethyl(methyl)amino)ethyl)carbamoyl)oxy)tridecanoyl)oxy)propane-1,3-diyl) di(nonanedioate))

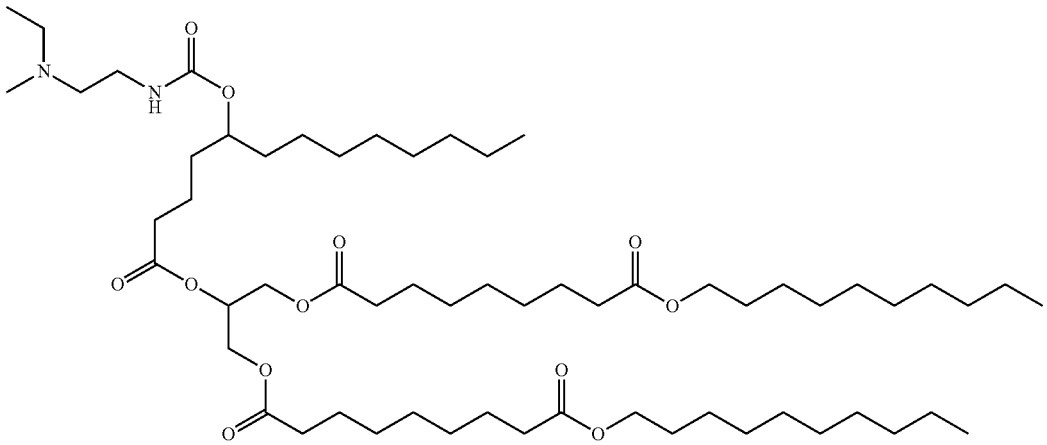 [SMILES: CCCCCCCCCCOC(=O)CCCCCCCC(=O)OCC(COC(=O)CCCCCCCC(=O)OCCCCCCCCCC)OC(=O)CCCC(CCCCCCCC)OC(=O)NCCN(C)CC]

Compound 58 was prepared in 60% yield from Intermediate 55d and Intermediate 56c using the method employed for Compound 52. $^1$H NMR (400 MHz, CDCl$_3$) δ 5.27-5.20 (m, 1H), 4.73 (s, 1H), 4.28 (ddd, J=11.9, 4.4, 2.8 Hz, 2H), 4.13 (ddd, J=11.9, 5.9, 2.6 Hz, 2H), 4.05 (t, J=6.7 Hz, 4H), 3.31 (s, 2H), 2.39-2.09 (m, 12H), 1.62 (dq, J=13.8, 7.2, 6.5 Hz, 22H), 1.41-0.99 (m, 54H), 0.88 (td, J=6.9, 2.0 Hz, 9H). MS: 1055.0 m/z [M+H].

Example 59—Compound 59

Intermediate 59a: 9-oxo-9-(undecyloxy)nonanoic acid

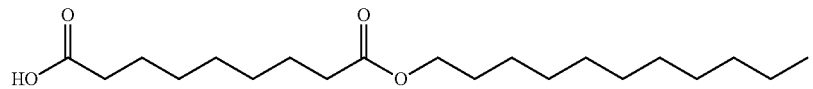 [SMILES: CCCCCCCCCCCOC(=O)CCCCCCCC(=O)O]

Intermediate 59a was prepared in 41% yield from nonanedioic acid and undecan-1-ol using the method employed for Intermediate 56a. $^1$H NMR (400 MHz, CDCl$_3$) δ 4.05 (t, J=6.7 Hz, 2H), 2.31 (dt, J=22.6, 7.5 Hz, 4H), 1.62 (q, J=7.1 Hz, 6H), 1.40-1.18 (m, 23H), 0.87 (t, J=6.7 Hz, 3H).

Intermediate 59b: O'1,O1-(2-oxopropane-1,3-diyl) 9,9'-diundecyl di(nonanedioate)

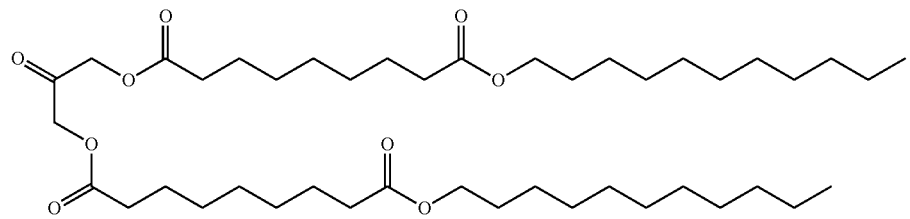 [SMILES: CCCCCCCCCCCOC(=O)CCCCCCCC(=O)OCC(=O)COC(=O)CCCCCCCC(=O)OCCCCCCCCCCC]

Intermediate 59b was prepared in 23% yield from 1,3-dihydroxypropan-2-one and Intermediate 59a using the method employed for Intermediate 56b. $^1$H NMR (400 MHz, CDCl$_3$) δ 3.98 (t, J=6.7 Hz, 2H), 2.35 (t, J=7.5 Hz, 2H), 2.22 (t, J=7.5 Hz, 2H), 1.57 (dt, J=18.6, 6.9 Hz, 6H), 1.36-1.12 (m, 23H), 0.89-0.76 (m, 3H).

Intermediate 59c: O'1,O1-(2-hydroxypropane-1,3-diyl) 9,9'-diundecyl di(nonanedioate)

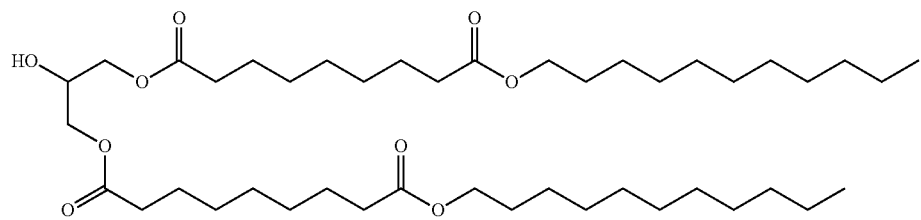 [SMILES: CCCCCCCCCCCOC(=O)CCCCCCCC(=O)OCC(O)COC(=O)CCCCCCCC(=O)OCCCCCCCCCCC]

Intermediate 59c was prepared in 47% yield from Intermediate 59b using the method employed for Intermediate 56c. $^1$H NMR (400 MHz, CDCl$_3$) δ 4.23-4.00 (m, 9H), 2.52 (d, J=4.7 Hz, 1H), 2.31 (dt, J=24.2, 7.5 Hz, 8H), 1.62 (q, J=7.0 Hz, 13H), 1.29 (d, J=23.9 Hz, 43H), 0.88 (t, J=6.7 Hz, 6H).

Compound 59: O'1,O1-(2-((3-(((2-(ethyl(methyl)amino)ethyl)carbamoyl)oxy)undecanoyl)oxy)propane-1,3-diyl) 9,9'-diundecyl di(nonanedioate)

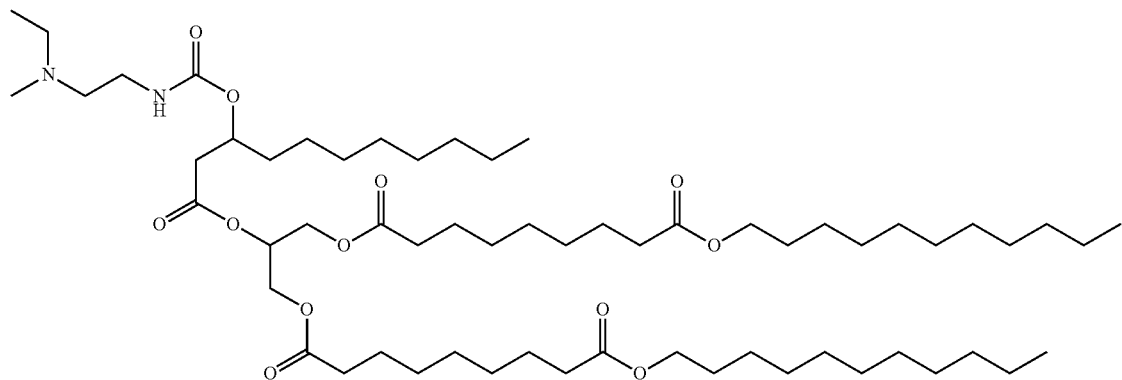 [SMILES: CCCCCCCCCCCOC(=O)CCCCCCCC(=O)OCC(COC(=O)CCCCCCCC(=O)OCCCCCCCCCCC)OC(=O)CC(CCCCCCCC)OC(=O)NCCN(C)CC]

Compound 59 was prepared in 35% yield from Intermediate 52d and Intermediate 59c using the method employed for Compound 52. $^1$H NMR (400 MHz, CDCl$_3$) δ 5.23 (s, 1H), 5.08 (d, J=6.5 Hz, 1H), 4.28 (ddd, J=15.0, 11.9, 4.5 Hz, 2H), 4.14 (dt, J=13.1, 6.7 Hz, 2H), 4.05 (t, J=6.8 Hz, 4H), 2.58 (qd, J=15.4, 6.6 Hz, 4H), 2.30 (dt, J=10.4, 7.5 Hz, 10H), 1.60 (q, J=7.7, 6.9 Hz, 20H), 1.43-0.97 (m, 58H), 0.88 (td, J=6.9, 1.9 Hz, 9H). MS: 1054.9 m/z [M+H].

Example 60—Compound 60

Compound 60: O'1,O1-(2-((4-(((2-(ethyl(methyl)amino)ethyl)carbamoyl)oxy)dodecanoyl)oxy)propane-1,3-diyl) 9,9'-diundecyl di(nonanedioate)

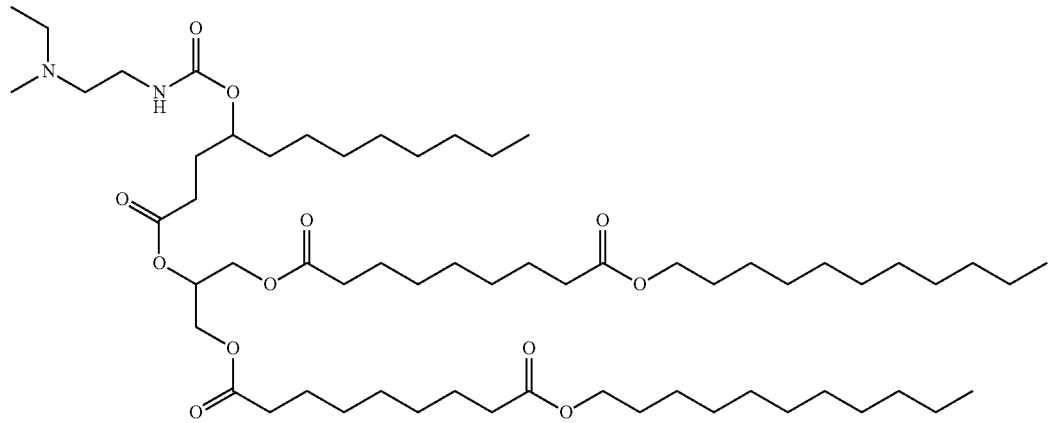 [SMILES: CCCCCCCCCCCOC(=O)CCCCCCCC(=O)OCC(COC(=O)CCCCCCCC(=O)OCCCCCCCCCCC)OC(=O)CCC(CCCCCCCC)OC(=O)NCCN(C)CC]

Compound 60 was prepared in 79% yield from Intermediate 54d and Intermediate 59c using the method employed for Compound 52. $^1$H NMR (400 MHz, CDCl$_3$) δ 5.25 (p, J=5.1 Hz, 1H), 4.76 (s, 1H), 4.28 (ddd, J=11.9, 4.5, 2.7 Hz, 2H), 4.15 (dt, J=11.7, 5.6 Hz, 2H), 4.05 (t, J=6.8 Hz, 4H), 2.38 (t, J=7.5 Hz, 5H), 2.35-2.11 (m, 10H), 1.98-1.41 (m, 23H), 1.41-0.96 (m, 57H), 0.88 (td, J=6.9, 1.8 Hz, 9H). MS: 1068.9 m/z [M+H].

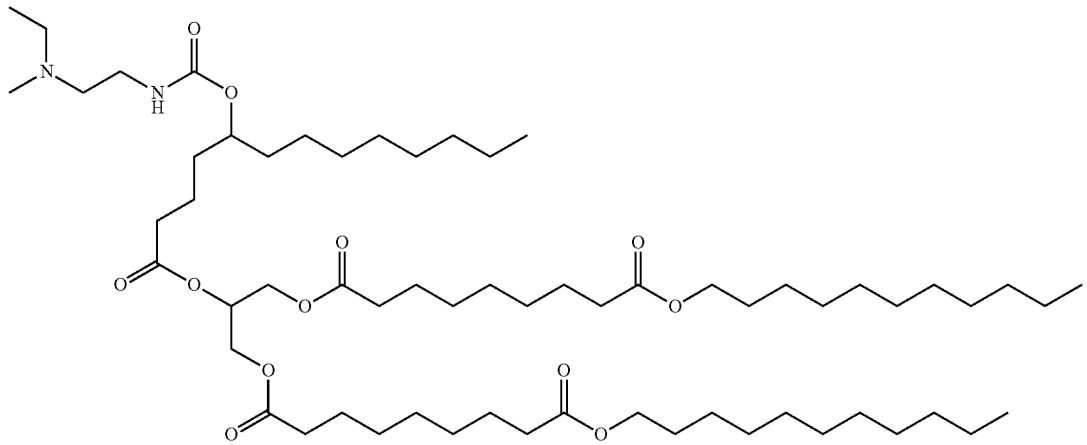 [SMILES: CCCCCCCCCCCOC(=O)CCCCCCCC(=O)OCC(COC(=O)CCCCCCCC(=O)OCCCCCCCCCCC)OC(=O)CCCC(CCCCCCCC)OC(=O)NCCN(C)CC]

Example 61—Compound 61

Compound 61: O'1,O1-(2-((5-(((2-(ethyl(methyl)amino)ethyl)carbamoyl)oxy)tridecanoyl)oxy)propane-1,3-diyl) 9,9'-diundecyl di(nonanedioate)

Compound 61 was prepared in 61% yield from Intermediate 55d and Intermediate 59c using the method employed for Compound 52. $^1$H NMR (400 MHz, CDCl$_3$) δ 5.29-5.20 (m, 1H), 4.72 (d, J=7.4 Hz, 1H), 4.28 (ddd, J=11.9, 4.4, 2.3 Hz, 2H), 4.14 (ddd, J=11.9, 5.9, 2.0 Hz, 2H), 4.05 (t, J=6.8 Hz, 4H), 2.82-2.13 (m, 15H), 1.82-1.39 (m, 21H), 1.39-0.97 (m, 56H), 0.88 (td, J=6.9, 1.9 Hz, 9H). MS: 1083.0 m/z [M+H].

Example 62—Compound 62

Intermediate 62a: 1-((tert-butyldimethylsilyl)oxy)-3-hydroxypropan-2-one

To a mixture of 1,3-dihydroxypropan-2-one (50 g, 1.0 equiv.), imidazole (37.79 g, 1.0 equiv.) in THF (40 mL) at 0° C. was added TBSCl (83.66 g, 1.0 equiv.), and the mixture was stirred at 20° C. for 2 h under N$_2$ atmosphere. Upon completion, the reaction mixture was concentrated under reduced pressure to give a residue, which was purified by column chromatography (EtOAc/hex) to afford product as a colorless oil (15 g, 13%).

Intermediate 62b: 1-(3-((tert-butyldimethylsilyl)oxy)-2-oxopropyl) 9-undecyl nonanedioate

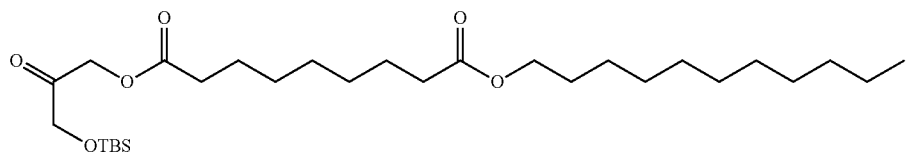 [SMILES: CCCCCCCCCCCOC(=O)CCCCCCCC(=O)OCC(=O)CO[Si](C)(C)C(C)(C)C]

To a mixture of Intermediate 62a (10 g, 1.0 equiv.), EDCI (9.38 g, 1.0 equiv.), and DMAP (5.98 g, 1.0 equiv.) in DCM (300 mL) at 0° C. was added Intermediate 59a (16.76 g, 1.0 equiv.), and the mixture was stirred at 20° C. for 12 h under $N_2$ atmosphere. Upon completion, the reaction mixture was concentrated under reduced pressure to remove DCM and the resulting residue was diluted with water. The crude material was extracted 3× with EtOAc, and the combined organic layers were dried over $Na_2SO_4$, filtered, and concentrated in vacuo. The crude residue was purified by column chromatography (EtOAc/hexanes) to afford product as a colorless oil (11 g, 43%). $^1$H NMR (400 MHz, $CDCl_3$) δ 4.84 (s, 2H), 4.16 (s, 2H), 3.95 (t, J=6.8 Hz, 2H), 2.32 (t, J=7.5 Hz, 2H), 2.18 (t, J=7.5 Hz, 2H), 1.61-1.48 (m, 6H), 1.30-1.12 (m, 22H), 0.82 (s, 9H), 0.78 (t, J=6.8 Hz, 3H).

Intermediate 62c: 1-(3-hydroxy-2-oxopropyl) 9-undecyl nonanedioate

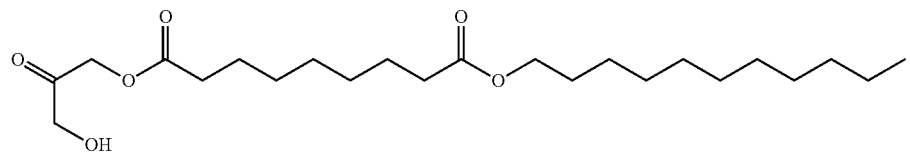 [SMILES: CCCCCCCCCCCOC(=O)CCCCCCCC(=O)OCC(=O)CO]

To a mixture of Intermediate 62b (11 g, 1.0 equiv.) in THF (50 mL) was added HF pyridine (3.75 mL, 8.0 equiv.). The mixture was stirred at 20° C. for 5 h under $N_2$ atmosphere. Upon completion, the reaction mixture was diluted with water and extracted 3× with EtOAc. The combined organic layers were dried over $Na_2SO_4$, filtered, and concentrated in vacuo. The crude residue was purified by column chromatography (EtOAc/hexanes) to afford product as a white solid (6 g, 70%). $^1$H NMR (400 MHz, $CDCl_3$) δ 4.70 (s, 2H), 4.30 (s, 2H), 3.98 (t, J=6.8 Hz, 2H), 2.95 (s, 1H), 2.36 (t, J=7.5 Hz, 2H), 2.22 (t, J=7.6 Hz, 2H), 1.57 (dt, J=20.3, 7.1 Hz, 6H), 1.37-1.10 (m, 22H), 0.81 (t, J=6.7 Hz, 3H).

Intermediate 62d: 1-(3-(((9Z,12Z)-octadeca-9,12-dienoyl)oxy)-2-oxopropyl) 9-undecyl nonanedioate

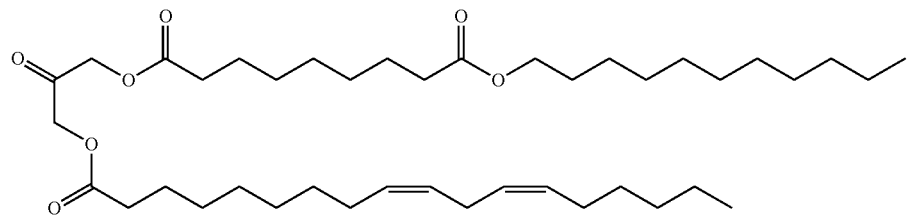 [SMILES: CCCCC/C=C\C/C=C\CCCCCCCC(=O)OCC(=O)COC(=O)CCCCCCCC(=O)OCCCCCCCCCCC]

To a solution of Intermediate 62c (6 g, 1.0 equiv.) in DCM (100 mL) at 0° C. was added EDCI (1.0 equiv.), DMAP (1.0 equiv.). The solution was degassed and purged 3× with $N_2$ followed by the addition of linoleic acid (4 mL, 1.0 equiv.). The mixture was stirred at 20° C. for 12 h under $N_2$ atmosphere. Upon completion, the reaction mixture was concentrated under reduced pressure to remove DCM and the resulting residue was diluted with water. The crude material was extracted 3× with EtOAc, and the combined organic layers were dried over $Na_2SO_4$, filtered, and concentrated in vacuo. The crude residue was purified by column chromatography (EtOAc/hexanes) to afford product as a colorless oil (7.5 g, 55%). $^1$H NMR (400 MHz, $CDCl_3$) δ 4.70 (s, 2H), 4.30 (s, 2H), 3.98 (t, J=6.8 Hz, 2H), 2.95 (s, 1H), 2.36 (t, J=7.5 Hz, 2H), 2.22 (t, J=7.6 Hz, 2H), 1.57 (dt, J=20.3, 7.1 Hz, 6H), 1.37-1.10 (m, 22H), 0.81 (t, J=6.7 Hz, 3H).

Intermediate 62e: 1-(2-hydroxy-3-(((9Z,12Z)-octa-deca-9,12-dienoyl)oxy)propyl) 9-undecyl nonane-dioate

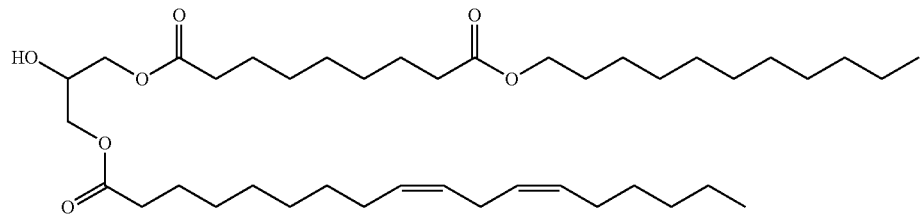 [SMILES: CCCCC/C=C\C/C=C\CCCCCCCC(=O)OCC(O)COC(=O)CCCCCCCC(=O)OCCCCCCCCCCC]

To a solution of Intermediate 62d (7 g, 1.0 equiv.) in THF/toluene/water (4:1:2, 0.04 M) at 0° C. was added NaBH$_4$ (5 equiv.), and the mixture was stirred at 20° C. for 5 h under N$_2$ atmosphere. Upon completion, the mixture was quenched with sat. NH$_4$Cl at 5° C. and extracted 3× with EtOAc. The combined organic layers were washed 2× with brine, dried over Na$_2$SO$_4$, filtered, and concentrated to afford a residue. The crude residue was purified by column chromatography (EtOAc/hex) to afford product as a colorless oil (6 g, 85%). $^1$H NMR (400 MHz, CDCl$_3$) δ 5.42-5.25 (m, 4H), 4.25-3.90 (m, 8H), 2.76 (t, J=6.4 Hz, 2H), 2.55 (s, 1H), 2.30 (dt, J=24.5, 7.6 Hz, 6H), 2.03 (q, J=6.8 Hz, 4H), 1.61 (q, J=7.0 Hz, 8H), 1.48-1.06 (m, 35H), 0.87 (td, J=6.8, 3.8 Hz, 6H).

Compound 62: 1-(3-methyl-13-((((9Z,12Z)-octa-deca-9,12-dienoyl)oxy)methyl)-9-octyl-7,11-dioxo-8,12-dioxa-3,6-diazatetradecan-14-yl) 9-undecyl nonanedioate

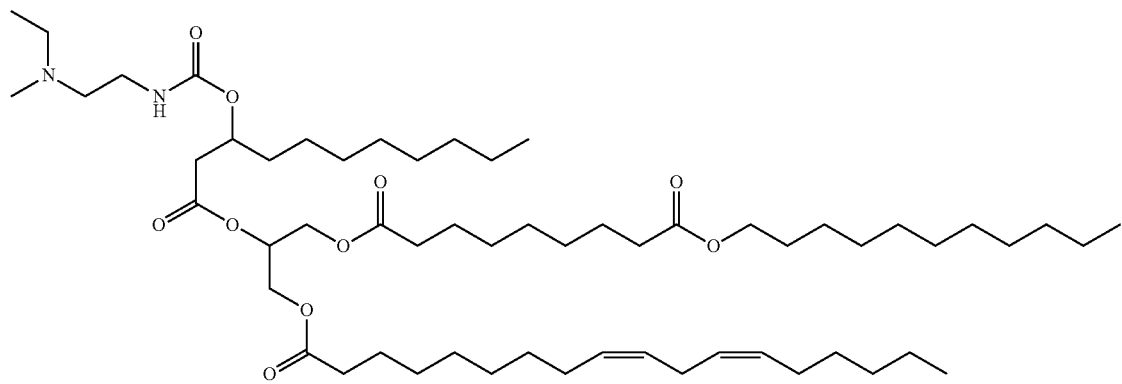 [SMILES: CCCCC/C=C\C/C=C\CCCCCCCC(=O)OCC(COC(=O)CCCCCCCC(=O)OCCCCCCCCCCC)OC(=O)CC(CCCCCCCC)OC(=O)NCCN(C)CC]

Compound 62 was prepared in 36% yield from Intermediate 52d and Intermediate 62e using the method employed for Compound 52. $^1$H NMR (400 MHz, CDCl$_3$) δ 5.47-5.28 (m, 4H), 5.23 (t, J=5.2 Hz, 1H), 5.14-5.04 (m, 1H), 4.28 (ddd, J=15.3, 11.9, 4.6 Hz, 2H), 4.14 (ddd, J=11.8, 7.5, 5.8 Hz, 2H), 4.05 (t, J=6.8 Hz, 2H), 3.38 (s, 2H), 2.77 (t, J=6.5 Hz, 2H), 2.58 (qd, J=15.2, 6.3 Hz, 5H), 2.37-2.22 (m, 7H), 2.05 (q, J=6.7 Hz, 4H), 1.62 (d, J=6.8 Hz, 14H), 1.48-0.97 (m, 50H), 0.97-0.79 (m, 9H). MS: 992.3 m/z [M+H].

Example 63—Compound 63

Compound 63: 1-(3-methyl-14-((((9Z,12Z)-octa-deca-9,12-dienoyl)oxy)methyl)-9-octyl-7,12-dioxo-8,13-dioxa-3,6-diazapentadecan-15-yl) 9-undecyl nonanedioate

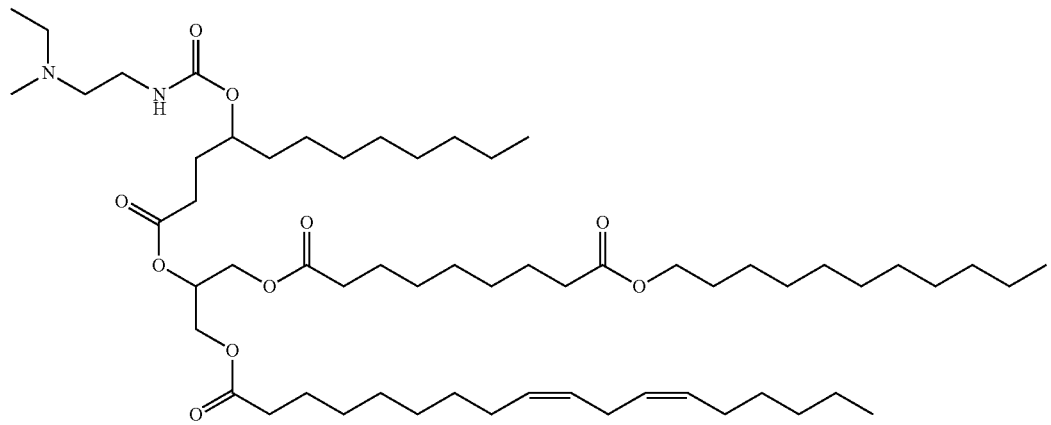 [SMILES: CCCCC/C=C\C/C=C\CCCCCCCC(=O)OCC(COC(=O)CCCCCCCC(=O)OCCCCCCCCCCC)OC(=O)CCC(CCCCCCCC)OC(=O)NCCN(C)CC]

Compound 63 was prepared in 79% yield from Intermediate 54d and Intermediate 62e using the method employed for Compound 52. $^1$H NMR (400 MHz, CDCl$_3$) δ 5.44-5.28 (m, 4H), 5.25 (ddd, J=5.8, 4.5, 1.4 Hz, 1H), 4.76 (s, 1H), 4.28 (dd, J=11.9, 4.4 Hz, 2H), 4.15 (ddd, J=11.9, 5.8, 4.2 Hz, 2H), 4.05 (t, J=6.8 Hz, 2H), 3.31 (s, 2H), 2.77 (t, J=6.7 Hz, 2H), 2.70-2.12 (m, 15H), 2.05 (q, J=6.9 Hz, 4H), 1.97-1.72 (m, 3H), 1.61 (h, J=6.5 Hz, 12H), 1.40-1.19 (m, 47H), 1.11 (s, 3H), 0.96-0.81 (m, 9H). MS: 1006.9 m/z [M+H].

Example 64—Compound 64

Compound 64: 1-(3-methyl-15-((((9Z,12Z)-octa-deca-9,12-dienoyl)oxy)methyl)-9-octyl-7,13-dioxo-8,14-dioxa-3,6-diazahexadecan-16-yl) 9-undecyl nonanedioate

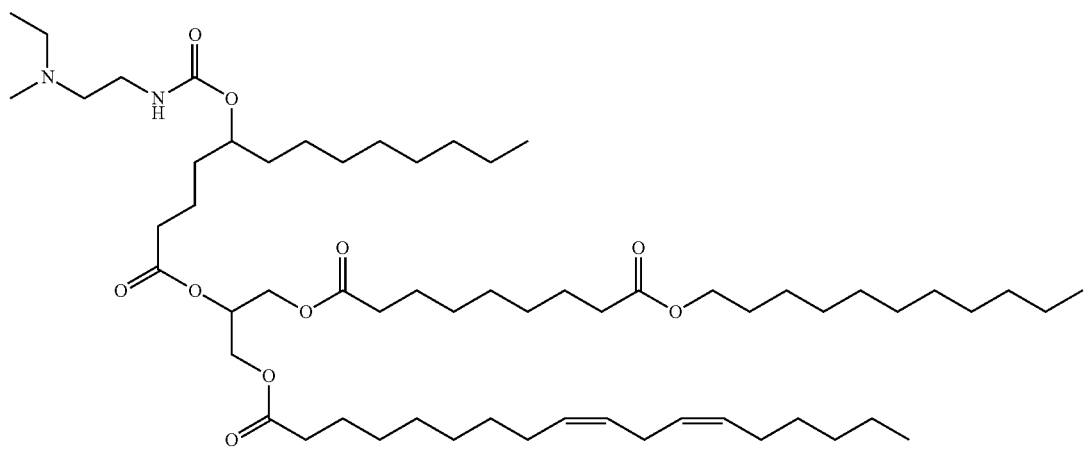 [SMILES: CCCCC/C=C\C/C=C\CCCCCCCC(=O)OCC(COC(=O)CCCCCCCC(=O)OCCCCCCCCCCC)OC(=O)CCCC(CCCCCCCC)OC(=O)NCCN(C)CC]

Compound 64 was prepared in 79% yield from Intermediate 55d and Intermediate 62e using the method employed for Compound 52. $^1$H NMR (400 MHz, CDCl$_3$) δ 5.48-5.28 (m, 4H), 5.24 (h, J=4.9, 4.4 Hz, 1H), 4.73 (s, 1H), 4.29 (ddd, J=11.9, 4.4, 3.3 Hz, 2H), 4.14 (ddd, J=11.9, 5.9, 3.1 Hz, 2H), 4.05 (t, J=6.8 Hz, 2H), 3.31 (s, 2H), 2.77 (t, J=6.5 Hz, 2H), 2.67-2.11 (m, 14H), 2.05 (q, J=6.8 Hz, 4H), 1.73-1.41 (m, 17H), 1.41-0.95 (m, 50H), 0.94-0.82 (m, 9H). MS: 1021.0 m/z [M+H].

Example 65—Compound 65

Compound 65: 2-((4-((((1-methylpyrrolidin-2-yl)methyl)carbamoyl)oxy)tetradecanoyl)oxy)propane-1,3-diyl (9Z,9'Z,12Z,12'Z)-bis(octadeca-9,12-dienoate)

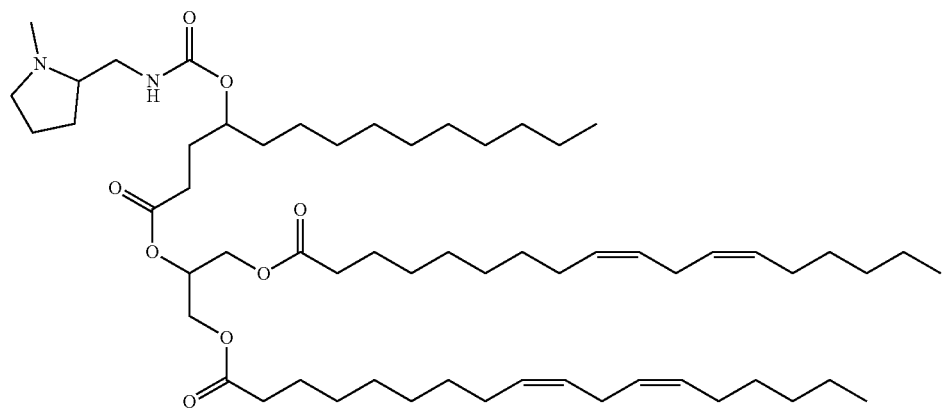 [SMILES: CCCCC/C=C\C/C=C\CCCCCCCC(=O)OCC(COC(=O)CCCCCCC/C=C\C/C=C\CCCCC)OC(=O)CCC(CCCCCCCCCC)OC(=O)NCC1CCCN1C]

Compound 65 was prepared in 75% yield from Intermediate 39d and 1-(1-methylpyrrolidin-2-yl)methanamine using the method employed for Example 1. $^1$H NMR (400 MHz, CDCl$_3$) δ 5.45-5.28 (m, 8H), 5.25 (ddd, J=10.2, 5.7, 4.4 Hz, 1H), 4.76 (s, 1H), 4.28 (dd, J=11.9, 4.4 Hz, 2H), 4.20-4.11 (m, 2H), 3.45 (s, 1H), 3.21 (s, 2H), 2.82-2.74 (m, 4H), 2.46-2.24 (m, 9H), 2.05 (q, J=6.8 Hz, 8H), 2.01-1.42 (m, 16H), 1.41-1.20 (m, 45H), 0.88 (td, J=7.0, 4.7 Hz, 9H). MS: 984.9 m/z [M+H].

Example 66—Compound 66

Compound 66: 2-((4-(((3-(pyrrolidin-1-yl)propoxy)carbonyl)oxy)tetradecanoyl)oxy)propane-1,3-diyl (9Z,9'Z,12Z,12'Z)-bis(octadeca-9,12-dienoate)

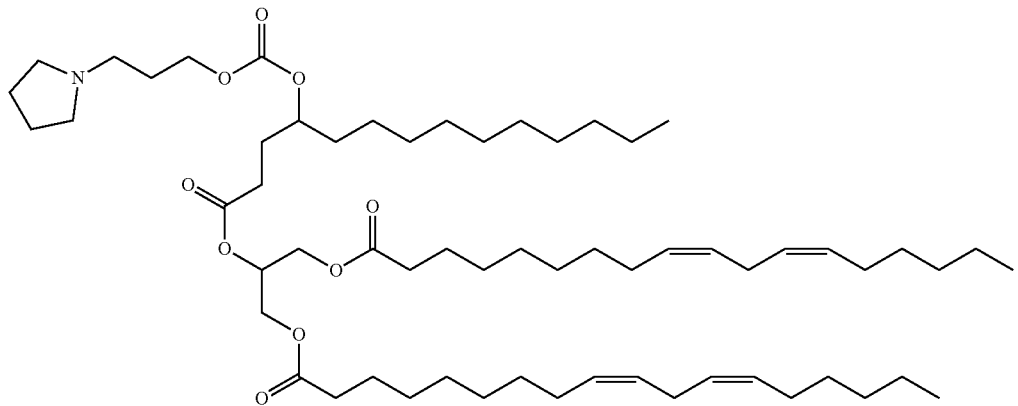 [SMILES: CCCCC/C=C\C/C=C\CCCCCCCC(=O)OCC(COC(=O)CCCCCCC/C=C\C/C=C\CCCCC)OC(=O)CCC(CCCCCCCCCC)OC(=O)OCCCN1CCCC1]

Compound 66 was prepared in 65% yield from Intermediate 39d and 3-(pyrrolidin-1-yl)propan-1-ol using the method employed for Example 1. ¹H NMR (400 MHz, CDCl₃) δ 5.57-5.21 (m, 9H), 4.72 (dt, J=12.2, 5.2 Hz, 1H), 4.29 (dd, J=11.9, 4.4 Hz, 2H), 4.24-4.07 (m, 4H), 2.82-2.74 (m, 4H), 2.60 (d, J=102.7 Hz, 5H), 2.45-2.38 (m, 2H), 2.38-2.26 (m, 4H), 2.13-1.73 (m, 16H), 1.73-1.43 (m, 9H), 1.41-1.16 (m, 42H), 1.04-0.74 (m, 9H). MS: 999.4 m/z [M+H].

Example 67—Compound 67

Compound 67: 2-((4-((((1-methylpyrrolidin-2-yl)methyl)carbamoyl)oxy)octanoyl)oxy)propane-1,3-diyl (9Z,9'Z,12Z,12'Z)-bis(octadeca-9,12-dienoate)

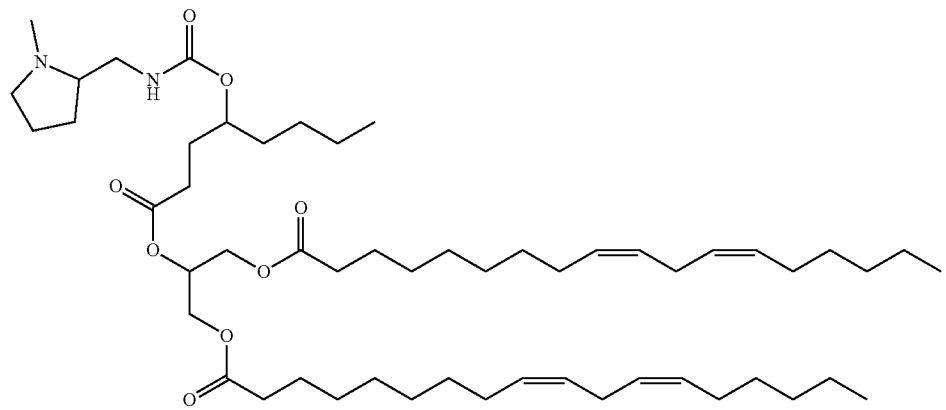 [SMILES: CCCCC/C=C\C/C=C\CCCCCCCC(=O)OCC(COC(=O)CCCCCCC/C=C\C/C=C\CCCCC)OC(=O)CCC(CCCC)OC(=O)NCC1CCCN1C]

Compound 67 was prepared in 50% yield from Intermediate 42d and 1-(1-methylpyrrolidin-2-yl)methanamine using the method employed for Example 1. ¹H NMR (400 MHz, CDCl₃) δ 5.42-5.08 (m, 9H), 4.77 (s, 1H), 4.28 (ddd, J=11.8, 4.5, 1.8 Hz, 2H), 4.20-4.12 (m, 2H), 3.48 (s, 1H), 3.33 (s, 2H), 2.77 (td, J=6.1, 1.2 Hz, 4H), 2.63-2.23 (m, 11H), 2.05 (q, J=6.8 Hz, 9H), 1.98-1.42 (m, 14H), 1.42-1.22 (m, 32H), 0.96-0.81 (m, 9H). MS: 900.0 m/z [M+H].

Example 68—Compound 68

Compound 68: 2-((4-(((3-(pyrrolidin-1-yl)propoxy)carbonyl)oxy)octanoyl)oxy)propane-1,3-diyl (9Z,9'Z,12Z,12'Z)-bis(octadeca-9,12-dienoate)

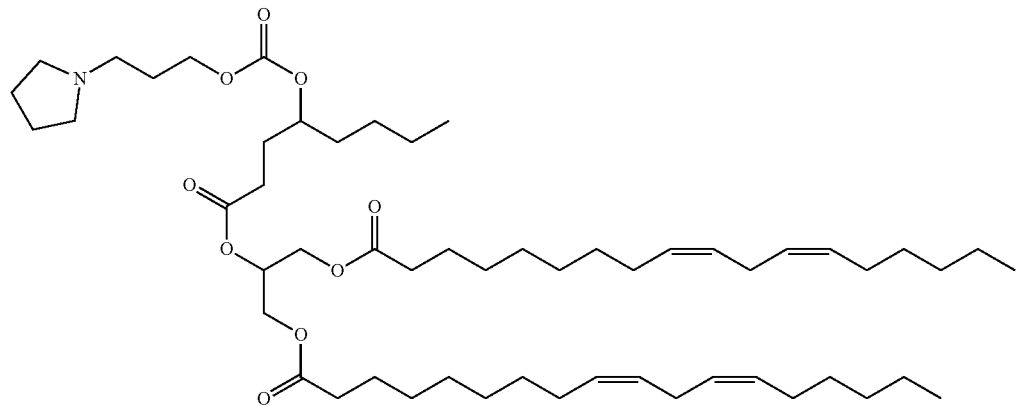 [SMILES: CCCCC/C=C\C/C=C\CCCCCCCC(=O)OCC(COC(=O)CCCCCCC/C=C\C/C=C\CCCCC)OC(=O)CCC(CCCC)OC(=O)OCCCN1CCCC1]

Compound 68 was prepared in 43% yield from Intermediate 42d and 3-(pyrrolidin-1-yl)propan-1-ol using the method employed for Example 1. $^1$H NMR (400 MHz, CDCl$_3$) δ 5.43-5.04 (m, 9H), 4.72 (tt, J=7.4, 5.1 Hz, 1H), 4.40-4.10 (m, 6H), 2.81-2.74 (m, 4H), 2.54 (d, J=58.1 Hz, 5H), 2.40 (ddd, J=8.4, 6.8, 4.4 Hz, 2H), 2.36-2.27 (m, 4H), 2.11-1.73 (m, 16H), 1.73-1.43 (m, 8H), 1.43-1.21 (m, 31H), 0.99-0.77 (m, 9H). MS: 915.7 m/z [M+H].

Example 69—Compound 69

Intermediate 69a: 4-oxononanoic acid

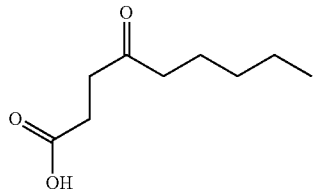

To a mixture of 5-pentyltetrahydrofuran-2-one (50 g, 1.0 equiv.) in 3:1 EtOH/H$_2$O (500 mL) was added NaOH (2.0 equiv.) in one portion at 15° C. under N$_2$. The mixture was stirred at 15° C. for 12 h. Upon completion, the reaction mixture was concentrated under reduced pressure, and the resulting residue was extracted 2× with DCM. The combined organic layers were dried over Na$_2$SO$_4$ and concentrated to afford a crude residue.

The crude residue was subsequently reconstituted in DCM (1 L), followed by the addition of DMP (3 equiv.) in one portion at 15° C. under N$_2$. The mixture was stirred at 15° C. for 4 h. Upon completion, the reaction was concentrated under reduced pressure and the solution was adjusted to pH=3 with 1 M HCl. The slurry was filtered and washed with H$_2$O. The resulting filter cake was dissolved in EtOAc, dried over Na$_2$SO$_4$, filtered, and concentrated to afford product as a white solid (22 g, 45%). $^1$H NMR (400 MHz, CDCl$_3$) δ 2.72 (dd, J=7.0, 5.4 Hz, 2H), 2.63 (ddd, J=7.2, 5.9, 1.2 Hz, 2H), 2.44 (t, J=7.4 Hz, 2H), 1.64-1.54 (m, 2H), 1.36-1.20 (m, 4H), 0.89 (t, J=6.9 Hz, 3H).

Intermediate 69b: 2-((4-oxononanoyl)oxy)propane-1,3-diyl (9Z,9'Z,12Z,12'Z)-bis(octadeca-9,12-dienoate)

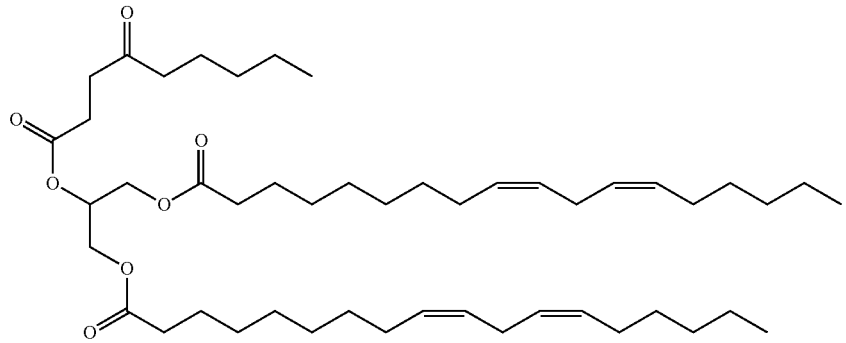

Intermediate 69b was synthesized in 74% yield from Intermediate 69a and Intermediate 1c using the method employed for Intermediate 1d. $^1$H NMR (400 MHz, CDCl$_3$) δ 5.46-5.16 (m, 9H), 4.29 (dd, J=11.9, 4.3 Hz, 2H), 4.14 (dt, J=11.8, 6.0 Hz, 2H), 2.74 (dt, J=21.5, 6.5 Hz, 6H), 2.59 (t, J=6.6 Hz, 2H), 2.43 (t, J=7.5 Hz, 2H), 2.32 (t, J=7.6 Hz, 4H), 2.04 (dd, J=8.6, 5.3 Hz, 8H), 1.60 (ddd, J=14.2, 8.4, 4.8 Hz, 6H), 1.50-1.06 (m, 32H), 0.89 (t, J=6.8 Hz, 9H).

Intermediate 69c: 2-((4-(((4-nitrophenoxy)carbonyl)oxy)nonanoyl)oxy)propane-1,3-diyl (9Z,9'Z,12Z,12'Z)-bis(octadeca-9,12-dienoate)

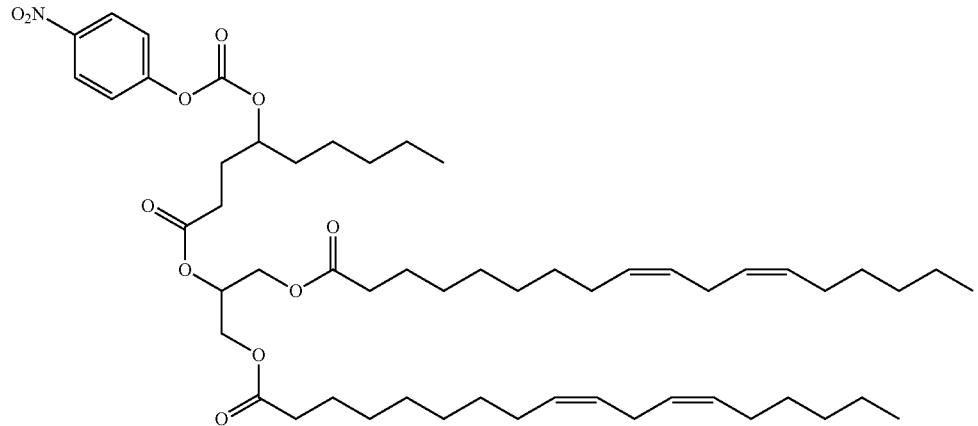 [SMILES: CCCCC/C=C\C/C=C\CCCCCCCC(=O)OCC(COC(=O)CCCCCCC/C=C\C/C=C\CCCCC)OC(=O)CCC(CCCCC)OC(=O)Oc1ccc([N+](=O)[O-])cc1]

To a solution of Intermediate 69b (10 g, 1.0 equiv.) in THF (300 mL), toluene (150 mL) and H$_2$O (75 mL) was added NaBH$_4$ (5.0 equiv.) at 5° C. The mixture was stirred at 15° C. for 3 h under N$_2$ atmosphere. Upon completion, Na$_2$SO$_4$ was added to the reaction mixture at 0° C., and the resulting mixture was filtered and concentrated under reduced pressure. The resulting residue was purified by column chromatography to afford alcohol intermediate as a colorless oil.

The intermediate was immediately reconstituted in DCM (80 mL), followed by the addition of pyridine (1.67 equiv.) and (4-nitrophenyl) carbonochloridate (2 equiv.) at 0° C. The mixture was stirred at 0° C. for 5 h under N$_2$ atmosphere. Upon completion, the reaction mixture was concentrated under reduced pressure to afford a residue that was purified by column chromatography to yield product as a colorless oil (4.05 g, 33%). $^1$H NMR (400 MHz, CDCl$_3$) δ 8.26-8.19 (m, 2H), 7.40-7.28 (m, 2H), 5.43-5.11 (m, 9H), 4.80 (tt, J=7.5, 4.4 Hz, 1H), 4.25 (dd, J=11.9, 4.3 Hz, 2H), 4.09 (dd, J=11.9, 5.8 Hz, 2H), 2.70 (t, J=6.4 Hz, 4H), 2.40 (t, J=7.4 Hz, 2H), 2.33-2.16 (m, 4H), 1.97 (q, J=6.8 Hz, 10H), 1.67 (ddt, J=13.4, 9.9, 4.7 Hz, 1H), 1.55 (dtd, J=15.7, 8.4, 7.4, 4.8 Hz, 5H), 1.43-1.16 (m, 36H), 0.83 (q, J=6.8 Hz, 9H).

Compound 69: 2-((4-(((2-(ethyl(methyl)amino)ethyl)carbamoyl)oxy)nonanoyl)oxy)propane-1,3-diyl (9Z,9'Z,12Z,12'Z)-bis(octadeca-9,12-dienoate)

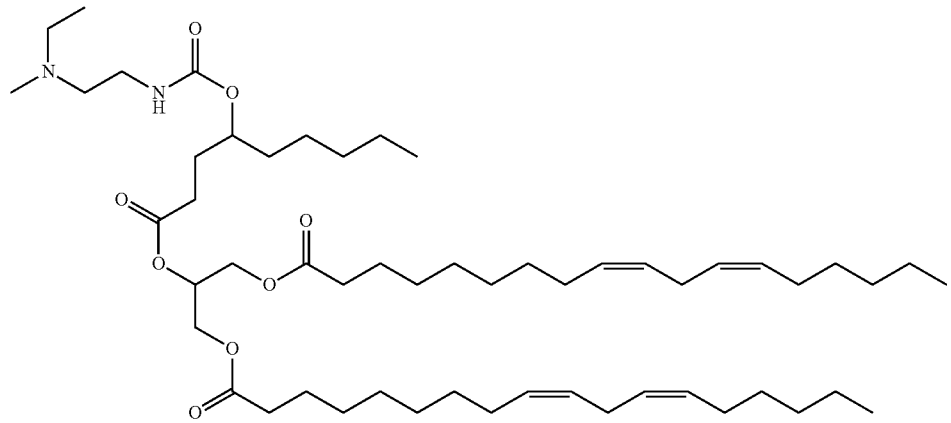 [SMILES: CCCCC/C=C\C/C=C\CCCCCCCC(=O)OCC(COC(=O)CCCCCCC/C=C\C/C=C\CCCCC)OC(=O)CCC(CCCCC)OC(=O)NCCN(C)CC]

Compound 69 was prepared in 77% yield from Intermediate 69c and N1-ethyl-N1-methylethane-1,2-diamine using the method employed for Example 1. ¹H NMR (500 MHz, CDCl₃) δ 5.35 (pt, J=8.8, 4.4 Hz, 8H), 5.25 (p, J=5.1 Hz, 1H), 4.76 (dt, J=12.3, 6.7 Hz, 1H), 4.28 (dd, J=11.9, 4.5 Hz, 2H), 4.15 (dh, J=11.4, 5.9 Hz, 2H), 3.31 (s, 2H), 2.77 (t, J=6.8 Hz, 4H), 2.62-2.45 (m, 4H), 2.38 (dt, J=9.0, 6.2 Hz, 2H), 2.30 (q, J=13.0, 10.4 Hz, 8H), 2.05 (q, J=7.0 Hz, 9H), 1.91 (tt, J=9.5, 4.5 Hz, 1H), 1.81 (dt, J=14.7, 7.8 Hz, 1H), 1.65-1.43 (m, 7H), 1.40-1.17 (m, 36H), 1.09 (q, J=8.8, 8.2 Hz, 3H), 0.88 (q, J=6.5 Hz, 9H). MS: 902.6 m/z [M+H].

Example 70—Compound 70

Compound 70: 2-((4-((((1-methylpyrrolidin-2-yl)methyl)carbamoyl)oxy)nonanoyl)oxy)propane-1,3-diyl (9Z,9'Z,12Z,12'Z)-bis(octadeca-9,12-dienoate)

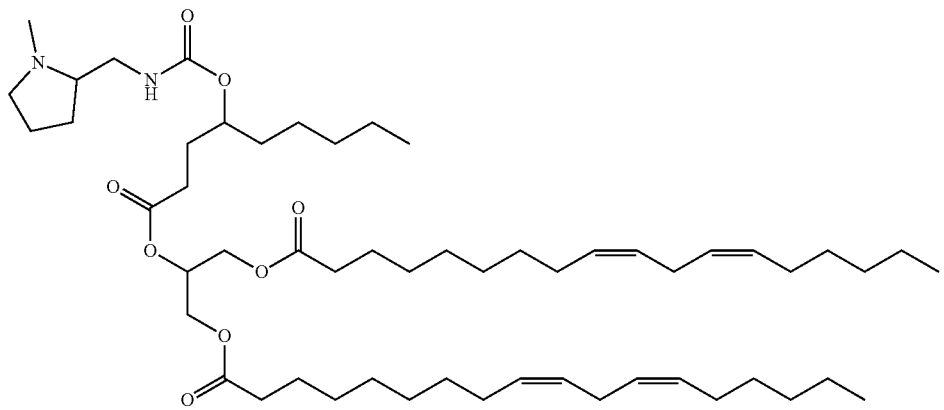 [SMILES: CCCCC/C=C\C/C=C\CCCCCCCC(=O)OCC(COC(=O)CCCCCCC/C=C\C/C=C\CCCCC)OC(=O)CCC(CCCCC)OC(=O)NCC1CCCN1C]

Compound 70 was prepared in 62% yield from Intermediate 69c and 1-(1-methylpyrrolidin-2-yl)methanamine using the method employed for Example 1. ¹H NMR (500 MHz, CDCl₃) δ 5.45-5.29 (m, 8H), 5.25 (p, J=5.2 Hz, 1H), 4.76 (s, 1H), 4.28 (dd, J=11.9, 4.5 Hz, 2H), 4.15 (dq, J=11.7, 5.8 Hz, 2H), 3.46 (d, J=25.9 Hz, 1H), 3.19 (s, 2H), 2.77 (t, J=6.8 Hz, 4H), 2.34 (dt, J=31.1, 8.3 Hz, 12H), 2.05 (q, J=7.0 Hz, 8H), 1.99-1.42 (m, 16H), 1.42-1.19 (m, 35H), 0.88 (q, J=6.8 Hz, 9H). MS: 914.4 m/z [M+H].

Example 71—Compound 71

Compound 71: 2-((4-(((3-(pyrrolidin-1-yl)propoxy)carbonyl)oxy)nonanoyl)oxy)propane-1,3-diyl (9Z,9'Z,12Z,12'Z)-bis(octadeca-9,12-dienoate)

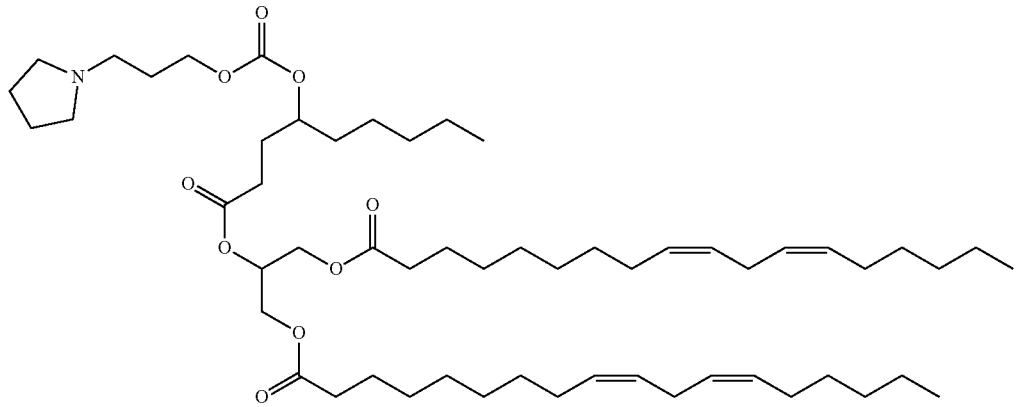 [SMILES: CCCCC/C=C\C/C=C\CCCCCCCC(=O)OCC(COC(=O)CCCCCCC/C=C\C/C=C\CCCCC)OC(=O)CCC(CCCCC)OC(=O)OCCCN1CCCC1]

Compound 71 was prepared in 78% yield from Intermediate 69c and 3-(pyrrolidin-1-yl)propan-1-ol using the method employed for Example 1. ¹H NMR (500 MHz, Chloroform-d) δ 5.50-5.28 (m, 8H), 5.25 (p, J=5.1 Hz, 1H), 4.72 (tt, J=7.8, 4.5 Hz, 1H), 4.36-4.26 (m, 2H), 4.23-4.11 (m, 4H), 2.77 (t, J=6.7 Hz, 4H), 2.41 (dt, J=15.0, 9.0 Hz, 2H), 2.31 (t, J=7.5 Hz, 5H), 2.05 (q, J=6.9 Hz, 8H), 2.00-1.75 (m, 9H), 1.72-1.48 (m, 8H), 1.43-1.20 (m, 35H), 1.00-0.75 (m, 9H). MS: 929.4 m/z [M+H].

Example 72—Compound 72

Compound 72: 2-((4-(((2-(pyrrolidin-1l-yl)ethyl)carbamoyl)oxy)nonanoyl)oxy)propane-1,3-diyl (9Z, 9'Z,12Z,12'Z)-bis(octadeca-9,12-dienoate)

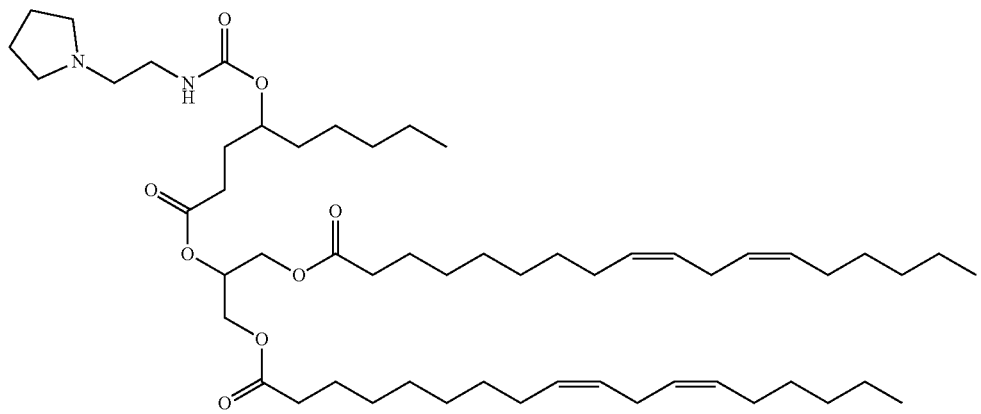 [SMILES: CCCCC/C=C\C/C=C\CCCCCCCC(=O)OCC(COC(=O)CCCCCCC/C=C\C/C=C\CCCCC)OC(=O)CCC(CCCCC)OC(=O)NCCN1CCCC1]

Compound 72 was prepared in 72% yield from Intermediate 69c and 2-(pyrrolidin-1-yl)ethan-1-amine using the method employed for Example 1. ¹H NMR (500 MHz, CDCl₃) δ 5.49 (s, 1H), 5.34 (dtt, J=18.0, 6.9, 3.9 Hz, 8H), 5.25 (p, J=5.1 Hz, 1H), 4.76 (s, 1H), 4.28 (dd, J=11.9, 4.4 Hz, 2H), 4.15 (dt, J=11.6, 5.4 Hz, 2H), 3.40-3.27 (m, 2H), 2.80-2.50 (m, 11H), 2.45-2.35 (m, 2H), 2.31 (t, J=7.6 Hz, 5H), 2.05 (q, J=7.0 Hz, 9H), 1.97-1.67 (m, 8H), 1.60 (q, J=7.3 Hz, 8H), 1.33 (d, J=26.5 Hz, 36H), 0.88 (q, J=6.5 Hz, 9H). MS: 914.7 m/z [M+H].

Example 73—Compound 73

Intermediate 73a: 4-oxoundecanoic acid

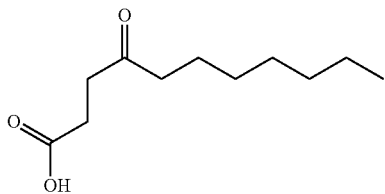

To a solution of 5-heptyltetrahydrofuran-2-one (20 g, 1.0 equiv.) in 2:1 EtOH/H₂O (400 mL) was added NaOH (1.1 equiv.). The mixture was degassed and purged 3× with N₂, and then the mixture was stirred at 20° C. for 12 h under N₂ atmosphere. Upon completion, the reaction mixture was concentrated under reduced pressure to remove solvent, and 1 N HCl was added to the resulting residue until pH=3. The resulting slurry was filtered, and the filtered cake was concentrated under reduced pressure to give a residue.

The resulting residue was reconstituted in DCM (200 mL), followed by the addition of DMP (3 equiv.). The mixture was stirred 20° C. for 5 h. Upon completion, the mixture was concentrated under reduced pressure, and the resulting residue was diluted with H₂O and extracted 3× with EtOAc. The combined organic layers were washed with brine, dried over Na₂SO₄, filtered, and concentrated. Crude material was purified by column chromatography to afford product as a white solid (10 g, 46%). ¹H NMR (400 MHz, CDCl₃) δ 2.65 (dd, J=7.0, 5.3 Hz, 2H), 2.56 (t, J=6.8 Hz, 2H), 2.37 (t, J=7.5 Hz, 2H), 1.51 (q, J=7.2 Hz, 2H), 1.27-1.13 (m, 8H), 0.86-0.76 (m, 3H).

Intermediate 73b: 2-((4-oxoundecanoyl)oxy)propane-1,3-diyl (9Z,9'Z,12Z,12'Z)-bis(octadeca-9,12-dienoate)

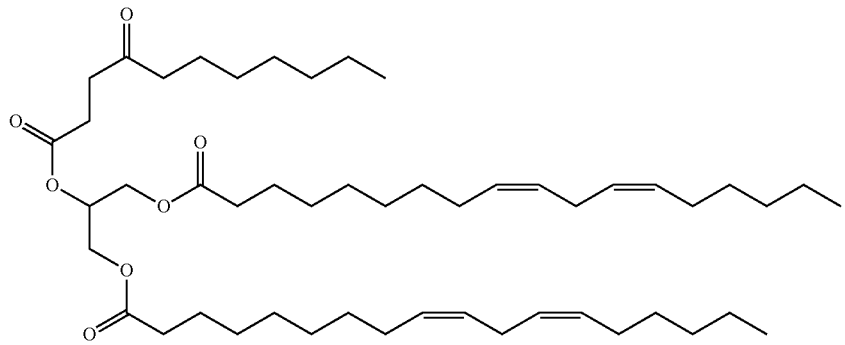 [SMILES: CCCCC/C=C\C/C=C\CCCCCCCC(=O)OCC(COC(=O)CCCCCCC/C=C\C/C=C\CCCCC)OC(=O)CCC(=O)CCCCCCC]

Intermediate 73b was synthesized in 42% yield from Intermediate 73a and Intermediate 1c using the method employed for Intermediate 1 d. $^1$H NMR (400 MHz, CDCl$_3$) δ 5.28 (dddd, J=12.3, 10.7, 8.7, 5.5 Hz, 8H), 5.21-5.15 (m, 1H), 4.22 (dd, J=11.9, 4.3 Hz, 2H), 4.13-4.05 (m, 2H), 2.70 (t, J=6.4 Hz, 4H), 2.64 (t, J=6.5 Hz, 2H), 2.52 (t, J=6.5 Hz, 2H), 2.36 (t, J=7.5 Hz, 2H), 2.25 (t, J=7.6 Hz, 4H), 2.02-1.95 (m, 8H), 1.53 (h, J=7.0 Hz, 6H), 1.33-1.16 (m, 37H), 0.81 (td, J=6.8, 4.7 Hz, 9H).

Intermediate 73c: 2-((4-(((4-nitrophenoxy)carbonyl)oxy)undecanoyl)oxy)propane-1,3-diyl (9Z,9'Z,12Z,12'Z)-bis(octadeca-9,12-dienoate)

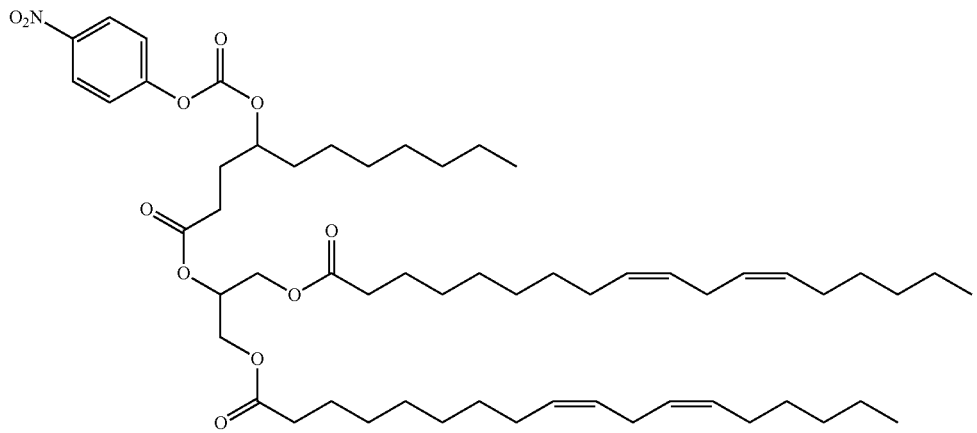 [SMILES: CCCCC/C=C\C/C=C\CCCCCCCC(=O)OCC(COC(=O)CCCCCCC/C=C\C/C=C\CCCCC)OC(=O)CCC(CCCCCCC)OC(=O)Oc1ccc([N+](=O)[O-])cc1]

To a solution of Intermediate 73b (25 g, 1.0 equiv.) in THF (500 mL), toluene (125 mL), and H$_2$O (250 mL) at 0° C. under N$_2$ was added NaBH$_4$ (5.0 equiv.). The mixture was stirred at 5° C. for 1 h under N$_2$ atmosphere. Upon completion, the residue was poured into saturated NH$_4$Cl solution and extracted 3× with EtOAc. The combined organic layers were washed with brine, dried over Na$_2$SO$_4$, filtered, and concentrated in vacuo. The residue was purified by column chromatography to afford intermediate alcohol as a colorless residue.

The intermediate was immediately reconstituted in DCM (100 mL), followed by the addition of pyridine (2 equiv.) and (4-nitrophenyl) carbonochloridate (2 equiv.) at 0° C. The mixture was stirred at 20° C. under N$_2$ atmosphere for 5 h, after which point the reaction mixture was concentrated under reduced pressure. The resulting residue was diluted with hexanes and filtered. The filtrate was washed 3× with water and 1× with brine before being dried over Na$_2$SO$_4$, filtered, and concentrated. Purification by column chromatography afforded product as a colorless oil (5.2 g, 40%). 1H NMR (400 MHz, Chloroform-d) δ 8.28 (d, J=8.8 Hz, 2H), 7.41 (dd, J=8.6, 6.1 Hz, 2H), 5.33 (tdd, J=23.5, 11.3, 6.1 Hz, 9H), 4.87 (tt, J=7.7, 4.6 Hz, 1H), 4.32 (dd, J=12.0, 4.4 Hz, 2H), 4.16 (dd, J=12.0, 5.8 Hz, 2H), 2.77 (t, J=6.4 Hz, 4H), 2.47 (t, J=7.5 Hz, 2H), 2.39-2.25 (m, 4H), 2.04 (q, J=6.9 Hz, 10H), 1.79-1.55 (m, 7H), 1.48-1.15 (m, 36H), 0.89 (t, J=6.7 Hz, 9H).

Compound 73: 2-((4-(((2-(ethyl(methyl)amino)ethyl)carbamoyl)oxy)undecanoyl)oxy)propane-1,3-diyl (9Z,9'Z,12Z,12'Z)-bis(octadeca-9,12-dienoate)

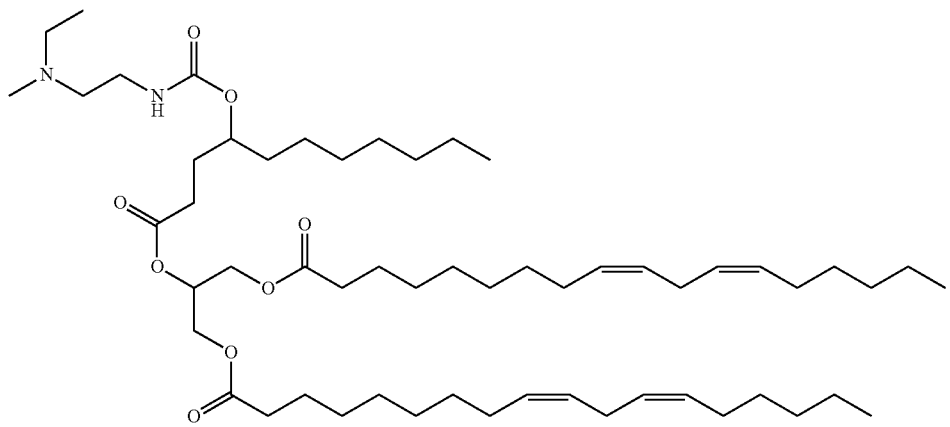 [SMILES: CCCCC/C=C\C/C=C\CCCCCCCC(=O)OCC(COC(=O)CCCCCCC/C=C\C/C=C\CCCCC)OC(=O)CCC(CCCCCCC)OC(=O)NCCN(C)CC]

Compound 73 was prepared in 53% yield from Intermediate 73c and (2-aminoethyl)(ethyl)methylamine using the method employed for Example 1. $^1$H NMR (500 MHz, CDCl$_3$) δ 5.47-5.27 (m, 8H), 5.24 (q, J=5.1 Hz, 1H), 4.76 (s, 1H), 4.28 (dd, J=11.9, 4.4 Hz, 2H), 4.15 (dt, J=11.6, 5.4 Hz, 2H), 3.31 (s, 2H), 2.77 (t, J=6.7 Hz, 4H), 2.61-2.35 (m, 6H), 2.31 (t, J=7.6 Hz, 7H), 2.05 (q, J=7.0 Hz, 8H), 1.90 (q, J=11.5, 9.0 Hz, 1H), 1.81 (dt, J=14.5, 7.6 Hz, 1H), 1.65-1.41 (m, 9H), 1.39-1.19 (m, 38H), 1.10 (s, 3H), 0.88 (q, J=7.0 Hz, 9H). MS: 930.3 m/z [M+H].

Example 74—Compound 74

Compound 74: 2-((4-((((1-methylpyrrolidin-2-yl)methyl)carbamoyl)oxy)undecanoyl)oxy)propane-1,3-diyl (9Z,9'Z,12Z,12'Z)-bis(octadeca-9,12-dienoate)

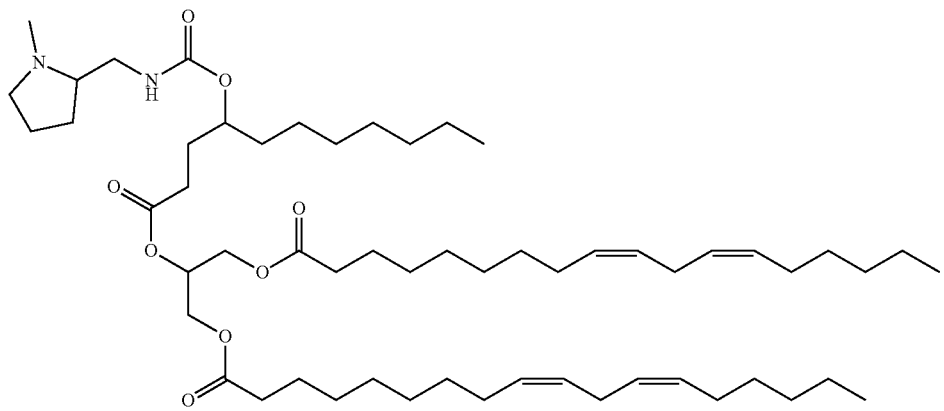 [SMILES: CCCCC/C=C\C/C=C\CCCCCCCC(=O)OCC(COC(=O)CCCCCCC/C=C\C/C=C\CCCCC)OC(=O)CCC(CCCCCCC)OC(=O)NCC1CCCN1C]

Compound 74 was prepared in 55% yield from Intermediate 73c and 1-(1-methylpyrrolidin-2-yl)methanamine using the method employed for Example 1. $^1$H NMR (500 MHz, CDCl$_3$) δ 5.34 (dtt, J=18.0, 6.9, 3.8 Hz, 8H), 5.25 (p, J=5.2 Hz, 1H), 4.81-4.72 (m, 1H), 4.28 (dd, J=11.9, 4.4 Hz, 2H), 4.15 (dt, J=11.7, 5.2 Hz, 2H), 3.43 (s, 1H), 3.17 (s, 2H), 2.77 (t, J=6.8 Hz, 4H), 2.34 (dt, J=31.2, 8.3 Hz, 11H), 2.05 (q, J=7.0 Hz, 8H), 1.99-1.43 (m, 16H), 1.43-1.13 (m, 39H), 0.88 (q, J=7.7, 7.2 Hz, 9H). MS: 942.8 m/z [M+H].

Example 75—Compound 75

Compound 75: 2-((4-(((3-(pyrrolidin-1-yl)propoxy)carbonyl)oxy)undecanoyl)oxy)propane-1,3-diyl (9Z,9'Z,12Z,12'Z)-bis(octadeca-9,12-dienoate)

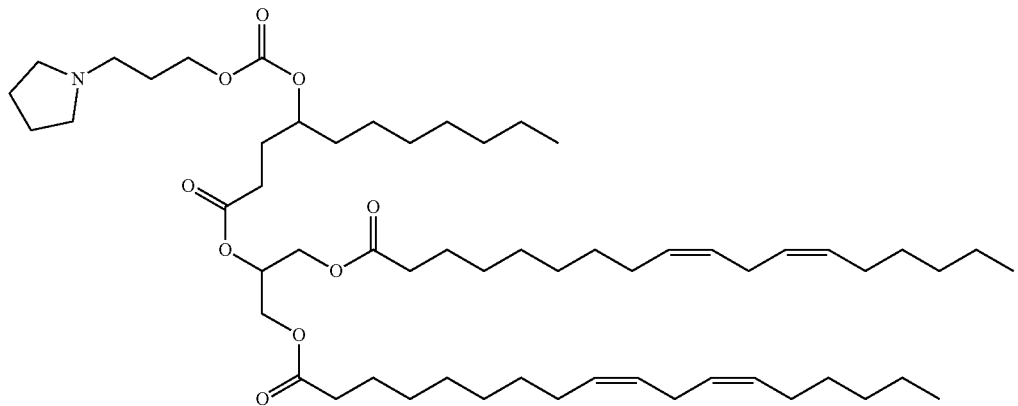 [SMILES: CCCCC/C=C\C/C=C\CCCCCCCC(=O)OCC(COC(=O)CCCCCCC/C=C\C/C=C\CCCCC)OC(=O)CCC(CCCCCCC)OC(=O)OCCCN1CCCC1]

Compound 75 was prepared in 73% yield from Intermediate 73c and 3-(pyrrolidin-1-yl)propan-1-ol using the method employed for Example 1. $^1$H NMR (500 MHz, CDCl$_3$) δ 5.46-5.28 (m, 8H), 5.25 (p, J=5.1 Hz, 1H), 4.72 (tt, J=7.8, 4.5 Hz, 1H), 4.29 (dd, J=11.9, 4.4 Hz, 2H), 4.22-4.11 (m, 4H), 2.77 (t, J=6.8 Hz, 4H), 2.45-2.37 (m, 2H), 2.31 (t, J=7.5 Hz, 4H), 2.05 (q, J=7.0 Hz, 8H), 2.01-1.91 (m, 3H), 1.91-1.78 (m, 5H), 1.67-1.50 (m, 9H), 1.39-1.22 (m, 39H), 0.88 (q, J=6.6 Hz, 9H). MS: 957.4 m/z [M+H].

Example 76—Compound 76

Compound 76: 2-((4-(((2-(pyrrolidin-1l-yl)ethyl)carbamoyl)oxy)undecanoyl)oxy)propane-1,3-diyl (9Z,9'Z,12Z,12'Z)-bis(octadeca-9,12-dienoate)

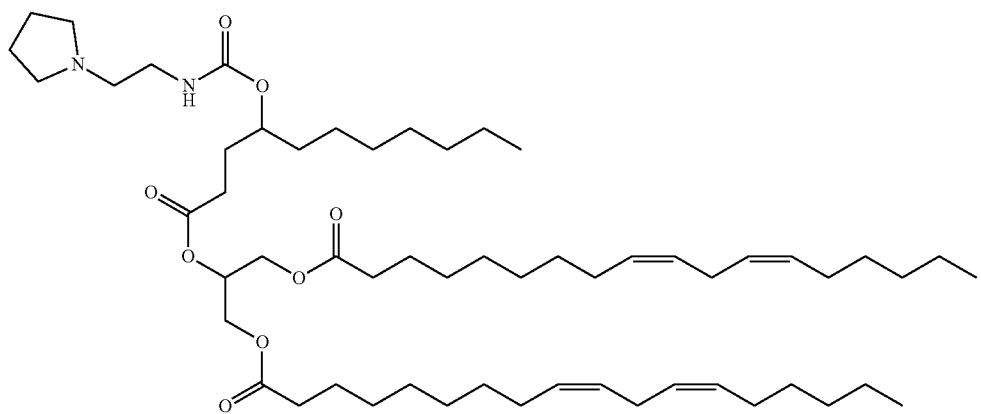 [SMILES: CCCCC/C=C\C/C=C\CCCCCCCC(=O)OCC(COC(=O)CCCCCCC/C=C\C/C=C\CCCCC)OC(=O)CCC(CCCCCCC)OC(=O)NCCN1CCCC1]

Compound 76 was prepared in 81% yield from Intermediate 73c and 2-(pyrrolidin-1-yl)ethan-1-amine using the method employed for Example 1. $^1$H NMR (500 MHz, CDCl$_3$) δ 5.56 (s, 1H), 5.46-5.28 (m, 8H), 5.25 (p, J=5.2 Hz, 1H), 4.76 (s, 1H), 4.28 (dd, J=11.9, 4.4 Hz, 2H), 4.15 (dt, J=11.7, 5.5 Hz, 2H), 3.43-3.31 (m, 2H), 2.77 (t, J=6.7 Hz, 11H), 2.45-2.35 (m, 2H), 2.31 (t, J=7.6 Hz, 4H), 2.05 (q, J=7.0 Hz, 8H), 1.97-1.74 (m, 7H), 1.69-1.43 (m, 8H), 1.43-1.09 (m, 39H), 0.88 (q, J=7.0 Hz, 9H). MS: 943.2 m/z [M+H].

Example 77—Compound 77

Compound 77: 2-((4-(((2-(azetidin-1-yl)ethyl)carbamoyl)oxy)decanoyl)oxy)propane-1,3-diyl (9Z,9'Z,12Z,12'Z)-bis(octadeca-9,12-dienoate)

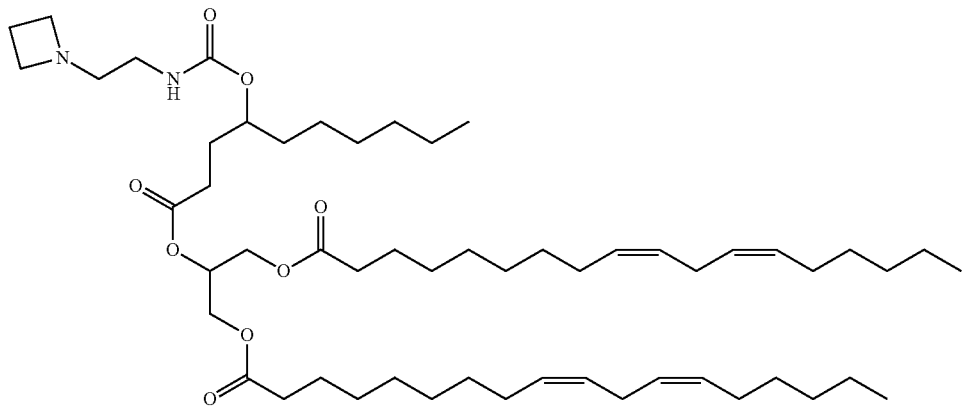 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NCCN1CCC1]

Compound 77 was prepared in 36% yield from Intermediate 40d and 2-(azetidin-1-yl)ethan-1-amine using the method employed for Example 1. $^1$H NMR (400 MHz, CDCl$_3$) δ 5.45-5.29 (m, 8H), 5.25 (h, J=4.6, 4.1 Hz, 1H), 4.75 (s, 1H), 4.28 (ddd, J=11.9, 4.5, 1.9 Hz, 2H), 4.15 (ddt, J=11.9, 5.8, 3.6 Hz, 2H), 3.74-3.54 (m, 3H), 3.48-3.38 (m, 1H), 3.31 (d, J=6.3 Hz, 1H), 2.86 (s, 1H), 2.81-2.73 (m, 4H), 2.41-2.26 (m, 7H), 2.05 (q, J=6.8 Hz, 8H), 1.97-1.87 (m, 2H), 1.87-1.77 (m, 2H), 1.60 (d, J=7.2 Hz, 8H), 1.44-1.15 (m, 37H), 0.96-0.84 (m, 9H). MS: 914.7 m/z [M+H].

Example 78—Compound 78

Compound 78: 2-((4-(((2-(piperidin-1-yl)ethyl)carbamoyl)oxy)decanoyl)oxy)propane-1,3-diyl (9Z,9'Z,12Z,12'Z)-bis(octadeca-9,12-dienoate)

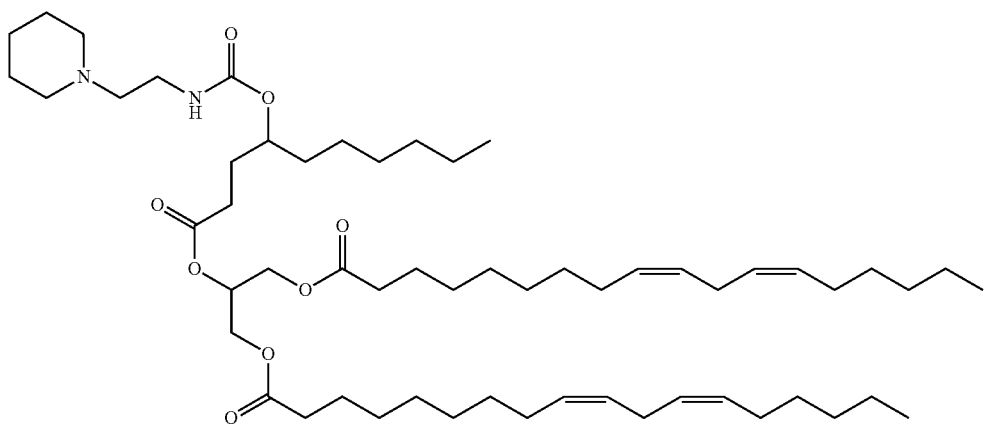 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NCCN1CCCCC1]

Compound 78 was prepared in 60% yield from Intermediate 40d and 2-(piperidin-1-yl)ethan-1-amine using the method employed for Example 1. $^1$H NMR (400 MHz, CDCl$_3$) δ 5.47-5.28 (m, 8H), 5.25 (h, J=4.8 Hz, 1H), 4.76 (s, 1H), 4.28 (ddd, J=11.9, 4.4, 1.3 Hz, 2H), 4.15 (dt, J=11.8, 5.7 Hz, 2H), 3.42 (s, 2H), 2.80-2.72 (m, 4H), 2.44 (d, J=6.7 Hz, 2H), 2.39 (ddd, J=8.6, 6.9, 2.5 Hz, 2H), 2.36-2.27 (m, 5H), 2.05 (q, J=6.9 Hz, 8H), 1.95-1.41 (m, 18H), 1.41-1.20 (m, 37H), 0.96-0.81 (m, 9H). MS: 942.4 m/z [M+H].

Example 79—Compound 79

Compound 79: 2-((4-(((2-methyl-1-(pyrrolidin-1-yl)propan-2-yl)carbamoyl)oxy)decanoyl)oxy)propane-1,3-diyl (9Z,9'Z,12Z,12'Z)-bis(octadeca-9,12-dienoate)

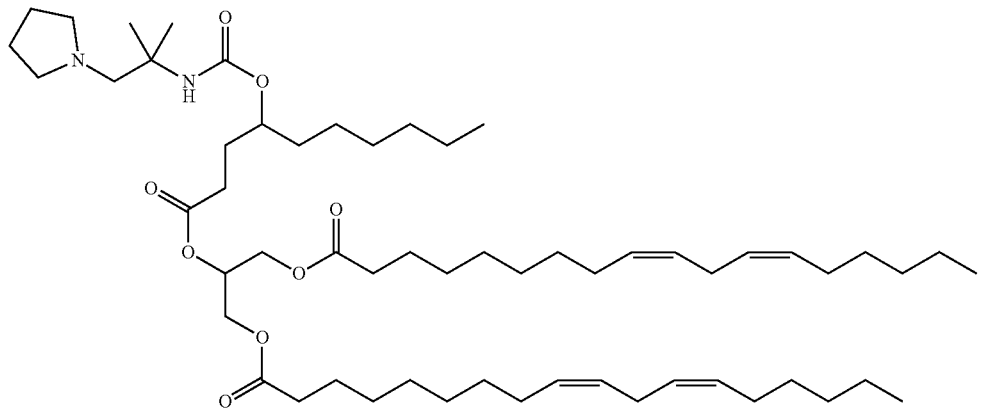 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NC(C)(C)CN1CCCC1]

Compound 79 was prepared in 48% yield from Intermediate 40d and 2-methyl-1-(pyrrolidin-1-yl)propan-2-amine using the method employed for Example 1. $^1$H NMR (400 MHz, CDCl$_3$) δ 5.42-5.21 (m, 9H), 4.72 (s, 1H), 4.28 (ddt, J=11.9, 4.4, 2.2 Hz, 2H), 4.15 (ddd, J=11.9, 5.8, 4.6 Hz, 2H), 2.86-2.49 (m, 8H), 2.39 (td, J=8.2, 7.4, 2.2 Hz, 1H), 2.31 (td, J=7.6, 1.8 Hz, 4H), 2.05 (q, J=6.8 Hz, 8H), 2.00-1.45 (m, 17H), 1.45-1.03 (m, 41H), 0.98-0.77 (m, 9H). MS: 956.5 m/z [M+H].

Example 80—Compound 80

Intermediate 80a: (5-methylhexyl)magnesium bromide

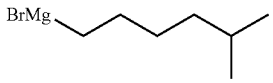

To a solution of Mg (1.63 g, 1.2 equiv.) and I$_2$ (0.1 equiv.) in THF (100 mL) was added 1-bromo-5-methyl-hexane (1.0 equiv.) at 15° C. The mixture was stirred at 40° C. for 2 h under N$_2$ atmosphere. No further work-up. The reaction mixture was used in next step directly. Bromo(5-methylhexyl)magnesium in THF was obtained as gray solution.

Intermediate 80b: ethyl 9-methyl-4-oxodecanoate

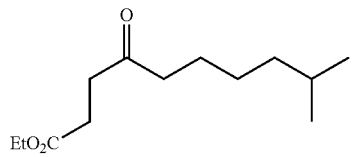

To a solution of ethyl 4-chloro-4-oxo-butanoate (16 g, 1.0 equiv.) in THF (150 mL) was added CuI (1.0 equiv.) and Intermediate 80a (2.0 equiv.) at −78° C. The mixture was stirred at −78° C. for 2 h under N$_2$ atmosphere. Upon completion, the reaction mixture was quenched with water and extracted 3× with EtOAc. The combined organic layers were washed 2× with brine, dried over Na$_2$SO$_4$, filtered and concentrated under reduced pressure to give a residue. Crude residue was purified by column chromatography to afford product (10 g, 45% yield) as a colorless oil. $^1$H NMR (400 MHz, CDCl$_3$) δ 4.06 (q, J=7.1 Hz, 2H), 2.64 (t, J=6.6 Hz, 2H), 2.50 (t, J=6.8 Hz, 2H), 2.38 (t, J=7.5 Hz, 2H), 1.55-1.45 (m, 3H), 1.28-1.15 (m, 6H), 1.15-1.06 (m, 2H), 0.79 (d, J=6.6 Hz, 6H).

Intermediate 80c: 9-methyl-4-oxodecanoic acid

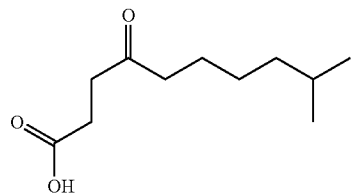

To a solution of intermediate 80b (10 g, 1.0 equiv.) in EtOH (100 mL) was added KOH (3.0 equiv.) at 20° C. The mixture was stirred at 50° C. for 12 h under N$_2$ atmosphere. The reaction was then concentrated to remove EtOH, and the pH was adjusted to 5.5 with HCl (1 M). The resulting mixture was diluted with water and extracted 2× with EtOAc. The combined organic layers were washed 2× with brine, dried over Na$_2$SO$_4$, filtered, and concentrated under reduced pressure. Crude material was purified by column chromatography to afford product (4.4 g, 50%) as a white solid. $^1$H NMR (400 MHz, CDCl$_3$) δ 2.71 (t, J=6.8 Hz, 2H), 2.63 (ddd, J=7.0, 5.8, 1.1 Hz, 2H), 2.44 (t, J=7.5 Hz, 2H), 1.53 (dq, J=19.8, 7.0, 6.6 Hz, 3H), 1.31-1.24 (m, 2H), 1.16 (dt, J=8.6, 6.7 Hz, 2H), 0.85 (d, J=6.6 Hz, 6H).

Intermediate 80d: 2-((9-methyl-4-oxodecanoyl)oxy)propane-1,3-diyl (9Z,9'Z,12Z,12'Z)-bis(octadeca-9,12-dienoate)

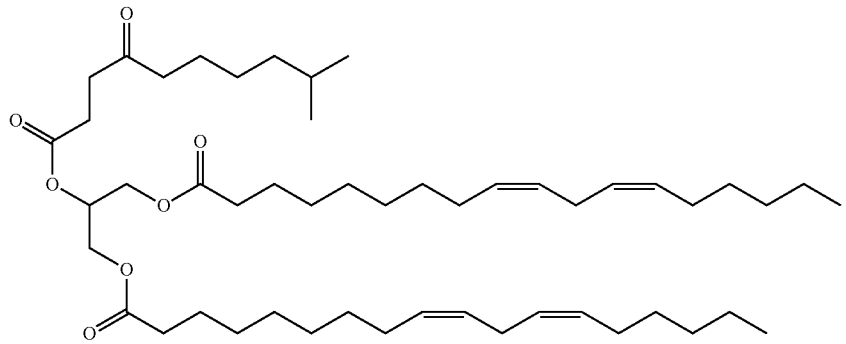 [SMILES: CCCCC/C=C\C/C=C\CCCCCCCC(=O)OCC(COC(=O)CCCCCCC/C=C\C/C=C\CCCCC)OC(=O)CCC(=O)CCCCC(C)C]

Intermediate 80d was synthesized in 40% yield from Intermediate 80c and Intermediate 1c using the method employed for Intermediate 1d. $^1$H NMR (400 MHz, CDCl$_3$) δ 5.45-5.28 (m, 8H), 5.24 (p, J=5.1 Hz, 1H), 4.28 (dd, J=11.9, 4.3 Hz, 2H), 4.14 (dd, J=11.9, 5.9 Hz, 2H), 2.76 (t, J=6.4 Hz, 4H), 2.71 (t, J=6.5 Hz, 2H), 2.59 (t, J=6.5 Hz, 2H), 2.43 (t, J=7.5 Hz, 2H), 2.31 (t, J=7.6 Hz, 4H), 2.04 (q, J=6.8 Hz, 8H), 1.67-1.50 (m, 8H), 1.39-1.21 (m, 29H), 1.22-1.12 (m, 3H), 0.93-0.82 (m, 12H).

Intermediate 80e: 2-((9-methyl-4-(((4-nitrophenoxy)carbonyl)oxy)decanoyl)oxy)propane-1,3-diyl (9Z,9'Z,12Z,12'Z)-bis(octadeca-9,12-dienoate)

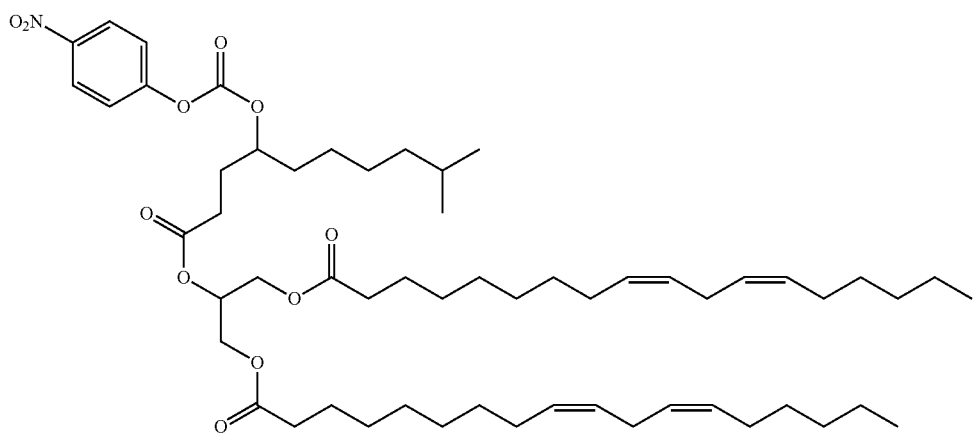 [SMILES: CCCCC/C=C\C/C=C\CCCCCCCC(=O)OCC(COC(=O)CCCCCCC/C=C\C/C=C\CCCCC)OC(=O)CCC(CCCCC(C)C)OC(=O)Oc1ccc([N+](=O)[O-])cc1]

To a solution of Intermediate 80d (1.5 g, 1.0 equiv.) in THF (30 mL), toluene (15 mL) and H$_2$O (7.5 mL) was added NaBH$_4$ (5.0 equiv.) at 0° C. The mixture was stirred at 5° C. for 5 h. Upon complete reduction, the reaction mixture was partitioned between THF and H$_2$O, and the resulting organic phase was separated, dried over Na$_2$SO$_4$, filtered, and concentrated under reduced pressure to give a residue. The residue was purified by column chromatography to afford intermediate alcohol was a yellow oil.

The resulting intermediate was immediately reconstituted in DCM (10 mL), followed by the addition of pyridine (2.0 equiv.) and (4-nitrophenyl) carbonochloridate (2.0 equiv.) at 0° C. The mixture was stirred at 0° C. for 5 h. The reaction mixture was then filtered and concentrated under reduced pressure to give a crude residue that was purified by column chromatography to afford product as a colorless oil. $^1$H NMR (400 MHz, CDCl$_3$) δ 8.25-8.18 (m, 2H), 7.38-7.28 (m, 2H), 5.39-5.15 (m, 9H), 4.80 (tt, J=7.1, 4.3 Hz, 1H), 4.25 (dd, J=12.0, 4.3 Hz, 2H), 4.13-4.04 (m, 2H), 2.70 (t, J=6.4 Hz, 4H), 2.40 (dd, J=8.3, 6.6 Hz, 2H), 2.33-2.19 (m, 4H), 2.05-1.85 (m, 10H), 1.67 (ddt, J=14.6, 9.4, 4.8 Hz, 1H), 1.52 (dddq, J=32.6, 26.2, 13.2, 6.6, 6.1 Hz, 8H), 1.37-1.17 (m, 30H), 1.11 (dt, J=9.0, 6.5 Hz, 2H), 0.94-0.66 (m, 12H).

Compound 80: 2-((4-(((2-(ethyl(methyl)amino)ethyl)carbamoyl)oxy)-9-methyldecanoyl)oxy)propane-1,3-diyl (9Z,9'Z,12Z,12'Z)-bis(octadeca-9,12-dienoate)

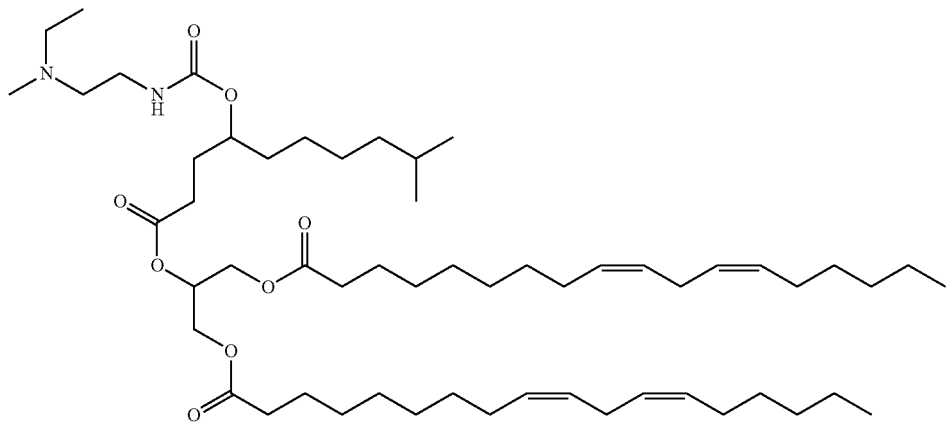

Compound 80 was prepared in 68% yield from Intermediate 80e and (2-aminoethyl)(ethyl)methylamine using the method employed for Example 1. $^1$H NMR (400 MHz, CDCl$_3$) δ 5.43-5.22 (m, 9H), 4.76 (s, 1H), 4.28 (ddd, J=12.0, 4.5, 1.5 Hz, 2H), 4.15 (ddd, J=11.9, 5.8, 4.7 Hz, 2H), 3.37 (s, 3H), 2.77 (td, J=6.0, 1.3 Hz, 4H), 2.39 (ddd, J=8.4, 6.9, 2.4 Hz, 2H), 2.35-2.28 (m, 5H), 2.05 (q, J=6.8 Hz, 8H), 1.86 (ddt, J=37.3, 14.4, 7.1 Hz, 3H), 1.77-1.38 (m, 12H), 1.39-1.19 (m, 34H), 1.15 (d, J=6.7 Hz, 3H), 0.94-0.79 (m, 12H). MS: 929.9 m/z [M+H].

Example 81—Compound 81

Intermediate 81a: 1-bromo-6-methylheptane

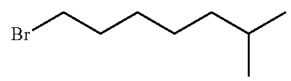

To a solution of PPh$_3$ (66.97 g, 1.33 equiv.) in DCM (300 mL) was added Br$_2$ (1.33 equiv.) at 0° C. Then, 6-methylheptan-1-ol (1.0 equiv.) was added in one portion. The mixture was stirred at 0° C. for 2 h under N$_2$ atmosphere. Upon completion, the reaction mixture was diluted with H$_2$O, and organic phase was separated. The organic layer was dried over Na$_2$SO$_4$, filtered, and concentrated under reduced pressure to give a residue. Pentane was added, and the precipitated triphenylphosphine oxide was filtered off. The organic phase was concentrated under reduced pressure to give a residue, which was purified by column chromatography to afford product as a yellow oil (30 g, 81%). $^1$H NMR (400 MHz, CDCl$_3$) δ 3.41 (td, J=6.9, 1.1 Hz, 2H), 1.91-1.79 (m, 2H), 1.59-1.49 (m, 1H), 1.45-1.35 (m, 2H), 1.34-1.25 (m, 3H), 1.21-1.12 (m, 2H), 0.86 (dd, J=6.6, 1.1 Hz, 6H).

Intermediate 81b: (6-methylheptyl)magnesium bromide

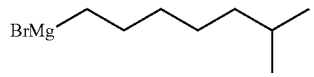

To a solution of Mg (4.53 g, 1.2 equiv.) and 12 (0.1 equiv.) in THF (300 mL) was added Intermediate 81a (1.0 equiv.) at 15° C. The mixture was stirred at 40° C. for 2 h under N$_2$ atmosphere. No further work-up. The reaction mixture was used directly in the next step. Bromo (6-methylheptyl) magnesium in THF was obtained as gray solution.

Intermediate 81c: ethyl 10-methyl-4-oxoundecanoate

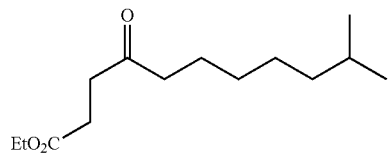 [SMILES: CCOC(=O)CCC(=O)CCCCCC(C)C]

To a solution of ethyl 4-chloro-4-oxo-butanoate (25 g, 1.0 equiv.) and CuI (1.0 equiv.) in THF (200 mL) was added Intermediate 81b (1.0 equiv.) at −78° C. The mixture was stirred at −78° C. for 5 h under N$_2$ atmosphere. The reaction mixture was then diluted with water and extracted 3× with EtOAc. The combined organic layers were separated, washed 2× with brine, dried over Na$_2$SO$_4$, filtered, and concentrated under reduced pressure to give a residue. The residue was purified by column chromatography to afford product as a yellow oil (10 g, 27%). $^1$H NMR (400 MHz, CDCl$_3$) δ 4.06 (q, J=7.1 Hz, 2H), 2.64 (t, J=6.6 Hz, 2H), 2.50 (t, J=6.7 Hz, 2H), 2.37 (t, J=7.5 Hz, 2H), 1.51 (q, J=7.5 Hz, 2H), 1.43 (dq, J=13.2, 6.6 Hz, 1H), 1.26-1.15 (m, 7H), 1.14-1.04 (m, 2H), 0.79 (d, J=6.6 Hz, 6H).

Intermediate 81d: 10-methyl-4-oxoundecanoic acid

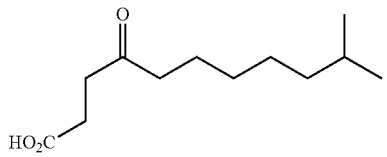

A mixture of Intermediate 81c (10 g, 1.0 equiv.) and KOH (3.0 equiv.) in EtOH (50 mL) was degassed and purged 3× with N$_2$, and then the mixture was stirred at 50° C. for 12 h under N$_2$ atmosphere. The mixture was concentrated to remove EtOH, then adjusted to pH 5.5 with HCl (1 M). Then the reaction mixture was diluted with water and extracted 3× with EtOAc. The combined organic layers were separated, washed 2× with brine, dried over Na$_2$SO$_4$, filtered, and concentrated under reduced pressure to give a residue. The residue was purified by column chromatography to afford product as a white solid (4 g, 45%). $^1$H NMR (400 MHz, CDCl$_3$) δ 2.65 (t, J=6.1 Hz, 2H), 2.56 (ddd, J=7.1, 5.9, 1.2 Hz, 2H), 2.37 (t, J=7.5 Hz, 2H), 1.51 (q, J=7.3 Hz, 2H), 1.42 (dt, J=13.2, 6.6 Hz, 1H), 1.20 (tt, J=4.9, 2.5 Hz, 4H), 1.14-1.05 (m, 2H), 0.79 (d, J=6.6 Hz, 6H).

Intermediate 81e: 2-((10-methyl-4-oxoundecanoyl)oxy)propane-1,3-diyl (9Z,9'Z,12Z,12'Z)-bis(octadeca-9,12-dienoate)

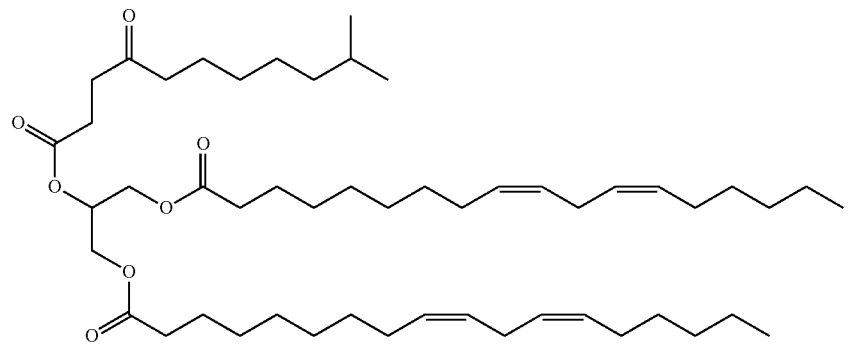 [SMILES: CCCCC/C=C\C/C=C\CCCCCCCC(=O)OCC(COC(=O)CCCCCCC/C=C\C/C=C\CCCCC)OC(=O)CCC(=O)CCCCCC(C)C]

Intermediate 81e was synthesized in 40% yield from Intermediate 81d and Intermediate 1c using the method employed for Intermediate 1d. $^1$H NMR (400 MHz, CDCl$_3$) δ 5.39-5.20 (m, 8H), 5.17 (ddd, J=10.1, 5.8, 4.3 Hz, 1H), 4.21 (dd, J=11.9, 4.3 Hz, 2H), 4.07 (dd, J=11.9, 5.9 Hz, 2H), 2.69 (t, J=6.4 Hz, 4H), 2.64 (t, J=6.5 Hz, 2H), 2.52 (t, J=6.5 Hz, 2H), 2.36 (t, J=7.5 Hz, 2H), 2.24 (t, J=7.5 Hz, 4H), 1.97 (q, J=6.8 Hz, 8H), 1.66-1.46 (m, 7H), 1.33-1.13 (m, 35H), 1.08 (q, J=6.9 Hz, 2H), 0.84-0.77 (m, 12H).

Intermediate 81f: 2-((10-methyl-4-(((4-nitrophenoxy)carbonyl)oxy)undecanoyl)oxy)propane-1,3-diyl (9Z,9'Z,12Z,12'Z)-bis(octadeca-9,12-dienoate)

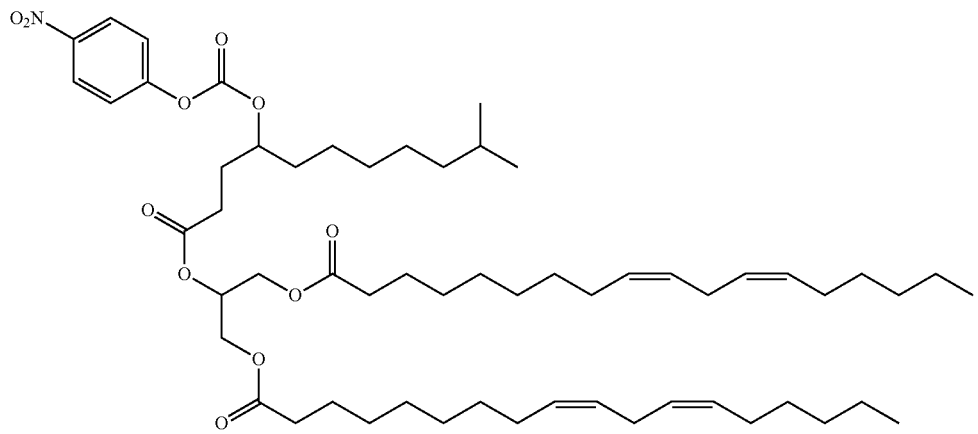 [SMILES: CCCCC/C=C\C/C=C\CCCCCCCC(=O)OCC(COC(=O)CCCCCCC/C=C\C/C=C\CCCCC)OC(=O)CCC(CCCCCC(C)C)OC(=O)Oc1ccc([N+](=O)[O-])cc1]

To a solution of Intermediate 81e (6 g, 1.0 equiv.) in THF (120 mL), toluene (30 mL) and H₂O (60 mL) was added NaBH₄ (5.0 equiv.) at 0° C. The mixture was stirred at 5° C. for 5 h.

Upon complete reduction, the reaction mixture was partitioned between THF and H₂O, and the resulting organic phase was separated, dried over Na₂SO₄, filtered, and concentrated under reduced pressure to give a residue. The residue was purified by column chromatography to afford intermediate alcohol was a yellow oil.

The resulting intermediate was immediately reconstituted in DCM (10 mL), followed by the addition of pyridine (2.0 equiv.) and (4-nitrophenyl) carbonochloridate (2.0 equiv.) at 0° C. The mixture was stirred at 0° C. for 1 h. The reaction mixture was then filtered and concentrated under reduced pressure to give a crude residue that was purified by column chromatography to afford product as a yellow oil (4.3 g, 59%). 1H NMR (400 MHz, CDCl₃) δ 8.27-8.16 (m, 2H), 7.37-7.29 (m, 2H), 5.43-5.12 (m, 9H), 4.80 (s, 1H), 4.25 (dd, J=11.9, 4.4 Hz, 2H), 4.14-4.06 (m, 2H), 2.70 (t, J=6.4 Hz, 4H), 2.40 (t, J=7.5 Hz, 2H), 2.24 (td, J=7.5, 4.1 Hz, 4H), 2.05-1.88 (m, 9H), 1.71-1.62 (m, 1H), 1.62-1.47 (m, 6H), 1.45-0.97 (m, 35H), 0.89-0.66 (m, 12H).

Compound 81: 2-((4-(((2-(ethyl(methyl)amino)ethyl)carbamoyl)oxy)-10-methylundecanoyl)oxy)propane-1,3-diyl (9Z,9'Z,12Z,12'Z)-bis(octadeca-9,12-dienoate)

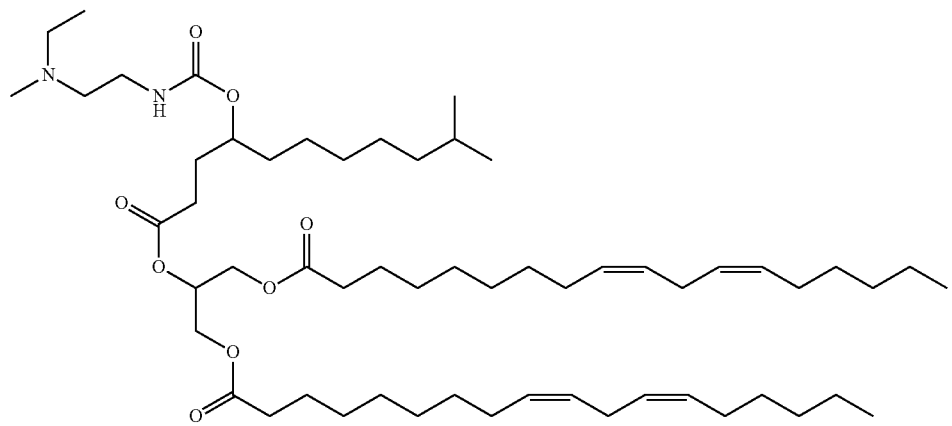 [SMILES: CCCCC/C=C\C/C=C\CCCCCCCC(=O)OCC(COC(=O)CCCCCCC/C=C\C/C=C\CCCCC)OC(=O)CCC(CCCCCC(C)C)OC(=O)NCCN(C)CC]

Compound 81 was prepared in 85% yield from Intermediate 81f and (2-aminoethyl)(ethyl)methylamine using the method employed for Example 1. ¹H NMR (400 MHz, CDCl₃) δ 5.42-5.21 (m, 9H), 4.76 (s, 1H), 4.33-4.23 (m, 2H), 4.15 (dt, J=11.8, 5.7 Hz, 2H), 3.38 (d, J=40.4 Hz, 3H), 2.77 (t, J=6.5 Hz, 4H), 2.38 (t, J=7.7 Hz, 2H), 2.32 (td, J=7.6, 1.1 Hz, 5H), 2.05 (q, J=6.7 Hz, 8H), 1.96-1.78 (m, 3H), 1.68-1.43 (m, 12H), 1.43-1.20 (m, 36H), 1.14 (d, J=6.6 Hz, 3H), 0.93-0.80 (m, 12H). MS: 944.5 m/z [M+H].

Example 82—Compound 82

Compound 82: 2-((9-methyl-4-(((2-(pyrrolidin-1-yl)ethyl)carbamoyl)oxy)decanoyl)oxy)propane-1,3-diyl (9Z,9'Z,12Z,12'Z)-bis(octadeca-9,12-dienoate)

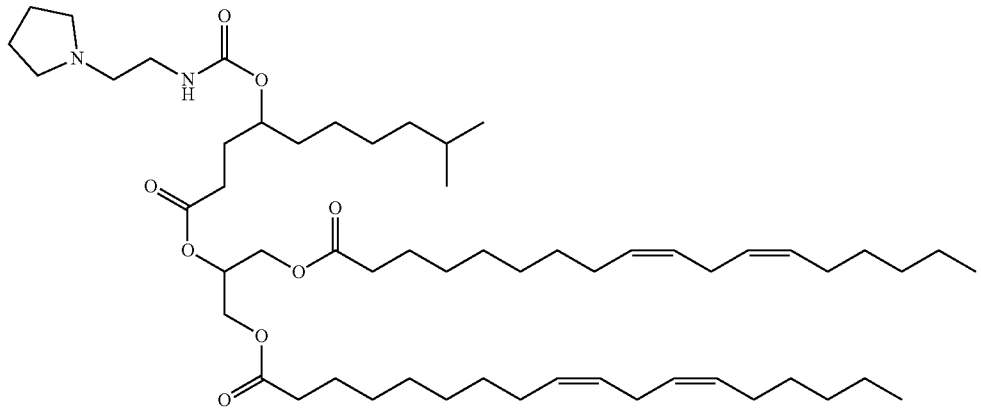 [SMILES: CCCCC/C=C\C/C=C\CCCCCCCC(=O)OCC(COC(=O)CCCCCCC/C=C\C/C=C\CCCCC)OC(=O)CCC(CCCCC(C)C)OC(=O)NCCN1CCCC1]

Compound 82 was prepared in 86% yield from Intermediate 80e and 2-(pyrrolidin-1-yl)ethan-1-amine using the method employed for Example 1. $^1$H NMR (400 MHz, CDCl$_3$) δ 5.87 (s, 1H), 5.43-5.23 (m, 9H), 4.76 (s, 1H), 4.28 (ddd, J=12.0, 4.5, 2.6 Hz, 2H), 4.15 (ddd, J=11.9, 5.8, 4.6 Hz, 2H), 3.52-3.42 (m, 2H), 2.94 (s, 5H), 2.82-2.75 (m, 4H), 2.39 (ddd, J=8.4, 6.9, 2.0 Hz, 2H), 2.36-2.29 (m, 4H), 2.05 (q, J=6.8 Hz, 8H), 2.01-1.76 (m, 7H), 1.67-1.45 (m, 8H), 1.40-1.21 (m, 33H), 1.15 (s, 2H), 0.93-0.81 (m, 12H). MS: 942.3 m/z [M+H].

Example 83—Compound 83

Compound 83: 2-((10-methyl-4-(((2-(pyrrolidin-1-yl)ethyl)carbamoyl)oxy)undecanoyl)oxy)propane-1,3-diyl (9Z,9'Z,12Z,12'Z)-bis(octadeca-9,12-dienoate)

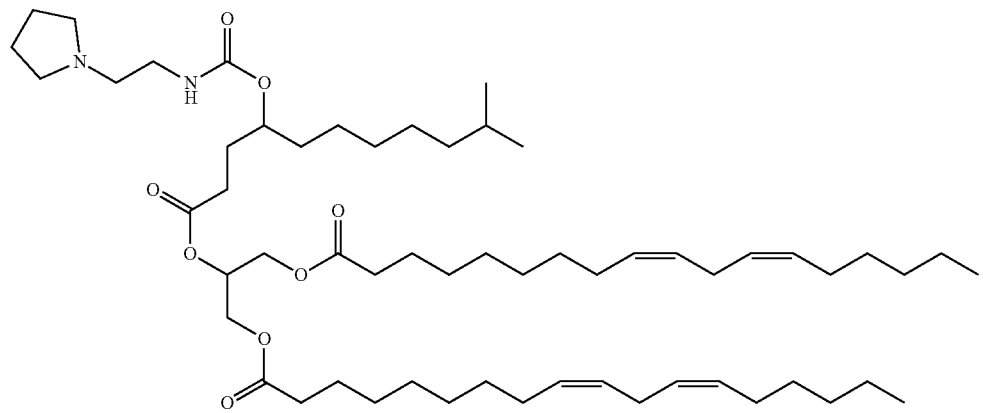

Compound 83 was prepared in 87% yield from Intermediate 81f and 2-(pyrrolidin-1-yl)ethan-1-amine using the method employed for Example 1. $^1$H NMR (400 MHz, CDCl$_3$) δ 5.99 (s, 1H), 5.45-5.19 (m, 9H), 4.76 (s, 1H), 4.28 (ddd, J=11.9, 4.5, 3.2 Hz, 2H), 4.15 (ddd, J=11.9, 5.8, 4.7 Hz, 2H), 3.50 (d, J=6.3 Hz, 2H), 2.99 (s, 5H), 2.81-2.73 (m, 4H), 2.39 (ddd, J=8.2, 6.9, 1.8 Hz, 2H), 2.35-2.28 (m, 4H), 2.05 (q, J=6.8 Hz, 8H), 2.02-1.77 (m, 7H), 1.66-1.43 (m, 8H), 1.41-1.20 (m, 35H), 1.14 (d, J=6.7 Hz, 2H), 0.95-0.81 (m, 12H). MS: 956.5 m/z [M+H].

Example 84—Compound 84

Compound 84: 2-((4-(((1-methylazetidin-3-yl)carbamoyl)oxy)decanoyl)oxy)propane-1,3-diyl (9Z,9'Z,12Z,12'Z)-bis(octadeca-9,12-dienoate)

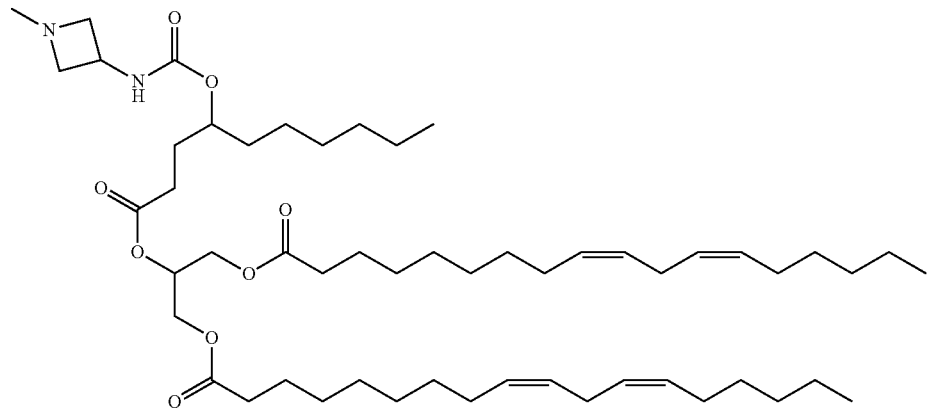 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)NC1CN(C)C1]

Compound 84 was prepared in 87% yield from Intermediate 40d and 1-methylazetidin-3-amine using the method employed for Example 1. $^1$H NMR (500 MHz, CDCl$_3$) δ 5.44-5.28 (m, 8H), 5.23 (p, J=5.2 Hz, 1H), 4.77 (d, J=7.0 Hz, 1H), 4.46 (s, 1H), 4.28 (dt, J=10.9, 5.2 Hz, 2H), 4.16 (ddd, J=8.7, 5.6, 2.8 Hz, 2H), 3.99 (s, 2H), 3.81 (s, 2H), 2.77 (t, J=6.7 Hz, 4H), 2.65 (s, 2H), 2.40-2.29 (m, 6H), 2.05 (q, J=7.0 Hz, 8H), 1.93 (dtd, J=15.1, 7.6, 3.8 Hz, 1H), 1.83 (q, J=7.4 Hz, 1H), 1.66-1.44 (m, 7H), 1.40-1.17 (m, 37H), 0.88 (q, J=7.0 Hz, 9H). MS: 900.4 m/z [M+H].

Example 85—Compound 85

Intermediate 85a: benzyl 4-hydroxyoctanoate

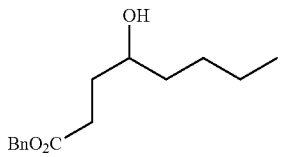

To a solution of 5-butyltetrahydrofuran-2-one (20 g, 1.0 equiv.) in H$_2$O (50 mL) was added NaOH (5.63 g, 1.0 equiv.). The mixture was stirred at 25° C. for 12 h. Upon completion, the reaction mixture was concentrated under reduced pressure to remove H$_2$O.

The resulting residue was reconstituted in DMF (100 mL) followed by the addition of BnBr (14.08 g, 1.0 equiv.). The mixture was stirred at 25° C. for 2 h. The reaction mixture was then concentrated under reduced pressure to remove DMF. The residue was diluted with H$_2$O (150 mL) and extracted with 3× with EtOAc, dried over Na$_2$SO$_4$, and filtered and the filtrate was concentrated under reduced pressure to give a residue. The residue was purified by column chromatography to afford product as a yellow oil (15 g, 43%).

Intermediate 85b: benzyl 4-(((4-nitrophenoxy)carbonyl)oxy)octanoate

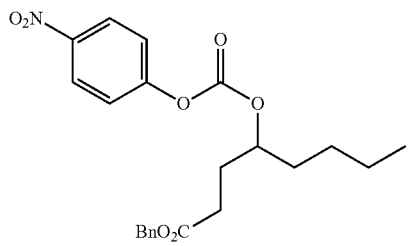

A mixture of Intermediate 85a (15 g, 1.0 equiv.) in DCM (150 mL) was added (4-nitrophenyl) carbonochloridate (32.21 g, 5.0 equiv.) under N$_2$, and then pyridine (5.16 mL, 2.0 equiv.) was added to the mixture. The reaction mixture was stirred at 20° C. for 1 h under N$_2$ atmosphere. The reaction mixture was concentrated under reduced pressure to remove solvent. The residue was diluted with hexanes and filtered. The filtrate was washed with 3× with H$_2$O. The organic layer was washed with 1× with brine, dried over Na$_2$SO$_4$, and filtered, and the filtrate was concentrated under reduced pressure to give a residue. The residue was purified by column chromatography to afford product as a colorless oil (12 g, 48%). $^1$H NMR (400 MHz, CDCl$_3$) δ 8.31-8.17 (m, 2H), 7.42-7.30 (m, 6H), 5.13 (s, 2H), 4.87 (qd, J=7.6, 4.8 Hz, 1H), 2.50 (t, J=7.4 Hz, 2H), 2.11 (dtd, J=15.3, 7.8, 4.0 Hz, 1H), 2.00 (dt, J=14.7, 7.6 Hz, 1H), 1.82-1.69 (m, 1H), 1.63 (ddt, J=14.3, 8.5, 5.0 Hz, 1H), 1.45-1.27 (m, 4H), 1.01-0.83 (m, 3H).

Intermediate 85c: benzyl 4-(((2-(pyrrolidin-1-yl)ethyl)carbamoyl)oxy)octanoate

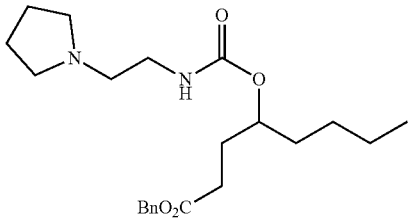

To a solution of Intermediate 85b (4 g, 2.0 equiv.) and 2-pyrrolidin-1-ylethanamine (550 mg, 1.0 equiv.) in MeCN (20 mL) was added DMAP (59 mg, 0.1 equiv.), then pyridine (1.17 mL, 3.0 equiv.) at 0° C. The mixture was stirred at 20° C. for 12 h under N$_2$ atmosphere. The reaction mixture was concentrated under reduced pressure to remove MeCN (20 mL). The residue was diluted with H$_2$O and extracted 3× with EtOAc. The combined organic layers were concentrated under reduced pressure to give a residue. The residue was purified by column chromatography to afford product as a colorless oil (1.8 g, 48%). $^1$H NMR (400 MHz, CDCl$_3$) δ 7.32-7.23 (m, 5H), 5.03 (d, J=10.2 Hz, 3H), 4.69 (s, 1H), 3.23 (dq, J=18.7, 5.9 Hz, 3H), 2.70 (s, 2H), 2.60-2.40 (m, 7H), 2.34 (td, J=8.3, 7.6, 2.7 Hz, 2H), 1.87 (d, J=10.5 Hz, 1H), 1.70 (t, J=3.8 Hz, 6H), 1.44 (d, J=24.4 Hz, 2H), 1.22 (q, J=11.9 Hz, 4H), 0.80 (t, J=4.2 Hz, 3H).

Compound 85: 2-((4-(((2-(pyrrolidin-1-yl)ethyl)
carbamoyl)oxy)octanoyl)oxy)propane-1,3-diyl (9Z,
9'Z,12Z,12'Z)-bis(octadeca-9,12-dienoate)

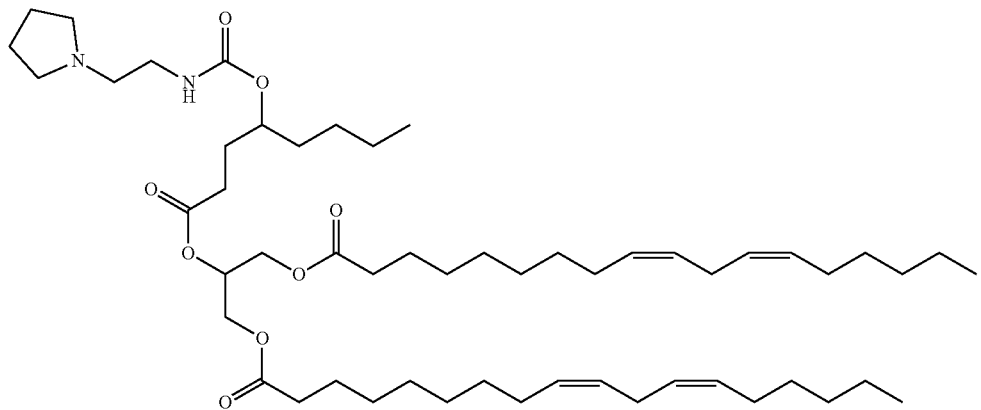 [SMILES: CCCCC/C=C\C/C=C\CCCCCCCC(=O)OCC(COC(=O)CCCCCCC/C=C\C/C=C\CCCCC)OC(=O)CCC(CCCC)OC(=O)NCCN1CCCC1]

To a solution of Intermediate 85c (1.8 g, 1.0 equiv.) in THF (9 mL) was added Pd/C (0.5 g, 10% w/w) under Ar atmosphere. The mixture was purged with 3× H2, and then the mixture was stirred at 20° C. for 5 h under H2 atmosphere (15 Psi). The reaction mixture was filtered and the filtrate was concentrated under reduced pressure to remove THF.

The resulting crude material was dissolved in DCM (10 mL), followed by the addition of DMAP (65 mg, 0.16 equiv.), DIPEA (1.74 mL, 3.0 equiv.), and EDCI (638 mg, 1.0 equiv.). Then, Intermediate 1c (2.05 g, 1.0 equiv.) was added at 0'° C. The mixture was stirred at 20° C. for 16 h under $N_2$ atmosphere. The reaction mixture was concentrated under reduced pressure to remove DCM. The residue was diluted with $H_2O$ and extracted 2× with EtOAc. The combined organic layers were concentrated under reduced pressure to give a residue. The residue was purified by column chromatography to afford product as a colorless oil (1.1 g, 50%). $^1$H NMR (400 MHz, CDCl$_3$) δ 5.39-5.21 (m, 7H), 5.18 (p, J=5.0 Hz, 1H), 5.09 (s, 1H), 4.76-4.65 (m, 1H), 4.22 (dd, J=12.0, 4.4 Hz, 2H), 4.08 (ddd, J=11.9, 5.9, 3.4 Hz, 2H), 3.21 (q, J=5.9 Hz, 2H), 2.70 (t, J=6.4 Hz, 4H), 2.51 (t, J=6.1 Hz, 2H), 2.43 (d, J=5.8 Hz, 4H), 2.32 (ddd, J=8.9, 6.6, 3.9 Hz, 2H), 2.25 (t, J=7.6 Hz, 4H), 1.98 (q, J=6.9 Hz, 7H), 1.91-1.66 (m, 6H), 1.63-1.35 (m, 8H), 1.25 (tq, J=7.2, 4.6, 3.6 Hz, 30H), 0.82 (t, J=6.7 Hz, 9H). MS: 900.4 m/z [M+H].

Example 86—Compound 86

Intermediate 86a: ethyl
1-nonanoylcyclopropane-1-carboxylate

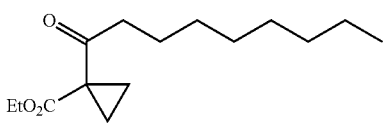 [SMILES: CCCCCCCCC(=O)C1(C(=O)OCC)CC1]

To a solution of diethyl cyclopropane-1,1-dicarboxylate (15 g, 1.0 equiv.) in THF (200 mL) was added a solution of bromo(octyl)magnesium (2 M, 40.28 mL, 1.0 equiv.) dropwise at −78° C. under $N_2$. The reaction mixture was stirred at −78° C. for 5 h under $N_2$ atmosphere. The reaction mixture was poured into aq. $NH_4Cl$. The aqueous phase was extracted 3× with ethyl acetate. The combined organic phase was washed with brine, dried with anhydrous $Na_2SO_4$, filtered and the filtrate was concentrated in vacuum. The residue was purified with another batch by column chromatography to afford product as a colorless oil (20 g, 48%). $^1$H NMR (400 MHz, CDCl$_3$) δ 4.13 (q, J=7.1 Hz, 2H), 2.75 (t, J=7.4 Hz, 2H), 1.57-1.49 (m, 2H), 1.35 (s, 4H), 1.21 (dd, J=8.7, 5.5 Hz, 16H), 0.81 (t, J=6.9 Hz, 6H).

Intermediate 86b:
1-nonanoylcyclopropane-1-carboxylic acid

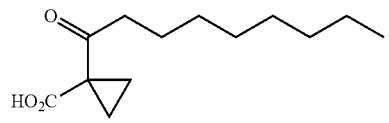 [SMILES: CCCCCCCCC(=O)C1(C(=O)O)CC1]

To a solution of Intermediate 86a (10 g, 1.0 equiv.) in EtOH (60 mL) and $H_2O$ (30 mL) was added NaOH (2.36 g, 1.5 equiv.) and LiOH (1.41 g, 1.5 equiv.) under $N_2$. Then the mixture was stirred at 20° C. for 12 h under $N_2$ atmosphere. The reaction mixture was concentrated under reduced pressure to give a residue. The residue was adjusted to pH=3 by adding 2 N HCl. Then the mixture was stirred at 20° C. for 1 h under $N_2$ atmosphere. The mixture was extracted 3× with EtOAc. The combined organic phase was washed with brine, dried with anhydrous $Na_2SO_4$, filtered and the filtrate was concentrated in vacuum. Product as collected as a colorless oil (5 g, 28%). $^1$H NMR (400 MHz, CDCl$_3$) δ 2.25 (t, J=7.3 Hz, 2H), 1.96 (q, J=4.4 Hz, 2H), 1.71 (q, J=4.4 Hz, 2H), 1.64-1.55 (m, 2H), 1.26 (d, J=3.7 Hz, 11H), 0.87 (t, J=6.8 Hz, 3H).

Intermediate 86c: 2-((1-nonanoylcyclopropane-1-carbonyl)oxy)propane-1,3-diyl (9Z,9'Z,12Z,12'Z)-bis(octadeca-9,12-dienoate)

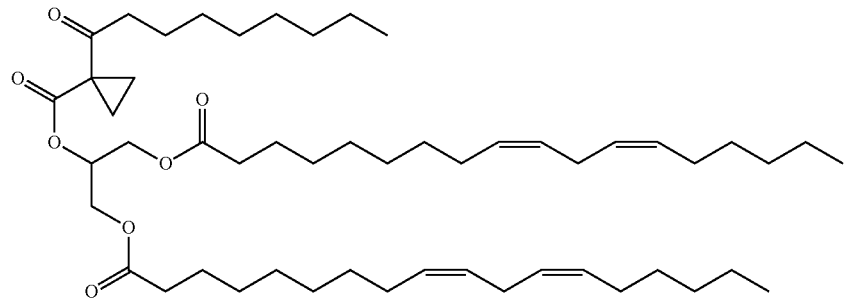 [SMILES: CCCCC/C=C\C/C=C\CCCCCCCC(=O)OCC(COC(=O)CCCCCCC/C=C\C/C=C\CCCCC)OC(=O)C1(C(=O)CCCCCCCC)CC1]

To a solution of Intermediate 86b (6 g, 1.0 equiv.), Int. 1C (16.36 g, 1.0 equiv.), EDCI (6.10 g, 1.5 equiv.), and DMAP (324 mg, 0.1 equiv.) in DCM (60 mL) was added $Et_3N$ (5.54 mL, 1.5 equiv.) at 0° C. The mixture was stirred at 20° C. for 12 h under $N_2$ atmosphere. Then it was poured into water and extracted 3× with EtOAc. The combined organic phase was washed with brine, dried with anhydrous $Na_2SO_4$, filtered and the filtrate was concentrated in vacuum to give a residue. The residue was purified by column chromatography to afford product as a colorless oil (8 g, 37%). $^1H$ NMR (400 MHz, $CDCl_3$) δ 5.28 (dtt, J=15.4, 10.8, 5.8 Hz, 8H), 4.26 (dd, J=12.1, 4.1 Hz, 2H), 4.08 (dd, J=12.0, 6.1 Hz, 2H), 2.76 (t, J=7.4 Hz, 2H), 2.70 (t, J=6.4 Hz, 4H), 2.24 (t, J=7.6 Hz, 4H), 1.98 (q, J=6.9 Hz, 8H), 1.54 (p, J=7.0 Hz, 9H), 1.43-1.33 (m, 4H), 1.33-1.15 (m, 40H), 0.85-0.79 (m, 9H).

Intermediate 86d: 2-((1-(1-hydroxynonyl)cyclopropane-1-carbonyl)oxy)propane-1,3-diyl (9Z,9'Z,12Z,12'Z)-bis(octadeca-9,12-dienoate)

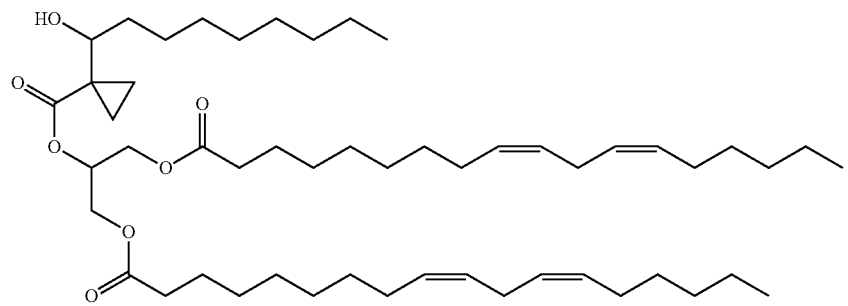 [SMILES: CCCCC/C=C\C/C=C\CCCCCCCC(=O)OCC(COC(=O)CCCCCCC/C=C\C/C=C\CCCCC)OC(=O)C1(C(O)CCCCCCCC)CC1]

A solution of Intermediate 86c (8 g, 1.0 equiv) in 4:2:1 THF/water/toluene (0.05-0.1 M) was cooled to 0-5° C., followed by the addition of $NaBH_4$ (5.0 equiv). The reaction was maintained at 0-25° C. for at least 2 h. The reaction was then diluted with water and EtOAc, and the resulting biphasic mixture was extracted 3× with EtOAc. The combined organic layers were dried over $Na_2SO_4$, filtered, and concentrated in vacuo. Crude material was purified by column chromatography (EtOAc/hexanes) to afford product as a colorless oil (4 g, 500%). $^1H$ NM/R (400 MHz, $CDCl_3$) δ 5.33 (tdq, J=20.3, 10.0, 5.6, 4.9 Hz, 9H), 4.28 (dt, J=12.0, 4.0 Hz, 2H), 4.15 (ddd, J=12.1, 8.0, 6.0 Hz, 2H), 3.18-3.12 (m, 1H), 2.77 (t, J=6.4 Hz, 4H), 2.68 (s, 1H), 2.31 (t, J=7.6 Hz, 4H), 2.05 (q, J=6.9 Hz, 8H), 1.68-1.48 (m, 9H), 1.40-1.16 (m, 43H), 0.98 (ddd, J=10.7, 6.7, 4.1 Hz, 1H), 0.93-0.84 (m, 9H), 0.81 (ddd, J=9.7, 6.8, 4.2 Hz, 1H).

Intermediate 86e: 2-((1-(1-(((4-nitrophenoxy)carbonyl)oxy)nonyl)cyclopropane-1-carbonyl)oxy)propane-1,3-diyl (9Z,9'Z,12Z,12'Z)-bis(octadeca-9,12-dienoate)

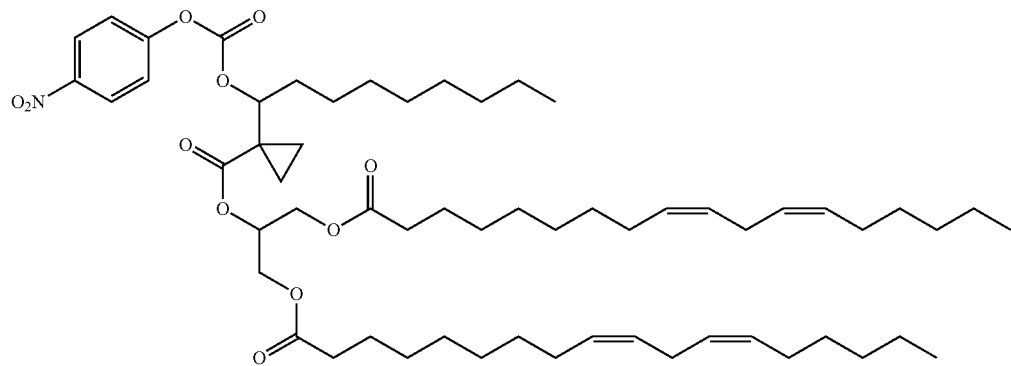 [SMILES: CCCCC/C=C\C/C=C\CCCCCCCC(=O)OCC(COC(=O)CCCCCCC/C=C\C/C=C\CCCCC)OC(=O)C1(C(CCCCCCCC)OC(=O)Oc2ccc([N+](=O)[O-])cc2)CC1]

To a solution of Intermediate 86d (4 g, 1.0 equiv.) in DCM (40 mL) was added (4-nitrophenyl) carbonochloridate (1.95 g, 2.0 equiv.), pyridine (781 uL, 2.0 equiv.) at 0° C. Then the reaction mixture was stirred at 20° C. for 5 h under $N_2$ atmosphere. The reaction mixture was concentrated under reduced pressure to remove solvent. The residue was reconstitituted in petroleum ether and filtered. The filtrate was washed with $H_2O$. The combined organic layers were washed with brine, dried over anhydrous $Na_2SO_4$, filtered and the filtrate was concentrated under reduced pressure to give a residue. The residue was purified by column chromatography to afford product (2.8 g, 59%) as a colorless oil. $^1$H NMR (400 MHz, $CDCl_3$) δ 8.25-8.16 (m, 2H), 7.36-7.26 (m, 2H), 5.27 (tdd, J=17.5, 8.5, 4.0 Hz, 9H), 4.84 (dd, J=9.1, 4.4 Hz, 1H), 4.24 (dt, J=11.9, 3.8 Hz, 2H), 4.08 (dd, J=11.8, 5.8 Hz, 2H), 2.70 (t, J=6.3 Hz, 4H), 2.23 (t, J=7.6 Hz, 4H), 2.02-1.93 (m, 8H), 1.82 (qd, J=9.4, 4.9 Hz, 1H), 1.69 (ddt, J=14.4, 10.0, 5.1 Hz, 1H), 1.53 (t, J=7.2 Hz, 5H), 1.35-1.16 (m, 41H), 1.07-1.01 (m, 1H), 0.95-0.89 (m, 1H), 0.81 (td, J=6.8, 3.8 Hz, 9H).

Compound 86: 2-((1-(1-(((2-(ethyl(methyl)amino)ethyl)carbamoyl)oxy)nonyl)cyclopropane-1-carbonyl)oxy)propane-1,3-diyl (9Z,9'Z,12Z,12'Z)-bis(octadeca-9,12-dienoate)

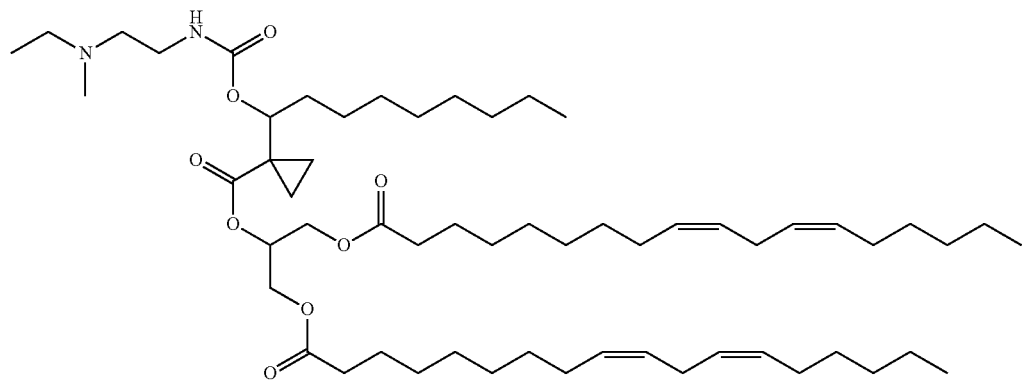 [SMILES: CCCCC/C=C\C/C=C\CCCCCCCC(=O)OCC(COC(=O)CCCCCCC/C=C\C/C=C\CCCCC)OC(=O)C1(C(CCCCCCCC)OC(=O)NCCN(C)CC)CC1]

Compound 86 was synthesized in 90% yield from Intermediate 86e and N1-ethyl-N1-methylethane-1,2-diamine using the method employed in Example 1. ¹H NMR (400 MHz, CDCl₃) δ 5.53-5.22 (m, 9H), 4.75 (dd, J=8.7, 4.5 Hz, 1H), 4.29 (ddd, J=22.5, 11.8, 4.3 Hz, 2H), 4.14 (dd, J=11.9, 5.9 Hz, 2H), 3.30 (s, 2H), 2.77 (t, J=6.5 Hz, 4H), 2.54 (d, J=13.7 Hz, 4H), 2.38-2.21 (m, 7H), 2.05 (q, J=6.7 Hz, 8H), 1.60 (t, J=7.4 Hz, 4H), 1.40-1.17 (m, 40H), 1.12-1.00 (m, 4H), 0.91-0.85 (m, 9H). MS: 956.1 m/z [M+H].

Example 87—Compound 87

Intermediate 87a:
5-hydroxy-1-methyl-5-octylpyrrolidin-2-one

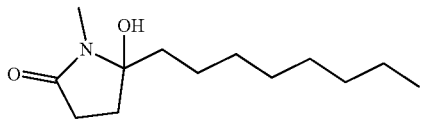 [SMILES: CCCCCCCCC1(O)CCC(=O)N1C]

To a solution of 1-methylpyrrolidine-2,5-dione (20 g, 1.0 equiv.) in THE (150 mL) was added bromo(octyl)magnesium (1 M, 265 mL, 1.5 equiv.) drop wise at 15° C. under N₂. The mixture was stirred at 15° C. for 12 h under N₂. The reaction mixture was quenched by addition NH₄Cl at 0° C. Then it was diluted with H₂O and extracted 3× with EtOAc. The combined organic layers were concentrated under reduced pressure to give a residue. The residue was purified by column chromatography to afford product as a white solid (20 g, 50%). ¹H NMR (400 MHz, CDCl₃) δ 3.75 (s, 1H), 2.68 (s, 3H), 2.43 (ddd, J=16.4, 10.0, 6.4 Hz, 1H), 2.24 (ddd, J=16.7, 10.0, 4.5 Hz, 1H), 2.13 (ddd, J=13.6, 10.0, 6.4 Hz, 1H), 1.93 (ddd, J=14.0, 10.0, 4.7 Hz, 1H), 1.73 (td, J=13.4, 3.7 Hz, 1H), 1.65-1.53 (m, 1H), 1.35-1.07 (m, 12H), 0.88-0.76 (m, 3H).

Intermediate 87b:
4-hydroxy-N-methyldodecanamide

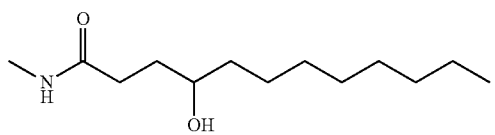 [SMILES: CCCCCCCCC(O)CCC(=O)NC]

To a solution of Intermediate 87a (15 g, 1.0 equiv.) in MeOH (150 mL) was added NaBH₄ (4.99 g, 2.0 equiv.) portion wise. The mixture was stirred at 15° C. for 1 h. The reaction mixture was quenched by addition NH₄Cl at 0° C., and then it was diluted with H₂O and extracted 3× with EtOAc. The combined organic layers were concentrated under reduced pressure to give a residue. The residue was purified by column chromatography to afford product as a white solid (8 g, 53%). ¹H NMR (400 MHz, CDCl₃) δ 5.93 (s, 1H), 3.60-3.50 (m, 1H), 3.11 (s, 1H), 2.73 (d, J=4.8 Hz, 3H), 2.36-2.20 (m, 2H), 1.78 (dddd, J=14.3, 7.7, 6.5, 3.1 Hz, 1H), 1.58 (ddt, J=13.8, 8.9, 6.7 Hz, 1H), 1.46-1.09 (m, 14H), 0.87-0.77 (m, 3H).

Intermediates 87c:
(R)-4-hydroxy-N-methyldodecanamide

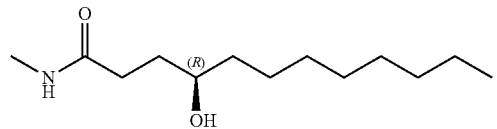

To a solution of Intermediate 87b (1.0 equiv.) in Et₂O (0.2-1 M) was added Novozym 435 (0.89 equiv.) and vinyl acetate (2.0 equiv.). The mixture was stirred at 40° C. for 96 h. The reaction mixture was concentrated under reduced pressure to give a residue, which was purified by column chromatography. The material collected from the column was subject to the reaction conditions above three additional times to afford (R)-88c as a yellow solid (24% yield). ¹H NMR (400 MHz, CDCl₃) δ 5.57 (s, 1H), 3.54 (tt, J=7.7, 3.6 Hz, 1H), 2.74 (d, J=4.8 Hz, 3H), 2.64 (d, J=4.6 Hz, 1H), 2.28 (td, J=6.9, 3.2 Hz, 2H), 1.79 (dtd, J=14.3, 7.0, 3.1 Hz, 1H), 1.60 (ddd, J=14.3, 8.8, 6.8 Hz, 2H), 1.47-1.12 (m, 14H), 0.87-0.74 (m, 3H).

Intermediate 87d:
(R)-5-octyldihydrofuran-2(3H)-one

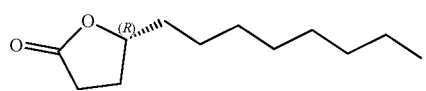

To a solution of Intermediate 87d (1.0 equiv.) in MeOH (0.1-1.0 M) was added NaOH (10 equiv.). The mixture was stirred at 80° C. for at least 2 h, after which point HCl (1-2 M, 10.0 equiv.) was added, and the mixture was stirred at 25° C. for 1 h. The reaction mixture was then diluted with H₂O and extracted 3× with EtOAc. The combined organic layers were concentrated under reduced pressure to give a residue. The residue was purified by column chromatography to afford product as a yellow oil. ¹H NMR (400 MHz, CDCl₃) δ 4.41 (p, J=6.9 Hz, 1H), 2.46 (dd, J=9.5, 6.8 Hz, 2H), 2.25 (dq, J=13.4, 6.7 Hz, 1H), 1.78 (dq, J=12.7, 9.3 Hz, 1H), 1.72-1.62 (m, 1H), 1.60-1.47 (m, 1H), 1.45-1.10 (m, 14H), 0.81 (t, J=6.6 Hz, 3H).

Intermediate 87e: (R)-4-hydroxydodecanoic acid

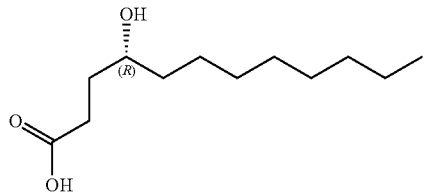

To a solution of Intermediate 87d (1.0 equiv.) in H₂O (0.1-0.5 M) was added NaOH (1.0-1.5 equiv.). The mixture was stirred at 20° C. for at least 12 h. The reaction mixture was concentrated under reduced pressure to afford a residue. The residue was used directly in the next step without additional purification.

Intermediate 88f: benzyl (R)-4-hydroxydodecanoate

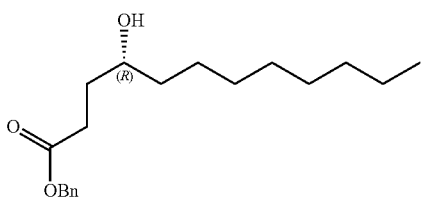

To a solution of Intermediate 87e (1.0 equiv.) in acetone (0.3 M) was added BnBr (1.0-1.5 equiv.) and TBAB (0.05 equiv.). The mixture was stirred at 60° C. for at least 12 h. The reaction mixture was concentrated under reduced pressure to give a residue. The residue was either (1) purified by column chromatography, or (2) diluted with sat. NaHCO$_3$, extracted 3× with EtOAc, dried over Na$_2$SO$_4$, filtered, and concentrated before being purified by column chromatography. Both methods afforded product as a yellow oil (54% yield).

Intermediate 87g: benzyl (R)-4-(((4-nitrophenoxy)carbonyl)oxy)dodecanoate

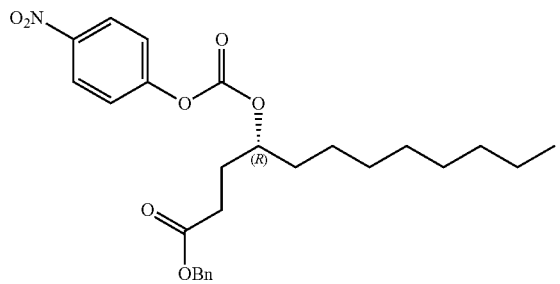

To a solution of Intermediate 87f (1.0 equiv.) and (4-nitrophenyl) carbonochloridate (3.0 equiv.) in DCM (0.3-1.2 M) was added pyridine (3.0 equiv.) at 0-20° C. The mixture was stirred at 20° C. for at least 1 h. The reaction mixture was concentrated under reduced pressure to give a residue. The residue was either (1) purified by column chromatography, or (2) used in the next step without additional purification. Product was collected as a pale yellow oil (36%). $^1$H NMR (400 MHz, CDCl$_3$) δ 8.22-8.13 (m, 2H), 7.29 (d, J=2.0 Hz, 2H), 5.06 (s, 2H), 4.80 (tt, J=7.6, 4.5 Hz, 1H), 2.43 (t, J=7.5 Hz, 2H), 2.04 (ddt, J=15.3, 7.8, 3.9 Hz, 1H), 1.92 (dq, J=14.8, 7.4 Hz, 1H), 1.71-1.61 (m, 1H), 1.55 (ddd, J=14.3, 9.1, 5.2 Hz, 1H), 1.36-1.13 (m, 11H), 0.81 (t, J=6.6 Hz, 3H).

Intermediate 87h: benzyl (R)-4-(((2-(ethyl(methyl)amino)ethyl)carbamoyl)oxy)dodecanoate

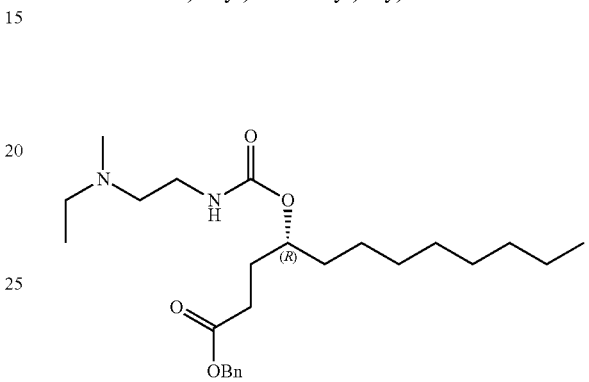

To a solution of Intermediate 87g (1.0 equiv.) and N'-ethyl-N'-methyl-ethane-1,2-diamine (3.0 equiv.) in MeCN (0.1-0.2 M) was added pyridine (3.0 equiv.) and DMAP (1.0 equiv.). The mixture was stirred at 20° C. for 12 h. The reaction mixture was then concentrated under reduced pressure to give a residue. The residue was purified by column chromatography to afford product as a yellow oil (88%). $^1$H NMR (400 MHz, CDCl$_3$) δ 7.60-7.23 (m, 5H), 5.04 (s, 2H), 4.77-4.64 (m, 1H), 3.15 (t, J=6.0 Hz, 2H), 2.36 (ddt, J=12.3, 8.2, 4.3 Hz, 5H), 2.13 (s, 3H), 1.96-1.70 (m, 3H), 1.55-1.33 (m, 2H), 1.29-1.10 (m, 13H), 0.96 (t, J=7.1 Hz, 3H), 0.80 (t, J=6.7 Hz, 4H).

Compound 87: 2-(((R)-4-(((2-(ethyl(methyl)amino)ethyl)carbamoyl)oxy)dodecanoyl)oxy)propane-1,3-diyl (9Z,9'Z,12Z,12'Z)-bis(octadeca-9,12-dienoate)

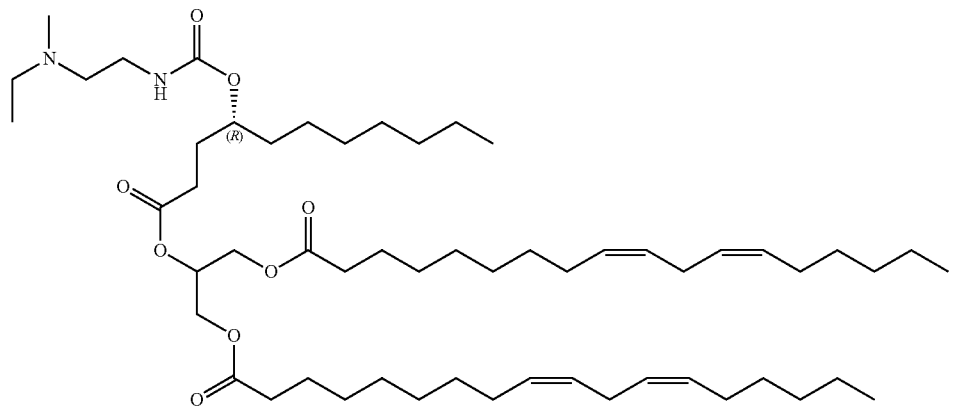

To a solution of Intermediate 87h (1.0 equiv.) in THF (0.1-0.3 M) was added Pd/C (10% w/w, 1.0 equiv.). The mixture was stirred at 15-20° C. for 5 h under H2 (15 Psi). Upon completion, the reaction mixture was filtered and concentrated under reduced pressure to give a residue.

To a solution of the residue and Intermediate 1c (1.0 equiv.) in DCM (10 mL) was added EDCI (1.0 equiv.), DMAP (0.1 equiv.) and Et₃N (1.05 equiv.). The mixture was stirred at 15-20° C. for at least 12 h. The reaction mixture was concentrated under reduced pressure to remove DCM. The residue was diluted with H₂O and extracted with 3× with EtOAc. The combined organic layers were dried over Na₂SO₄, filtered, and the filtrate was concentrated under reduced pressure to give a residue. The residue was purified by column chromatography to afford product as a pale yellow oil (61%). ¹H NMR (400 MHz, CDCl₃) δ 5.40-5.14 (m, 8H), 5.08 (s, 1H), 4.69 (s, 1H), 4.21 (dd, J=11.9, 4.4 Hz, 2H), 4.08 (ddd, J=12.0, 5.9, 3.3 Hz, 2H), 3.17 (q, J=6.0 Hz, 2H), 2.70 (t, J=6.4 Hz, 4H), 2.43-2.28 (m, 5H), 2.24 (t, J=7.6 Hz, 4H), 2.14 (s, 3H), 1.98 (q, J=6.8 Hz, 7H), 1.79 (ddd, J=42.6, 15.1, 7.5 Hz, 3H), 1.53 (q, J=7.6 Hz, 8H), 1.33-1.06 (m, 37H), 0.97 (t, J=7.1 Hz, 3H), 0.81 (q, J=6.3 Hz, 9H). MS: 944.1 m/z [M+H].

Example 88—Compound 88

Intermediate 88a:
(S)-1-(methylamino)-1-oxododecan-4-yl acetate

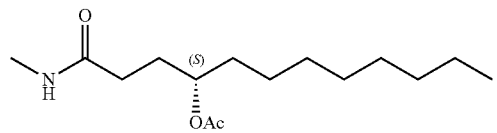

Intermediate 88a was synthesized in 23% yield from Intermediate 87b using the method employed for Intermediate 87c. ¹H NMR (400 MHz, CDCl₃) δ 5.81 (s, 1H), 4.79 (tq, J=8.5, 3.8 Hz, 1H), 2.73 (d, J=4.8 Hz, 3H), 2.17-2.03 (m, 2H), 1.98 (s, 3H), 1.95-1.63 (m, 3H), 1.56-1.36 (m, 2H), 1.19 (d, J=8.4 Hz, 11H), 0.81 (t, J=6.8 Hz, 3H).

Intermediate 88b:
(S)-5-octyldihydrofuran-2(3H)-one

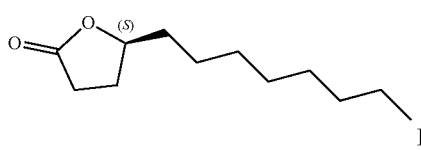

Intermediate 88b was prepared from Intermediate 88a using the method employed for Intermediate 87d.

Intermediate 88c: benzyl (S)-4-hydroxydodecanoate

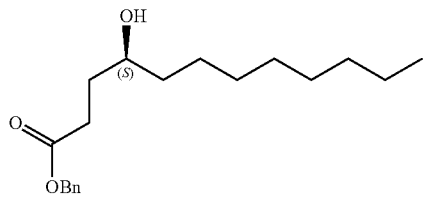

Intermediate 88c was prepared from Intermediate 88b using the methods employed for Intermediate 87e and 87f.

Intermediate 88d: benzyl (S)-4-(((4-nitrophenoxy)carbonyl)oxy)dodecanoate

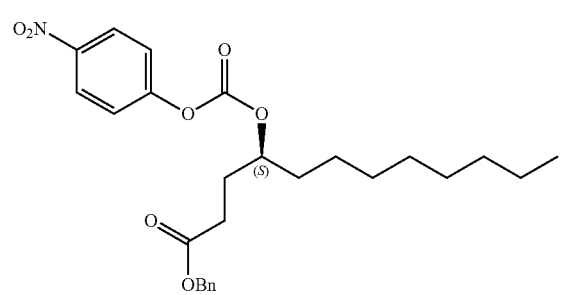

Intermediate 88d was prepared from Intermediate 88c using the method employed for Intermediate 88g.

Intermediate 88e: benzyl (S)-4-(((2-(ethyl(methyl)amino)ethyl)carbamoyl)oxy)dodecanoate

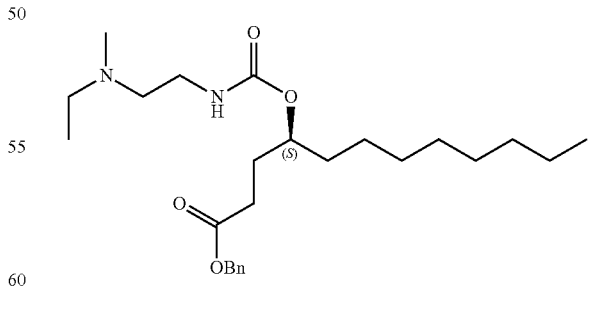

Intermediate 88e was synthesized in 47% yield from Intermediate 88e using the method employed for Intermediate 87h.

Compound 88: 2-(((S)-4-(((2-(ethyl(methyl)amino)ethyl)carbamoyl)oxy)dodecanoyl)oxy)propane-1,3-diyl (9Z,9'Z,12Z,12'Z)-bis(octadeca-9,12-dienoate)

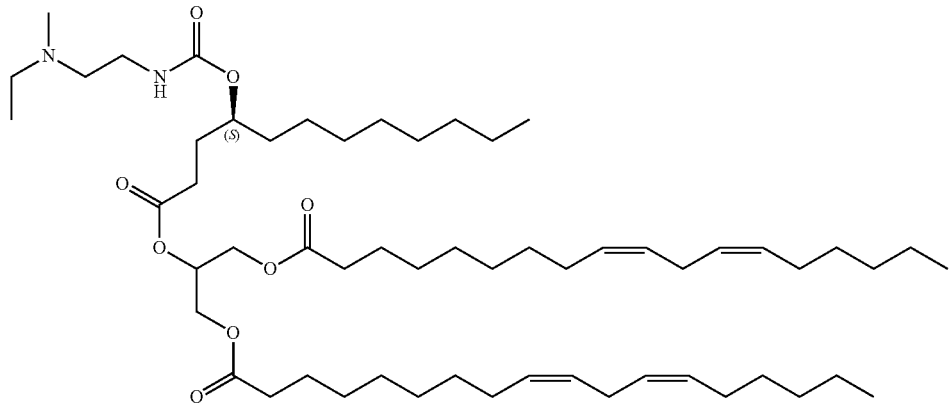

Compound 88 was synthesized in 42% yield from Intermediate 88d using the method employed in Compound 87.

Example 89—Compound 89

Intermediate 89a: 4-hydroxy-N-methyldecanamide

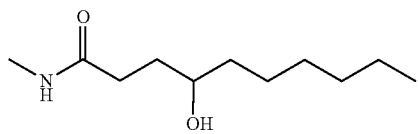

To a mixture of methanamine hydrochloride (19.83 g, 2.0 equiv.) in DCM (250 mL) was added AlMe$_3$ (2 M, 152.72 mL, 2.08 equiv.) drop-wise at 0° C. under N$_2$. The mixture was stirred at 0° C. for 2 h under N$_2$ atmosphere. This solution was then added drop-wise to a solution of 5-hexyltetrahydrofuran-2-one (25 g, 1.0 equiv.) in DCM (100 ml) under N$_2$. The mixture was stirred at 20° C. for 12 h under N$_2$ atmosphere. The reaction mixture was quenched by adding HCl (1 N) at 0° C. The organic layer was separated and the aqueous layer was extracted 3× with DCM. The combined organic phase was washed 3× with brine, dried with anhydrous Na$_2$SO$_4$, filtered and the filtrate was concentrated in vacuum. The residue was purified by column chromatography to afford product as a white solid (67%). $^1$H NMR (400 MHz, CD$_3$OD) δ 3.50 (td, J=7.7, 3.8 Hz, 1H), 2.70 (s, 3H), 2.29 (ddt, J=25.9, 16.6, 6.8 Hz, 2H), 1.77 (dddd, J=13.3, 9.2, 6.8, 3.9 Hz, 1H), 1.66-1.55 (m, 1H), 1.42 (h, J=4.0 Hz, 3H), 1.39-1.25 (m, 8H), 0.95-0.87 (m, 3H).

Intermediate 89b: (S)-1-(methylamino)-1-oxodecan-4-yl acetate

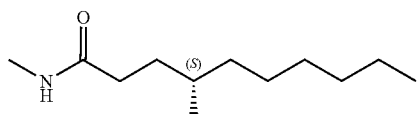

Intermediate 89b was synthesized in 23% yield using the method employed in Intermediate 87c. $^1$H NMR (400 MHz, CDCl$_3$) δ 5.70 (s, 1H), 4.79 (tt, J=8.4, 4.4 Hz, 1H), 2.74 (d, J=4.8 Hz, 3H), 2.11 (dp, J=21.3, 7.7, 7.2 Hz, 2H), 1.98 (s, 3H), 1.86 (tdd, J=13.6, 6.7, 3.2 Hz, 1H), 1.81-1.70 (m, 1H), 1.45 (ddp, J=19.0, 13.6, 6.6, 6.1 Hz, 2H), 1.27-1.12 (m, 8H), 0.80 (t, J=6.7 Hz, 3H).

Intermediate 89c: (S)-5-hexyldihydrofuran-2(3H)-one

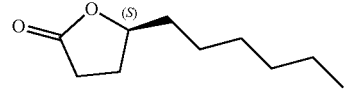

Intermediate 89c was synthesized in 78% yield from Intermediate 89b using the method employed in Intermediate 87d. $^1$H NMR (400 MHz, CDCl$_3$) δ 4.48 (ddd, J=13.7, 7.5, 5.6 Hz, 1H), 2.52 (dd, J=9.5, 6.9 Hz, 2H), 2.31 (dq, J=13.4, 6.7 Hz, 1H), 1.91-1.80 (m, 1H), 1.80-1.68 (m, 1H), 1.58 (dq, J=13.8, 5.2 Hz, 1H), 1.51-1.21 (m, 8H), 0.87 (t, J=6.6 Hz, 3H).

Intermediate 89d: benzyl (S)-4-hydroxydecanoate

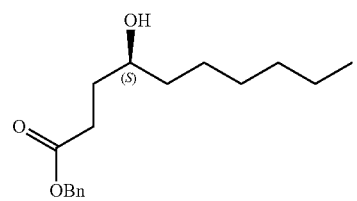

To a solution of Intermediate 89c (3 g, 1.0 equiv.) in EtOH (25 mL) and H$_2$O (5 mL) was added NaOH (1.1 equiv.) under N$_2$. Then the mixture was stirred at 20° C. for 12 h under N$_2$ atmosphere. The reaction mixture was concentrated under reduced pressure to remove solvent.

The resulting residue was subjected to the method employed in Intermediate 87f to afford product as a colorless oil (3 g, 50%).

437

Intermediate 89e: benzyl (S)-4-(((4-nitrophenoxy) carbonyl)oxy)decanoate

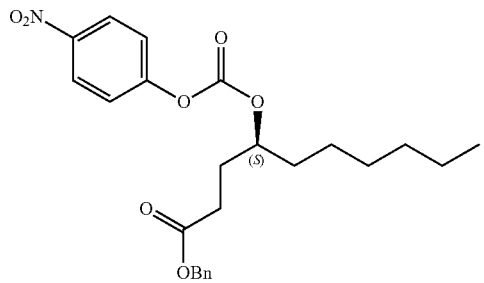

To a solution of Intermediate 89d (3 g, 1.0 equiv.) in DCM (30 mL) was added (4-nitrophenyl) carbonochloridate (3.26 g, 1.5 equiv.) under $N_2$. Then pyridine (1.74 mL, 2.0 equiv.) was added to the mixture at 0° C. The reaction mixture was stirred at 20° C. for 1 h under $N_2$ atmosphere. The reaction mixture was concentrated under reduced pressure to remove solvent to give a residue. The residue was diluted with hexanes and filtered. The filtrate was washed 3× with $H_2O$. The combined organic layers were washed with brine, dried over $Na_2SO_4$, filtered and the filtrate was concentrated under reduced pressure to give a residue. The residue was purified by column chromatography to afford product as a colorless oil (2 g, 42%). $^1$H NMR (400 MHz, $CD_3OD$) δ 8.23-8.13 (m, 2H), 7.37-7.18 (m, 7H), 5.39 (s, 1H), 5.03 (s, 2H), 4.47 (s, 1H), 4.00 (q, J=7.1 Hz, 2H), 2.42 (t, J=7.1 Hz, 2H), 2.00 (ddt, J=15.0, 7.6, 3.8 Hz, 1H), 1.85 (dt, J=14.7, 7.3 Hz, 1H), 1.57 (ddt, J=21.1, 14.0, 6.8 Hz, 2H), 1.35-1.16 (m, 8H), 0.91-0.75 (m, 3H).

438

Intermediate 89f: benzyl (S)-4-(((2-(pyrrolidin-1-yl) ethyl)carbamoyl)oxy)decanoate

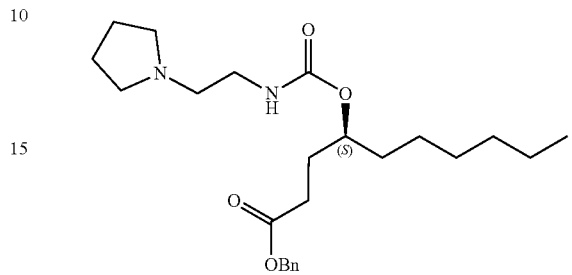

To a solution of Intermediate 89e (1.5 g, 1.0 equiv.) in MeCN (15 mL) was added 2-pyrrolidin-1-ylethanamine (1.16 g, 3.0 equiv.), pyridine (819 uL, 3.0 equiv.), DMAP (413 mg, 1.0 equiv.) under $N_2$. The mixture was stirred at 20° C. for 5 h under $N_2$ atmosphere. The reaction mixture was concentrated under reduced pressure to remove solvent. The residue was diluted with EtOAc and washed 5× with 1 N $NaHCO_3$ and 3× with $H_2O$. The organic layer was dried over $Na_2SO_4$, filtered and the filtrate was concentrated under reduced pressure to give a residue. The residue was purified by column chromatography to afford product as a pale yellow oil (0.65 g, 41%). $^1$H NMR (400 MHz, $CD_3OD$) δ 7.41-7.26 (m, 5H), 5.11 (d, J=1.1 Hz, 2H), 4.73 (dd, J=10.9, 5.7 Hz, 1H), 3.26 (dd, J=6.7, 1.7 Hz, 2H), 2.79-2.57 (m, 7H), 2.41 (t, J=7.4 Hz, 2H), 1.99-1.74 (m, 7H), 1.53 (s, 3H), 1.36-1.24 (m, 9H), 0.92-0.86 (m, 3H).

Compound 89: 2-(((S)-4-(((2-(pyrrolidin-1-yl)ethyl) carbamoyl)oxy)decanoyl)oxy)propane-1,3-diyl (9Z, 9'Z,12Z,12'Z)-bis(octadeca-9,12-dienoate)

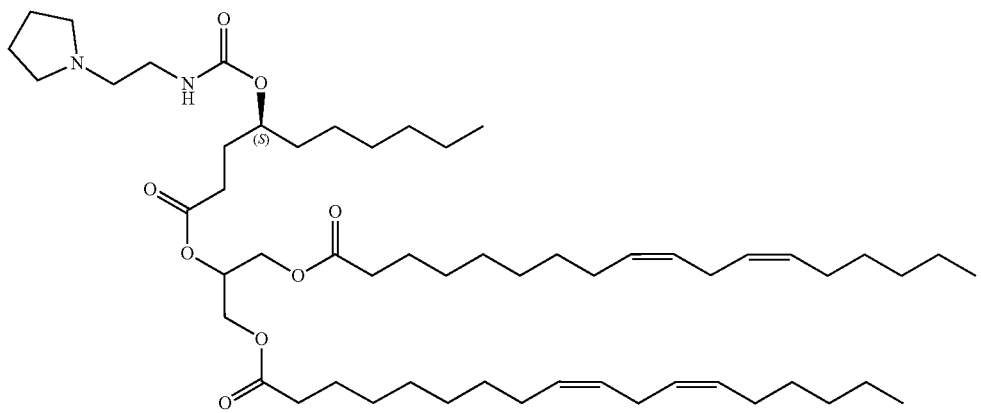

To a suspension of Pd/C (10% w/w, 1.0-3.0 equiv.) in THF (0.2-0.5 M) was added Intermediate 89f (1.0 equiv.). The mixture was stirred at 15-25° C. for at least 5 h under H2 atmosphere. The reaction mixture was filtered, and the filtrate was concentrated to give a residue. The residue was purified by column chromatography to afford product as a thick brown oil.

The brown oil was immediately reconstituted in DCM (0.2-0.5 M) followed by the addition of Intermediate 1c (1.0 equiv.), EDCI (1.2 equiv.), DMAP (0.1-0.2 equiv.) and Et$_3$N (1.5 equiv.) at 0° C. under N$_2$. The mixture was stirred at 20° C. for at least 12 h under N$_2$ atmosphere. The mixture was diluted with H$_2$O and extracted 3× with EtOAc. The combined organic phase was washed with brine, dried with anhydrous Na$_2$SO$_4$, filtered and the filtrate was concentrated in vacuum. The residue was purified by column chromatography to afford product as a colorless oil (23%). $^1$H NMR (400 MHz, CDCl$_3$) δ 5.49-5.22 (m, 8H), 5.18 (t, J=5.0 Hz, 1H), 5.08 (s, 1H), 4.69 (s, 1H), 4.22 (dd, J=11.9, 4.4 Hz, 2H), 4.12-4.04 (m, 2H), 3.28-3.15 (m, 2H), 2.70 (t, J=6.5 Hz, 4H), 2.50 (d, J=6.4 Hz, 2H), 2.44 (s, 3H), 2.32 (s, 2H), 2.25 (t, J=7.6 Hz, 4H), 1.98 (q, J=6.9 Hz, 8H), 1.83 (s, 1H), 1.70 (s, 5H), 1.38-0.94 (m, 37H), 0.81 (q, J=6.6 Hz, 9H). MS: 928.4 m/z [M+H].

Example 90—Compound 90

Intermediate 90a: benzyl (R)-4-hydroxydecanoate

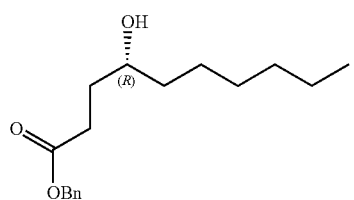

Intermediate 90a was synthesized in 27% yield from (5R)-5-hexyltetrahydrofuran-2-one using the method employed in Intermediate 89d.

Intermediate 90b: benzyl (R)-4-(((4-nitrophenoxy)carbonyl)oxy)decanoate

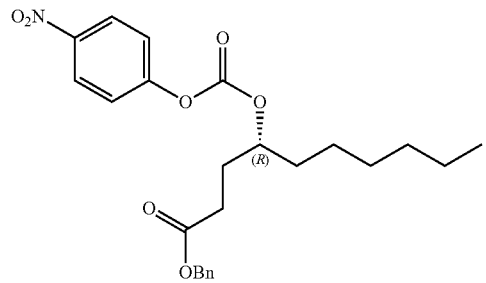

Intermediate 90b was synthesized in 57% yield from Intermediate 90a using the method employed in Intermediate 89e.

Intermediate 90c: benzyl (R)-4-(((2-(pyrrolidin-1-yl)ethyl)carbamoyl)oxy)decanoate

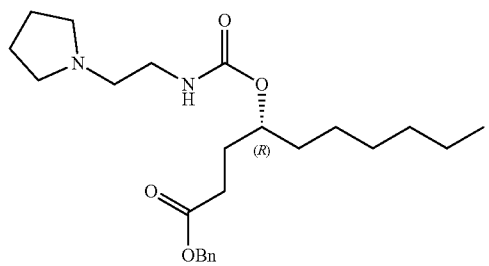

Intermediate 90c was synthesized in 47% yield from Intermediate 90b using the method employed in Intermediate 89f.

Compound 90: 2-(((R)-4-(((2-(pyrrolidin-1-yl)ethyl)carbamoyl)oxy)decanoyl)oxy)propane-1,3-diyl (9Z, 9'Z,12Z,12'Z)-bis(octadeca-9,12-dienoate)

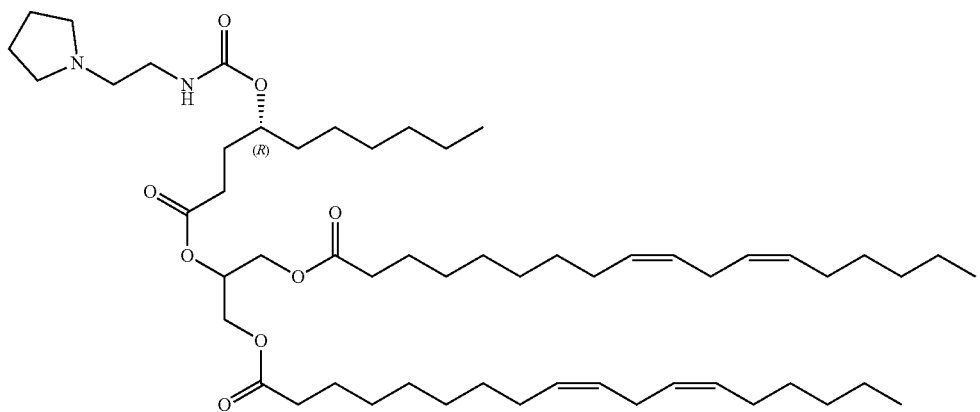

Compound 90 was synthesized in 27% yield from Intermediate 90c using the method employed in Compound 89.

Example 91—Compound 91

Intermediate 91a. 4-hydroxydodecanoic acid

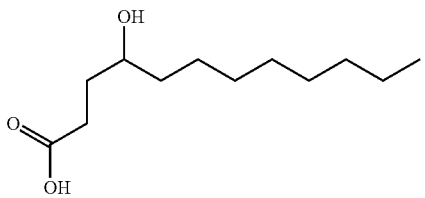

To a solution of 5-octyltetrahydrofuran-2-one (20 g, 1.0e quiv.) in H$_2$O (200 mL) was added NaOH (4.03 g, 1.0 equiv.). The mixture was stirred at 20° C. for 12 h under N$_2$ atmosphere. The reaction mixture was concentrated under reduced pressure to remove H$_2$O. This afforded crude product as a white solid (14 g, 65%). $^1$H NMR (400 MHz, D$_2$O) δ 3.55 (ddd, J=9.5, 7.5, 4.6 Hz, 1H), 2.19 (qdd, J=15.0, 9.3, 6.3 Hz, 2H), 1.69 (dddd, J=13.9, 9.4, 6.4, 4.4 Hz, 1H), 1.59 (dddd, J=14.0, 9.2, 7.7, 6.4 Hz, 1H), 1.46-1.30 (m, 3H), 1.23 (d, J=6.6 Hz, 11H), 0.86-0.77 (m, 3H).

Intermediate 91b: benzyl 4-hydroxydodecanoate

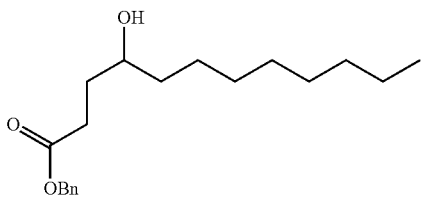 [SMILES: CCCCCCCCC(O)CCC(=O)OCc1ccccc1]

To a solution of Intermediate 91a (10 g, 1.0 equiv.) in DMF (100 mL) was added BnBr (7.91 g, 1.0 equiv.). The mixture was stirred at 20° C. for 2 h under N$_2$ atmosphere. The mixture was diluted with H$_2$O and extracted 2× with EtOAc. The combined organic layers were concentrated under reduced pressure to give a residue. The residue was purified by column chromatography to afford product as a colorless oil (5.7 g, 40%). $^1$H NMR (400 MHz, CDCl$_3$) δ 7.46-7.28 (m, 5H), 5.12 (s, 2H), 3.61 (h, J=4.6 Hz, 1H), 2.51 (td, J=7.3, 2.9 Hz, 2H), 1.86 (dtd, J=14.6, 7.4, 3.5 Hz, 1H), 1.76-1.59 (m, 3H), 1.42 (q, J=12.1, 9.1 Hz, 4H), 1.28 (d, J=11.9 Hz, 12H), 0.88 (t, J=6.8 Hz, 3H).

Intermediate 91c: benzyl 4-(((4-nitrophenoxy)carbonyl)oxy)dodecanoate

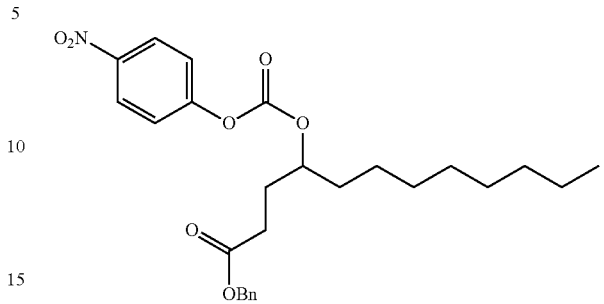

To a solution of Intermediate 91b (10 g, 1.0 equiv.) and (4-nitrophenyl) carbonochloridate (9.87 g, 1.05 equiv.) in DCM (100 mL) was added pyridine (3.95 mL, 1.5 equiv.) at 0° C. The mixture was stirred at 20° C. for 1 h under N$_2$ atmosphere. The reaction mixture was concentrated under reduced pressure to remove DCM. The residue was diluted with H$_2$O and extracted 3× with EtOAc. The combined organic layers were concentrated under reduced pressure to give a residue. The residue was purified by column chromatography to afford product as a colorless oil (7.5 g, 49%). $^1$H NMR (400 MHz, CDCl$_3$) δ 8.30-8.21 (m, 2H), 7.48-7.26 (m, 7H), 5.22 (d, J=69.6 Hz, 2H), 4.87 (tt, J=7.5, 4.5 Hz, 1H), 2.59-2.42 (m, 2H), 1.80-1.57 (m, 2H), 1.52-1.16 (m, 13H), 0.88 (t, J=6.6 Hz, 3H).

Intermediate 91d: benzyl 4-(((2-(dimethylamino)ethyl)carbamoyl)oxy)dodecanoate

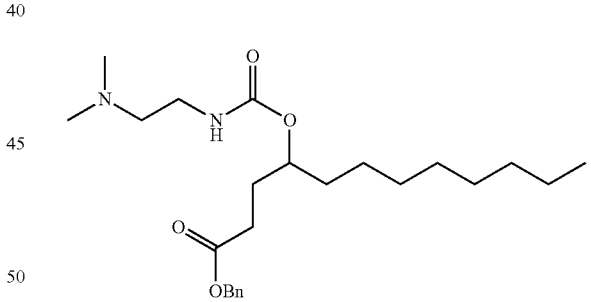

To a solution of Intermediate 91c (1.0 equiv.) in MeCN (0.1-0.5 M) was added diamine or amino alcohol (N',N'-dimethylethane-1,2-diamine (2.0-3.0 equiv.)), pyridine (3.0 equiv.), and DMAP (0.1 equiv.) at 0° C. The mixture was stirred at 15-25° C. for at least 2 h. Upon completion, the reaction mixture was concentrated under reduced pressure, diluted with H$_2$O, and extracted 3× with EtOAc. The combined organic layers were concentrated to afford a residue, which was purified by column chromatography to afford product as a yellow oil (79%). $^1$H NMR (400 MHz, CDCl$_3$) δ 7.46-7.28 (m, 5H), 5.08 (s, 1H), 4.76 (s, 1H), 3.23 (q, J=5.9 Hz, 2H), 2.40 (ddt, J=12.0, 8.9, 4.5 Hz, 4H), 2.21 (s, 7H), 1.94 (d, J=9.9 Hz, 1H), 1.82 (p, J=7.6 Hz, 1H), 1.61-1.40 (m, 3H), 1.39-1.16 (m, 14H), 0.87 (t, J=6.7 Hz, 3H).

Compound 91: 2-((4-(((2-(dimethylamino)ethyl)carbamoyl)oxy)dodecanoyl)oxy)propane-1,3-diyl (9Z,9'Z,12Z,12'Z)-bis(octadeca-9,12-dienoate)

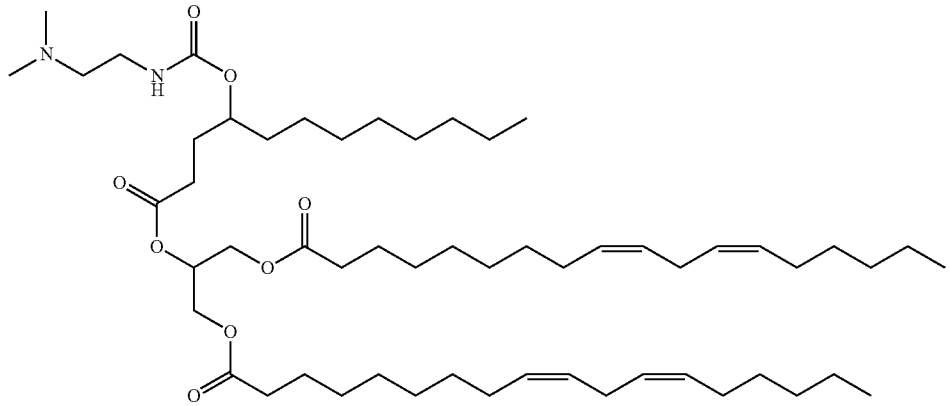 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCCN(C)C]

To a solution of Intermediate 91d in THF (0.1-0.5 M) was added Pd/C (10% w/w). The mixture was stirred at 25° C. for at least 5 h under H2 atmosphere at 15 Psi. The resulting product was diluted in THF and filtered to remove the solid. The filtrate was concentrated in vacuo. The residue was purified by column chromatography to afford carboxylic acid intermediate as a brown oil.

From the resulting oil, Compound 91 was subsequently synthesized in 15% yield using the method employed in Intermediate 90f. $^1$H NMR (400 MHz, CDCl$_3$) δ 5.44-5.26 (m, 8H), 5.27-5.20 (m, 1H), 5.12 (s, 1H), 4.75 (s, 1H), 4.28 (ddd, J=11.9, 4.5, 1.3 Hz, 2H), 4.14 (ddd, J=11.9, 5.8, 3.4 Hz, 2H), 3.24 (q, J=5.7 Hz, 2H), 2.77 (t, J=6.7 Hz, 4H), 2.44-2.35 (m, 4H), 2.31 (t, J=7.6 Hz, 4H), 2.22 (s, 6H), 2.04 (q, J=6.9 Hz, 8H), 1.97-1.84 (m, 2H), 1.80 (dt, J=14.9, 7.7 Hz, 1H), 1.67-1.42 (m, 8H), 1.42-1.14 (m, 39H), 0.88 (td, J=6.8, 5.2 Hz, 9H). MS: 930.4 m/z [M+H].

Example 92—Compound 92

Intermediate 92a: benzyl 4-((((1-methylpiperidin-4-yl)oxy)carbonyl)oxy)dodecanoate

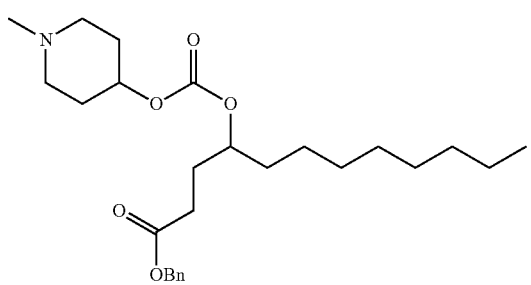 [SMILES: CCCCCCCCC(CCC(=O)OCc1ccccc1)OC(=O)OC1CCN(C)CC1]

Intermediate 92a was synthesized in 94% yield from Intermediate 91c and 1-methylpiperidin-4-ol using the method employed in Intermediate 91d. $^1$H NMR (400 MHz, CDCl$_3$) δ 7.39-7.28 (m, 5H), 5.11 (s, 2H), 4.73 (dtd, J=11.8, 5.4, 4.6, 2.7 Hz, 1H), 4.62 (tt, J=8.6, 4.2 Hz, 1H), 2.68 (s, 2H), 2.48-2.37 (m, 2H), 2.29 (s, 5H), 2.01-1.84 (m, 4H), 1.78 (dtt, J=12.5, 8.2, 3.5 Hz, 2H), 1.67-1.58 (m, 1H), 1.58-1.46 (m, 1H), 1.27 (d, J=15.6 Hz, 13H), 0.87 (t, J=6.8 Hz, 3H).

Compound 92: 2-((4-((((1-methylpiperidin-4-yl)oxy)carbonyl)oxy)dodecanoyl)oxy)propane-1,3-diyl (9Z,9'Z,12Z,12'Z)-bis(octadeca-9,12-dienoate)

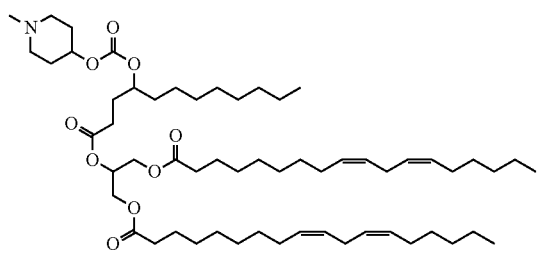 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OC1CCN(C)CC1]

Compound 92 was synthesized in 28% yield from Intermediate 92a using the method employed in Compound 91. $^1$H NMR (400 MHz, CDCl$_3$) δ 5.39-5.21 (m, 8H), 5.21-5.16 (m, 1H), 4.65 (d, J=6.9 Hz, 1H), 4.57-4.52 (m, 1H), 4.22 (dd, J=11.9, 4.3 Hz, 2H), 4.08 (ddd, J=11.9, 5.8, 4.1 Hz, 2H), 2.70 (t, J=6.5 Hz, 4H), 2.61 (s, 2H), 2.36-2.29 (m, 2H), 2.29-2.18 (m, 7H), 2.14 (s, 2H), 1.98 (q, J=6.8 Hz, 8H), 1.93-1.84 (m, 4H), 1.83-1.77 (m, 1H), 1.77-1.65 (m, 3H), 1.54 (t, J=7.3 Hz, 13H), 1.33-1.12 (m, 41H), 0.81 (td, J=6.9, 5.3 Hz, 9H). MS: 957.4 m/z [M+H].

Example 93—Compound 93

Intermediate 93a: benzyl 4-(((2-(azetidin-1-yl)ethyl)carbamoyl)oxy)dodecanoate

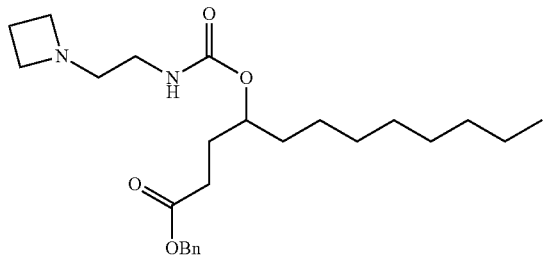 [SMILES: CCCCCCCCC(CCC(=O)OCc1ccccc1)OC(=O)NCCN1CCC1]

Intermediate 93a was synthesized in 80% yield from Intermediate 91c and 2-(azetidin-1-yl)ethanamine using the method employed in Intermediate 92d. $^1$H NMR (400 MHz, CDCl$_3$) δ 7.49-7.26 (m, 5H), 5.11 (s, 2H), 5.04 (s, 1H), 4.74 (s, 1H), 3.20 (t, J=7.0 Hz, 4H), 3.11 (q, J=5.8 Hz, 2H), 2.50 (t, J=5.9 Hz, 2H), 2.41 (ddd, J=8.6, 6.7, 3.2 Hz, 2H), 2.10-2.00 (m, 2H), 1.96-1.88 (m, 1H), 1.82 (d, J=15.4 Hz, 4H), 1.46 (d, J=6.9 Hz, 3H), 1.34-1.18 (m, 14H), 0.87 (t, J=6.8 Hz, 3H).

Compound 93: 2-((4-(((2-(azetidin-1-yl)ethyl)carbamoyl)oxy)dodecanoyl)oxy)propane-1,3-diyl (9Z,9'Z,12Z,12'Z)-bis(octadeca-9,12-dienoate)

Compound 93 was synthesized in 18% yield from Intermediate 93a using the method employed in Compound 91. $^1$H NMR (400 MHz, CDCl$_3$) δ 5.36-5.22 (m, 8H), 5.18 (p, J=5.0 Hz, 1H), 4.98 (t, J=5.6 Hz, 1H), 4.68 (s, 1H), 4.22 (ddd, J=11.9, 4.5, 1.6 Hz, 2H), 4.08 (ddq, J=11.7, 5.8, 2.8 Hz, 2H), 3.12 (t, J=7.0 Hz, 4H), 3.05 (q, J=5.9 Hz, 2H), 2.70 (t, J=6.4 Hz, 4H), 2.43 (t, J=5.9 Hz, 2H), 2.31 (ddd, J=8.8, 6.6, 4.2 Hz, 2H), 2.25 (t, J=7.6 Hz, 4H), 1.99 (dq, J=10.0, 6.9 Hz, 10H), 1.88-1.68 (m, 3H), 1.59-1.36 (m, 7H), 1.34-1.11 (m, 42H), 0.86-0.77 (m, 9H). MS: 942.1 m/z [M+H].

Example 94—Compound 94

Intermediate 94a: benzyl 4-(((2-(piperidin-1-yl)ethyl)carbamoyl)oxy)dodecanoate

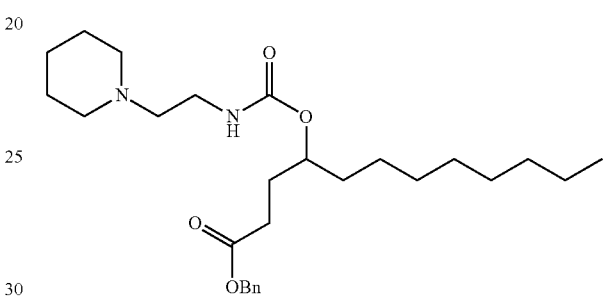

Intermediate 94a was synthesized in 68% yield from Intermediate 91c and 2-(piperidin-1-yl)ethan-1-amine using the method employed in Intermediate 91d. $^1$H NMR (400 MHz, CDCl$_3$) δ 7.38-7.28 (m, 5H), 5.10 (s, 3H), 4.75 (s, 1H), 3.22 (t, J=6.0 Hz, 2H), 2.64 (s, 1H), 2.45-2.29 (m, 8H), 1.99-1.88 (m, 1H), 1.82 (dq, J=15.0, 8.0 Hz, 1H), 1.48 (dt, J=53.9, 5.8 Hz, 9H), 1.34-1.17 (m, 12H), 0.86 (t, J=6.7 Hz, 3H).

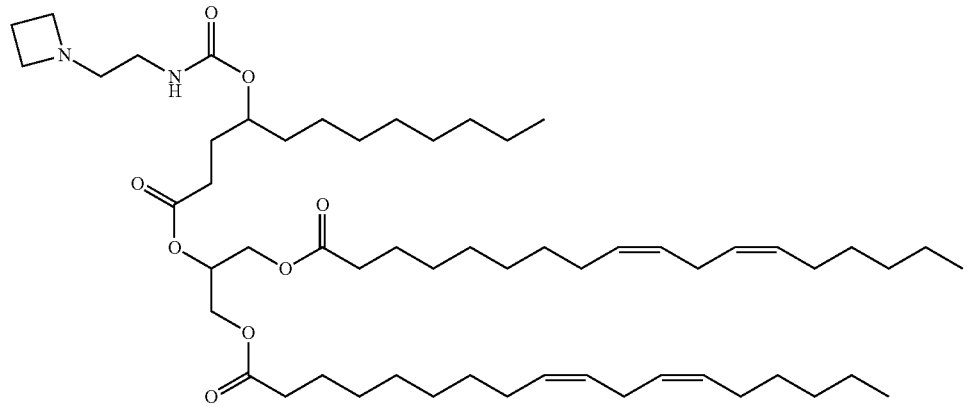 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCCN1CCC1]

447

Compound 94: 2-((4-(((2-(piperidin-1-yl)ethyl)carbamoyl)oxy)dodecanoyl)oxy)propane-1,3-diyl (9Z,9'Z,12Z,12'Z)-bis(octadeca-9,12-dienoate)

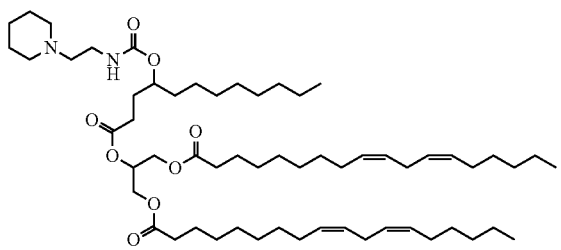 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)NCCN1CCCCC1]

Compound 94 was synthesized in 22% yield from Intermediate 94a using the method employed in Compound 91. ¹H NMR (400 MHz, CDCl₃) δ 5.29 (qq, J=11.7, 6.7 Hz, 8H), 5.18 (p, J=5.1 Hz, 1H), 5.08 (s, 1H), 4.69 (s, 1H), 4.22 (ddd, J=11.9, 4.5, 2.2 Hz, 2H), 4.08 (ddd, J=11.9, 5.9, 3.6 Hz, 2H), 3.18 (q, J=5.9 Hz, 2H), 2.70 (t, J=6.5 Hz, 4H), 2.39-2.18 (m, 12H), 1.98 (q, J=6.9 Hz, 8H), 1.91-1.79 (m, 1H), 1.79-1.68 (m, 1H), 1.61-1.33 (m, 15H), 1.33-1.10 (m, 42H), 0.81 (q, J=6.4 Hz, 9H). MS: 970.2 m/z [M+H].

448

Example 95—Compound 95

Intermediate 95a: benzyl 4-(((4-(diethylamino)butoxy)carbonyl)oxy)dodecanoate

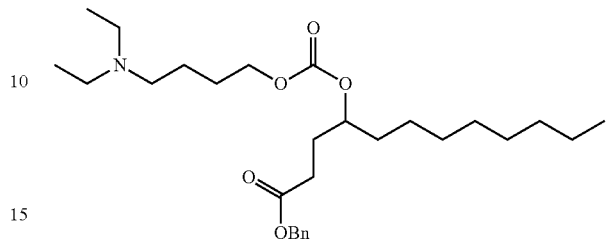

Intermediate 95a was synthesized in 83% yield from Intermediate 91c and 4-(diethyl amino)butan-1-ol using the method employed in Intermediate 92d. ¹H NMR (400 MHz, CDCl₃) δ 7.44-7.28 (m, 5H), 5.11 (s, 2H), 4.72 (tdd, J=7.6, 5.4, 4.0 Hz, 1H), 4.11 (td, J=6.7, 3.8 Hz, 2H), 2.49 (q, J=7.1 Hz, 4H), 2.42 (dtd, J=7.7, 5.1, 4.4, 2.5 Hz, 4H), 1.99 (dddd, J=14.4, 8.9, 7.0, 4.1 Hz, 1H), 1.89 (dtd, J=14.7, 8.4, 6.5 Hz, 1H), 1.64 (ddt, J=17.4, 10.5, 6.2 Hz, 3H), 1.56-1.46 (m, 3H), 1.34-1.21 (m, 13H), 1.00 (t, J=7.1 Hz, 6H), 0.87 (t, J=6.8 Hz, 3H).

Compound 95: 2-((4-(((4-(diethyl amino)butoxy)carbonyl)oxy)dodecanoyl)oxy)propane-1,3-diyl (9Z,9'Z,12Z,12'Z)-bis(octadeca-9,12-dienoate)

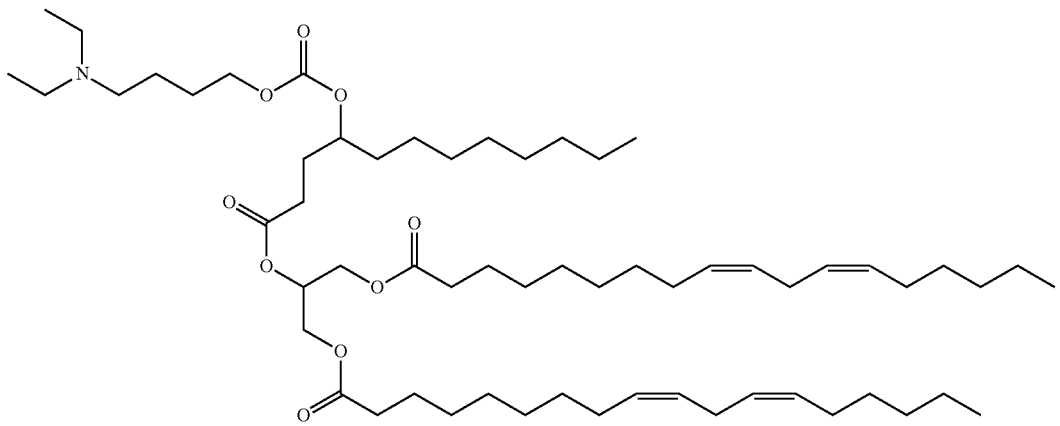 [SMILES: CCCCC/C=C\C/C=C\CCCCCCCC(=O)OCC(COC(=O)CCCCCCC/C=C\C/C=C\CCCCC)OC(=O)CCC(CCCCCCCC)OC(=O)OCCCCN(CC)CC]

Compound 95 was prepared in 27% yield from Intermediate 95a using the method employed in Compound 91. ¹H NMR (400 MHz, CDCl₃) δ 5.35 (qdd, J=10.6, 4.4, 1.7 Hz, 8H), 5.27-5.22 (m, 1H), 4.71 (tt, J=7.6, 2.7 Hz, 1H), 4.28 (dd, J=11.9, 4.3 Hz, 2H), 4.13 (dtt, J=10.4, 6.6, 3.7 Hz, 4H), 2.76 (t, J=6.6 Hz, 4H), 2.50 (q, J=7.2 Hz, 4H), 2.41 (ddd, J=15.2, 8.0, 6.4 Hz, 4H), 2.31 (t, J=7.6 Hz, 4H), 2.04 (q, J=6.8 Hz, 8H), 1.98-1.82 (m, 3H), 1.72-1.47 (m, 12H), 1.39-1.21 (m, 42H), 1.00 (t, J=7.1 Hz, 6H), 0.88 (td, J=6.8, 4.8 Hz, 9H). MS: 987.5 m/z [M+H].

Example 96—Compound 96

Intermediate 96a: benzyl 4-(((2-(diethylamino)ethyl)carbamoyl)oxy)dodecanoate

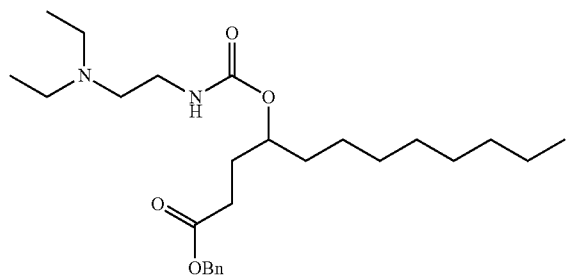 [SMILES: CCCCCCCCC(CCC(=O)OCc1ccccc1)OC(=O)NCCN(CC)CC]

Intermediate 96a was synthesized in 58% yield from Intermediate 91c and N',N'-diethylethane-1,2-diamine using the method employed in Intermediate 91d. $^1$H NMR (400 MHz, CDCl$_3$) δ 7.39-7.28 (m, 5H), 5.19 (s, 1H), 5.11 (s, 2H), 4.76 (s, 1H), 3.51 (s, 2H), 3.27-3.15 (m, 2H), 2.54 (dd, J=8.7, 5.9 Hz, 6H), 2.41 (ddd, J=9.0, 6.9, 2.6 Hz, 2H), 1.94 (d, J=7.5 Hz, 1H), 1.83 (p, J=7.3 Hz, 1H), 1.63-1.40 (m, 3H), 1.35-1.17 (m, 13H), 1.01 (t, J=7.1 Hz, 6H), 0.87 (t, J=6.8 Hz, 3H).

Compound 96: 2-((4-(((2-(diethylamino)ethyl)carbamoyl)oxy)dodecanoyl)oxy)propane-1,3-diyl (9Z,9'Z,12Z,12'Z)-bis(octadeca-9,12-dienoate)

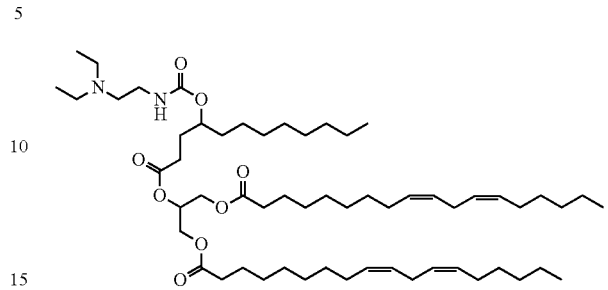

Compound 96 was prepared in 42% yield from Intermediate 96a using the method employed in Compound 91. $^1$H NMR (400 MHz, CDCl$_3$) δ 5.29 (qq, J=11.4, 6.5 Hz, 8H), 5.18 (p, J=5.2 Hz, 1H), 5.08 (s, 1H), 4.69 (s, 1H), 4.21 (ddd, J=11.8, 4.5, 2.0 Hz, 2H), 4.08 (ddd, J=12.0, 5.9, 2.7 Hz, 2H), 3.12 (dt, J=13.0, 6.3 Hz, 2H), 2.70 (t, J=6.5 Hz, 4H), 2.45 (q, J=7.3 Hz, 6H), 2.28 (dt, J=27.2, 8.0 Hz, 6H), 1.98 (q, J=6.9 Hz, 8H), 1.83 (s, 1H), 1.78-1.68 (m, 1H), 1.54 (t, J=7.2 Hz, 9H), 1.35-1.11 (m, 42H), 0.81 (q, J=6.3 Hz, 9H). MS: 958.4 m/z [M+H].

Example 97—Compound 97

Compound 97: 2-((5-(((2-(ethyl(methyl)amino)ethyl)carbamoyl)oxy)tridecanoyl)oxy)propane-1,3-diyl (9Z,9'Z,12Z,12'Z)-bis(octadeca-9,12-dienoate)

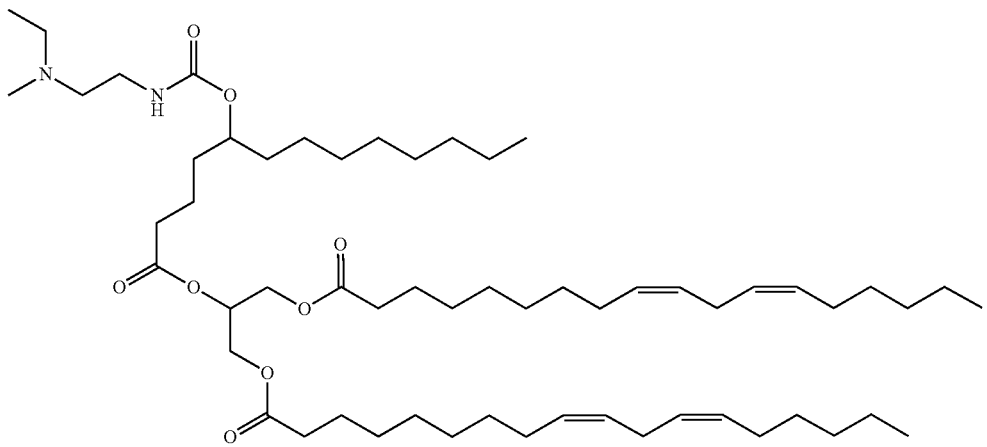 [SMILES: CCCCC/C=C\C/C=C\CCCCCCCC(=O)OCC(COC(=O)CCCCCCC/C=C\C/C=C\CCCCC)OC(=O)CCCC(CCCCCCCC)OC(=O)NCCN(C)CC]

Compound 96 was prepared in 75% yield from Intermediate 55d and Intermediate 1c using the method employed for Compound 52. $^1$H NMR (400 MHz, CDCl$_3$) δ 5.42-5.28 (m, 8H), 5.27-5.22 (m, 1H), 5.12 (d, J=5.7 Hz, 1H), 4.76-4.67 (m, 1H), 4.28 (dt, J=11.9, 4.5 Hz, 2H), 4.13 (ddd, J=12.0, 5.9, 4.5 Hz, 2H), 3.23 (h, J=7.2, 6.2 Hz, 2H), 2.76 (t, J=6.6 Hz, 4H), 2.43 (dt, J=14.5, 6.6 Hz, 4H), 2.35-2.27 (m, 6H), 2.19 (s, 3H), 2.04 (q, J=6.8 Hz, 8H), 1.71-1.46 (m, 13H), 1.40-1.19 (m, 42H), 1.03 (t, J=7.1 Hz, 3H), 0.92-0.83 (m, 9H). MS: 958.5 m/z [M+H].

Example 98

Intermediate 98a: ethyl 2,2-dimethyl-3-oxoundecanoate

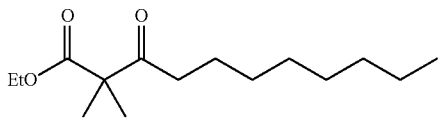 [SMILES: CCCCCCCCC(=O)C(C)(C)C(=O)O]

To a solution of N-isopropylpropan-2-amine (20.0 mL, 1.0 equiv.) in THF (1-3 M) was added n-BuLi (2.5 M, 56.60 mL, 1.0 equiv.) at −78° C. under $N_2$. The mixture was stirred at −78° C. for 20 min. Then ethyl 2-methylpropanoate (18.96 mL, 1.0 equiv.) was added at −78° C. The mixture was stirred at −78° C. for another 20 min. Nonanoyl chloride (26.60 mL, 1.0 equiv.) in THF (200 mL) was added dropwise to the above solution. The mixture was allowed to warm to 15° C. and stirred at 15° C. for 12 h under $N_2$ atmosphere. The reaction mixture was quenched by addition ice water, filtered and concentrated under reduced pressure to give a residue. The residue was diluted with $H_2O$ and extracted 3× with EtOAc. The organic phase was separated, washed with brine, dried over anhydrous $Na_2SO_4$, filtered and concentrated under reduced pressure to give a residue. The residue was purified by column chromatography to afford product as a yellow oil (15 g, 41%). $^1$H NMR (400 MHz, $CDCl_3$) δ 4.11 (q, J=7.2 Hz, 2H), 2.36 (t, J=7.3 Hz, 2H), 1.56-1.46 (m, 2H), 1.28 (s, 6H), 1.25-1.13 (m, 13H), 0.80 (t, J=6.7 Hz, 3H).

Intermediate 98b: 2,2-dimethyl-3-oxoundecanoic acid

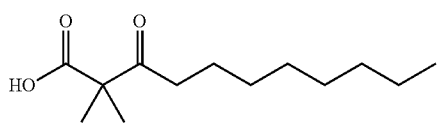

A mixture of Intermediate 98a (15 g, 1.0 equiv.), LiOH (2.10 g, 1.5 equiv.), KOH (4.92 g, 1.5 equiv.) in EtOH (120 mL) and $H_2O$ (40 mL) was degassed and purged 3× with $N_2$, and then the mixture was stirred at 40° C. for 3 h under $N_2$ atmosphere. The mixture was concentrated to remove EtOH. Then, the pH was adjusted to 5-6 with HCl (1 M). The mixture was partitioned between $H_2O$ and EtOAc. The organic phase was separated, washed with brine, dried over anhydrous $Na_2SO_4$, filtered and concentrated under reduced pressure to give a residue. The residue was purified by column chromatography to afford product as a yellow oil (5 g, 37%). $^1$H NMR (400 MHz, Chloroform-d) δ 2.46 (t, J=7.3 Hz, 2H), 1.58-1.47 (m, 2H), 1.33 (s, 6H), 1.20 (s, 10H), 0.81 (t, J=6.6 Hz, 3H).

Example 99—Compound 99

Intermediate 99a: 2-(((2,2-dimethyl-3-oxoundecanoyl)oxy)methyl)propane-1,3-diyl (9Z,9′Z,12Z,12′Z)-bis(octadeca-9,12-dienoate)

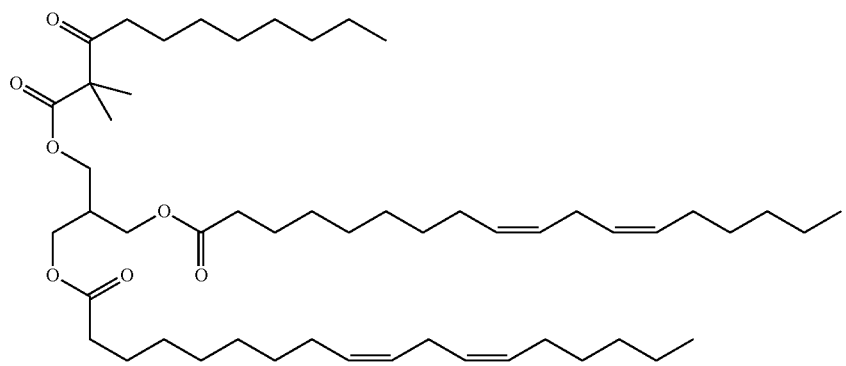 [SMILES: CCCCC/C=C\C/C=C\CCCCCCCC(=O)OCC(COC(=O)CCCCCCC/C=C\C/C=C\CCCCC)COC(=O)C(C)(C)C(=O)CCCCCCCC]

To a solution of Intermediate 53a (12.16 g, 1.1 equiv.) in THF (20 mL) was added Intermediate 98b (4 g, 1.0 equiv.), DBAD (8.07 g, 2.0 equiv.) and $PPh_3$ (9.19 g, 2.0 equiv.) at 0° C. The mixture was stirred at 0° C. for 15 min. Then the mixture was stirred at 15° C. for 16 h under $N_2$ atmosphere. The reaction mixture was diluted with $H_2O$ and extracted 3× with EtOAc. The organic phase was separated, washed with brine, dried over anhydrous $Na_2SO_4$, filtered and concentrated under reduced pressure to give a residue. The residue was purified by column chromatography to afford product as a yellow oil (3 g, 20%). $^1$H NMR (400 MHz, $CDCl_3$) δ 5.27 (dtt, J=10.8, 8.7, 6.1 Hz, 8H), 4.10 (d, J=6.0 Hz, 2H), 4.03 (d, J=6.0 Hz, 4H), 2.70 (t, J=6.4 Hz, 4H), 2.37 (t, J=7.3 Hz, 2H), 2.23 (t, J=7.6 Hz, 4H), 1.98 (q, J=6.8 Hz, 8H), 1.52 (tt, J=14.2, 7.4 Hz, 8H), 1.31-1.17 (m, 46H), 0.85-0.77 (m, 12H).

Intermediate 99b: 2-(((3-hydroxy-2,2-dimethylundecanoyl)oxy)methyl)propane-1,3-diyl (9Z,9'Z,12Z,12'Z)-bis(octadeca-9,12-dienoate)

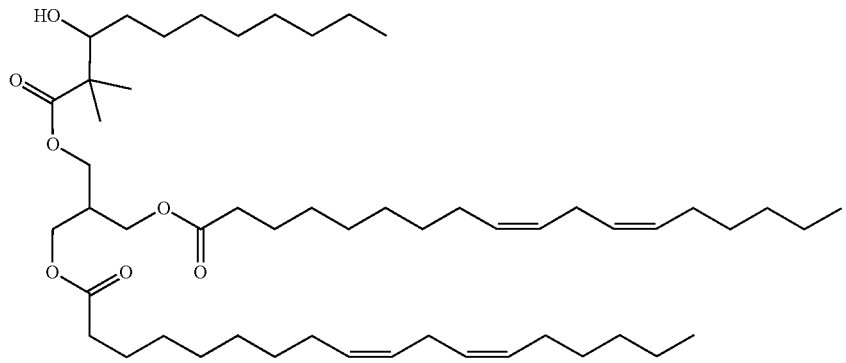 [SMILES: CCCCC/C=C\C/C=C\CCCCCCCC(=O)OCC(COC(=O)CCCCCCC/C=C\C/C=C\CCCCC)COC(=O)C(C)(C)C(O)CCCCCCCC]

To a solution of Intermediate 99a (1.0 equiv.) in 4:2:1 THF:H₂O:toluene (0.025-0.1 was added NaBH₄ (5.0 equiv.) at 0° C. The mixture was stirred at 15° C. for 5 h under N₂ atmosphere. The reaction mixture was partitioned between THF and H₂O, and the organic phase was concentrated under reduced pressure to give a residue. The residue was purified by column chromatography to afford product as a colorless oil (33%). ¹H NMR (400 MHz, CDCl₃) δ 5.41-5.25 (m, 8H), 4.20-4.07 (m, 7H), 3.63 (dd, J=10.2, 6.7 Hz, 1H), 2.76 (t, J=6.4 Hz, 4H), 2.40 (t, J=6.0 Hz, 2H), 2.30 (t, J=7.6 Hz, 4H), 2.04 (q, J=6.8 Hz, 8H), 1.59 (q, J=7.3 Hz, 6H), 1.40-1.22 (m, 40H), 1.16 (d, J=4.5 Hz, 6H), 0.88 (td, J=6.8, 4.0 Hz, 9H).

Intermediate 99c: 2-(((2,2-dimethyl-3-(((4-nitrophenoxy)carbonyl)oxy)undecanoyl)oxy)methyl)propane-1,3-diyl (9Z,9'Z,12Z,12'Z)-bis(octadeca-9,12-dienoate)

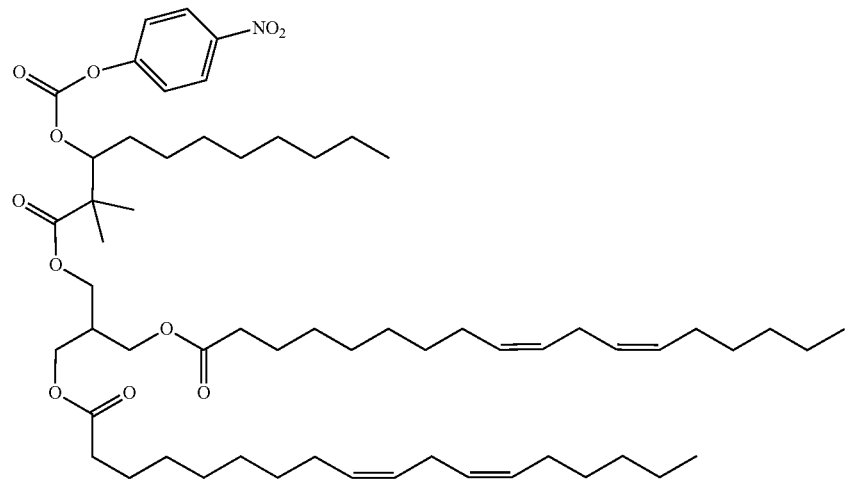 [SMILES: CCCCC/C=C\C/C=C\CCCCCCCC(=O)OCC(COC(=O)CCCCCCC/C=C\C/C=C\CCCCC)COC(=O)C(C)(C)C(CCCCCCCC)OC(=O)Oc1ccc([N+](=O)[O-])cc1]

To a solution of Intermediate 99b (1 g, 1.0 equiv.) and (4-nitrophenyl) carbonochloridate (478 mg, 2.0 equiv.) in DCM (10 mL) was added pyridine (191 uL, 2.0 equiv.) at 0° C. under N₂. The mixture was stirred at 15-25° C. for 5 h under N₂ atmosphere. The reaction mixture was concentrated under reduced pressure to give a residue. The residue was purified by column chromatography to afford product as a colorless oil (0.8 g, 67%). ¹H NMR (400 MHz, CDCl₃) δ 8.20 (d, J=8.8 Hz, 2H), 7.30 (d, J=8.9 Hz, 2H), 5.29 (dq, J=13.1, 7.1, 6.1 Hz, 8H), 5.03 (dd, J=10.4, 2.3 Hz, 1H), 4.08 (dd, J=6.0, 2.5 Hz, 6H), 2.69 (t, J=6.4 Hz, 4H), 2.35 (p, J=6.0 Hz, 1H), 2.23 (q, J=8.4, 7.7 Hz, 4H), 1.97 (q, J=6.9 Hz, 8H), 1.53 (h, J=7.1, 5.9 Hz, 8H), 1.36-1.12 (m, 56H), 0.85-0.77 (m, 12H).

Compound 99: 2-(4,4,11-trimethyl-5-octyl-3,7-di-oxo-2,6-dioxa-8,11-diazatridecyl)propane-1,3-diyl (9Z,9'Z,12Z,12'Z)-bis(octadeca-9,12-dienoate)

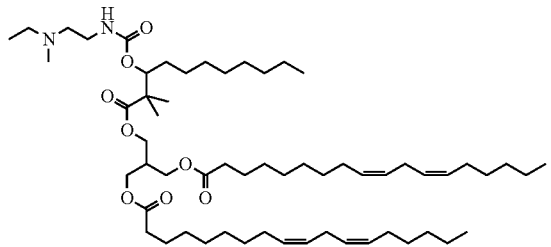 [SMILES: CCCCC/C=C\C/C=C\CCCCCCCC(=O)OCC(COC(=O)CCCCCCC/C=C\C/C=C\CCCCC)COC(=O)C(C)(C)C(CCCCCCCC)OC(=O)NCCN(C)CC]

To a solution of Intermediate 99c (1.0 equiv.) in MeCN (0.1 M) was added diamine (N'-ethyl-N'-methyl-ethane-1,2-diamine (3.0 equiv.)), DMAP (1.0 equiv.), and pyridine (3.0 equiv.) at 0° C. The mixture was stirred at 15° C. for at least 2 h under N₂ atmosphere. The reaction mixture was concentrated under reduced pressure to give a residue. The residue was diluted with H₂O and extracted 3× with EtOAc. The organic phase was separated, washed with brine, dried over anhydrous Na₂SO₄, filtered and concentrated under reduced pressure to give a residue. The residue was purified by column chromatography to afford product as a yellow oil (66%). ¹H NMR (400 MHz, CDCl₃) δ 5.28 (pt, J=11.5, 5.8 Hz, 8H), 4.90 (t, J=6.4 Hz, 1H), 4.11-4.02 (m, 5H), 3.17 (dt, J=13.4, 7.3 Hz, 2H), 2.70 (t, J=6.4 Hz, 4H), 2.37 (dq, J=12.3, 6.2 Hz, 5H), 2.23 (t, J=7.6 Hz, 4H), 2.14 (s, 3H), 1.98 (q, J=6.8 Hz, 7H), 1.54 (p, J=6.8 Hz, 4H), 1.37-1.06 (m, 49H), 0.97 (t, J=7.1 Hz, 3H), 0.81 (q, J=6.9 Hz, 9H). MS: 973.5 m/z [M+H].

Example 100—Compound 100

Intermediate 100a: ethyl 2,2-dimethyl-3-oxononanoate

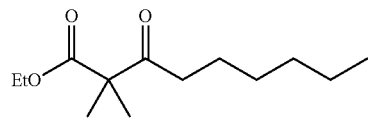 [SMILES: CCCCCCC(=O)C(C)(C)C(=O)OCC]

Intermediate 100a was synthesized in 26% yield from N-isopropylpropan-2-amine, ethyl 2-methylpropanoate, and heptanoyl chloride using the method employed in Intermediate 99a. ¹H NMR (400 MHz, CDCl₃) δ 4.14 (q, J=7.1 Hz, 2H), 2.40 (t, J=7.3 Hz, 2H), 1.60-1.47 (m, 2H), 1.36-1.14 (m, 13H), 0.84 (t, J=6.8 Hz, 3H).

Intermediate 100b: 2,2-dimethyl-3-oxononanoic acid

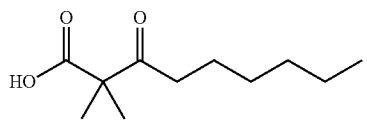

A mixture of Intermediate 100a (20 g, 1.0 equiv.), LiOH (3.15 g, 1.5 equiv.), KOH (7.37 g, 1.5 equiv.) in EtOH (6 mL) and H₂O (2 mL) was stirred at 40° C. for 4 h under N₂ atmosphere. The mixture was concentrated to remove EtOH. Then, the pH was adjusted to 5-6 with HCl (1 M). The mixture was partitioned between H₂O and EtOAc and extracted 2× with EtOAc. The organic phase was separated, washed with brine, dried over anhydrous Na₂SO₄, filtered and concentrated under reduced pressure to give a residue. The residue was purified by column chromatography to afford product as a colorless oil (6 g, 34%). ¹H NMR (400 MHz, CDCl₃) δ 2.53 (t, J=7.3 Hz, 2H), 1.58 (p, J=7.2 Hz, 2H), 1.40 (s, 6H), 1.34-1.23 (m, 6H), 0.92-0.81 (m, 3H).

Intermediate 100c: 2-(((2,2-dimethyl-3-oxononanoyl)oxy)methyl)propane-1,3-diyl (9Z,9'Z, 12Z,12'Z)-bis(octadeca-9,12-dienoate)

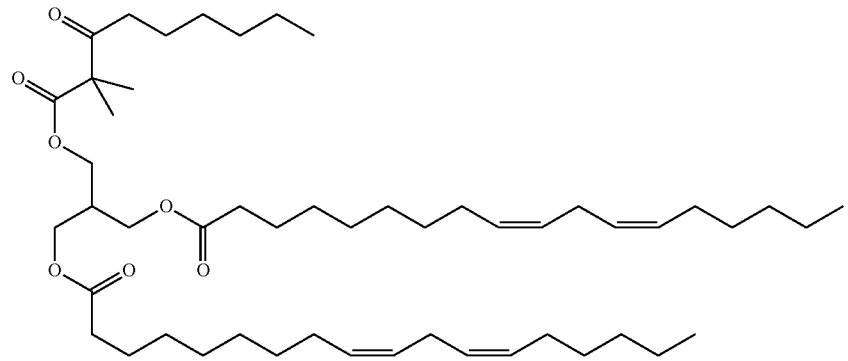 [SMILES: CCCCC/C=C\C/C=C\CCCCCCCC(=O)OCC(COC(=O)CCCCCCC/C=C\C/C=C\CCCCC)COC(=O)C(C)(C)C(=O)CCCCCC]

To a solution of Intermediate 1c (19.06 g, 1.1 equiv.) in THF (50 mL) was added PPh₃ (14.41 g, 2.0 equiv.) and DBAD (12.65 g, 2.0 equiv.), and Intermediate 100b (5.5 g, 1.0 equiv.) at 0° C. The mixture was stirred at 0° C. for 20 min, and the mixture was allowed to warm to 15° C. and stirred at 15° C. for 16 hr under N₂ atmosphere. The reaction mixture was diluted with H₂O and extracted 3× with EtOAc. The organic phase was separated, washed with brine, dried over anhydrous Na₂SO₄, filtered and concentrated under reduced pressure to give a residue. The residue was purified by column chromatography to afford product as a yellow oil (4 g, 18%). ¹H NMR (400 MHz, CDCl₃) δ 5.28 (tt, J=11.1, 5.4 Hz, 8H), 4.10 (d, J=6.0 Hz, 2H), 4.05 (dd, J=10.4, 6.0 Hz, 4H), 2.70 (t, J=6.4 Hz, 4H), 2.34 (dt, J=17.5, 6.6 Hz, 3H), 2.23 (t, J=7.6 Hz, 4H), 1.98 (q, J=6.8 Hz, 8H), 1.61-1.44 (m, 8H), 1.39 (d, J=14.2 Hz, 3H), 1.35-1.14 (m, 41H), 0.85-0.76 (m, 9H).

Intermediate 100d: 2-(((3-hydroxy-2,2-dimethyl-nonanoyl)oxy)methyl)propane-1,3-diyl (9Z,9'Z,12Z,12'Z)-bis(octadeca-9,12-dienoate)

Intermediate 100e: 2-(((2,2-dimethyl-3-(((4-nitrophenoxy)carbonyl)oxy)nonanoyl)oxy)methyl)propane-1,3-diyl (9Z,9'Z,12Z,12'Z)-bis(octadeca-9,12-dienoate)

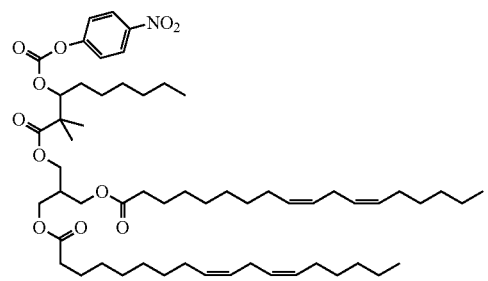

To a solution of Intermediate 100d (0.4 g, 1.0 equiv.) and (4-nitrophenyl)carbonochloridate (890 mg, 9.0 equiv.) in DCM (5 mL) was added pyridine (119 uL, 3.0 equiv.) at 0°

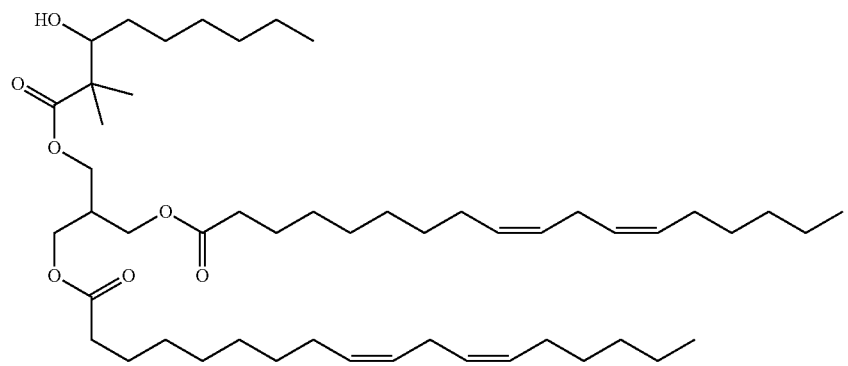 [SMILES: CCCCC/C=C\C/C=C\CCCCCCCC(=O)OCC(COC(=O)CCCCCCC/C=C\C/C=C\CCCCC)COC(=O)C(C)(C)C(O)CCCCCC]

To a solution of Intermediate 100c (1.0 equiv.) in 4:2:1 THF:H₂O:toluene (0.025-0.1 was added NaBH₄ (5.0 equiv.) at 0° C. The mixture was stirred at 5° C. for 5 h under N₂ atmosphere. The reaction mixture was partitioned between THF and H₂O, and the organic phase was dried over Na₂SO₄, filtered, and concentrated under reduced pressure to give a residue. The residue was purified by column chromatography to afford product as a colorless oil (20%).

C. The mixture was stirred at 15° C. for 3 h under N₂ atmosphere. Then the mixture was stirred at 25° C. for 2 h under N₂ atmosphere. The reaction mixture was filtered and concentrated under reduced pressure to give a residue. The residue was purified by column chromatography to afford product as a colorless oil (0.2 g, 42%). ¹H NMR (400 MHz, CDCl₃) δ 8.21 (dd, J=9.3, 2.5 Hz, 2H), 7.31 (dd, J=9.4, 2.8 Hz, 2H), 5.43-5.16 (m, 8H), 5.03 (dd, J=10.3, 2.3 Hz, 1H), 4.12-3.99 (m, 6H), 2.70 (t, J=6.4 Hz, 4H), 2.35 (h, J=6.0 Hz, 1H), 2.22 (t, J=7.6 Hz, 4H), 1.97 (t, J=6.9 Hz, 7H), 1.63-1.47 (m, 6H), 1.40-1.12 (m, 41H), 0.82 (t, J=6.7 Hz, 9H).

Compound 100: 2-(((2,2-dimethyl-3-(((2-(pyrrolidin-1-yl)ethyl)carbamoyl)oxy)nonanoyl)oxy)methyl)propane-1,3-diyl (9Z,9'Z,12Z,12'Z)-bis(octadeca-9,12-dienoate)

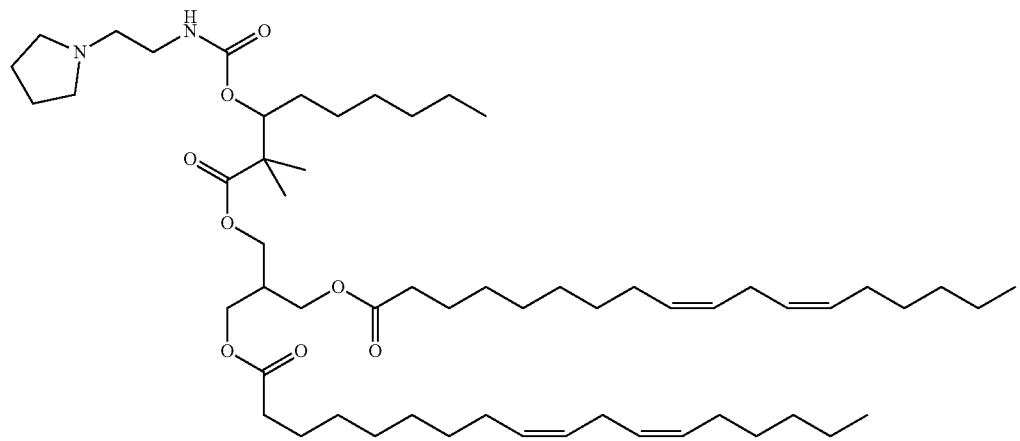 [SMILES: CCCCC/C=C\C/C=C\CCCCCCCC(=O)OCC(COC(=O)CCCCCCC/C=C\C/C=C\CCCCC)COC(=O)C(C)(C)C(CCCCCC)OC(=O)NCCN1CCCC1]

Compound 100 was synthesized in 90% yield from Intermediate 100e and 2-pyrrolidin-1-ylethanamine using the method employed in Compound 99. $^1$H NMR (400 MHz, CDCl$_3$) δ 5.28 (tdq, J=17.2, 12.4, 5.8, 5.3 Hz, 8H), 4.90 (t, J=6.4 Hz, 1H), 4.13-4.00 (m, 6H), 3.22 (ddq, J=19.5, 12.8, 6.3, 5.8 Hz, 2H), 2.70 (t, J=6.4 Hz, 4H), 2.51 (t, J=6.3 Hz, 2H), 2.44 (d, J=6.0 Hz, 4H), 2.34 (p, J=6.0 Hz, 1H), 2.23 (t, J=7.6 Hz, 4H), 1.98 (q, J=6.8 Hz, 8H), 1.70 (h, J=7.5 Hz, 4H), 1.54 (p, J=7.0 Hz, 4H), 1.41-1.06 (m, 44H), 0.81 (dt, J=9.6, 6.7 Hz, 9H). MS: 956.4 m/z [M+H].

Example 101—Compound 101

Compound 101: 2-((4-(((3-(azetidin-1-yl)propoxy)carbonyl)oxy)decanoyl)oxy)propane-1,3-diyl (9Z,9'Z,12Z,12'Z)-bis(octadeca-9,12-dienoate)

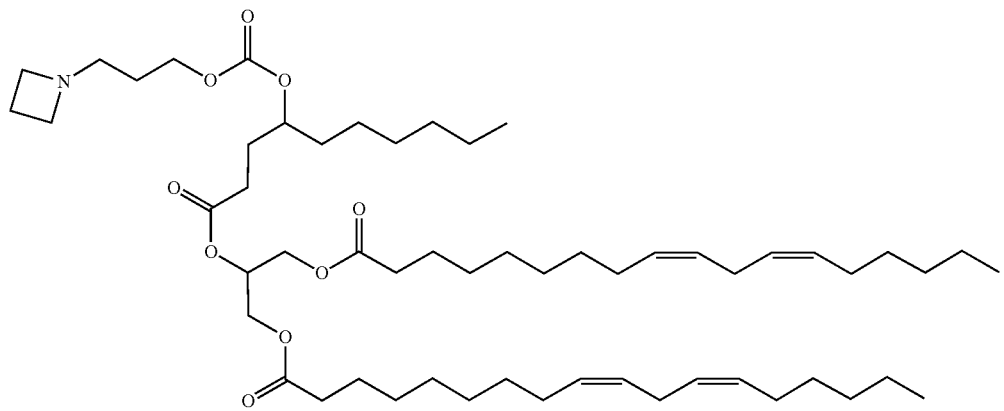 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)OCCCN1CCC1]

Compound 101 was synthesized in 65% yield from Intermediate 40d and 3-(azetidin-1-yl)propan-1-ol using the method employed for Example 1. $^1$H NMR (400 MHz, CDCl$_3$) δ 5.45-5.28 (m, 8H), 5.25 (tt, J=5.8, 4.3 Hz, 1H), 4.71 (ddd, J=11.5, 7.6, 4.7 Hz, 1H), 4.29 (dd, J=11.9, 4.3 Hz, 2H), 4.15 (dddd, J=13.3, 7.2, 5.5, 3.2 Hz, 4H), 3.18 (t, J=7.0 Hz, 4H), 2.82-2.72 (m, 4H), 2.48 (t, J=7.3 Hz, 2H), 2.40 (dt, J=8.8, 6.8 Hz, 2H), 2.31 (td, J=7.6, 1.2 Hz, 4H), 2.10-1.99 (m, 10H), 1.99-1.84 (m, 2H), 1.77-1.50 (m, 15H), 1.42-1.21 (m, 37H), 0.88 (td, J=6.9, 5.4 Hz, 9H). MS: 929.3 m/z [M+H].

Example 102—Compound 102

Compound 102: 2-((4-(((3-(piperidin-1-yl)propoxy)carbonyl)oxy)decanoyl)oxy)propane-1,3-diyl (9Z,9'Z,12Z,12'Z)-bis(octadeca-9,12-dienoate)

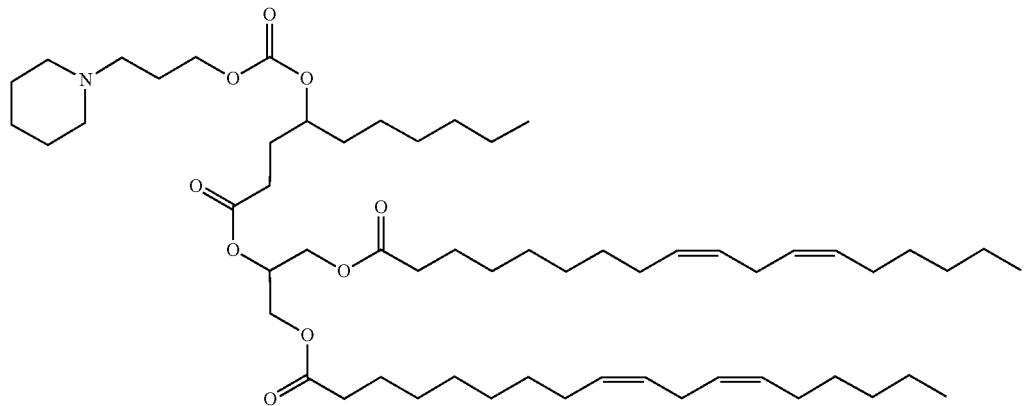 [SMILES: CCCCC/C=C\C/C=C\CCCCCCCC(=O)OCC(COC(=O)CCCCCCC/C=C\C/C=C\CCCCC)OC(=O)CCC(CCCCCC)OC(=O)OCCCN1CCCCC1]

Compound 102 was synthesized in 72% yield from Intermediate 40d and 3-(piperidin-1-yl)propan-1-ol using the method employed for Example 1. $^1$H NMR (400 MHz, CDCl$_3$) δ 5.44-5.28 (m, 8H), 5.25 (ddd, J=5.8, 4.3, 1.5 Hz, 1H), 4.76-4.69 (m, 1H), 4.37-4.24 (m, 2H), 4.24-4.10 (m, 4H), 2.82-2.71 (m, 4H), 2.48-2.26 (m, 12H), 2.05 (q, J=6.8 Hz, 8H), 2.01-1.81 (m, 4H), 1.71-1.49 (m, 17H), 1.43 (s, 2H), 1.40-1.24 (m, 37H), 0.88 (td, J=6.9, 5.0 Hz, 9H). MS: 957.1 m/z [M+H].

Example 103—Compound 103

Intermediate 103a: (2-ethylbutyl)magnesium bromide

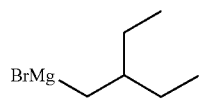

To a solution of Mg (1.1 equiv.) and I$_2$ (0.1 equiv.) in THF (0.4-0.5 M) was added 3-(bromomethyl)pentane (1.0 equiv.) dropwise. The mixture was stirred at 40° C. for at least 1 h. The reaction mixture was used directly in the next step without additional purification.

Intermediate 103b: ethyl 6-ethyl-4-oxooctanoate

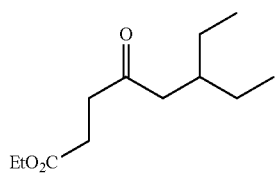

To a solution of ethyl 4-chloro-4-oxo-butanoate (1.0 equiv.) in THF (0.3 M) was added CuI (1-2 equiv.) and Intermediate 103a (1-2 equiv. equiv.) at −78° C. dropwise. The mixture was stirred at −78° C. for at least 1.5 h. Upon completion, saturated NH$_4$Cl was added, and the reaction was extracted 3× with EtOAc. The organic layer was concentrated under reduced pressure to give a residue. The residue was purified by column chromatography to afford product as a brown oil (82%). $^1$H NMR (400 MHz, CDCl$_3$) δ 4.05 (q, J=7.1 Hz, 2H), 2.65 (t, J=6.6 Hz, 2H), 2.49 (d, J=13.1 Hz, 2H), 2.30 (d, J=6.8 Hz, 2H), 1.82-1.71 (m, J=6.5 Hz, 1H), 1.33-1.13 (m, 7H), 0.78 (t, J=7.4 Hz, 6H).

Intermediate 103c: 6-ethyl-4-oxooctanoic acid

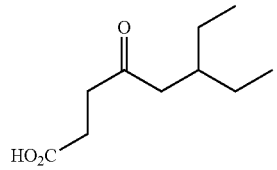

To a solution of Intermediate 103c (1.0 equiv.) in 3:1 EtOH/H$_2$O (0.2 M) was added NaOH (1.5 equiv), LiOH (1.5 equiv.). The mixture was stirred at 40° C. for at least 1 h. Upon completion, the pH of the reaction was adjusted to 3 using 1 M HCl, and the reaction was diluted with H$_2$O and extracted 3× with EtOAc. The organic layer was dried over Na$_2$SO$_4$, filtered and concentrated under reduced pressure to give a residue. The residue was purified by column chromatography to afford product as a yellow oil (46%). $^1$H NMR (400 MHz, CDCl$_3$) δ 2.69-2.60 (m, 2H), 2.56 (t, J=6.6 Hz, 2H), 2.30 (d, J=6.7 Hz, 2H), 1.75 (hept, J=6.4 Hz, 1H), 1.22 (qp, J=13.8, 6.6 Hz, 4H), 0.78 (t, J=7.4 Hz, 6H).

Intermediate 103d: 2-((6-ethyl-4-oxooctanoyl)oxy)propane-1,3-diyl (9Z,9'Z,12Z,12'Z)-bis(octadeca-9,12-dienoate)

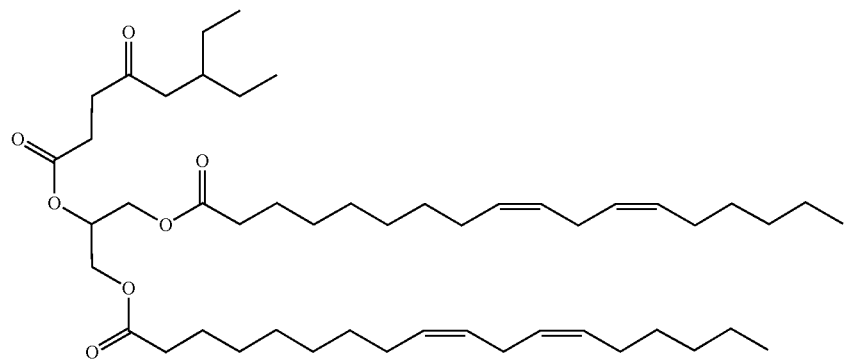 [SMILES: CCCCC/C=C\C/C=C\CCCCCCCC(=O)OCC(COC(=O)CCCCCCC/C=C\C/C=C\CCCCC)OC(=O)CCC(=O)CC(CC)CC]

To a solution of Intermediate 103c (1.0 equiv.) in DCM (0.2-0.5 M) was added Intermediate 1c (1.0 equiv.), EDCI (1.2 equiv.), DMAP (0.1-0.2 equiv.) and Et$_3$N (1.5 equiv.) at 0° C. under N$_2$. The mixture was stirred at 20-25° C. for at least 12 h under N$_2$ atmosphere. The mixture was diluted with H$_2$O and extracted 3× with EtOAc. The combined organic phase was dried with anhydrous Na$_2$SO$_4$, filtered and the filtrate was concentrated in vacuum. The residue was purified by column chromatography to afford product as a yellow oil (40%). $^1$H NMR (400 MHz, CDCl$_3$) δ 5.40-5.21 (m, 8H), 5.18 (p, J=5.0 Hz, 1H), 4.23 (dt, J=11.9, 5.0 Hz, 2H), 4.08 (dd, J=11.9, 5.9 Hz, 2H), 2.67 (dt, J=20.4, 6.5 Hz, 6H), 2.51 (td, J=6.5, 2.9 Hz, 2H), 2.32-2.22 (m, 5H), 1.98 (q, J=6.8 Hz, 8H), 1.75 (p, J=6.4 Hz, 1H), 1.53 (q, J=7.2 Hz, 4H), 1.35-1.09 (m, 31H), 0.80 (dt, J=16.7, 6.9 Hz, 12H).

Intermediate 103e: 2-((6-ethyl-4-(((4-nitrophenoxy)carbonyl)oxy)octanoyl)oxy)propane-1,3-diyl (9Z,9'Z,12Z,12'Z)-bis(octadeca-9,12-dienoate)

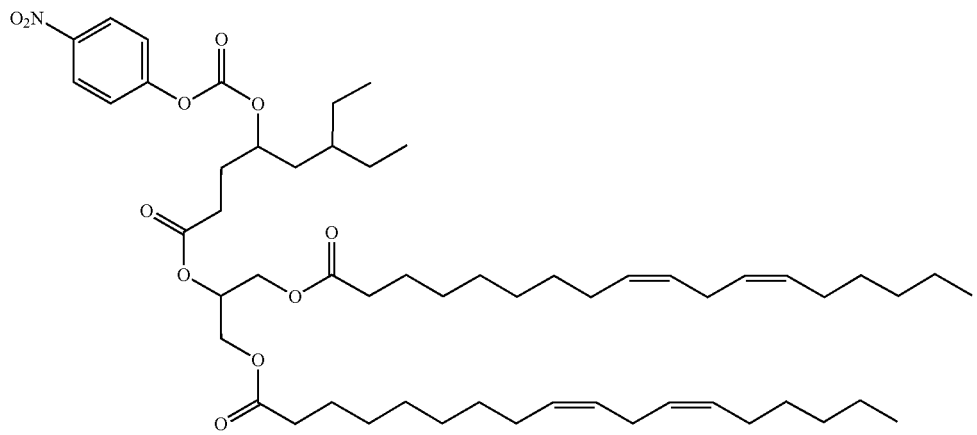 [SMILES: CCCCC/C=C\C/C=C\CCCCCCCC(=O)OCC(COC(=O)CCCCCCC/C=C\C/C=C\CCCCC)OC(=O)CCC(CC(CC)CC)OC(=O)Oc1ccc([N+](=O)[O-])cc1]

Intermediate 103e was synthesized in 46% yield from Intermediate 103d using the method employed in Intermediate 1e. $^1$H NMR (400 MHz, CDCl$_3$) δ 8.21 (d, J=8.1 Hz, 2H), 7.32 (d, J=8.4 Hz, 2H), 5.27 (tt, J=14.1, 7.8 Hz, 8H), 4.89 (p, J=7.4 Hz, 1H), 4.32-4.02 (m, 4H), 2.70 (t, J=6.5 Hz, 4H), 2.41 (t, J=7.5 Hz, 2H), 2.32-2.19 (m, 4H), 1.98 (q, J=7.2 Hz, 10H), 1.69-1.40 (m, 7H), 1.39-1.16 (m, 36H), 0.82 (t, J=6.9 Hz, 12H).

Compound 103: 2-((6-ethyl-4-(((2-(ethyl(methyl)amino)ethyl)carbamoyl)oxy)octanoyl)oxy)propane-1,3-diyl (9Z,9'Z,12Z,12'Z)-bis(octadeca-9,12-dienoate)

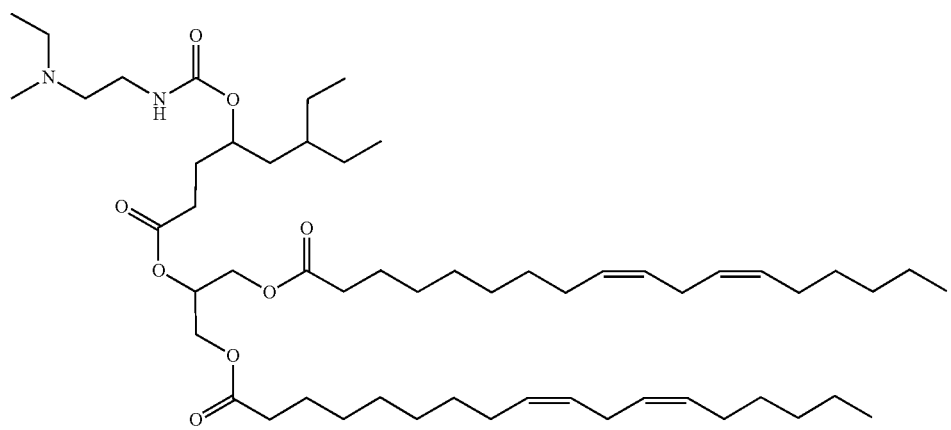 [SMILES: CCCCC/C=C\C/C=C\CCCCCCCC(=O)OCC(COC(=O)CCCCCCC/C=C\C/C=C\CCCCC)OC(=O)CCC(CC(CC)CC)OC(=O)NCCN(C)CC]

Compound 103 was synthesized in 98% yield from Intermediate 103e and and N'-ethyl-N'-methyl-ethane-1,2-diamine using the method employed in Intermediate 91d. $^1$H NMR (400 MHz, CDCl$_3$) δ 5.42-5.21 (m, 8H), 5.18 (q, J=5.0 Hz, 1H), 5.07 (s, 1H), 4.79 (s, 1H), 4.21 (ddd, J=11.8, 4.4, 1.8 Hz, 2H), 4.08 (ddd, J=11.9, 5.8, 3.4 Hz, 2H), 3.17 (d, J=6.2 Hz, 2H), 2.70 (t, J=6.4 Hz, 4H), 2.44-2.27 (m, 6H), 2.24 (t, J=7.6 Hz, 4H), 2.13 (s, 3H), 1.98 (q, J=6.8 Hz, 8H), 1.84 (dq, J=8.4, 4.4 Hz, 1H), 1.71 (dd, J=14.8, 7.5 Hz, 1H), 1.58-1.43 (m, 8H), 1.29-1.16 (m, 38H), 0.96 (d, J=7.2 Hz, 3H), 0.80 (ddd, J=13.4, 6.7, 3.7 Hz, 13H). MS: 916.3 m/z [M+H].

Example 104

Intermediate 104a: (3,7-dimethyloctyl)magnesium bromide

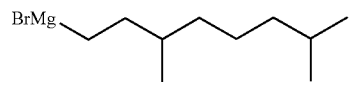

Intermediate 104a was synthesized from 1-bromo-3,7-dimethyl-octane using the method employed in Intermediate 104a.

Intermediate 104b: ethyl 7,11-dimethyl-4-oxododecanoate

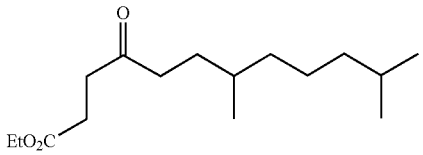 [SMILES: CCOC(=O)CCC(=O)CCC(C)CCCC(C)C]

Intermediate 104b was synthesized in 66% yield from Intermediate 104a using the method employed in Intermediate 103b. $^1$H NMR (400 MHz, CDCl$_3$) δ 4.11 (qd, J=7.1, 2.5 Hz, 2H), 2.71 (t, J=6.6 Hz, 2H), 2.56 (t, J=6.6 Hz, 2H), 2.49-2.35 (m, 2H), 1.68-1.54 (m, 1H), 1.49 (dq, J=13.2, 6.6 Hz, 1H), 1.43-1.31 (m, 2H), 1.24 (td, J=8.0, 7.1, 3.6 Hz, 6H), 1.10 (dddd, J=16.9, 9.9, 4.7, 2.0 Hz, 3H), 0.84 (d, J=6.5 Hz, 9H).

Intermediate 104c: 7,11-dimethyl-4-oxododecanoic acid

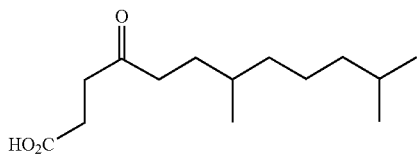 [SMILES: CC(C)CCCC(C)CCC(=O)CCC(=O)O]

Intermediate 104c was synthesized in 51% yield from Intermediate 104b using the method employed in Intermediate 103c. $^1$H NMR (400 MHz, CDCl$_3$) δ 2.72 (t, J=6.1 Hz, 2H), 2.63 (t, J=6.5 Hz, 2H), 2.50-2.36 (m, 2H), 1.61 (ddt, J=11.8, 9.0, 4.3 Hz, 1H), 1.51 (hept, J=6.6 Hz, 1H), 1.45-1.34 (m, 2H), 1.24 (ddt, J=16.2, 13.5, 4.2 Hz, 4H), 1.11 (ddt, J=16.0, 9.6, 5.9 Hz, 3H), 0.91-0.81 (m, 9H).

Intermediate 104d: 2-((7,11-dimethyl-4-oxododecanoyl)oxy)propane-1,3-diyl (9Z,9'Z,12Z,12'Z)-bis(octadeca-9,12-dienoate)

Intermediate 104d was synthesized in 58% yield from Intermediate 104c using the method employed in Intermediate 103d. $^1$H NMR (400 MHz, CDCl$_3$) δ 5.41-5.28 (m, 8H), 5.24 (ddd, J=10.2, 5.8, 4.3 Hz, 1H), 4.28 (dd, J=11.9, 4.4 Hz, 2H), 4.14 (dd, J=11.9, 5.8 Hz, 2H), 2.74 (dt, J=17.5, 6.5 Hz, 6H), 2.58 (t, J=6.5 Hz, 2H), 2.48-2.37 (m, 2H), 2.31 (t, J=7.6 Hz, 4H), 2.04 (q, J=6.9 Hz, 8H), 1.60 (ddd, J=10.0, 5.6, 2.6 Hz, 6H), 1.54-1.47 (m, 1H), 1.42-1.19 (m, 34H), 1.10 (ddt, J=19.6, 10.0, 6.9 Hz, 4H), 0.93-0.80 (m, 15H).

Intermediate 104e: 2-((7,11-dimethyl-4-(((4-nitrophenoxy)carbonyl)oxy)dodecanoyl)oxy)propane-1,3-diyl (9Z,9'Z,12Z,12'Z)-bis(octadeca-9,12-dienoate)

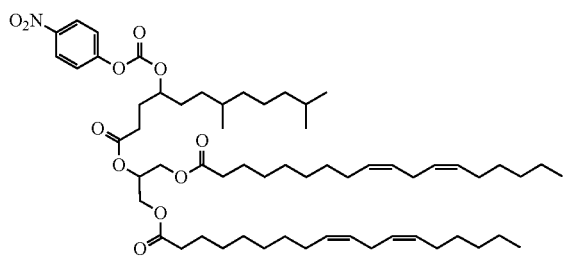

Intermediate 104e was synthesized in 58% yield from Intermediate 104d using the method employed in Intermediate 1e. $^1$H NMR (400 MHz, CDCl$_3$) δ 8.27-8.11 (m, 2H), 7.36-7.29 (m, 2H), 5.36-5.16 (m, 9H), 4.78 (ddq, J=12.5, 7.0, 3.4 Hz, 1H), 4.25 (dd, J=12.0, 4.3 Hz, 2H), 4.12-4.05 (m, 2H), 2.70 (t, J=6.3 Hz, 4H), 2.40 (t, J=7.5 Hz, 2H), 2.24 (tt, J=7.7, 4.0 Hz, 4H), 2.07-1.88 (m, 10H), 1.72-1.48 (m, 7H), 1.44 (ddd, J=13.3, 6.6, 1.3 Hz, 1H), 1.39-1.14 (m, 34H), 1.06 (dtd, J=8.6, 6.7, 4.7 Hz, 3H), 0.86-0.76 (m, 15H).

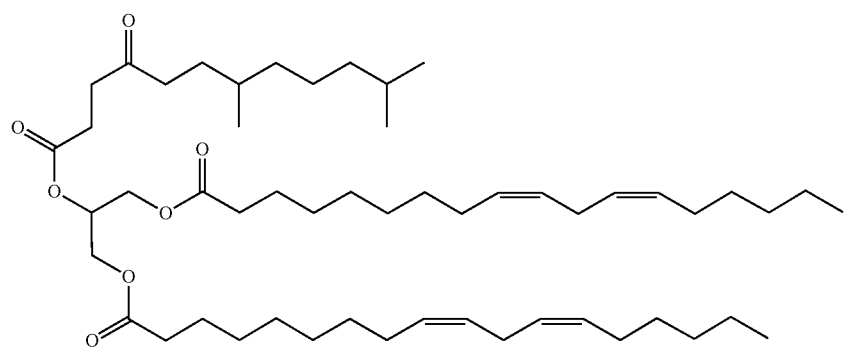 [SMILES: CCCCC/C=C\C/C=C\CCCCCCCC(=O)OCC(COC(=O)CCCCCCC/C=C\C/C=C\CCCCC)OC(=O)CCC(=O)CCC(C)CCCC(C)C]

Example 105—Compound 105

Compound 105: 2-((7,11-dimethyl-4-(((2-(pyrrolidin-1l-yl)ethyl)carbamoyl)oxy)dodecanoyl)oxy)propane-1,3-diyl (9Z,9'Z,12Z,12'Z)-bis(octadeca-9,12-dienoate)

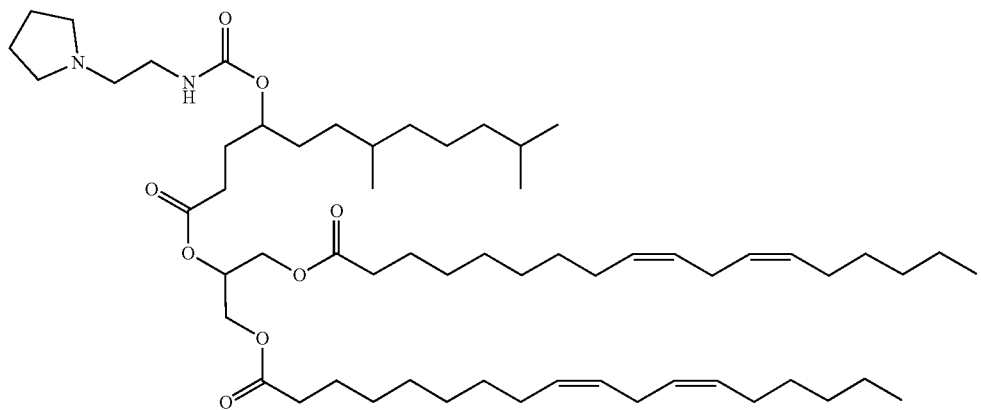 [SMILES: CCCCC/C=C\C/C=C\CCCCCCCC(=O)OCC(COC(=O)CCCCCCC/C=C\C/C=C\CCCCC)OC(=O)CCC(CCC(C)CCCC(C)C)OC(=O)NCCN1CCCC1]

Compound 105 was synthesized in 62% yield from Intermediate 104e and 2-pyrrolidin-1-ylethanamine using the method employed in Intermediate 91d. H NMR (400 MHz, CDCl$_3$) δ 5.38-5.22 (m, 8H), 5.22-5.16,), 0.78-5.08 (s, 1H), 4.67 (s, 1H), 4.22 (dd, J=12.0, 4.4 Hz, 2H), 4.08 (ddd, J=11.9, 5.9, 3.5 Hz, 2H), 3.20 (t, J=6.0 Hz, 2H), 2.70 (t, J=6.4 Hz, 4H), 2.51 (t, J=6.1 Hz, 2H), 2.43 (d, J=5.9 Hz, 4H), 2.32 (ddd, J=9.2, 6.7, 3.7 Hz, 2H), 2.25 (t, J=7.6 Hz, 4H), 1.98 (q, J=6.8 Hz, 8H), 1.84 (d, J=7.5 Hz, 1H), 1.77-1.66 (m, 5H), 1.54 (p, J=7.1 Hz, 7H), 1.44 (p, J=6.6 Hz, 3H), 1.35-1.10 (m, 34H), 1.10-0.96 (m, 5H), 0.86-0.74 (m, 15H). MS: 984.2 m/z [M+H].

Example 106—Compound 106

Compound 106: 2-(((6-ethyl-4-(((2-(pyrrolidin-1-yl)ethyl)carbamoyl)oxy)octanoyl)oxy)propane-1,3-diyl (9Z,9'Z,12Z,12'Z)-bis(octadeca-9,12-dienoate)

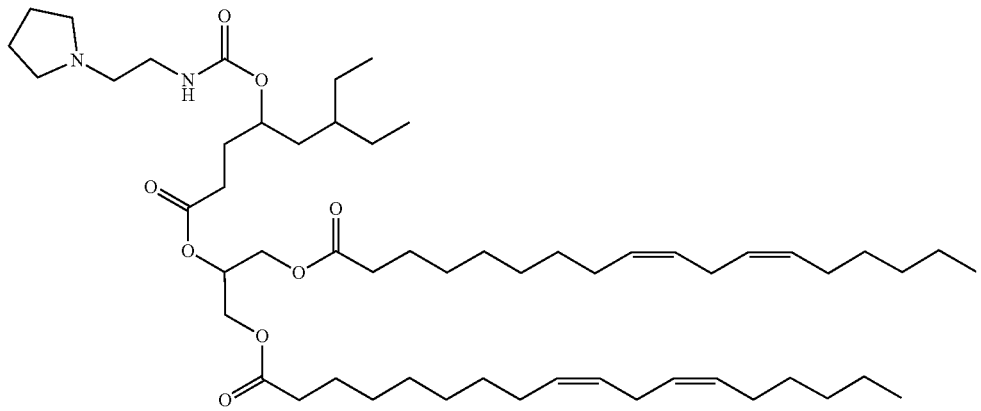 [SMILES: CCCCC/C=C\C/C=C\CCCCCCCC(=O)OCC(COC(=O)CCCCCCC/C=C\C/C=C\CCCCC)OC(=O)CCC(CC(CC)CC)OC(=O)NCCN1CCCC1]

Compound 106 was prepared in 78% yield from Intermediate 103e and 2-pyrrolidin-1-ylethanamine using the method employed in Intermediate 91d. ¹H NMR (400 MHz, CDCl₃) δ 5.28 (qt, J=11.5, 6.0 Hz, 8H), 5.19 (q, J=5.0 Hz, 1H), 4.79 (s, 1H), 4.22 (dd, J=12.2, 4.5 Hz, 2H), 4.08 (ddd, J=11.8, 5.8, 3.5 Hz, 2H), 3.22 (q, J=5.9 Hz, 2H), 2.70 (t, J=6.4 Hz, 4H), 2.53 (t, J=6.2 Hz, 2H), 2.46 (s, 3H), 2.33 (dd, J=9.6, 7.0 Hz, 2H), 2.25 (t, J=7.6 Hz, 4H), 1.98 (q, J=6.8 Hz, 7H), 1.89-1.80 (m, 2H), 1.76-1.61 (m, 7H), 1.60-1.45 (m, 6H), 1.34-1.16 (m, 33H), 0.87-0.72 (m, 12H). MS: 928.4 m/z [M+H].

Example 107—Compound 107

Intermediate 107a: (Z)-1-bromonon-3-ene

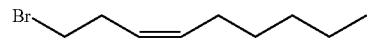

To a solution of PPh₃ (36.79 g, 1.33 equiv.) in DCM (1 M) was added Br₂ (7.23 mL, 1.33 eq) at 0° C. (Z)-non-3-en-1-ol (15 g, 1.0 equiv.) was added to the reaction mixture and the mixture was stirred at 0° C. for 2 h. The reaction mixture was quenched by addition of H₂O at 0° C. and extracted 3× with EtOAc. The combined organic layers were concentrated under reduced pressure to give a residue. The residue was purified by column chromatography to afford product as a colorless oil (15 g, 69%). ¹H NMR (400 MHz, CDCl₃) δ 5.47-5.30 (m, 2H), 3.64 (t, J=6.7 Hz, 2H), 2.18-2.06 (m, 2H), 2.02 (q, J=6.7 Hz, 2H), 1.77 (s, 1H), 1.62 (p, J=6.9 Hz, 2H), 1.38-1.20 (m, 6H), 0.87 (t, J=6.8 Hz, 3H).

Intermediate 107b: (Z)-non-3-en-1-ylmagnesium bromide

To a suspension of Mg (2.13 g, 1.2 equiv.) in THF (150 mL) was added I₂ (1.86 g, 0.1 equiv.). Then Intermediate 107a (15 g, 1.0 equiv.) was added to the mixture and the mixture was stirred at 45° C. for 2 h. The reaction mixture was used for next step directly without additional purification.

Intermediate 107c: ethyl (Z)-4-oxotridec-7-enoate

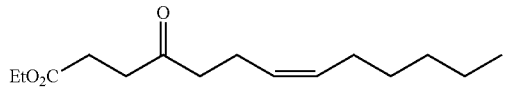

Intermediate 107c was synthesized in 75% yield from Intermediate 107b using the method employed in Intermediate 103b. ¹H NMR (400 MHz, CDCl₃) δ 5.43-5.23 (m, 2H), 4.10 (qd, J=7.1, 3.2 Hz, 3H), 2.69 (t, J=6.6 Hz, 2H), 2.55 (t, J=6.6 Hz, 2H), 2.47 (t, J=7.4 Hz, 2H), 2.30 (q, J=7.3 Hz, 2H), 2.01-1.95 (m, 2H), 1.34-1.18 (m, 11H), 0.86 (t, J=6.8 Hz, 3H).

Intermediate 107d: (Z)-4-oxotridec-7-enoic acid

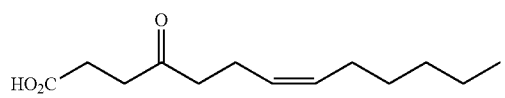 [SMILES: CCCCC/C=C\CCC(=O)CCC(=O)O]

Intermediate 107d was synthesized in 80% yield from Intermediate 107c using the method employed in Intermediate 103c. ¹H NMR (400 MHz, CDCl₃) δ 5.23 (ddt, J=34.8, 17.4, 7.8 Hz, 2H), 4.27-3.96 (m, 2H), 2.58 (t, J=6.1 Hz, 2H), 2.38 (t, J=7.4 Hz, 2H), 2.31-2.08 (m, 4H), 1.92 (q, J=6.9 Hz, 2H), 1.75 (s, 2H), 1.21 (dq, J=15.0, 9.2, 8.0 Hz, 6H), 0.80 (t, J=6.7 Hz, 3H).

Intermediate 107e: 2-(((Z)-4-oxotridec-7-enoyl)oxy) propane-1,3-diyl (9Z,9'Z,12Z,12'Z)-bis(octadeca-9, 12-dienoate)

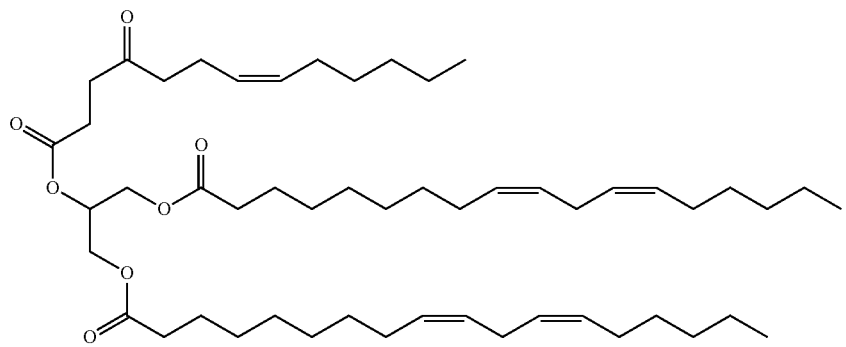 [SMILES: CCCCC/C=C\C/C=C\CCCCCCCC(=O)OCC(COC(=O)CCCCCCC/C=C\C/C=C\CCCCC)OC(=O)CCC(=O)CC/C=C\CCCCC]

Intermediate 107e was synthesized in 80% yield from Intermediate 107d and Intermediate 1c using the method employed in Intermediate 104c. $^1$H NMR (400 MHz, CDCl$_3$) δ 5.35-5.22 (m, 9H), 5.21-5.15 (m, 1H), 4.23 (dt, J=11.9, 4.8 Hz, 2H), 4.12-4.01 (m, 4H), 2.76-2.67 (m, 4H), 2.65 (t, J=6.5 Hz, 2H), 2.55-2.49 (m, 2H), 2.42 (t, J=7.5 Hz, 2H), 2.25 (t, J=7.6 Hz, 6H), 1.98 (q, J=7.2 Hz, 13H), 1.54 (p, J=7.6 Hz, 4H), 1.32-1.18 (m, 37H), 0.82 (td, J=7.0, 1.7 Hz, 9H).

Intermediate 107f: 2-(((Z)-4-(((4-nitrophenoxy)carbonyl)oxy)tridec-7-enoyl)oxy)propane-1,3-diyl (9Z,9'Z,12Z,12'Z)-bis(octadeca-9,12-dienoate)

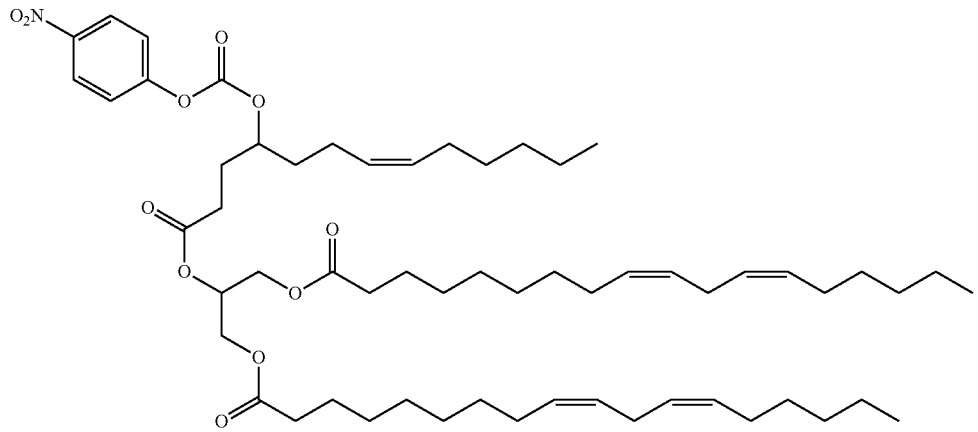 [SMILES: CCCCC/C=C\C/C=C\CCCCCCCC(=O)OCC(COC(=O)CCCCCCC/C=C\C/C=C\CCCCC)OC(=O)CCC(CC/C=C\CCCCC)OC(=O)Oc1ccc([N+](=O)[O-])cc1]

Intermediate 107f was synthesized in 21% yield from Intermediate 107e using the method employed in Intermediate 1e. $^1$H NMR (400 MHz, CDCl$_3$) δ 8.48-8.20 (m, 2H), 7.56-7.32 (m, 2H), 5.45-5.20 (m, 10H), 4.88 (tt, J=7.9, 4.6 Hz, 1H), 4.30 (ddd, J=12.1, 10.3, 4.5 Hz, 2H), 4.15 (ddd, J=11.9, 5.8, 2.1 Hz, 2H), 2.74 (dt, J=19.6, 6.5 Hz, 5H), 2.59 (t, J=6.5 Hz, 1H), 2.48 (q, J=7.1 Hz, 2H), 2.41-2.24 (m, 5H), 2.15 (q, J=7.7 Hz, 1H), 2.09-1.96 (m, 10H), 1.61 (q, J=12.7, 9.4 Hz, 5H), 1.39-1.20 (m, 30H), 0.99-0.69 (m, 9H).

Compound 107: 2-(((Z)-4-(((2-(ethyl(methyl)amino)ethyl)carbamoyl)oxy)tridec-7-enoyl)oxy)propane-1,3-diyl (9Z,9'Z,12Z,12'Z)-bis(octadeca-9,12-dienoate)

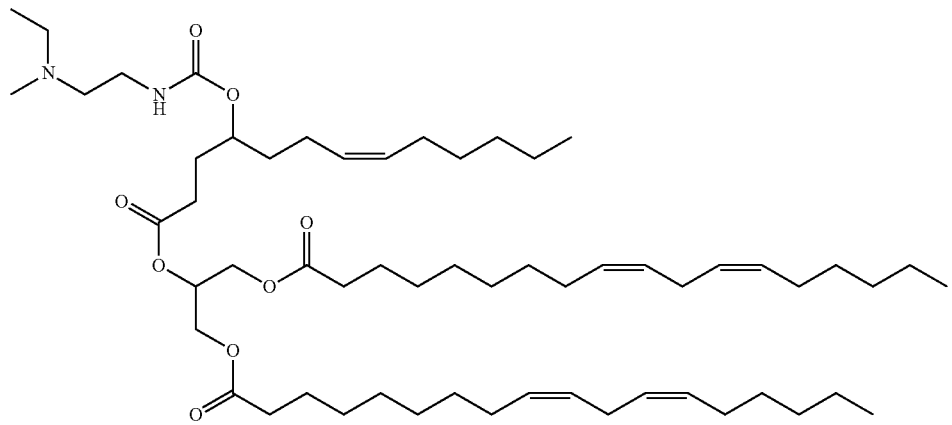 [SMILES: CCCCC/C=C\C/C=C\CCCCCCCC(=O)OCC(COC(=O)CCCCCCC/C=C\C/C=C\CCCCC)OC(=O)CCC(CC/C=C\CCCCC)OC(=O)NCCN(C)CC]

Compound 107 was synthesized in 56% yield from Intermediate 107f and N'-ethyl-N'-methyl-ethane-1,2-diamine using the method employed in Intermediate 91d. $^1$H NMR (400 MHz, CDCl$_3$) δ 5.41-5.29 (m, 9H), 5.24 (p, J=5.0 Hz, 1H), 5.16 (d, J=5.3 Hz, 1H), 4.81-4.74 (m, 1H), 4.28 (dd, J=11.9, 4.4 Hz, 2H), 4.14 (ddd, J=11.9, 5.8, 3.3 Hz, 2H), 3.23 (q, J=5.9 Hz, 2H), 2.76 (t, J=6.4 Hz, 4H), 2.48-2.36 (m, 6H), 2.31 (t, J=7.6 Hz, 4H), 2.20 (s, 3H), 2.02 (dq, J=20.4, 7.0 Hz, 12H), 1.96-1.87 (m, 2H), 1.81 (dd, J=14.7, 7.3 Hz, 1H), 1.65-1.55 (m, 7H), 1.39-1.22 (m, 35H), 1.03 (t, J=7.1 Hz, 3H), 0.88 (td, J=7.0, 2.3 Hz, 9H). MS: 955.3 m/z [M+H].

Example 108—Compound 108

Compound 108: 2-(((Z)-4-(((2-(pyrrolidin-1-yl)ethyl)carbamoyl)oxy)tridec-7-enoyl)oxy)propane-1,3-diyl (9Z,9'Z,12Z,12'Z)-bis(octadeca-9,12-dienoate)

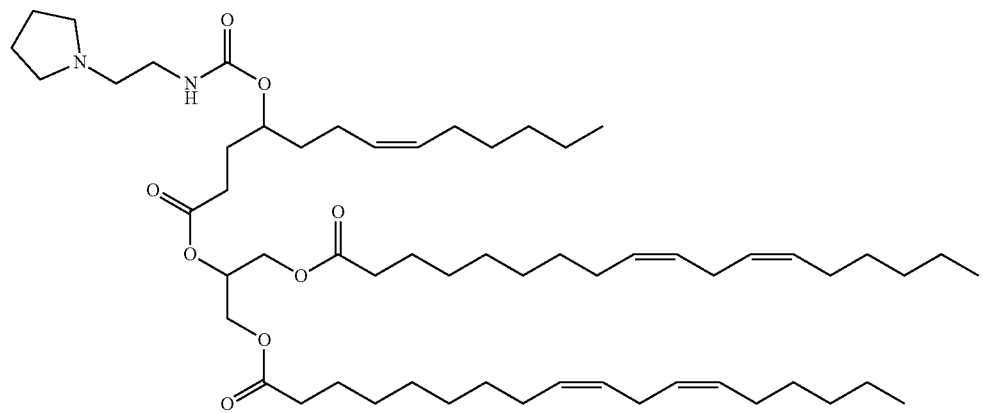 [SMILES: CCCCC/C=C\C/C=C\CCCCCCCC(=O)OCC(COC(=O)CCCCCCC/C=C\C/C=C\CCCCC)OC(=O)CCC(CC/C=C\CCCCC)OC(=O)NCCN1CCCC1]

Compound 108 was synthesized in 51% yield from Intermediate 107f and 2-pyrrolidin-1-ylethanamine using the method employed in Intermediate 91d. H NMR (400 MHz, CDCl$_3$) δ 5.43-5.26 (m, 9H), 5.24 (q, J=5.1 Hz, 1H), 4.78 (tt, J=8.6, 4.6 Hz, 1H), 4.28 (dd, J=11.9, 4.4 Hz, 2H), 4.14 (ddd, J=11.9, 5.8, 3.5 Hz, 2H), 3.29 (q, J=5.9 Hz, 2H), 2.76 (t, J=6.4 Hz, 4H), 2.66-2.50 (m, 5H), 2.39 (ddd, J=9.6, 6.7, 3.6 Hz, 2H), 2.31 (t, J=7.6 Hz, 4H), 2.01 (dq, J=20.4, 7.1 Hz, 12H), 1.87-1.72 (m, 5H), 1.59 (q, J=7.3 Hz, 6H), 1.40-1.15 (m, 31H), 0.88 (td, J=6.9, 2.2 Hz, 9H). MS: 967.3 m/z [M+H].

Example 109—Compound 109

Intermediate 109a: 3-((tert-butyldimethylsilyl)oxy)-2-oxopropyl (9Z,12Z)-octadeca-9,12-dienoate

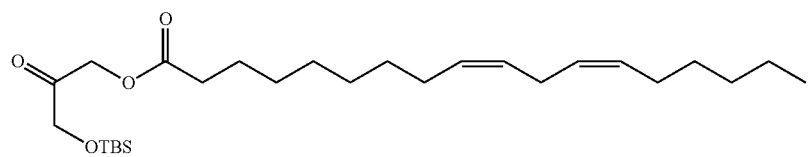 [SMILES: CCCCC/C=C\C/C=C\CCCCCCCC(=O)OCC(=O)CO[Si](C)(C)C(C)(C)C]

Intermediate 109a was synthesized in 63% yield from Intermediate 62a and linoleic acid using the method employed in Intermediate 62b. H NMR (400 MHz, CDCl$_3$) δ 5.31-5.19 (m, 4H), 4.84 (s, 2H), 4.16 (s, 2H), 2.67 (t, J=6.7 Hz, 2H), 2.32 (t, J=7.5 Hz, 2H), 1.94 (q, J=6.9 Hz, 4H), 1.57 (q, J=7.4 Hz, 2H), 1.31-1.13 (m, 15H), 0.80 (d, J=15.1 Hz, 12H).

Intermediate 109b: 3-hydroxy-2-oxopropyl (9Z,12Z)-octadeca-9,12-dienoate

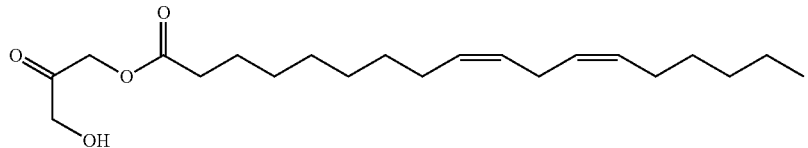 [SMILES: CCCCC/C=C\C/C=C\CCCCCCCC(=O)OCC(=O)CO]

To a solution of Intermediate 109a (1.0 equiv.) in THF (180 mL) was added HF-pyridine (5.0 equiv.). The mixture was stirred at 25° C. for 1 h. The reaction mixture was concentrated under reduced pressure to remove THF. The residue was diluted with $H_2O$ and extracted 3× with EtOAc. The combined organic layers were dried over $Na_2SO_4$, filtered and the filtrate was concentrated under reduced pressure to give a residue. The residue was purified by column chromatography to afford product as a colorless oil (66%). $^1$H NMR (400 MHz, $CDCl_3$) δ 5.33 (dtd, J=12.5, 10.3, 9.5, 5.6 Hz, 4H), 4.74 (s, 1H), 4.36 (s, 1H), 2.76 (t, J=6.4 Hz, 2H), 2.41 (t, J=7.5 Hz, 1H), 2.37-2.27 (m, 1H), 2.03 (q, J=6.9 Hz, 4H), 1.65 (p, J=7.1 Hz, 2H), 1.41-1.24 (m, 14H), 0.87 (t, J=6.7 Hz, 3H).

Intermediate 109c: 3-(oleoyloxy)-2-oxopropyl (9Z,12Z)-octadeca-9,12-dienoate

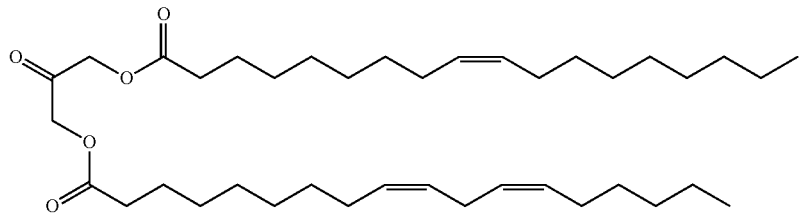 [SMILES: CCCCC/C=C\C/C=C\CCCCCCCC(=O)OCC(=O)COC(=O)CCCCCCC/C=C\CCCCCCCC]

Intermediate 109c was synthesized in 50% yield from Intermediate 109b and oleic acid using the method employed in Compound 52. $^1$H NMR (400 MHz, $CDCl_3$) δ 5.37-5.22 (m, 6H), 4.68 (s, 4H), 2.70 (t, J=6.4 Hz, 2H), 2.35 (t, J=7.5 Hz, 4H), 2.02-1.91 (m, 8H), 1.60 (q, J=7.3 Hz, 4H), 1.33-1.17 (m, 33H), 0.81 (dt, J=7.0, 3.3 Hz, 6H).

Intermediate 109d: 2-hydroxy-3-(oleoyloxy)propyl (9Z,12Z)-octadeca-9,12-dienoate

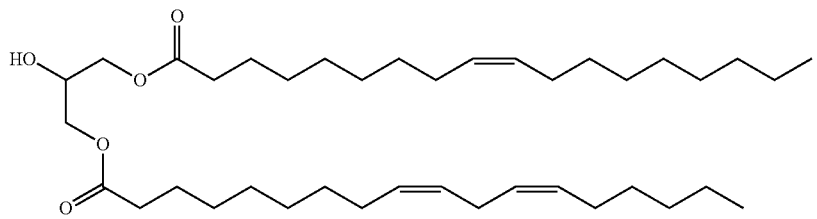 [SMILES: CCCCC/C=C\C/C=C\CCCCCCCC(=O)OCC(O)COC(=O)CCCCCCC/C=C\CCCCCCCC]

Intermediate 109d was synthesized in 50% yield from Intermediate 109c using the method employed in Intermediate 1c. $^1$H NMR (400 MHz, $CDCl_3$) δ 5.37-5.21 (m, 6H), 4.15-4.00 (m, 4H), 2.70 (t, J=6.3 Hz, 2H), 2.28 (t, J=7.6 Hz, 4H), 2.04-1.89 (m, 8H), 1.56 (t, J=7.4 Hz, 4H), 1.23 (dt, J=13.9, 7.0 Hz, 34H), 0.82 (td, J=6.8, 3.8 Hz, 6H).

Compound 109: 3-(oleoyloxy)-2-((4-(((2-(pyrrolidin-1-yl)ethyl)carbamoyl)oxy)octanoyl)oxy)propyl (9Z,12Z)-octadeca-9,12-dienoate

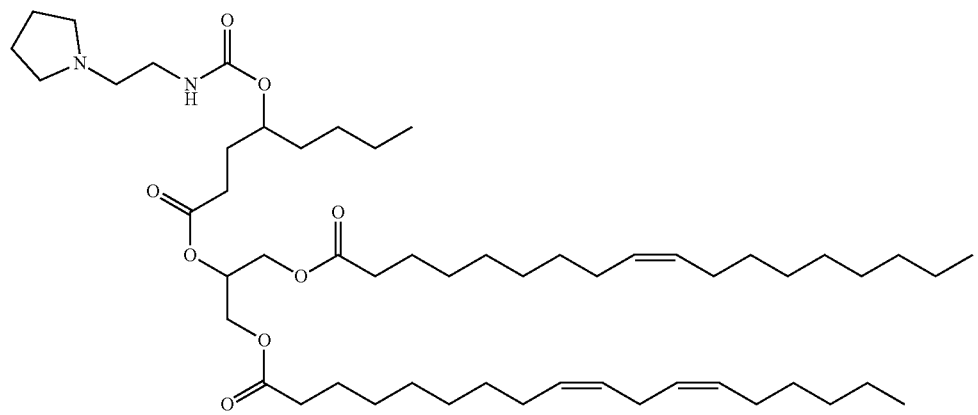 [SMILES: CCCCC/C=C\C/C=C\CCCCCCCC(=O)OCC(COC(=O)CCCCCCC/C=C\CCCCCCCC)OC(=O)CCC(CCCC)OC(=O)NCCN1CCCC1]

Compound 109 was synthesized from Intermediate 109d and Intermediate 85c using the method employed in Compound 85. $^1$H NMR (400 MHz, CDCl$_3$) δ 5.35 (tdd, J=8.8, 6.5, 3.6 Hz, 5H), 5.28-5.22 (m, 1H), 5.16 (s, 1H), 4.29 (dd, J=11.9, 4.4 Hz, 2H), 4.15 (ddd, J=11.9, 5.8, 3.3 Hz, 2H), 3.34-3.22 (m, 2H), 2.77 (t, J=6.5 Hz, 2H), 2.55 (d, J=30.6 Hz, 5H), 2.39 (ddd, J=8.8, 6.6, 3.8 Hz, 2H), 2.31 (t, J=7.6 Hz, 4H), 2.09-1.97 (m, 7H), 1.91 (d, J=7.2 Hz, 1H), 1.78 (d, J=6.0 Hz, 4H), 1.61 (t, J=7.2 Hz, 6H), 1.30 (td, J=10.5, 9.4, 4.7 Hz, 30H), 0.91-0.87 (m, 6H). MS: 902.3 m/z [M+H].

Example 110—Compound 110

Intermediate 110a: 2-oxopropane-1,3-diyl dioleate

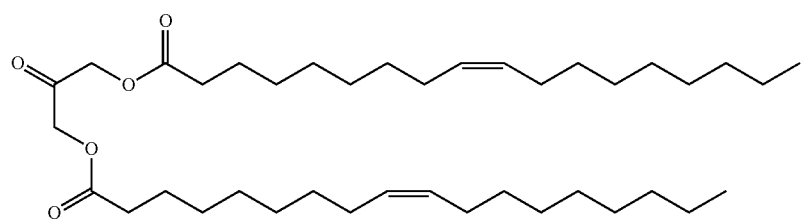 [SMILES: CCCCCCCC/C=C\CCCCCCCC(=O)OCC(=O)COC(=O)CCCCCCC/C=C\CCCCCCCC]

To a solution of 1,3-dihydroxypropan-2-one (5 g, 0.5 equiv.) in DCM (300 mL) was added DMAP (1.1 equiv.) and EDCI (1.0 equiv.). Then the above mixture was added oleic acid (1.0 equiv.) and stirred at 25° C. for 12 h. The reaction mixture was concentrated under reduced pressure to remove DCM. The residue was diluted with H$_2$O and extracted 3× with EtOAc. The combined organic layers were dried over Na$_2$SO$_4$, filtered, and the filtrate was concentrated under reduced pressure to give a residue. The residue was purified by column chromatography to afford product as a colorless oil (8 g, 12%). $^1$H NMR (400 MHz, CDCl$_3$) δ 5.34-5.21 (m, 4H), 4.68 (s, 4H), 2.35 (t, J=7.5 Hz, 4H), 1.94 (q, J=6.4 Hz, 8H), 1.60 (q, J=7.4 Hz, 4H), 1.31-1.14 (m, 38H), 0.89-0.75 (m, 6H).

Intermediate 110b: 2-hydroxypropane-1,3-diyl dioleate

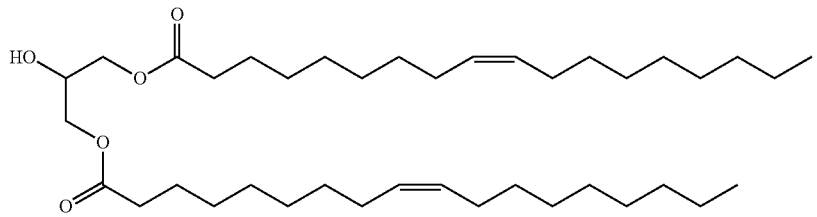 [SMILES: CCCCCCCC/C=C\CCCCCCCC(=O)OCC(O)COC(=O)CCCCCCC/C=C\CCCCCCCC]

Intermediate 110b was synthesized in 47% yield from Intermediate 110a using the method employed in Intermediate 1c. ¹H NMR (400 MHz, CDCl₃) δ 5.41-5.26 (m, 4H), 4.22-4.06 (m, 4H), 2.34 (t, J=7.6 Hz, 4H), 2.01 (q, J=6.4 Hz, 7H), 1.63 (p, J=7.2 Hz, 4H), 1.28 (d, J=14.2 Hz, 33H), 0.90-0.81 (m, 6H).

Compound 110: 2-((4-(((2-(pyrrolidin-1-yl)ethyl)carbamoyl)oxy)octanoyl)oxy)propane-1,3-diyl dioleate

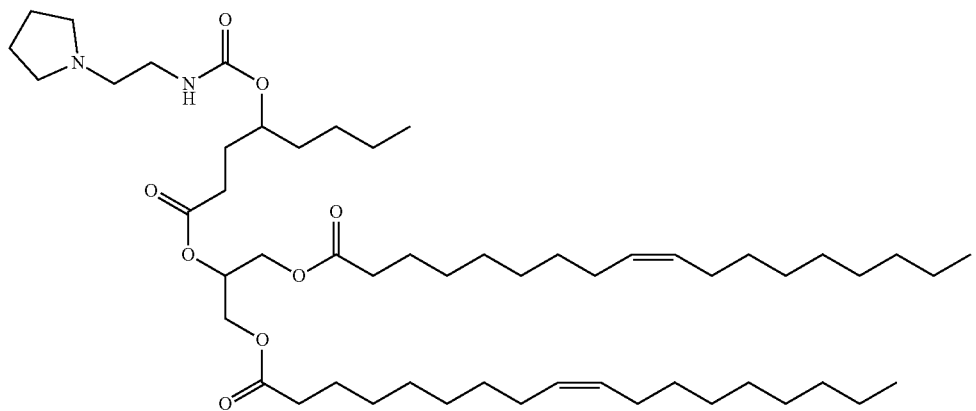 [SMILES: CCCCCCCC/C=C\CCCCCCCC(=O)OCC(COC(=O)CCCCCCC/C=C\CCCCCCCC)OC(=O)CCC(CCCC)OC(=O)NCCN1CCCC1]

Compound 110 was synthesized from Intermediate 110b and Intermediate 85c using the method employed in Compound 85. ¹H NMR (400 MHz, CDCl₃) δ 5.33-5.22 (m, 4H), 5.22-5.15 (m, 1H), 5.08 (s, 1H), 4.69 (s, 1H), 4.28-4.17 (m, 2H), 4.08 (ddq, J=12.2, 6.4, 2.9 Hz, 2H), 3.21 (d, J=6.8 Hz, 2H), 2.51 (t, J=6.2 Hz, 2H), 2.43 (d, J=6.0 Hz, 4H), 2.32 (ddd, J=8.6, 6.6, 3.7 Hz, 2H), 2.24 (t, J=7.6 Hz, 4H), 1.94 (q, J=6.7 Hz, 8H), 1.87-1.78 (m, 1H), 1.70 (p, J=3.1 Hz, 5H), 1.61-1.36 (m, 9H), 1.22 (d, J=13.2 Hz, 45H), 0.82 (td, J=6.9, 3.7 Hz, 9H). MS: 904.2 m/z [M+H].

Example 111—Compound 111

Compound 111—3-((4-(((2-(pyrrolidin-1-yl)ethyl)carbamoyl)oxy)octanoyl)oxy)propane-1,2-diyl (9Z,9'Z,12Z,12'Z)-bis(octadeca-9,12-dienoate)

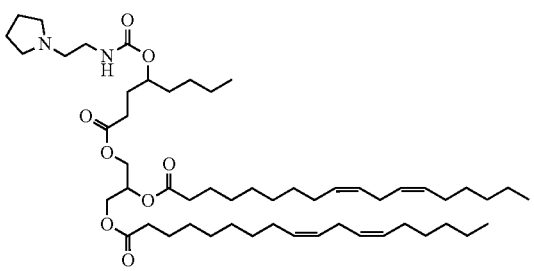 [SMILES: CCCCC/C=C\C/C=C\CCCCCCCC(=O)OCC(COC(=O)CCC(CCCC)OC(=O)NCCN1CCCC1)OC(=O)CCCCCCC/C=C\C/C=C\CCCCC]

Compound 111 was synthesized from Intermediate 85c and Intermediate 30a using the method employed in Compound 85. $^1$H NMR (400 MHz, CDCl$_3$) δ 5.43-5.27 (m, 8H), 5.24 (t, J=5.2 Hz, 1H), 5.14 (s, 1H), 4.74 (s, 1H), 4.27 (ddd, J=12.2, 8.2, 4.2 Hz, 2H), 4.18-4.09 (m, 2H), 3.27 (q, J=5.9 Hz, 2H), 2.75 (t, J=6.4 Hz, 4H), 2.57 (t, J=6.2 Hz, 2H), 2.50 (s, 4H), 2.37 (td, J=8.9, 7.8, 3.5 Hz, 2H), 2.30 (td, J=7.5, 4.4 Hz, 4H), 2.03 (q, J=6.9 Hz, 8H), 1.98-1.86 (m, 2H), 1.76 (h, J=3.1 Hz, 5H), 1.59 (tt, J=9.8, 5.1 Hz, 7H), 1.38-1.21 (m, 30H), 0.87 (t, J=6.7 Hz, 9H). MS: 900.1 m/z [M+H].

Example 112—Compound 112

Compound 112: 2-(((4-(((2-(pyrrolidin-1l-yl)ethyl)carbamoyl)oxy)octanoyl)oxy)methyl)propane-1,3-diyl (9Z,9'Z,12Z,12'Z)-bis(octadeca-9,12-dienoate)

Compound 112 was synthesized from Intermediate 86c and Intermediate 53a using the method employed in Compound 84. $^1$H NMR (400 MHz, CDCl$_3$) δ 5.44-5.28 (m, 8H), 5.19 (s, 1H), 4.75 (s, 1H), 4.12 (d, J=5.9 Hz, 6H), 3.29 (q, J=6.1 Hz, 2H), 2.77 (t, J=6.4 Hz, 4H), 2.64-2.49 (m, 6H), 2.38 (ddd, J=10.1, 8.5, 4.8 Hz, 3H), 2.30 (t, J=7.6 Hz, 4H), 2.05 (q, J=6.8 Hz, 8H), 1.90 (s, 2H), 1.86-1.72 (m, 6H), 1.61 (t, J=7.3 Hz, 7H), 1.32 (tq, J=7.6, 4.9, 3.7 Hz, 33H), 0.89 (t, J=6.7 Hz, 9H). MS: 914.1 m/z [M+H].

Example 113—Compound 113

Intermediate 113a: benzyl 3-hydroxyheptanoate

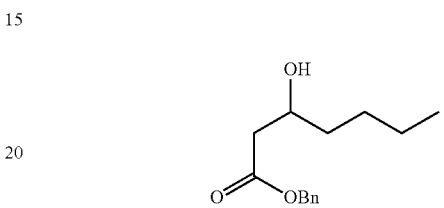

Zn was poured into HCl (1 M) and stirred for 30 min. The mixture was filtered, and the precipitate was washed with EtOH. The solid was dried under reduced pressure to afford freshly prepared Zn. To a suspension of Zn (15.18 g, 2.0 equiv.) in THF (50 mL) was added pentanal (1.0 equiv.) and benzyl 2-bromoacetate (1.5 equiv.) dropwise at 66° C. for 0.5 h. The reaction mixture was filtered, and the filtrate was concentrated under reduced pressure to give a residue. The residue was diluted with H$_2$O and extracted 3× with EtOAc. The combined organic layers were concentrated under reduced pressure to give a residue. The residue was purified by column chromatography to afford product as a colorless oil (10 g, 36%). $^1$H NMR (400 MHz, CDCl$_3$) δ 7.34 (d,

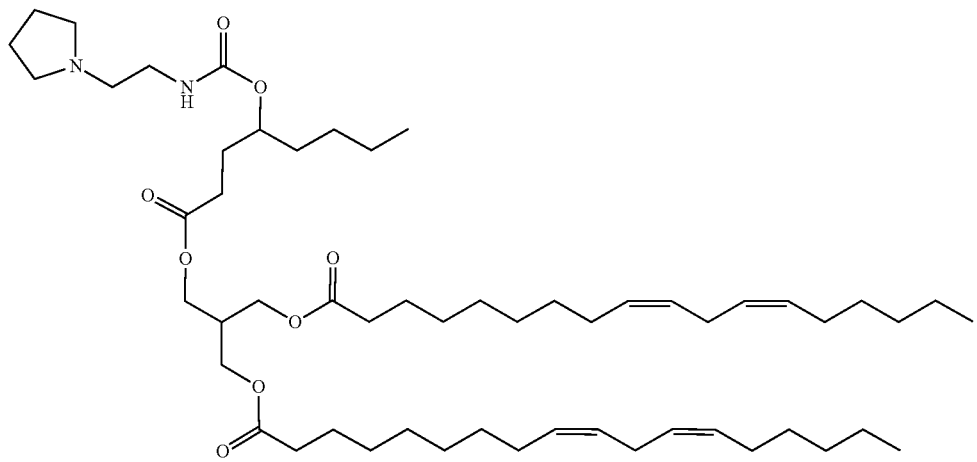 [SMILES: CCCCC/C=C\C/C=C\CCCCCCCC(=O)OCC(COC(=O)CCCCCCC/C=C\C/C=C\CCCCC)COC(=O)CCC(CCCC)OC(=O)NCCN1CCCC1]

J=4.1 Hz, 5H), 5.14 (s, 2H), 4.01 (tt, J=8.4, 3.6 Hz, 1H), 2.87 (s, 1H), 2.59-2.41 (m, 2H), 1.57-1.47 (m, 1H), 1.43 (qd, J=9.6, 8.9, 4.6 Hz, 2H), 1.37-1.24 (m, 4H), 0.93-0.87 (m, 3H).

Intermediate 113b: benzyl 3-(((4-nitrophenoxy)carbonyl)oxy)heptanoate

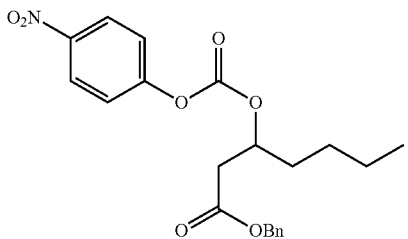 [SMILES: CCCCC(CC(=O)OCc1ccccc1)OC(=O)Oc1ccc([N+](=O)[O-])cc1]

To a solution of Intermediate 113a (8 g, 1.0 equiv.) and (4-nitrophenyl) carbonochloridate (2.0 equiv.) in DCM (10 mL) was added pyridine (3.0 equiv.) at 0° C. The mixture was stirred at 20° C. for 2 h under N₂ atmosphere. The reaction mixture was concentrated under reduced pressure to remove DCM. The residue was diluted with H₂O and extracted 3× with EtOAc. The combined organic layers were concentrated under reduced pressure to give a residue. The residue was purified by column chromatography to afford product as a colorless oil (8 g, 59% yield). ¹H NMR (400 MHz, CDCl₃) δ 8.30-8.21 (m, 2H), 7.39-7.28 (m, 7H), 5.16 (d, J=3.3 Hz, 2H), 2.82-2.69 (m, 2H), 1.81-1.68 (m, 2H), 1.43-1.30 (m, 5H), 0.94-0.89 (m, 3H).

Intermediate 113c: benzyl 3-(((2-(pyrrolidin-1-yl)ethyl)carbamoyl)oxy)heptanoate

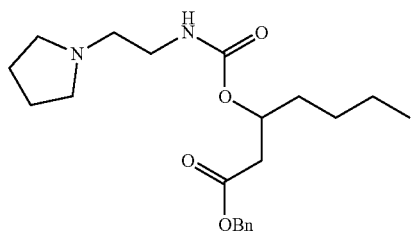 [SMILES: CCCCC(CC(=O)OCc1ccccc1)OC(=O)NCCN1CCCC1]

To a solution of Intermediate 113b (0.5 g, 1.0 equiv.) and 2-pyrrolidin-1-ylethanamine (3.0 equiv.) in MeCN (10 mL) was added DMAP (0.1 equiv.) and pyridine (3.0 equiv.) at 0° C. The mixture was stirred at 20° C. for 2 h. The reaction mixture was concentrated under reduced pressure to remove MeCN. The residue was diluted with H₂O and extracted 3× with EtOAc. The combined organic layers were concentrated under reduced pressure to give a residue. The residue was purified by column chromatography to afford product as a colorless oil (0.4 g, 85%). ¹H NMR (400 MHz, CDCl₃) δ 7.36-7.20 (m, 5H), 5.05 (s, 2H), 3.17 (dt, J=13.3, 6.4 Hz, 2H), 2.56 (td, J=13.2, 11.4, 6.3 Hz, 2H), 2.50-2.37 (m, 6H), 1.72-1.63 (m, J=4.0, 3.5 Hz, 4H), 1.49 (s, 2H), 1.28-1.20 (m, 4H), 0.81 (q, J=4.2, 3.2 Hz, 3H).

Intermediate 113d: 3-(((2-(pyrrolidin-1-yl)ethyl)carbamoyl)oxy)heptanoic acid

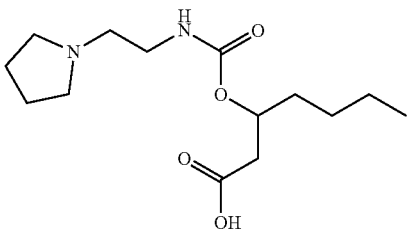 [SMILES: CCCCC(CC(=O)O)OC(=O)NCCN1CCCC1]

To a solution of Intermediate 113c (3.5 g, 1.0 equiv.) in THF (10 mL) was added Pd/C (10% w/w). The mixture was purged 3× with H2, and then the mixture was stirred at 20° C. for 12 h under H2 atmosphere. The reaction mixture was filtered, and the filtrate was concentrated under reduced pressure to give a residue. The residue was purified by column chromatography to afford product as a colorless oil (2 g, 75%). ¹H NMR (400 MHz, CDCl₃) δ 10.00 (s, 1H), 6.46 (t, J=6.0 Hz, 1H), 5.02 (dt, J=10.0, 5.2 Hz, 1H), 3.43-3.25 (m, 3H), 2.92 (dt, J=21.7, 6.5 Hz, 6H), 2.37 (qd, J=14.9, 6.4 Hz, 2H), 1.87 (q, J=4.4, 2.9 Hz, 4H), 1.64-1.45 (m, 2H), 1.24 (h, J=7.7, 6.7 Hz, 4H), 0.88-0.75 (m, 3H).

Compound 113: 2-(((3-(((2-(pyrrolidin-1-yl)ethyl)carbamoyl)oxy)heptanoyl)oxy)methyl)propane-1,3-diyl (9Z,9'Z,12Z,12'Z)-bis(octadeca-9,12-dienoate)

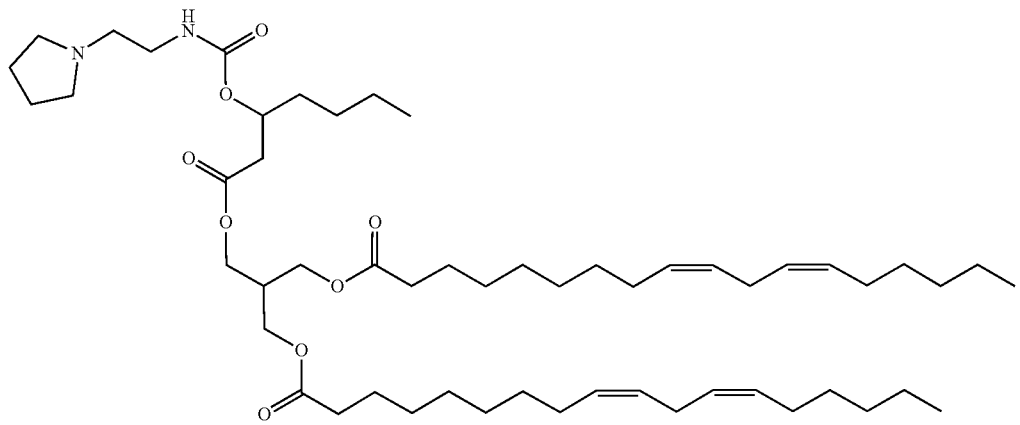 [SMILES: CCCCC/C=C\C/C=C\CCCCCCCC(=O)OCC(COC(=O)CCCCCCC/C=C\C/C=C\CCCCC)COC(=O)CC(CCCC)OC(=O)NCCN1CCCC1]

Compound 113 was synthesized from Intermediate 113c and Intermediate 53a using the method employed in Compound 52. $^1$H NMR (400 MHz, CDCl$_3$) δ 5.37-5.18 (m, 8H), 5.00 (q, J=6.4 Hz, 1H), 4.06 (p, J=6.5, 6.1 Hz, 6H), 3.21 (p, J=7.3, 6.8 Hz, 2H), 2.70 (t, J=6.5 Hz, 4H), 2.55-2.39 (m, 7H), 2.32 (p, J=6.0 Hz, 1H), 2.23 (t, J=7.6 Hz, 4H), 1.98 (q, J=6.8 Hz, 7H), 1.76-1.63 (m, 5H), 1.54 (t, J=7.3 Hz, 6H), 1.33-1.15 (m, 30H), 0.82 (t, J=6.7 Hz, 9H). MS: 900.1 m/z [M+H].

Example 114—Comparative Compound 114

Compound 114: 2-(((2-(ethyl(methyl)amino)ethyl)carbamoyl)oxy)propane-1,3-diyl (9Z,9'Z,12Z,12'Z)-bis(octadeca-9,12-dienoate)

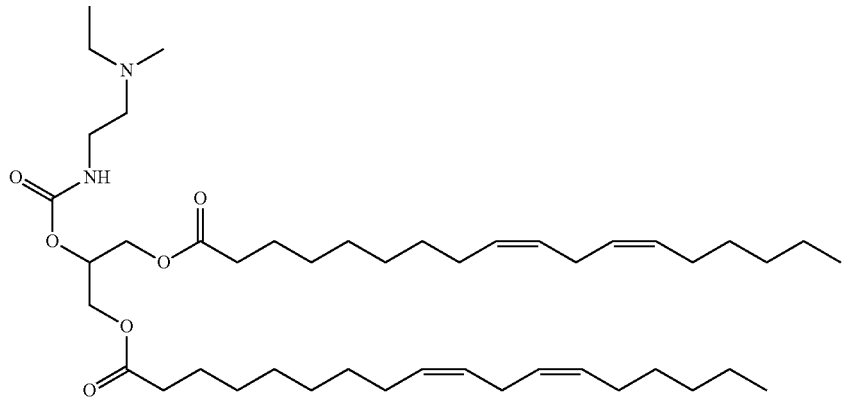 [SMILES: CCCCC/C=C\C/C=C\CCCCCCCC(=O)OCC(COC(=O)CCCCCCC/C=C\C/C=C\CCCCC)OC(=O)NCCN(C)CC]

To a solution of Intermediate 1c (250 mg, 1.0 equiv) in DCM (2 mL) was added pyridine (3.0 equiv) and 4-nitrophenyl chloroformate (1.1 equiv). The reaction was stirred at 25° C. for 2 h, after which point the reaction was quenched by the addition of water and extracted 3× with DCM. The organic layers were dried over Na$_2$SO$_4$, filtered, and concentrated. The resulting crude residue was reconstituted in MeCN (2 mL) followed by the addition of pyridine (3.0 equiv), N1-ethyl-N1-methylethane-1,2-diamine (1.5 equiv), and DMAP (1.0 equiv). The reaction was stirred at 25° C. for 16 h. Heptane was then added to the reaction mixture, and the heptane layer was washed 3× with MeCN. The combined MeCN layers were back-extracted three times with heptane, and the combined heptane layers were washed one final time with MeCN. Heptane was then removed in vacuo, and crude material was purified by column chromatography (MeOH/DCM) to afford product as a colorless oil (138 mg, 46%). 1H NMR (400 MHz, CDCl$_3$) δ 5.49-5.27 (m, 8H), 5.14 (p, J=5.0 Hz, 1H), 4.33-4.12 (m, 4H), 3.29 (q, J=5.7 Hz, 2H), 2.83-2.71 (m, 4H), 2.60-2.38 (m, 5H), 2.38-2.16 (m, 7H), 2.04 (q, J=6.9 Hz, 8H), 1.69-1.56 (m, 4H), 1.42-1.22 (m, 28H), 1.07 (t, J=7.2 Hz, 3H), 0.96-0.85 (m, 6H).

Example 115—Materials and Methods

LNP Compositions

LNPs were prepared using various amine lipids in a 4-component lipid system consisting of an ionizable lipid (e.g. an amine lipid), DSPC, cholesterol and PEG-2k-DMG. In assays for percent liver editing in mice, Cas9 mRNA and chemically modified sgRNA targeting a mouse sequence were formulated in LNPs, at either a 1:1 w/w ratio or a 1:2 w/w ratio.

LNP Formulation—Cross Flow

The lipid components were dissolved in 100% ethanol with the lipid component molar ratios described below. The chemically modified sgRNA and Cas9 mRNA were combined and dissolved in 25 mM citrate, 100 mM NaCl, pH 5.0, resulting in a concentration of total RNA cargo of approximately 0.45 mg/mL. The LNPs were formulated with an N/P ratio of about 6, with the ratio of chemically modified sgRNA: Cas9 mRNA at either a 1:1 or 1:2 w/w ratio as described below.

The LNPs were formed by an impinging jet mixing of the lipid in ethanol with two volumes of RNA solutions and one volume of water. The lipid in ethanol is mixed through a mixing cross with the two volumes of RNA solution. A fourth stream of water is mixed with the outlet stream of the cross through an inline tee. (See, e.g., WO2016010840, FIG. 2.) The LNPs were held for 1 hour at room temperature, and further diluted with water (approximately 1:1 v/v). Diluted LNPs were concentrated using tangential flow filtration on a flat sheet cartridge (Sartorius, 100 kD MWCO) and then buffer exchanged by diafiltration into 50 mM Tris, 45 mM NaCl, 5% (w/v) sucrose, pH 7.5 (TSS). Alternatively, the final buffer exchange into TSS was completed with PD-10 desalting columns (GE). If required, compositions were concentrated by centrifugation with Amicon 100 kDa centrifugal filters (Millipore). The resulting mixture was then filtered using a 0.2 m sterile filter. The final LNP was stored at 4° C. or −80° C. until further use.

LNP Composition Analytics

Dynamic Light Scattering ("DLS") is used to characterize the polydispersity index ("pdi") and size of the LNPs of the present disclosure. DLS measures the scattering of light that results from subjecting a sample to a light source. PDI, as determined from DLS measurements, represents the distribution of particle size (around the mean particle size) in a population, with a perfectly uniform population having a PDI of zero. Electrophoretic light scattering is used to characterize the surface charge of the LNP at a specified pH. The surface charge, or the zeta potential, is a measure of the magnitude of electrostatic repulsion/attraction between particles in the LNP suspension. Asymmetric-Flow Field Flow Fractionation—Multi-Angle Light Scattering (AF4-MALS) is used to separate particles in the composition by hydrodynamic radius and then measure the molecular weights, hydrodynamic radii and root mean square radii of the fractionated particles. This allows the ability to assess molecular weight and size distributions as well as secondary characteristics such as the Burchard-Stockmeyer Plot (ratio of root mean square ("rms") radius to hydrodynamic radius over time suggesting the internal core density of a particle) and the rms conformation plot (log of rms radius vs log of molecular weight where the slope of the resulting linear fit gives a degree of compactness vs elongation). Nanoparticle tracking analysis (NTA, Malvern Nanosight) can be used to determine particle size distribution as well as particle concentration. LNP samples are diluted appropriately and injected onto a microscope slide. A camera records the scattered light as the particles are slowly infused through field of view. After the movie is captured, the Nanoparticle Tracking Analysis processes the movie by tracking pixels and calculating a diffusion coefficient. This diffusion coefficient can be translated into the hydrodynamic radius of the particle. The instrument also counts the number of individual particles counted in the analysis to give particle concentration.

Cryo-electron microscopy ("cryo-EM") can be used to determine the particle size, morphology, and structural characteristics of an LNP.

Lipid compositional analysis of the LNPs can be determined from liquid chromatography followed by charged aerosol detection (LC-CAD). This analysis can provide a comparison of the actual lipid content versus the theoretical lipid content.

LNP compositions are analyzed for average particle size, polydispersity index (pdi), total RNA content, encapsulation efficiency of RNA, and zeta potential. LNP compositions may be further characterized by lipid analysis, AF4-MALS, NTA, and/or cryo-EM. Average particle size and polydispersity are measured by dynamic light scattering (DLS) using a Malvern Zetasizer DLS instrument. LNP samples were diluted with PBS buffer prior to being measured by DLS. Z-average diameter which is an intensity-based measurement of average particle size was reported along with number average diameter and pdi. A Malvern Zetasizer instrument is also used to measure the zeta potential of the LNP. Samples are diluted 1:17 (50 µL into 800 µL) in 0.1×PBS, pH 7.4 prior to measurement.

A fluorescence-based assay (Ribogreen®, ThermoFisher Scientific) is used to determine total RNA concentration and free RNA. Encapsulation efficiency is calculated as (Total RNA—Free RNA)/Total RNA. LNP samples are diluted appropriately with 1× TE buffer containing 0.2% Triton-X 100 to determine total RNA or 1× TE buffer to determine free RNA. Standard curves are prepared by utilizing the starting RNA solution used to make the compositions and diluted in 1× TE buffer+/−0.2% Triton-X 100. Diluted RiboGreen® dye (according to the manufacturer's instructions) is then added to each of the standards and samples and allowed to incubate for approximately 10 minutes at room temperature, in the absence of light. A SpectraMax M5 Microplate Reader (Molecular Devices) is used to read the samples with excitation, auto cutoff and emission wavelengths set to 488 nm, 515 nm, and 525 nm respectively. Total RNA and free RNA are determined from the appropriate standard curves.

Encapsulation efficiency is calculated as (Total RNA–Free RNA)/Total RNA. The same procedure may be used for determining the encapsulation efficiency of a DNA-based cargo component. For single-strand DNA, Oligreen Dye may be used and for double-strand DNA, Picogreen Dye.

AF4-MALS is used to look at molecular weight and size distributions as well as secondary statistics from those calculations. LNPs are diluted as appropriate and injected into a AF4 separation channel using an HPLC autosampler where they are focused and then eluted with an exponential gradient in cross flow across the channel. All fluid is driven by an HPLC pump and Wyatt Eclipse Instrument. Particles eluting from the AF4 channel flow through a UV detector, multi-angle light scattering detector, quasi-elastic light scattering detector and differential refractive index detector. Raw data is processed by using a Debeye model to determine molecular weight and rms radius from the detector signals.

Lipid components in LNPs are analyzed quantitatively by HPLC coupled to a charged aerosol detector (CAD). Chromatographic separation of 4 lipid components is achieved by reverse phase HPLC. CAD is a destructive mass based detector which detects all non-volatile compounds and the signal is consistent regardless of analyte structure.

Cas9 mRNA and gRNA Cargos

The Cas9 mRNA cargo was prepared by in vitro transcription. Capped and polyadenylated Cas9 mRNA comprising 1×NLS (SEQ ID NO: 3) or a sequence of Table 24 of PCT/US2019/053423 (which is hereby incorporated by reference) was generated by in vitro transcription using a linearized plasmid DNA template and T7 RNA polymerase. For example, plasmid DNA containing a T7 promoter and a 100 nt poly(A/T) region can be linearized by incubating at 37° C. for 2 hours with XbaI with the following conditions: 200 ng/µL plasmid, 2 U/µL XbaI (NEB), and 1× reaction buffer. The XbaI can be inactivated by heating the reaction at 65° C. for 20 min. The linearized plasmid can be purified from enzyme and buffer salts using a silica maxi spin column (Epoch Life Sciences) and analyzed by agarose gel to confirm linearization. The IVT reaction to generate Cas9 modified mRNA can be performed by incubating at 37° C. for 4 hours in the following conditions: 50 ng/µL linearized plasmid; 2 mM each of GTP, ATP, CTP, and N1-methyl pseudo-UTP (Trilink); 10 mM ARCA (Trilink); 5 U/µL T7 RNA polymerase (NEB); 1 U/µL Murine RNase inhibitor (NEB); 0.004 U/µL Inorganic *E. coli* pyrophosphatase (NEB); and 1× reaction buffer. After the 4 h incubation, TURBO DNase (ThermoFisher) was added to a final concentration of 0.01 U/µL, and the reaction was incubated for an additional 30 minutes to remove the DNA template. The Cas9 mRNA was purified with an LiCi precipitation-containing method.

The sgRNAs in the following examples were chemically synthesized.

LNP Delivery In Vivo

CD-1 female mice, ranging from 6-10 weeks of age were used in each study. Animals were weighed and grouped according to body weight for preparing dosing solutions based on group average weight. LNPs were dosed via the lateral tail vein in a volume of 0.2 mL per animal (approximately 10 mL per kilogram body weight). The animals were periodically observed for adverse effects for at least 24 hours post dose.

For studies measuring in vivo editing in liver, CD-1 female mice were dosed at 0.1 mpk unless otherwise noted. Animals were euthanized at 6 or 7 days by exsanguination-via cardiac puncture under isoflourane anesthesia. Liver tissue was collected from each animal for DNA extraction and analysis. Blood was collected into serum separator tubes or into tubes containing buffered sodium citrate for plasma as described herein. Cohorts of mice were measured for editing by Next-Generation Sequencing (NGS).

NGS Sequencing

In brief, to quantitatively determine the efficiency of editing at the target location in the genome, genomic DNA was isolated and deep sequencing was utilized to identify the presence of insertions and deletions introduced by gene editing.

PCR primers were designed around the target site (e.g., B2M), and the genomic area of interest was amplified. Additional PCR was performed according to the manufacturer's protocols (Illumina) to add the necessary chemistry for sequencing. The amplicons were sequenced on an Illumina MiSeq instrument. The reads were aligned to the relevant reference genome (e.g., GRCm38) after eliminating those having low quality scores. The resulting files containing the reads were mapped to the reference genome (BAM files), where reads that overlapped the target region of interest were selected and the number of wild type reads versus the number of reads which contain an insertion, substitution, or deletion was calculated.

The editing percentage (e.g., the "editing efficiency" or "percent editing") is defined as the total number of sequence reads with insertions or deletions over the total number of sequence reads, including wild type.

Transthyretin (TTR) ELISA Analysis

Blood was collected and the serum was isolated as indicated. The total mouse TTR serum levels were determined using a Mouse Prealbumin (Transthyretin) ELISA Kit (Aviva Systems Biology, Cat. OKIA00111). Briefly, sera were serial diluted with kit sample diluent, e.g. to a final dilution of 10,000-fold and/or 2,500-fold. The diluted sample was then added to the ELISA plates and the assay was then carried out according to directions. Serum TTR data from treatment groups are expressed as a percentage of vehicle control levels.

Example 116—Assessing Lipid Efficacy by In Vivo Editing

We assessed in vivo editing efficiency for materials delivered with formulations including various amine lipid compounds. Editing was measured using either G282 (SEQ ID No: 1) which targets the mouse TTR gene or G650 (SEQ ID No: 2) which targets the mouse B2M gene. Lipids described above were assessed for efficacy through in vivo editing experiments. LNPs were formulated at a 1:1 w/w ratio of sgRNA to Cas9 mRNA, and at an N/P ratio of about 6. Molar concentrations of lipids in the lipid component of the LNPs are expressed as mol % amine lipid/DSPC/cholesterol/PEG-2k-DMG, e.g. 50/10/38.5/1.5. The final LNPs were characterized to determine the encapsulation efficiency, polydispersity index, and average particle size according to the analytical methods provided above. Analysis of average particle size, polydispersity (PDI), total RNA content and encapsulation efficiency of RNA are shown in Table 2. The pKa values of the following ionizable lipids was also measured and are provided in Table 1.

Figure 1B:
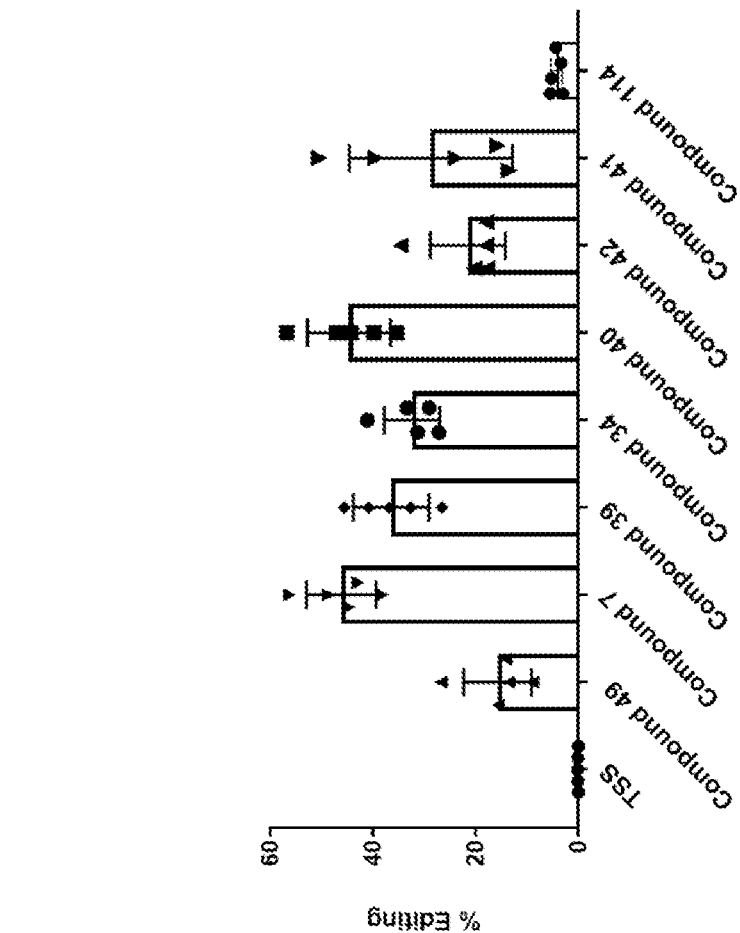
Figure 1C:
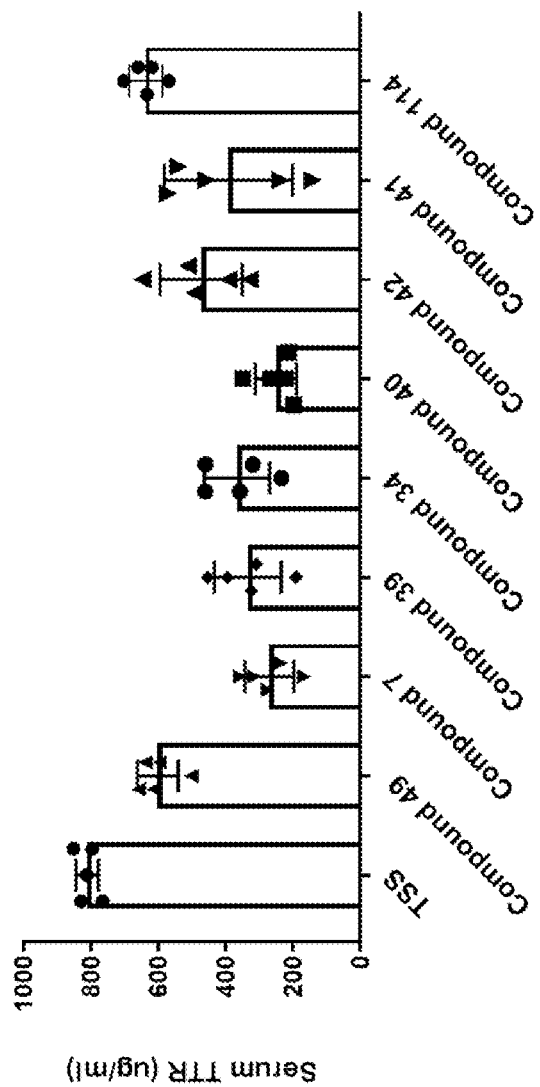

In Experiment 9, below, a series of compounds were tested that are based on compound 7 and which vary by inclusion of either a $C_6$ cycloalkyl or a $C_{4-12}$ alkyl at the $R^3$ position of Formula (1A), as illustrated in FIG. 1A. As shown in Table 3 and FIGS. 1B and 1C, all six compounds tested were efficacious for in vivo editing. Additional $R^3$ groups in the compound series based on compound 7 are also tested in Example 119 below.

TABLE 2

Composition Analytics.

| Cmpnd No. | Composition ratio (mol %) | Encapsulation (%) | Z-Ave Size (nm) | PDI | Num Ave Size (nm) | Exp. |
| --- | --- | --- | --- | --- | --- | --- |
| 1 | 50/10/38.5/1.5 | 99 | 79.25 | 0.085 | 57.00 | 1 |
| 3 | 50/10/38.5/1.5 | 98 | 83.58 | 0.042 | 67.38 | 1 |
| 7 | 50/10/38.5/1.5 | 98 | 87.93 | 0.052 | 70.97 | 1 |
| 8 | 50/10/38.5/1.5 | 98 | 94.18 | 0.066 | 71.54 | 1 |
| 9 | 50/10/38.5/1.5 | 97 | 83.72 | 0.049 | 67.39 | 1 |
| 30 | 50/10/38.5/1.5 | 98 | 116.20 | 0.040 | 97.58 | 1 |
| 49 | 50/9/38/3 | 99 | 86.06 | 0.033 | 71.23 | 1 |
| 5 | 50/10/38.5/1.5 | 97 | 88.86 | 0.003 | 73.37 | 2 |
| 6 | 50/10/38.5/1.5 | 98 | 68.98 | 0.075 | 50.12 | 2 |
| 10 | 50/10/38.5/1.5 | 98 | 68.38 | 0.079 | 51.46 | 2 |
| 49 | 50/9/38/3 | 98 | 75.34 | 0.052 | 59.17 | 2 |
| 11 | 50/10/38.5/1.5 | 98 | 92.55 | 0.063 | 70.42 | 3 |
| 12 | 50/10/38.5/1.5 | 98 | 73.87 | 0.051 | 56.58 | 3 |
| 49 | 50/9/38/3 | 97 | 78.85 | 0.036 | 64.05 | 3 |
| 14 | 50/10/38.5/1.5 | 96 | 95.77 | 0.023 | 77.66 | 4 |
| 15 | 50/10/38.5/1.5 | 97 | 90.90 | 0.055 | 71.35 | 4 |
| 16 | 50/10/38.5/1.5 | 98 | 84.13 | 0.039 | 66.00 | 4 |
| 49 | 50/9/38/3 | 98 | 82.71 | 0.056 | 64.97 | 4 |
| 1 | 50/9/39.5/1.5 | 96 | 89.37 | 0.041 | 70.27 | 5 |
| 17 | 50/10/38.5/1.5 | 98 | 91.32 | 0.037 | 72.26 | 5 |
| 18 | 50/10/38.5/1.5 | 99 | 77.64 | 0.057 | 58.93 | 5 |
| 19 | 50/10/38.5/1.5 | 99 | 82.31 | 0.011 | 66.83 | 5 |
| 20 | 50/10/38.5/1.5 | 98 | 88.10 | 0.056 | 70.77 | 5 |
| 21 | 50/10/38.5/1.5 | 99 | 80.80 | 0.041 | 65.00 | 5 |
| 31 | 50/10/38.5/1.5 | 98 | 93.72 | 0.009 | 76.38 | 5 |
| 32 | 50/10/38.5/1.5 | 98 | 78.88 | 0.054 | 62.21 | 5 |
| 33 | 50/10/38.5/1.5 | 98 | 87.33 | 0.036 | 70.78 | 5 |
| 34 | 50/10/38.5/1.5 | 96 | 90.69 | 0.044 | 73.81 | 5 |
| 35 | 50/10/38.5/1.5 | 97 | 85.62 | 0.063 | 68.07 | 5 |
| 36 | 50/10/38.5/1.5 | 97 | 76.38 | 0.058 | 60.24 | 5 |
| 49 | 50/9/38/3 | 98 | 82.71 | 0.056 | 64.97 | 5 |
| 7 | 50/10/38.5/1.5 | 98 | 95.20 | 0.020 | 76.61 | 6 |
| 9 | 50/10/38.5/1.5 | 98 | 85.62 | 0.048 | 68.63 | 6 |
| 22 | 50/10/38.5/1.5 | 98 | 98.32 | 0.026 | 79.28 | 6 |

TABLE 2-continued

Composition Analytics.

| Cmpnd No. | Composition ratio (mol %) | Encapsulation (%) | Z-Ave Size (nm) | PDI | Num Ave Size (nm) | Exp. |
|---|---|---|---|---|---|---|
| 23 | 50/10/38.5/1.5 | 97 | 94.38 | 0.048 | 75.29 | 6 |
| 24 | 50/10/38.5/1.5 | 98 | 109.50 | 0.133 | 72.78 | 6 |
| 49 | 50/9/38/3 | 99 | 75.92 | 0.040 | 60.22 | 6 |
| 1 | 50/9/39.5/1.5 | 97 | 90.24 | 0.002 | 74.63 | 7 |
| 25 | 50/10/38.5/1.5 | 99 | 81.90 | 0.029 | 64.59 | 7 |
| 26 | 50/10/38.5/1.5 | 99 | 79.29 | 0.047 | 62.17 | 7 |
| 27 | 50/10/38.5/1.5 | 99 | 85.38 | 0.040 | 65.81 | 7 |
| 28 | 50/10/38.5/1.5 | 98 | 90.56 | 0.029 | 73.19 | 7 |
| 29 | 50/10/38.5/1.5 | 83 | 90.05 | 0.002 | 74.44 | 7 |
| 49 | 50/9/38/3 | 98 | 80.07 | 0.019 | 64.16 | 7 |
| 34 | 50/10/38.5/1.5 | 98 | 92.98 | 0.014 | 75.69 | 8 |
| 38 | 50/10/38.5/1.5 | 98 | 87.14 | 0.045 | 68.11 | 8 |
| 49 | 50/9/38/3 | 98 | 86.84 | 0.020 | 71.49 | 8 |
| 7 | 50/10/38.5/1.5 | 97 | 89.00 | 0.034 | 73.67 | 9 |
| 34 | 50/10/38.5/1.5 | 97 | 85.93 | 0.043 | 68.07 | 9 |
| 39 | 50/10/38.5/1.5 | 98 | 89.19 | 0.004 | 73.72 | 9 |
| 40 | 50/10/38.5/1.5 | 97 | 98.55 | 0.023 | 81.09 | 9 |
| 41 | 50/10/38.5/1.5 | 98 | 109.00 | 0.036 | 88.36 | 9 |
| 42 | 50/10/38.5/1.5 | 98 | 113.80 | 0.014 | 93.70 | 9 |
| 43 | 50/10/38.5/1.5 | 97 | 136.60 | 0.014 | 113.90 | 9 |
| 49 | 50/9/38/3 | 99 | 86.26 | 0.017 | 70.81 | 9 |
| 49 | 50/9/38/3 | 96 | 83.65 | 0.031 | 67.22 | 9 |
| 114 | 50/10/38.5/1.5 | 95 | 120.3 | 0.011 | 100.5 | 9 |
| 34 | 50/10/38.5/1.5 | 98 | 92.98 | 0.014 | 75.69 | 10 |
| 38 | 50/10/38.5/1.5 | 98 | 87.14 | 0.045 | 68.11 | 10 |
| 49 | 50/9/38/3 | 98 | 86.84 | 0.020 | 71.49 | 10 |
| 49 | 50/9/38/3 | 96 | 83.65 | 0.031 | 67.22 | 10 |

Table 3 shows editing percentages in mouse liver as measured by NGS.

TABLE 3

Editing efficiency in mouse liver, providing % indel formation for G282 and G650 experiments and serum TTR levels for G282 experiments.

| Cmpnd No. | Editing Mean % Indel | SD | N | Serum TTR (ug/ml) | SD | Sample number (n) | Serum TTR (% TSS) | Guide | Exp. |
|---|---|---|---|---|---|---|---|---|---|
| TSS | 0.1 | 0.1 | 4 | 884 | 113 | 5 | 100% | G282 | 1 |
| 1 | 13.1 | 8.2 | 5 | 671 | 201 | 5 | 76% | G282 | 1 |
| 3 | 23.7 | 8.5 | 5 | 691 | 182 | 5 | 78% | G282 | 1 |
| 7 | 45.3 | 8.3 | 5 | 270 | 132 | 5 | 31% | G282 | 1 |
| 8 | 0.1 | 0.1 | 5 | 745 | 97 | 5 | 84% | G282 | 1 |
| 9 | 44.1 | 13.3 | 5 | 339 | 184 | 5 | 38% | G282 | 1 |
| 30 | 10.4 | 4.8 | 5 | 841 | 89 | 5 | 95% | G282 | 1 |
| 49 | 33.5 | 8.9 | 5 | 388 | 103 | 5 | 44% | G282 | 1 |
| TSS | 0.1 | 0.1 | 5 | | | | | G650 | 2 |
| 5 | 17.5 | 4.4 | 5 | | | | | G650 | 2 |
| 6 | 0.4 | 0.1 | 5 | | | | | G650 | 2 |
| 10 | 5.3 | 1.3 | 5 | | | | | G650 | 2 |
| 49 | 10.2 | 2.8 | 4 | | | | | G650 | 2 |
| TSS | 0.1 | 0.1 | 5 | | | | | G650 | 3 |
| 11 | 9.2 | 1.2 | 5 | | | | | G650 | 3 |
| 12 | 5.5 | 2.4 | 5 | | | | | G650 | 3 |
| 49 | 15.7 | 5.5 | 5 | | | | | G650 | 3 |
| TSS | 0.1 | 0.0 | 5 | | | | | G650 | 4 |
| 14 | 20.6 | 8.7 | 5 | | | | | G650 | 4 |
| 15 | 18.0 | 2.4 | 5 | | | | | G650 | 4 |
| 16 | 10.1 | 1.7 | 5 | | | | | G650 | 4 |
| 49 | 15.4 | 3.5 | 5 | | | | | G650 | 4 |
| TSS | 0.2 | 0.1 | 5 | | | | | G650 | 5 |
| 1 | 18.6 | 3.9 | 5 | | | | | G650 | 5 |
| 17 | 12.3 | 4.4 | 5 | | | | | G650 | 5 |
| 18 | 4.5 | 1.4 | 5 | | | | | G650 | 5 |
| 19 | 13.0 | 4.1 | 5 | | | | | G650 | 5 |
| 20 | 15.4 | 5.1 | 5 | | | | | G650 | 5 |

TABLE 3-continued

Editing efficiency in mouse liver, providing % indel formation for G282 and G650 experiments and serum TTR levels for G282 experiments.

| Cmpnd No. | Editing Mean % Indel | SD | N | Serum TTR (ug/ml) | SD | Sample number (n) | Serum TTR (% TSS) | Guide | Exp. |
|---|---|---|---|---|---|---|---|---|---|
| 21 | 12.1 | 1.4 | 5 | | | | | G650 | 5 |
| 31 | 15.6 | 1.8 | 5 | | | | | G650 | 5 |
| 32 | 11.6 | 2.0 | 5 | | | | | G650 | 5 |
| 33 | 20.0 | 5.0 | 5 | | | | | G650 | 5 |
| 34 | 44.8 | 8.3 | 5 | | | | | G650 | 5 |
| 35 | 35.5 | 6.6 | 5 | | | | | G650 | 5 |
| 36 | 30.0 | 8.4 | 5 | | | | | G650 | 5 |
| 49 | 22.3 | 4.6 | 5 | | | | | G650 | 5 |
| TSS | 0.0 | 0.0 | 5 | | | | | G650 | 6 |
| 7 | 22.6 | 5.6 | 5 | | | | | G650 | 6 |
| 9 | 20.3 | 2.0 | 5 | | | | | G650 | 6 |
| 22 | 6.7 | 2.4 | 5 | | | | | G650 | 6 |
| 23 | 7.3 | 2.0 | 5 | | | | | G650 | 6 |
| 24 | 6.8 | 0.9 | 5 | | | | | G650 | 6 |
| 49 | 11.4 | 2.2 | 5 | | | | | G650 | 6 |
| TSS | 0.0 | 0.1 | 5 | | | | | G650 | 7 |
| 1 | 3.2 | 0.8 | 5 | | | | | G650 | 7 |
| 25 | 10.2 | 5.5 | 5 | | | | | G650 | 7 |
| 26 | 5.2 | 1.4 | 5 | | | | | G650 | 7 |
| 27 | 13.0 | 2.8 | 5 | | | | | G650 | 7 |
| 28 | 17.8 | 2.5 | 5 | | | | | G650 | 7 |
| 29 | 3.6 | 0.7 | 5 | | | | | G650 | 7 |
| 49 | 20.5 | 4.3 | 5 | | | | | G650 | 7 |
| TSS | 0.1 | 0 | 5 | 777 | 89 | 5 | 100% | G282 | 8 |
| 34 | 50.4 | 6.3 | 5 | 101 | 62 | 5 | 13% | G282 | 8 |
| 38 | 26.7 | 6.1 | 5 | 301 | 51 | 5 | 39% | G282 | 8 |
| 49 | 38.6 | 8.0 | 5 | 247 | 82 | 5 | 32% | G282 | 8 |
| TSS | 0.1 | 0.1 | 5 | 812 | 33 | 5 | 100% | G282 | 9 |
| 7 | 46.1 | 6.8 | 5 | 271 | 73 | 5 | 33% | G282 | 9 |
| 34 | 32.4 | 5.4 | 5 | 367 | 97 | 5 | 45% | G282 | 9 |
| 39 | 36.5 | 7.3 | 5 | 335 | 99 | 5 | 41% | G282 | 9 |
| 40 | 44.7 | 8.1 | 5 | 251 | 61 | 5 | 31% | G282 | 9 |
| 41 | 28.8 | 15.9 | 5 | 393 | 190 | 5 | 48% | G282 | 9 |
| 42 | 21.6 | 7.3 | 5 | 473 | 122 | 5 | 58% | G282 | 9 |
| 49 | 15.8 | 6.6 | 5 | 602 | 60 | 5 | 74% | G282 | 9 |
| 49 | 30.7 | 6.7 | 5 | 527 | 145 | 5 | 65% | G282 | 9 |
| 114 | 0.8 | 1.1 | 5 | 637 | 49 | 5 | 78% | G282 | 9 |
| TSS | 0.1 | 0 | 5 | 777 | 89 | 5 | 100% | G282 | 10 |
| 34 | 50.4 | 6.3 | 5 | 101 | 62 | 5 | 13% | G282 | 10 |
| 38 | 26.7 | 6.1 | 5 | 301 | 51 | 5 | 39% | G282 | 10 |
| 49 | 38.6 | 8.0 | 5 | 247 | 82 | 5 | 32% | G282 | 10 |
| 49 | 30.4 | 5.1 | 5 | 311 | 76 | 5 | 38% | G282 | 10 |

Example 117—Dose Responsiveness of Editing in Liver

To assess whether the editing was dose responsive, experiments were performed in vivo at various LNP dose levels. Cas9 mRNA of Example 115 was formulated as LNPs with an sgRNA targeting TTR (G00282; SEQ TD NO: 1). These LNPs were formulated at a 1:1 w/w ratio of a sgRNA and Cas9 mRNA. The LNPs were formulated using the cross flow procedure with lipid molar compositions as described in Table 4 at an N/P ratio of 6.0. LNP compositions were analyzed for average particle size, polydispersity (pdi), total RNA content and encapsulation efficiency of RNA as described in Example 115. Analysis of average particle size, polydispersity (PDI), total RNA content and encapsulation efficiency of RNA are shown in Table 4.

TABLE 4

Composition Analytics

| Compound Number | Composition ratio (mol %) | Encapsulation (%) | Z-Ave Size (nm) | PDI | Num Ave Size (nm) |
|---|---|---|---|---|---|
| 7 | 50/10/38.5/1.5 | 97 | 85.09 | 0.033 | 68.39 |
| 9 | 50/10/38.5/1.5 | 97 | 74.83 | 0.033 | 59.99 |
| 49 | 50/9/38/3 | 98 | 84.93 | 0.007 | 69.51 |

Figure 2:
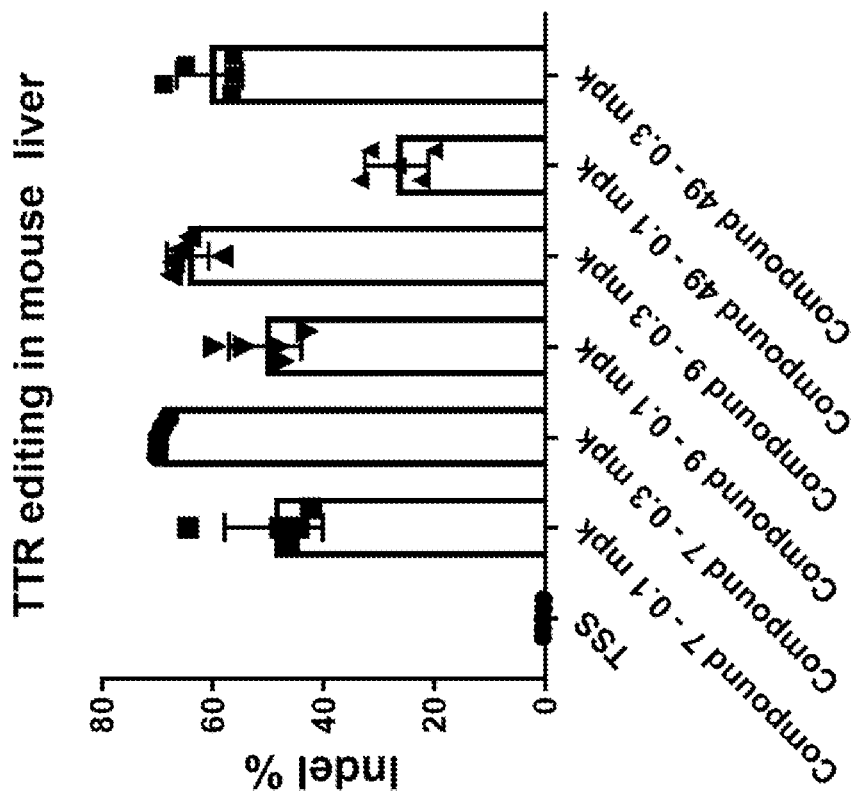
FIG. 2 is a graph showing percentage of editing of TTR in mouse liver cells after delivery using LNPs comprising a compound of Formula (IA) or a control compound. Dose response data are also shown.

CD-1 female mice were dosed i.v. at 0.1 mpk or 0.3 mpk and assessed for editing in liver. Results are shown in FIG. 2 and Table 5.

TABLE 5

TTR liver editing and serum TTR levels for dose response

| Compound Number | Dose (mpk) | Mean % Indel | SD | N |
|---|---|---|---|---|
| TSS | n/a | 0.4 | 0.1 | 5 |
| 7 | 0.1 | 49.1 | 8.9 | 5 |
| 7 | 0.3 | 69.4 | 0.8 | 5 |
| 9 | 0.1 | 50.6 | 6.5 | 5 |
| 9 | 0.3 | 64.5 | 3.8 | 5 |
| 49 | 0.1 | 26.8 | 5.7 | 5 |
| 49 | 0.3 | 60.6 | 5.9 | 5 |

Example 118

To assess the scalability of dosing, dose response experiments were performed in vivo. Cas9 mRNA of Example 115 was formulated as LNPs with a gRNA targeting TTR (G00282; SEQ ID NO: 1). These LNPs were formulated, prepared and analyzed as described in Example 115 using a 1:1 w/w ratio of a sgRNA and Cas9 mRNA. Composition analysis for these LNPs are described in Table 6.

TABLE 6

Composition Analytics

| Compound Number | Composition ratio (mol %) | Encapsulation (%) | Z-Ave Size (nm) | PDI | Num Ave Size (nm) |
|---|---|---|---|---|---|
| Compound 5 | 50/10/38.5/1.5 | 99 | 76.02 | 0.009 | 62.64 |
| Compound 34 | 50/10/38.5/1.5 | 98 | 86.45 | 0.015 | 71.97 |
| Compound 49 | 50/9/38/3 | 99 | 83.63 | 0.011 | 69.75 |

Figure 3A:
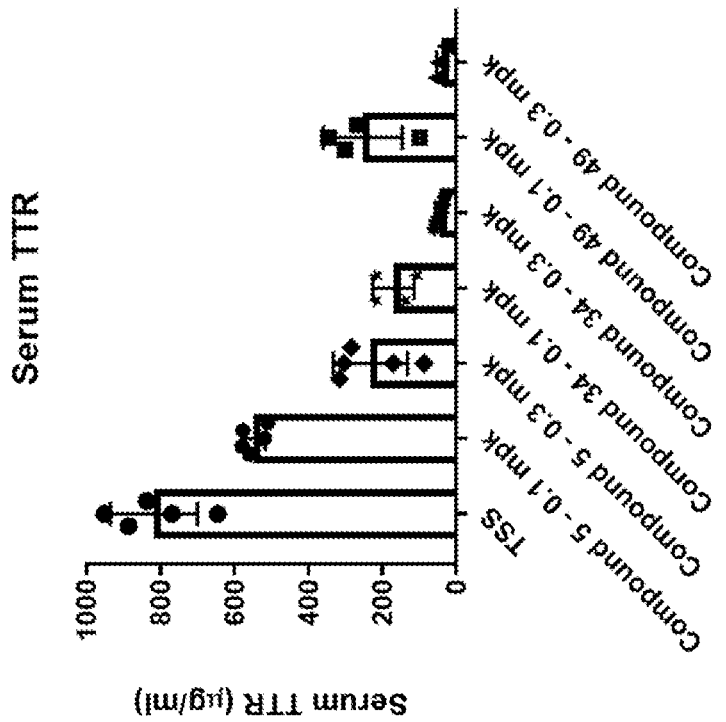
FIGS. 3A-3B show results after delivering using LNPs comprising a compound of Formula (IA).
Figure 3B:
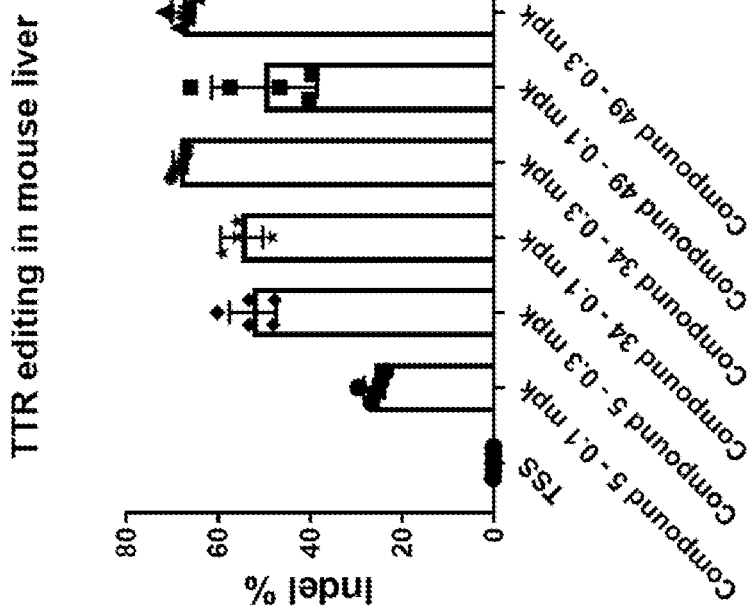

CD-1 female mice were dosed i.v. at 0.1 mpk or 0.3 mpk and assessed for editing in liver. Results are shown in FIG. 3A and FIG. 3B and Table 7.

TABLE 7

Editing and serum TTR levels

| Compound Number | Dose (mpk) | Editing | | | Serum TTR | | | |
|---|---|---|---|---|---|---|---|---|
| | | Mean % Indel | SD | N | Serum TTR (ug/ml) | SD | N | % TSS |
| TSS | TSS | 0.1 | 0.0 | 5 | 818 | 118 | 5 | 100% |
| 5 | 0.1 | 26.1 | 2.2 | 5 | 549 | 33 | 5 | 67% |
| 5 | 0.3 | 52.5 | 5.1 | 5 | 233 | 100 | 5 | 28% |
| 34 | 0.1 | 54.9 | 4.6 | 4 | 170 | 55 | 4 | 21% |
| 34 | 0.3 | 68.3 | 1.5 | 5 | 45 | 12 | 5 | 5% |
| 49 | 0.1 | 50.0 | 11.5 | 5 | 254 | 107 | 4 | 31% |
| 49 | 0.3 | 67.7 | 2.5 | 5 | 40 | 13 | 3 | 5% |

Example 119—Evaluating Lipid Delivery Efficacy by In Vivo Editing

We assessed in vivo editing efficiency for materials delivered with formulations with variable tail lengths through in vivo editing experiments. LNPs were formulated as described above with G502 (SEQ ID No: 4), which targets the mouse TTR gene, that was used to measure editing. Formulations contained a 1:2 w/w ratio of sgRNA to Cas9 mRNA. The characterization of the final LNPs is shown in Table 8. The pKa values of the ionizable lipids were measured and are shown in Table 1.

Figure 4A:
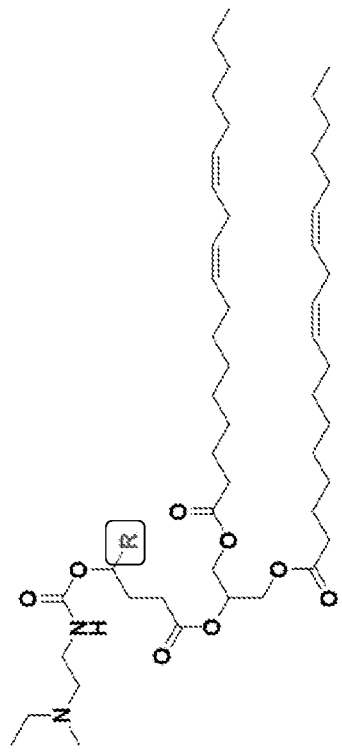
FIGS. 4A-4C show in vivo editing at the TTR locus and the compounds tested in the assay.
Figure 4B:
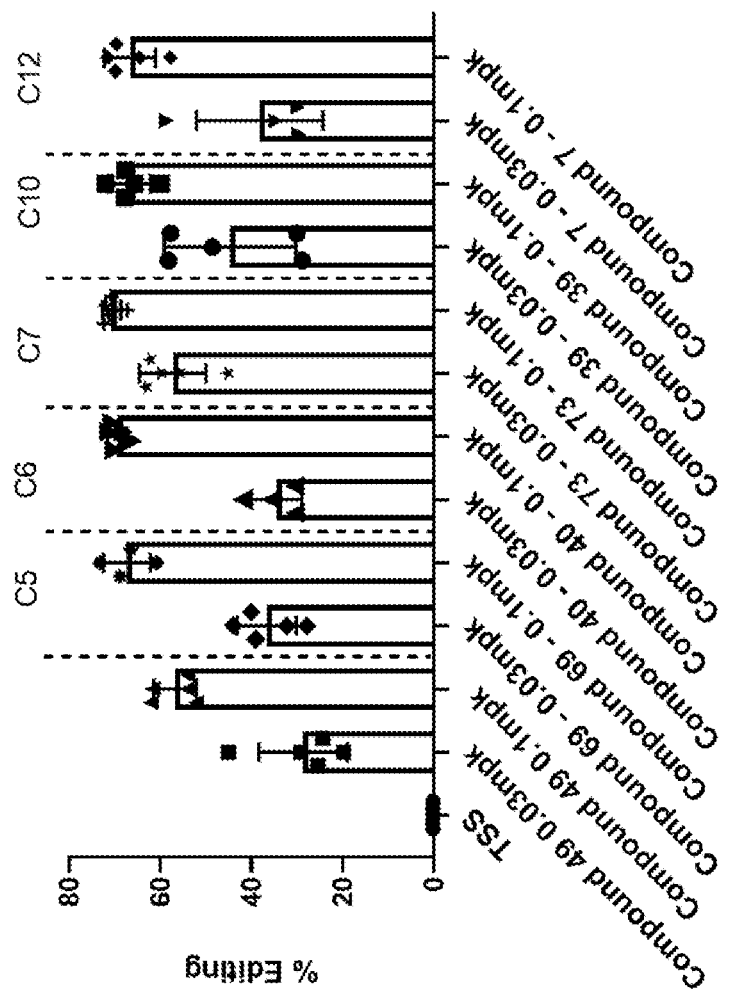
Figure 4C:
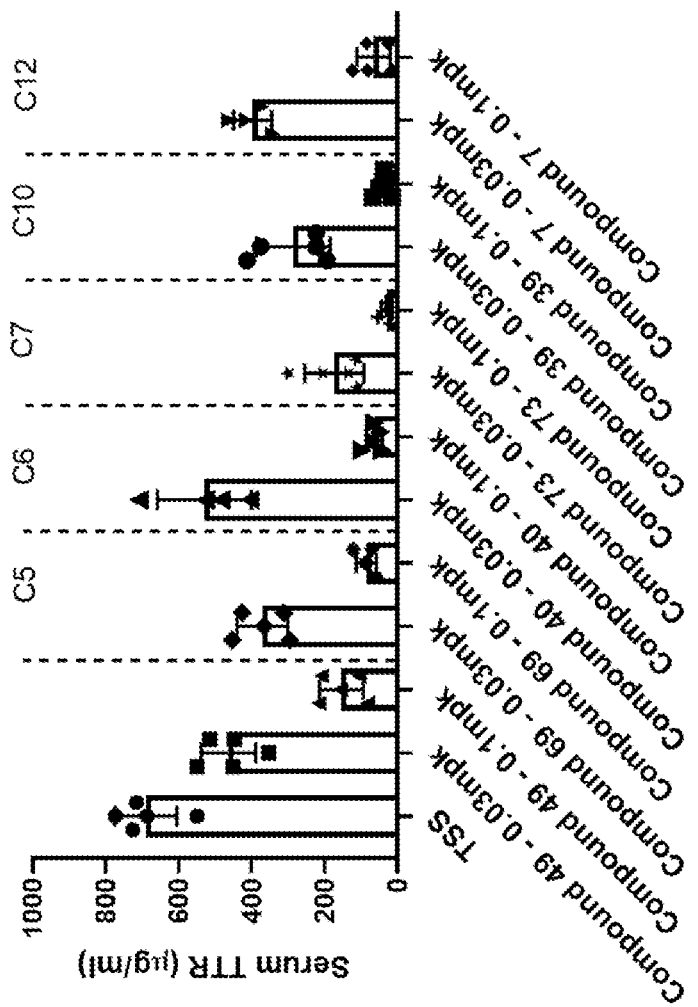

In Experiment 4, a series of compounds based on Compound 7 were tested that vary by the inclusion of a $C_{5-12}$ alkyl at the $R^3$ position of Formula (1A), as illustrated in FIG. 4A. As shown in Table 9 and FIGS. 4B and 4C, all five compounds tested were efficacious for in vivo editing.

Figure 5A:
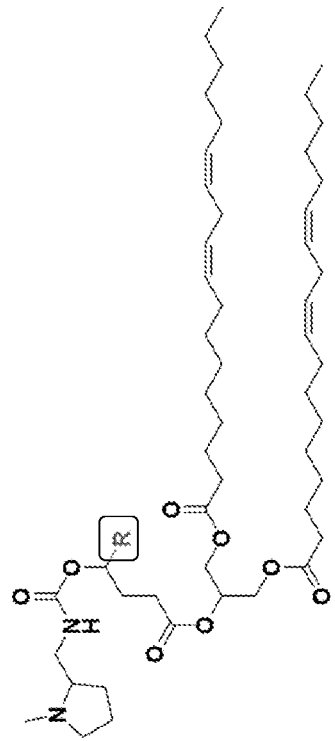
FIGS. 5A-5C show compounds of Formula (IA) and results of delivery using the compounds.
Figure 5B:
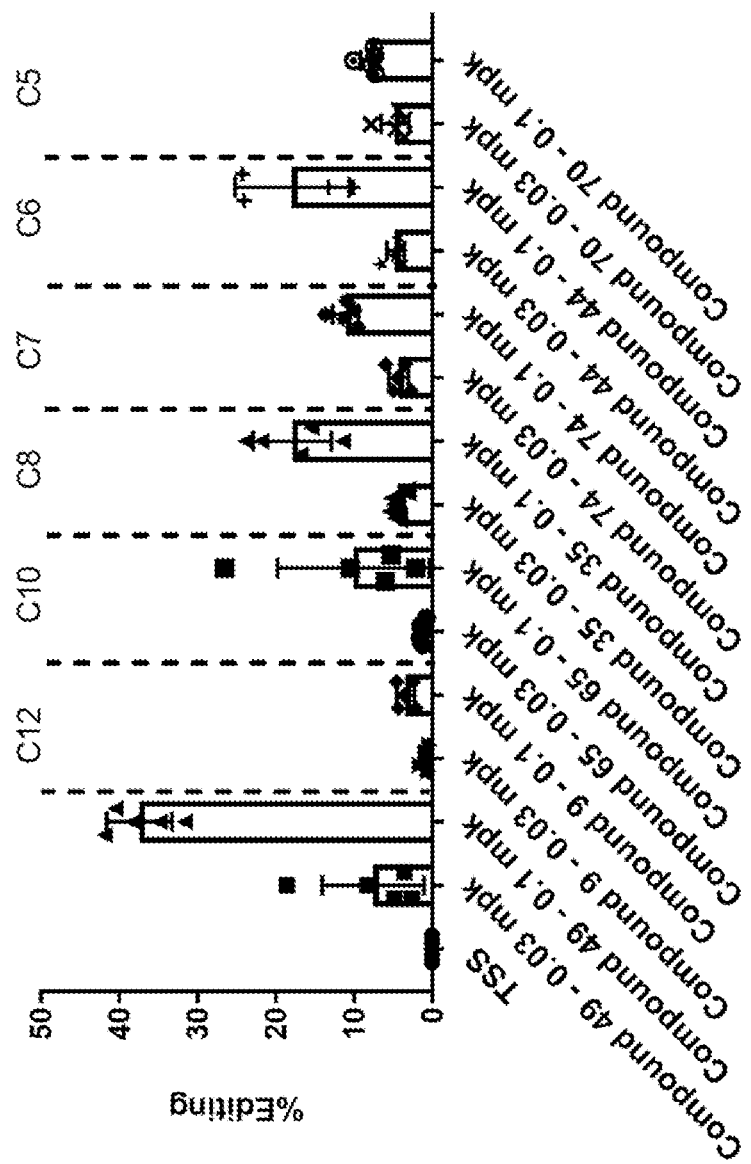
Figure 5C:
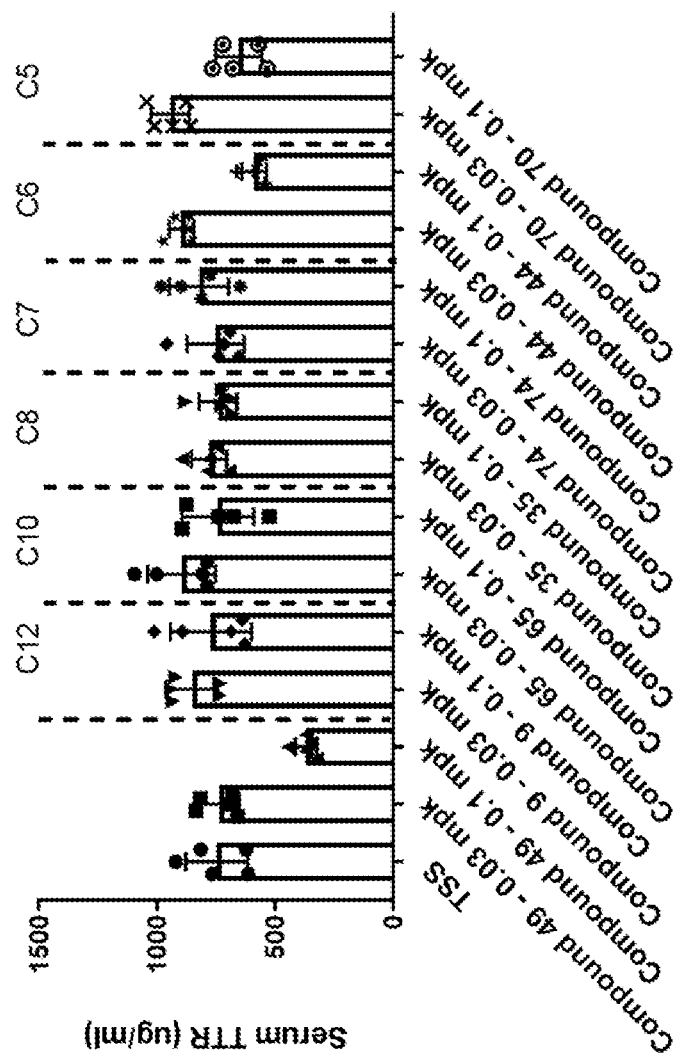

In Experiment 8, a series of compounds based on Compound 9 were tested that vary by the inclusion of a $C_{5-12}$ alkyl at the $R^3$ position of Formula (1A), as illustrated in FIG. 5A. Experiment 2 tested Compound 287 of this series which included a $C_4$ alkyl at the $R^3$ position. As shown in Table 9 and FIGS. 5B and 5C, all compounds in this series tested were efficacious for in vivo editing.

Figure 6A:
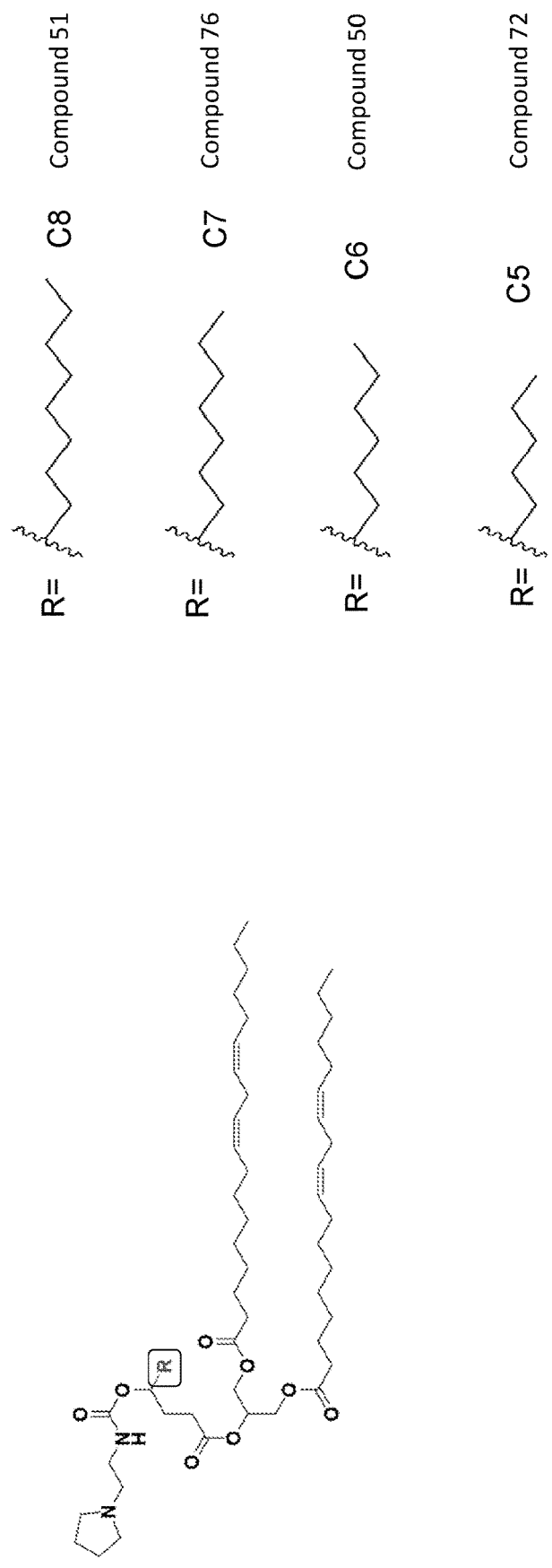
FIGS. 6A-6C show compounds of Formula (IA) and results delivery using the compounds.
Figure 6B:
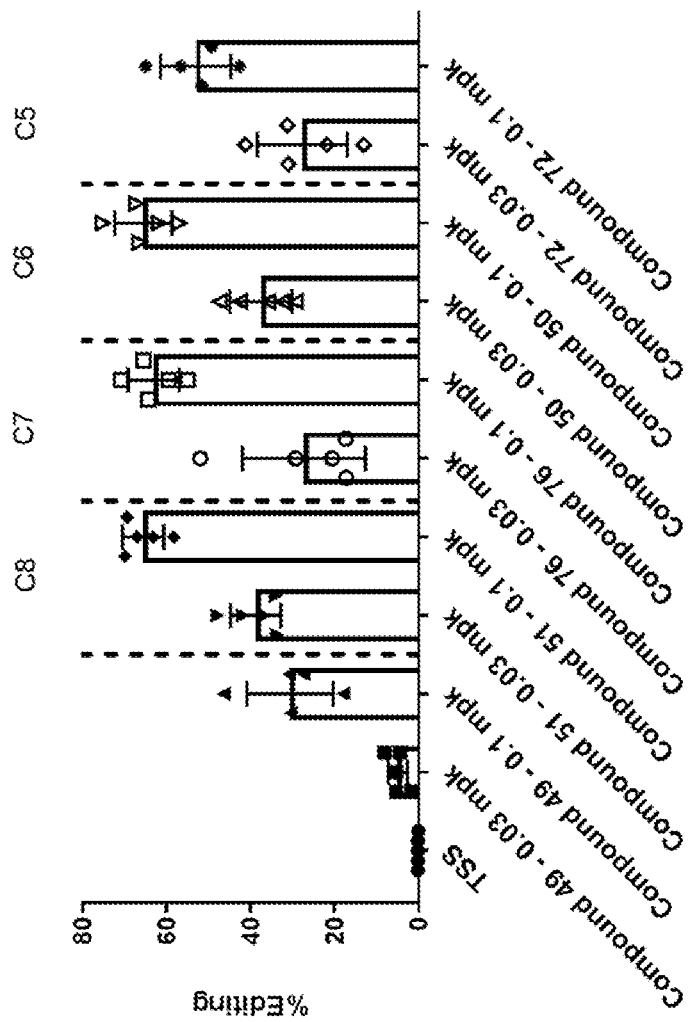
Figure 6C:
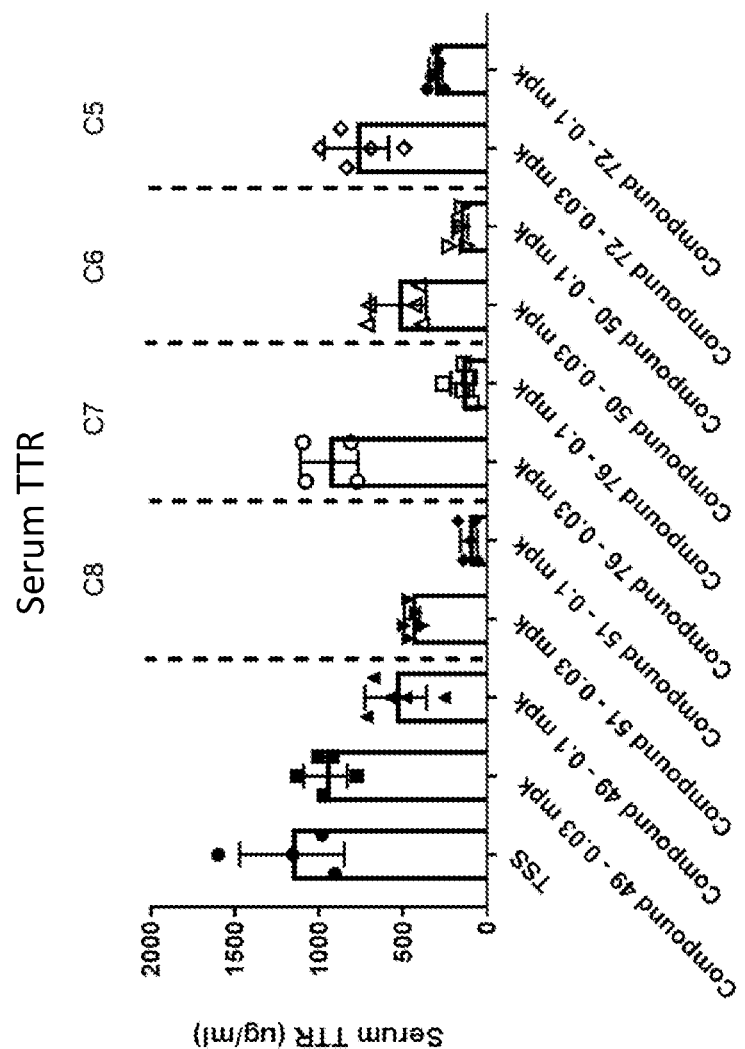

In Experiment 3, a series of compounds based on Compound 46 were tested that vary by the inclusion of a $C_{5-8}$ alkyl at the $R^3$ position of Formula (1A), as illustrated in FIG. 6A. Compound 46 includes a $C_{12}$ alkyl at the $R^3$ position, and compounds varying the tail length were tested. As shown in Table 9 and FIGS. 6B and 6C, compounds with $C_5$ (Compound 72), $C_6$ (Compound 50), $C_7$ (Compound 76), and $C_8$ (Compound 51) $R^3$ groups were efficacious for in vivo editing.

Figure 7A:
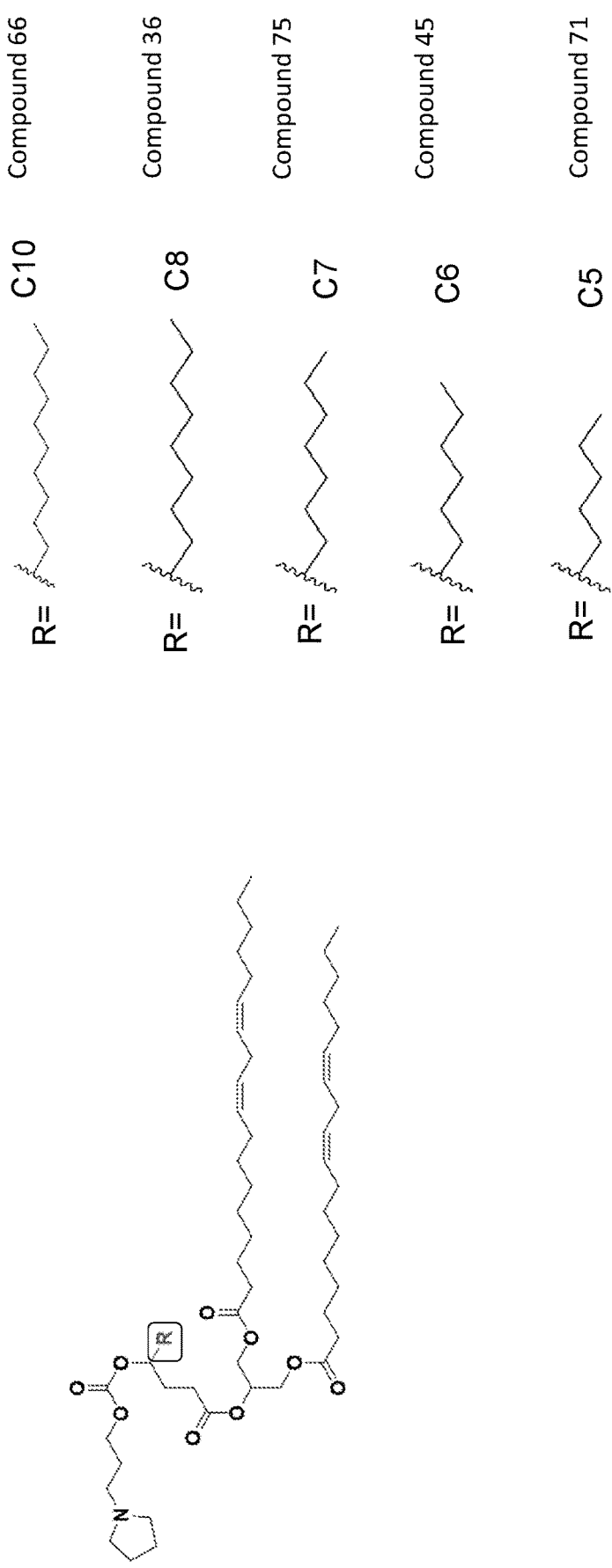
FIGS. 7A-7C show compounds of Formula (IA) and results of delivery using the compounds.
Figure 7B:
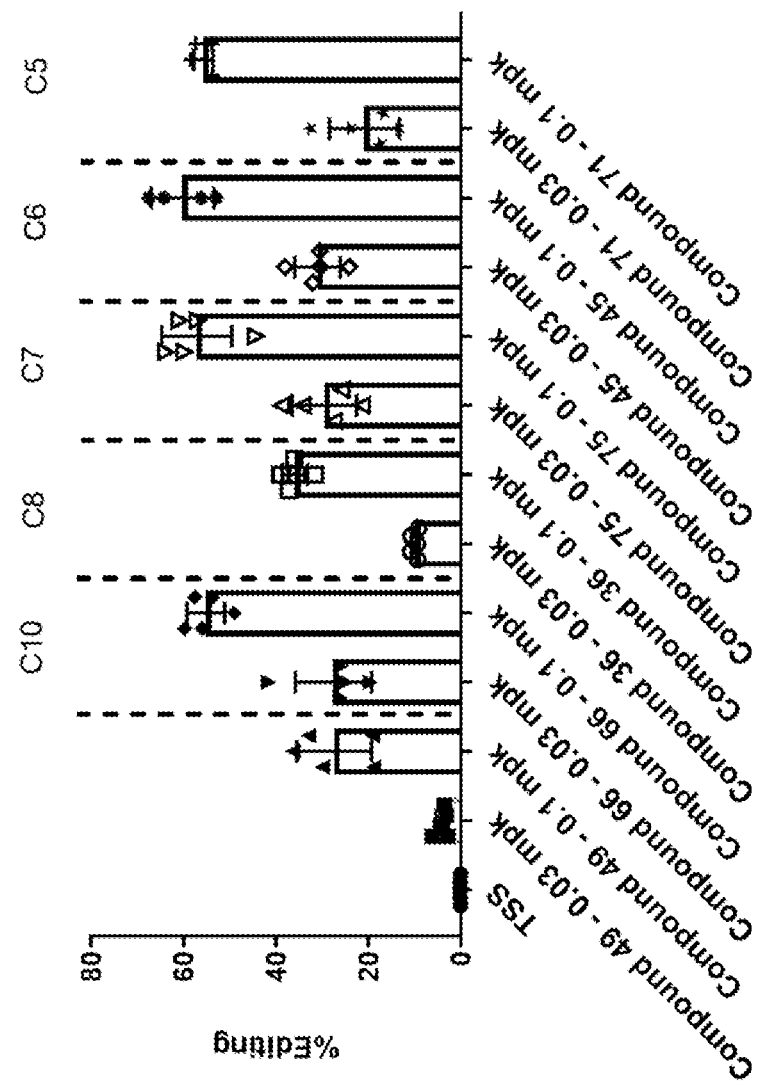
Figure 7C:
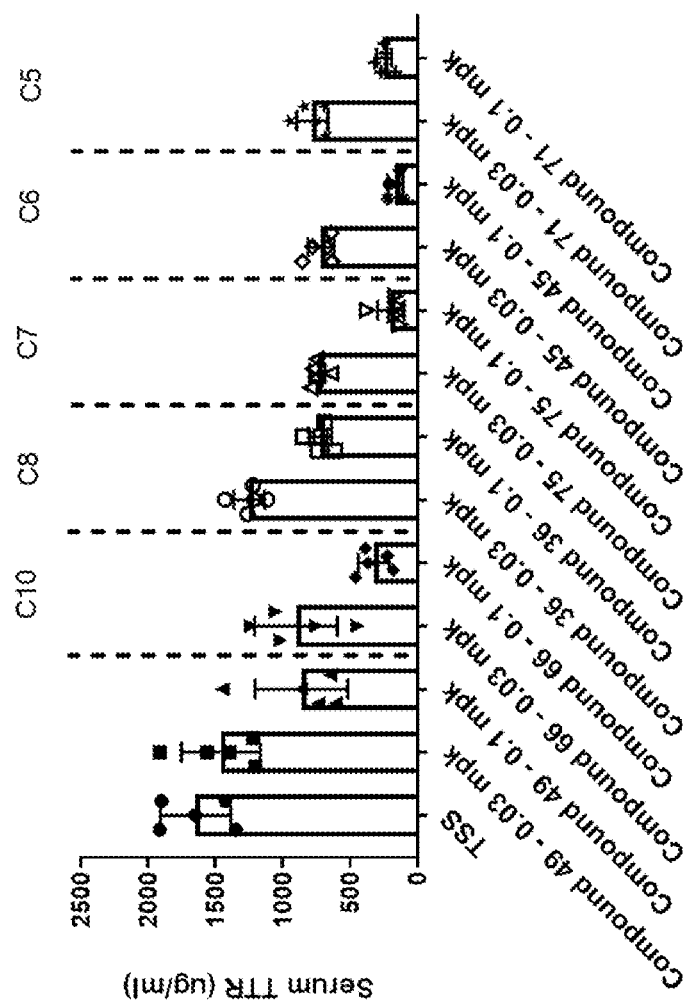
Figure 8A:
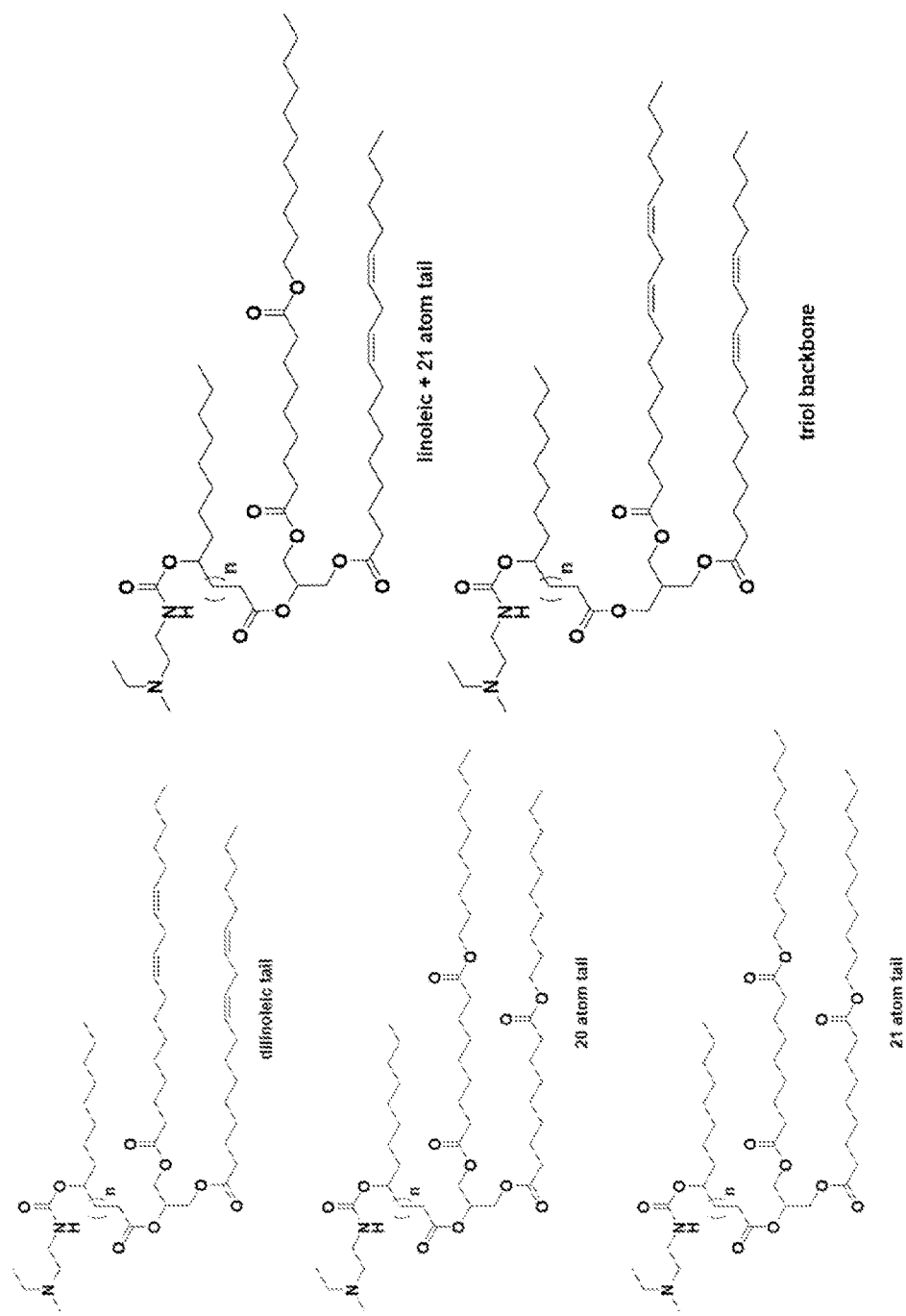
FIGS. 8A-8C show compounds of Formula (IA) and results of delivery using the compounds.
Figure 8B:
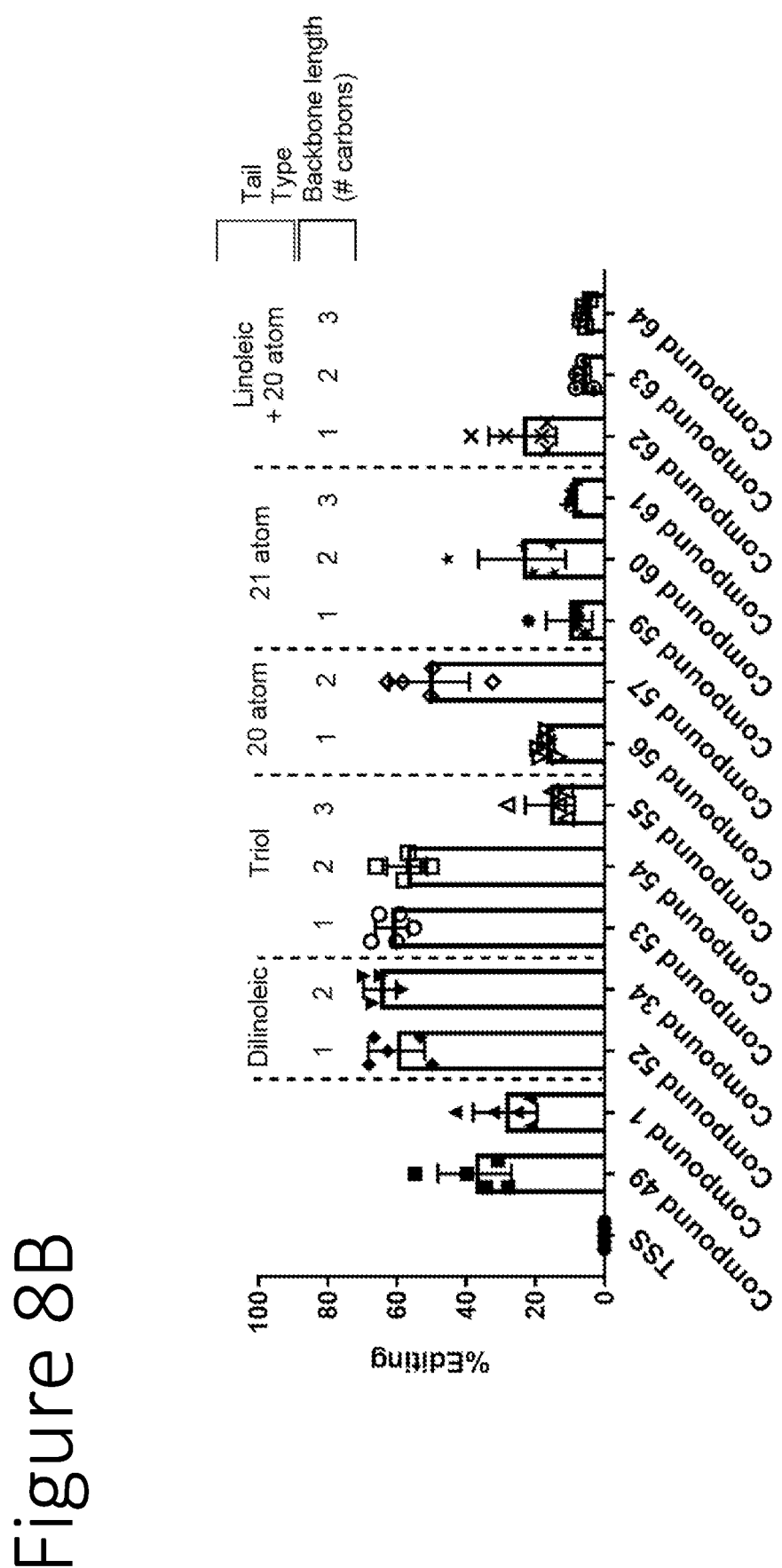
Figure 8C:
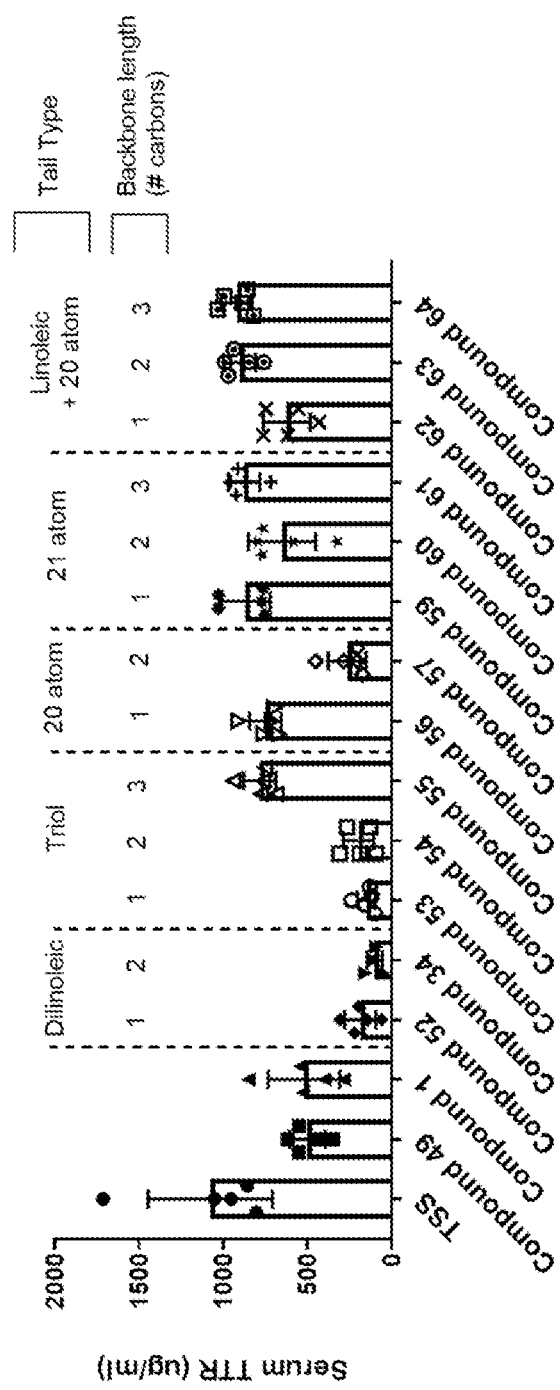

In Experiment 7, a series of compounds based on Compound 5 were tested that vary by the inclusion of a $C_{5-10}$ alkyl at the $R^3$ position of Formula (1A), as illustrated in FIG. 7A. Experiment 2 tested Compound 66 of this series which includes a $C_4$ alkyl at the $R^3$ position. Compound 5 includes a $C_{12}$ alkyl at the $R^3$ position and was shown to be efficacious for in vivo editing in Examples 116 and 118. As shown in Table 9 and FIGS. 7B and 7C, all additional compounds tested in this series were efficacious for in vivo editing. In Experiment 1, series of compounds based on Compound 34 were tested that vary at positions $X^1$ and $Y^1$ of Formula (1A) as illustrated in FIG. 8A. Compound 52 and Compound 34 shared dilinoleic groups at position $Y^1$ and vary by the inclusion of a $C_{0-1}$ alkylene groups at position $X^1$. Compound 53, Compound 54, and Compound 55 shared triol groups at position $Y^1$ and vary by the inclusion of a $C_{0-2}$ alkylene groups at position $X^1$. Compound 56, Compound 57, and Compound 58 shared 20 atom groups at position $Y^1$ and vary by the inclusion of a $C_{0-1}$ alkylene groups at position $X^1$. Compound 59, Compound 60 and Compound 61 shared 21 atom groups at position $Y^1$ and vary by the inclusion of a $C_{0-2}$ alkylene groups at position $X^1$. Compound 62, Compound 63 and Compound 64 shared heterogeneous linoleic and 21 atom groups at position $Y^1$ and vary by the inclusion of a $C_{0-2}$ alkylene groups at position $X^1$. As shown in Table 9 and FIGS. 8B and 8C, all compounds tested were efficacious for in vivo editing.

Figure 9A:
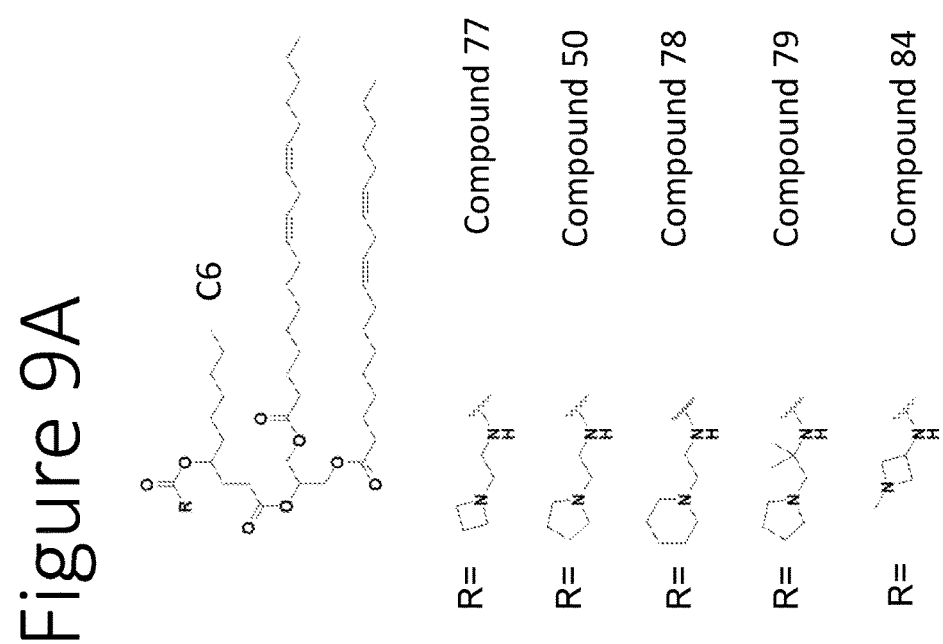
FIGS. 9A-9C show compounds of Formula (IA) and results of delivery using the compounds.
Figure 9A:
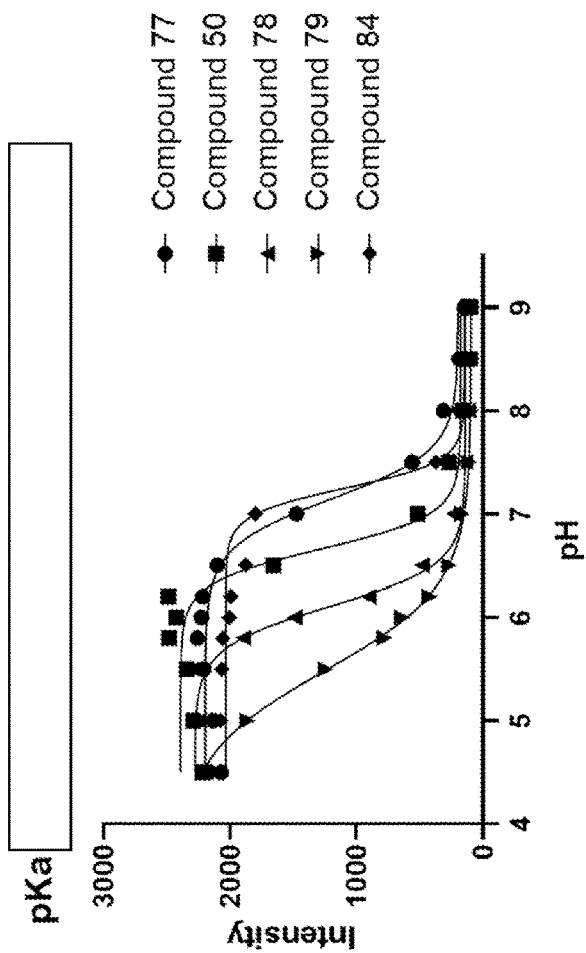
Figure 9B:
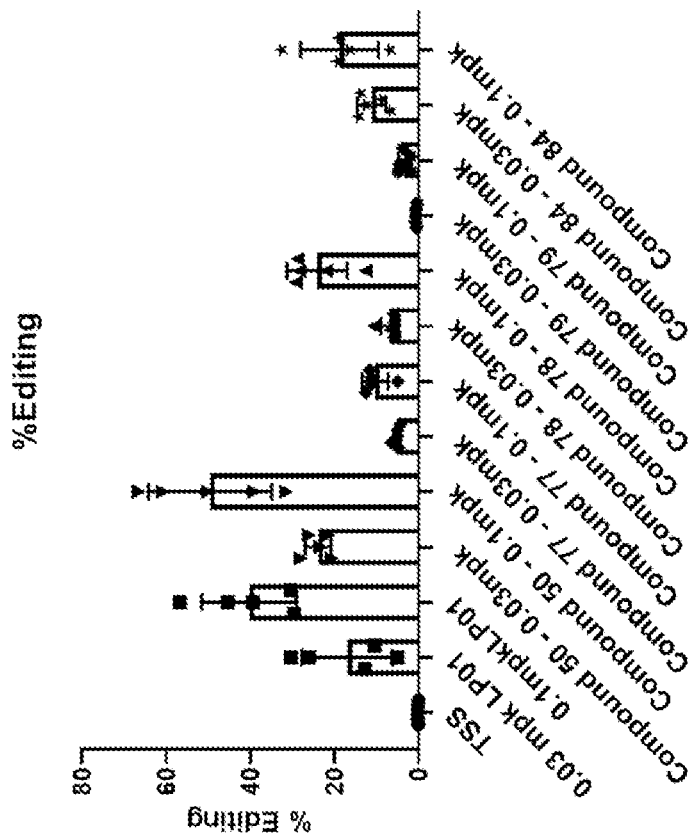
Figure 9C:
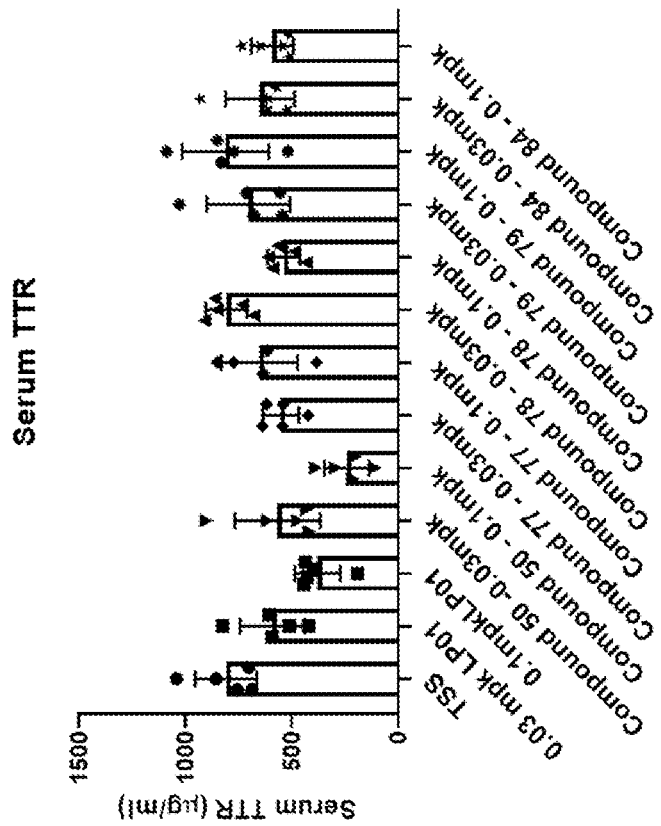

In Experiment 5, series of compounds based on Compound 50 were tested that vary at positions $X^2$ of Formula (1A) as illustrated in FIG. 9A. As shown in Table 9 and FIGS. 9B and 9C, all compounds tested were efficacious for in vivo editing at the 0.1 mpk dose.

Figure 10A:
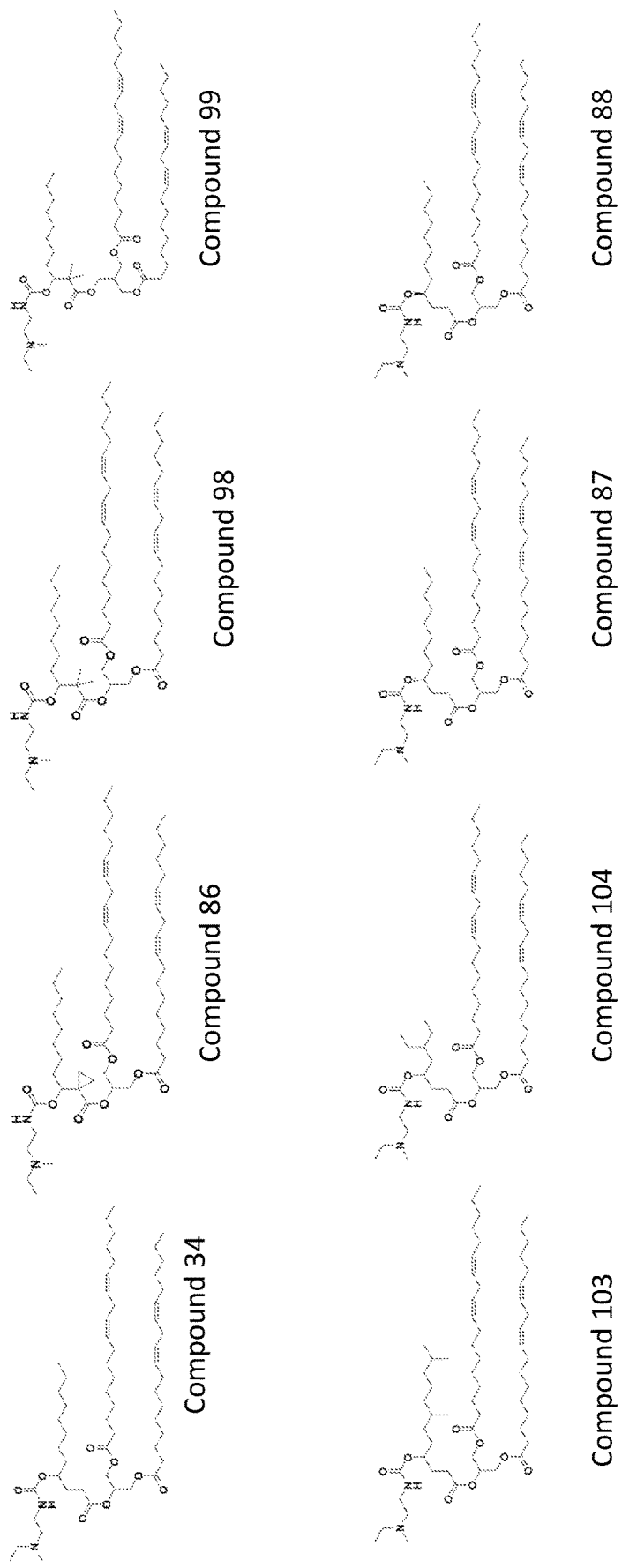
FIGS. 10A-10C show compounds of Formula (IA) and results of delivery using the compounds.
Figure 10B:
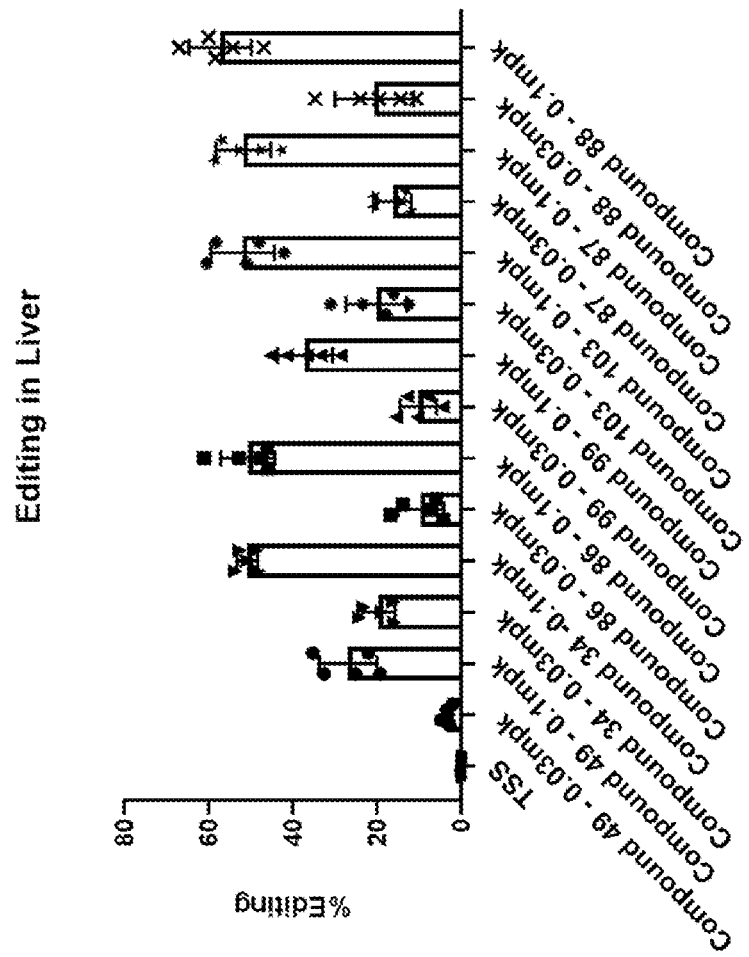
Figure 10C:
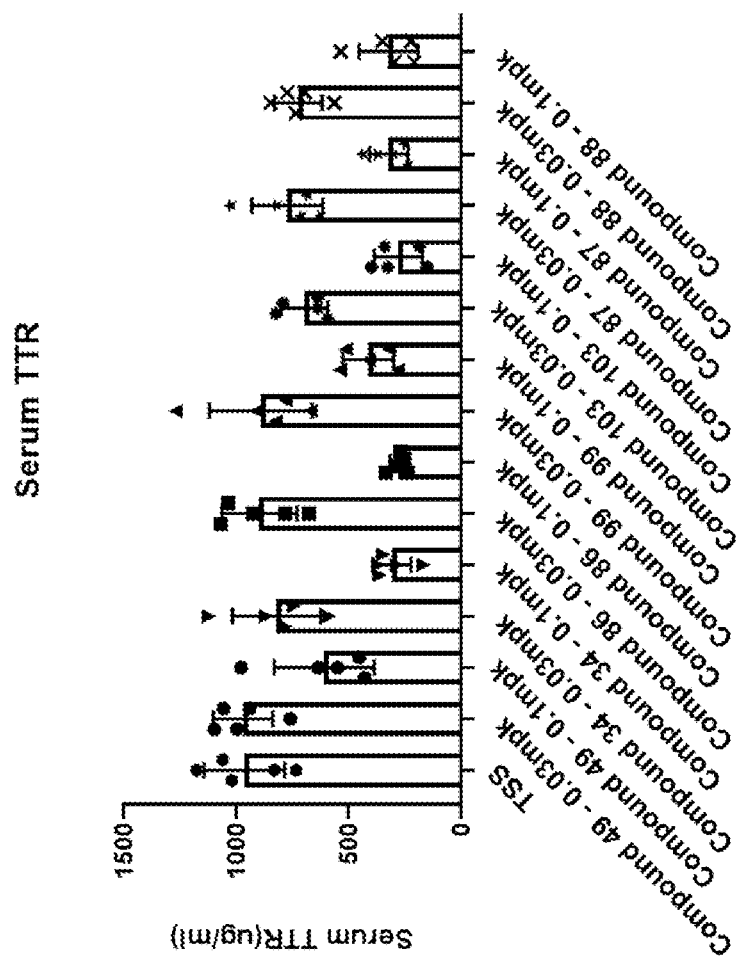

In Experiment 6, series of compounds based on Compound 34 were tested as illustrated in FIG. 10A. Compound 86 and Compound 99 vary from Compound 34 at the $X^1$ position of Formula (1A). Compound 103 vary from Compound 34 at the $R^3$ position of Formula (1A). Compound 87 and Compound 88 represent R- and S-enantiomers at carbon between the $R^3$ and the $X^1$ positions of the racemic Compound 34. Data are shown in Table 9 and FIGS. 10B and 10C. All compounds in this series tested in mice were efficacious for in vivo editing.

Figure 11A:
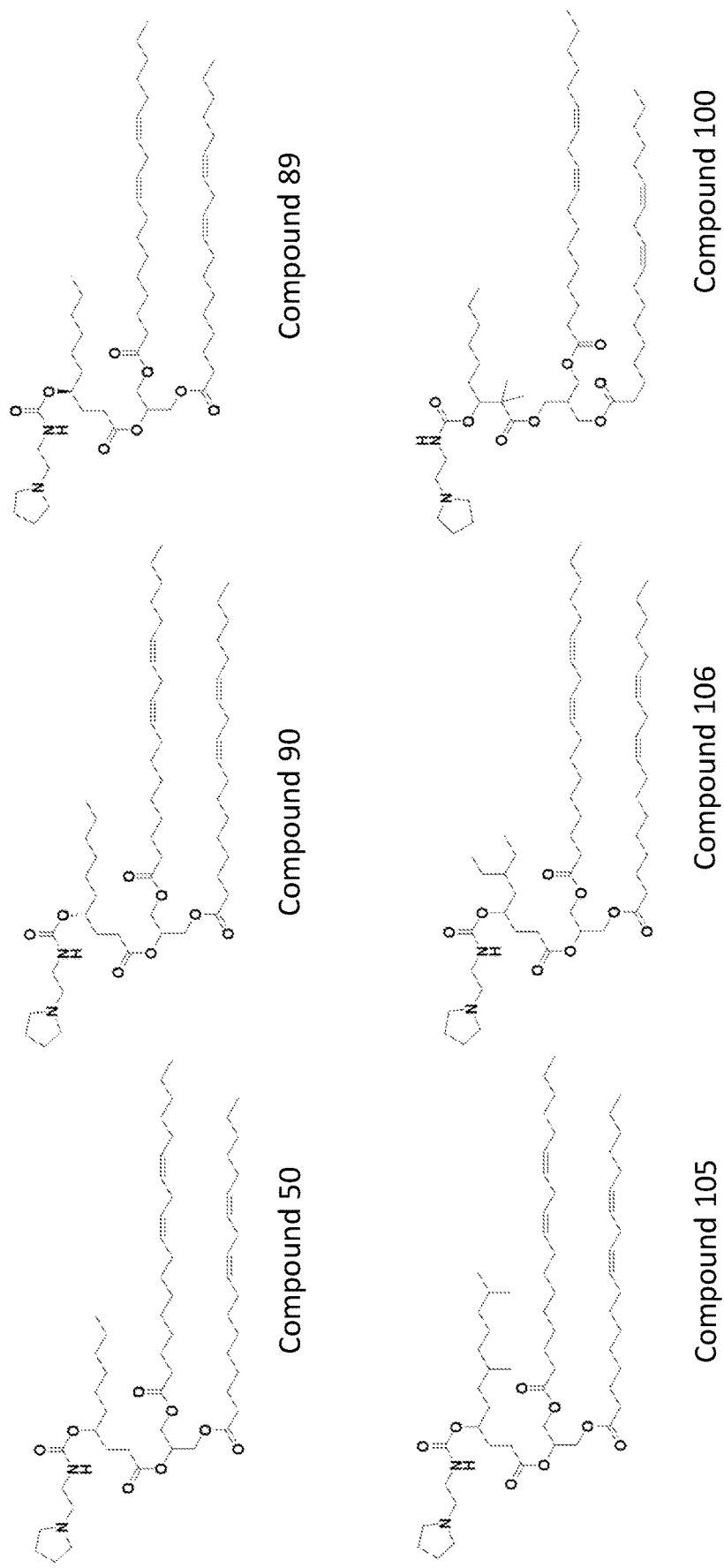
FIGS. 11A-11D show compounds of Formula (IA) and results of delivery using the compounds.
Figure 11B:
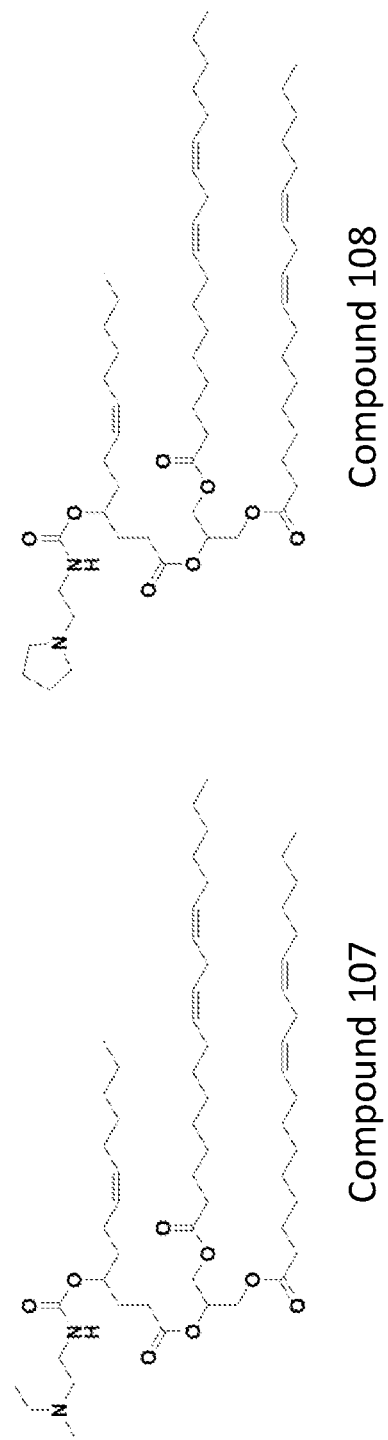
Figure 11C:
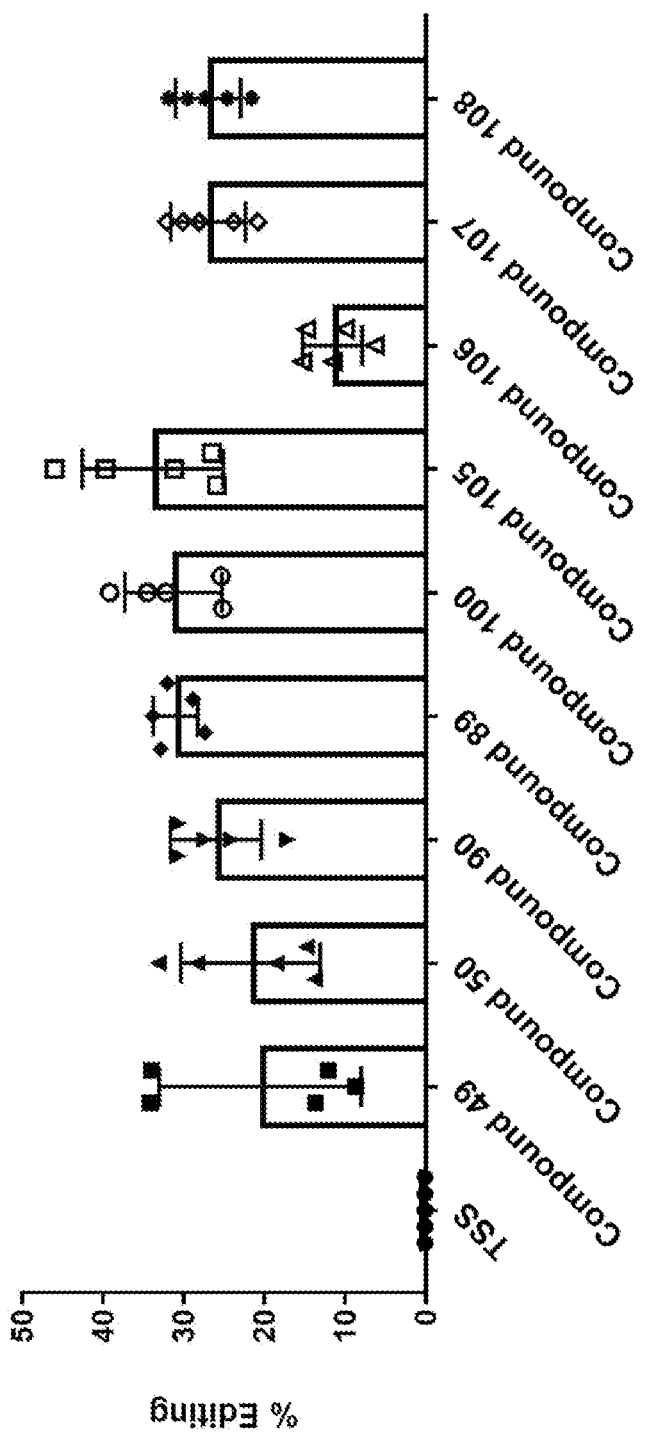
Figure 11D:
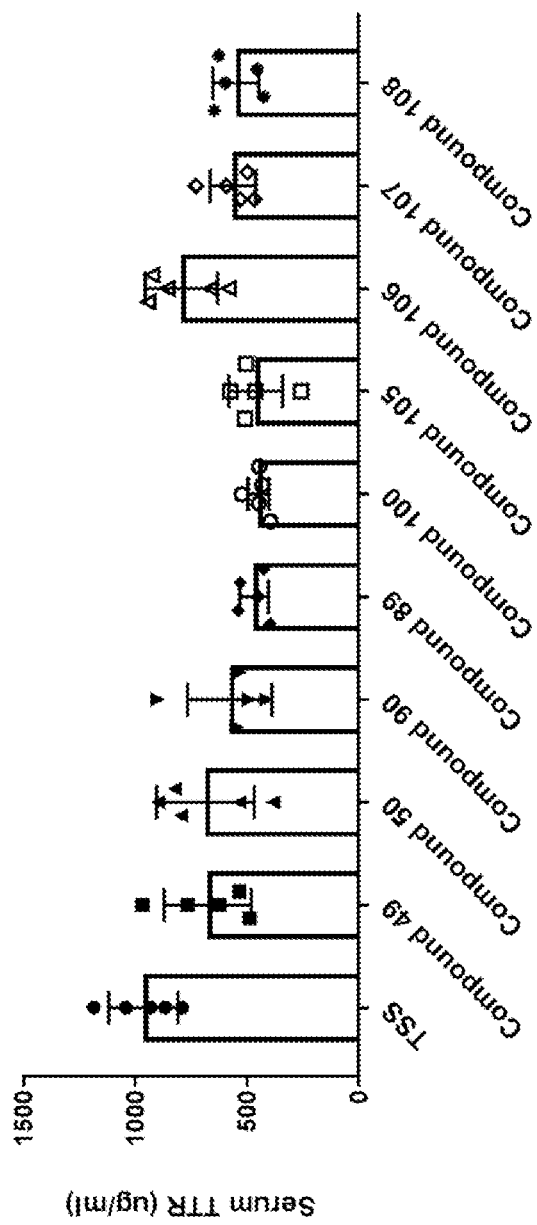

In Experiment 9, a series of compounds based on Compound 50 was tested as illustrated in FIG. 11A. Compound 90 and Compound 89 represent R- and S-enantiomers at carbon between the $R^3$ and the $X^1$ positions of the racemic Compound 50. Compound 100 and Compound 107 vary from Compound 50 and both the $R^3$ and the $X^1$ positions. Compound 105, Compound 106 and Compound 108 vary from Compound 50 at the $R^3$ position. Data are shown in Table 9 and FIGS. 11B and 11C. All compounds in this series tested in mice were efficacious for in vivo editing.

TABLE 8

Composition Analytics

| Cmpnd No. | Composition ratio (mol %) | Encapsulation (%) | Z-Ave Size (nm) | PDI | Num Ave Size (nm) | Expt. |
|---|---|---|---|---|---|---|
| 49 | 50/9/38/3 | 98% | 87.92 | 0.05 | 69.84 | 1 |
| 1 | 50/10/38.5/1.5 | 99% | 68.63 | 0.04 | 54.84 | 1 |
| 34 | 50/10/38.5/1.5 | 98% | 93.66 | 0.02 | 76.32 | 1 |
| 52 | 50/10/38.5/1.5 | 98% | 90.75 | 0.03 | 74.35 | 1 |
| 53 | 50/10/38.5/1.5 | 99% | 92.99 | 0.05 | 75.76 | 1 |
| 54 | 50/10/38.5/1.5 | 99% | 94.16 | 0.04 | 75.05 | 1 |
| 55 | 50/10/38.5/1.5 | 97% | 117.30 | 0.02 | 99.29 | 1 |
| 56 | 50/10/38.5/1.5 | 96% | 112.50 | 0.03 | 91.81 | 1 |
| 57 | 50/10/38.5/1.5 | 98% | 100.40 | 0.02 | 83.73 | 1 |
| 59 | 50/10/38.5/1.5 | 97% | 109.90 | 0.03 | 88.36 | 1 |
| 60 | 50/10/38.5/1.5 | 97% | 103.40 | 0.07 | 79.57 | 1 |
| 61 | 50/10/38.5/1.5 | 97% | 102.00 | 0.06 | 79.7 | 1 |
| 62 | 50/10/38.5/1.5 | 97% | 106.40 | 0.04 | 87.26 | 1 |
| 63 | 50/10/38.5/1.5 | 98% | 106.00 | 0.04 | 82.18 | 1 |
| 64 | 50/10/38.5/1.5 | 97% | 106.40 | 0.02 | 86.19 | 1 |
| 49 | 50/9/39.5/3 | 98% | 88.36 | 0.014 | 73.13 | 2 |
| 44 | 50/9/39.5/1.5 | 99% | 97.65 | 0.034 | 78.34 | 2 |
| 45 | 50/9/39.5/1.5 | 99% | 102.70 | 0.021 | 85.54 | 2 |
| 67 | 50/9/39.5/1.5 | 99% | 102.20 | 0.043 | 82.14 | 2 |
| 68 | 50/9/39.5/1.5 | 99% | 122.30 | 0.051 | 100.4 | 2 |
| 49 | 50/9/38/3 | 93 | 77.07 | 0.03 | 63.19 | 3 |
| 50 | 50/10/38.5/1.5 | 98 | 94.33 | 0.02 | 76.57 | 3 |
| 51 | 50/10/38.5/1.5 | 98 | 96.78 | 0.02 | 80.57 | 3 |
| 72 | 50/10/38.5/1.5 | 98 | 106.80 | 0.02 | 88.38 | 3 |
| 76 | 50/10/38.5/1.5 | 98 | 94.32 | 0.01 | 78.11 | 3 |
| 49 | 50/9/38/3 | 98 | 81.83 | 0.026 | 66.26 | 4 |
| 7 | 50/10/38.5/1.5 | 98 | 87.61 | 0.002 | 73.07 | 4 |
| 39 | 50/10/38.5/1.5 | 98 | 89.83 | 0.015 | 73.52 | 4 |
| 40 | 50/10/38.5/1.5 | 97 | 101.10 | 0.027 | 81.51 | 4 |
| 69 | 50/10/38.5/1.5 | 96 | 108.90 | 0.017 | 88.76 | 4 |
| 73 | 50/10/38.5/1.5 | 97 | 95.81 | 0.029 | 76.59 | 4 |
| 49 | 50/10/38.5/1.5 | 98 | 83.00 | 0.03 | 65 | 5 |
| 50 | 50/10/38.5/1.5 | 98 | 103.00 | 0.06 | 77 | 5 |
| 77 | 50/10/38.5/1.5 | 98 | 104.00 | 0.08 | 78 | 5 |
| 78 | 50/10/38.5/1.5 | 97 | 91.00 | 0.13 | 59 | 5 |
| 79 | 50/10/38.5/1.5 | 98 | 75.00 | 0.09 | 55 | 5 |
| 84 | 50/10/38.5/1.5 | 99 | 91.00 | 0.03 | 75 | 5 |
| 49 | 50/9/38/3 | 99% | 90.00 | 0.02 | 74 | 6 |
| 34 | 50/10/38.5/1.5 | 98% | 89.00 | 0.03 | 73 | 6 |
| 86 | 50/10/38.5/1.5 | 98% | 87.00 | 0.04 | 68 | 6 |
| 99 | 50/10/38.5/1.5 | 99% | 79.00 | 0.03 | 64 | 6 |
| 103 | 50/10/38.5/1.5 | 91% | 102.00 | 0.01 | 82 | 6 |
| 87 | 50/10/38.5/1.5 | 98% | 83.00 | 0.06 | 63 | 6 |
| 88 | 50/10/38.5/1.5 | 98% | 88.00 | 0.02 | 73 | 6 |
| 49 | 50/9/38/3 | 93 | 77.07 | 0.026 | 63.19 | 7 |
| 66 | 50/10/38.5/1.5 | 98 | 79.79 | 0.035 | 65.07 | 7 |
| 36 | 50/10/38.5/1.5 | 98 | 75.9 | 0.058 | 58.34 | 7 |
| 75 | 50/10/38.5/1.5 | 98 | 89.78 | 0.02 | 73.46 | 7 |
| 45 | 50/10/38.5/1.5 | 98 | 95.26 | 0.012 | 77.92 | 7 |
| 71 | 50/10/38.5/1.5 | 97 | 104.5 | 0.035 | 86.63 | 7 |
| 49 | 50/9/38/3 | 98% | 84.47 | 0.026 | 69.01 | 8 |
| 9 | 50/10/38.5/1.5 | 98% | 64.83 | 0.074 | 48.82 | 8 |
| 65 | 50/10/38.5/1.5 | 99% | 69.67 | 0.056 | 52.04 | 8 |
| 35 | 50/10/38.5/1.5 | 99% | 81.51 | 0.068 | 62.82 | 8 |
| 74 | 50/10/38.5/1.5 | 99% | 92.14 | 0.024 | 74.58 | 8 |
| 44 | 50/10/38.5/1.5 | 99% | 104.3 | 0.034 | 85.76 | 8 |
| 70 | 50/10/38.5/1.5 | 99% | 124.2 | 0.018 | 102 | 8 |
| 49 | 50/9/38/3 | 98 | 87 | 0.04 | 70 | 9 |
| 50 | 50/10/38.5/1.5 | 97 | 98 | 0.04 | 78 | 9 |
| 90 | 50/10/38.5/1.5 | 98 | 99 | 0.02 | 81 | 9 |
| 89 | 50/10/38.5/1.5 | 98 | 88 | 0.01 | 73 | 9 |

TABLE 8-continued

| | Composition Analytics | | | | | |
|---|---|---|---|---|---|---|
| Cmpnd No. | Composition ratio (mol %) | Encapsulation (%) | Z-Ave Size (nm) | PDI | Num Ave Size (nm) | Expt. |
| 100 | 50/10/38.5/1.5 | 99 | 102 | 0.05 | 83 | 9 |
| 105 | 50/10/38.5/1.5 | 99 | 80 | 0.02 | 64 | 9 |
| 106 | 50/10/38.5/1.5 | 99 | 91 | 0.01 | 74 | 9 |
| 107 | 50/10/38.5/1.5 | 98 | 89 | 0.03 | 72 | 9 |
| 108 | 50/10/38.5/1.5 | 99 | 89 | 0.03 | 73 | 9 |
| 49 | 50/9/38/3 | 0.98 | 90 | 0.04 | 75 | 10 |
| 34 | 50/10/38.5/1.5 | 0.98 | 95 | 0.03 | 77 | 10 |
| 91 | 50/10/38.5/1.5 | 0.98 | 97 | 0.01 | 82 | 10 |
| 92 | 50/10/38.5/1.5 | 0.98 | 67 | 0.06 | 51 | 10 |
| 93 | 50/10/38.5/1.5 | 0.98 | 103 | 0.01 | 86 | 10 |
| 94 | 50/10/38.5/1.5 | 0.98 | 70 | 0.06 | 53 | 10 |
| 95 | 50/10/38.5/1.5 | 0.98 | 105 | 0.01 | 88 | 10 |
| 51 | 50/10/38.5/1.5 | 0.98 | 98 | 0.02 | 82 | 10 |
| 96 | 50/10/38.5/1.5 | 0.98 | 89 | 0.03 | 73 | 10 |
| 97 | 50/10/38.5/1.5 | 0.98 | 92 | 0.03 | 75 | 10 |

Table 9 shows editing percentages in mouse liver as measured by NGS.

TABLE 9

Editing efficiency in mouse liver, providing % indel formation for G502 experiments and serum TTR levels.

| | | Editing | | | Serum TTR | | | | |
|---|---|---|---|---|---|---|---|---|---|
| Cmpnd No. | Dose (mpk) | % Editing | SD | N | Serum TTR (ug/ml) | SD | N | % TSS | Expt. |
| TSS | n/a | 0.1 | 0.00 | 5 | 1076.77 | 368.43 | 5 | 100.00 | 1 |
| 49 | 0.1 | 37.58 | 10.65 | 5 | 501.07 | 107.20 | 5 | 46.53 | 1 |
| 1 | 0.1 | 28.82 | 9.24 | 5 | 522.07 | 212.60 | 5 | 48.49 | 1 |
| 34 | 0.1 | 64.95 | 4.74 | 5 | 101.04 | 45.14 | 5 | 9.38 | 1 |
| 52 | 0.1 | 60.14 | 8.13 | 5 | 186.42 | 92.64 | 5 | 17.31 | 1 |
| 53 | 0.1 | 61.50 | 4.89 | 5 | 150.43 | 53.66 | 5 | 13.97 | 1 |
| 54 | 0.1 | 57.22 | 5.81 | 5 | 197.28 | 90.55 | 5 | 18.32 | 1 |
| 55 | 0.1 | 15.86 | 7.12 | 5 | 783.74 | 94.62 | 5 | 72.79 | 1 |
| 56 | 0.1 | 16.94 | 2.41 | 5 | 750.53 | 94.88 | 5 | 69.70 | 1 |
| 57 | 0.1 | 50.76 | 11.63 | 5 | 264.64 | 112.65 | 5 | 24.58 | 1 |
| 59 | 0.1 | 10.28 | 6.63 | 5 | 868.93 | 145.85 | 5 | 80.70 | 1 |
| 60 | 0.1 | 23.88 | 12.59 | 5 | 651.52 | 199.20 | 5 | 60.51 | 1 |
| 61 | 0.1 | 9.40 | 1.17 | 5 | 877.31 | 93.63 | 5 | 81.48 | 1 |
| 62 | 0.1 | 23.74 | 9.69 | 5 | 623.37 | 138.65 | 5 | 57.89 | 1 |
| 63 | 0.1 | 6.53 | 2.41 | 5 | 902.96 | 96.13 | 5 | 83.86 | 1 |
| 64 | 0.1 | 5.84 | 1.04 | 5 | 919.42 | 90.82 | 5 | 85.39 | 1 |
| TSS | n/a | 0.24 | 0.05 | 5 | 1232.25 | 259.96 | 5 | 100.00 | 2 |
| 49 | 0.03 | 6.5 | 0.39 | 5 | 1128.34 | 197.52 | 5 | 91.56 | 2 |
| 4 | 0.03 | 8.6 | 1.00 | 5 | 900.69 | 291.61 | 5 | 73.09 | 2 |
| 45 | 0.03 | 5.16 | 1.38 | 5 | 965.93 | 156.29 | 5 | 78.39 | 2 |
| 67 | 0.03 | 5.94 | 1.63 | 5 | 806 | 219.39 | 5 | 65.41 | 2 |
| 68 | 0.03 | 6.48 | 0.05 | 5 | 845.04 | 259.96 | 5 | 68.58 | 2 |
| TSS | n/a | 0.18 | 0.04 | 5 | 1161.07 | 311.28 | 5 | 100.00 | 3 |
| 49 | 0.03 | 5.02 | 2.30 | 5 | 960.376 | 129.68 | 5 | 82.71 | 3 |
| 49 | 0.1 | 30.66 | 10.27 | 5 | 544.37 | 183.72 | 5 | 46.89 | 3 |
| 50 | 0.03 | 37.54 | 24.51 | 5 | 528.43 | 165.52 | 5 | 45.51 | 3 |
| 50 | 0.1 | 65.56 | 3.59 | 5 | 160.42 | 44.32 | 5 | 13.82 | 3 |
| 51 | 0.03 | 38.8 | 5.98 | 5 | 447.172 | 44.70 | 5 | 38.51 | 3 |
| 51 | 0.1 | 65.62 | 4.90 | 5 | 108.258 | 49.36 | 5 | 9.32 | 3 |
| 72 | 0.03 | 27.72 | 10.69 | 5 | 777 | 191.77 | 5 | 66.92 | 3 |
| 72 | 0.1 | 53.06 | 8.34 | 5 | 306.856 | 39.10 | 5 | 26.43 | 3 |
| 76 | 0.03 | 27.32 | 14.64 | 5 | 939.50 | 171.63 | 5 | 69.72 | 3 |
| 76 | 0.1 | 63.08 | 6.07 | 5 | 148.554 | 67.25 | 5 | 12.79 | 3 |
| TSS | n/a | 0.24 | 0.05 | 5 | 690.45 | 84.84 | 5 | 100% | 4 |
| 49 | 0.03 | 28.78 | 9.67 | 5 | 464.17 | 74.74 | 5 | 67% | 4 |
| 49 | 0.1 | 56.82 | 4.70 | 5 | 154.53 | 60.30 | 5 | 22% | 4 |
| 7 | 0.03 | 38.23 | 13.85 | 4 | 397.92 | 52.45 | 4 | 58% | 4 |
| 7 | 0.1 | 66.72 | 5.63 | 5 | 66.59 | 45.44 | 5 | 10% | 4 |
| 69 | 0.03 | 36.68 | 6.47 | 5 | 370.88 | 69.44 | 5 | 54% | 4 |
| 69 | 0.1 | 67.38 | 5.13 | 4 | 85.93 | 27.44 | 4 | 12% | 4 |
| 40 | 0.03 | 34.53 | 5.48 | 4 | 529.70 | 128.79 | 4 | 77% | 4 |
| 40 | 0.1 | 69.44 | 2.12 | 5 | 64.65 | 21.93 | 5 | 9% | 4 |

TABLE 9-continued

Editing efficiency in mouse liver, providing % indel
formation for G502 experiments and serum TTR levels.

| | | Editing | | | Serum TTR | | | | |
|---|---|---|---|---|---|---|---|---|---|
| Cmpnd No. | Dose (mpk) | % Editing | SD | N | Serum TTR (ug/ml) | SD | N | % TSS | Expt. |
| 73 | 0.03 | 57.32 | 7.29 | 5 | 173.78 | 81.14 | 5 | 25% | 4 |
| 73 | 0.1 | 70.76 | 2.03 | 5 | 30.62 | 14.97 | 5 | 4% | 4 |
| 39 | 0.03 | 44.74 | 14.44 | 5 | 286.24 | 100.55 | 5 | 41% | 4 |
| 39 | 0.1 | 66.66 | 4.44 | 5 | 39.85 | 20.49 | 5 | 6% | 4 |
| TSS | n/a | 0.16 | 0.05 | 5 | 809.30 | 145.45 | 5 | 100 | 5 |
| 49 | 0.03 | 16.98 | 10.77 | 5 | 592.00 | 150.58 | 5 | 73.1 | 5 |
| 49 | 0.1 | 40.32 | 11.31 | 5 | 379.70 | 106.18 | 5 | 46.9 | 5 |
| 77 | 0.03 | 5.18 | 0.79 | 5 | 552.80 | 84.36 | 5 | 68.3 | 5 |
| 77 | 0.1 | 10.36 | 3.05 | 5 | 652.20 | 179.50 | 5 | 80.6 | 5 |
| 78 | 0.03 | 7 | 2.04 | 5 | 807.50 | 97.21 | 5 | 99.8 | 5 |
| 78 | 0.1 | 24.2 | 7.13 | 5 | 537.90 | 74.96 | 5 | 66.5 | 5 |
| 79 | 0.03 | 0.58 | 0.19 | 5 | 703.50 | 195.81 | 5 | 86.9 | 5 |
| 79 | 0.1 | 3.34 | 1.51 | 5 | 812.20 | 203.80 | 5 | 100.4 | 5 |
| 84 | 0.03 | 11.24 | 3.37 | 5 | 649.70 | 161.07 | 5 | 80.3 | 5 |
| 84 | 0.1 | 18.86 | 9.21 | 5 | 592.10 | 98.42 | 5 | 73.2 | 5 |
| 50 | 0.03 | 23.92 | 3.08 | 5 | 567.70 | 202.13 | 5 | 70.1 | 5 |
| 50 | 0.1 | 49.6 | 14.63 | 5 | 241.90 | 104.88 | 5 | 29.9 | 5 |
| TSS | n/a | 0.1 | 0.07 | 5 | 964.34 | 179.38 | 5 | 100.00 | 6 |
| 49 | 0.03 | 3.28 | 1.05 | 5 | 969.91 | 131.91 | 5 | 100.57 | 6 |
| 49 | 0.1 | 26.88 | 6.84 | 5 | 609.23 | 222.39 | 5 | 63.17 | 6 |
| 34 | 0.03 | 19.66 | 3.87 | 5 | 820.73 | 196.33 | 5 | 85.10 | 6 |
| 34 | 0.1 | 50.82 | 2.43 | 5 | 306.74 | 84.07 | 5 | 31.80 | 6 |
| 86 | 0.03 | 9.62 | 5.42 | 5 | 897.846 | 166.96 | 5 | 93.10 | 6 |
| 86 | 0.1 | 50.7 | 6.45 | 5 | 277.696 | 38.44 | 5 | 28.80 | 6 |
| 99 | 0.03 | 10.2 | 4.30 | 5 | 891.268 | 228.52 | 5 | 92.42 | 6 |
| 99 | 0.1 | 37.12 | 6.54 | 5 | 413.382 | 113.60 | 5 | 42.87 | 6 |
| 103 | 0.03 | 20.16 | 7.23 | 5 | 696.58 | 103.62 | 5 | 72.23 | 6 |
| 103 | 0.1 | 51.98 | 7.53 | 5 | 280.156 | 106.56 | 5 | 29.05 | 6 |
| 87 | 0.03 | 16.08 | 4.23 | 5 | 773.57 | 157.56 | 5 | 80.21 | 6 |
| 87 | 0.1 | 51.78 | 6.51 | 5 | 321.386 | 85.50 | 5 | 33.33 | 6 |
| 88 | 0.03 | 20.66 | 9.33 | 5 | 723.87 | 105.48 | 5 | 75.06 | 6 |
| 88 | 0.1 | 57.32 | 7.41 | 5 | 322.566 | 132.08 | 5 | 33.45 | 6 |
| TSS | n/a | 0.16 | 0.05 | 5 | 1648.15 | 261.09 | 5 | 100 | 7 |
| 49 | 0.03 | 4.08 | 1.33 | 5 | 1459.99 | 292.22 | 5 | 88.584 | 7 |
| 49 | 0.1 | 27.5 | 8.04 | 5 | 860.90 | 343.62 | 5 | 52.234 | 7 |
| 66 | 0.03 | 27.64 | 8.25 | 5 | 901.24 | 307.33 | 5 | 54.682 | 7 |
| 66 | 0.1 | 55.26 | 4.08 | 5 | 324.25 | 115.30 | 5 | 19.674 | 7 |
| 36 | 0.03 | 9.96 | 0.82 | 5 | 1249.04 | 115.28 | 5 | 75.785 | 7 |
| 36 | 0.1 | 35.92 | 2.78 | 5 | 722.28 | 85.81 | 5 | 43.824 | 7 |
| 75 | 0.03 | 29.6 | 6.95 | 5 | 743.29 | 58.71 | 5 | 45.098 | 7 |
| 75 | 0.1 | 57.22 | 7.58 | 5 | 197.72 | 99.45 | 5 | 11.996 | 7 |
| 45 | 0.03 | 31.1 | 4.96 | 5 | 715.87 | 97.41 | 5 | 43.435 | 7 |
| 45 | 0.1 | 60.3 | 6.80 | 5 | 166.30 | 55.94 | 5 | 10.09 | 7 |
| 71 | 0.03 | 20.94 | 7.55 | 5 | 781.63 | 115.04 | 5 | 47.425 | 7 |
| 71 | 0.1 | 55.78 | 2.10 | 5 | 248.13 | 55.94 | 5 | 15.055 | 7 |
| TSS | n/a | 0.1 | 0.00 | 5 | 748.33 | 130.95 | 5 | 100.00 | 8 |
| 49 | 0.03 | 7.62 | 6.50 | 5 | 735.41 | 83.84 | 5 | 98.27 | 8 |
| 49 | 0.1 | 37.46 | 4.17 | 5 | 369.43 | 45.54 | 5 | 49.37 | 8 |
| 9 | 0.03 | 0.84 | 0.46 | 5 | 853.25 | 107.87 | 5 | 114.02 | 8 |
| 9 | 0.1 | 3.46 | 1.09 | 5 | 772.22 | 172.17 | 5 | 103.19 | 8 |
| 65 | 0.03 | 1.32 | 0.31 | 5 | 896.77 | 143.42 | 5 | 119.84 | 8 |
| 65 | 0.1 | 10.12 | 9.68 | 5 | 742.52 | 151.70 | 5 | 99.22 | 8 |
| 35 | 0.03 | 4.46 | 0.70 | 5 | 780.47 | 74.29 | 5 | 104.30 | 8 |
| 35 | 0.1 | 17.94 | 4.99 | 5 | 741.82 | 79.87 | 5 | 99.13 | 8 |
| 74 | 0.03 | 4.36 | 1.25 | 5 | 752.38 | 120.29 | 5 | 100.54 | 8 |
| 74 | 0.1 | 11.12 | 1.63 | 5 | 823.58 | 126.35 | 5 | 110.06 | 8 |
| 44 | 0.03 | 4.76 | 1.10 | 5 | 897.76 | 51.74 | 5 | 119.97 | 8 |
| 44 | 0.1 | 17.97 | 7.30 | 5 | 589.60 | 52.34 | 5 | 78.79 | 8 |
| 70 | 0.03 | 4.84 | 1.77 | 5 | 945.08 | 81.30 | 5 | 126.29 | 8 |
| 70 | 0.1 | 8.04 | 1.17 | 5 | 654.70 | 98.42 | 5 | 87.49 | 8 |
| TSS | n/a | 0.1 | 0.00 | 5 | 964.50 | 154.71 | 5 | 100 | 9 |
| 49 | 0.03 | 20.54 | 12.51 | 5 | 677.31 | 194.76 | 5 | 70.22 | 9 |
| 50 | 0.03 | 21.74 | 8.62 | 5 | 687.70 | 218.46 | 5 | 71.3 | 9 |
| 90 | 0.03 | 26.02 | 5.64 | 5 | 578.26 | 188.44 | 5 | 59.95 | 9 |
| 89 | 0.03 | 31.02 | 2.76 | 5 | 469.27 | 63.53 | 5 | 48.65 | 9 |
| 100 | 0.03 | 31.3 | 6.03 | 5 | 450.19 | 47.05 | 5 | 46.68 | 9 |
| 105 | 0.03 | 33.86 | 8.75 | 5 | 462.70 | 120.85 | 5 | 47.97 | 9 |
| 106 | 0.03 | 11.58 | 3.69 | 5 | 795.41 | 161.67 | 5 | 82.47 | 9 |
| 106 | 0.03 | 1.98 | 1.16 | 5 | 855.49 | 158.34 | 5 | 88.7 | 9 |
| 107 | 0.03 | 26.98 | 4.62 | 5 | 564.55 | 102.79 | 5 | 58.53 | 9 |
| 108 | 0.03 | 27 | 4.04 | 5 | 550.89 | 102.92 | 5 | 57.12 | 9 |
| TSS | n/a | 0.14 | 0.05 | 5 | 767.76 | 98.15 | 5 | 100% | 10 |

TABLE 9-continued

Editing efficiency in mouse liver, providing % indel formation for G502 experiments and serum TTR levels.

| Cmpnd No. | Dose (mpk) | % Editing | SD | N | Serum TTR (ug/ml) | SD | N | % TSS | Expt. |
|---|---|---|---|---|---|---|---|---|---|
| 49 | 0.03 | 10.33 | 2.15 | 4 | 704.2 | 126.26 | 4 | 92% | 10 |
| 34 | 0.03 | 37.44 | 10.7 | 5 | 419.07 | 133.1 | 5 | 55% | 10 |
| 91 | 0.03 | 22.7 | 6.77 | 5 | 681.26 | 63.6 | 5 | 89% | 10 |
| 92 | 0.03 | 2.38 | 0.79 | 5 | 923.39 | 226.76 | 5 | 120% | 10 |
| 93 | 0.03 | 12.68 | 1.94 | 5 | 765.38 | 95.14 | 5 | 100% | 10 |
| 95 | 0.03 | 37.96 | 13.54 | 5 | 589.77 | 283.04 | 5 | 77% | 10 |
| 51 | 0.03 | 30.86 | 4.36 | 5 | 619.84 | 114.91 | 5 | 81% | 10 |
| 96 | 0.03 | 28.04 | 3.67 | 5 | 540.39 | 120 | 5 | 70% | 10 |
| 97 | 0.03 | 28.26 | 3.88 | 5 | 603.03 | 177.26 | 5 | 79% | 10 |

Example 120. Editing Efficacy and Tolerability of Lipids In Vivo

To assess lipid efficacy, dose response experiments were performed in vivo. Cas9 mRNA of Example 115 was formulated as LNPs with a gRNA targeting TTR (G00534; SEQ ID NO: 5). These LNPs were formulated, prepared and analyzed as described in Example 115 using a 1:2 w/w ratio of a sgRNA and Cas9 mRNA. Composition analysis for these LNPs are described in Table 10.

TABLE 10

Composition analytics

| Compound Number | Composition | Encapsulation (%) | Z-Avg Size (nm) | PDI | Num Avg Size (nm) |
|---|---|---|---|---|---|
| 49 | 50/9/38/3 | 97 | 87.84 | 0.028 | 69.85 |
| 34 | 50/10/38.5/1.5 | 93 | 96.43 | 0.052 | 76.08 |
| 45 | 50/10/38.5/1.5 | 95 | 101.00 | 0.052 | 83.48 |
| 50 | 50/10/38.5/1.5 | 87 | 98.55 | 0.050 | 79.18 |

Figure 12A:
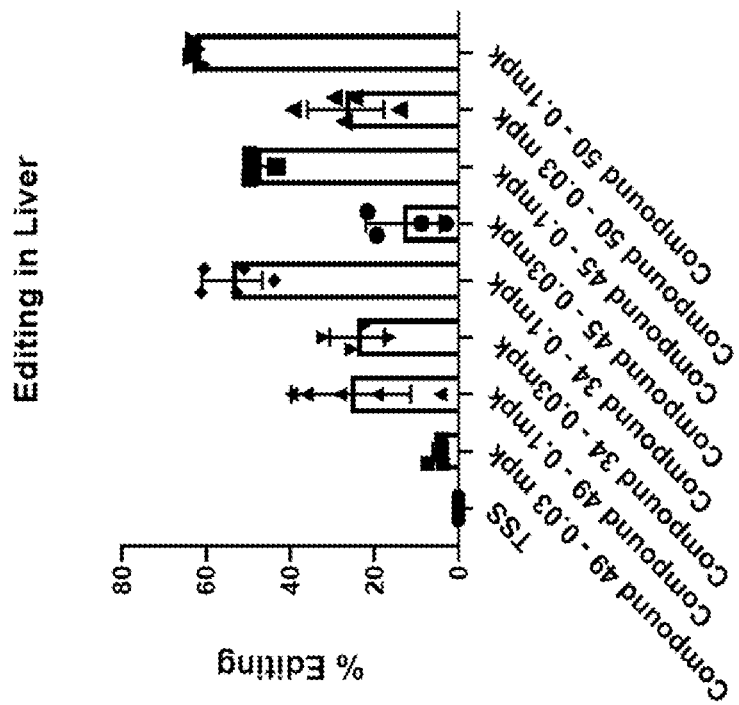
FIGS. 12A-12B show compounds of Formula (IA) and results of delivery using the compounds.
Figure 12B:
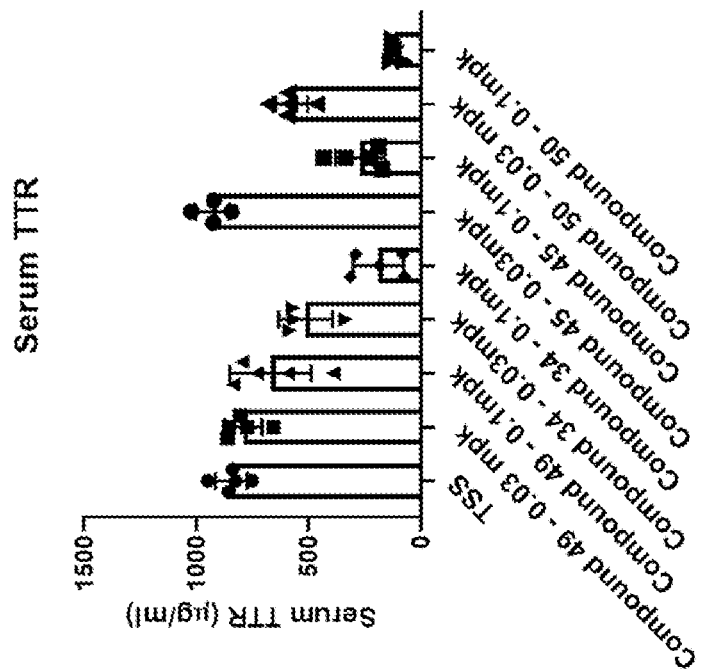

For efficacy, Sprague Dawley female rats were dosed i.v. at 0.1 mpk or 0.03 mpk. 6-7 days post dose, rats were euthanized by CO2 asphyxiation. Blood was collected into serum separator tubes. Liver biopsy processed for gDNA and assessed for editing by NGS methods described in Example 115. Results are shown in Table 11 and FIGS. 12A and 12B. For tolerability, Sprague Dawley female rats were dosed at 6 mpk and 24 hours post dose the animals were euthanized by CO2 asphyxiation. Blood was collected into serum separator tubes and sent to an external CRO for quantitation of liver enzymes via a liver enzyme panel. Results are shown in Table 12.

TABLE 11

Editing efficiency in rat, providing % indel formation for G534 experiments and serum TTR levels.

| Cmpnd No. | Dose (mpk) | % Editing | SD | N | Serum TTR (ug/ml) | SD | N | % TSS | Guides (gRNA) | Expt. |
|---|---|---|---|---|---|---|---|---|---|---|
| TSS |  | 0.1 | 0.00 | 5 | 845.3 | 70.69 | 5 | 100% | G534 | 1 |
| 49 | 0.03 | 4.76 | 1.49 | 5 | 790.9 | 82.94 | 5 | 94% | G534 | 1 |
| 49 | 0.1 | 25.62 | 14.18 | 5 | 669.5 | 181.13 | 5 | 79% | G534 | 1 |
| 34 | 0.03 | 21.22 | 6.54 | 5 | 514.2 | 119.36 | 5 | 61% | G534 | 1 |
| 34 | 0.1 | 53.9 | 7.17 | 5 | 188.9 | 112.67 | 5 | 22% | G534 | 1 |
| 45 | 0.03 | 10.76 | 8.80 | 5 | 910.4 | 73.77 | 5 | 110% | G534 | 1 |
| 45 | 0.1 | 48.16 | 2.90 | 5 | 270.7 | 109.71 | 5 | 32% | G534 | 1 |
| 50 | 0.03 | 26.9 | 9.04 | 5 | 581.7 | 76.89 | 5 | 69% | G534 | 1 |
| 50 | 0.1 | 62.6 | 1.04 | 5 | 116.6 | 24.78 | 5 | 14% | G534 | 1 |

TABLE 12

Results of liver enzyme panel of rat liver

| Cmpnd No. | Dose (mg/kg) | ALT (U/L) | AST (U/L) | Creatine kinase (U/L) | GGT (U/L) | ALP (U/L) | Total Bilirubin (mg/dL) |
|---|---|---|---|---|---|---|---|
| TSS |  | 47 | 72 | 132.2 | 0 | 318.4 | 0.1 |
| 49 | 6 | 408.5 | 534.8 | 157.5 | 2 | 784.3 | 0.6 |
| 34 | 6 | 179.6 | 349.6 | 184.8 | 3.4 | 542 | 0.2 |
| 45 | 6 | 163.2 | 681 | 1103 | 2.4 | 439.8 | 0.3 |
| 50 | 6 | 250.8 | 820.8 | 272 | 11 | 508.6 | 0.4 |

Example 121—In Vitro Editing with $R^3$ Alkyl Series Compounds

Figure 13A:
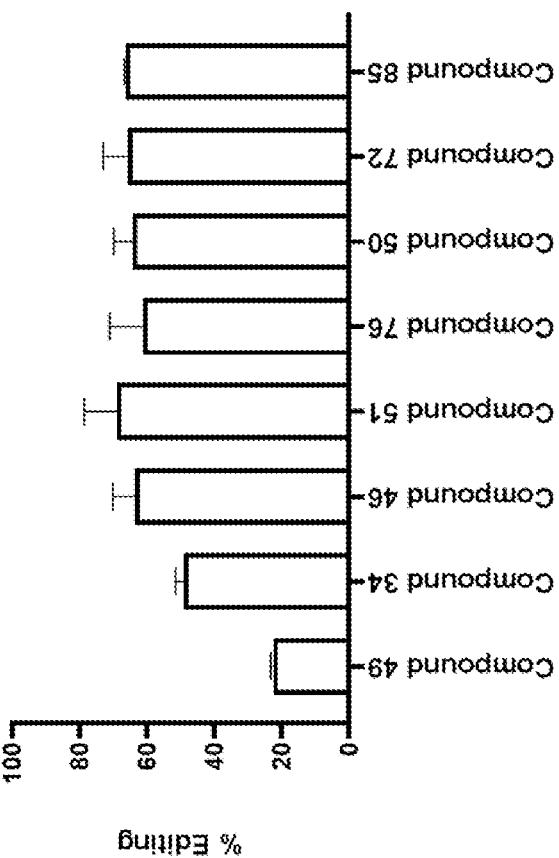
FIGS. 13A-13B show compounds of Formula (IA) and results of delivery using the compounds.
Figure 13B:
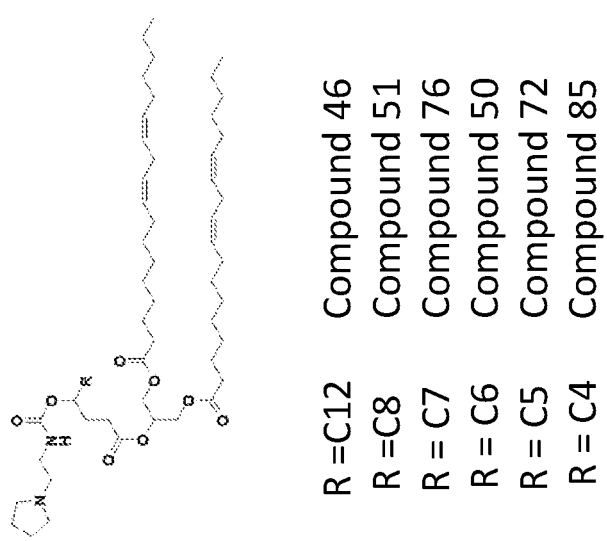

A series of compounds based on Compound 46 that vary by the inclusion of a $C_{4-12}$ alkyl at the $R^3$ position of Formula (IA) (as illustrated in FIG. 13A) were tested for in vitro editing. The human hepatocellular carcinoma cell line HUH17 (Japanese Collection of Research Bioresources Cell Bank, Cat. JCRB0403) was cultured in DMEM media supplemented with 10% fetal bovine serum and 1% Penicillin-Streptomycin. Cells were plated at a density of 20,000 cells/well in a 96-well plate 24 hours prior to transfection (~80% confluent at time of transfection). The LNPs were formulated at a 1:2 w/w ratio of sgRNA and Cas9 mRNA using the cross flow procedure with lipid molar compositions as described in Table 13 at an N/P ratio of 6.0. LNP compositions were analyzed for average particle size, polydispersity (pdi), total RNA content and encapsulation efficiency of RNA as described in Example 115. Analysis of average particle size, polydispersity (PDI), total RNA content and encapsulation efficiency of RNA are shown in Table 13. LNPs were diluted into media, incubated for 5 minutes at 37 C and pipetted onto cells at a dose of 2000 ng RNA per well. Each condition was assayed in biological duplicate. Cells were harvested post-transfection at 6 hours. Genomic DNA was extracted using 50 μL/well BuccalAmp DNA Extraction solution (Epicentre, Cat. QE09050) according to manufacturer's protocol. All DNA samples were subjected to PCR and subsequent NGS analysis for editing at the G000502 target locus, as described above. As shown in Table 14 and FIG. 13B, all compounds tested were efficacious for in vitro editing.

TABLE 13

Composition Analytics

| Cmpnd No. | Composition ratio (mol %) | Z-Ave Size [nm] | PDI | Number Average [nm] | % E |
|---|---|---|---|---|---|
| 49 | 50/9/38/3 | 93.14 | 0.015 | 74.82 | 98 |
| 34 | 50/10/38.5/1.5 | 93.01 | 0.009 | 75.88 | 97 |

TABLE 13-continued

Composition Analytics

| Cmpnd No. | Composition ratio (mol %) | Z-Ave Size [nm] | PDI | Number Average [nm] | % E |
|---|---|---|---|---|---|
| 46 | 50/10/38.5/1.5 | 94.54 | 0.003 | 76.76 | 99 |
| 51 | 50/10/38.5/1.5 | 97.21 | 0.009 | 80 | 98 |
| 76 | 50/10/38.5/1.5 | 98.79 | 0.024 | 81.12 | 97 |
| 50 | 50/10/38.5/1.5 | 102.8 | 0.021 | 84.16 | 97 |
| 72 | 50/10/38.5/1.5 | 111.4 | 0.018 | 91.47 | 94 |
| 85 | 50/10/38.5/1.5 | 117.1 | 0.045 | 93.05 | 96 |

TABLE 14

In vitro editing

| Cmpnd No. | Editing | SD |
|---|---|---|
| 49 | 22.6 | 0.8 |
| 34 | 49.0 | 2.5 |
| 46 | 63.7 | 6.4 |
| 51 | 69.0 | 9.7 |
| 76 | 61.2 | 9.9 |
| 50 | 64.3 | 5.6 |
| 72 | 65.8 | 7.3 |
| 85 | 66.4 | 0.4 |

SEQUENCE TABLE

| Description | Sequence | SEQ ID No. |
|---|---|---|
| G00282 sgRNA targeting mouse TTR | mU*mU*mA*CAGCCACGUCUACAGCAGUUUUAGAmGmCmUmAm GmAmAmUmAmGmCAAGUUAAAAUAAGGCUAGUCCGUUAUC AmAmCmUmUmGmAmAmAmAmGmUmGmGmCmAmCmCm GmAmGmUmCmGmGmUmGmCmU*mU*mU*mU | 1 |
| G00650 sgRNA targeting human B2M | mG*mA*mC*AAGCACCAGAAAGACCAGUUUUAGAmGmCmUmAm GmAmAmUmAmGmCAAGUUAAAAUAAGGCUAGUCCGUUAUC AmAmCmUmUmGmAmAmAmAmGmUmGmGmCmAmCmCm GmAmGmUmCmGmGmUmGmCmU*mU*mU*mU | 2 |
| mRNA encoding Cas9 | GGGUCCCGCAGUCGGCGUCCAGCGGCUCUGCUUGUUCGUGUGUGU GUCGUUGCAGGCCUUAUUCGGAUCCGCCACCAUGGACAAGAAGUA CAGCAUCGGACUGGACAUCGGAACAAACAGCGUCGAUGGGCAGU CAUCACAGACGAAUACAAGGUCCCGAGCAAGAAGUUCAAGGUCCU GGGAAACACAGACAGACACAGCCAUCAAGAAGAACCUGAUCGGAGC ACUGCUGUUCGACAGCGGAGAAACAGCAGAAGCAACAAGACUGAA GAGAACAGCAAGAAGAAGAUACACAAGAAGAAAGAACAGAAUCUG CUACCUGCAGGAAAUCUUCAGCAACGAAAUGGCAAAGGUCGACGA CAGCUUCUUCCACAGACUGGAAGAAAGCUUCCUGGUCGAAGAAGA CAAGAAGCACGAAAGACACCCGAUCUUCGGAAACAUCGUCGACGA AGUCGCAUACCACGAAAAGUACCCGACAAUCUACCACCUGAGAAA GAAGCUGGUCGACAGCACAGACAAGGCAGACCUGAGACUGAUCUA CCUGGCACUGGCACACAUGAUCAAGUUCAGAGGACACUUCCUGAU CGAAGGAGACCUGAACCCGGACAACAGCGACGUCGACAAGCUGUU CAUCCAGCUGGUCCAGACAUACAACCAGCUGUUCGAAGAAAACCC GAUCAACGCAAGCGGAGUCGACGCAAAGGCAAUCCUGAGCGCAAG ACUGAGCAAGAGCAGAAGACUGGAAAACCUGAUCGCACAGCUGCC GGGAGAAAAGAAGAACGGACUGUUCGGAAACCUGAUCGCACUGAG CCUGGGACUGACACCGAACUUCAAGAGCAACUUCGACCUGGCAGA AGACGCAAAGCUGCAGCUGAGCAAGGACACAUACGACGACGACCU GGACAACCUGCUGGCACAGAUCGGAGACCAGUACGCAGACCUGUU CCUGGCAGCAAAGAACCUGAGCGACGCAAUCCUGCUGAGCGACAU CCUGAGAGUCAACACAGAAAUCACAAAGGCACCGCUGAGCGCAAG CAUGAUCAAGAGAUACGACGAACACCACCAGGACCUGACACUGCU GAAGGCACUGGUCAGACAGCAGCUGCCGGAAAAGUACAAGGAAAU | 3 |

| Description | Sequence | SEQ ID No. |
|---|---|---|
| | CUUCUUCGACCAGAGCAAGAACGGAUACGCAGGAUACAUCGACGG | |
| | AGGAGCAAGCCAGGAAGAAUUCUACAAGUUCAUCAAGCCGAUCCU | |
| | GGAAAAGAUGGACGGAACAGAAGAACUGCUGGUCAAGCUGAACAG | |
| | AGAAGACCUGCUGAGAAAGCAGAGAACAUUCGACAACGGAAGCAU | |
| | CCCGCACCAGAUCCACCUGGGAGAACUGCACGCAAUCCUGAGAAG | |
| | ACAGGAAGACUUCUACCCGUUCCUGAAGGACAACAGAGAAAAGAU | |
| | CGAAAAGAUCCUGACAUUCAGAAUCCCGUACUACGUCGGACCGCU | |
| | GGCAAGAGGAAACAGCAGAUUCGCAUGGAUGACAAGAAAGAGCGA | |
| | AGAAACAAUCACACCGUGGAACUUCGAAGAAGUCGUCGACAAGGG | |
| | AGCAAGCGCACAGAGCUUCAUCGAAAGAAUGACAAACUUCGACAA | |
| | GAACCUGCCGAACGAAAAGGUCCUGCCGAAGCACAGCCUGCUGUA | |
| | CGAAUACUUCACAGUCUACAACGAACUGACAAAGGUCAAGUACGU | |
| | CACAGAAGGAAUGAGAAAGCCGGCAUUCCUGAGCGGAGAACAGAA | |
| | GAAGGCAAUCGUCGACCUGCUGUUCAAGACAAACAGAAAGGUCAC | |
| | AGUCAAGCAGCUGAAGGAAGACUACUUCAAGAAGAUCGAAUGCUU | |
| | CGACAGCGUCGAAAUCAGCGGAGUCGAAGACAGAUUCAACGCAAG | |
| | CCUGGGAACAUACCACGACCUGCUGAAGAUCAUCAAGGACAAGGA | |
| | CUUCCUGGACAACGAAGAAAACGAAGACAUCCUGGAAGACAUCGU | |
| | CCUGACACUGACACUGUUCGAAGACAGAGAAAUGAUCGAAGAAAG | |
| | ACUGAAGACAUACGCACACCUGUUCGACGACAAGGUCAUGAAGCA | |
| | GCUGAAGAGAAGAAGAUACACAGGAUGGGGAAGACUGAGCAGAAA | |
| | GCUGAUCAACGGAAUCAGAGACAAGCAGAGCGGAAAGACAAUCCU | |
| | GGACUUCCUGAAGAGCGACGGAUUCGCAAACAGAAACUUCAUGCA | |
| | GCUGAUCCACGACGACAGCCUGACAUUCAAGGAAGACAUCCAGAA | |
| | GGCACAGGUCAGCGGACAGGGAGACAGCCUGCACGAACACAUCGC | |
| | AAACCUGGCAGGAAGCCCGGCAAUCAAGAAGGGAAUCCUGCAGAC | |
| | AGUCAAGGUCGUCGACGAACUGGUCAAGGUCAUGGGAAGACACAA | |
| | GCCGGAAAACAUCGUCAUCGAAAUGGCAAGAGAAAACCAGACAAC | |
| | ACAGAAGGGACAGAAGAACAGCAGAGAAAGAAUGAAGAGAAUCGA | |
| | AGAAGGAAUCAAGGAACUGGGAAGCCAGAUCCUGAAGGAACACCC | |
| | GGUCGAAAACACACAGCUGCAGAACGAAAAGCUGUACCUGUACUA | |
| | CCUGCAGAACGGAAGAGACAUGUACGUCGACCAGGAACUGGACAU | |
| | CAACAGACUGAGCGACUACGACGUCGACCACAUCGUCCCGCAGAGC | |
| | UUCCUGAAGGACGACAGCCAUCGACAACAAGGUCCUGACAAGAAGC | |
| | GACAAGAACAGAGGAAAGAGCGACAACGUCCCGAGCGAAGAAGUC | |
| | GUCAAGAAGAUGAAGAACUACUGGAGACAGCUGCUGAACGCAAAG | |
| | CUGAUCACACAGAGAAAGUUCGACAACCUGACAAAGGCAGAGAGA | |
| | GGAGGACUGAGCGAACUGGACAAGGCAGGAUUCAUCAAGAGACAG | |
| | CUGGUCGAAACAAGACAGAUCACAAAGCACGUCGCACAGAUCCUG | |
| | GACAGCAGAAUGAACACAAAGUACGACGAAAACGACAAGCUGAUC | |
| | AGAGAAGUCAAGGUCAUCACACUGAAGAGCAAGCUGGUCAGCGAC | |
| | UUCAGAAAGGACUUCCAGUUCUACAAGGUCAGAGAAAUCAACAAC | |
| | UACCACCACGCACACGACGCAUACCUGAACGCAGUCGUCGGAACAG | |
| | CACUGAUCAAGAAGUACCCGAAGCUGGAAAGCGAAUUCGUCUACG | |
| | GAGACUACAAGGUCUACGACGUCAGAAAGAUGAUCGCAAAGAGCG | |
| | AACAGGAAAUCGGAAAGGCAACAGCAAAGUACUUCUUCUACAGCA | |
| | ACAUCAUGAACUUCUUCAAGACAGAAAUCACACUGGCAAACGGAG | |
| | AAAUCAGAAAGAGACCGCUGAUCGAAACAAACGGAGAAACAGGAG | |
| | AAAUCGUCUGGGACAAGGGAAGAGACUUCGCAACAGUCAGAAAGG | |
| | UCCUGAGCAUGCCGCAGGUCAACAUCGUCAAGAAGACAGAAGUCC | |
| | AGACAGGAGGAUUCAGCAAGGAAAGCAUCCUGCCGAAGAGAAACA | |
| | GCGACAAGCUGAUCGCAAGAAAGAAGGACUGGGACCCGAAGAAGU | |
| | ACGGAGGAUUCGACAGCCCGACAGUCGCAUACAGCGUCCUGGUCG | |
| | UCGCAAAGGUCGAAAAGGGAAAGAGCAAGAAGCUGAAGAGCGUCA | |
| | AGGAACUGCUGGGAAUCACAAUCAUGGAAAAGAAGCAGCUUCGAAA | |
| | AGAACCCGAUCGACUUCCUGGAAGCAAAGGGAUACAAGGAAGUCA | |
| | AGAAGGACCUGAUCAUCAAGCUGCCGAAGUACAGCCUGUUCGAAC | |
| | UGGAAAACGGAAGAAAGAGAAUGCUGGCAAGCGCAGGAGAACUGC | |
| | AGAAGGGAAACGAACUGGCACUGCCGAGCAAGUACGUCAACUUCC | |
| | UGUACCUGGCAAGCCACUACGAAAAGCUGAAGGGAAGCCCGGAAG | |
| | ACAACGAACAGAAGCAGCUGUUCGUCGAACAGCACAAGCACUACC | |
| | UGGACGAAAUCAUCGAACAGAUCAGCGAAUUCAGCAAGAGAGUCA | |
| | UCCUGGCAGACGCAAACCUGGACAAGGUCCUGAGCGCAUACAACA | |
| | AGCACAGAGACAAGCCGAUCAGAGAACAGGCAGAAAACAUCAUCC | |
| | ACCUGUUCACACUGACAAACCUGGGAGCACCGGCAGCAUUCAAGU | |
| | ACUUCGACACAACAAUCGACAGAAAGAGAUACACAAGCACAAAGG | |
| | AAGUCCUGGACGCAACACUGAUCCACCAGAGCAUCACAGGACUGU | |
| | ACGAAACAAGAAUCGACCUGAGCCAGCUGGGAGGAGACGGAGGAG | |
| | GAAGCCCGAAGAAGAAGAGAAAGGUCUAGCUAGCCAUCACAUUUA | |
| | AAAGCAUCUCAGCCUACCAUGAGAAUAAGAGAAAGAAAAUGAAGA | |
| | UCAAUAGCUUAUUCAUCUCUUUUUCUUUUUCGUUGGUGUAAAGC | |

SEQUENCE TABLE

| Description | Sequence | SEQ ID No. |
|---|---|---|
| | CAACACCCUGUCUAAAAAACAUAAAUUUCUUUAAUCAUUUUGCC UCUUUUCUCUGUGCUUCAAUUAAUAAAAAAUGGAAAGAACCUCG AGAAAAAAAAAAAAAAAAAAAAAAAAAAAAAAAAAAAAAAAA AAAAAAAAAAAAAAUCUAG | |
| G000502 sgRNA targeting mouse TTR | mA*mC*mA*CAAAUACCAGUCCAGCGGUUUUAGAmGmCmUmAm GmAmAmAmUmAmGmCAAGUUAAAAUAAGGCUAGUCCGUUAUC AmAmCmUmUmGmAmAmAmAmAmGmUmGmCmAmCmCm GmAmGmUmCmGmGmUmGmCmU*mU*mU*mU | 4 |
| G000534 sgRNA targeting rat TTR | mA*mC*mG*CAAAUAUCAGUCCAGCGGUUUUAGAmGmCmUmAm GmAmAmAmUmAmGmCAAGUUAAAAUAAGGCUAGUCCGUUAUC AmAmCmUmUmGmAmAmAmAmAmGmUmGmCmAmCmCm GmAmGmUmCmGmGmUmGmCmU*mU*mU*mU | 5 |

2'-O-methyl modifications and phosphorothioate linkages as represented below (m = 2'-OMe; * = phosphorothioate).

---

What is claimed is:

1. A compound of Formula IA;

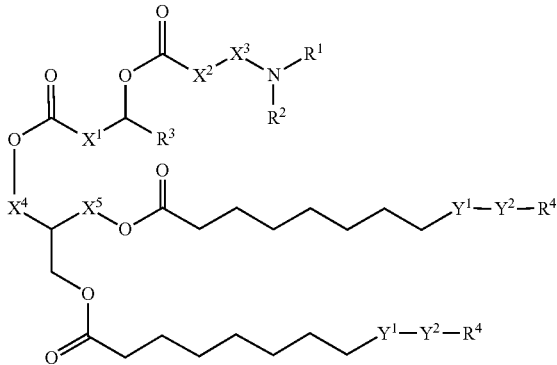

(IA)

wherein, independently for each occurrence, $X_1$ is $C_{1-3}$ alkylene or

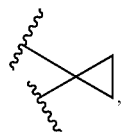

$X_2$ is selected from O, NH, NMe, and a bond, provided that when $X_2$ is O, $R^2$ taken together with the nitrogen atom and either $R^1$ or a carbon atom of $X_3$ form a 4-membered, 5-membered, or 6-membered ring;

$X_3$ is $C_{2-4}$ alkylene, $X_4$ is $C_1$ alkylene or a bond, $X_5$ is $C_1$ alkylene or a bond, $R^1$ is $C_{1-3}$ alkyl, $R^2$ is $C_{1-3}$ alkyl, or $R^2$ taken together with the nitrogen atom and either $R^1$ or a carbon atom of $X_3$ form a 4-membered, 5-membered, or 6-membered ring, $Y_1$ is selected from a bond, —CH=CH—, —(C=O)O—, and —O(C=O)—, $Y_2$ is selected from —CH$_2$—CH=CH— and $C_3$-$C_4$ alkylene, $R^3$ is selected from H, $C_{5-7}$ cycloalkyl, $C_8$-$C_{10}$ alkenyl, and $C_{3-18}$ alkyl, and $R^4$ is $C_{4-8}$ alkyl, or a salt thereof.

2. The compound of claim 1, wherein $X_1$ is $C_2$ alkylene or $C_1$ alkylene.

3. The compound of claim 1, wherein $X_2$ is NH.

4. The compound of claim 1, wherein $X_2$ is O, and $R^2$ taken together with the nitrogen atom and either $R^1$ or a carbon atom of $X_3$ form a 4-membered, 5-membered, or 6-membered ring.

5. The compound of claim 1, wherein $X_3$ is $C_{2-3}$ alkylene.

6. The compound of claim 1, wherein $R^2$ and a carbon atom of $X_3$ taken together form a 4- to 6-membered ring.

7. The compound of claim 1, wherein $R^1$ and $R^2$ together form a 4- to 6-membered ring.

8. The compound of claim 1, wherein $R^3$ is linear $C_{8-16}$ alkyl or branched $C_{6-10}$ alkyl.

9. The compound of claim 1, wherein $R^4$ is linear $C_{5-6}$ alkyl.

10. The compound of claim 1, wherein $X^4$ is a bond.

11. The compound of claim 1, wherein $X^5$ is a $C_1$ alkylene.

12. The compound of claim 1, wherein $Y_2$—$R^4$ is —CH$_2$—CH=CH—$R^4$.

13. The compound of claim 1, wherein the compound is a compound of Formula II:

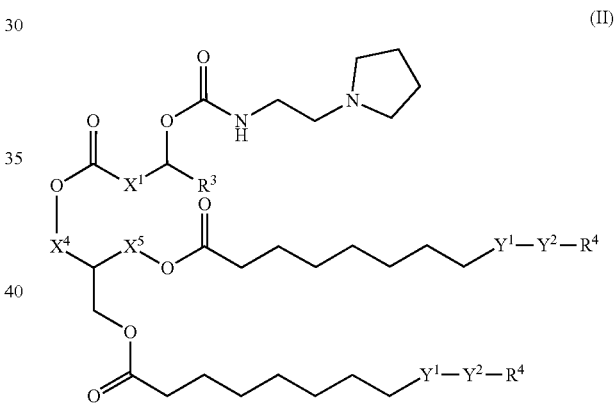

(II)

or the compound is a compound of Formula III:

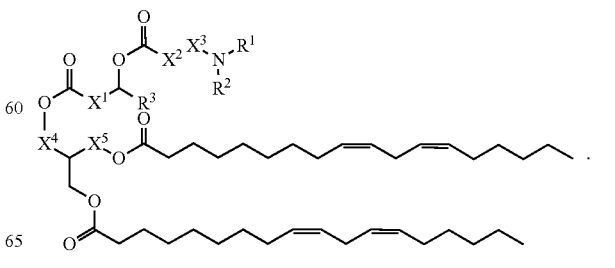

(III)

14. The compound of claim 1, wherein the compound is selected from:
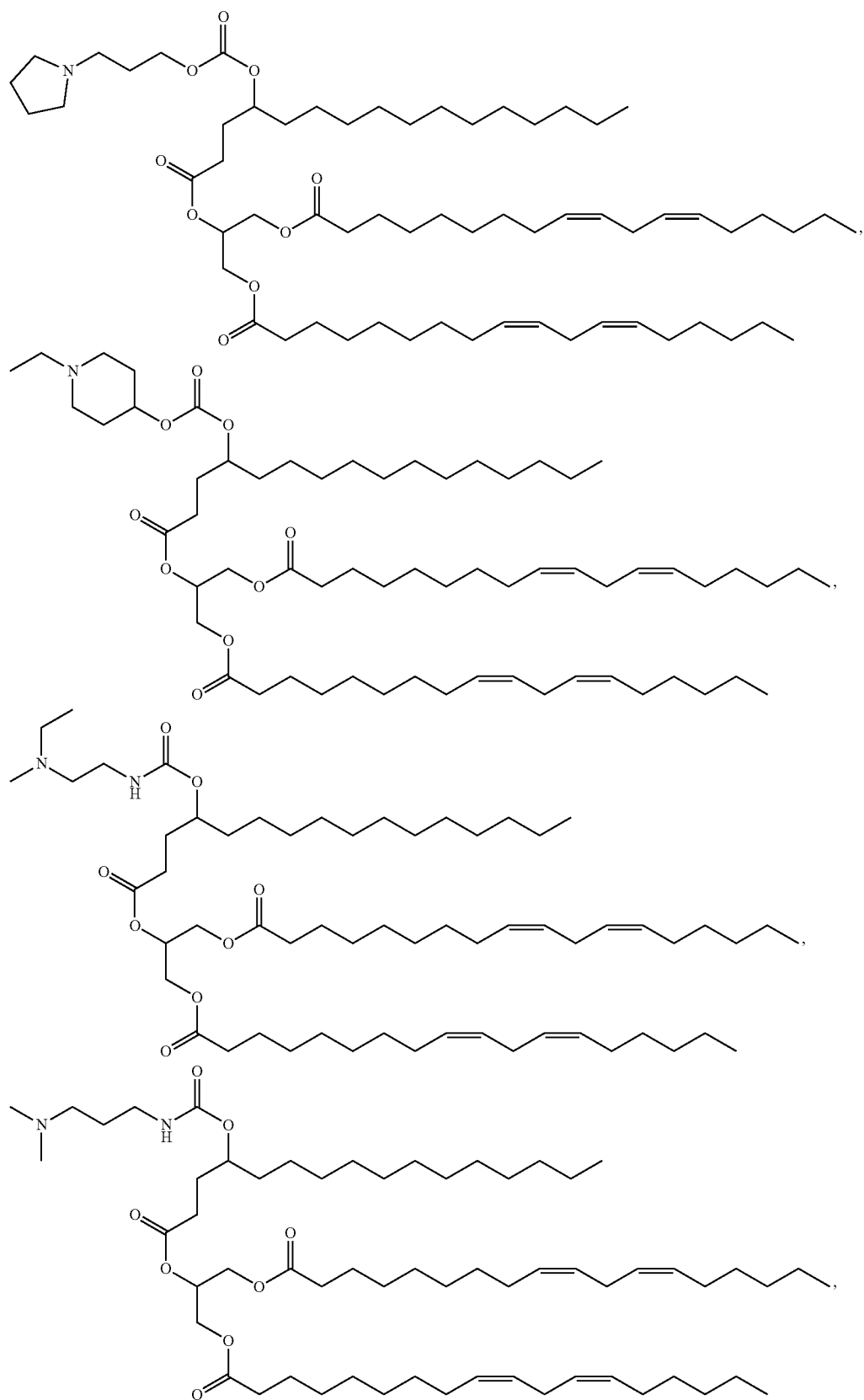

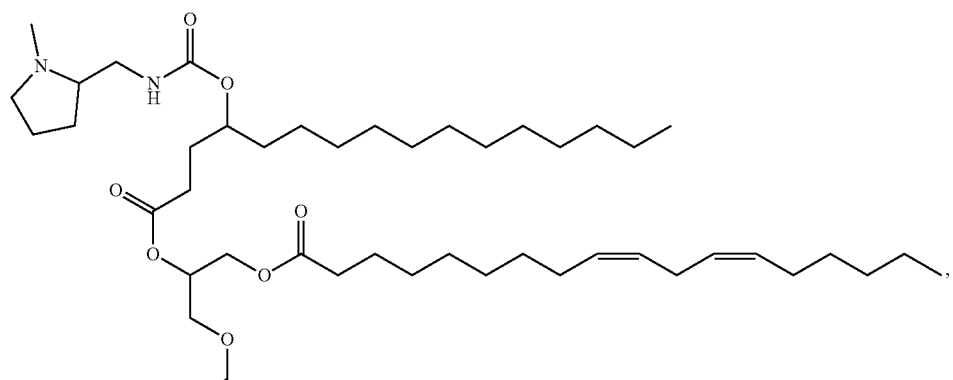
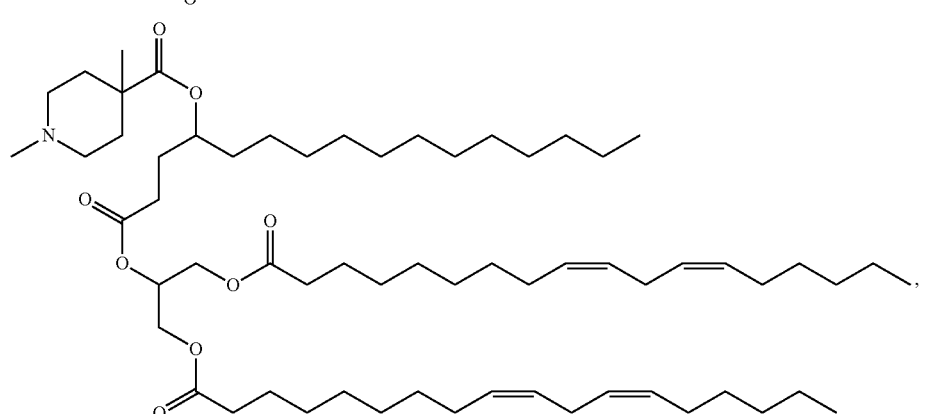
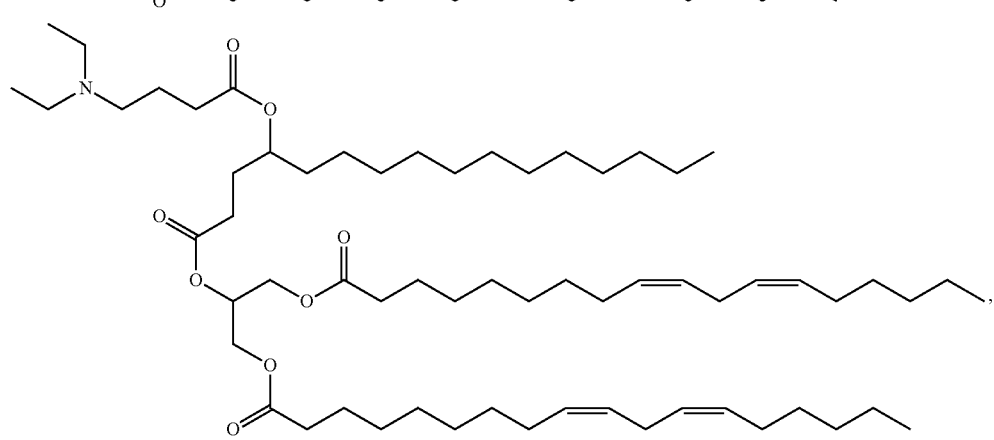
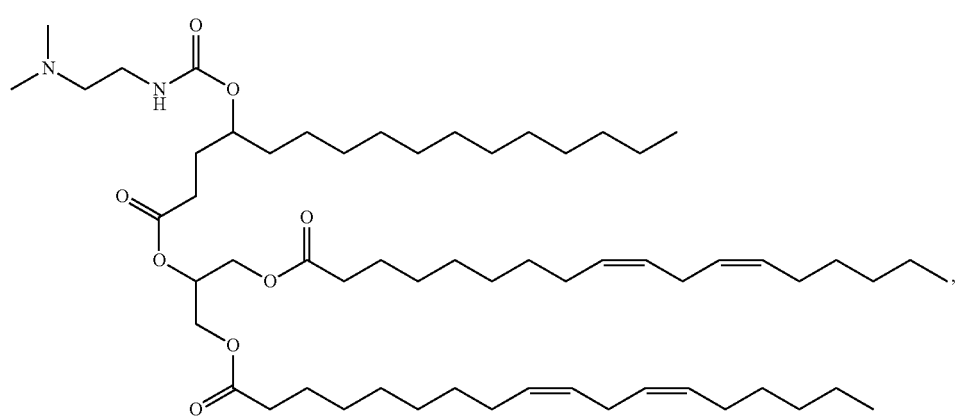

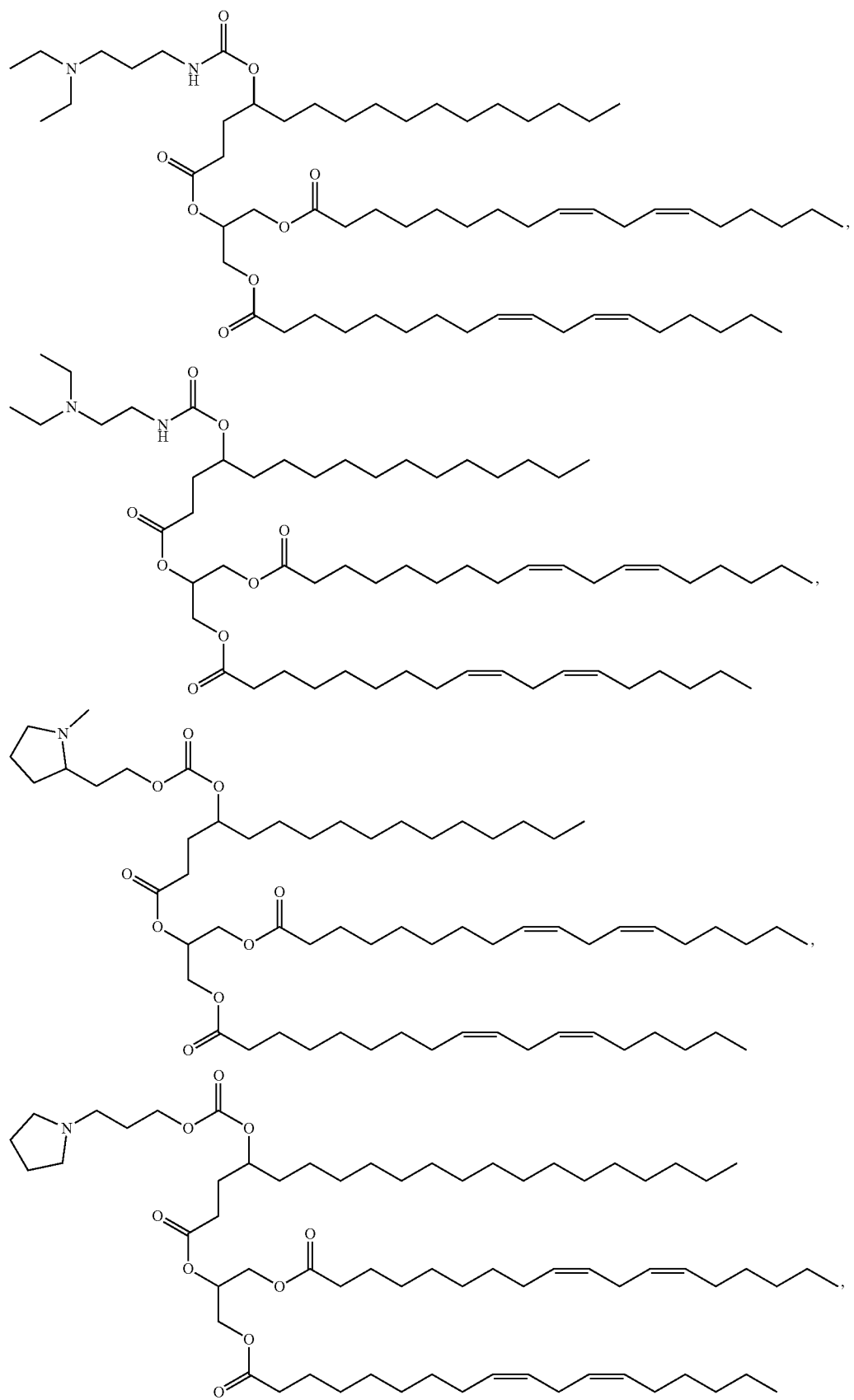

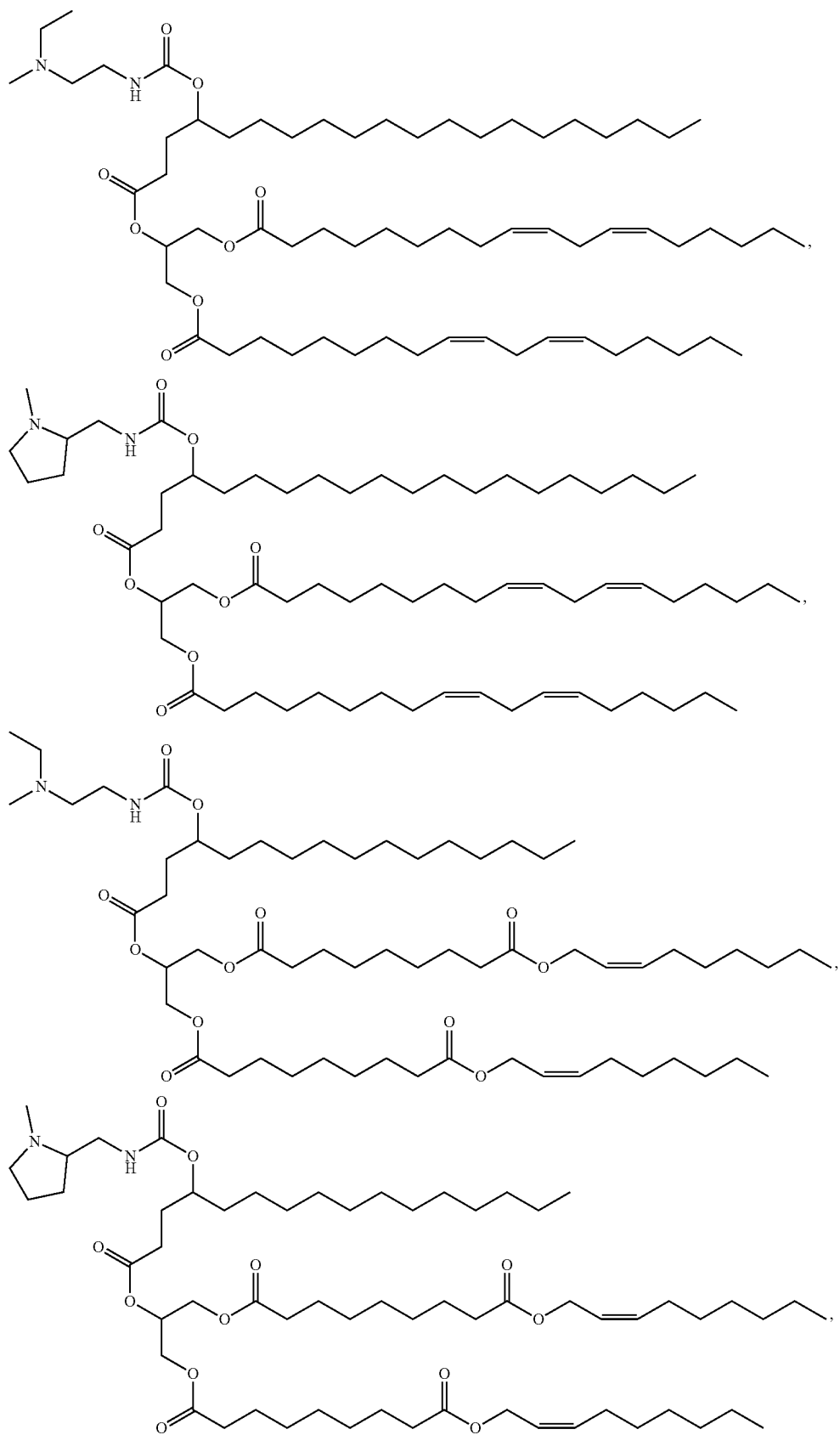

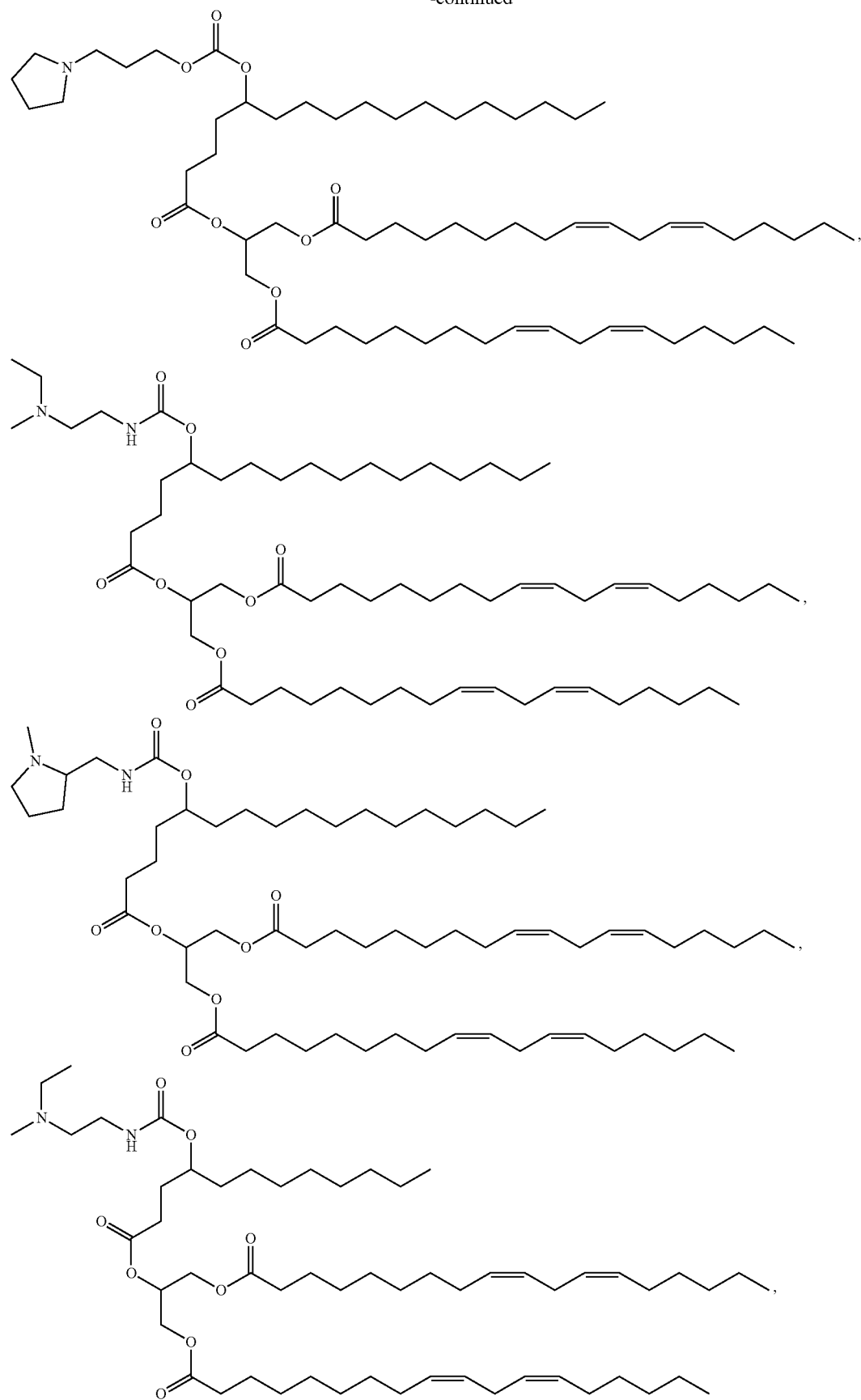

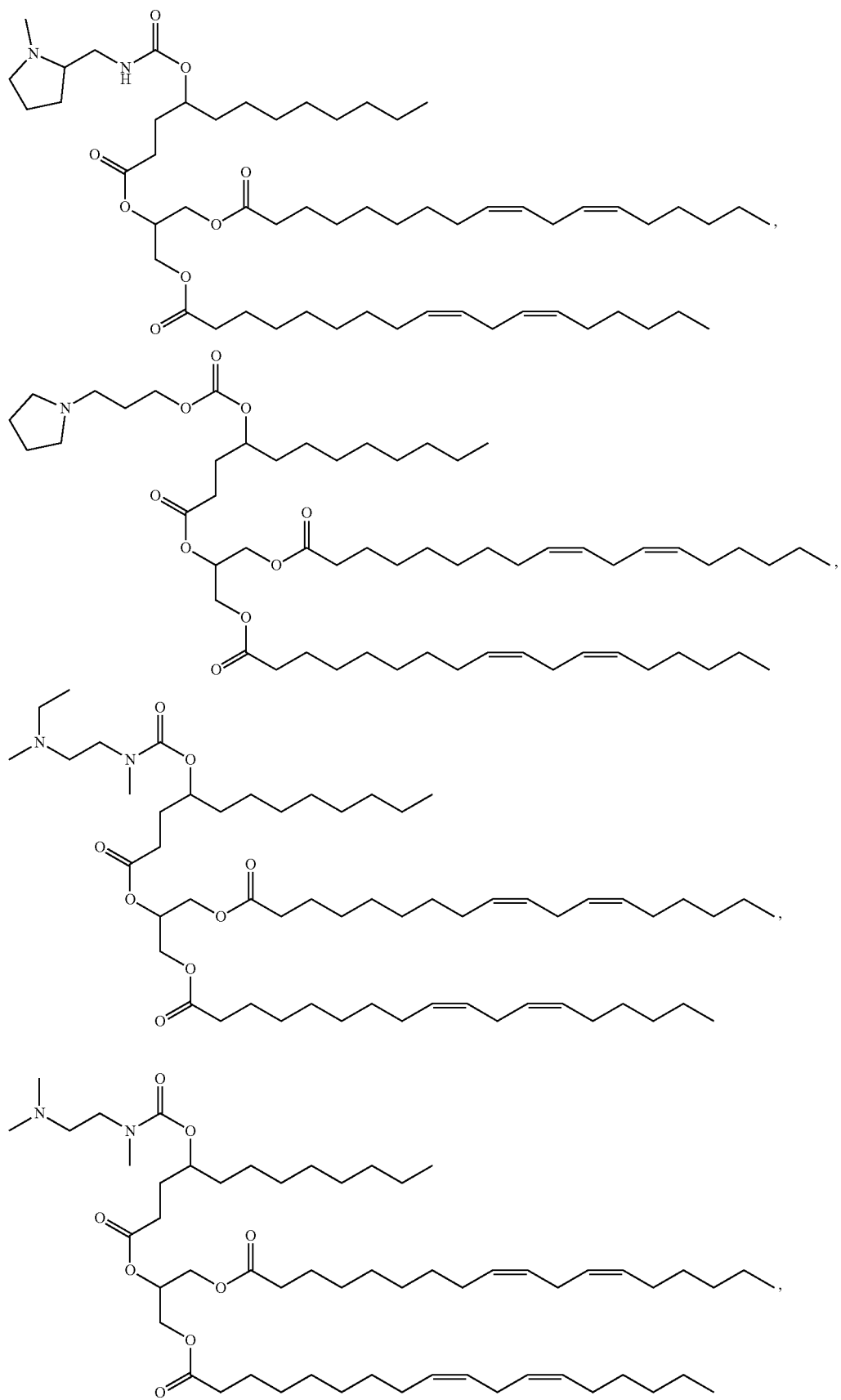

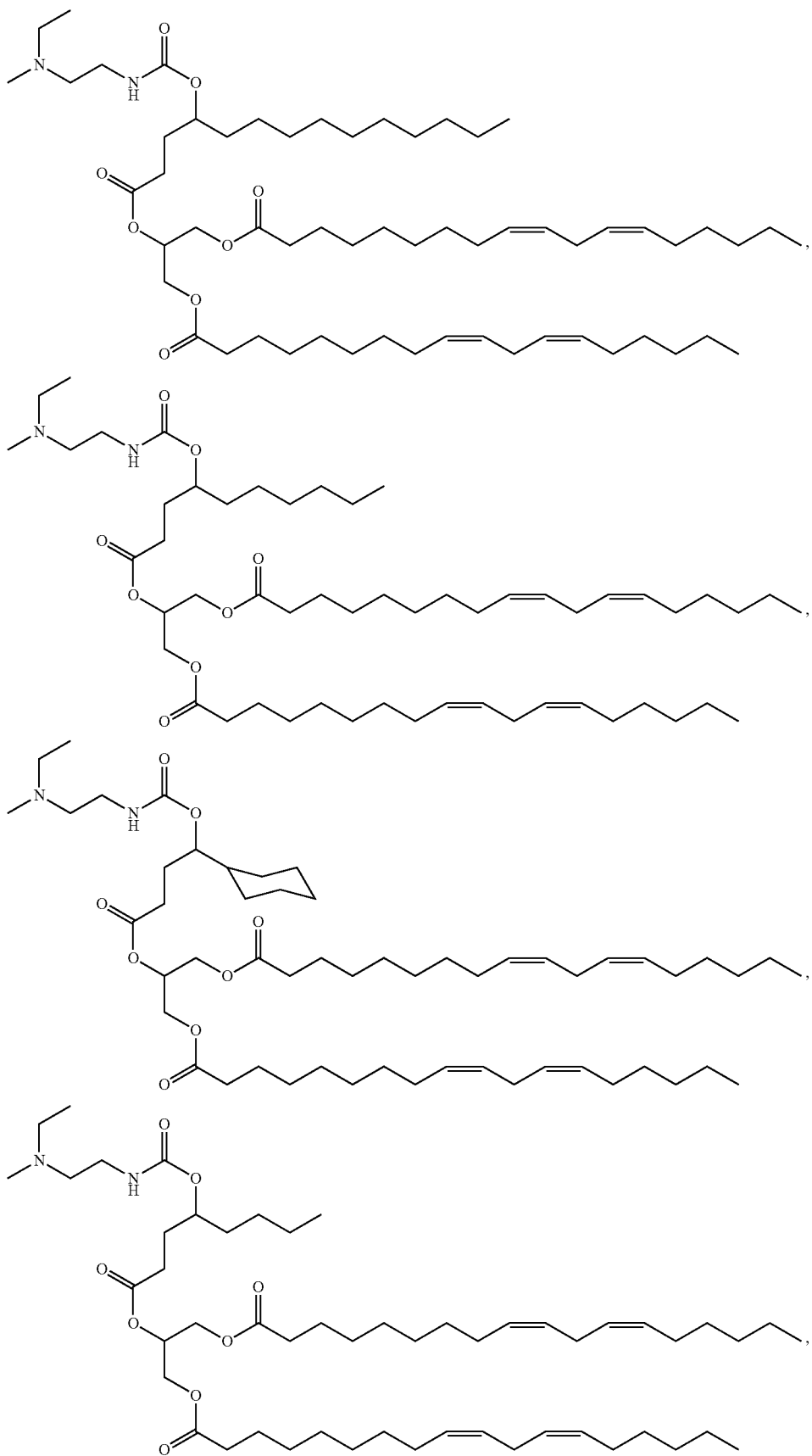

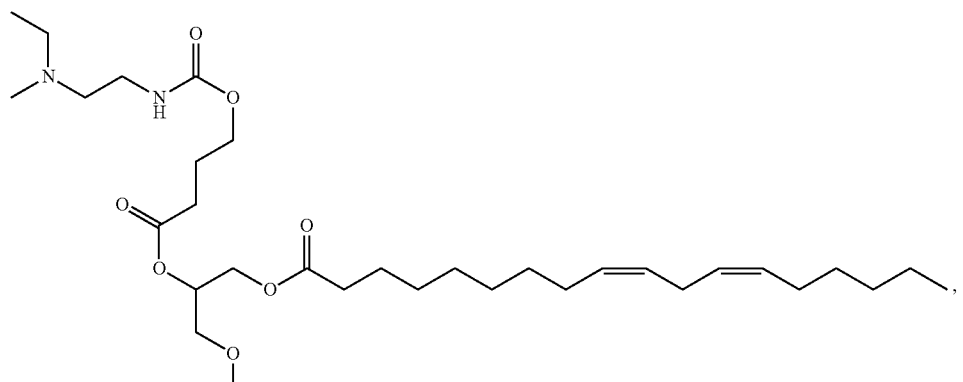
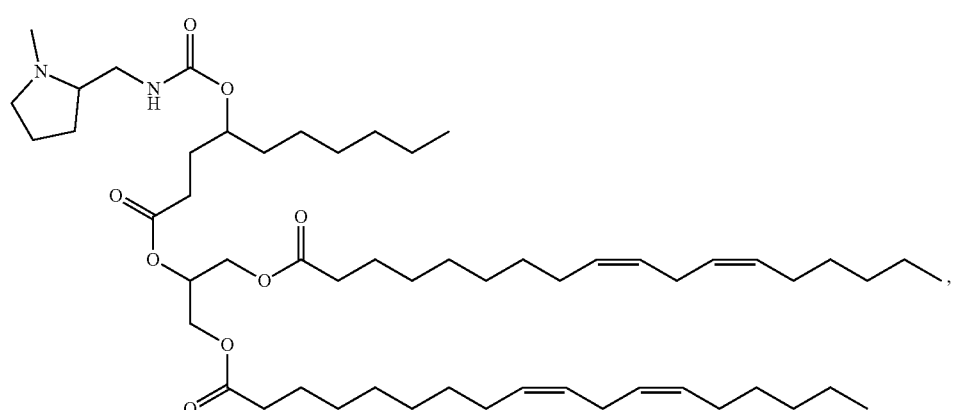
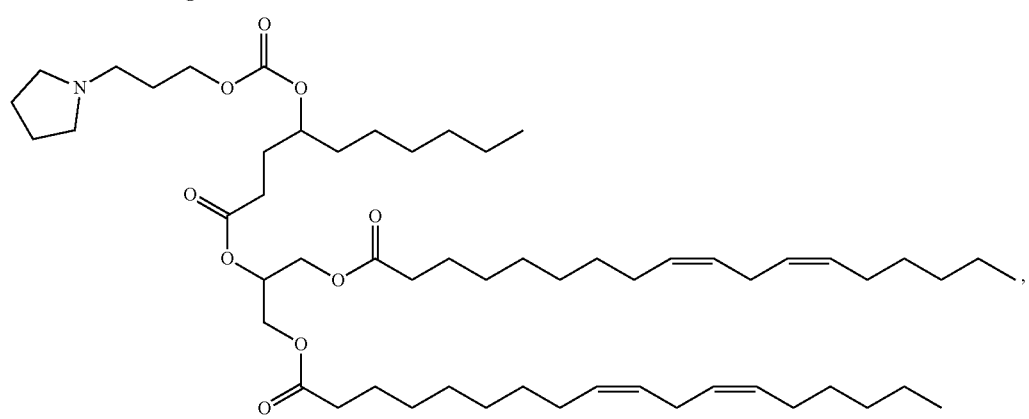
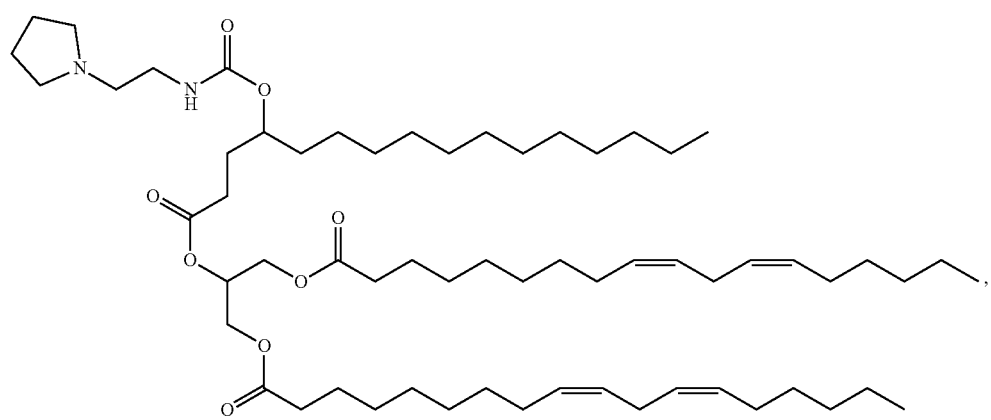

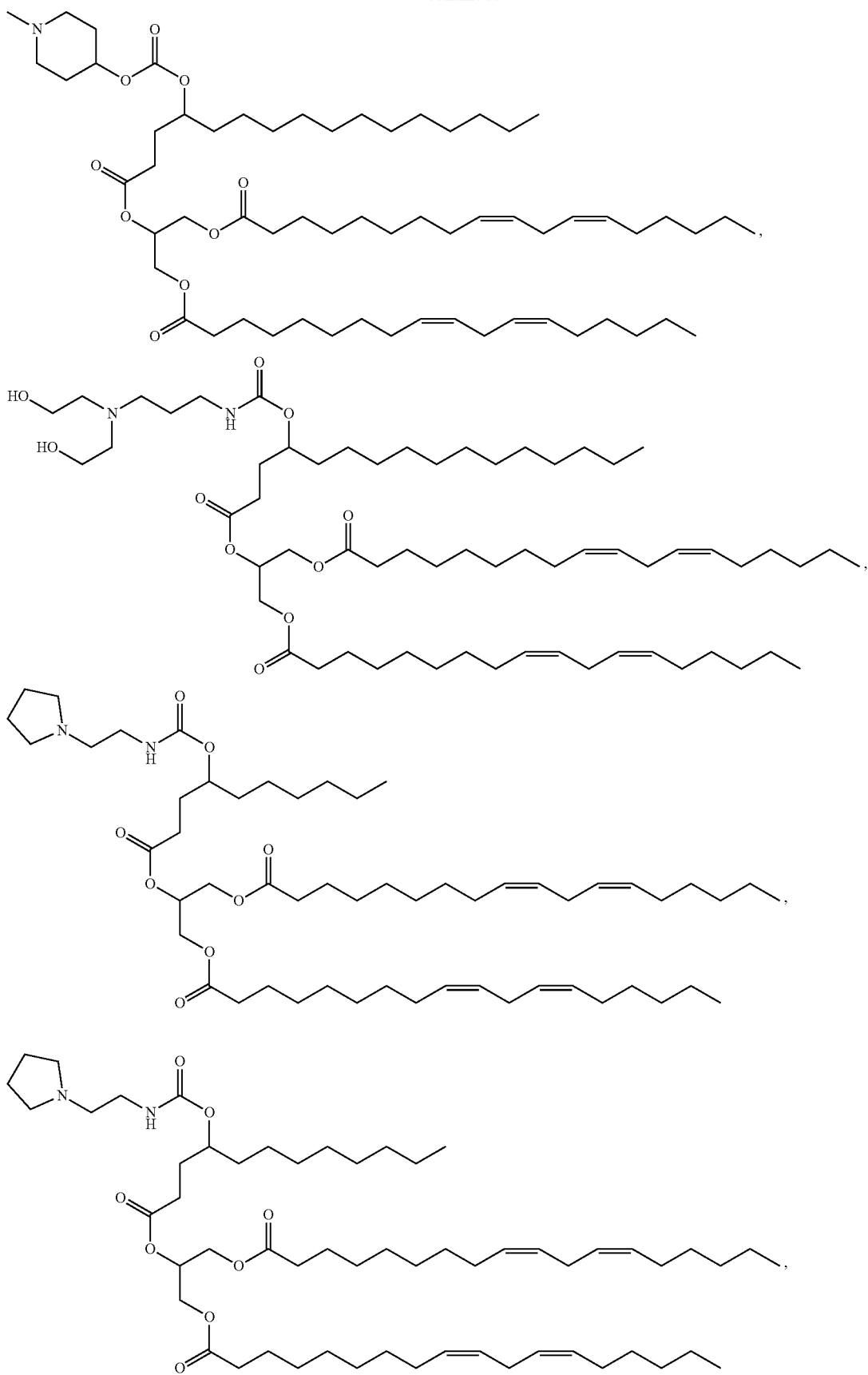

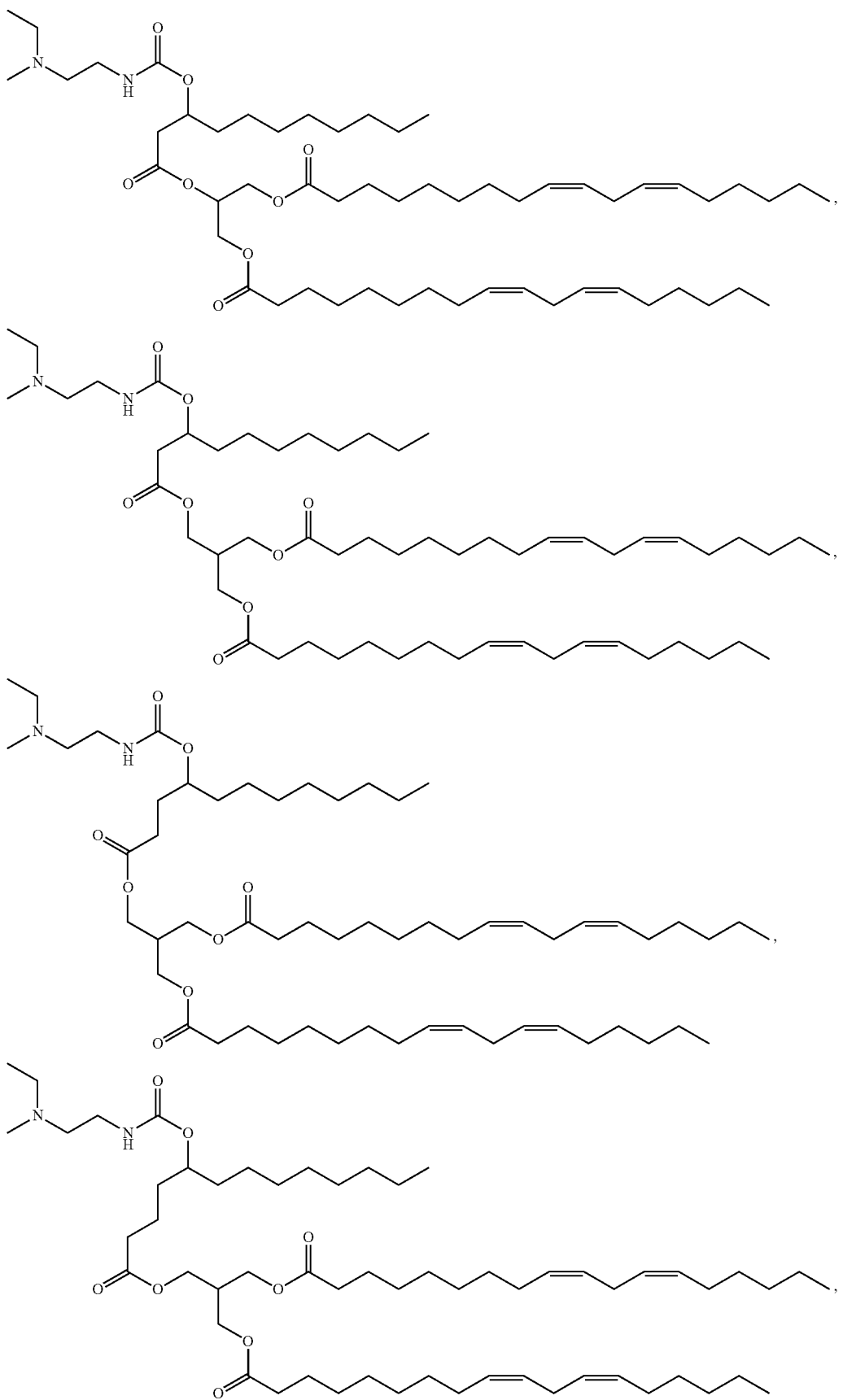

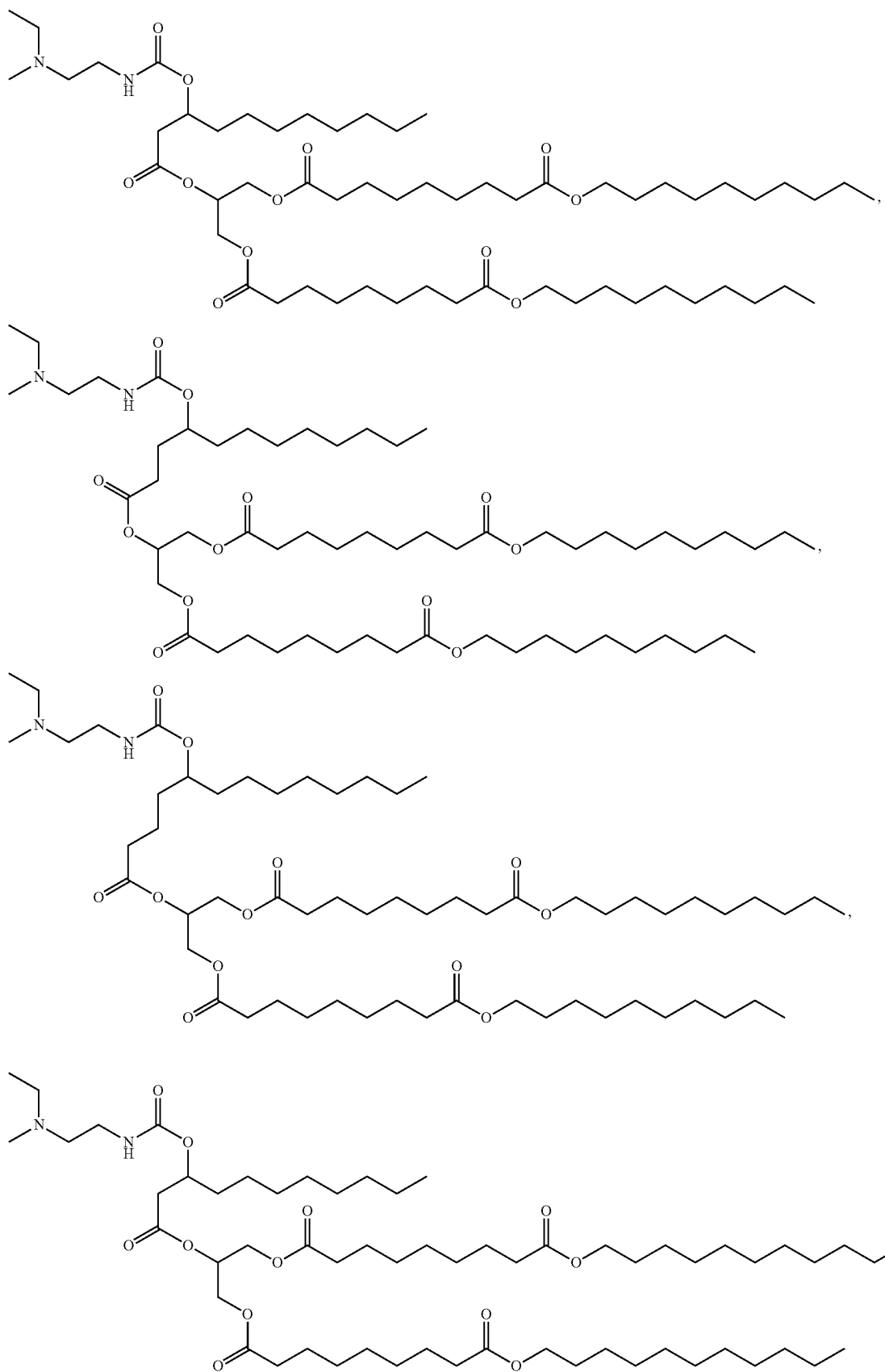

-continued
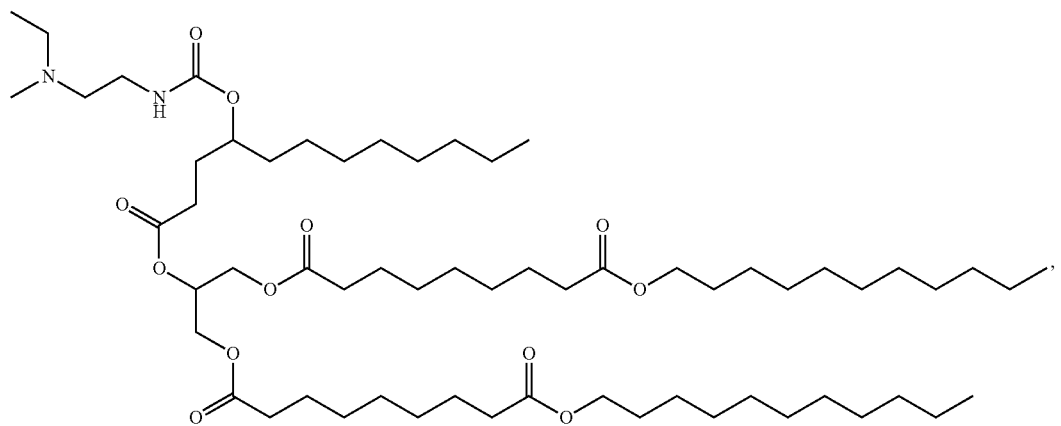
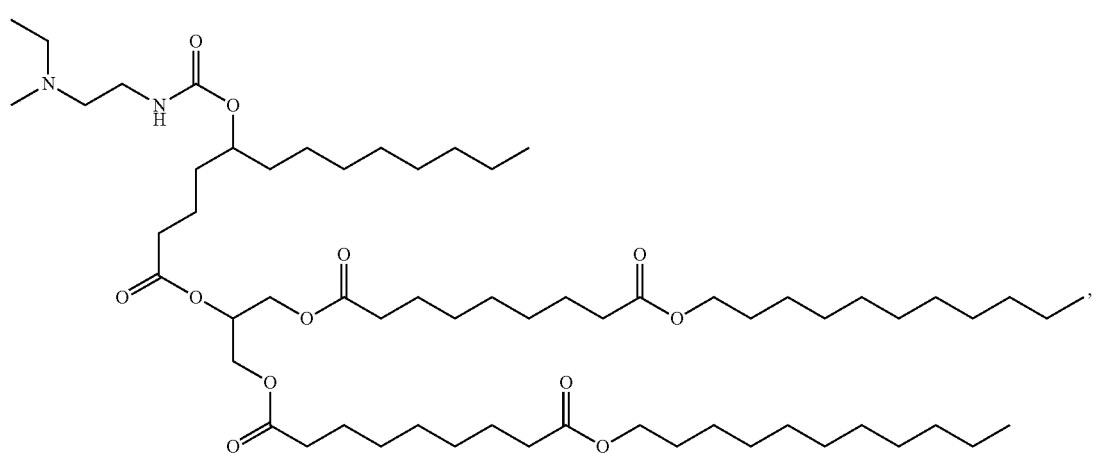
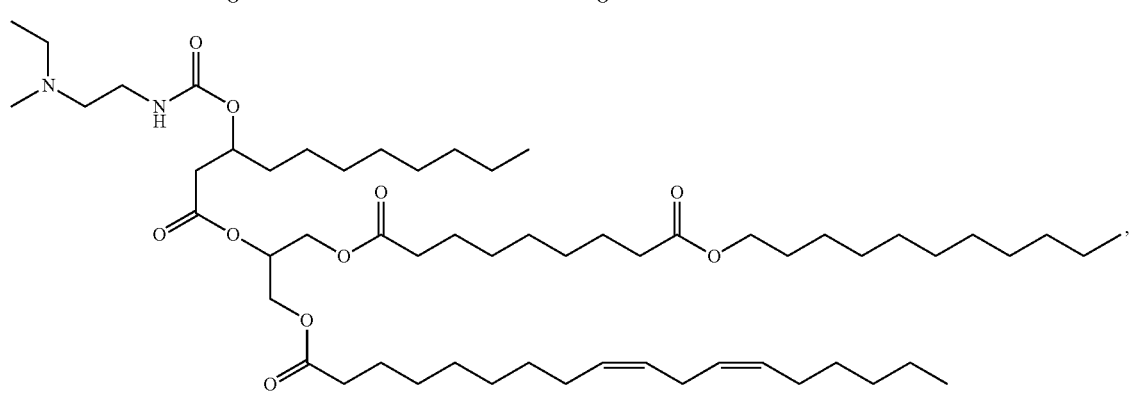
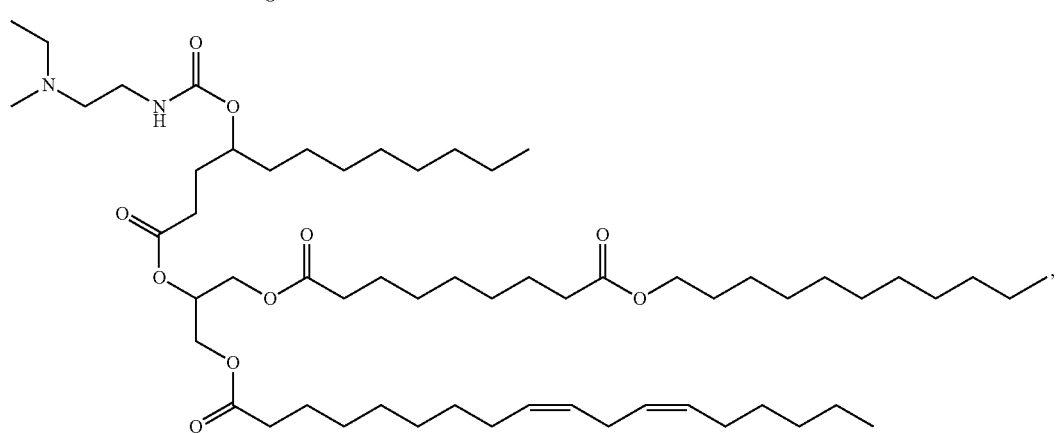

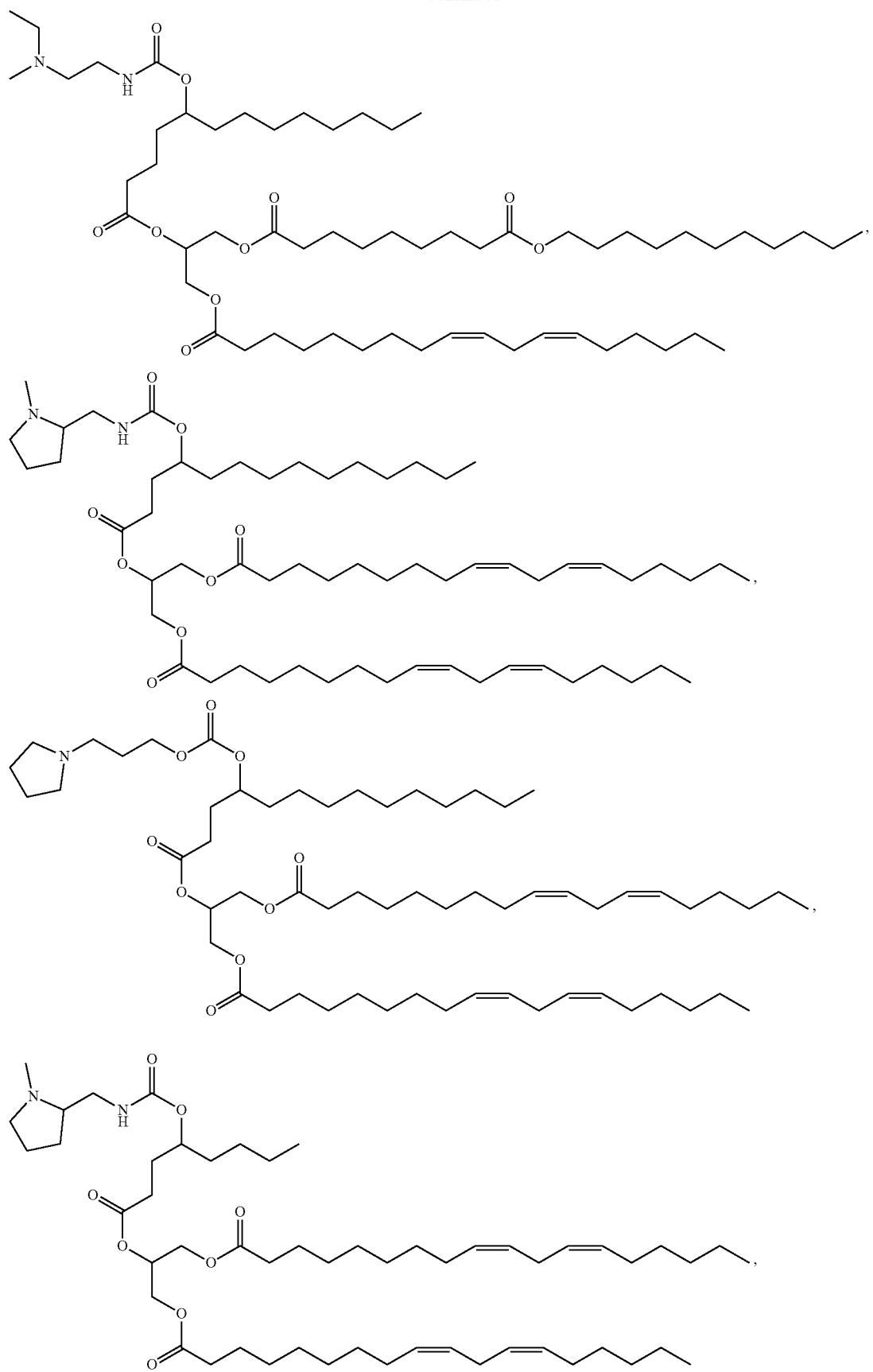

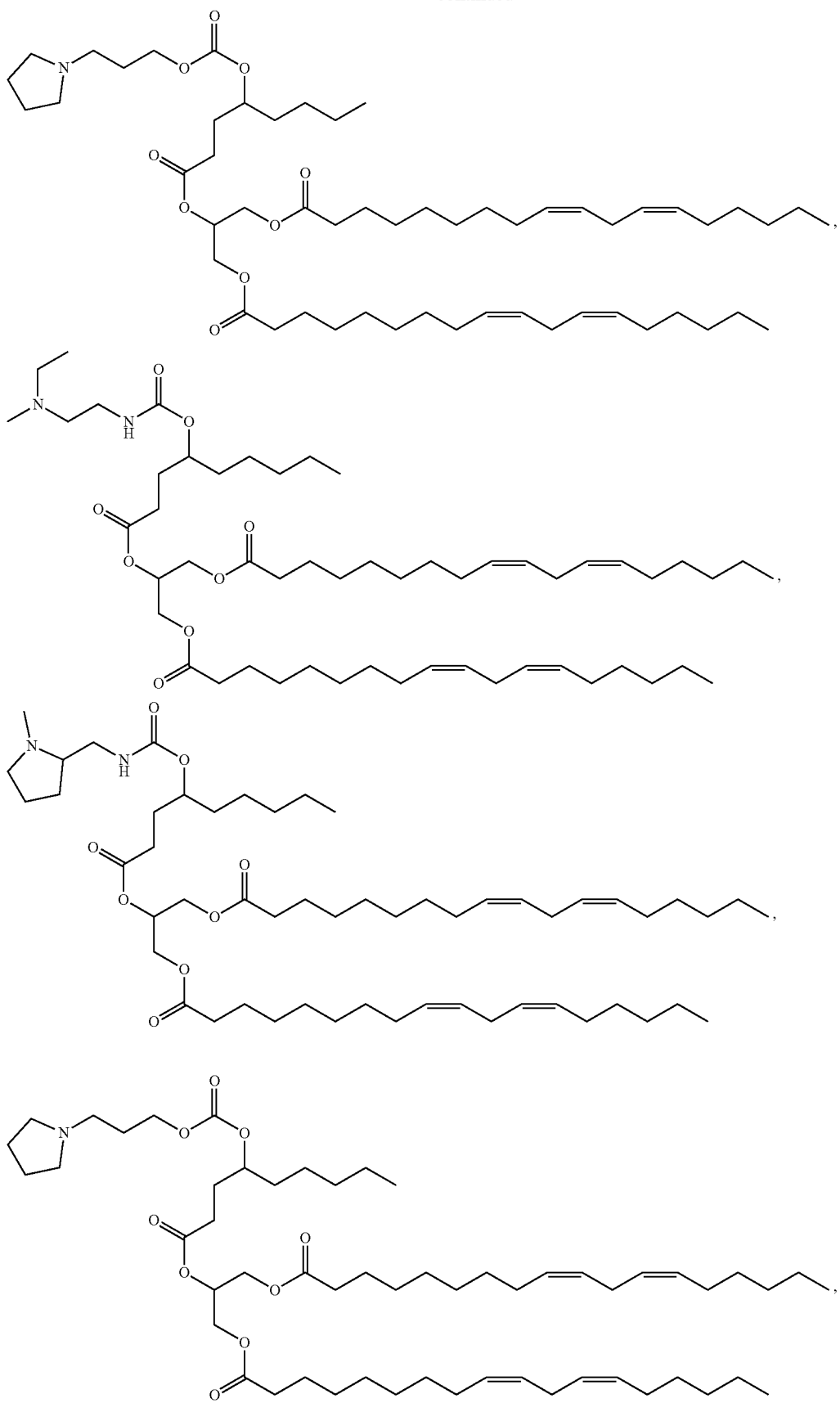

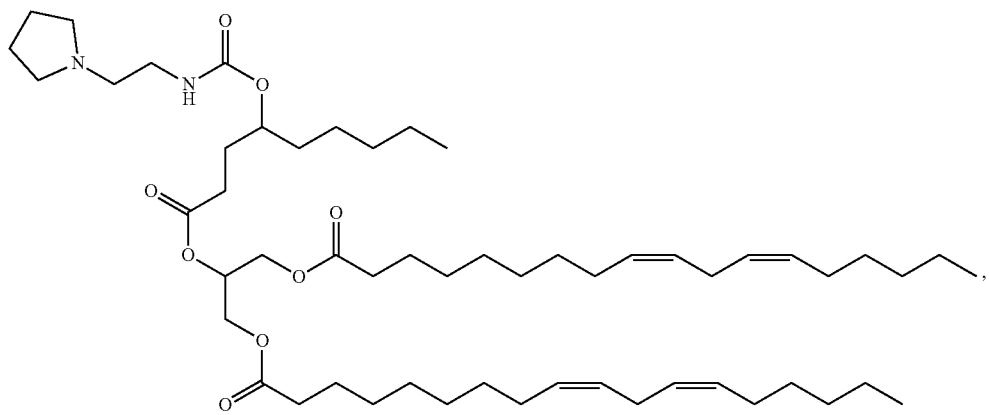
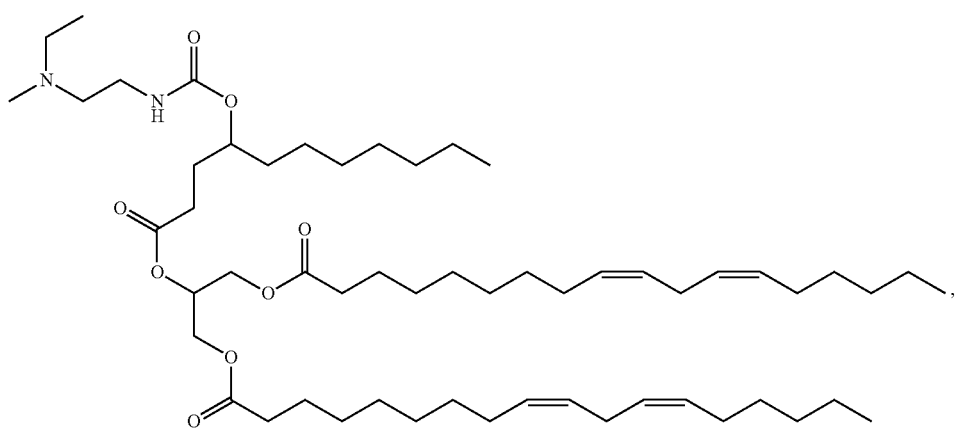
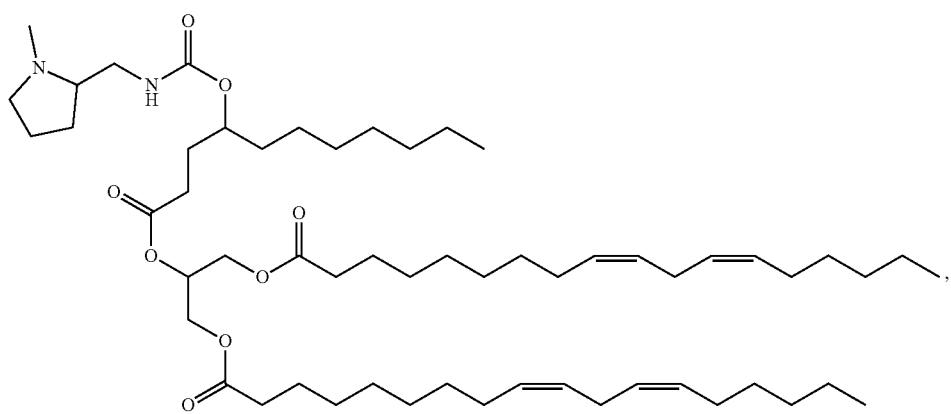
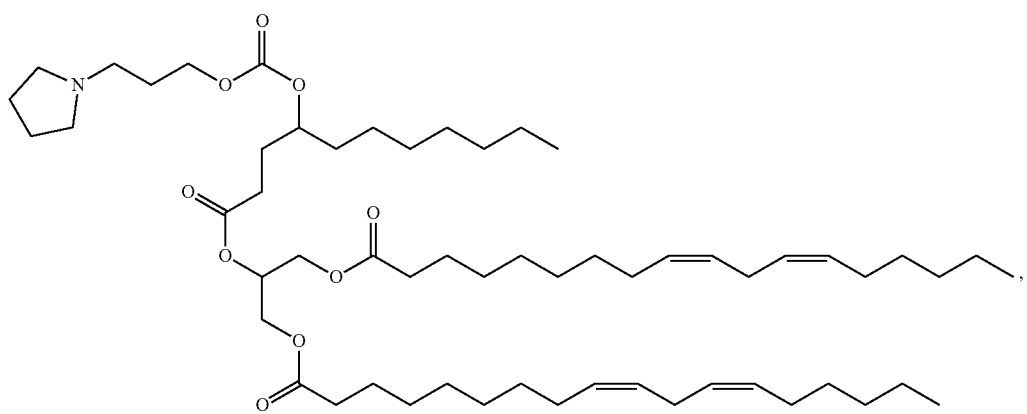

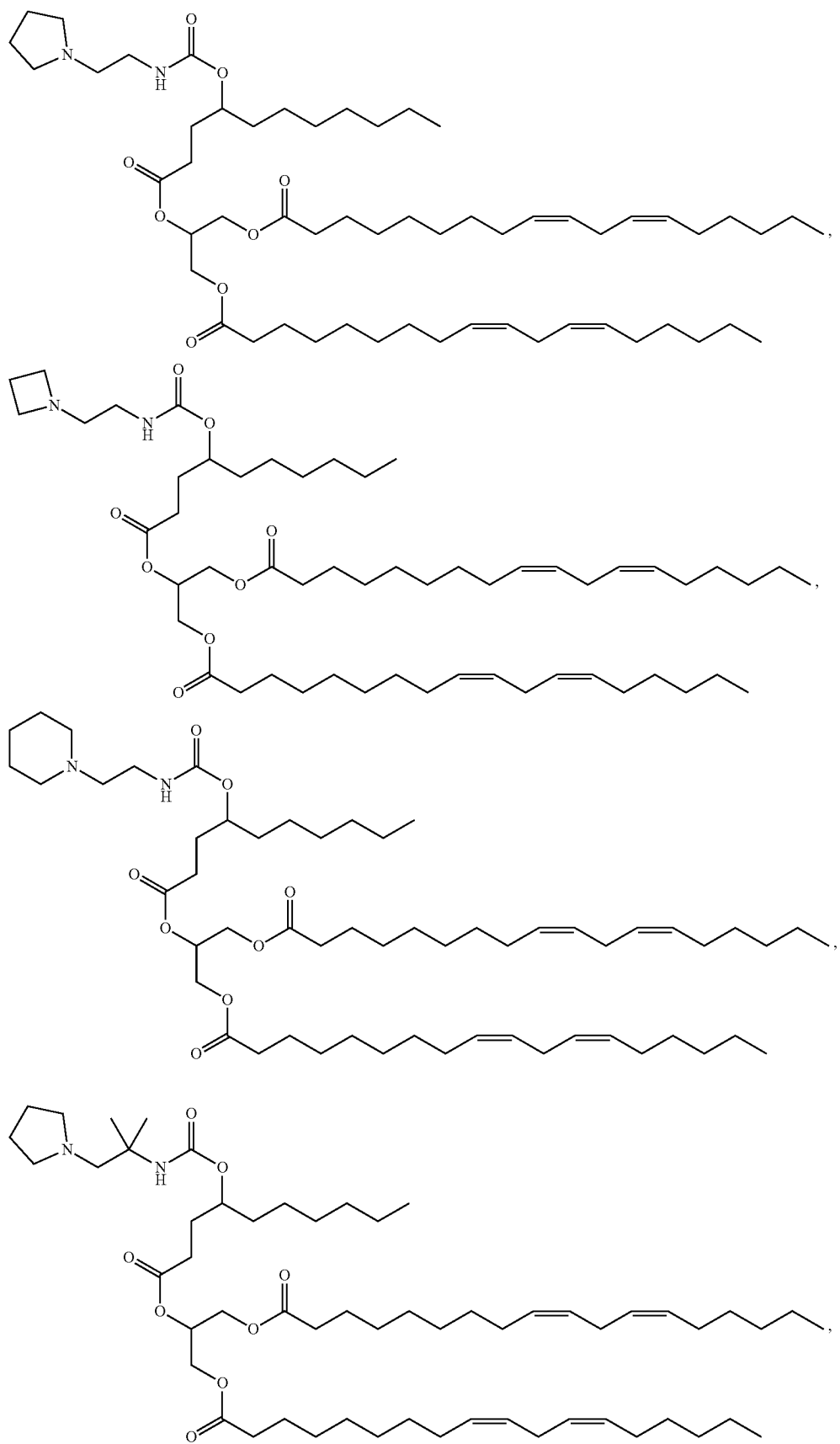

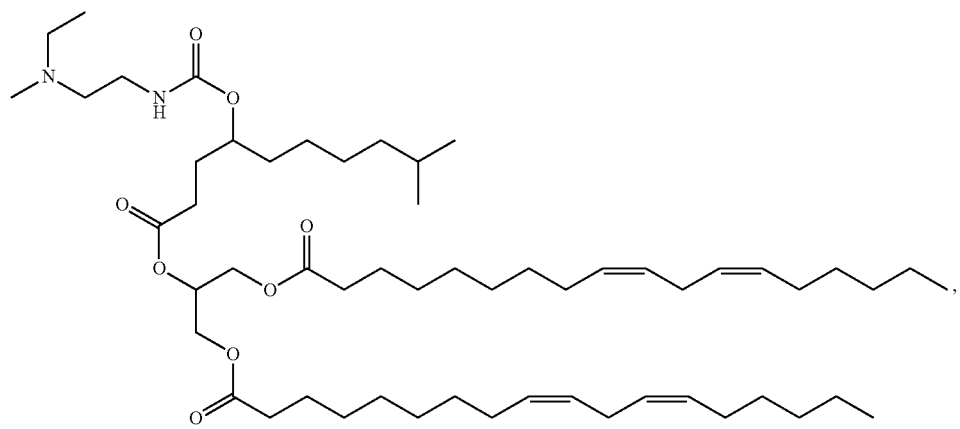

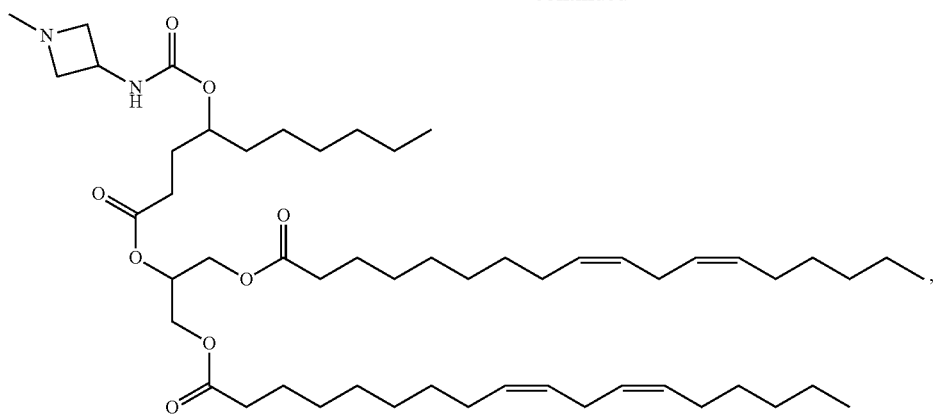,
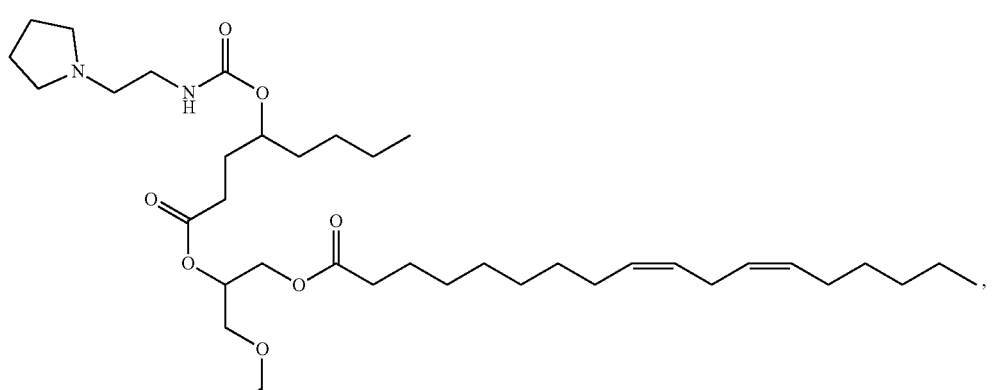,
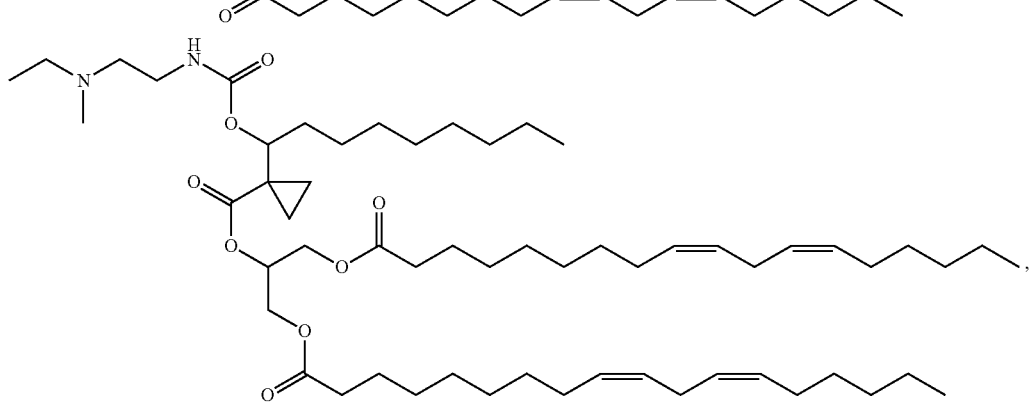,
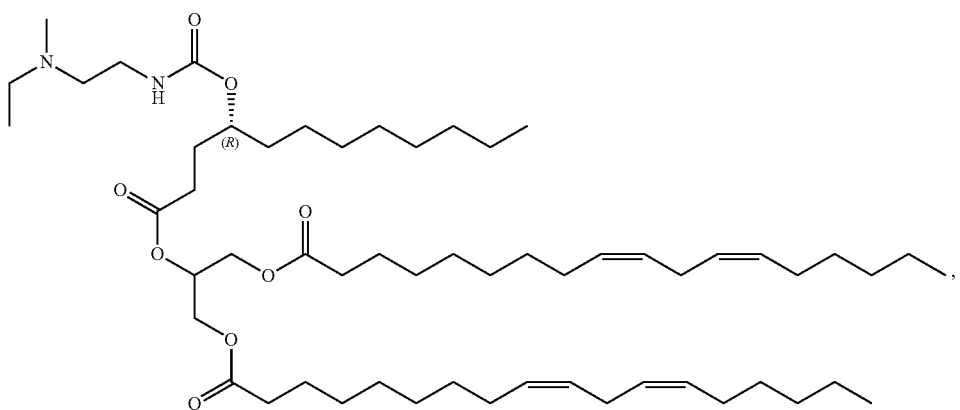,

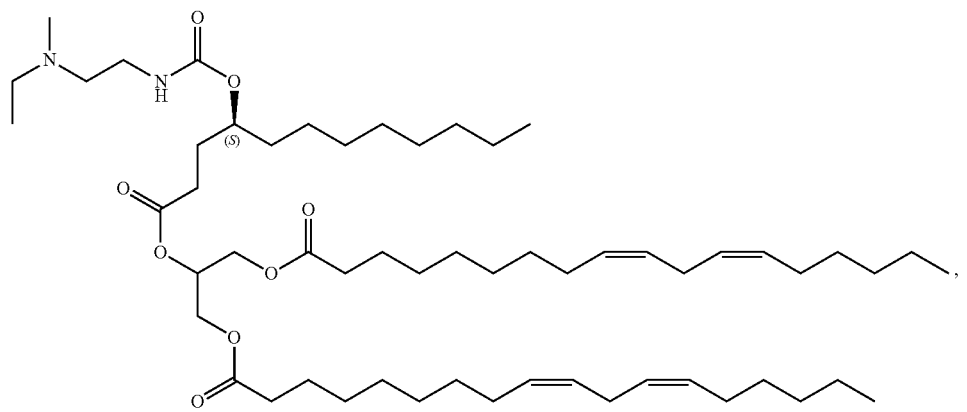
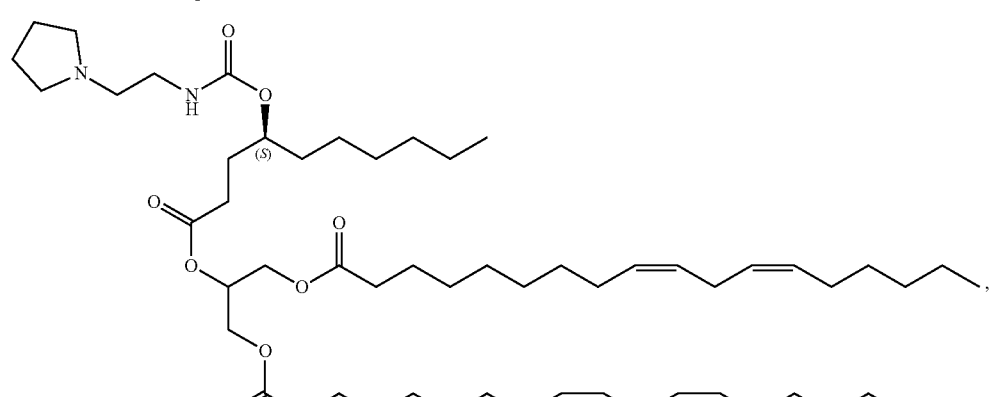
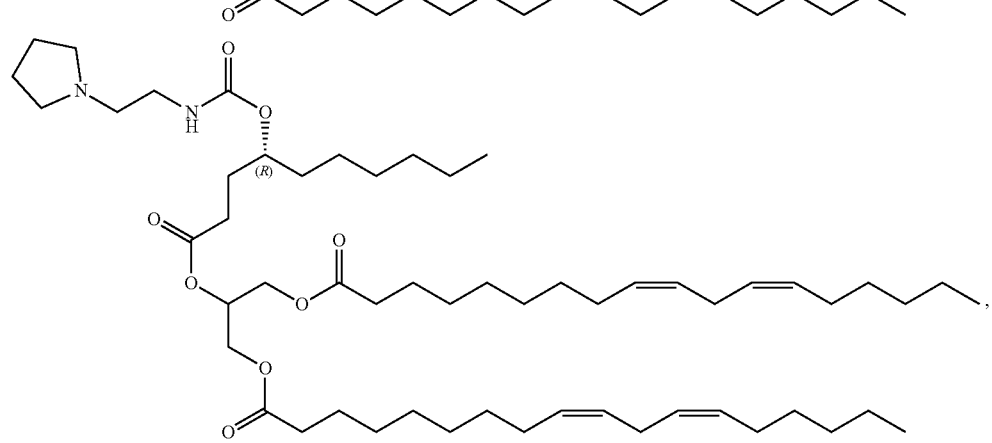
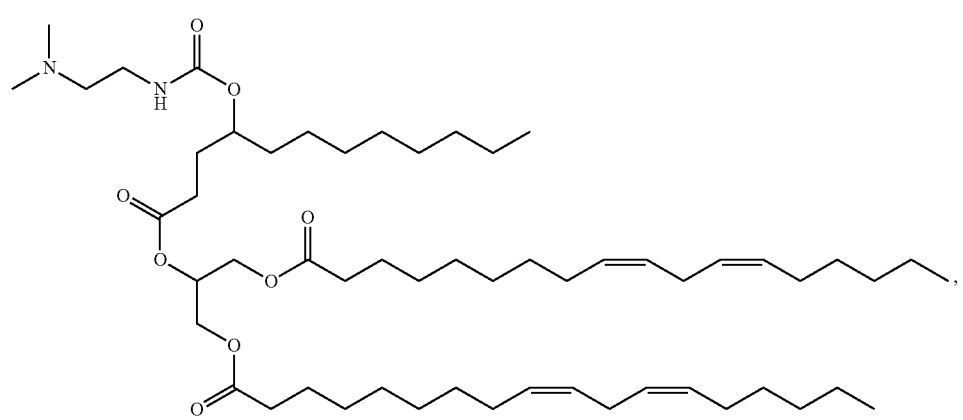

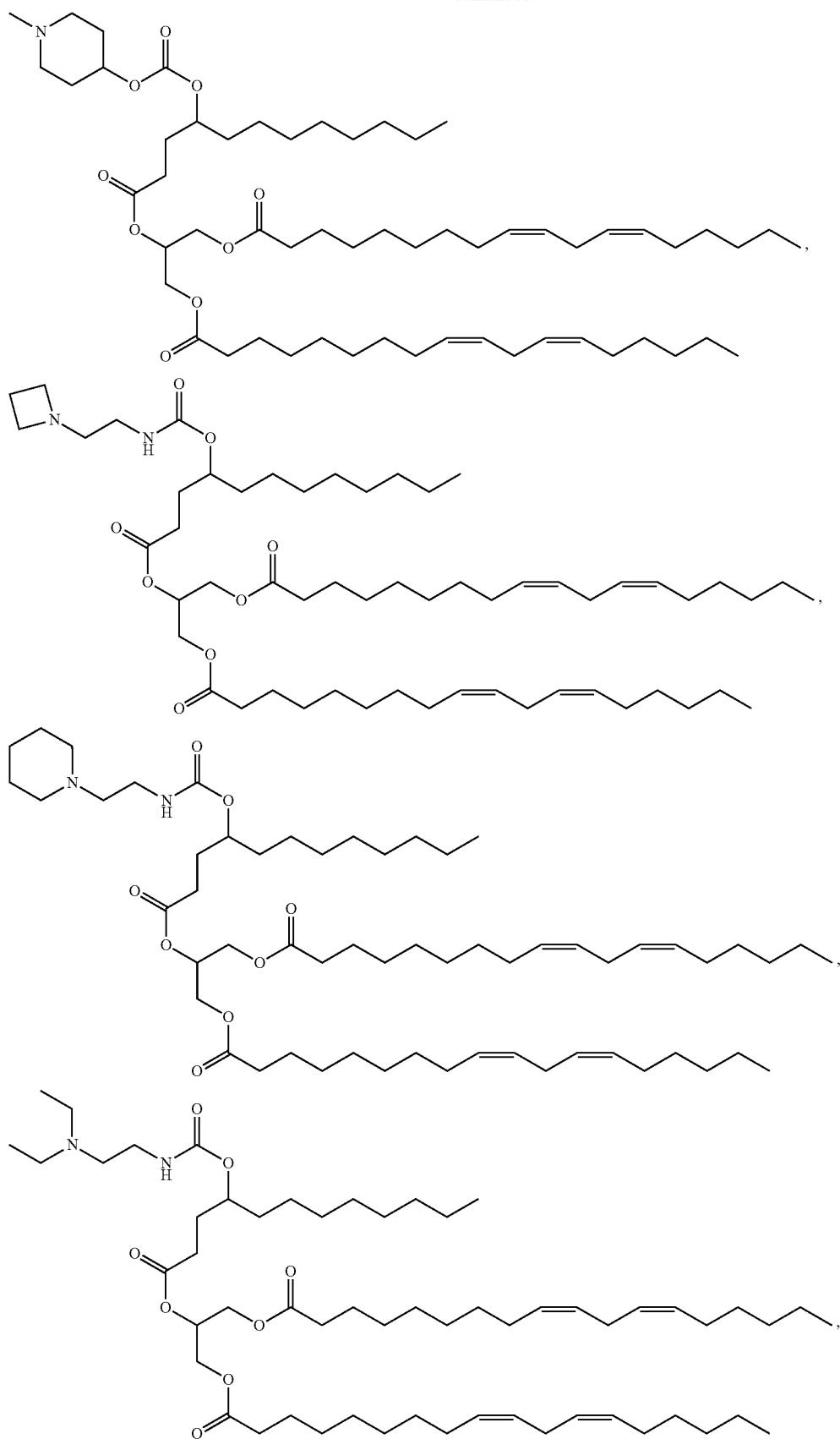

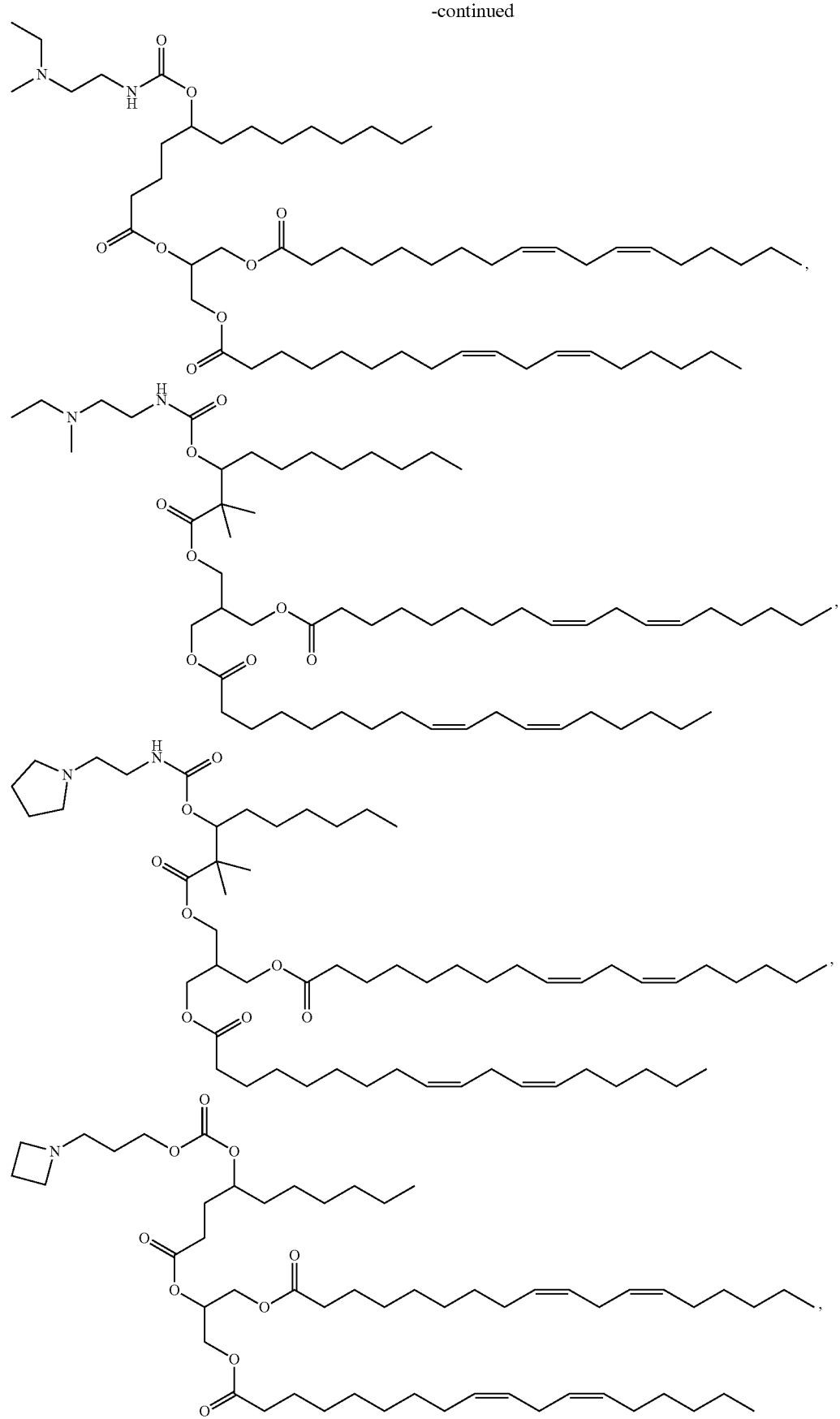

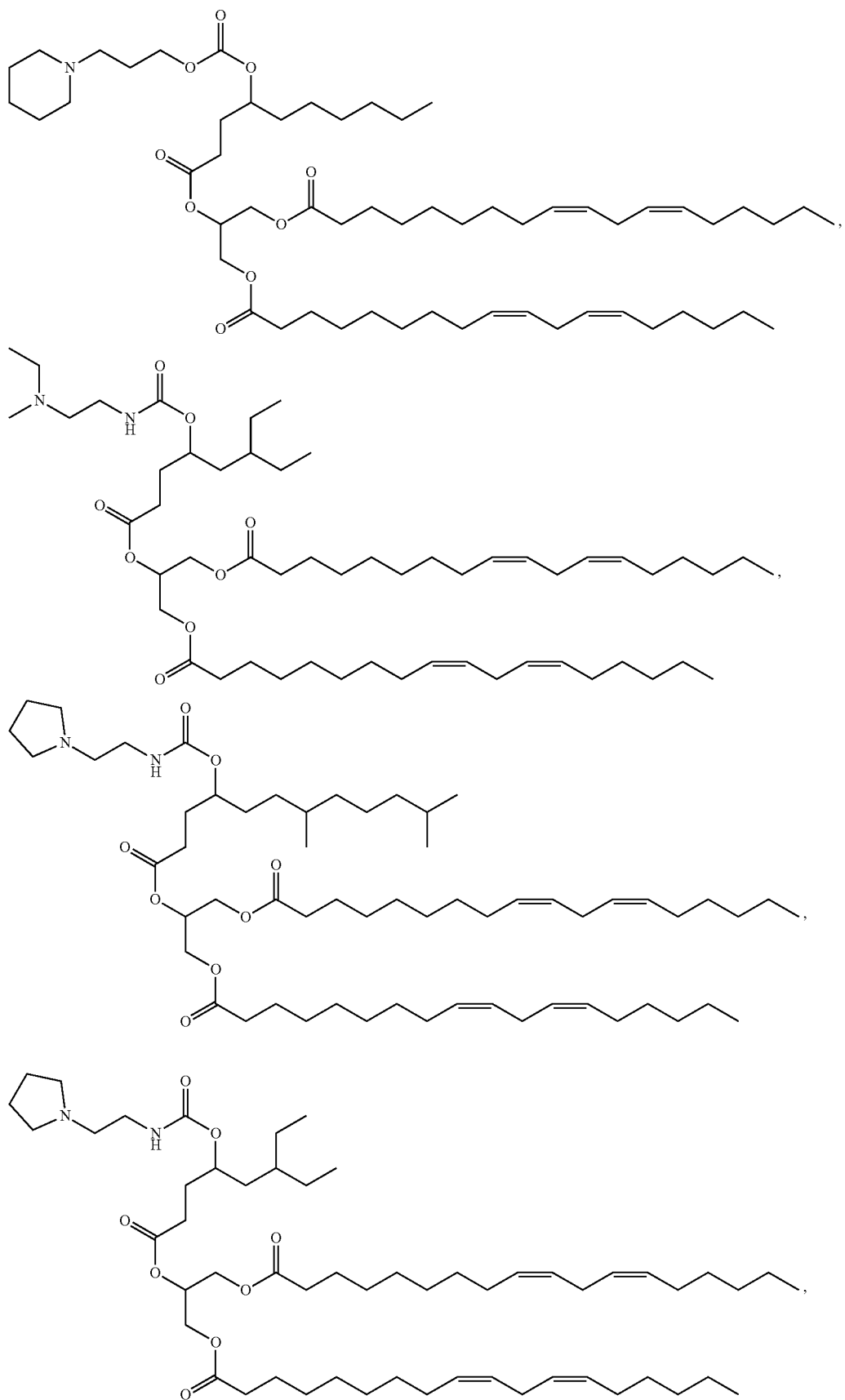

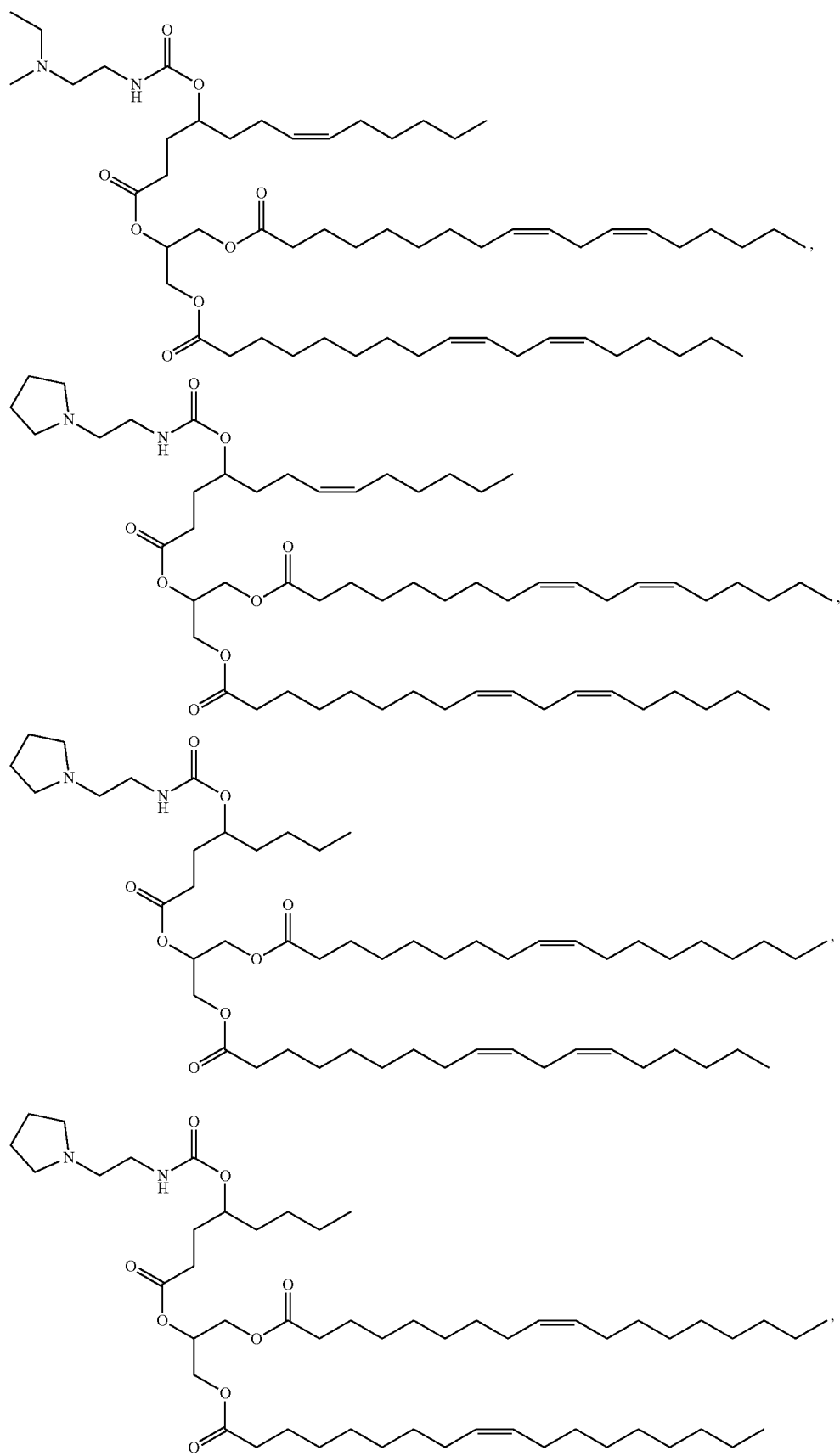

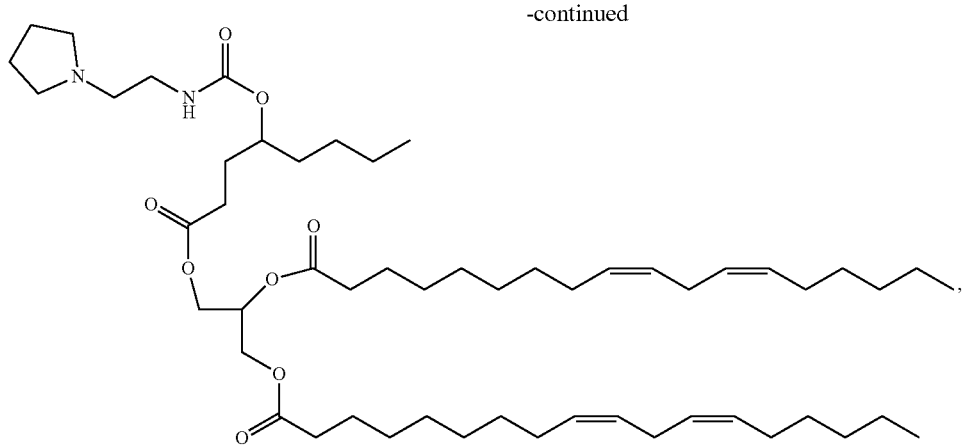

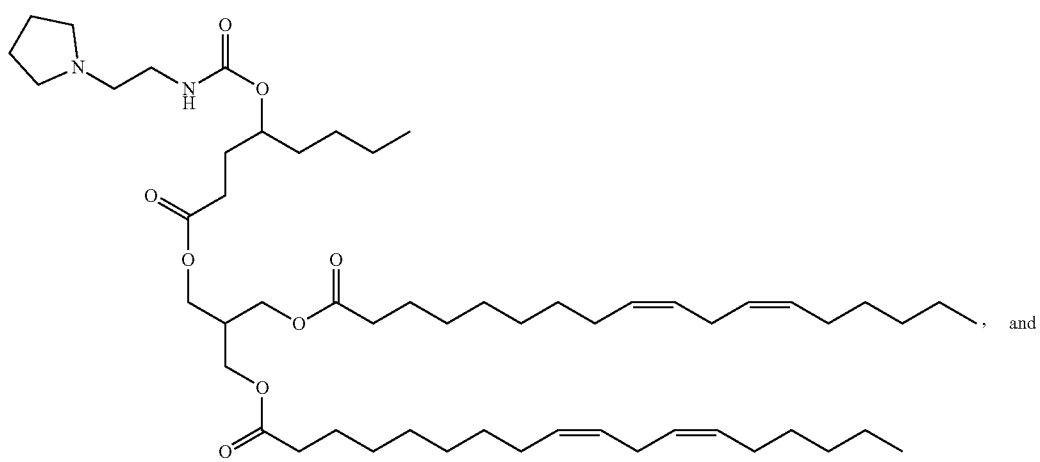, and

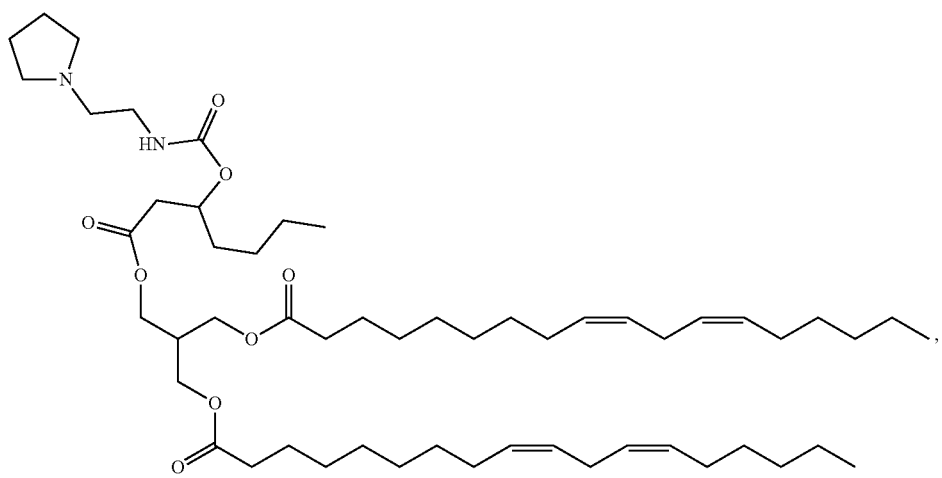, or a salt thereof.

15. A lipid nanoparticle (LNP) composition comprising a compound of claim 1 in a lipid component.

16. The LNP composition of claim 15, wherein the lipid component comprises a helper lipid, a PEG lipid, and a neutral lipid.

17. The LNP composition of claim 16, further comprising an RNA component, wherein the RNA component comprises a Class 2 Cas nuclease mRNA.

18. The LNP composition of claim 17, wherein the RNA component further comprises a gRNA-nucleic acid.

19. A method of gene editing, comprising contacting a cell with an LNP composition of claim 17.

20. A method of cleaving a DNA, comprising contacting a cell with an LNP composition of claim 17.

21. The compound of claim 14, wherein the compound is:
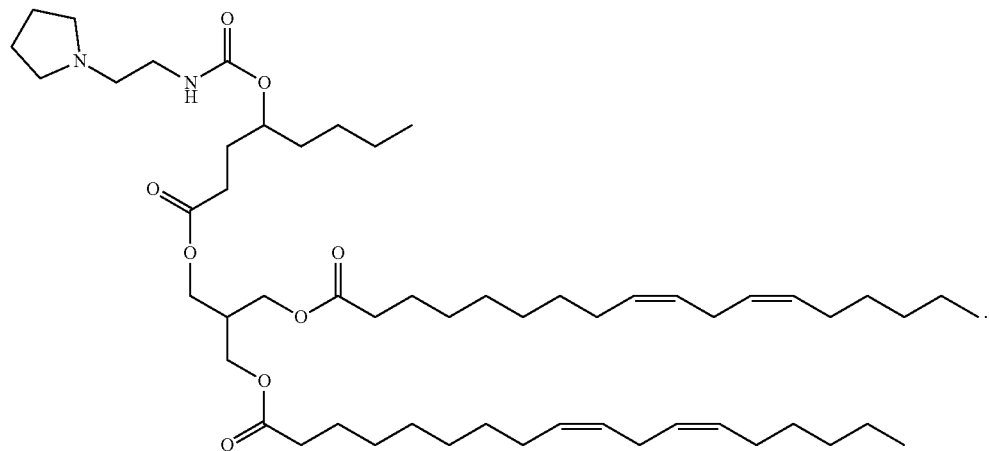 [SMILES: CCCCC/C=C\C/C=C\CCCCCCCC(=O)OCC(COC(=O)CCCCCCC/C=C\C/C=C\CCCCC)COC(=O)CCC(CCCC)OC(=O)NCCN1CCCC1 ; "."]
* * * * *

UNITED STATES PATENT AND TRADEMARK OFFICE
CERTIFICATE OF CORRECTION

| | | |
|---|---|---|
| PATENT NO. | : 12,077,483 B2 | Page 1 of 1 |
| APPLICATION NO. | : 17/299925 | |
| DATED | : September 3, 2024 | |
| INVENTOR(S) | : Stephen S. Scully et al. | |

It is certified that error appears in the above-identified patent and that said Letters Patent is hereby corrected as shown below:

In the Claims

In Column 519, Claim 1, "$X_1$" should be changed to --$X^1$--; "$X_2$" should be changed to --$X^2$-- for each occurrence; "$X_3$" should be changed to --$X^3$-- for each occurrence; "$X_4$" should be changed to --$X^4$--; "$X_5$" should be changed to --$X^5$--; "$Y_1$" should be changed to --$Y^1$--; "$Y_2$" should be changed to --$Y^2$--.

In Column 520, Claim 2, "$X_1$" should be changed to --$X^1$--; Claim 3, "$X_2$" should be changed to --$X^2$--; Claim 4, "$X_2$" should be changed to --$X^2$--; Claim 4, "$X_3$" should be changed to --$X^3$--; Claim 5, "$X_3$" should be changed to --$X^3$--; Claim 6, "$X_3$" should be changed to --$X^3$--; Claim 12, "$Y_2$—$R^4$" should be changed to --$Y^2$—$R^4$--.

In Column 568, Claim 18, "gRNA-nucleic acid" should be changed to --gRNA--.

Signed and Sealed this
Eleventh Day of November, 2025

John A. Squires
*Director of the United States Patent and Trademark Office*

SEQUENCE LISTING

<160> NUMBER OF SEQ ID NOS: 7

<210> SEQ ID NO 1
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1
uuacagccac gucuacagca guuuuagagc uagaaauagc aaguuaaaau aaggcuaguc    60
cguuaucaac uugaaaaagu ggcaccgagu cggugcuuuu    100

<210> SEQ ID NO 2
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2
gacaagcacc agaaagacca guuuuagagc uagaaauagc aaguuaaaau aaggcuaguc    60
cguuaucaac uugaaaaagu ggcaccgagu cggugcuuuu    100

<210> SEQ ID NO 3
<211> LENGTH: 4516
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3 ggucccgca gucggcgucc agcggcucug cuuguucgug ugugucgu ugcaggccuu    60 auucggaucc gccaccaugg acaagaagua cagcaucgga cuggacaucg aacaaacag    120 cgucggaugg gcagucauca cagacgaaua caagguccog agcaagaagu ucaagguccu    180
gggaaacaca gacagacaca gcaucaagaa gaaccugauc ggagcacugc uguucgacag    240

```
cggagaaaca gcagaagcaa caagacugaa gagaacagca agaagaagau acacaagaag    300
aaagaacaga aucugcuacc ugcaggaaau cuucagcaac gaaauggcaa aggucgacga    360
cagcuucuuc cacagacugg aagaaagcuu ccuggucgaa gaagacaaga agcacgaaag    420
acacccgauc uucggaaaca ucgucgacga agucgcauac cacgaaaagu acccgacaau    480
cuaccaccug agaaagaagc uggucgacag cacagacaag gcagaccuga gacugaucua    540
ccuggcacug gcacacauga ucaaguucag aggacacuuc cugaucgaag agaccugaa     600 cccggacaac agcgacgucg acaagcuguu cauccagcug guccagacau acaaccagcu    660
guucgaagaa aacccgauca acgcaagcgg agucgacgca aaggcaaucc ugagcgcaag    720
acugagcaag agcagaagac uggaaaaccu gaucgcacag cugccgggag aaaagaagaa    780
cggacuguuc ggaaaccuga ucgcacgag ccugggacu acaccgaacu ucaagagcaa      840
cuucgaccug gcagaagacg caaagcugca gcugagcaag gacacauacg acgacgaccu    900
ggacaaccug cuggcacaga ucggagacca guacgcagac cuguuccugg cagcaaagaa    960
ccugagcgac gcaauccugc ugagcgacau ccugagaguc aacacagaaa ucacaaaggc   1020
accgcugagc gcaagcauga ucaagagaua cgacgaacac caccaggacc ugacacugcu   1080
gaaggcacug gucagacagc agcugccgga aaaguacaag gaaaucuucu ucgaccagag   1140
caagaacgga uacgcaggau acaucgacgg aggagcaagc caggaagaau ucuacaaguu   1200
caucaagccg auccuggaaa gauggacgg aacagaagaa cugcugguca agcugaacag    1260
agaagaccug cugagaaagc agaacauu cgacaacgga agcaucccgc accagaucca     1320
ccugggagaa cugcacgcaa uccugagaag acaggaagac uucuacccgu uccugaagga   1380
caacagagaa aagaucgaaa agauccgac auucagaauc ccguacacg ucggaccgcu     1440 ggcaagagga aacagcagau cgcauggau gacaagaaag agcgaagaaa caaucacacc    1500
guggaacuuc gaagaagucg ucgacaaggg agcaagcgca cagagcuuca ucgaaagaau   1560
gacaaacuuc gacaagaacc ugccgaacga aaagguccug ccgaagcaca gccugcugua   1620
cgaauacuuc acagucuaca cgaacugac aaaggucaag uacgucacag aaggaaugag    1680
aaagccggca uucugagcg agaacagaa gaaggcaauc gucgaccugc uguucaagac     1740
aaacagaaag gucacaguca agcagcugaa ggaagacuac uucaagaaga ucgaaugcuu   1800
cgacagcguc gaaaucagcg gagucgaaga cagauucaac gcaagccugg aacauacca    1860 cgaccugcug aagaucauca aggacaagga cuuccuggac aacgaagaaa acgaagacau   1920
ccuggaagac aucguccuga cacugacacu guucgaagac agaaaauga ucgaagaaag    1980 acugaagaca uacgcacacc uguucgacga caaggucaug aagcagcuga agagaagaag   2040
auacacagga uggggaagac ugagcagaaa gcugaucaac ggaaucagag acaagcagag   2100
cggaaagaca auccuggacu uccugaagag cgacggauuc gcaaacagaa acuucaugca   2160
gcugauccac gacgacagcc ugacauucaa ggaagacauc cagaaggcac aggucagcgg   2220 acaggggagac agccugcacg aacacaucgc aaaccuggca ggaagcccgg caaucaagaa   2280
gggaauccug cagacaguca aggucgucga cgaacugguc aaggucaugg aagacacaa    2340 gccgaaaaac aucgucaucg aaauggcaag agaaaaccag acaacacaga agggacgaa    2400 gaacagcaga gaaagaauga agagaaucga agaaggaauc aaggaacugg aagccagau    2460 ccugaaggaa cacccggucg aaaacacaca gcugcagaac gaaaagcugu accuguacua   2520
ccugcagaac ggaagagaca uguacgucga ccaggaacug gacaucaaca gacugagcga   2580
```

-continued

```
cuacgacguc gaccacaucg ucccgcagag cuuccugaag gacgacagca ucgacaacaa   2640
gguccugaca agaagcgaca agaacagagg aaagagcgac aacgucccga gcgaagaagu   2700
cgucaagaag augaagaacu acuggagaca gcugcugaac gcaaagcuga ucacacagag   2760
aaaguucgac aaccugacaa aggcagagag aggaggacug agcgaacugg acaaggcagg   2820
auucaucaag agacagcugg ucgaaacaag acagaucaca aagcacgucg cacagauccu   2880
ggacagcaga augaacacaa aguacgacga aaacgacaag cugaucagag aagucaaggu   2940
caucacacug aagagcaagc uggucagcga cuucagaaag gacuuccagu ucuacaaggu   3000
cagagaaauc aacaacuacc accacgcaca cgacgcauac cugaacgcag ucgucggaac   3060
agcacugauc aagaaguacc cgaagcugga aagcgaauuc gucuacggag acuacaaggu   3120
cuacgacguc agaaagauga ucgcaaagag cgaacaggaa aucggaaagg caacagcaaa   3180
guacuucuuc uacagcaaca ucaugaacuu cuucaagaca gaaaucacac uggcaaacgg   3240
agaaaucaga aagagaccgc ugaucgaaac aaacggagaa acaggagaaa cgucuggga   3300 caagggaaga gacuucgcaa cagucagaaa gguccugagc augccgcagg ucaacaucgu   3360
caagaagaca gaaguccaga caggaggauu cagcaaggaa agcauccugc gaagagaaa   3420 cagcgacaag cugaucgcaa gaaagaagga cugggacccg aagaaguacg gaggauucga   3480
cagcccgaca gucgcauaca gcguccuggu cgucgcaaag gucgaaaagg gaaagagcaa   3540
gaagcugaag agcgucaagg aacugcuggg aaucacaauc auggaaagaa gcagcuucga   3600
aaagaacccg aucgacuucc uggaagcaaa gggauacaag gaagucaaga aggaccugau   3660
caucaagcug ccgaaguaca gccuguucga acuggaaaac ggaagaaaga gaaugcuggc   3720
aagcgcagga gaacugcaga agggaaacga acuggcacug ccgagcaagu acgucaacuu   3780
ccuguaccug gcaagccacu acgaaaagcu gaagggaagc ccggaagaca acgaacagaa   3840
gcagcuguuc gucgaacagc acaagcacua ccuggacgaa aucaucgaac agaucagcga   3900
auucagcaag agagucaucc uggcagacgc aaaccuggac aaggaccuga gcgcauacaa   3960
caagcacaga gacaagccga ucagagaaca ggcagaaaac aucauccacc uguucacacu   4020
gacaaaccug ggagcaccgg cagcauucaa guacuucgac acaacaaucg acagaaagag   4080
auacacaagc acaaaggaag uccuggacgc aacacugauc caccagagca ucacaggacu   4140
guacgaaaca agaaucgacc ugagccagcu gggaggagac ggaggaggaa gcccgaagaa   4200
gaagagaaag gucuagcuag ccaucacauu uaaaagcauc ucagccuacc augaauaa    4260 gagaaagaaa augaagauca auagcuuauu caucucuuuu ucuuuuucgu ugguguaaag   4320
ccaacacccu gucuaaaaaa cauaaauuuc uuuaaucauu uugccucuuu ucucugugcu   4380
ucaauuaaua aaaauggaa agaaccucga gaaaaaaaaa aaaaaaaaaa aaaaaaaaaa   4440
aaaaaaaaaa aaaaaaaaaa aaaaaaaaaa aaaaaaaaaa aaaaaaaaaa aaaaaaaaaa   4500
aaaaaaaaaa aucuag                                                  4516
```

<210> SEQ ID NO 4
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
acacaaauac caguccagcg guuuuagagc uagaaauagc aaguuaaaau aaggcuaguc      60
cguuaucaac uugaaaaagu ggcaccgagu cggugcuuuu                          100

<210> SEQ ID NO 5
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
acgcaaauau caguccagcg guuuuagagc uagaaauagc aaguuaaaau aaggcuaguc      60
cguuaucaac uugaaaaagu ggcaccgagu cggugcuuuu                          100

<210> SEQ ID NO 6
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa                          100

<210> SEQ ID NO 7
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
tttttttttt tttttttttt tttttttttt tttttttttt tttttttttt tttttttttt      60
tttttttttt tttttttttt tttttttttt tttttttttt                          100